US012612386B2

(12) United States Patent
Jeschke et al.

(10) Patent No.: US 12,612,386 B2
(45) Date of Patent: Apr. 28, 2026

(54) HETEROARYL-TRIAZOLE COMPOUNDS AS PESTICIDES

(71) Applicant: Bayer Aktiengesellschaft, Leverkusen (DE)

(72) Inventors: Peter Jeschke, Bergisch Gladbach (DE); Martin Fuesslein, Duesseldorf (DE); Hans-Georg Schwarz, Dorsten (DE); Joachim Telser, Wuppertal (DE); Yolanda Cancho Grande, Leverkusen (DE); Alexander Arlt, Cologne (DE); Steffen Mueller, Muelheim an der Ruhr (DE); Ulrich Ebbinghaus-Kintscher, Dortmund (DE); Peter Loesel, Leverkusen (DE); Marc Linka, Duesseldorf (DE); Arunas Jonas Damijonaitis, Chapel Hill, NC (US); Iring Heisler, Duesseldorf (DE); Andreas Turberg, Haan (DE); Oleksandr Mandzhulo, Kiev (UA)

(73) Assignee: Bayer Aktiengesellschaft, Leverkusen (DE)

( * ) Notice: Subject to any disclaimer, the term of this patent is extended or adjusted under 35 U.S.C. 154(b) by 652 days.

(21) Appl. No.: 17/997,884

(22) PCT Filed: May 5, 2021

(86) PCT No.: PCT/EP2021/061834

§ 371 (c)(1),
(2) Date: Nov. 3, 2022

(87) PCT Pub. No.: WO2021/224323

PCT Pub. Date: Nov. 11, 2021

(65) Prior Publication Data

US 2023/0348432 A1 Nov. 2, 2023

(30) Foreign Application Priority Data

May 6, 2020 (EP) .................................... 20173275
Nov. 2, 2020 (EP) .................................... 20205300
Feb. 15, 2021 (EP) .................................... 21157134

(51) Int. Cl.

| | |
|---|---|
| ***C07D 403/04*** | (2006.01) |
| ***A01N 43/707*** | (2006.01) |
| ***A01P 5/00*** | (2006.01) |
| ***A01P 7/02*** | (2006.01) |
| ***A01P 7/04*** | (2006.01) |
| ***C07D 401/14*** | (2006.01) |

(52) U.S. Cl.

CPC ......... *C07D 403/04* (2013.01); *A01N 43/707* (2013.01); *A01P 5/00* (2021.08); *A01P 7/02* (2021.08); *A01P 7/04* (2021.08); *C07D 401/14* (2013.01)

(58) Field of Classification Search

CPC .... A01N 43/653; A01N 43/707; A01N 47/02; A01N 53/00; C07D 401/14
See application file for complete search history.

(56) References Cited

U.S. PATENT DOCUMENTS

| | | | | |
|---|---|---|---|---|
| 11,528,907 | B2 * | 12/2022 | Arlt | A01N 43/00 |
| 11,864,557 | B2 * | 1/2024 | Arlt | C07D 471/04 |
| 12,187,705 | B2 * | 1/2025 | Arlt | A01N 55/00 |
| 2020/0404919 | A1 | 12/2020 | Schwarz et al. | |
| 2021/0147387 | A1 | 5/2021 | Arlt et al. | |
| 2021/0155608 | A1 | 5/2021 | Arlt et al. | |
| 2021/0386070 | A1 | 12/2021 | Arlt et al. | |
| 2022/0002268 | A1 | 1/2022 | Arlt et al. | |
| 2022/0274947 | A1 | 9/2022 | Schwarz et al. | |

FOREIGN PATENT DOCUMENTS

| | | | |
|---|---|---|---|
| WO | 2017192385 | A1 | 11/2017 |
| WO | 2019170626 | A1 | 9/2019 |
| WO | 2019201835 | A1 | 10/2019 |
| WO | 2019202077 | A1 | 10/2019 |

(Continued)

OTHER PUBLICATIONS

International Search Report received in international application No. PCT/EP2021/061834, mailed Jun. 2, 2021.

*Primary Examiner* — Mark V Stevens
(74) *Attorney, Agent, or Firm* — Michael Vanengelen

(57) ABSTRACT

The present invention relates to novel heteroaryl-triazole compounds of the general formula (I), in which the structural elements X, $R^1$, $R^2$, $R^3$ and $R^4$ have the meaning given in the description, to formulations and compositions comprising such compounds and for their use in the control of animal pests including arthropods and insects in plant protection and to their use for control of ectoparasites on animals.

(I)

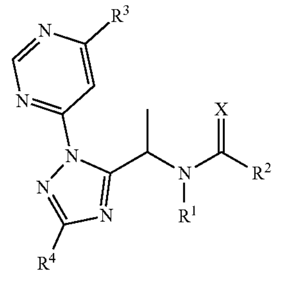

21 Claims, No Drawings

(56) References Cited

FOREIGN PATENT DOCUMENTS

| | | | | | |
|---|---|---|---|---|---|
| WO | WO-2019197468 | A1 | * | 10/2019 | ........... A01N 43/653 |
| WO | WO-2019206799 | A1 | * | 10/2019 | ............. A01N 43/00 |
| WO | 2019215198 | A1 | | 11/2019 | |
| WO | 2020002563 | A1 | | 1/2020 | |
| WO | 2020013720 | A2 | | 1/2020 | |
| WO | 2020053364 | A1 | | 3/2020 | |
| WO | 2020053365 | A2 | | 3/2020 | |
| WO | WO-2020079198 | A1 | * | 4/2020 | ........... A01N 43/653 |
| WO | 2020094363 | A1 | | 5/2020 | |
| WO | 2020169445 | A1 | | 8/2020 | |
| WO | 2020182649 | A1 | | 9/2020 | |
| WO | 2020188014 | A1 | | 9/2020 | |
| WO | 2020188027 | A1 | | 9/2020 | |
| WO | 2020193341 | A1 | | 10/2020 | |
| WO | 2021013719 | A1 | | 1/2021 | |

* cited by examiner

HETEROARYL-TRIAZOLE COMPOUNDS AS PESTICIDES

CROSS-REFERENCE TO RELATED APPLICATIONS

This application is the National Stage entry of International Application No. PCT/EP2021/061834, filed 5 May 2021, which claims priority to European Patent Application No. 20173275.7, filed 6 May 2020, European Patent Application No. 20205300.5, filed 2 Nov. 2020 and European Patent Application No. 21157134.4, filed 15 Feb. 2021.

BACKGROUND

Field

The present invention relates to novel heteroaryl-triazole compounds, to formulations and compositions comprising such compounds and to their use in the control of animal pests including arthropods and insects in plant protection and to their use for the control of ectoparasites on animals.

DESCRIPTION OF RELATED ART

Certain heteroaryl-triazole compounds are disclosed for the use in controlling ectoparasites on animals in WO 2017/192385 and for the use in controlling animal pests including arthropods and insects in the field of plant protection in WO 2019/170626 and WO 2019/215198. Further, the patent applications WO 2019/197468, WO 2019/201835, WO 2019/202077, WO 2019/206799, WO 2021/013719 and WO 2021/013720 disclose certain heteroaryl-triazole compounds for the use in controlling ectoparasites on animals and for the control of animal pests including arthropods and insects in the field of plant protection. WO 2020/002563, WO 2020/053364, WO 2020/053365, WO 2020/079198, WO 2020/094363, WO 2020/169445, WO 2020/182649, WO 2020/188014, WO 2020/188027 and WO 2020/193341 describe azole-amide compounds all of which can be used as insecticides.

Modern plant protection products and veterinary ectoparasiticides have to meet many demands, for example in relation to efficacy, persistence, spectrum and resistance breaking properties. Questions of toxicity, the combinability with other active compounds or formulation auxiliaries play a role, as well as the question of the expense that the synthesis of an active compound requires. Furthermore, resistances may occur. For all these reasons, the search for novel crop protection compositions or veterinary ectoparasiticides cannot be considered to be complete, and there is a constant need for novel compounds having properties which, compared to the known compounds, are improved at least in respect of individual aspects.

SUMMARY

It was an object of the present invention to provide compounds which widen the spectrum of the pesticides in various aspects.

The present invention therefore provides compounds of the general formula (I)

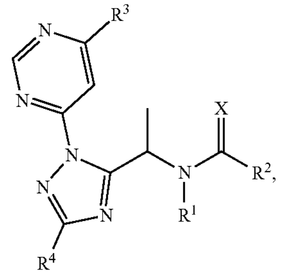

(I)

in which (Configuration 1-1):

X is O or S;

$R^1$ is hydrogen; $R^2$ is selected from the following substructures Q1 and Q2, in which the bond to the C═X-group is marked with a #:

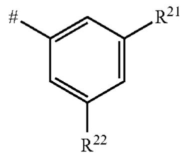

Q1

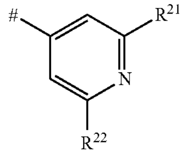

Q2 wherein $R^{21}$ is halogen, —CN, —$SF_5$, $C_1$-$C_3$haloalkyl, $C_1$-$C_3$haloalkoxy, $C_1$-$C_3$haloalkylthio, $C_1$-$C_3$haloalkylsulfinyl, $C_1$-$C_3$haloalkylsulfonyl, $C_1$-$C_3$alkylthio, $C_1$-$C_3$alkylsulfinyl, $C_1$-$C_3$alkylsulfonyl, $C_3$-$C_4$cycloalkylthio, $C_3$-$C_4$cycloalkylsulfinyl, $C_3$-$C_4$cycloalkylsulfonyl, phenylsulfonyl, wherein the phenyl is optionally substituted with one to two substituent(s) selected from the group of halogen, —CN, methyl, trifluoromethyl or trifluoromethoxy; or cyclopropyl wherein the cyclopropyl is optionally substituted with one to two substituent(s) selected from the group of halogen, —CN, methyl or trifluoromethyl;

$R^{22}$ is hydrogen, halogen, —CN, $C_1$-$C_3$haloalkyl, $C_1$-$C_3$haloalkoxy or $C_1$-$C_3$haloalkylsulfonyl;

$R^3$ is —CN or a substituent selected from the following substructure S1, in which the bond to the pyrimidine is marked with a #:

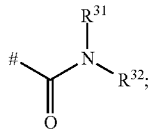

S1

$R^{31}$ is hydrogen or $C_1$-$C_3$alkyl;

$R^{32}$ is hydrogen, $C_3$-$C_6$cycloalkyl or $C_1$-$C_3$alkyl, wherein $C_3$-$C_6$cycloalkyl and $C_1$-$C_3$alkyl are optionally substituted with one to two substituent selected from the group of halogen, —CN, $C_3$-$C_6$cycloalkyl and $C_1$-$C_3$alkoxy;

$R^4$ is hydrogen, $C_1$-$C_3$alkyl, $C_1$-$C_3$alkoxy or $C_3$-$C_4$cycloalkyl.

DETAILED DESCRIPTION OF A PREFERRED EMBODIMENT

The compounds of the formula (I) likewise encompass any diastereomers or enantiomers and E/Z isomers which exist, and also salts and N-oxides of compounds of the formula (I), and the use thereof for control of animal pests.

Preferred radical definitions for the formulae specified above and hereinafter are given below.

The present invention furthermore provides compounds of the general formula (I) in which (Configuration 1-2):

X is O or S;

$R^1$ is hydrogen;

$R^2$ is selected from the following substructures Q1 and Q2, in which the bond to the C═X-group is marked with a #:

Q1

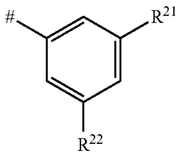

Q2

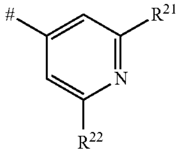

wherein $R^{21}$ is halogen, —CN, —$SF_5$, $C_1$-$C_3$haloalkyl, $C_1$-$C_3$haloalkoxy, $C_1$-$C_3$haloalkylthio, $C_1$-$C_3$haloalkylsulfinyl, $C_1$-$C_3$haloalkylsulfonyl, $C_1$-$C_3$alkylthio, $C_1$-$C_3$alkylsulfinyl, $C_1$-$C_3$alkylsulfonyl, $C_3$-$C_4$cycloalkylthio, $C_3$-$C_4$cycloalkylsulfinyl, $C_3$-$C_4$cycloalkylsulfonyl, phenylsulfonyl, wherein the phenyl is optionally substituted with one to two substituent(s) selected from the group of halogen, —CN, methyl, trifluoromethyl or trifluoromethoxy; or cyclopropyl wherein the cyclopropyl is optionally substituted with one to two substituent(s) selected from the group of halogen, —CN, methyl or trifluoromethyl;

$R^{22}$ is hydrogen, halogen, —CN, $C_1$-$C_3$haloalkyl, $C_1$-$C_3$haloalkoxy or $C_1$-$C_3$haloalkylsulfonyl;

$R^3$ is —CN or a substituent selected from the following substructure S1, in which the bond to the pyrimidine is marked with a #:

S1

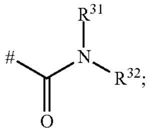

$R^{31}$ is hydrogen or $C_1$-$C_3$alkyl;

$R^{32}$ is hydrogen, $C_3$-$C_6$cycloalkyl or $C_1$-$C_3$alkyl, wherein $C_3$-$C_6$cycloalkyl and $C_1$-$C_3$alkyl are optionally substituted with one to three substituents selected from the group of halogen, —CN, $C_3$-$C_6$cycloalkyl and $C_1$-$C_3$alkoxy;

$R^4$ is hydrogen, $C_1$-$C_3$alkyl, $C_1$-$C_3$alkoxy or $C_3$-$C_4$cycloalkyl.

Preference (Configuration 2-1) is given to the compounds of formula (I) in which X is O or S;

$R^1$ is hydrogen;

$R^2$ is selected from the following substructures Q1 and Q2, in which the bond to the C═X-group is marked with a #:

Q1

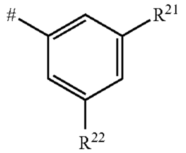

Q2

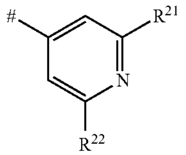

wherein $R^{21}$ is fluorine, chlorine, bromine, iodine, —CN, cyclopropyl, 1-cyanocyclopropyl, 2,2-dichlorocyclopropyl, difluoromethyl, trifluoromethyl, difluoromethoxy, trifluoromethoxy, 1,1,2,2-tetrafluoroethoxy, 1,1,2,2-tetrafluoro-2-iodoethoxy difluoromethylthio, trifluoromethylthio, 1,1,2,2-tetrafluoroethylthio difluoromethylsulfonyl, trifluoromethylsulfonyl, 1,1,2,2-tetrafluoroethylsulfonyl, methylsulfonyl, ethylsulfonyl, cyclopropylsulfonyl or 4-chlorophenyl-sulfonyl;

$R^{22}$ is hydrogen, fluorine, chlorine, bromine, iodine, —CN, difluoromethyl, trifluoromethyl, difluoromethoxy, trifluoromethoxy, difluoromethylsulfonyl, trifluoromethylsulfonyl;

$R^3$ is —CN or a substituent selected from the following substructure S1, in which the bond to the pyrimidine is marked with a #:

S1

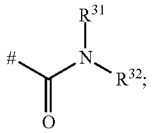

$R^{31}$ is hydrogen or methyl;

$R^{32}$ is hydrogen, cyclopropyl or $C_1$-$C_3$alkyl, wherein $C_1$-$C_3$alkyl is optionally substituted with one substituent selected from the group of halogen, —CN, cyclopropyl and methoxy;

$R^4$ is hydrogen, methyl or cyclopropyl.

Preference (Configuration 2-2) is also given to the compounds of the formula (I) in which X is O or S;

$R^1$ is hydrogen;

$R^2$ is selected from the following substructures Q1 and Q2, in which the bond to the C═X-group is marked with a #:

Q1

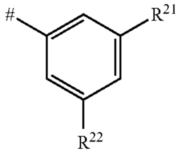

Q2

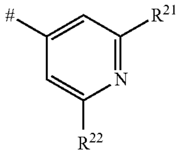

wherein $R^{21}$ is fluorine, chlorine, bromine, iodine, —CN, cyclopropyl, 1-cyanocyclopropyl, 2,2-dichlorocyclopropyl, difluoromethyl, 1,1-difluoroethyl, trifluoromethyl, chlorodifluoromethyl, 2-fluoropropan-2-yl, difluoromethoxy, trifluoromethoxy, 1,1,2,2-tetrafluoroethoxy, 1,1,2,2-tetrafluoro-2-iodoethoxy difluoromethylthio, trifluoromethylthio, 1,1,2,2-tetrafluoroethylthio, difluoromethylsulfonyl, trifluoromethylsulfonyl, 1,1,2,2-tetrafluoroethylsulfonyl, methylsulfanyl, methylsulfinyl, methylsulfonyl, ethylsulfonyl, cyclopropylsulfonyl or 4-chlorophenyl-sulfonyl;

$R^{22}$ is hydrogen, fluorine, chlorine, bromine, iodine, —CN, difluoromethyl, trifluoromethyl, difluoromethoxy, trifluoromethoxy, difluoromethylsulfonyl, trifluoromethylsulfonyl;

$R^3$ is —CN or a substituent selected from the following substructure S1, in which the bond to the pyrimidine is marked with a #:

S1

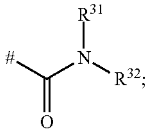

$R^{31}$ is hydrogen or methyl;

$R^{32}$ is hydrogen, cyclopropyl or $C_1$-$C_3$alkyl, wherein $C_1$-$C_3$alkyl is optionally substituted with one to three substituents selected from the group of fluorine, chlorine, —CN, cyclopropyl and methoxy;

$R^4$ is hydrogen, methyl or cyclopropyl.

Further preferred (Configuration 3-1) are the compounds of the formula (I) in which X is O;

$R^1$ is hydrogen;

$R^2$ is (3,5-dibromophenyl), (3,5-dichlorophenyl), (3-chloro-5-methylsulfonylphenyl), (3-cyano-5-fluorophenyl), (3-fluorophenyl), (3-iodophenyl), 3-(1,1,2,2-tetrafluoroethylthio)phenyl, 3-(1-cyanocyclopropyl)-5-(trifluoromethoxy)phenyl, 3-(difluoromethoxy)-5-fluorophenyl, 3-(difluoromethylsulfonyl)-5-(trifluoromethoxy)phenyl, 3-(trifluoromethoxy)-5-(trifluoromethylsulfonyl)phenyl, 3-(trifluoromethoxy)phenyl, 3-(trifluoromethyl)phenyl, 3,5-bis(difluoromethoxy)phenyl, 3,5-bis(trifluoromethoxy)phenyl, 3,5-bis(trifluoromethyl)phenyl, 3,5-bis(trifluoromethylsulfonyl)phenyl, 3-bromo-5-(1,1,2,2-tetrafluoroethoxy)phenyl, 3-bromo-5-(2,2-dichlorocyclopropyl)phenyl, 3-bromo-5-(difluoromethoxy)phenyl, 3-bromo-5-(trifluoromethoxy)phenyl, 3-chloro-5-(1,1,2,2-tetrafluoro-2-iodoethoxy)phenyl, 3-chloro-5-(1,1,2,2-tetrafluoroethoxy)phenyl, 3-chloro-5-(4-chlorophenyl)sulfonylphenyl, 3-chloro-5-(difluoromethylsulfonyl)phenyl, 3-chloro-5-(trifluoromethoxy)phenyl, 3-chloro-5-(trifluoromethyl)phenyl, 3-chloro-5-(trifluoromethylsulfonyl)phenyl, 3-chloro-5-(trifluoromethylthio)phenyl, 3-cyano-5-(trifluoromethoxy)phenyl, 3-cyclopropyl-5-(difluoromethoxy)phenyl, 3-cyclopropyl-5-(trifluoromethoxy)phenyl, 3-cyclopropylsulfonyl-5-(trifluoromethoxy)phenyl, 3-fluoro-5-(trifluoromethoxy)phenyl, 3-methylsulfonyl-5-(trifluoromethoxy)phenyl, 3-methylsulfonyl-5-(trifluoromethyl)phenyl or 2-chloro-6-(1-cyanocyclopropyl)pyridin-4-yl.

$R^3$ is —CN, aminocarbonyl, methylcarbamoyl, [ethyl(methyl)amino]carbonyl, [isopropyl(methyl)amino]carbonyl or [cyclopropylmethyl(methyl)amino]carbonyl;

$R^4$ is hydrogen, methyl or cyclopropyl.

Also further preferred (Configuration 3-2) are the compounds of the formula (I) in which X is O;

$R^1$ is hydrogen;

$R^2$ is (3-fluorophenyl), (3-iodophenyl), (3,5-dibromophenyl), (3,5-dichlorophenyl), (3-chloro-5-methylsulfonylphenyl), 3-bromo-5-methylsulfonylphenyl, (3-cyano-5-fluorophenyl), 3-chloro-5-cyanophenyl, 3-bromo-5-cyanophenyl, 3,5-dicyanophenyl, 3-(1,1,2,2-tetrafluoroethylthio)phenyl, 3-(1-cyanocyclopropyl)-5-(trifluoromethoxy)phenyl, 3-(difluoromethoxy)-5-fluorophenyl, 3-(difluoromethoxy)-5-iodophenyl, 3-(difluoromethylsulfonyl)-5-(trifluoromethoxy)phenyl, 3-(trifluoromethoxy)-5-(trifluoromethylsulfonyl)phenyl, 3-(trifluoromethoxy)phenyl, 3-(trifluoromethyl)phenyl, 3-(trifluoromethylsulfonyl)phenyl, 3,5-bis(difluoromethoxy)phenyl, 3-(2-fluoropropan-2-yl)-5-(trifluoromethoxy)phenyl, 3,5-bis(trifluoromethoxy)phenyl, 3,5-bis(difluoromethyl)phenyl, 3,5-bis(trifluoromethyl)phenyl, 3-(difluoromethoxy)-5-(trifluoromethoxy)phenyl, 3,5-bis(difluoromethylsulfonyl)phenyl, 3,5-bis(trifluoromethylsulfonyl)phenyl, 3-bromo-5-(1,1,2,2-tetrafluoroethoxy)phenyl, 3-bromo-5-(2,2-dichlorocyclopropyl)phenyl, 3-bromo-5-(difluoromethoxy)phenyl, 3-bromo-5-(trifluoromethoxy)phenyl, 3-chloro-5-(1,1,2,2-tetrafluoro-2-iodoethoxy)phenyl, 3-chloro-5-(1,1,2,2-tetrafluoroethoxy)phenyl, 3-chloro-5-(4-chlorophenyl)sulfonylphenyl, 3-chloro-5-(difluoromethylsulfonyl)phenyl, 3-chloro-5-(trifluoromethoxy)phenyl, 3-chloro-5-(trifluoromethyl)phenyl, 3-chloro-5-(1,1-difluoroethyl)phenyl, 3-chloro-5-(chlorodifluoromethyl)phenyl, 3-chloro-5-(trifluoromethylsulfonyl)phenyl, 3-bromo-5-(trifluoromethylsulfonyl)phenyl, 3-chloro-5-(trifluoromethylthio)phenyl, 3-cyano-5-(trifluoromethoxy)phenyl, 3-cyclopropyl-5-(difluoromethoxy)phenyl, 3-cyclopropyl-5-(trifluoromethoxy)phenyl, 3-cyclopropylsulfonyl-5-(trifluoromethoxy)phenyl, 3-fluoro-5-(trifluoromethoxy)phenyl, 3-methylsulfonylphenyl, 3-(difluoromethoxy)-5-methylsulfanylphenyl, 3-(difluoromethoxy)-5-methylsulfonylphenyl, 3-methylsulfonyl-5-(trifluoromethoxy)phenyl, 3-methylsulfonyl-5-(trifluoromethyl)phenyl, 2,6-dibromopyridin-4-yl, 2-(trifluoromethoxy)pyridin-4-yl, 2-chloro-6-(trifluoromethoxy)pyridin-4-yl, 2-bromo-6-methylsulfonyl-pyridin-4-yl or 2-chloro-6-(1-cyanocyclopropyl)pyridin-4-yl;

$R^3$ is —CN, aminocarbonyl, methylcarbamoyl, ethylcarbamoyl, (isopropylamino)carbonyl, (difluoroethylamino)carbonyl, (3,3,3-trifluoropropylamino)carbonyl, (cyclopropylamino)carbonyl, dimethylaminocarbonyl, [ethyl(methyl)amino]carbonyl, [isopropyl(methyl)amino]carbonyl or [cyclopropylmethyl(methyl)amino]carbonyl;

$R^4$ is hydrogen, methyl or cyclopropyl.

In a further preferred embodiment, the invention relates to compounds of the formula (I')

(I')

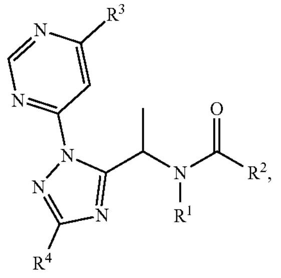

in which the structural elements $R^1$, $R^2$, $R^3$ and $R^4$ have the meanings given in Configuration (1-1) or the meanings given in Configuration (2-1) or the meanings given in Configuration (3-1) or the meanings given in Configuration (1-2) or the meanings given in Configuration (2-2) or the meanings given in Configuration (3-2).

In a further preferred embodiment, the invention relates to compounds of the formula (I'') in which $R^1$ is hydrogen and (I'')

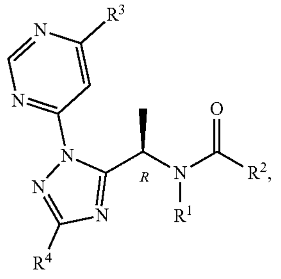

in which the structural elements $R^2$, $R^3$ and $R^4$ have the meanings given in Configuration (1-1) or the meanings given in Configuration (2-1) or the meanings given in Configuration (3-1) or the meanings given in Configuration (1-2) or the meanings given in Configuration (2-2) or the meanings given in Configuration (3-2).

In a further preferred embodiment, the invention relates to compounds of the formula (I''') in which $R^1$ is hydrogen and (I''')

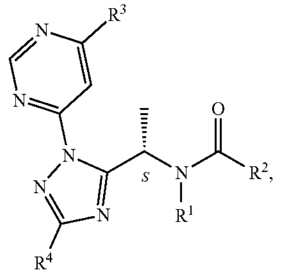

in which the structural elements $R^2$, $R^3$ and $R^4$ have the meanings given in Configuration (1-1) or the meanings given in Configuration (2-1) or the meanings given in Configuration (3-1) or the meanings given in Configuration (1-2) or the meanings given in Configuration (2-2) or the meanings given in Configuration (3-2).

In accordance with a further aspect, the present invention covers intermediate compounds which are useful for the preparation of the compounds of general formula (I), supra.

Particularly, the invention covers the intermediate compounds of general formula (a) and salts thereof:

(a)

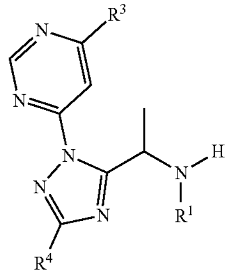

in which $R^1$, $R^3$ and $R^4$ have the meanings given in Configuration (1-1) or the meanings given in Configuration (2-1) or the meanings given in Configuration (3-1) or the meanings given in Configuration (1-2) or the meanings given in Configuration (2-2) or the meanings given in Configuration (3-2).

Particularly, the invention covers the intermediate compound(s) INT-1 to INT-23, in case of amines and acids also the salts thereof and in case of amine hydrochlorides also the free amines (see table 2):

INT-1: 6-[5-(1-aminoethyl)-1H-1,2,4-triazol-1-yl]pyrimidine-4-carbonitrile hydrochloride INT-2: tert-butyl {1-[1-(6-cyanopyrimidin-4-yl)-1H-1,2,4-triazol-5-yl]ethyl}carbamate INT-3: tert-butyl N-[(1S)-1-[2-(6-cyanopyrimidin-4-yl)-1,2,4-triazol-3-yl]ethyl]carbamate INT-4: 6-[5-[(1S)-1-aminoethyl]-1,2,4-triazol-1-yl]pyrimidine-4-carbonitrile; 2,2,2-trifluoroacetic acid INT-5: tert-butyl N-[(1S)-1-[2-(6-cyanopyrimidin-4-yl)-5-methyl-1,2,4-triazol-3-yl]ethyl]carbamate INT-6: 6-[5-[(1S)-1-aminoethyl]-3-methyl-1,2,4-triazol-1-yl]pyrimidine-4-carbonitrile hydrochloride INT-7: tert-butyl N-[(1S)-1-[2-(6-cyanopyrimidin-4-yl)-5-cyclopropyl-1,2,4-triazol-3-yl]ethyl]-carbamate INT-8: 6-[5-[(1S)-1-aminoethyl]-3-cyclopropyl-1,2,4-triazol-1-yl]pyrimidine-4-carbonitrile hydro-chloride INT-9: 6-[5-[(1S)-1-aminoethyl]-1,2,4-triazol-1-yl]pyrimidine-4-carboxamide hydrochloride INT-10: 6-[5-[(1S)-1-aminoethyl]-3-methyl-1,2,4-triazol-1-yl]pyrimidine-4-carboxamide hydrochloride INT-11: 6-[5-[(1S)-1-aminoethyl]-3-cyclopropyl-1,2,4-triazol-1-yl]pyrimidine-4-carboxamide hydro-chloride INT-17: methyl 6-[5-[(1S)-1-(tert-butoxycarbonylamino)ethyl]-3-cyclopropyl-1,2,4-triazol-1-yl]pyrimidine-4-carboxylate INT-18: tert-butyl N-[(1S)-1-[2-(6-carbamoylpyrimidin-4-yl)-5-cyclopropyl-1,2,4-triazol-3-yl]ethyl]carbamate INT-19: tert-butyl N-[(1S)-1-[5-cyclopropyl-2-[6-(methylcarbamoyl)pyrimidin-4-yl]-1,2,4-triazol-3-yl]ethyl]carbamate INT-20: tert-butyl N-[(1S)-1-[5-cyclopropyl-2-[6-(dimethylcarbamoyl)pyrimidin-4-yl]-1,2,4-triazol-3-yl]ethyl]carbamate INT-21: 6-[5-[(1S)-1-aminoethyl]-3-cyclopropyl-1,2,4-triazol-1-yl]-N-methyl-pyrimidine-4-carboxamide hydrochloride INT-22: 6-[5-[(1S)-1-aminoethyl]-3-cyclopropyl-1,2,4-triazol-1-yl]-N,N-dimethyl-pyrimidine-4-carboxamide hydrochloride INT-12: 2-chloro-6-(1-cyanocyclopropyl)pyridine-4-carboxylic acid INT-13: 3-(trifluoromethoxy)-5-(trifluoromethylsulfonyl)benzoic acid INT-14: 3-bromo-5-(2,2-dichlorocyclopropyl)benzoic acid INT-15: 3-bromo-5-(1,1,2,2-tetrafluoroethoxy)benzoic acid INT-16: 3-(1-fluoro-1-methyl-ethyl)-5-(trifluoromethoxy)benzoic acid INT-23: 3,5-bis(difluoromethylsulfonyl)benzoic acid The compounds of the formula (I) may possibly also, depending on the nature of the substituents, be in the form of stereoisomers, i.e. in the form of geometric and/or optical isomers or isomer mixtures of varying composition. This invention provides both the pure stereoisomers and any desired mixtures of these isomers, even though it is generally only compounds of the formula (I) that are discussed here.

However, preference is given in accordance with the invention to using the optically active, stereoisomeric forms of the compounds of the formula (I) and salts thereof.

The invention therefore relates both to the pure enantiomers and diastereomers and to mixtures thereof for controlling animal pests, including arthropods and particularly insects.

If appropriate, the compounds of the formula (I) may be present in various polymorphic forms or as a mixture of various polymorphic forms. Both the pure polymorphs and the polymorph mixtures are provided by the invention and can be used in accordance with the invention.

Definitions

The person skilled in the art is aware that, if not stated explicitly, the expressions "a" or "an" as used in the present application may, depending on the situation, mean "one (1)", "one (1) or more" or "at least one (1)".

For all the structures described herein, such as ring systems and groups, adjacent atoms must not be —O—O— or —O—S—.

Structures having a variable number of possible carbon atoms (C atoms) may be referred to in the present application as $C_{lower\ limit\ of\ carbon\ atoms}$-$C_{upper\ limit\ of\ carbon\ atoms}$ structures ($C_{LL}$-$C_{UL}$ structures), in order thus to be stipulated more specifically. Example: an alkyl group may consist of 3 to 10 carbon atoms and in that case corresponds to $C_3$-$C_{10}$alkyl. Ring structures composed of carbon atoms and heteroatoms may be referred to as "LL- to UL-membered" structures. One example of a 6-membered ring structure is toluene (a 6-membered ring structure substituted by a methyl group).

If a collective term for a substituent, for example $C_{LL}$-$C_{UL}$ alkyl, is at the end of a composite substituent, for example $C_{LL}$-$C_{UL}$cycloalkyl-$C_{LL}$-$C_{UL}$alkyl, the constituent at the start of the composite substituent, for example the $C_{LL}$-$C_{UL}$cycloalkyl, may be mono- or polysubstituted identically or differently and independently by the latter substituent, for example $C_{LL}$-$C_{UL}$alkyl. All the collective terms used in this application for chemical groups, cyclic systems and cyclic groups can be stipulated more specifically through the addition "$C_{LL}$-$C_{UL}$" or "LL- to UL-membered".

In the definitions of the symbols given in the above formulae, collective terms which are generally representative of the following substituents were used: Halogen relates to elements of the 7th main group, preferably fluorine, chlorine, bromine and iodine, more preferably fluorine, chlorine and bromine, and even more preferably fluorine and chlorine.

Examples of heteroatom are N, O, S, P, B, Si. Preferably, the term "heteroatom" relates to N, S and O.

According to the invention, "alkyl"—on its own or as part of a chemical group—represents straight-chain or branched hydrocarbons preferably having 1 to 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preference is also given to alkyls having 1 to 4 carbon atoms such as, inter alia, methyl, ethyl, ethyl, n-propyl, isopropyl, n-butyl, isobutyl, s-butyl or t-butyl. The inventive alkyls may be substituted by one or more identical or different radicals.

According to the invention, "alkenyl"—on its own or as part of a chemical group—represents straight-chain or branched hydrocarbons preferably having 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preference is also given to alkenyls having 2 to 4 carbon atoms such as, inter alia, 2-propenyl, 2-butenyl or 1-methyl-2-propenyl. The inventive alkenyls may be substituted by one or more identical or different radicals.

According to the invention, "alkynyl"—on its own or as part of a chemical group—represents straight-chain or branched hydrocarbons preferably having 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Preference is also given to alkynyls having 2 to 4 carbon atoms such as, inter alia, ethynyl, 2-propynyl or 2-butynyl-2-propenyl. The inventive alkynyls may be substituted by one or more identical or different radicals.

According to the invention, "cycloalkyl"—on its own or as part of a chemical group—represents mono-, bi- or tricyclic hydrocarbons preferably having 3 to 10 carbons, for example cyclopropyl, cyclobutyl, cyclopentyl, cyclohexyl, cycloheptyl, cyclooctyl, bicyclo[2.2.1]heptyl, bicyclo[2.2.2]octyl or adamantyl. Preference is also given to cycloalkyls having 3, 4, 5, 6 or 7 carbon atoms such as, inter alia, cyclopropyl or cyclobutyl. The inventive cycloalkyls may be substituted by one or more identical or different radicals.

According to the invention, "alkylcycloalkyl" represents mono-, bi- or tricyclic alkylcycloalkyl preferably having 4 to 10 or 4 to 7 carbon atoms, for example methylcyclopropyl, ethylcyclopropyl, isopropylcyclobutyl, 3-methylcyclopentyl and 4-methylcyclohexyl. Preference is also given to alkylcycloalkyls having 4, 5 or 7 carbon atoms such as, inter alia, ethylcyclopropyl or 4-methylcyclohexyl. The inventive alkylcycloalkyls may be substituted by one or more identical or different radicals.

According to the invention, "cycloalkylalkyl" represents mono-, bi- or tricyclic cycloalkylalkyl preferably having 4 to 10 or 4 to 7 carbon atoms, for example cyclopropylmethyl, cyclobutylmethyl, cyclopentylmethyl, cyclohexylmethyl and cyclopentylethyl. Preference is also given to cycloalkylalkyls having 4, 5 or 7 carbon atoms such as, inter alia, cyclopropylmethyl or cyclobutylmethyl. The inventive cycloalkylalkyls may be substituted by one or more identical or different radicals.

According to the invention, "hydroxyalkyl" represents a straight-chain or branched alcohol preferably having 1 to 6 carbon atoms, for example methanol, ethanol, n-propanol, isopropanol, n-butanol, isobutanol, s-butanol and t-butanol. Preference is also given to hydroxyalkyl groups having 1 to 4 carbon atoms. The inventive hydroxyalkyl groups may be substituted by one or more identical or different radicals.

According to the invention, "alkoxy" represents a straight-chain or branched O-alkyl preferably having 1 to 6 carbon atoms, for example methoxy, ethoxy, n-propoxy, isopropoxy, n-butoxy, isobutoxy, s-butoxy and t-butoxy. Preference is also given to alkoxy groups having 1 to 4 carbon atoms. The inventive alkoxy groups may be substituted by one or more identical or different radicals.

According to the invention, "alkylthio", or "alkylsulfanyl" represents straight-chain or branched S-alkyl preferably having 1 to 6 carbon atoms, for example methylthio, ethylthio, n-propylthio, isopropylthio, n-butylthio, isobutylthio, s-butylthio and t-butylthio. Preference is also given to alkylthio groups having 1 to 4 carbon atoms. The inventive alkylthio groups may be substituted by one or more identical or different radicals.

According to the invention, "alkylsulfinyl" represents straight-chain or branched alkylsulfinyl preferably having 1 to 6 carbon atoms, for example methylsulfinyl, ethylsulfinyl, n-propylsulfinyl, isopropylsulfinyl, n-butylsulfinyl, isobutylsulfinyl, s-butylsulfinyl and t-butylsulfinyl. Preference is also given to alkylsulfinyl groups having 1 to 4 carbon atoms. The inventive alkylsulfinyl groups may be substituted by one or more identical or different radicals and embrace both enantiomers.

According to the invention, "alkylsulfonyl" represents straight-chain or branched alkylsulfonyl preferably having 1 to 6 carbon atoms, for example methylsulfonyl, ethylsulfonyl, n-propylsulfonyl, isopropylsulfonyl, n-butylsulfonyl, isobutylsulfonyl, s-butylsulfonyl and t-butylsulfonyl. Preference is also given to alkylsulfonyl groups having 1 to 4 carbon atoms. The inventive alkylsulfonyl groups may be substituted by one or more identical or different radicals.

According to the invention, "cycloalkylthio" or "cycloalkylsulfanyl" represents —S-cycloalkyl preferably having 3 to 6 carbon atoms, for example cyclopropylthio, cyclobutylthio, cyclopentylthio, cyclohexylthio.

Preference is also given to cycloalkylthio groups having 3 to 5 carbon atoms. The inventive cycloalkylthio groups may be substituted by one or more identical or different radicals.

According to the invention, "cycloalkylsulfinyl" represents —S(O)-cycloalkyl preferably having 3 to 6 carbon atoms, for example cyclopropylsulfinyl, cyclobutylsulfinyl, cyclopentylsulfinyl, cyclohexylsulfinyl. Preference is also given to cycloalkylsulfinyl groups having 3 to 5 carbon atoms. The inventive cycloalkylsulfinyl groups may be substituted by one or more identical or different radicals and embrace both enantiomers.

According to the invention, "cycloalkylsulfonyl" represents —$SO_2$-cycloalkyl preferably having 3 to 6 carbon atoms, for example cyclopropylsulfonyl, cyclobutylsulfonyl, cyclopentylsulfonyl, cyclohexylsulfonyl. Preference is also given to cycloalkylsulfonyl groups having 3 to 5 carbon atoms. The inventive cycloalkylsulfonyl groups may be substituted by one or more identical or different radicals.

According to the invention, "phenylthio", or "phenylsulfanyl" represents —S-phenyl, for example phenylthio. The inventive phenylthio groups may be substituted by one or more identical or different radicals.

According to the invention, "phenylsulfinyl" represents —S(O)-phenyl, for example phenylsulfinyl. The inventive phenylsulfinyl groups may be substituted by one or more identical or different radicals and embrace both enantiomers.

According to the invention, "phenylsulfonyl" represents —$SO_2$-phenyl for example phenylsulfonyl. The inventive phenylsulfonyl groups may be substituted by one or more identical or different radicals.

According to the invention, "alkylcarbonyl" represents straight-chain or branched alkyl-C(═O) preferably having 2 to 7 carbon atoms such as methylcarbonyl, ethylcarbonyl, n-propylcarbonyl, isopropylcarbonyl, s-butylcarbonyl and t-butylcarbonyl. Preference is also given to alkylcarbonyls having 1 to 4 carbon atoms. The inventive alkylcarbonyls may be substituted by one or more identical or different radicals.

According to the invention, "alkoxycarbonyl"—alone or as a constituent of a chemical group—represents straight-chain or branched alkoxycarbonyl, preferably having 1 to 6 carbon atoms or having 1 to 4 carbon atoms in the alkoxy moiety, for example methoxycarbonyl, ethoxycarbonyl, n-propoxycarbonyl, isopropoxycarbonyl, s-butoxycarbonyl and t-butoxycarbonyl. The inventive alkoxycarbonyl groups may be substituted by one or more identical or different radicals.

According to the invention, "alkylaminocarbonyl" represents straight-chain or branched alkylaminocarbonyl having preferably 1 to 6 carbon atoms or 1 to 4 carbon atoms in the alkyl moiety, for example methylaminocarbonyl, ethylaminocarbonyl, n-propylaminocarbonyl, isopropylaminocarbonyl, s-butylaminocarbonyl and t-butylaminocarbonyl. The inventive alkylaminocarbonyl groups may be substituted by one or more identical or different radicals.

According to the invention, "N,N-dialkylaminocarbonyl" represents straight-chain or branched N,N-dialkylaminocarbonyl having preferably 1 to 6 carbon atoms or 1 to 4 carbon atoms in the alkyl moiety, for example N,N-dimethylaminocarbonyl, N,N-diethylaminocarbonyl, N,N-di(n-propylamino)carbonyl, N,N-di(isopropylamino)carbonyl and N,N-di-(s-butylamino)carbonyl. The inventive N,N-dialkylaminocarbonyl groups may be substituted by one or more identical or different radicals.

According to the invention, "aryl" represents a mono-, bi- or polycyclic aromatic system having preferably 6 to 14, especially 6 to 10, ring carbon atoms, for example phenyl, naphthyl, anthryl, phenanthrenyl, preferably phenyl. In addition, aryl also represents fused polycyclic systems such as tetrahydronaphthyl, indenyl, indanyl, fluorenyl, biphenyl, where the bonding site is on the aromatic system. The inventive aryl groups may be substituted by one or more identical or different radicals.

Examples of substituted aryls are the arylalkyls, which may likewise be substituted by one or more identical or different radicals in the $C_1$-$C_4$alkyl and/or $C_6$-$C_{14}$aryl moiety. Examples of such arylalkyls include benzyl and phenyl-1-ethyl.

According to the invention the term "polycyclic" ring refers to fused, bridged and spirocyclic carbocyclic and heterocyclic rings as well as ring systems linked through single or double bonds.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may be unsubstituted or substituted, where the bonding site is on a ring atom. Unless defined differently, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group consisting of N, O, and S, although no two oxygen atoms should be directly adjacent. The heterocyclic rings usually contain not more than 4 nitrogen atoms and/or not more than 2 oxygen atoms and/or not more than 2 sulphur atoms. In the case of optionally substituted heterocyclyl, the invention also embraces polycyclic ring systems, for example 8-azabicyclo[3.2.1]octanyl, 1-azabicyclo[2.2.1]heptyl, 1-oxa-5-azaspiro[2.3]hexyl or 2,3-dihydro-1H-indole.

Inventive heterocyclyl groups are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Of particular significance are heteroaryls, i.e. heteroaromatic systems. According to the invention, the term heteroaryl represents heteroaromatic compounds, i.e. completely unsaturated aromatic heterocyclic compounds which fall under the above definition of heterocycles. Preference is given to 5- to 7-membered rings having 1 to 3, preferably 1 or 2, identical or different heteroatoms from the group above. Inventive heteroaryls are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The inventive heteroaryl groups may also be substituted by one or more identical or different radicals.

According to the invention, the substituent =O (oxo) can replace two hydrogen atoms of a methylene ($CH_2$) group or the lone pairs of a sulfur, nitrogen and phosphorous atom which bears only substituents other than hydrogen. For example the radical $C_2$-alkyl becomes for example —$COCH_3$ through substitution by =O (oxo) while the heterocycle thietan-3-yl-becomes for example 1-oxothietan-3-yl through substitution by one =O (oxo) group or 1,1-dioxothietan-3-yl through substitution by two =O (oxo) groups.

According to the invention, the substituent=S (thiono) can replace two hydrogen atoms of a methylene ($CH_2$) group. For example the radical $C_2$-alkyl becomes for examples —$CSCH_3$ through substitution by =S (thiono).

The expression "optionally substituted" as used herein means that the optionally substituted group either is substituted with further substituents or is not substituted with further substituents.

The term "in each case optionally substituted" means that a group/substituent, such as a alkyl, alkenyl, alkynyl, alkoxy, alkylthio, alkylsulfinyl, alkylsulfonyl, cycloalkyl, aryl, phenyl, benzyl, heterocyclyl and heteroaryl radical, is substituted, meaning, for example, a substituted radical derived from the unsubstituted base structure, where the substituents, for example, one (1) substituent or a plurality of substituents, preferably 1, 2, 3, 4, 5, 6 or 7, are selected from a group consisting of amino, hydroxyl, halogen, nitro, cyano, isocyano, mercapto, isothiocyanato, $C_1$-$C_4$carboxyl, carbonamide, $SF_5$, aminosulphonyl, $C_1$-$C_4$alkyl, $C_1$-$C_4$haloalkyl, $C_3$-$C_4$cycloalkyl, $C_2$-$C_4$alkenyl, $C_5$-$C_6$cycloalkenyl, $C_2$-$C_4$alkynyl, N-mono-$C_1$-$C_4$alkylamino, N,N-di-$C_1$-$C_4$alkylamino, N—$C_1$-$C_4$alkanoylamino, $C_1$-$C_4$alkoxy, $C_1$-$C_4$haloalkoxy, $C_2$-$C_4$alkenyloxy, $C_2$-$C_4$alkynyloxy, $C_3$-$C_4$cycloalkoxy, $C_5$-$C_6$cycloalkenyloxy, $C_1$-$C_4$alkoxycarbonyl, $C_2$-$C_4$alkenyloxycarbonyl, $C_2$-$C_4$alkynyloxycarbonyl, $C_6$-, $C_{10}$-, $C_{14}$-aryloxycarbonyl, $C_1$-$C_4$alkanoyl, $C_2$-$C_4$alkenylcarbonyl, $C_2$-$C_4$alkynylcarbonyl, $C_6$-, $C_{10}$-, $C_{14}$-arylcarbonyl, $C_1$-$C_4$alkylthio, $C_1$-$C_4$haloalkylthio, $C_3$-$C_4$cycloalkylthio, $C_2$-$C_4$alkenylthio, $C_5$-$C_6$cycloalkenylthio, $C_2$-$C_4$alkynylthio, $C_1$-$C_4$alkylsulfinyl, including both enantiomers of the $C_1$-$C_4$alkylsulfinyl group, $C_1$-$C_4$haloalkylsulfinyl, including both enantiomers of the $C_1$-$C_4$haloalkylsulfinyl group, $C_1$-$C_4$alkylsulfonyl, $C_1$-$C_4$haloalkylsulfonyl, N-mono-$C_1$-$C_4$alkylaminosulfonyl, N,N-di-$C_1$-$C_4$alkylaminosulfonyl, $C_1$-$C_4$alkylphosphinyl, $C_1$-$C_4$alkylphosphonyl, including both enantiomers of $C_1$-$C_4$alkylphosphinyl and $C_1$-$C_4$alkylphosphonyl, N—$C_1$-$C_4$alkylaminocarbonyl, N,N-di-$C_1$-$C_4$alkylaminocarbonyl, N—$C_1$-$C_4$alkanoylaminocarbonyl, N—$C_1$-$C_4$alkanoyl-N—$C_1$-$C_4$alkylaminocarbonyl, $C_6$-, $C_{10}$-, $C_{14}$-aryl, $C_6$-, $C_{10}$-, $C_{14}$-aryloxy, benzyl, benzyloxy, benzylthio, $C_6$-, $C_{10}$-, $C_{14}$-arylthio, $C_6$-, $C_{10}$-, $C_{14}$-arylamino, benzylamino, heterocyclyl and trialkylsilyl, substituents bonded via a double bond, such as $C_1$-$C_4$alkylidene (e.g. methylidene or ethylidene), an oxo group, an imino group and a substituted imino group. When two or more radicals form one or more rings, these may be carbocyclic, heterocyclic, saturated, partly saturated, unsaturated, for example including aromatic rings and with further substitution. The substituents mentioned by way of example ("first substituent level") may, if they contain hydrocarbonaceous components, optionally have further substitution therein ("second substituent level"), for example by one or more of the substituents each independently selected from halogen, hydroxyl, amino, nitro, cyano, isocyano, azido, acylamino, an oxo group and an imino group. The term "(optionally) substituted" group preferably embraces just one or two substituent levels.

The inventive halogen-substituted chemical groups or halogenated groups (for example alkyl or alkoxy) are mono- or polysubstituted by halogen up to the maximum possible number of substituents. Such groups are also referred to as halo groups (for example haloalkyl). In the case of polysubstitution by halogen, the halogen atoms may be the same or different, and may all be bonded to one carbon atom or may be bonded to a plurality of carbon atoms. Halogen is especially fluorine, chlorine, bromine or iodine, preferably fluorine, chlorine or bromine and more preferably fluorine. More particularly, halogen-substituted groups are monohalocycloalkyl such as 1-fluorocyclopropyl, 2-fluorocyclopropyl or 1-fluorocyclobutyl, monohaloalkyl such as 2-chloroethyl, 2-fluoroethyl, 1-chloroethyl, 1-fluoroethyl, chloromethyl, or fluoromethyl; perhaloalkyl such as trichloromethyl or trifluoromethyl or $CF_2CF_3$, polyhaloalkyl such as difluoromethyl, 2-fluoro-2-chloroethyl, dichloromethyl, 1,1,2,2-tetrafluoroethyl or 2,2,2-trifluoroethyl. Further examples of haloalkyls are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl, 3,3,3-trifluoropropyl and pentafluoro-t-butyl. Preference is given to haloalkyls having 1 to 4 carbon atoms and 1 to 9, preferably 1 to 5, identical or different halogen atoms selected from fluorine, chlorine and bromine. Particular preference is given to haloalkyls having 1 or 2 carbon atoms and 1 to 5 identical or different halogen atoms selected from fluorine and chlorine, such as, inter alia, difluoromethyl, trifluoromethyl or 2,2-difluoroethyl. Further examples of halogen-substituted compounds are haloalkoxy such as $OCF_3$, $OCHF_2$, $OCH_2F$, $OCF_2CF_3$, $OCH_2CF_3$, $OCH_2CHF_2$ und $OCH_2CH_2Cl$, haloalkylsulfanyls such as difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio, haloalkylsulfinyls such as difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluoroethylsulfinyl and 2-chloro-1,1,2-trifluoroethylsulfinyl, haloalkylsulfinyls such as difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluoroethylsulfinyl and 2-chloro-1,1,2-trifluoroethylsulfinyl, haloalkylsulfonyl groups such as difluoromethylsulfonyl, trifluoromethylsulfonyl, trichloromethylsulfonyl, chlorodifluoromethylsulfonyl, 1-fluoroethylsulfonyl, 2-fluoroethylsulfonyl, 2,2-difluoroethylsulfonyl, 1,1,2,2-tetrafluoroethylsulfonyl, 2,2,2-trifluoroethylsulfonyl and 2-chloro-1,1,2-trifluoroethylsulfonyl.

In the case of radicals having carbon atoms, preference is given to those having 1 to 4 carbon atoms, especially 1 or 2 carbon atoms. Preference is generally given to substituents from the group of halogen, e.g. fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given here to the substituents methyl, methoxy, fluorine and chlorine.

Substituted amino such as mono- or disubstituted amino means a radical from the group of the substituted amino radicals which are N-substituted, for example, by one or two identical or different radicals from the group of alkyl, hydroxy, amino, alkoxy, acyl and aryl; preferably N-mono- and N,N-dialkylamino, (for example methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (for example N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and also saturated N-heterocycles; preference is given here to alkyl radicals having 1 to 4 carbon atoms; here, aryl is preferably phenyl or substituted phenyl; for acyl, the definition given further below applies, preferably $(C_1-C_4)$-alkanoyl. The same applies to substituted hydroxylamino or hydrazino.

Substituted amino also includes quaternary ammonium compounds (salts) having four organic substituents on the nitrogen atom.

Optionally substituted phenyl is preferably phenyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, $(C_1-C_4)$alkylthio, $(C_1-C_4)$haloalkylthio, $(C_1-C_4)$alkylsulfinyl $(C_1-C_4)$haloalkylsulfinyl, $(C_1-C_4)$alkylsulfonyl $(C_1-C_4)$haloalkylsulfonyl, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and 4-trichloromethylphenyl, 2,4-, 3,5-, 2,5- and 2,3-dichlorophenyl, o-, m- and p-methoxyphenyl, 4-heptafluorophenyl.

Optionally substituted cycloalkyl is preferably cycloalkyl which is unsubstituted or mono- or polysubstituted, preferably up to trisubstituted, by identical or different radicals from the group of halogen, cyano, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl and $(C_1-C_4)$haloalkoxy, especially by one or two $(C_1-C_4)$alkyl radicals.

Inventive compounds may occur in preferred embodiments. Individual embodiments described herein may be combined with one another. Not included are combinations which contravene the laws of nature and which the person skilled in the art would therefore rule out on the basis of his/her expert knowledge. Ring structures having three or more adjacent oxygen atoms, for example, are excluded.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixture of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded herefrom are methods for the surgical or therapeutic treatment of the human or animal body and diagnostic methods carried out on the human or animal body.

The invention furthermore relates to the use of the compounds of the formula (I) as pesticides, in particular crop protection agents.

In the context of the present application, the term "pesticide" in each case also always comprises the term "crop protection agent".

The compounds of the formula (I), having good plant tolerance, favourable homeotherm toxicity and good environmental compatibility, are suitable for protecting plants and plant organs against biotic and abiotic stressors, for increasing harvest yields, for improving the quality of the harvested material and for controlling animal pests, especially insects, arachnids, helminths, in particular nematodes, and molluscs, which are encountered in agriculture, in horticulture, in animal husbandry, in aquatic cultures, in forests, in gardens and leisure facilities, in the protection of stored products and of materials, and in the hygiene sector.

Within the context of the present patent application, the term "hygiene" is understood to mean any and all measures, procedures and practices which aim to prevent disease, in particular infectious disease, and which serve to protect the health of humans and animals and/or to protect the environment, and/or which maintain cleanliness. In accordance with the invention, this especially includes measures for cleaning, disinfection and sterilisation of, for example, textiles or hard surfaces, especially surfaces of glass, wood, concrete, porcelain, ceramics, plastic or also of metal(s), and for ensuring that these are kept free of hygiene pests and/or their excretions. Preferably excluded from the scope of the invention in this regard are surgical or therapeutic treatment procedures applicable to the human body or to the bodies of animals and diagnostic procedures which are carried out on the human body or on the bodies of animals.

The term "hygiene sector" thus covers all areas, technical fields and industrial applications in which these hygiene measures, procedures and practices are important, in relation for example to hygiene in kitchens, bakeries, airports, bathrooms, swimming pools, department stores, hotels, hospitals, stables, animal husbandries, etc.

The term "hygiene pest" is therefore understood to mean one or more animal pests whose presence in the hygiene sector is problematic, in particular for health reasons. It is therefore a primary objective to avoid or minimize the presence of hygiene pests, and/or exposure to them, in the hygiene sector. This can be achieved in particular through the application of a pesticide that can be used both to prevent infestation and to tackle an infestation which is already present. Preparations which avoid or reduce exposure to pests can also be used. Hygiene pests include, for example, the organisms mentioned below.

The term "hygiene protection" thus covers all actions to maintain and/or improve these hygiene measures, procedures and practices.

The compounds of the formula (I) can preferably be used as pesticides. They are active against normally sensitive and resistant species and against all or some stages of development. The abovementioned pests include:

pests from the phylum of the Arthropoda, in particular from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agrilus* spp., for example *Agrilus planipennis, Agrilus coxalis, Agrilus bilineatus, Agrilus anxius, Agriotes* spp., for example *Agriotes linneatus, Agriotes mancus, Agriotes obscurus, Alphitobius diaperinus, Amphimallon solstitialis, Anobium punctatum, Anomala dubia, Anoplophora* spp., for example *Anoplophora glabripennis, Anthonomus* spp., for example *Anthonomus grandis, Anthrenus* spp., *Apion* spp., *Apogonia* spp., *Athous haemorrhoidales, Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dendroctonus* spp., for example *Dendroctonus ponderosae, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hoplia argentea, Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Limonius ectypus, Lissorhoptrus oryzophilus, Listronotus* (=*Hyperodes*) spp., *Lixus* spp., *Luperodes* spp., *Luperomorpha xanthodera, Lyctus* spp., *Megacyllene* spp., for example *Megacyllene robiniae, Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., for example *Scolytus multistriatus, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Dermaptera, for example *Anisolabis maritime, Forficula auricularia, Labidura riparia;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* or *Pegomyia* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda;* from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., for example *Coccus hesperidum, Coccus*

*longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lopholeucaspis japonica, Lycorma delicatula, Macrosiphum* spp., *for example Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., for example *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., *for example Pemphigus bursarius, Pemphigus populivenae, Peregrinus maidis, Perkinsiella* spp., *Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pulvinaria* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., *for example Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Megacopta cribraria, Miridae, Monalonion atratum, Nezara* spp., for example *Nezara viridula, Nysius* spp., *Oebalus* spp., *Pentomidae, Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Camponotus* spp., *Dolichovespula* spp., *Diprion* spp., for example *Diprion similis, Hoplocampa* spp., for example *Hoplocampa cookei, Hoplocampa testudinea, Lasius* spp., *Linepithema* (*Iridiomyrmex*) *humile, Monomorium pharaonis, Paratrechina* spp., *Paravespula* spp., *Plagiolepis* spp., *Sirex* spp., for example *Sirex noctilio, Solenopsis invicta, Tapinoma* spp., *Technomyrmex albipes, Urocerus* spp., *Vespa* spp., for example *Vespa crabro, Wasmannia auropunctata, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diparopsis* spp., *Diatraea saccharalis, Dioryctria* spp., for example *Dioryctria zimmermani, Earias* spp., *Ecdytolopha aurantium, Elasmopalpus lignosellus, Eldana saccharina, Ephestia* spp., for example *Ephestia elu-*

*tella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hepialus* spp., for example *Hepialus humuli, Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., *for example Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., for example *Ostrinia nubilalis, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Podesia* spp., for example *Podesia syringae, Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Chaetanaphothrips leeuweni, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., for example *Thrips palmi, Thrips tabaci;* from the order of the Zygentoma (=*Thysanura*), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, for example from the class of the Bivalvia, for example *Dreissena* spp., and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

plant pests from the phylum of the Nematoda, i.e. phytoparasitic nematodes, in particular *Aglenchus* spp., for example *Aglenchus agricola, Anguina* spp., for example *Anguina tritici, Aphelenchoides* spp., *for example Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., *for example Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., *for example Helicotylenchus dihystera, Hemicriconemoides* spp., *Hemicycliophora* spp., *Heterodera* spp., *for example Heterodera avenae, Heterodera glycines, Heterodera schachtii, Hirschmanniella* spp., *Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., for example *Paratrichodorus minor, Paratylenchus* spp., *Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example *Tylenchorhynchus annulatus, Tylenchulus* spp., for example *Tylenchulus semipenetrans, Xiphinema* spp., for example *Xiphinema index.*

The compounds of the formula (I) can optionally, at certain concentrations or application rates, also be used as herbicides, safeners, growth regulators or agents to improve plant properties, as microbicides or gametocides, for example as fungicides, antimycotics, bactericides, viricides (including agents against viroids) or as agents against MLO (*mycoplasma*-like organisms) and RLO (*rickettsia*-like organisms). If appropriate, they can also be used as intermediates or precursors for the synthesis of other active compounds.

Formulations/Use Forms

The present invention further relates to formulations, in particular formulations for controlling unwanted controlling animal pests. The formulation may be applied to the animal pest and/or in their habitat.

The formulation of the invention may be provided to the end user as "ready-for-use" use form, i.e. the formulations may be directly applied to the plants or seeds by a suitable device, such as a spraying or dusting device. Alternatively, the formulations may be provided to the end user in the form of concentrates which have to be diluted, preferably with water, prior to use. Unless otherwise indicated, the wording "formulation" therefore means such concentrate, whereas the wording "use form" means the end user as "ready-for-use" solution, i.e. usually such diluted formulation.

The formulation of the invention can be prepared in conventional manners, for example by mixing the compound of the invention with one or more suitable auxiliaries, such as disclosed herein.

The formulation comprises at least one compound of the invention and at least one agriculturally suitable auxiliary, e.g. carrier(s) and/or surfactant(s).

A carrier is a solid or liquid, natural or synthetic, organic or inorganic substance that is generally inert. The carrier generally improves the application of the compounds, for instance, to plants, plants parts or seeds. Examples of suitable solid carriers include, but are not limited to, ammonium salts, in particular ammonium sulfates, ammonium phosphates and ammonium nitrates, natural rock flours, such as kaolins, clays, talc, chalk, quartz, attapulgite, montmorillonite and diatomaceous earth, silica gel and synthetic rock flours, such as finely divided silica, alumina and silicates. Examples of typically useful solid carriers for preparing granules include, but are not limited to crushed and fractionated natural rocks such as calcite, marble, pumice, sepiolite and dolomite, synthetic granules of inorganic and organic flours and granules of organic material such as paper, sawdust, coconut shells, maize cobs and tobacco stalks. Examples of suitable liquid carriers include, but are not limited to, water, organic solvents and combinations thereof.

Examples of suitable solvents include polar and nonpolar organic chemical liquids, for example from the classes of aromatic and nonaromatic hydrocarbons (such as cyclohexane, paraffins, alkylbenzenes, xylene, toluene, tetrahydronaphthalene, alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as ethanol, propanol, butanol, benzylalcohol, cyclohexanol or glycol), ketones (such as acetone, methyl ethyl ketone, methyl isobutyl ketone, acetophenone, or cyclohexanone), esters (including fats and oils) and (poly)ethers, unsubstituted and substituted amines, amides (such as dimethylformamide or fatty acid amides) and esters thereof, lactams (such as N-alkylpyrrolidones, in particular N-methylpyrrolidone) and lactones, sulfones and sulfoxides (such as dimethyl sulfoxide), oils of vegetable or animal origin, nitriles (alkyl nitriles such as acetonitrile, propionotrilie, butyronitrile, or aromatic nitriles, such as benzonitrile), carbonic acid esters (cyclic carbonic acid esters, such as ethylene carbonate, propylene carbonate, butylene carbonate, or dialkyl carbonic acid esters, such as dimethyl carbonate, diethyl carbonate, dipropyl carbonate, dibutyl carbonate, dioctyl carbonate). The carrier may also be a liquefied gaseous extender, i.e. liquid which is gaseous at standard temperature and under standard pressure, for example aerosol propellants such as halohydrocarbons, butane, propane, nitrogen and carbon dioxide.

Preferred solid carriers are selected from clays, talc and silica.

Preferred liquid carriers are selected from water, fatty acid amides and esters thereof, aromatic and nonaromatic hydrocarbons, lactams, lactones, carbonic acid esters, ketones, (poly)ethers.

The amount of carrier typically ranges from 1 to 99.99%, preferably from 5 to 99.9%, more preferably from 10 to 99.5%, and most preferably from 20 to 99% by weight of the formulation.

Liquid carriers are typically present in a range of from 20 to 90%, for example 30 to 80% by weight of the formulation.

Solid carriers are typically present in a range of from 0 to 50%, preferably 5 to 45%, for example 10 to 30% by weight of the formulation.

If the formulation comprises two or more carriers, the outlined ranges refer to the total amount of carriers.

The surfactant can be an ionic (cationic or anionic), amphoteric or non-ionic surfactant, such as ionic or non-ionic emulsifier(s), foam former(s), dispersant(s), wetting agent(s), penetration enhancer(s) and any mixtures thereof. Examples of suitable surfactants include, but are not limited to, salts of polyacrylic acid, ethoxylated polya(alpha-substituted)acrylate derivatives, salts of lignosulfonic acid (such as sodium lignosulfonate), salts of phenolsulfonic acid or naphthalenesulfonic acid, polycondensates of ethylene oxide and/or propylene oxide with or without alcohols, fatty acids or fatty amines (for example, polyoxyethylene fatty acid esters such as castor oil ethoxylate, polyoxyethylene fatty alcohol ethers, for example alkylaryl polyglycol ethers), substituted phenols (preferably alkylphenols or arylphenols), salts of sulfosuccinic esters, taurine derivatives (preferably alkyl taurates), phosphoric esters of polyethoxylated alcohols or phenols, fatty esters of polyols (such a fatty acid esters of glycerol, sorbitol or sucrose), sulfates (such as alkyl sulfates and alkyl ether sulfates), sulfonates (for example, alkylsulfonates, arylsulfonates and alkylbenzene sulfonates), sulfonated polymers of naphthalene/formaldehyde, phosphate esters, protein hydrolysates, lignosulfite waste liquors and methylcellulose. Any reference to salts in this paragraph refers preferably to the respective alkali, alkaline earth and ammonium salts.

Preferred surfactants are selected from ethoxylated polya (alpha-substituted)acrylate derivatives, polycondensates of ethylene oxide and/or propylene oxide with alcohols, polyoxyethylene fatty acid esters, alkylbenzene sulfonates, sulfonated polymers of naphthalene/formaldehyde, polyoxyethylene fatty acid esters such as castor oil ethoxylate, sodium lignosulfonate and arylphenol ethoxylate.

The amount of surfactants typically ranges from 5 to 40%, for example 10 to 20%, by weight of the formulation.

Further examples of suitable auxiliaries include water repellents, siccatives, binders (adhesive, tackifier, fixing agent, such as carboxymethylcellulose, natural and synthetic polymers in the form of powders, granules or latices, such as gum arabic, polyvinyl alcohol and polyvinyl acetate, natural phospholipids such as cephalins and lecithins and synthetic phospholipids, polyvinylpyrrolidone and tylose), thickeners and secondary thickeners (such as cellulose ethers, acrylic acid derivatives, xanthan gum, modified clays, e.g. the products available under the name Bentone, and finely divided silica), stabilizers (e.g. cold stabilizers, preservatives (e.g. dichlorophene, benzyl alcohol hemiformal, 1,2-Benzisothiazolin-3-on, 2-methyl-4-isothiazolin-3-one), antioxidants, light stabilizers, in particular UV stabilizers, or other agents which improve chemical and/or physical stability), dyes or pigments (such as inorganic pigments, e.g. iron oxide, titanium oxide and Prussian Blue; organic dyes, e.g. alizarin, azo and metal phthalocyanine dyes), antifoams (e.g. silicone antifoams and magnesium stearate), antifreezes, stickers, gibberellins and processing auxiliaries, mineral and vegetable oils, perfumes, waxes, nutrients (including trace nutrients, such as salts of iron, manganese, boron, copper, cobalt, molybdenum and zinc), protective colloids, thixotropic substances, penetrants, sequestering agents and complex formers.

The choice of the auxiliaries depends on the intended mode of application of the compound of the invention and/or on the physical properties of the compound(s). Furthermore, the auxiliaries may be chosen to impart particular properties (technical, physical and/or biological properties) to the formulations or use forms prepared therefrom. The choice of auxiliaries may allow customizing the formulations to specific needs.

The formulation comprises an insecticidal/acaricidal/nematicidal effective amount of the compound(s) of the invention. The term "effective amount" denotes an amount, which is sufficient for controlling harmful insects/mites/nematodes on cultivated plants or in the protection of materials and which does not result in a substantial damage to the treated plants. Such an amount can vary in a broad range and is dependent on various factors, such as the insect/mite/nematode species to be controlled, the treated cultivated plant or material, the climatic conditions and the specific compound of the invention used. Usually, the formulation according to the invention contains from 0.01 to 99% by weight, preferably from 0.05 to 98% by weight, more preferred from 0.1 to 95% by weight, even more preferably from 0.5 to 90% by weight, most preferably from 1 to 80% by weight of the compound of the invention. It is possible that a formulation comprises two or more compounds of the invention. In such case the outlined ranges refer to the total amount of compounds of the present invention.

The formulation of the invention may be in any customary formulation type, such as solutions (e.g aqueous solutions), emulsions, water- and oil-based suspensions, powders (e.g. wettable powders, soluble powders), dusts, pastes, granules (e.g. soluble granules, granules for broadcasting), suspoemulsion concentrates, natural or synthetic products impregnated with the compound of the invention, fertilizers and also microencapsulations in polymeric substances. The compound of the invention may be present in a suspended, emulsified or dissolved form. Examples of particular suitable formulation types are solutions, watersoluble concentrates (e.g. SL, LS), dispersible concentrates (DC), suspensions and suspension concentrates (e.g. SC, OD, OF, FS), emulsifiable concentrates (e.g. EC), emulsions (e.g. EW, EO, ES, ME, SE), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GW, GF). These and further formulations types are defined by the Food and Agriculture Organization of the United Nations (FAO). An overview is given in the "Catalogue of pesticide formulation types and international coding system", Technical Monograph No. 2, 6th Ed. May 2008, Croplife International.

Preferably, the formulation of the invention is in form of one of the following types: EC, SC, FS, SE, OD, WG, WP, CS, more preferred EC, SC, OD, WG, CS.

Further details about examples of formulation types and their preparation are given below. If two or more compounds of the invention are present, the outlined amount of compound of the invention refers to the total amount of compounds of the present invention. This applies mutatis mutandis for any further component of the formulation, if two or more representatives of such component, e.g. wetting agent, binder, are present.

i) Water-Soluble Concentrates (SL, LS)

10-60% by weight of at least one compound of the invention and 5-15% by weight surfactant (e.g. polycondensates of ethylene oxide and/or propylene oxide with alcohols) are dissolved in such amount of water and/or water-soluble solvent (e.g. alcohols such as propylene glycol or carbonates such as propylene carbonate) to result in a total amount of 100% by weight. Before application the concentrate is diluted with water.

ii) Dispersible Concentrates (DC)

5-25% by weight of at least one compound of the invention and 1-10% by weight surfactant and/or binder (e.g. polyvinylpyrrolidone) are dissolved in such amount of organic solvent (e.g. cyclohexanone) to result in a total amount of 100% by weight. Dilution with water gives a dispersion.

iii) Emulsifiable Concentrates (EC)

15-70% by weight of at least one compound of the invention and 5-10% by weight surfactant (e.g. a mixture of calcium dodecylbenzenesulfonate and castor oil ethoxylate) are dissolved in such amount of water-insoluble organic solvent (e.g. aromatic hydrocarbon or fatty acid amide) and if needed additional water-soluble solvent to result in a total amount of 100% by weight. Dilution with water gives an emulsion.

iv) Emulsions (EW, EO, ES)

5-40% by weight of at least one compound of the invention and 1-10% by weight surfactant (e.g. a mixture of calcium dodecylbenzenesulfonate and castor oil ethoxylate, or polycondensates of ethylene oxide and/or propylene oxide with or without alcohols) are dissolved in 20-40% by weight water-insoluble organic solvent (e.g. aromatic hydrocarbon). This mixture is added to such amount of water by means of an emulsifying machine to result in a total amount of 100% by weight. The resulting formulation is a homogeneous emulsion. Before application the emulsion may be further diluted with water.

v) Suspensions and Suspension Concentrates v-1) Water-Based (SC, FS)

In a suitable grinding equipment, e.g. an agitated ball mill, 20-60% by weight of at least one compound of the invention are comminuted with addition of 2-10% by weight surfactant (e.g. sodium lignosulfonate and polyoxyethylene fatty alcohol ether), 0.1-2% by weight thickener (e.g. xanthan gum) and water to give a fine active substance suspension. The water is added in such amount to result in a total amount of 100% by weight. Dilution with water gives a stable suspension of the active substance. For FS type formulations up to 40% by weight binder (e.g. polyvinylalcohol) is added.

v-2) Oil-Based (OD, OF)

In a suitable grinding equipment, e.g. an agitated ball mill, 20-60% by weight of at least one compound of the invention are comminuted with addition of 2-10% by weight surfactant (e.g. sodium lignosulfonate and polyoxyethylene fatty alcohol ether), 0.1-2% by weight thickener (e.g. modified clay, in particular Bentone, or silica) and an organic carrier to give a fine active substance oil suspension. The organic carrier is added in such amount to result in a total amount of 100% by weight. Dilution with water gives a stable dispersion of the active substance.

vi) Water-Dispersible Granules and Water-Soluble Granules (WG, SG)

1-90% by weight, preferably 20-80%, most preferably 50-80% by weight of at least one compound of the invention are ground finely with addition of surfactant (e.g. sodium lignosulfonate and sodium alkylnaphthylsulfonates) and potentially carrier material and converted to water-dispersible or water-soluble granules by means of typical technical appliances like e.g. extrusion, spray drying, fluidized bed granulation. The surfactant and carrier material is used in such amount to result in a total amount of 100% by weight. Dilution with water gives a stable dispersion or solution of the active substance.

vii) Water-Dispersible Powders and Water-Soluble Powders (WP, SP, WS)

50-80% by weight of at least one compound of the invention are ground in a rotor-stator mill with addition of 1-20% by weight surfactant (e.g. sodium lignosulfonate, sodium alkylnaphthylsulfonates) and such amount of solid carrier, e.g. silica gel, to result in a total amount of 100% by weight. Dilution with water gives a stable dispersion or solution of the active substance.

viii) Gel (GW, GF)

In an agitated ball mill, 5-25% by weight of at least one compound of the invention are comminuted with addition of 3-10% by weight surfactant (e.g. sodium lignosulfonate), 1-5% by weight binder (e.g. carboxymethylcellulose) and such amount of water to result in a total amount of 100% by weight. This results in a fine suspension of the active substance. Dilution with water gives a stable suspension of the active substance.

ix) Microemulsion (ME)

5-20% by weight of at least one compound of the invention are added to 5-30% by weight organic solvent blend (e.g. fatty acid dimethylamide and cyclohexanone), 10-25% by weight surfactant blend (e.g. polyoxyethylene fatty alcohol ether and arylphenol ethoxylate), and such amount of water to result in a total amount of 100% by weight. This mixture is stirred for 1 h to produce spontaneously a thermodynamically stable microemulsion.

x) Microcapsules (CS)

An oil phase comprising 5-50% by weight of at least one compound of the invention, 0-40% by weight water-insoluble organic solvent (e.g. aromatic hydrocarbon), 2-15% by weight acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50% by weight of at least one compound of the invention, 0-40% by weight water-insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol), this resulting in the formation of polyurea microcapsules. Optionally, the addition of a polyamine (e.g. hexamethylenediamine) is also used to result in the formation of polyurea microcapsules. The monomers amount to 1-10% by weight of the total CS formulation.

xi) Dustable Powders (DP, DS)

1-10% by weight of at least one compound of the invention are ground finely and mixed intimately with such amount of solid carrier, e.g. finely divided kaolin, to result in a total amount of 100% by weight.

xii) Granules (GR, FG)

0.5-30% by weight of at least one compound of the invention are ground finely and associated with such amount of solid carrier (e.g. silicate) to result in a total amount of 100% by weight.

xiii) Ultra-Low Volume Liquids (UL)

1-50% by weight of at least one compound of the invention are dissolved in such amount of organic solvent, e.g. aromatic hydrocarbon, to result in a total amount of 100% by weight.

The formulations types i) to xiii) may optionally comprise further auxiliaries, such as 0.1-1% by weight preservatives, 0.1-1% by weight antifoams, 0.1-1% by weight dyes and/or pigments, and 5-10% by weight antifreezes.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, such active compound combinations may improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellants and/or plant activators and/or growth regulators and/or fertilizers. Likewise, the compounds of the formula (I) can be used to improve plant properties such as, for example, growth, yield and quality of the harvested material.

In a particular embodiment according to the invention, the compounds of the formula (I) are present in formulations or the use forms prepared from these formulations in a mixture with further compounds, preferably those as described below.

If one of the compounds mentioned below can occur in different tautomeric forms, these forms are also included even if not explicitly mentioned in each case. Further, all named mixing partners can, if their functional groups enable this, optionally form salts with suitable bases or acids.

Insecticides/Acaricides/Nematicides

The active compounds identified here by their common names are known and are described, for example, in the pesticide handbook ("The Pesticide Manual" 16th Ed., British Crop Protection Council 2012) or can be found on the Internet (e.g. http://www.alanwood.net/pesticides). The classification is based on the current IRAC Mode of Action Classification Scheme at the time of filing of this patent application.

(1) Acetylcholinesterase (AChE) inhibitors, preferably carbamates selected from alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb, or organophosphates selected from acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, preferably cyclodiene-organochlorines selected from chlordane and endosulfan, or phenylpyrazoles (fiproles) selected from ethiprole and fipronil.

(3) Sodium channel modulators, preferably pyrethroids selected from acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin, or DDT or methoxychlor.

(4) Nicotinic acetylcholine receptor (nAChR) competitive modulators, preferably neonicotinoids selected from acetamiprid, clothianidin, dinotefuran, imidacloprid, nitenpyram, thiacloprid and thiamethoxam, or nicotine, or sulfoximines selected from sulfoxaflor, or butenolids selected from flupyradifurone, or mesoionics selected from triflumezopyrim.

(5) Nicotinic acetylcholine receptor (nAChR) allosteric modulators (Site I), preferably spinosyns selected from spinetoram and spinosad.

(6) Glutamate-gated chloride channel (GluCl) allosteric modulators, preferably avermectins/milbemycins selected from abamectin, emamectin benzoate, lepimectin and milbemectin.

(7) Juvenile hormone mimics, preferably juvenile hormone analogues selected from hydroprene, kinoprene and methoprene, or fenoxycarb or pyriproxyfen.

(8) Miscellaneous non-specific (multi-site) inhibitors, preferably alkyl halides selected from methyl bromide and other alkyl halides, or chloropicrine or sulphuryl fluoride or borax or tartar emetic or methyl isocyanate generators selected from diazomet and metam.

(9) Chordotonal organ TRPV channel modulators, preferably pyridine azomethanes selected from pymetrozine and pyrifluquinazone, or pyropenes selected from afidopyropen.

(10) Mite growth inhibitors affecting CHS1 selected from clofentezine, hexythiazox, diflovidazin and etoxazole.

(11) Microbial disruptors of the insect gut membranes selected from *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and B.t. plant proteins selected from Cry1Ab, Cry1Ac, Cry1Fa, Cry1A.105, Cry2Ab, Vip3A, mCry3A, Cry3Ab, Cry3Bb and Cry34Ab1/35Ab1.

(12) Inhibitors of mitochondrial ATP synthase, preferably ATP disruptors selected from diafenthiuron, or organotin compounds selected from azocyclotin, cyhexatin and fenbutatin oxide, or propargite or tetradifon.

(13) Uncouplers of oxidative phosphorylation via disruption of the proton gradient selected from chlorfenapyr, DNOC and sulfluramid.

(14) Nicotinic acetylcholine receptor channel blockers selected from bensultap, cartap hydrochloride, thiocylam and thiosultap-sodium.

(15) Inhibitors of chitin biosynthesis affecting CHS1, preferably benzoylureas selected from bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1 selected from buprofezin.

(17) Moulting disruptor (in particular for Diptera, i.e. dipterans) selected from cyromazine.

(18) Ecdysone receptor agonists, preferably diacylhydrazines selected from chromafenozide, halofenozide, methoxyfenozide and tebufenozide.

(19) Octopamine receptor agonists selected from amitraz.

(20) Mitochondrial complex III electron transport inhibitors selected from hydramethylnone, acequinocyl, fluacrypyrim and bifenazate.

(21) Mitochondrial complex I electron transport inhibitors, preferably METI acaricides and insecticides selected from fenazaquin, fenpyroximate, pyrimidifen, pyridaben, tebufenpyrad and tolfenpyrad, or rotenone (Derris).

(22) Voltage-dependent sodium channel blockers, preferably oxadiazines selected from indoxacarb, or semicarbazones selected from metaflumizone.

(23) Inhibitors of acetyl CoA carboxylase, preferably tetronic and tetramic acid derivatives selected from spirodiclofen, spiromesifen, spiropidion and spirotetramat.

(24) Mitochondrial complex IV electron transport inhibitors, preferably phosphides selected from aluminium phosphide, calcium phosphide, phosphine and zinc phosphide, or cyanides selected from calcium cyanide, potassium cyanide and sodium cyanide.

(25) Mitochondrial complex II electron transport inhibitors, preferably beta-ketonitrile derivatives selected from cyenopyrafen and cyflumetofen, or carboxanilides selected from pyflubumide.

(28) Ryanodine receptor modulators, preferably diamides selected from chlorantraniliprole, cyantraniliprole, cyclaniliprole, flubendiamide and tetraniliprole.

(29) Chordotonal organ Modulators (with undefined target site) selected from flonicamid.

(30) GABA-gated chlorid channel allosteric modulators, preferably meta-diamides selected from broflanilide, or isoxazoles selected from fluxametamide.

(31) Baculovisuses, preferably Granuloviruses (GVs) selected from *Cydia pomonella* GV and *Thaumatotibia leucotreta* (GV), or Nucleopolyhedroviruses (NPVs) selected from *Anticarsia gemmatalis* MNPV and *Helicoverpa armigera* NPV.

(32) Nicotinic acetylcholine receptor allosteric modulators (Site II) selected from GS-omega/kappa HXTX-Hv1a peptide.

(33) further active compounds selected from Acynonapyr, Afoxolaner, Azadirachtin, Benclothiaz, Benzoximate, Benzpyrimoxan, Bromopropylate, Chinomethionat, Chloroprallethrin, Cryolite, Cyclobutrifluram or Cyclobutrifen (CAS 1460292-16-3), Cycloxaprid, Cyetpyrafen, Cyhalodiamide, Dicloromezotiaz, Dicofol, Dimpropyridaz, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Flupyrimin, Fluralaner, Fufenozide, Fupentiofenox (CAS 1472050-04-6), Guadipyr, Heptafluthrin, Imidaclothiz, Iprodione, Isocycloseram, kappa-Bifenthrin, kappa-Tefluthrin, Lotilaner, Meperfluthrin, Oxazosulfyl, Paichongding, Pyridalyl, Pyrifluquinazon, Pyriminostrobin, Sarolaner, Spirobudiclofen, Tetramethylfluthrin, Tetrachlorantraniliprole, Tigolaner, Tioxazafen, Thiofluoximate, Tyclopyrazoflor, Iodomethane, Triflupentoxide (CAS 1472050-04-6); furthermore preparations based on *Bacillus firmus* (I-1582, Votivo) and azadirachtin (BioNeem), and also the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), PF1364 (known from JP2010/018586) (CAS 1204776-60-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl) benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)-N-[3-chloro-1-(3-pyridinyl)-1H-pyrazol-4-yl]-N-ethyl-3-[(3,3,3-trifluoropropyl) sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl) amino]carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl) phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy) phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8), N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1,8-diazaspiro[4.5]dec-3-en-4-yl-carbonic acid ethyl ester (known from WO 2010/066780 A1, WO 2011151146 A1) (CAS 1229023-00-0), N-[1-(2,6-difluorophenyl)-1H-pyrazol-3-yl]-2-(trifluoromethyl)benzamide (known from WO 2014/053450 A1) (CAS 1594624-87-9), N-[2-(2,6-difluorophenyl)-2H-1,2,3-triazol-4-yl]-2-(trifluoromethyl)benzamide (known from WO 2014/053450 A1) (CAS 1594637-65-6), N-[1-(3,5-difluoro-2-pyridinyl)-1H-pyrazol-3-yl]-2-(trifluoromethyl) benzamide (known from WO 2014/053450 A1) (CAS 1594626-19-3).

Fungicides

The active ingredients specified herein by their Common Name are known and described, for example, in The Pesticide Manual (16th Ed. British Crop Protection Council) or can be searched in the internet (e.g. www.alanwood.net/pesticides).

All named fungicidal mixing partners of the classes (1) to (15) can, if their functional groups enable this, optionally form salts with suitable bases or acids. All named mixing partners of the classes (1) to (15) can include tautomeric forms, where applicable.

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) Mefentrifluconazole, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2- methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) ipfentrifluconazole, (1.082) 2-[4-(4-chlorophenoxy)-2-(trifluoromethyl)phenyl]-1-(1H-1,2,4-triazol-1-yl)propan-2-ol, (1.083) 2-[6-(4-bromophenoxy)-2-(trifluoromethyl)-3-pyridyl]-1-(1,2,4-triazol-1-yl)propan-2-ol, (1.084) 2-[6-(4-chlorophenoxy)-2-(trifluoromethyl)-3-pyridyl]-1-(1,2,4-triazol-1-yl)propan-2-ol, (1.085) 3-[2-(1-chlorocyclopropyl)-3-(3-chloro-2-fluoro-phenyl)-2-hydroxy-propyl]imidazole-4-carbonitrile and (1.086) 4-[[6-[rac-(2R)-2-(2,4-difluorophenyl)-1,1-difluoro-2-hydroxy-3-(5-thioxo-4H-1,2,4-triazol-1-yl)propyl]-3-pyridyl]oxy]benzonitrile.

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028)inpyrfluxam, (2.029) 3-(difluoromethyl)-1-methyl-N-[(3S)-1,1,3-trimethyl-2,3-dihydro-1H-inden-4-yl]-1H-pyrazole-4-carboxamide, (2.030) fluindapyr, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide, (2.057) pyrapropoyne.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5- dimethylphenoxy)methyl]phenyl}-2-methoxy-N-methylacetamide, (3.025) fenpicoxamid, (3.026) mandestrobin, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate, (3.030) metyltetraprole, (3.031) florylpicoxamid.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl) pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable to induce a host defence, for example (6.001) acibenzolar-S-methyl, (6.002) isotianil, (6.003) probenazole, (6.004) tiadinil.

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) Inhibitors of the ATP production, for example (8.001) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.001) propamocarb, (10.002) propamocarb hydrochloride, (10.003) tolclofos-methyl.

11) Inhibitors of the melanin biosynthesis, for example (11.001) tricyclazole, (11.002) 2,2,2-trifluoroethyl {3-methyl-1-[(4-methylbenzoyl)amino]butan-2-yl}carbamate.

12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).

13) Inhibitors of the signal transduction, for example (13.001) fludioxonil, (13.002) iprodione, (13.003) procymidone, (13.004) proquinazid, (13.005) quinoxyfen, (13.006) vinclozolin.

14) Compounds capable to act as an uncoupler, for example (14.001) fluazinam, (14.002) meptyldinocap.

15) Further fungicides selected from the group consisting of (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) Oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl] ethanone, (15.033) 2-(6-benzylpyridin-2-yl) quinazoline, (15.034) dipymetitrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl] quinazoline, (15.039) 2-{(5R)-3-[2-(1-{[3,5-bis (difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulfonate, (15.040) 2-{(5S)-3-[2-(1-{[3,5-bis(difluoromethyl)-1H-pyrazol-1-yl]

acetyl}piperidin-4-yl)-1,3-thiazol-4-yl]-4,5-dihydro-1,2-oxazol-5-yl}-3-chlorophenyl methanesulfonate, (15.041) Ipflufenoquin, (15.042) 2-{2-fluoro-6-[(8-fluoro-2-methylquinolin-3-yl)oxy]phenyl}propan-2-ol, (15.043)fluoxapiprolin, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) quinofumelin, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one, (15.063) aminopyrifen, (15.064) (N'-[2-chloro-4-(2-fluorophenoxy)-5-methylphenyl]-N-ethyl-N-methylimidoformamide), (15.065) (N'-(2-chloro-5-methyl-4-phenoxyphenyl)-N-ethyl-N-methylimido-formamide), (15.066) (2-{2-[(7,8-difluoro-2-methylquinolin-3-yl)oxy]-6-fluorophenyl}propan-2-ol), (15.067) (5-bromo-1-(5,6-dimethylpyridin-3-yl)-3,3-dimethyl-3,4-dihydroisoquinoline), (15.068) (3-(4,4-difluoro-5,5-dimethyl-4,5-dihydrothieno[2,3-c]pyridin-7-yl)quinoline), (15.069) (1-(4,5-dimethyl-1H-benzimidazol-1-yl)-4,4-difluoro-3,3-dimethyl-3,4-dihydroisoquinoline), (15.070) 8-fluoro-3-(5-fluoro-3,3-dimethyl-3,4-dihydroisoquinolin-1-yl)quinolone, (15.071) 8-fluoro-3-(5-fluoro-3,3,4,4-tetramethyl-3,4-dihydroisoquinolin-1-yl)quinolone, (15.072) 3-(4,4-difluoro-3,3-dimethyl-3,4-dihydroisoquinolin-1-yl)-8-fluoroquinoline, (15.073) (N-methyl-N-phenyl-4-[5-(trifluoromethyl)-1,2,4-oxadiazol-3-yl]benzamide), (15.074) (methyl{4-[5-(trifluoromethyl)-1,2,4-oxadiazol-3-yl]phenyl}carbamate), (15.075) (N-{4-[5-(trifluoromethyl)-1,2,4-oxadiazol-3-yl]benzyl}-cyclopropane-carboxamide), (15.076) N-methyl-4-(5-(trifluoromethyl)-1,2,4-oxadiazol-3-yl]-benzamide, (15.077) N-[(E)-methoxyiminomethyl]-4-[5-(trifluoromethyl)-1,2,4-oxadiazol-3-yl]benzamide, (15.078) N-[(Z)-methoxyiminomethyl]-4-[5-(trifluoromethyl)-1,2,4-oxadiazol-3-yl]benzamide, (15.079) N-[4-[5-(trifluoromethyl)-1,2,4-oxadiazol-3-yl]phenyl]-cyclopropane-carboxamide, (15.080) N-(2-fluorophenyl)-4-[5-(trifluoromethyl)-1,2,4-oxadiazol-3-yl]benzamide, (15.081) 2,2-difluoro-N-methyl-2-[4-[5-(trifluoromethyl)-1,2,4-oxadiazol-3-yl]phenyl]-acetamide, (15.082) N-allyl-N-[[4-[5-(trifluoromethyl)-1,2,4-oxadiazol-3-yl)phenyl]methyl]acetamide, (15.083) N-[(E)-N-methoxy-C-methyl-carbonimidoyl]-4-(5-(trifluoromethyl)-1,2,4-oxadiazol-3-yl]-benzamide, (15.084) N-[(Z)-N-methoxy-C-methyl-carbonimidoyl]-4-[5-(trifluoromethyl)-1,2,4-oxadiazol-3-yl]benzamide, (15.085) N-allyl-N-[[4-[5-(trifluoromethyl)-1,2,4-oxadiazol-3-yl]phenyl]-methyl]-propanamide, (15.086) 4,4-dimethyl-1-[[4-[5-(trifluoromethyl)-1,2,4-oxadiazol-3-yl]phenyl]methyl]-pyrrolidin-2-one, (15.087) N-methyl-4-[5-(trifluoromethyl)-1,2,4-oxadiazol-3-yl]-benzenecarbothioamide, (15.088) 5-methyl-1-[[4-[5-(trifluoromethyl)-1,2,4-oxadiazol-3-yl]phenyl]methyl]pyrrolidin-2-one, (15.089) N-((2,3-difluoro-4-[5-(trifluoromethyl)-1,2,4-oxadiazol-3-yl]phenyl]methyl]-3,3,3-trifluoro-propanamide, (15.090) 1-methoxy-1-methyl-3-[[4-[5-(trifluoromethyl}-1,2,4-oxadiazol-3-yl]phenyl]-methyl]urea, (15.091) 1,1-diethyl-3-[[4-[5-(trifluoromethyl}-1,2,4-oxadiazol-3-yl]phenyl]methyl]urea, (15.092) N-[[4-[5-(trifluoromethyl)-1,2,4-oxadiazol-3-yl]phen-yl]methyl]propanamide, (15.093) N-methoxy-N-[[4-[5-(trifluoromethyl)-1,2,4-oxadiazol-3-yl]phenyl]methyl]cyclopropanecarboxamide, (15.094) 1-methoxy-3-methyl-1-[[4-[5-(trifluoromethyl)-1,2,4-oxadiazol-3-yl]phenyl]methyl]urea, (15.095) N-methoxy-N-[[4-[5-(trifluoromethyl)-1,2,4-oxadiazol-3-yl]phenyl]-methyl)-cyclopropane-carboxamide, (15.096) N,2-dimethoxy-N-[[4-[5-(trifluoromethyl}-1,2,4-oxadiazol-3-yl]phenyl]-methyl]-propanamide, (15.097) N-ethyl-2-methyl-N-[[4-[5-(trifluoromethyl)-1,2,4-oxadiazol-3-yl)phenyl]methyl]-propanamide, (15.098) 1-methoxy-3-methyl-1-[[4-[5-(trifluoromethyl)-1,2,4-oxadiazol-3-yl]phenyl]-methyl]-urea, (15.099) 1,3-dimethoxy-1-[[4-[5-(trifluoromethyl)-1,2,4-oxadiazol-3-yl]phenyl]methyl]urea, (15.100) 3-ethyl-1-methoxy-1-[[4-[5-(trifluoromethyl)-1,2,4-oxadiazol-3-yl]phenyl]methyl]urea, (15.101) 1-[[4-[5-(trifluoromethyl)-1,2,4-oxadiazol-3-yl]phenyl]methyl]piperidin-2-one, (15.102) 4,4-dimethyl-2-[[4-[5-(trifluoromethyl)-1,2,4-oxadiazol-3-yl]phenyl]methyl]isooxazolidin-3-one, (15.103) 5,5-dimethyl-2-[[4-[5-(trifluoromethyl)-1,2,4-oxadiazol-3-yl]phenyl]methyl]isoxazolidin-3-one, (15.104) 3,3-dimethyl-1-[[4-[5-(trifluoromethyl)-1,2,4-oxadiazol-3-yl]-phenyl]-methyl]-piperidin-2-one, (15.105) 1-[[3-fluoro-4-(5-(trifluoromethyl)-1,2,4-oxadiazol-3-yl]-phenyl]-methyl]-azepan-2-one, (15.106) 4,4-dimethyl-2-[[4-(5-(trifluoromethyl)-1,2,4-oxadiazol-3-yl]-phenyl]-methyl]isoxazolidin-3-one (15.107) 5,5-dimethyl-2-[[4-[5-(trifluoromethyl)-1,2,4-oxadiazol-3-yl]-phenyl]methyl]isoxazolidin-3-one, (15.108) ethyl (1-{4-[5-(trifluoromethyl)-1,2,4-oxadiazol-3-yl]benzyl}-1H-pyrazol-4-yl)acetate, (15.109) N,N-dimethyl-1-{4-[5-(trifluoromethyl)-1,2,4-oxadiazol-3-yl]benzyl}-1H-1,2,4-triazol-3-amine and (15.110) N-{2,3-difluoro-4-[5-(trifluoromethyl)-1,2,4-oxadiazol-3-yl]benzyl}butanamide.

Biological Pesticides as Mixing Components

The compounds of the formula (I) can be combined with biological pesticides.

Biological pesticides comprise in particular bacteria, fungi, yeasts, plant extracts and products formed by microorganisms, including proteins and secondary metabolites.

Biological pesticides comprise bacteria such as spore-forming bacteria, root-colonising bacteria and bacteria which act as biological insecticides, fungicides or nematicides.

Examples of such bacteria which are employed or can be used as biological pesticides are:

*Bacillus amyloliquefaciens*, strain FZB42 (DSM 231179), or *Bacillus cereus*, in particular *B. cereus* strain CNCM I-1562 or *Bacillus firmus*, strain I-1582 (Accession number CNCM I-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. kurstaki strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are employed or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), Metschnikowia fructicola, in particular strain NRRL Y-30752, *Paecilomyces fumosoroseus* (now: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma* atroviride, in particular strain SCI (Accession Number CBS 122089), *Trichoderma harzianum*, in particular *T. harzianum rifai* T39. (Accession Number CNCM I-952).

Examples of viruses which are employed or can be used as biological pesticides are: *Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:

*Agrobacterium* spp., *Azorhizobium caulinodans, Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., in particular *Rhizobium trifolii, Rhizopogon* spp., *Scleroderma* spp., *Suillus* spp., *Streptomyces* spp.

Examples of plant extracts and products formed by microorganisms including proteins and secondary metabolites which are employed or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), Pyrethrum/Pyrethrins, *Quassia amara, Quercus, Quillaja, Regalia*, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, Viscum album, Brassicaceae extract, in particular oilseed rape powder or mustard powder, as well as bioinsecticidal/acaricidal active substances obtained from olive oil, in particular unsaturated fatty/carboxylic acids having carbon chain lengths $C_{16}$-$C_{20}$ as active ingredients, such as, for example, contained in the product with the trade name FLiPPER®.

Safener as Mixing Components

The compounds of the formula (I) can be combined with safeners such as, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Here, plants are to be understood to mean all plants and plant parts such as wanted and unwanted wild plants or crop plants (including naturally occurring crop plants), for example cereals (wheat, rice, triticale, barley, rye, oats), maize, soya bean, potato, sugar beet, sugar cane, tomatoes, pepper, cucumber, melon, carrot, watermelon, onion, lettuce, spinach, leek, beans, *Brassica oleracea* (e.g. cabbage) and other vegetable species, cotton, tobacco, oilseed rape, and also fruit plants (with the fruits apples, pears, citrus fruits and grapevines). Crop plants can be plants which can be obtained by conventional breeding and optimization methods or by biotechnological and genetic engineering methods or combinations of these methods, including the transgenic plants and including the plant varieties which can or cannot be protected by varietal property rights. Plants should be understood to mean all developmental stages, such as seeds, seedlings, young (immature) plants up to mature plants. Plant parts should be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested plants or harvested plant parts and vegetative and generative propagation material, for example seedlings, tubers, rhizomes, cuttings and seeds.

Treatment according to the invention of the plants and plant parts with the compounds of the formula (I) is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. The invention is used with particular preference to treat plants of the respective commercially customary cultivars or those that are in use. Plant cultivars are to be understood as meaning plants having new properties ("traits") and which have been obtained by conventional breeding, by mutagenesis or by recombinant DNA techniques. They can be cultivars, varieties, bio- or genotypes.

Transgenic Plant, Seed Treatment and Integration Events

According to the invention, the compounds of formula (I) can be advantageously used to treat transgenic plants, plant cultivars or plant parts that received genetic material which imparts advantageous and/or useful properties (traits) to these plants, plant cultivars or plant parts. Therefore, it is contemplated that the present invention may be combined with one or more recombinant traits or transgenic event(s) or a combination thereof. For the purposes of this application, a transgenic event is created by the insertion of a specific recombinant DNA molecule into a specific position (locus) within the chromosome of the plant genome. The insertion creates a novel DNA sequence referred to as an "event" and is characterized by the inserted recombinant DNA molecule and some amount of genomic DNA immediately adjacent to/flanking both ends of the inserted DNA. Such trait(s) or transgenic event(s) include, but are not limited to, pest resistance, water use efficiency, yield performance, drought tolerance, seed quality, improved nutritional quality, hybrid seed production, and herbicide tolerance, in which the trait is measured with respect to a plant lacking such trait or transgenic event. Concrete examples of such advantageous and/or useful properties (traits) are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products, and increased resistance or tolerance against animal and microbial pests, such as against insects, arachnids, nematodes, mites, slugs and snails.

Among DNA sequences encoding proteins which confer properties of resistance or tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the Cry1A, CryIAb, CryIAc, CryIIA, CryIIIA, CryIIIB2, Cry9c Cry2Ab, Cry3Bb and CryIF proteins or toxic fragments thereof and also hybrids or combinations thereof, especially the CryIF protein or hybrids derived from a CryIF protein (e.g. hybrid CryIA-CryIF proteins or toxic fragments thereof), the CryIA-type proteins or toxic fragments thereof, preferably the CryIAc protein or hybrids derived from the CryIAc protein (e.g. hybrid CryIAb-CryIAc proteins) or the CryIAb or Bt2 protein or toxic fragments thereof, the Cry2Ae, Cry2Af or Cry2Ag proteins or toxic fragments thereof, the CryIA.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci US A. 28; 93(11):5389-94, the Cry proteins as described in WO2001/47952, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-enolpyruvylshikimat-3-phosphat-synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g. WO2007/024782), a mutated *Arabidopsis* ALS/AHAS gene (e.g. U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further and particularly emphasized examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLRI (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); EventEE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1

(sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control—herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control—herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession N° PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession No PTA-13025, WO2013/012775A1).

Further, a list of such transgenic event(s) is provided by the United States Department of Agriculture's (USDA) Animal and Plant Health Inspection Service (APHIS) and can be found on their website on the world wide web at aphis.usda.gov. For this application, the status of such list as it is/was on the filing date of this application, is relevant.

The genes/events which impart the desired traits in question may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. the compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This may be done, for example, by drenching, or by mixing into the soil or the nutrient solution, i.e. the locus of the plant (e.g. soil or hydroponic systems) is impregnated with a liquid form of the compounds of the formula (I), or by soil application, i.e. the compounds of the formula (I) according to the invention are introduced in solid form (e.g. in the form of granules) into the locus of the plants, or by drip application (often also referred to as "chemigation"), i.e. the liquid application of the compounds of the formula (I) according to the invention from surface or sub-surface driplines over a certain period of time together with varying amounts of water at defined locations in the vicinity of the plants. In the case of paddy rice crops, this can also be done by metering the compound of the formula (I) in a solid application form (for example as granules) into a flooded paddy field.

Digital Technologies

The compounds of the invention can be used in combination with models e.g. embedded in computer programs for site specific crop management, satellite farming, precision farming or precision agriculture. Such models support the site specific management of agricultural sites with data from various sources such as soils, weather, crops (e.g. type, growth stage, plant health), weeds (e.g. type, growth stage), diseases, pests, nutrients, water, moisture, biomass, satellite data, yield etc. with the purpose to optimize profitability, sustainability and protection of the environment. In particular, such models can help to optimize agronomical decisions, control the precision of pesticide applications and record the work performed.

As an example, the compounds of the invention can be applied to a crop plant according to an appropriate dose regime if a model models the development of a pest and calculates that a threshold has been reached for which it is recommendable to apply the compound of the invention to the crop plant.

Commercially available systems which include agronomic models are e.g. FieldScripts™ from The Climate Corporation, Xarvio™ from BASF, AGLogic™ from John Deere, etc.

The compounds of the invention can also be used in combination with smart spraying equipment such as e.g. spot spraying or precision spraying equipment attached to or housed within a farm vehicle such as a tractor, robot, helicopter, airplane, unmanned aerial vehicle (UAV) such as a drone, etc. Such an equipment usually includes input sensors (such as e.g. a camera) and a processing unit configured to analyze the input data and configured to provide a decision based on the analysis of the input data to apply the compound of the invention to the crop plants (respectively the weeds) in a specific and precise manner. The use of such smart spraying equipment usually also requires positions systems (e.g. GPS receivers) to localize recorded data and to guide or to control farm vehicles; geographic information systems (GIS) to represent the information on intelligible maps, and appropriate farm vehicles to perform the required farm action such as the spraying.

In an example, pests can be detected from imagery acquired by a camera. In an example the pests can be identified and/or classified based on that imagery. Such identification and/classification can make use of image processing algorithms. Such image processing algorithms can utilize machine learning algorithms, such as trained neutral networks, decision trees and utilize artificial intelligence algorithms. In this manner, the compounds described herein can be applied only where needed.

Treatment of Seed

The control of animal pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is furthermore desirable to optimize the amount of active compound employed in such a way as to provide optimum protection for the seed and the germinating plant from attack by animal pests, but without damaging the plant itself by the active compound employed. In particular, methods for the treatment of seed should also take into consideration the intrinsic insecticidal or nematicidal properties of pest-resistant or -tolerant transgenic plants in order to achieve optimum protection of the seed and also the germinating plant with a minimum of pesticides being employed.

The present invention therefore in particular also relates to a method for the protection of seed and germinating plants, from attack by pests, by treating the seed with one of the compounds of the formula (I). The method according to the invention for protecting seed and germinating plants against attack by pests furthermore comprises a method where the seed is treated simultaneously in one operation or sequentially with a compound of the formula (I) and a mixing component. It also comprises a method where the seed is treated at different times with a compound of the formula (I) and a mixing component.

The invention likewise relates to the use of the compounds of the formula (I) for the treatment of seed for protecting the seed and the resulting plant from animal pests.

Furthermore, the invention relates to seed which has been treated with a compound of the formula (I) according to the invention so as to afford protection from animal pests. The invention also relates to seed which has been treated simultaneously with a compound of the formula (I) and a mixing component. The invention furthermore relates to seed which has been treated at different times with a compound of the formula (I) and a mixing component. In the case of seed which has been treated at different points in time with a compound of the formula (I) and a mixing component, the individual substances may be present on the seed in different layers. Here, the layers comprising a compound of the formula (I) and mixing components may optionally be separated by an intermediate layer. The invention also relates to seed where a compound of the formula (I) and a mixing component have been applied as component of a coating or as a further layer or further layers in addition to a coating.

Furthermore, the invention relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this manner, the immediate treatment of the crop at the time of sowing or shortly thereafter can be dispensed with.

It has to be considered a further advantage that by treatment of the seed with a compound of the formula (I), germination and emergence of the treated seed may be enhanced.

It is likewise to be considered advantageous that compounds of the formula (I) can be used in particular also for transgenic seed.

Furthermore, compounds of the formula (I) can be employed in combination with compositions or compounds of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. In particular, this takes the form of seed of cereals (for example wheat, barley, rye, millet and oats), corn, cotton, soya beans, rice, potatoes, sunflowers, coffee, tobacco, canola, oilseed rape, beets (for example sugarbeets and fodder beets), peanuts, vegetables (for example tomatoes, cucumbers, bean, cruciferous vegetables, onions and lettuce), fruit plants, lawns and ornamental plants. The treatment of the seed of cereals (such as wheat, barley, rye and oats), maize, soya beans, cotton, canola, oilseed rape, vegetables and rice is of particular importance.

As already mentioned above, the treatment of transgenic seed with a compound of the formula (I) is also of particular importance. This takes the form of seed of plants which, as a rule, comprise at least one heterologous gene which governs the expression of a polypeptide with in particular insecticidal and/or nematicidal properties. The heterologous genes in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. It is particularly preferably a heterologous gene derived from *Bacillus thuringiensis*.

In the context of the present invention, the compound of the formula (I) is applied to the seed. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water to a certain stage of the rice embryo ('pigeon breast stage'), stimulating the germination and a more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This must be ensured particularly in the case of active compounds which can exhibit phytotoxic effects at certain application rates.

In general, the compounds of the formula (I) are applied to the seed in a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing the compounds of the formula (I) with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of agrochemically active compounds. Preference is given to using alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are in particular lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Preference is given to using silicone antifoams and magnesium stearate.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions.

Cellulose derivatives, acrylic acid derivatives, xanthan, modified clays and finely divided silica are preferred.

Adhesives which may be present in the seed dressing formulations usable in accordance with the invention are all customary binders usable in seed dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel", vol. 2, Springer Verlag, 1970, pp. 401-412).

The seed dressing formulations usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom by adding water, all mixing units usable customarily for the seed dressing are useful. Specifically, the procedure in the seed dressing is to place the seed into a mixer, operated batch-wise or continuously, to add the particular desired amount of seed dressing formulations, either as such or after prior dilution with water, and to mix everything until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. in the field of veterinary medicine, the compounds of the formula (I) are active against animal parasites, in particular ectoparasites or endoparasites. The term endoparasite includes in particular helminths and protozoae, such as coccidia. Ectoparasites are typically and preferably arthropods, in particular insects or acarids.

In the field of veterinary medicine the compounds of the formula (I) are suitable, with favourable toxicity in warm blooded animals, for controlling parasites which occur in animal breeding and animal husbandry in livestock, breeding, zoo, laboratory, experimental and domestic animals. They are active against all or specific stages of development of the parasites.

Agricultural livestock include, for example, mammals, such as, sheep, goats, horses, donkeys, camels, buffaloes, rabbits, reindeers, fallow deers, and in particular cattle and pigs; or poultry, such as turkeys, ducks, geese, and in particular chickens; or fish or crustaceans, e.g. in aquaculture; or, as the case may be, insects such as bees.

Domestic animals include, for example, mammals, such as hamsters, guinea pigs, rats, mice, chinchillas, ferrets or in particular dogs, cats; cage birds; reptiles; amphibians or aquarium fish.

According to a particular embodiment, the compounds of the formula (I) are administered to mammals.

According to another particular embodiment, the compounds of the formula (I) are administered to birds, namely cage birds or in particular poultry.

By using the compounds of the formula (I) to control animal parasites, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means that the compounds of the formula (I) are effective in reducing the incidence of the respective parasite in an animal infected with such parasites to innocuous levels. More specifically, "controlling", as used herein, means that the compounds of the formula (I) are effective in killing the respective parasite, inhibiting its growth, or inhibiting its proliferation.

Exemplary arthropods include, without any limitation from the order of the Anoplurida, for example, *Haematopinus* spp., *Linognathus* spp., *Pediculus* spp., *Phtirus* spp., *Solenopotes* spp.;

from the order of the Mallophagida and the suborders Amblycerina and Ischnocerina, for example *Bovicola* spp., *Damalina* spp., *Felicola* spp., *Lepikentron* spp., *Menopon* spp., *Trichodectes* spp., *Trimenopon* spp., *Trinoton* spp., *Werneckiella* spp.;

from the order of the Diptera and the suborders Nematocerina and Brachycerina, for example *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.

from the order of the Siphonapterida, for example *Ceratophyllus* spp.; *Ctenocephalides* spp., *Pulex* spp., *Tunga* spp., *Xenopsylla* spp.;

from the order of the Heteropterida, for example *Cimex* spp., *Panstrongylus* spp., *Rhodnius* spp., *Triatoma* spp.; as well as nuisance and hygiene pests from the order of the Blattarida.

Further, among the arthropods, the following acari may be mentioned by way of example, without any limitation:

from the subclass of the Acari (Acarina) and the order of the Metastigmata, for example, from the family of argasidae like *Argas* spp., *Ornithodorus* spp., *Otobius* spp., from the family of Ixodidae like *Amblyomma* spp., *Dermacentor* spp., *Haemaphysalis* spp., *Hyalomma* spp., *Ixodes* spp., *Rhipicephalus* (*Boophilus*) spp, *Rhipicephalus* spp. (the original genus of multi host ticks); from the order of mesostigmata like *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Exemplary parasitic protozoa include, without any limitation:

Mastigophora (*Flagellata*) such as:

Metamonada: from the order Diplomonadida, for example, *Giardia* spp., *Spironucleus* spp.

Parabasala: from the order Trichomonadida, for example, *Histomonas* spp., *Pentatrichomonas* spp., *Tetratrichomonas* spp., *Trichomonas* spp., *Tritrichomonas* spp.

Euglenozoa: from the order Trypanosomatida, for example, *Leishmania* spp., *Trypanosoma* spp

*Sarcomastigophora* (Rhizopoda), such as Entamoebidae, for example, *Entamoeba* spp., Centramoebidae, for example, *Acanthamoeba* sp., Euamoebidae, e.g. Hartmanella sp.

Alveolata such as *Apicomplexa* (*Sporozoa*): e.g. *Cryptosporidium* spp.; from the order Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; *from the order Adeleida* e.g. *Hepatozoon* spp., *Klossiella* spp.; from the order Haemosporida e.g. *Leucocytozoon* spp., *Plasmodium* spp.; from the order Piroplasmida e.g. *Babesia* spp., *Ciliophora* spp., *Echinozoon* spp., *Theileria* spp.; from the order Vesibuliferida e.g. *Balantidium* spp., *Buxtonella* spp.

*Microspora* such as *Encephalitozoon* spp., *Enterocytozoon* spp., *Globidium* spp., *Nosema* spp., and furthermore, e.g. *Myxozoa* spp.

Helminths pathogenic for humans or animals include, for example, acanthocephala, nematodes, pentastoma and platyhelmintha (e.g. monogenea, cestodes and trematodes).

Exemplary helminths include, without any limitation:

Monogenea: e.g.: *Dactylogyrus* spp., *Gyrodactylus* spp., Microbothrium spp., Polystoma spp., Troglocephalus spp.

Cestodes: from the order of the Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

from the order of the Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of the Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of the Trichinellida, for example: *Capillaria* spp., *Eucoleus* spp., *Paracapillaria* spp., *Trichinella* spp., *Trichomosoides* spp., *Trichuris* spp.

from the order of the Tylenchida, for example: *Micronema* spp., *Parastrongyloides* spp., *Strongyloides* spp.

from the order of the Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

from the order of the Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acantocephala: from the order of the Oligacanthorhynchida, for example: *Macracanthorhynchus* spp., *Prosthenorchis* spp.; from the order of the Moniliformida, for example: *Moniliformis* spp.

from the order of the Polymorphida, for example: *Filicollis* spp.; from the order of the Echinorhynchida, for example: *Acanthocephalus* spp., *Echinorhynchus* spp., *Leptorhynchoides* spp.

Pentastoma: from the order of the Porocephalida, for example: *Linguatula* spp.

In the veterinary field and in animal keeping, the administration of the compounds of the formula (I) is carried out by methods generally known in the art, such as enterally, parenterally, dermally or nasally, in the form of suitable preparations. Administration can be carried out prophylactically, methaphylactically or therapeutically.

Thus, one embodiment of the present invention refers to the compounds of the formula (I) for use as a medicament.

Another aspect refers to the compounds of the formula (I) for use as an antiendoparasitical agent.

Another particular aspect refers to the compounds of the formula (I) for use as a anthelmintic agent, more particular for use as a nematicidal agent, a platyhelminthicidal agent, an acanthocephalicidal agent, or a pentastomicidal agent.

Another particular aspect refers to the compounds of the formula (I) for use as an antiprotozoal agent.

Another aspect refers to the compounds of the formula (I) for use as an antiectoparasitical agent, in particular an arthropodicidal agent, more particular an insecticidal agent or acaricidal agent.

Further aspects of the invention are veterinary formulations, comprising an effective amount of at least one compound of the formula (I) and at least one of the following: pharmaceutically acceptable excipient (e.g. solid or liquid diluents), pharmaceutically acceptable auxiliary (e.g. surfactants), in particular a pharmaceutically acceptable excipient and/or pharmaceutically acceptable auxiliary which is normally used in veterinary formulations.

A related aspect of the invention is a method for preparing a veterinary formulation as described herein, comprising the step of mixing at least one compound of the formula (I) with pharmaceutically acceptable excipients and/or auxiliaries, in particular with pharmaceutically acceptable excipients and/or auxiliaries which are normally used in veterinary formulations.

Another particular aspect of the invention are veterinary formulations, selected from the group of ectoparasiticidal and endoparasiticidal formulations, more particular selected from the group of anthelmintic, antiprotozoal, and arthropodicidal formulations, even more particular selected from the group of nematicidal, platyhelminthicidal, acanthocephalicidal, pentastomicidal, insecticidal, and acaricidal formulations, in accordance with the mentioned aspects, as well as their methods for preparation.

Another aspect refers to a method for treatment of a parasitic infection, in particular an infection by a parasite selected from the group of ectoparasites and endoparasites mentioned herein, by applying an effective amount of a compound of the formula (I) to an animal, in particular a non-human animal, in need thereof.

Another aspect refers to a method for treatment of a parasitic infection, in particular an infection by a parasite selected from the group of ectoparasites and endoparasites mentioned herein, by applying a veterinary formulation as defined herein to an animal, in particular a non-human animal, in need thereof.

Another aspect refers to the use of the compounds of the formula (I) in the treatment of a parasitic infection, in particular an infection by a parasite selected from the group of ectoparasites and endoparasites mentioned herein, in an animal, in particular a non-human animal.

In the present context of the animal health or veterinary field, the term "treatment" includes prophylactic, metaphylactic or therapeutical treatment.

In a particular embodiment, mixtures of at least one compound of the formula (I) with other active ingredients, particularly with endo- and ectoparasiticides, for the veterinary field are provided herewith.

In the field of animal health "mixture" not only means that two (or more) different active ingredients are formulated in a joint formulation and are accordingly applied together but also refers to products which comprise separate formulations for each active compound. Accordingly, if more than two active compounds are to be applied, all active compounds may be formulated in a joint formulation or all active compounds may be formulated in separate formulations; also feasible are mixed forms where some of the active compounds are formulated jointly and some of the active compounds are formulated separately. Separate formulations allow the separate or successive application of the active compounds in question.

The active compounds specified herein by their common names are known and described, for example, in the Pesticide Manual (see above) or can be searched in the internet (e.g. http://www.alanwood.net/pesticides).

Exemplary active ingredients from the group of ectoparasiticides, as mixing partners, include, without limitation insecticides and acaricides listed in detail above. Further active ingredients which may be used are listed below following the aforementioned classification which is based on the current IRAC Mode of Action Classification Scheme: (1) Acetylcholinesterase (AChE) inhibitors; (2) GABA-gated chloride channel blockers; (3) Sodium channel modulators; (4) Nicotinic acetylcholine receptor (nAChR) competitive modulators; (5) Nicotinic acetylcholine receptor (nAChR) allosteric modulators; (6) Glutamate-gated chloride channel (GluCl) allosteric modulators; (7) Juvenile hormone mimics; (8) Miscellaneous non-specific (multi-site) inhibitors; (9) Modulators of Chordotonal Organs; (10) Mite growth inhibitors; (12) Inhibitors of mitochondrial ATP synthase, such as, ATP disruptors; (13) Uncouplers of oxidative phosphorylation via disruption of the proton gradient; (14) Nicotinic acetylcholine receptor channel blockers; (15) Inhibitors of chitin biosynthesis, type 0; (16) Inhibitors of chitin biosynthesis, type 1; (17) Moulting disruptor (in particular for Diptera, i.e. dipterans); (18) Ecdysone receptor agonists; (19) Octopamine receptor agonists; (21) Mitochondrial complex I electron transport inhibitors; (25) Mitochondrial complex II electron transport inhibitors; (20) Mitochondrial complex III electron transport inhibitors; (22) Voltage-dependent sodium channel blockers; (23) Inhibitors of acetyl CoA carboxylase; (28) Ryanodine receptor modulators; (30) GABA-gated chloride channel allosteric modulators.

Active compounds with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite;

Compounds from other classes, e.g. butacarb, dimetilan, cloethocarb, phosphocarb, pirimiphos (-ethyl), parathion (-ethyl), methacrifos, isopropyl o-salicylate, trichlorfon, tigolaner, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos;

organochlorines, e.g. camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

Biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz Bee hive *varroa* acaricides, for example organic acids, e.g. formic acid, oxalic acid.

Exemplary active ingredients from the group of endoparasiticides, as mixing partners, include, without limitation, anthelmintically active compounds and antiprotozoal active compounds.

Anthelmintically active compounds, including, without limitation, the following nematicidally, trematicidally and/or cestocidally active compounds:

from the class of macrocyclic lactones, for example: eprinomectin, abamectin, nemadectin, moxidectin, doramectin, selamectin, lepimectin, latidectin, milbemectin, ivermectin, emamectin, milbemycin;

from the class of benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, flubendazole;

from the class of depsipeptides, preferably cyclic depsipetides, in particular 24-membered cyclic depsipeptides, for example: emodepside, PF1022A;

from the class of tetrahydropyrimidines, for example: morantel, pyrantel, oxantel;
from the class of imidazothiazoles, for example: butamisole, levamisole, tetramisole;
from the class of aminophenylamidines, for example: amidantel, deacylated amidantel (dAMD), tribendimidine;
from the class of aminoacetonitriles, for example: monepantel;
from the class of paraherquamides, for example: paraherquamide, derquantel;
from the class of salicylanilides, for example: tribromsalan, bromoxanide, brotianide, clioxanide, closantel, niclosamide, oxyclozanide, rafoxanide;
from the class of substituted phenols, for example: nitroxynil, bithionol, disophenol, hexachlorophene, niclofolan, meniclopholan;
from the class of organophosphates, for example: trichlorfon, naphthalofos, dichlorvos/DDVP, crufomate, coumaphos, haloxon;
from the class of piperazinones/quinolines, for example: praziquantel, epsiprantel;
from the class of piperazines, for example: piperazine, hydroxyzine;
from the class of tetracyclines, for example: tetracyclin, chlorotetracycline, doxycyclin, oxytetracyclin, rolitetracyclin;
from diverse other classes, for example: bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, clorsulon.

Antiprotozoal active compounds, including, without limitation, the following active compounds:
from the class of triazines, for example: diclazuril, ponazuril, letrazuril, toltrazuril;
from the class of polylether ionophore, for example: monensin, salinomycin, maduramicin, narasin;
from the class of macrocyclic lactones, for example: milbemycin, erythromycin;
from the class of quinolones, for example: enrofloxacin, pradofloxacin;
from the class of quinines, for example: chloroquine;
from the class of pyrimidines, for example: pyrimethamine;
from the class of sulfonamides, for example: sulfaquinoxaline, trimethoprim, sulfaclozin;
from the class of thiamines, for example: amprolium;
from the class of lincosamides, for example: clindamycin;
from the class of carbanilides, for example: imidocarb;
from the class of nitrofuranes, for example: nifurtimox;
from the class of quinazolinone alkaloids, for example: halofuginon; from diverse other classes, for example: oxamniquin, paromomycin;
from the class of vaccines or antigenes from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All named mixing partners can, if their functional groups enable this, optionally form salts with suitable bases or acids.

Vector Control

The compounds of the formula (I) can also be used in vector control. For the purpose of the present invention, a vector is an arthropod, in particular an insect or arachnid, capable of transmitting pathogens such as, for example, viruses, worms, single-cell organisms and bacteria from a reservoir (plant, animal, human, etc.) to a host. The pathogens can be transmitted either mechanically (for example trachoma by non-stinging flies) to a host, or by injection (for example malaria parasites by mosquitoes) into a host.

Examples of vectors and the diseases or pathogens they transmit are:

1) Mosquitoes
*Anopheles*: malaria, filariasis;
*Culex*: Japanese encephalitis, other viral diseases, filariasis, transmission of other worms;
*Aedes*: yellow fever, dengue fever, other viral diseases, filariasis;
Simuliidae: transmission of worms, in particular *Onchocerca volvulus;*
Psychodidae: transmission of leishmaniasis
2) Lice: skin infections, epidemic typhus;
3) Fleas: plague, endemic typhus, cestodes;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia burgdorferi* sensu lato, *Borrelia* duttoni, tick-borne encephalitis, Q fever (*Coxiella burnetii*), babesioses (*Babesia canis canis*), ehrlichiosis.

Examples of vectors in the sense of the present invention are insects, for example aphids, flies, leafhoppers or *thrips*, which are capable of transmitting plant viruses to plants. Other vectors capable of transmitting plant viruses are spider mites, lice, beetles and nematodes.

Further examples of vectors in the sense of the present invention are insects and arachnids such as mosquitoes, in particular of the genera *Aedes, Anopheles*, for example *A. gambiae, A. arabiensis, A. funestus, A. dirus* (malaria) and *Culex*, psychodids such as *Phlebotomus, Lutzomyia*, lice, fleas, flies, mites and ticks capable of transmitting pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protecting wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. Likewise, the compounds of the formula (I), alone or in combinations with other active compounds, can be used as antifouling agents.

Control of Animal Pests in the Hygiene Sector

The compounds of the formula (I) are suitable for controlling animal pests in the hygiene sector. In particular, the invention can be applied in the domestic sector, in the hygiene sector and in the protection of stored products, especially for controlling insects, arachnids, ticks and mites encountered in enclosed spaces such as dwellings, factory halls, offices, vehicle cabins, animal husbandries. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

They are used, for example, in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Abbreviations and Symbols

AcOH: acetic acid
aq.: aqueous
br: broad
d: doublet
DABCO 1,4-diazabicyclo[2.2.2]octane
DCC: N,N'-dicyclohexylcarbodiimide
DCM: dichloromethane
DIPEA: N,N-diisopropylethylamine
DMF: N,N-dimethylformamide
DMSO: dimethylsulfoxide
ee: enantiomeric excess
eq.: equivalent
ES: electrospray ionization
$Et_3N$ triethylamine
EtOAc: ethyl acetate
h(rs) hour(s)
HATU: 1-[bis(dimethylamino)methylene]-1H-1,2,3-triazolo[4,5-b]pyridinium-3-oxid hexafluorophosphate
HOBt: 1-hydroxybenzotriazole hydrate
HPLC: high performance liquid chromatography
iPrOH: isopropanol
J: coupling constant
LCMS: liquid chromatography-mass spectrometry
m z: mass-to-charge ratio
M: molarity
m: multiplet
MeCN acetonitrile
MeOH: methanol
$NaH_2PO_4$ monosodium phosphate
NaOH sodium hydroxide
$Na_2SO_4$ sodium sulfate
$NH_4Cl$ ammonium chloride
NMR: nuclear magnetic resonance
q: quartet
r. t.: room temperature
Rt: retention time
s: singlet
sat.: saturated
T: temperature
t: triplet
T3P®: propylphosphonic anhydride
THF: tetrahydrofuran
TMSOK potassium trimethylsilanolate
wt.: weight
xantphos: 4,5-bis(diphenylphosphino)-9,9-dimethylxanthene
δ: chemical shift
λ: wavelength Description of the Processes and Intermediates Compounds of formula (I') may be prepared as illustrated in the following scheme 1 where $R^1$, $R^2$, $R^3$ and $R^4$ are as previously defined and $X^1$ stands for OH or Cl.

Scheme 1

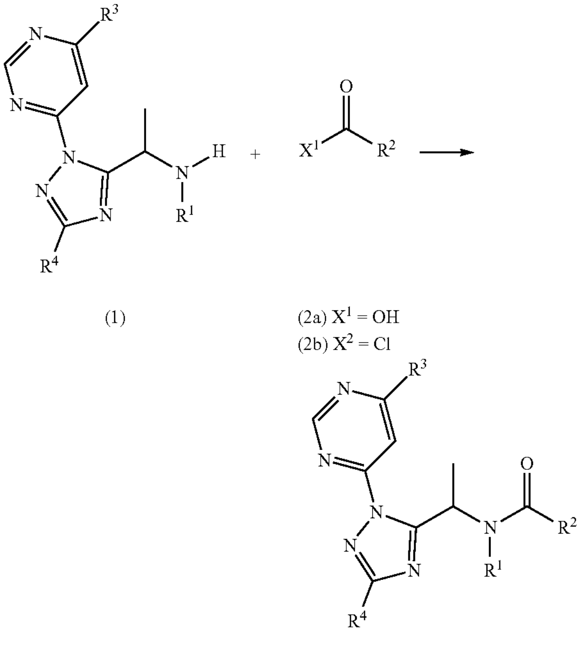

(1)

(2a) $X^1$ = OH
(2b) $X^2$ = Cl (I')

$X^1$═OH: A triazole compound of formula (1) is reacted with a carboxylic acid of formula (2a) ($X^1$═OH) to form compounds of formula (I'). For example, a mixture of a triazole of formula (1), a carboxylic acid of formula (2a) ($X^1$═OH), a suitable coupling reagent, such as T3P®, HATU or DCC/HOBt, a suitable base such as triethylamine or DIPEA, in a suitable solvent, such as ethyl acetate or DMF are mixed at temperatures ranging from around 0 to 100° C. to provide compounds of formula (I') which may then be isolated and, if necessary and desired, purified using techniques well known in the art, such as chromatography. $X^1$=Cl: A triazole compound of formula (1) is reacted with a carboxylic acid chloride of formula (2b) ($X^1$=Cl) to form compounds of formula (I'). For example, a mixture of a triazole of formula (1), a carboxylic acid chloride of formula (2b) ($X^1$=Cl), a suitable base such as triethylamine or DIPEA, in a suitable solvent, such as dichloromethane or THF are mixed at temperatures ranging from around 0 to 100° C. to provide compounds of formula (I') which may then be isolated and, if necessary and desired, purified using techniques well known in the art, such as chromatography.

Thioamides of formula (I) (in which X=S) can be obtained by treatment of compounds of formula (I') with the Lawesson's reagent in boiling toluene as described for example in WO 2005009435.

Carboxylic acids of formula (2a) ($X^1$=OH) and carboxylic acid chlorides of formula (2b) ($X^1$=Cl) are commercially available or may be synthesized by methods known to a person skilled in the state of the art. The synthesis of certain carboxylic acids of formula (2a) ($X^1$=OH) has been described in WO 2019/197468.

3-[(1,1,2,2-Tetrafluoroethyl)sulfanyl]benzoic acid: synthesis described in J. Org. Chem. 1964, vol 29, 895-898. An alternative synthesis is possible starting with 3-sulfanylbenzoic acid, the latter being converted into the methyl ester with HCl in MeOH, followed by alkylation with 1,2-dibromo-1,1,2,2-tetrafluoroethane in the presence of cesium carbonate in DMSO at 60° C. The resulting methyl 3-[(2-bromo-1,1,2,2-tetrafluoroethyl)sulfanyl]benzoate is debrominated with Zn in AcOH at 50° C. Hydrolysis of the methyl ester yields 3-[(1,1,2,2-tetrafluoroethyl)sulfanyl]benzoic acid.

Compounds of formula (I) may be prepared as illustrated in the following scheme 2 where $R^1$ and $R^3$ are as previously defined and $R^4$ is hydrogen or $C_1$-$C_3$alkyl.

Scheme 2

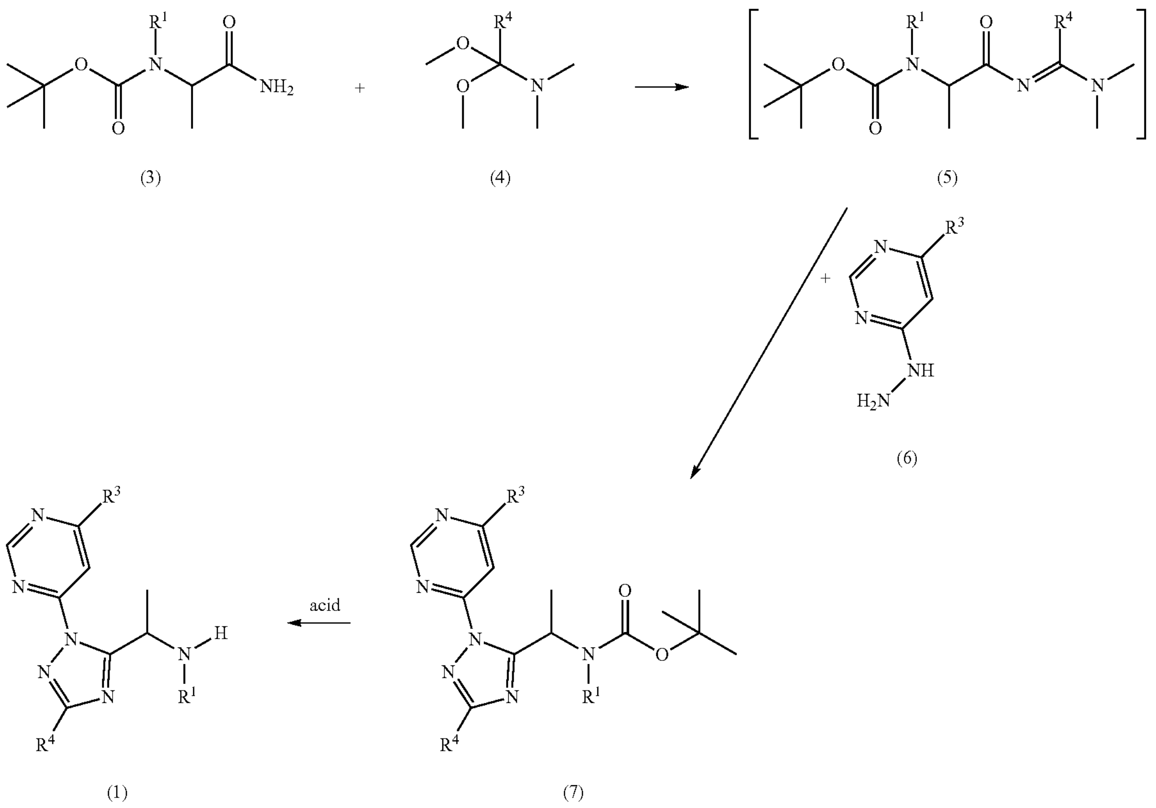

An amide of formula (3) is reacted with an N,N-dimethylamide dimethyl acetal of formula (4) to form compounds of formula (5) which are subsequently reacted with substituted hydrazines of formula (6) or suitable salt thereof (e.g. hydrochloric acid salts) under acidic conditions to form compounds of formula (7). For example, a compound of formula (3) and a N,N-dimethylamide dimethyl acetal of formula (4) are reacted in a suitable solvent, such as $CH_2Cl_2$ at reflux to provide compounds of formula (5). After removal of the solvent, compounds of formula (5) are reacted with a substituted hydrazine of formula (6) or a suitable salt thereof (e.g. hydrochloric acid salt) in a suitable solvent such as 1,4-dioxane, acetic acid or a mixture of such solvents at temperatures ranging from around 20 to 80° C. The resulting compounds of formula (7) may then be isolated and, if necessary and desired, purified using techniques well known in the art, such as chromatography.

A carbamate of formula (7) is treated with an acid to form amines of formula (1). For example, a carbamate of formula (7) and a suitable acid, such as hydrogen chloride or trifluoracetic acid, are reacted in a suitable solvent, such as 1,4-dioxane or in the case of trifluoroacetic acid without an additional solvent at temperatures ranging from around 0 to 80° C. The resulting amines of formula (1) may then be isolated as their acid salts or after base treatment as free amines and, if necessary and desired, purified using techniques well known in the art, such as chromatography.

The requisite amides of formula (3) and hydrazines of formula (6) or suitable salts thereof (e.g. hydrochloric acid salts) are commercially available or may be synthesized by methods described in this application or methods known to the skilled artisan.

For example, hydrazines of formula (6) can be obtained as follows:

6-hydroxypyrimidine-4-carboxylic acid is obtained as described in J. Org. Chem. 1961, 2755; WO2010/20432 A2; US2011/21500 A1 or US2007/259860 A1 and converted to 6-chloropyrimidine-4-carbonyl chloride in analogy to WO2010/20432 A2. The acid chloride function of the latter is then converted into an amide by reaction with an appropriate amine in a solvent as THF at 0° C. If the reacting amine is different from ammonia, only one equivalent of reacting amine is used and a suitable base as triethyl amine is used additionally. Amides of such type are known from Chemistry of heterocyclic compounds 1972, vol 8, p 509. Finally, the chloropyrimidine function is converted into a hydrazinopyrimidine by reaction with hydrazine hydrate in a solvent as methanol at RT or elevated temperature as up to 65° C. in analogy to Ukrainskii Khimicheskii Zhurnal 1982, 48(1), 67-69.

Compounds of formula (I') may alternatively be prepared as illustrated in the following scheme 3 where $R^1$, $R^2$, $R^3$ and $R^4$ are as previously defined and $R^5$ is hydrogen or $C_1$-$C_3$alkyl.

An amide of formula (8) is reacted with an N,N-dimethylamide dimethyl acetal of formula (4) to form compounds of formula (9) which are subsequently reacted with substituted hydrazines of formula (6) or suitable salts thereof (e.g. hydrochloric acid salts) under acidic conditions to form compounds of formula (I'). For example, a compound of formula (8) and an N,N-dimethylamide dimethyl acetal of formula (4) are reacted in a suitable solvent, such as $CH_2Cl_2$ at reflux to provide compounds of formula (9). Upon removal of the solvent, compounds of formula (9) are reacted with a substituted hydrazine of formula (6) or a suitable salt thereof (e.g. hydrochloric acid salt) in a suitable solvent such as 1,4-dioxane, acetic acid or a mixture of such solvents at temperatures ranging from around 20 to 100° C. The resulting compounds of formula (I') may then be isolated and, if necessary and desired, purified using techniques well known in the art, such as chromatography.

The requisite hydrazines of formula (6) or suitable salts thereof (e.g. hydrochloric acid salts) are commercially available or may be synthesized by methods described in this application or methods known to the skilled artisan.

The required amides of formula (8) may be prepared as illustrated in the following scheme 4, where $R^1$ and $R^2$ are as previously described (see also WO 2017/192385).

Scheme 3

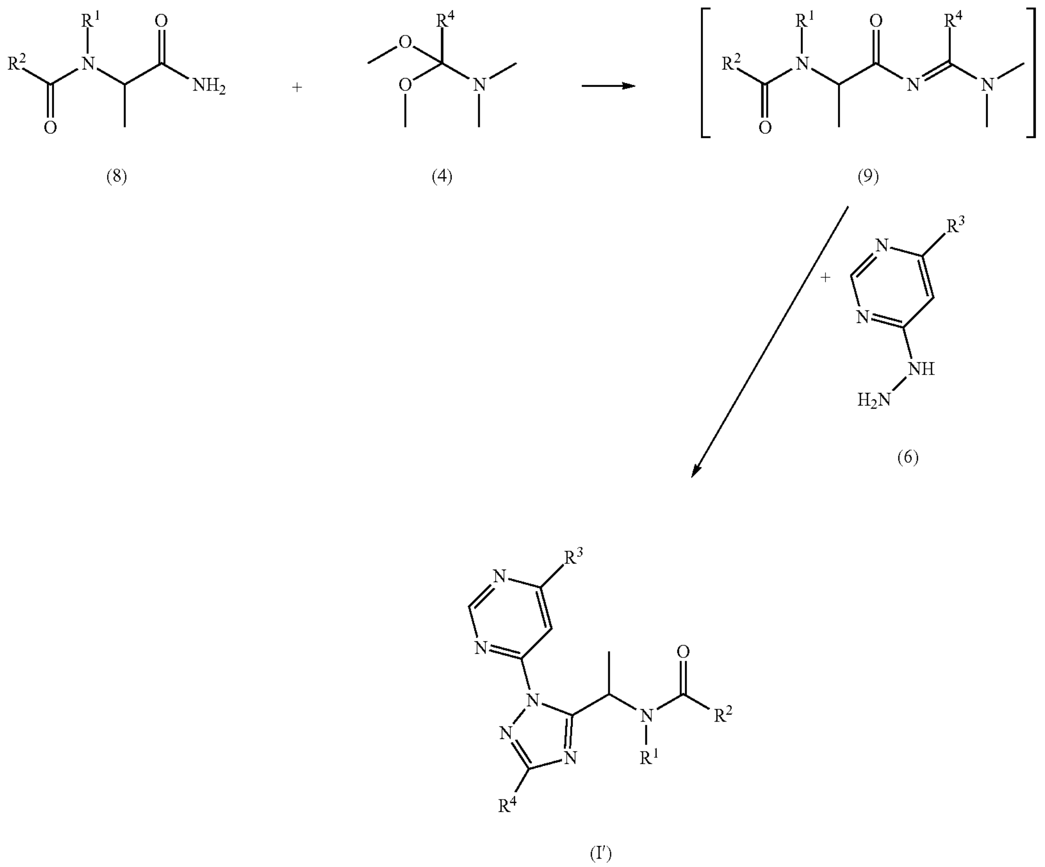

(8) (4) (9) (6) (I')

Scheme 4

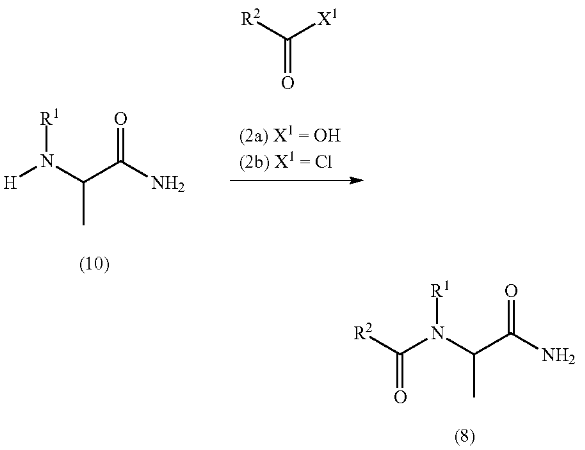

(10)

(8)

An amino amide of formula (10) is reacted with a carboxylic acid of formula (2a) ($X^1$═OH) to form compounds of formula (8). For example, a mixture of an amino amide of formula (10), a carboxylic acid (2a) ($X^1$═OH), a suitable coupling reagent, such as T3P®, HATU or DCC/HOBt, a suitable base such as triethylamine or DIPEA, in a suitable solvent such as ethyl acetate or DMF are mixed at temperatures ranging from around 0 to 100° C. to provide compounds of formula (8) which may then be isolated and, if necessary and desired, purified using techniques well known in the art, such as chromatography.

Alternatively, an amino amide of formula (10) is reacted with a carboxylic acid chloride of formula (2b) ($X^1$═Cl) to form compounds of formula (8). For example, a mixture of an amino amide of formula (10), a carboxylic acid chloride of formula (2b) ($X^1$═Cl), a suitable base such as triethylamine or DIPEA, in a suitable solvent, such as dichloromethane or THF are mixed at temperatures ranging from around 0 to 100° C. to provide compounds of formula (8) which may then be isolated and, if necessary and desired, purified using techniques well known in the art, such as chromatography.

Compounds of formula (10) are commercially available or may be synthesized by methods known to the skilled artisan. Carboxylic acids of formula (2a) ($X^1$═OH) and carboxylic acid chlorides of formula (2b) ($X^1$═Cl) are commercially available or may be synthesized by methods known to the skilled artisan. The synthesis of certain carboxylic acids of formula (2a) ($X^1$═OH) has been described in WO 2019/197468. Scheme 5 illustrates the preparation of alkyltriazole and cycloalkyltriazole containing amines (1a) where $R^4$ is $C_1$-$C_3$alkyl or $C_3$-$C_4$cycloalkyl. Z is $NH_2$ or $OC_1$-$C_6$alkyl.

Scheme 5

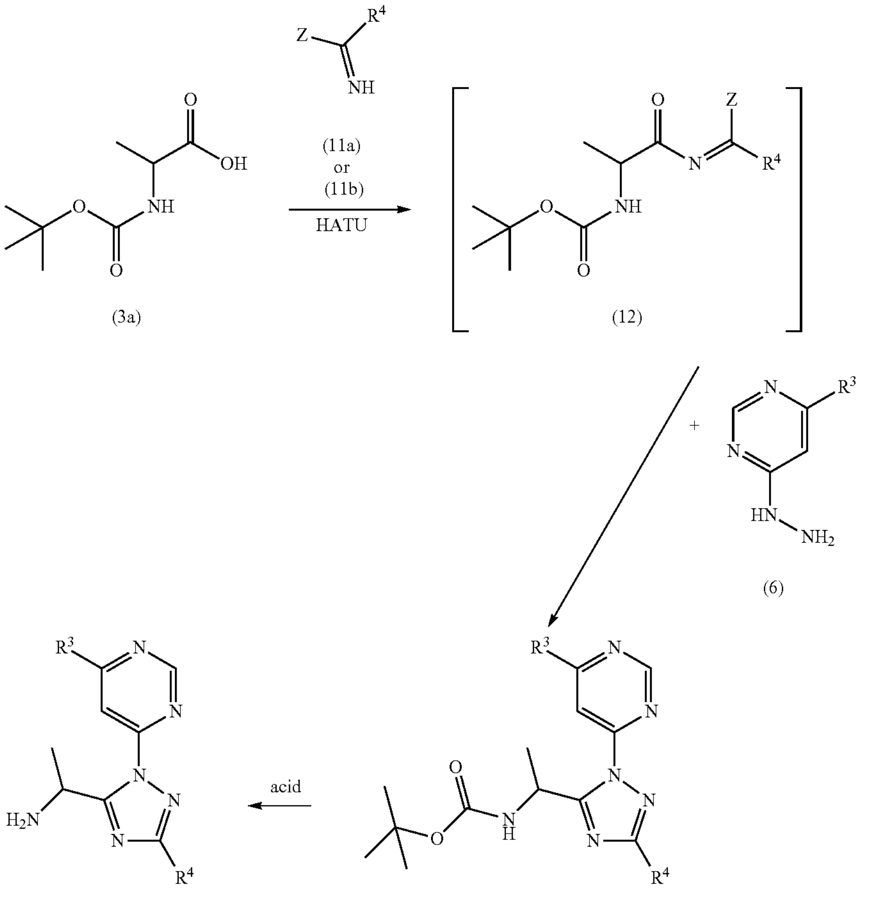

(3a)

(12)

(6)

(1a)

(7a)

N-(tert-butoxycarbonyl)-alanine (3a) is reacted with an alkylamidine (11a, Z═$NH_2$) or an alkylimidate (11b, Z═$OC_1$-$C_6$alkyl) to form intermediates of formula (12) which are subsequently reacted with substituted hydrazines of formula (6) to form alkyltriazoles of formula (7a).

For example in the case of (11a, Z═$NH_2$) (compare *J. Org. Chem.* 2011, 76, 1177-1179) N-(tert-butoxycarbonyl)-alanine and an alkylamidine of formula (11a) are reacted in the presence of a suitable coupling reagent, such as HATU, a suitable base such as triethylamine or DIPEA, in a suitable solvent, such as DMF, at temperatures ranging from 0 to 50° C. to form acylamidine intermediates of formula (12). After removal of the solvent, the intermediates of formula (12) are reacted with a substituted hydrazine of formula (6) or a suitable salt thereof (e.g. hydrochloric acid salt) in a suitable solvent such as acetic acid at temperatures ranging from around 20 to 80° C. The resulting alkyltriazoles of formula (7a) may then be isolated and, if necessary and desired, purified using techniques well known in the art, such as chromatography.

In the case of Z═$OC_1$-$C_6$alkyl N-(tert-butoxycarbonyl)-alanine and an alkylimidate of formula (11b) or a suitable salt thereof are reacted in the presence of a suitable coupling reagent, such as HATU, a suitable base such as triethylamine or DIPEA, in a suitable solvent, such as THF at temperatures ranging from around 0 to 25° C. to form acyl imidate intermediates of formula (12b). Upon addition of a substituted hydrazine of formula (6) or a suitable salt thereof (e.g. hydrochloric acid salt) the intermediate of formula (12b) reacts at temperatures ranging from around 20 to 80° C. to give alkyltriazoles of formula (7a) which may then be isolated and, if necessary and desired, purified using techniques well known in the art, such as chromatography.

A carbamate of formula (7a) is treated with an acid to form amines or the associated salts of formula (1a) as described in scheme 2 for amines of general formula (1).

The requisite alkylamidines (11a) and alkylimidates (11 b) or their suitable salts and hydrazines of formula (6) or suitable salts thereof (e.g. hydrochloric acid salts) are commercially available or may be synthesized by methods described in this application or methods known to the skilled artisan (see for example WO 2011/133447 for the synthesis of methyl cyclopropanecarboximidate hydrochloride).

Compounds of formula (1b) in which alkyl is $C_1$-$C_3$alkyl and $R^3$ is as previously defined, may be prepared as illustrated in the following scheme 6.

Scheme 6

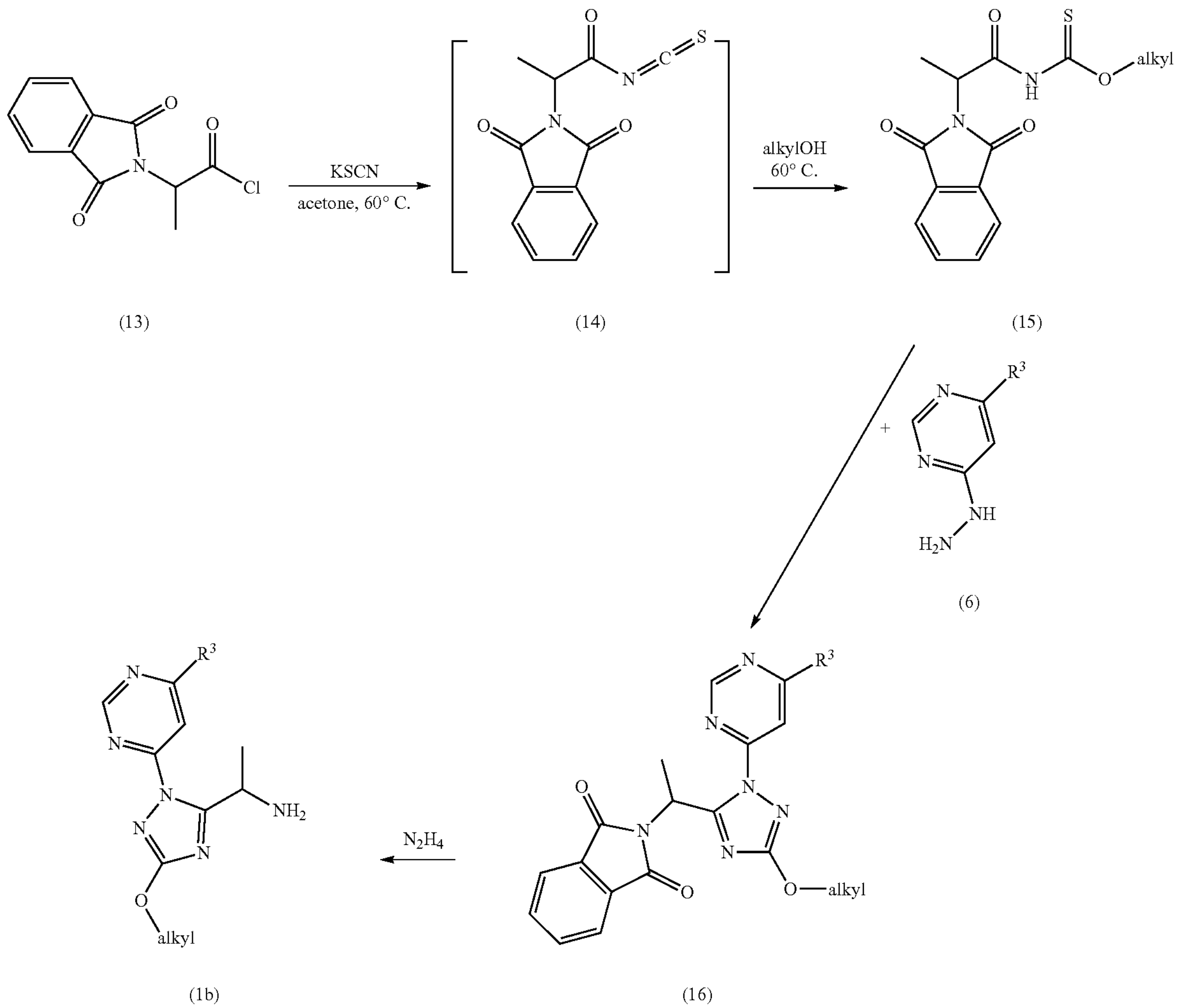

(13) (14) (15) (6) (1b) (16)

2-(1,3-Dioxo-1,3-dihydro-2H-isoindol-2-yl)propanoyl chloride (13), prepared from 2-(1,3-dioxo-1,3-dihydro-2H-isoindol-2-yl)propanoic acid and oxalyl chloride according to *Tetrahedron: Asymmetry,* 21(8), 936-942, 2010, is reacted with potassium thiocyanate (KSCN) in acetone to yield the corresponding isocyanate intermediate (14) which is treated in the next step with the corresponding alcohol (alkylOH) to afford the O-alkyl [2-(1,3-dioxo-1,3-dihydro-2H-isoindol-2-yl)propanoyl]carbamothioates (15). The reaction between the intermediate of formula (15) and a hydrazine of formula (6) or it's hydrohalic acid salt in ethanol affords cyclized products of formula (16) as described in Bioorganic & Medicinal Chemistry 26 (2018) 3321-3344.). In a final step, the phthalimide protecting group is removed by reaction with hydrazine hydrate in a suitable solvent, like ethanol, as described in WO 2018/086605. The obtained amine (1b) is then reacted with a carboxylic acid as described in scheme 1 to form the example compounds.

Compounds of formula (21) may be prepared as illustrated in the following scheme 7 wherein E is H or $C_1$-$C_6$alkyl, Hal is bromine or iodine, $R^{22}$ is as previously described, and G is cyclopropyl wherein the cyclopropyl is optionally substituted with one to two substituent(s) selected from the group of halogen, —CN, methyl or trifluoromethyl.

Scheme 7

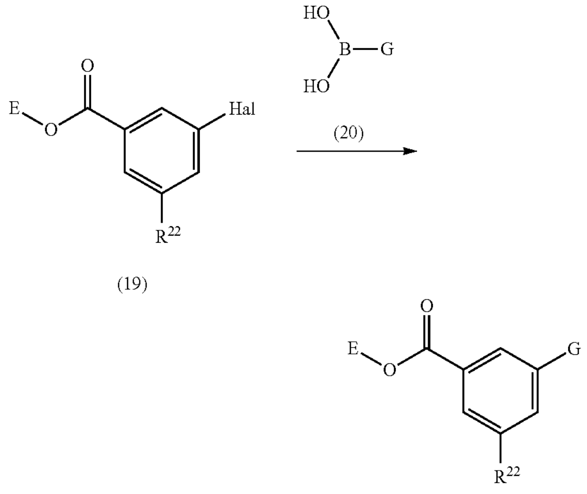

(19)

(21)

A halogen containing compound of formula (19) is reacted with a boronic acid of formula (20) or a corresponding boronic acid ester to form compounds of formula (21). For example, a mixture of a halogen containing compound of formula (19), a boronic acid (20), a suitable catalyst, such as palladium(II) acetate in combination with tricyclohexylphosphine, a suitable base such as tripotassium phosphate, in a suitable solvent or solvent mixture such as toluene and water are reacted at temperatures ranging from around 0 to 100° C. to provide compounds of formula (21) which may then be isolated and, if necessary and desired, purified using techniques well known in the art, such as chromatography. Compounds of formula (21) in which E is $C_1$-$C_6$alkyl can be transformed to compounds of formula (21) in which E is H by treatment with an alkali hydroxide in a suitable solvent or solvent mixture such as/containing tetrahydrofuran, ethanol or water at temperatures ranging from around 0 to 100° C.

Compounds of formula (23) may be prepared as illustrated in the following scheme 8 wherein E is H or $C_1$-$C_6$alkyl, Hal is iodine or bromine, Ra is $C_1$-$C_3$alkyl or cylopropyl and $R^{22}$ is as previously described.

Scheme 8

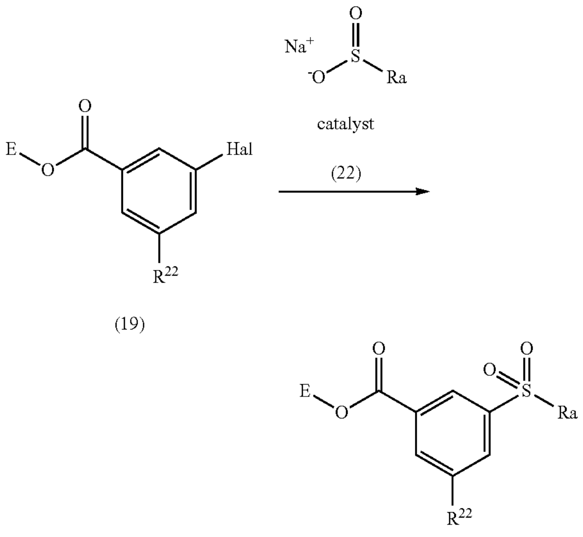

(19)

(23)

An aryl halide of formula (20) is reacted with a sulfinate salt of formula (22) under copper salt catalysis to form sulfones of formula (23).

For example, a mixture of a compound of formula (20), a sodium sulfinate salt of formula (22), copper(J) iodide, proline and sodium hydroxide are reacted in a suitable solvent, such as dimethyl sulfoxide at temperatures ranging from 40 to 140° C. (compare WO 2019/197468). In an alternative approach a mixture of a compound of formula (20), a sodium sulfinate salt of formula (22), copper(I) iodide, trans-N,N-dimethylcyclohexane-1-2-diamine and cesium carbonate are reacted in a suitable solvent, such as DMF at temperatures ranging from 40 to 140° C.

The resulting compounds of formula (23) may then be isolated and, if necessary and desired, purified using techniques well known in the art, such as chromatography. Compounds of formula (23) in which E is $C_1$-$C_6$alkyl can be transformed to compounds of formula (23) in which E is H by treatment with an alkali hydroxide in a suitable solvent or solvent mixture such as/containing tetrahydrofuran, ethanol or water at temperatures ranging from around 0 to 100° C. In case E is a tert-butyl group this ester can be cleaved under acidid conditions in a suitable solvent such as dichloromethane in the presence of a suitable acid such as trifluoroacetic acid at temperatures ranging from 0-40° C.

The aryl halides (20) and sulfinate salts of formula (22) are commercially available or may be synthesized by methods known to the skilled artisan.

In an alternative approach compounds of formula (23a) may be prepared as illustrated in the following scheme 9a wherein Hal is fluorine or chlorine, Ra is $C_1$-$C_3$alkyl or cylopropyl and $R^{22}$ is as previously described.

Scheme 9a

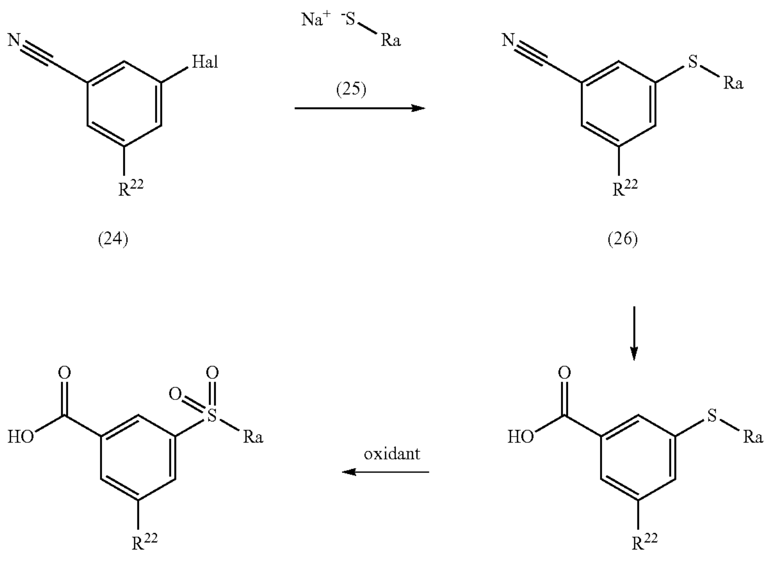

(24) (26) (23a) (27)

An aryl halide of formula (24) is reacted with a thiolate salt of formula (25) to form thioethers of formula (26) which are then hydrolised to form carboxylic acids of formula (27). In a third step thioethers of formula (27) are oxidized to sulfones of formula (23a).

For example, a mixture of a halide of formula (24) and a sodium thiolate of formula (25), is reacted in a suitable solvent, such as N,N-dimethylformamide at temperatures ranging from −20 to 50° C. The resulting nitriles of formula (26) are then hydrolyzed either under basic conditions, using for example aqueous sodium hydroxide in a suitable solvent or solvent mixture, such as isopropanol or methanol/THF at temperatures ranging from 40 to 100° C. or under acidic conditions in a suitable strong acid, such as sulfuric acid or hydrochloric acid either neat or diluted with a suitable dilutant such as water at temperatures ranging from 40 to 100° C. The obtained carboxylic acids (27) are then if necessary and desired, purified using techniques well known in the art, such as chromatography (see also the syntheses of 3-chloro-5-(difluoromethyl)benzoic acid described in this application for conditions of basic hydrolysis and US 20060276536 for conditions of acidic hydrolysis).

A thioether containing compound of formula (27) is reacted with an oxidizing reagent such as 3-chloroperoxybenzoic acid or a combination of formic acid and hydrogenperoxide in a suitable solvent such as dichloromethane at temperatures ranging from 0 to 50° C. to form sulfones of formula (23). The obtained sulfones of formula (23a) are then if necessary and desired, purified using techniques well known in the art, such as chromatography.

The requisite aryl halides (24) and thiolate salts of formula (25) are commercially available or may be synthesized by methods known to the skilled artisan (e.g. WO 2013/049250 for the synthesis of cyclopropanethiol). Thiolate salts may be synthesized form the corresponding thiols through deprotonation with sodium hydride in a suitable solvent such as N,N-dimethylformamide.

In a further alternative approach compounds of formula (23b) may be prepared as illustrated in the following scheme 9b wherein Hal is chlorine, bromine or iodine, Ra is $C_1$-$C_3$alkyl or $C_1$-$C_3$haloalkyl and $R^{22}$ is as previously described.

Scheme 9b

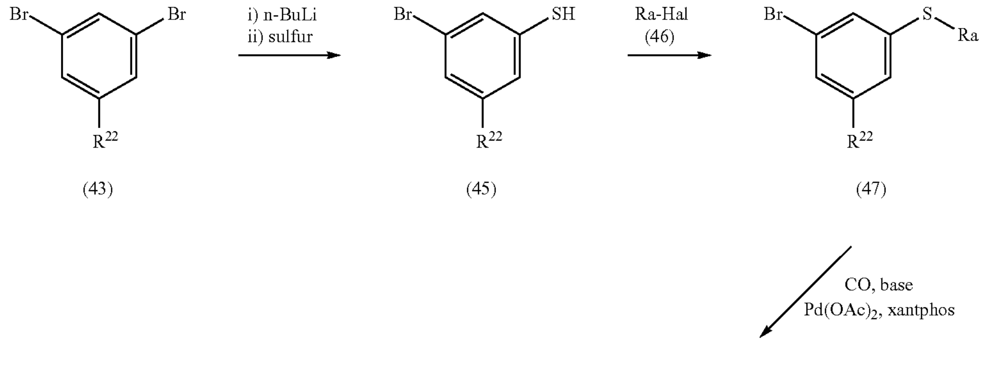

(43) (45) (47)

-continued

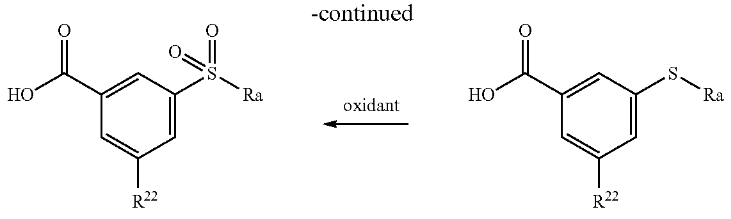

(23b) (48)

Dirbromobenzenes of formula (43) may be lithiated at low temperatures, ranging from −78 to 0° C. in the presence of a lithium transferring reagent, e.g. n-butyllithium, as described in WO2009148052, followed by a reaction with sulfur. The resulting thiols of formula (45) may be alkylated with alkylation reagents (46) in the presence of a base and in case of $CF_3Hal$ in the presence of a phase transfer catalyst, for example 1,1'-dimethyl-[4,4'-bipyridine]-1,1'-diium dichloride.

The resulting sulfanes of formula (47) may be carbonylated and subsequently oxidized by methods known to the skilled artisan to obtain sulfones of formula (23b).

Compounds of formula (34) may be prepared as illustrated in the following scheme 10. $R_f$ is $C_1$-$C_3$haloalkyl and $R^{21}$ is as previously described. Hal is iodine or chlorine in case $R_f$ is difluoromethyl. If $R^{21}$ is iodine or bromine it can be converted to an optionally substituted cyclopropyl as described in scheme 7.

hydrolyzed to form carboxylic acids of formula (33). In an additional step thioethers of formula (33) are oxidized to sulfones of formula (34).

For example, a mixture of an aryl fluoride of formula (28) and sodium sulfide (29), is reacted in a suitable solvent, such as N,N-dimethylformamide at temperatures ranging from −20 to 50° C. The resulting thiols of formula (30) are then alkylated with trifluoromethyliodide in the presence of e.g. triethylamine and 1,1'-dimethyl-4,4'-bipyridinium dichloride in a suitable solvent, such as N,N-dimethylformamide at temperatures ranging from −20 to 50° C.

The obtained thioethers of formula (32) are hydrolyzed either under basic conditions, using for example aqueous sodium hydroxide in a suitable solvent, such as methanol at temperatures ranging from 40 to 100° C. or under acidic conditions in a suitable strong acid, such as sulfuric acid or hydrochloric acid either neat or diluted with a suitable dilutant such as water at temperatures ranging from 40 to Scheme 10

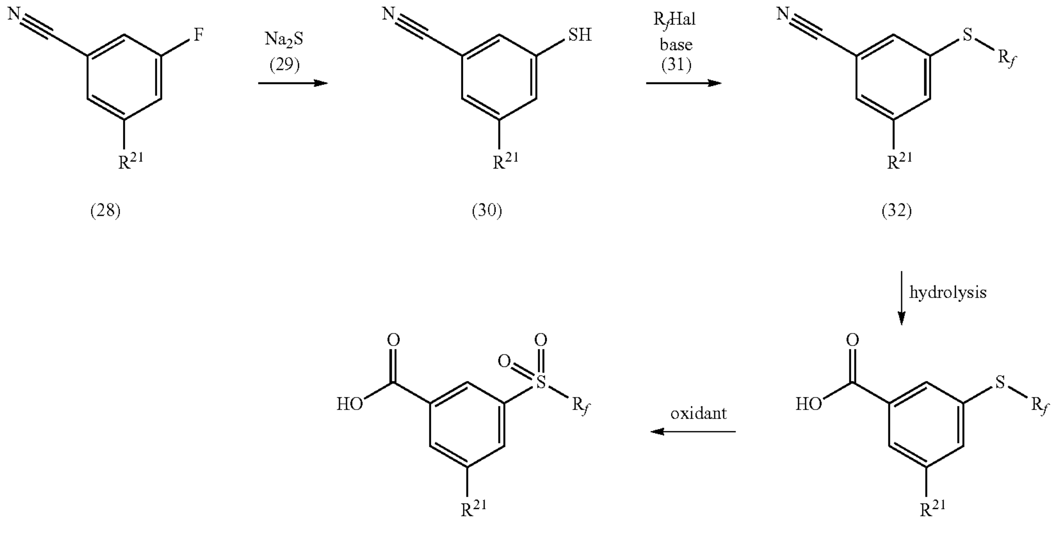

(28) (30) (32)

(34) (33)

An aryl fluoride of formula (28) is reacted with sodium sulfide (29) to form thiols of formula (30) described for example in *Tetrahedron Letters,* 2012, 53(20), 2548-2551. Subsequently, a haloalkylthioether (32) is formed under alkylation conditions using e.g. haloalkyliodides or difluoromethylchloride and suitable bases. In case of trifluoromethyliodide an additional catalyst as described for example in WO 2015035223 is used. The nitrile function is then 100° C. The obtained carboxylic acids (33) are then if necessary and desired, purified using techniques well known in the art, such as chromatography.

A thioether containing compound of formula (33) is reacted with an oxidizing reagent such as 3-chloroperoxybenzoic acid in a suitable solvent such as dichloromethane or a combination of acetic acid and hydrogenperoxide at temperatures ranging from 0 to 50° C. to form sulfones of formula (34). The obtained sulfones of formula (34) are then if necessary and desired, purified using techniques well known in the art, such as chromatography.

The requisite aryl fluorides (28) are commercially available or may be synthesized by methods known to the skilled artisan.

In an alternative approach acids of formula (38) containing substituted cyclopropyl groups may be prepared as illustrated in the following scheme 11 wherein $R^{22}$ is as previously described and $Z^1$ is either —CN or —$CO_2C_1$-$C_6$alkyl. $Z^2$ and $Z^3$ are independently selected from the group of hydrogen, halogen, —CN, methyl or trifluoromethyl with the prerequisite that only up to three of the substituents $Z^2$ and $Z^3$ are different from hydrogen. L is iodo or trifluoroacetate. M is a transition metal complex fragment containing iron, copper, palladium or rhodium and a suitable ligand substitution.

Scheme 11

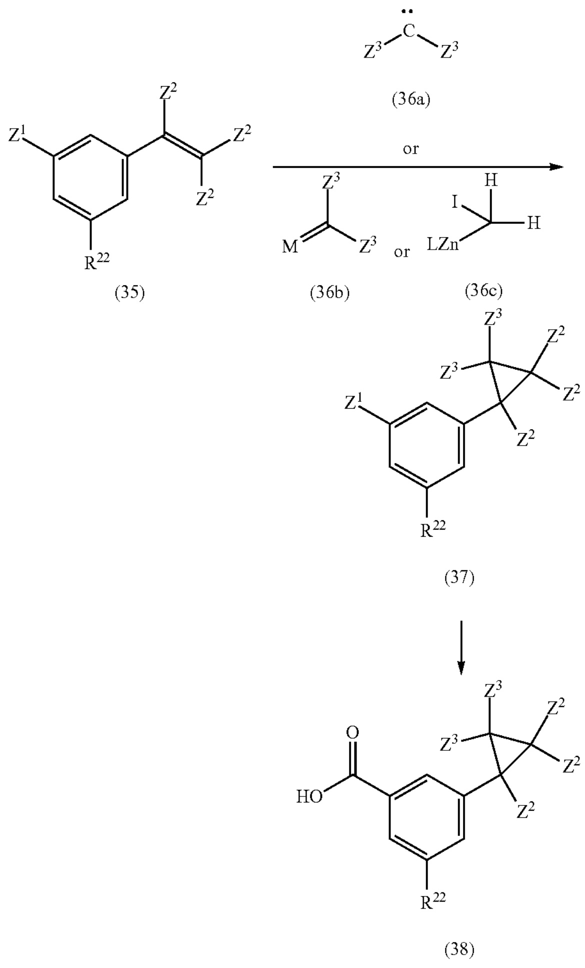

(35) (36a) (36b) (36c) (37) (38)

Alkene containing compounds of formula (35) react with free carbenes (36a), zinc carbenoids (36c) and certain transition metal carbene complexes (36b) to yield cyclopropyl containing compounds of formula (37). These may then be transformed to acids of formula (38) either by ester cleavage (in case $Z^1$ is —$CO_2C_1$-$C_6$alkyl) or by hydrolysis of a cyano group (in case $Z^1$ is —CN). Different cyclopropanation reactions are known to persons skilled in the art and have been reviewed in the literature (for example in *Chem. Rev.* 2017, 117, 11651-11679).

For a reaction with a zinc carbenoid (36c) the zinc carbenoid is generated upon first reacting $Et_2Zn$ with trifluoro acetic acid in a suitable solvent such as absolute dichloromethane at 0° C. followed by the addition of $CH_2$12. Upon addition of the alkene (35) the preformed zinc carbenoid reacts with the alkene to form the cyclopropane at temperature ranging from 20-40° C. (see also WO 2012/139775).

Different transition metal carbene complexes (36b) have been found suitable for cyclopropanation reactions. Examples of suitable precursors for such complexes are CuBr, $Pd(OAc)_2$, $Rh(OAc)_4$ or iron(III)-5,10,15,20-tetraphenyl-porphyrin (Fe(TPP)Cl).

For a reaction via a palladium carbene complex, a solution of an alkene (35) in a suitable solvent such as tetrahydrofurane or diethyl ether is treated with a solution of diazomethane in a suitable solvent such as diethyl ether in the presence of a suitable palladium salt such as $Pd(OAc)_2$ at temperatures ranging from 0° C.-20° C. (see also WO 2014/023367). A trifluoromethyl substituted cyclopropyl group can be obtained through reaction of an alkene (35) with iron carbene complexes obtained from in situ generated trifluoromethyl diazomethane and Fe(TPP)Cl as described in *Angew. Chem. Int. Ed.* 2010, 49, 938-941.

For a reaction with a free carbene (36a), a solution of an alkene (35) in a suitable solvent is mixed with a carbene precursor from which the free carbene is generated in situ. For example a solution of an alkene (35) in diglyme is heated in the presence of sodium bromo(difluoro)acetate at temperatures ranging from 60-80° C. An alternative carbene precursor is for example trimethyl(trifluoromethyl)silane which is used in combination with sodium iodide (as described in WO 2017/040742).

The final hydrolysis of the cyano groups to the corresponding acid (38) may be conducted under basic or acidic conditions as described in scheme 9. The hydrolysis of esters may be conducted as described in scheme 8.

The requisite alkenes (35) and reagents needed for the generation of free carbenes (36a), zinc carbenoids (36c) and certain transition metal carbene complexes (36b) are either commercially available or may be synthesized by methods known to the skilled artisan. For the synthesis of substituted alkenes (35) via palladium catalyzed coupling reactions see for example WO 2013/178362 (1-bromo-3-(1,1-dimethylethyl)-5-(1-methylethenyl)benzene) and WO 2012/035011 (1,5-dichloro-2-fluoro-3-(3,3,3-trifluoroprop-1-en-2-yl) benzene).

The preparation and use examples which follow illustrate the invention without limiting it.

Scheme 12 illustrates the preparation of triazole-containing amines (1b) where $R^4$, $R^{31}$ and $R^{32}$ are as previously described, Alk is $C_1$-$C_3$alkyl and Hal is chlorine, bromine or iodine.

Intermediates of formula (5a) or (12) are reacted with a substituted hydrazine of formula (39) or a suitable salt thereof (e.g. hydrochloric acid salt) in a suitable solvent such as acetic acid at temperatures ranging from around 20 to 80° C. The resulting 4-halogen-pyrimidin-6-yl-triazoles of formula (40) may then be isolated and, if necessary and desired, purified using techniques well known in the art, such as chromatography.

Subsequently, 4-halogen-pyrimidin-6-yl-triazoles of formula (40) are pressurized with carbon monoxide in suitable $C_1$-$C_3$ alcohols like methanol or ethanol in the presence of a palladium catalyst, for example [1,1'-bis(diphenylphosphino)ferrocene]dichloropalladium, likewise described in WO 2012/035039. The resulting ester of formula (41) can be converted into amides of formula (42) by methods described in this application or methods known to the skilled artisan.

A carbamate of formula (42) is treated with an acid to form amines or the associated salts of formula (1b) as described in scheme 2 for amines of general formula (1).

The requisite amidines (5a) and imidates (12) are described in scheme 2 and scheme 5 and hydrazines of formula (39) or suitable salts thereof (e.g. hydrochloric acid salts) are commercially available or may be synthesized by methods described in this application or methods known to the skilled artisan.

Scheme 12

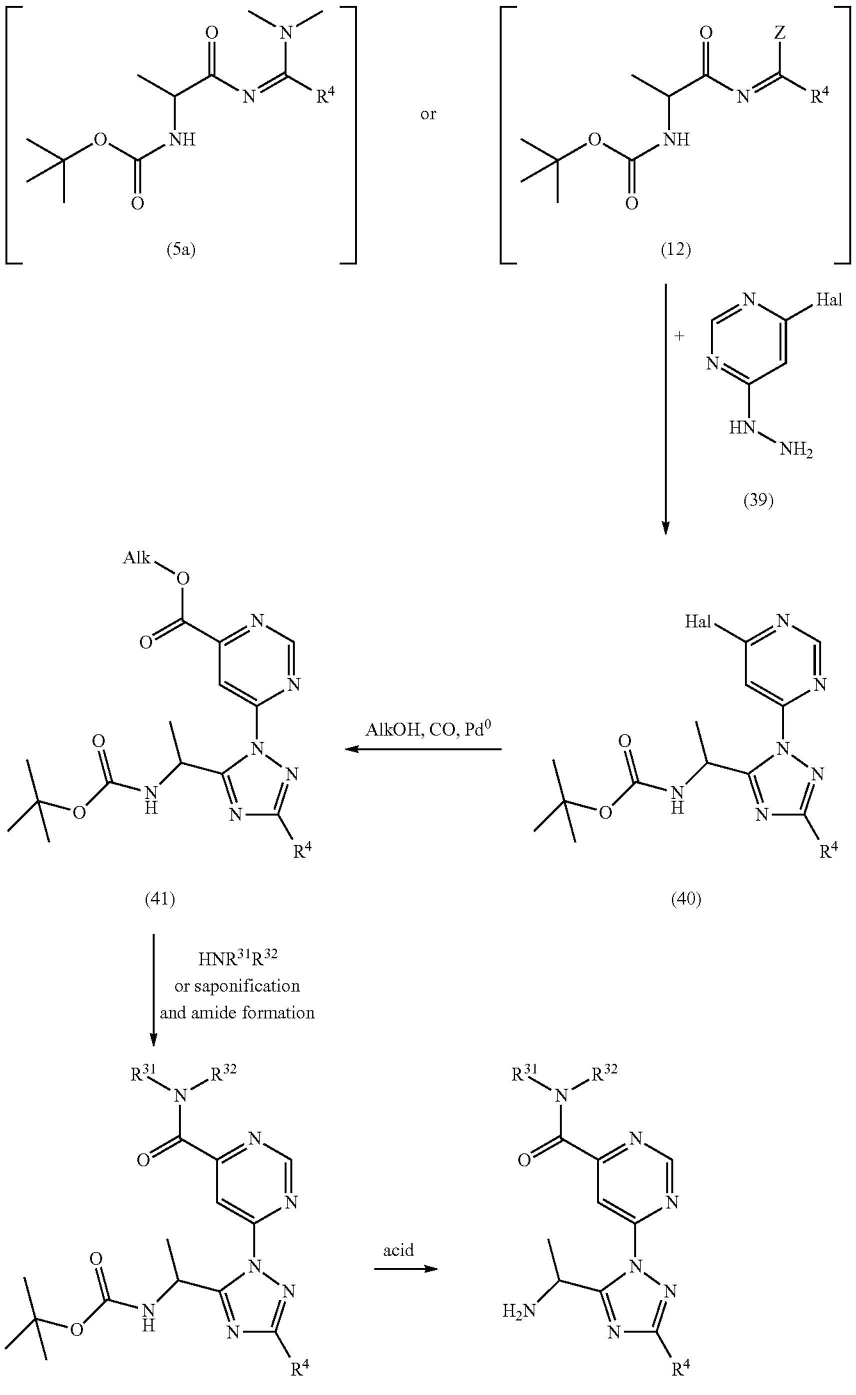

(5a) (12) (39) (41) (40) (42) (1b)

Compounds of formula (53) may be prepared as illustrated in the following scheme 13. $R^{22}$ is as previously described.

Scheme 13

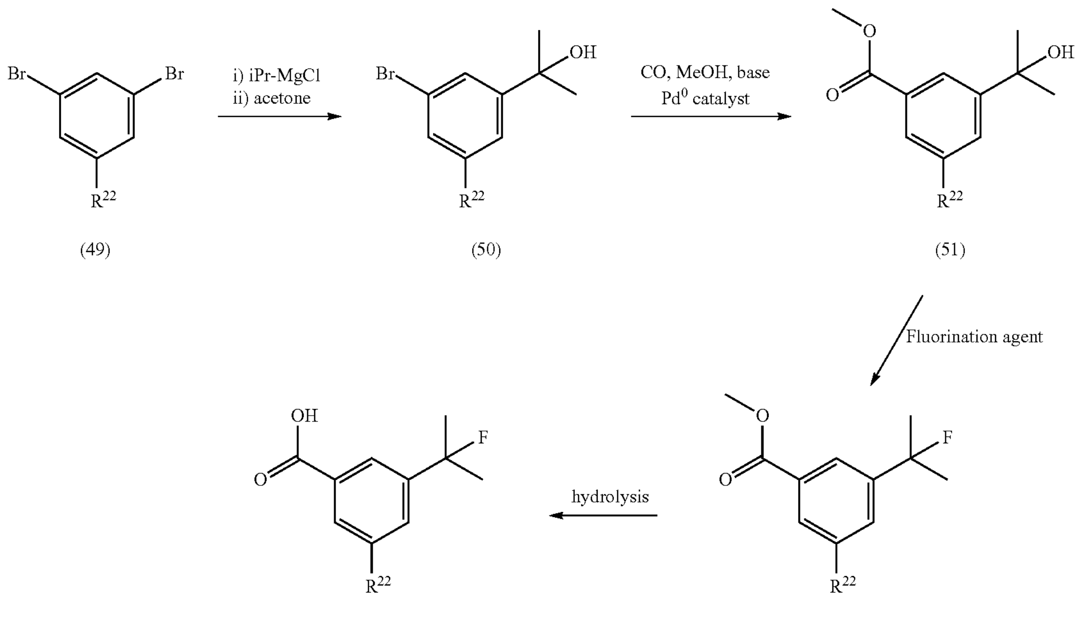

(49) (50) (51) (52) (53)

Aryl bromides of formula (49) are easily converted into 1-hydroxy-1-methyl-ethyl aryl compounds of formula (50) with Grignard reagents like isopropyl magnesium chloride and acetone as electrophile, likewise described in WO 2017/055859. The resulting compounds (50) may be carbonylated and subsequently fluorinated (fluorination: see for example Journal of Medicinal Chemistry (2019), 62(9), 4350-4369) and hydrolyzed by methods known to the skilled artisan to obtain benzoic acids of formula (52).

Compounds of formula (59) may be prepared as illustrated in the following scheme 14. $R_f$ is $C_1$-$C_3$haloalkyl, LG describes a leaving group, for example chlorine, bromine, iodine or methyl sulfonate.

Scheme 14

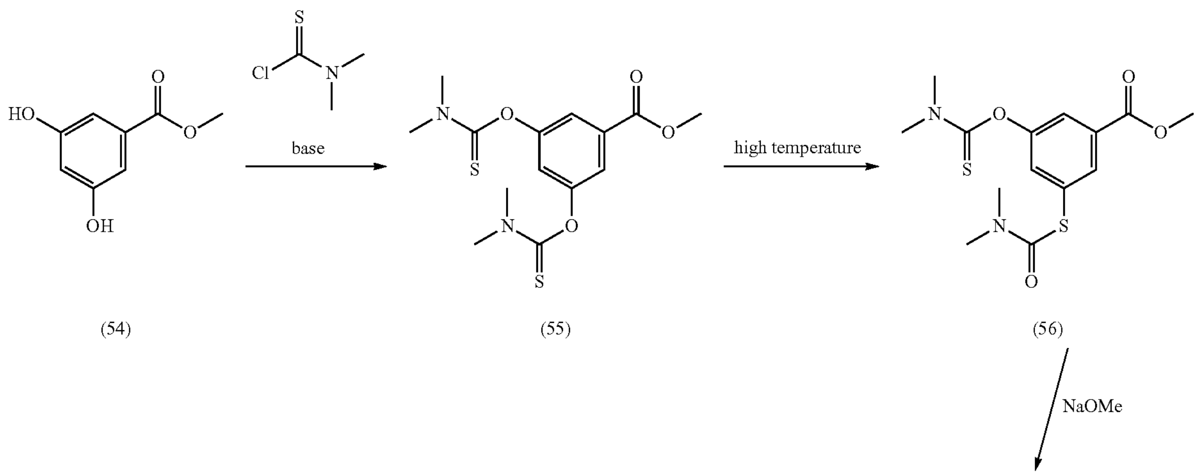

(54) (55) (56)

-continued

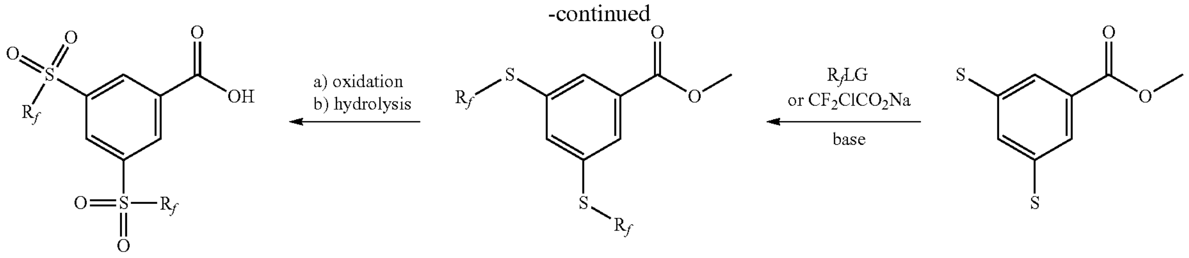

(59) (58) (57)

Methyl 3,5-dimercaptobenzoate (57) can readily be prepared according to known procedures described in US 20020072583. Haloalkylation with $R_fLG$ is described for example in WO 2004/007444 or with $CF_2ClCO_2Na$ described in WO 2020/002563. The resulting thioether compounds (58) may be oxidized and subsequently hydrolyzed by methods known to the skilled artisan to obtain benzoic acids of formula (59).

PREPARATION OF EXAMPLES

Synthesis of 3-bromo-N-{(1S)-1-[1-(6-cyanopyrimidin-4-yl)-1H-1,2,4-triazol-5-yl]ethyl}-5-(trifluoromethoxy)benzamide (example I-1)

Step 1: 2 N-[(2S)-1-amino-1-oxopropan-2-yl]-3-bromo-5-(trifluoromethoxy)benzamide

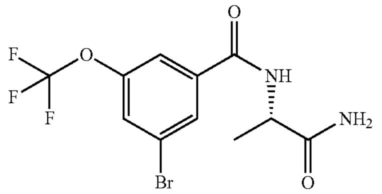 [SMILES: C[C@H](NC(=O)c1cc(Br)cc(OC(F)(F)F)c1)C(N)=O]

1.75 g (14.0 mmol) L-alaninamide-hydrochloride, 1.0 g (3.5 mmol) 3-bromo-5-(trifluoromethoxy)benzoic acid and 3.1 mL triethylamine were stirred in 10 mL DMF at ice-water cooling. To the mixture were added 3.1 ml (5.3 mmol) of T3P (cyclic propanphosphonic acid anhydride) 50% in EtOAc. The mixture was stirred overnight at room temperature. Water was added to the reaction mixture upon which a white precipitate formed. The precipitate was separated by filtration and dissolved in ethyl acetate. The solution was washed consecutively with dilute hydrochloric acid (10%), water, saturated aq. $NaHCO_3$ solution and brine. Evaporation of the solvent provided 1.13 g N-[(2S)-1-amino-1-oxopropan-2-yl]-3-bromo-5-(trifluoromethoxy)benzamide.

ESI mass [m/z]: 355.0 $[M+H]^+$

Step 2: 3-bromo-N-{(1S)-1-[1-(6-cyanopyrimidin-4-yl)-1H-1,2,4-triazol-5-yl]ethyl}-5-(trifluoromethoxy)benzamide (example I-1)

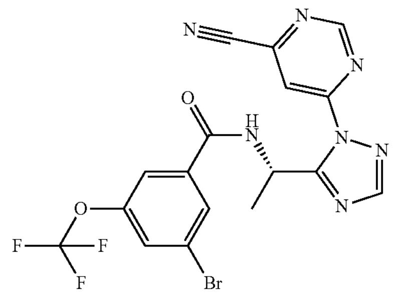 [SMILES: C[C@H](NC(=O)c1cc(Br)cc(OC(F)(F)F)c1)c1ncnn1-c1cc(C#N)ncn1]

To a solution of 160 mg (0.45 mmol) N-[(2S)-1-amino-1-oxopropan-2-yl]-3-bromo-5-(trifluoromethoxy)benzamide in 3 mL $CH_2Cl_2$ were added 0.09 mL (0.67 mmol) N,N-dimethylformamide dimethylacetal. The solution was heated at reflux for 2 h after which the solvent was removed under reduced pressure. The residue was dissolved in 3 mL glacial acetic acid. 93 mg (0.54 mmol) 6-hydrazinopyrimidine-4-carbonitrile hydrochloride were added and the mixture was stirred for 2 h at 80° C. The solvent was then removed under reduced pressure and the residue was purified by reversed phase chromatography (water/acetonitrile) to provide 159 mg of 3-bromo-N-{(1S)-1-[1-(6-cyanopyrimidin-4-yl)-1H-1,2,4-triazol-5-yl]ethyl}-5-(trifluoromethoxy)benzamide.

$^1$H-NMR (400 MHz, DMSO-$d_6$): δ=9.42 (d, J=6.8 Hz, 1H), 9.38 (d, J=1.2 Hz, 1H), 8.61 (d, J=1.2 Hz, 1H), 8.36 (s, 1H), 8.14 (s, 1H), 7.90 (s, 1H), 7.80 (s, 1H), 6.22-6.13 (m, 1H), 1.63 (d, J=6.8 Hz, 3H).

ESI mass [m/z]: 484.1 $[M+H]^+$

Synthesis of N-{1-[1-(6-cyanopyrimidin-4-yl)-1H-1,2,4-triazol-5-yl]ethyl}-3-cyclopropyl-5-(trifluoromethoxy)benzamide (example I-8)

Step 1: 6-hydrazinopyrimidine-4-carbonitrile

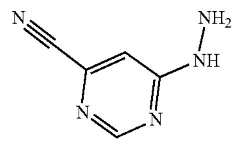

A mixture of 500 mg (3.58 mmol) 6-chloropyrimidine-4-carbonitrile and 7.2 ml (7.2 mmol) of a 1 M solution of hydrazine in THF was refluxed for 2 h and then stirred overnight at room temperature. After cooling to room temperature, the mixture was evaporated and the residue was suspended in 15 ml of hot water. After cooling to room temperature the resulting precipitate was separated by filtration, washed with water, dissolved in acetonitrile and dried under vacuo to yield 159 mg 6-hydrazinopyrimidine-4-carbonitrile hydrochloride. The mother liquor obtained from the filtration step was then basified using an aqueous solution of $NaHCO_3$. This led to the incomplete dissolution of some solid precipitate which had formed after filtration. The complete suspension was transferred to a separatory funnel and extracted three times with ethyl acetate. The combined organic layers were washed with brine, dried using $Na_2SO_4$ and filtered. Evaporation of the solvent under reduced pressure led to the isolation of 120 mg 6-hydrazino-pyrimidine-4-carbonitrile. The obtained 6-hydrazinopyrimidine-4-carbonitrile hydrochloride and 6-hydrazinopyrimidine-4-carbonitrile were combined and used in the next step without further purification.

ESI mass [m/z]: 136.1 $[M+H]^+$

Step 2: tert-butyl {1-[1-(6-cyanopyrimidin-4-yl)-1H-1,2,4-triazol-5-yl]ethyl}carbamate

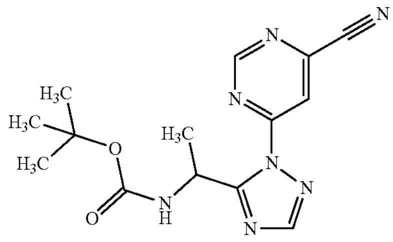 [SMILES: CC(NC(=O)OC(C)(C)C)c1ncnn1-c1cc(C#N)ncn1]

To a solution of 0.26 g (1.35 mmol) $N^2$-(tert-butoxycarbonyl)-alaninamide in 10 mL $CH_2Cl_2$ were added 0.27 mL (2.0 mmol) N,N-dimethylformamide dimethylacetal. The solution was heated at reflux for 2 h after which the solvent was removed under reduced pressure. The residue was dissolved in a mixture of 3 mL glacial acetic acid and 3 ml 1,4-dioxane. 0.27 g of the mixture of 6-hydrazinopyrimidine-4-carbonitrile and 6-hydrazinopyrimidine-4-carbonitrile hydrochloride obtained in the first step were added as a solution in a mixture of 2 ml glacial acetic acid and 2 mL 1,4-dioxane. The mixture was stirred for 72 h at room temperature. The solvent was then removed under reduced pressure and the residue was purified by chromatography on silica (ethyl acetate/cyclohexane) to provide 201 mg of tert-butyl {1-[1-(6-cyanopyrimidin-4-yl)-1H-1,2,4-triazol-5-yl]ethyl}carbamate.

$^1$H-NMR (400 MHz, DMSO-$d_6$): δ=9.38 (s, 1H), 8.58 (s, 1H), 8.33 (s, 1H), 7.61 (d, J=7.6 Hz, 1H), 5.78-5.68 (m, 1H), 1.44 (d, J=7.6 Hz, 3H), 1.33 (s, 9H).

ESI mass [m/z]: 316.1 $[M+H]^+$

Step 3: 6-[5-(1-aminoethyl)-1H-1,2,4-triazol-1-yl]pyrimidine-4-carbonitrile hydrochloride

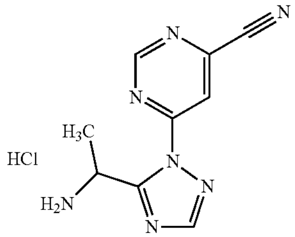 [SMILES: Cl ; CC(N)c1ncnn1-c1cc(C#N)ncn1]

To a solution of 100 mg (0.31 mmol) tert-butyl {1-[1-(6-cyanopyrimidin-4-yl)-1H-1,2,4-triazol-5-yl]ethyl}carbamate in 3 ml 1,4-dioxane was added 0.79 ml (3.2 mmol) of a 4 M solution of HCl in 1,4-dioxane and the mixture was stirred at room temperature overnight. Then further 0.50 ml (2.0 mmol) of a 4 M solution of HCl in 1,4-dioxane was added and the mixture stirred at room temperature overnight. The reaction mixture was evaporated to give the title compound (100 mg, 80% purity) which was used in the next step without further purification.

$^1$H-NMR (400 MHz, DMSO-$d_6$): δ=9.42 (d, J=1.2 Hz, 1H), 8.74 (brs, 3H), 8.67 (d, J=1.2 Hz, 1H), 8.56 (s, 1H), 5.50-5.40 (m, 1H), 1.64 (d, J=6.8 Hz, 3H).

ESI mass [m/z]: 216.1 $[amine+H]^+$

Step 4: N-{1-[1-(6-cyanopyrimidin-4-yl)-1H-1,2,4-triazol-5-yl]ethyl}-3-cyclopropyl-5-(trifluoromethoxy)benzamide (example I-8)

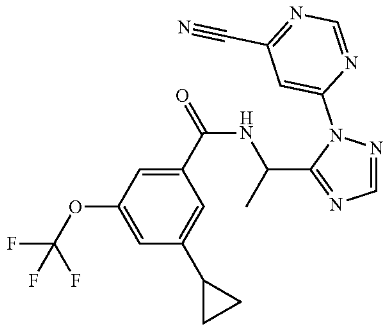 [SMILES: CC(NC(=O)c1cc(OC(F)(F)F)cc(C2CC2)c1)c1ncnn1-c1cc(C#N)ncn1]

To a solution of 67 mg (64% purity, 0.18 mmol) 3-cyclopropyl-5-(trifluoromethoxy)benzoic acid in 2 mL N,N-dimethylformamide (DMF) were added 0.1 mL (0.6 mmol) N,N-diisopropylethylamine (Hünig's Base) and 121 mg (318 μmol) [O-(7-azabenzotriazol-1-yl)-N,N,N,N'-tetramethyluronium-hexafluorophosphate] (HATU). The mixture was stirred for 1 h at room temperature. Then 50 mg (80% purity, 0.15 mmol) 6-[5-(1-aminoethyl)-1H-1,2,4-triazol-1-yl]pyrimidine-4-carbonitrile hydrochloride were added and the reaction mixture was stirred at room temperature for three days. The reaction mixture was then directly purified by reversed phase chromatography (water/acetonitrile) to afford 31 mg of the title compound.

ESI mass [m/z]: 444.1 $[M+H]^+$ $^1$H-NMR (400 MHz, DMSO-$d_6$): δ=9.38 (d, J=0.8 Hz, 1H), 9.24 (d, J=6.8 Hz, 1H), 8.61 (d, J=0.8 Hz, 1H), 8.35 (s, 1H), 7.54 (s, 1H), 7.52 (s, 1H), 7.28 (s, 1H), 6.22-6.12 (m, 1H), 2.10-2.00 (m, 1H), 1.63 (d, J=7.2 Hz, 3H), 1.07-1.00 (m, 2H), 0.81-0.75 (m, 2H).

Synthesis of methyl 3-bromo-5-(difluoromethoxy)benzoate

Step 1: methyl 3-bromo-5-hydroxybenzoate

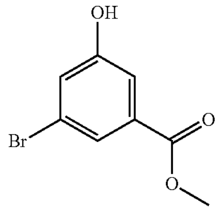

A solution of 3-bromo-5-hydroxybenzoic acid (49.9 g, 230 mmol) in MeOH (325 mL) was cooled by an ice bath to 7-8° C. Then $SOCl_2$ (27.4 g, 16.79 mL, 230 mmol) was added dropwise to this solution over 25 min. The reaction mixture was warmed to room temperature, stirred under reflux for 3 h, cooled down to room temperature and then stirred for another 48 h at this temperature. All volatiles were removed in vacuo and the residue dissolved in ethyl acetate (400 mL). The solution was washed with $NaHCO_3$, brine, dried over $Na_2SO_4$ and the volatiles were removed under reduced pressure. The residue was triturated with hexanes (400 mL). The precipitate was filtered off, washed with hexanes/diethyl ether (1:1), dried at 110° C. to afford methyl 3-bromo-5-hydroxybenzoate (50.5 g) as a dark yellow powder.

$^1H$ NMR (400 MHz, $CDCl_3$) δ=7.73 (m, 1H), 7.51 (m, 1H), 7.26 (s, 1H), 7.23 (t, J=2.1 Hz, 1H), 6.05 (br s, 1H), 3.92 (s, 3H). Recorded on a Varian Gemini 2000 machine.

Step 2: methyl 3-bromo-5-(difluoromethoxy)benzoate

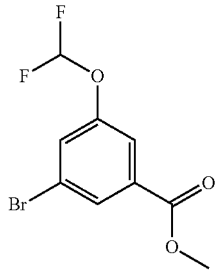

A mixture of methyl 3-bromo-5-hydroxybenzoate (23.1 g, 100 mmol), $K_2CO_3$ (41.5 g, 300 mmol) and $ClF_2CCOONa$ (45.7 g, 300 mmol) in DMF (350 mL) was stirred at 60-65° C. for 2 hrs. The precipitate was then separated, washed with acetone and the filtrate was evaporated under reduced pressure. The residue was dissolved in diethyl ether (300 mL) and the solution was left to stand at r.t. for 12 hrs. A precipitate formed which was filtered off and washed with water. The filtrate was washed with brine (300 mL) and the organic layer was evaporated under reduced pressured. The oily residue was dissolved in hexanes (250 mL) and kept at r.t. for 2 hrs. A precipitate formed which was removed by filtration and the filtrate was evaporated under reduced pressure. The residue was distilled under reduced pressure (3 torr) and the fraction with a boiling point between 80 and 85° C. was collected to afford 15.75 g methyl 3-bromo-5-(difluoromethoxy)benzoate.

$^1H$ NMR (400 MHz, $CDCl_3$) δ=8.03 (t, J=1.6 Hz, 1H), 7.75-7.70 (m, 1H), 7.49 (t, J=2.1 Hz, 1H), 6.55 (t, J=72.6 Hz, 1H), 3.93 (s, 3H). Recorded on a Varian Gemini 2000 machine.

$^{19}F$ NMR (376 MHz, $CDCl_3$) δ=−84.89 (d, J=72.7 Hz). (recorded on a Varian Gemini 2000 machine)

Synthesis of 3-methylsulfonyl-5-(trifluromethoxy)benzoic acid

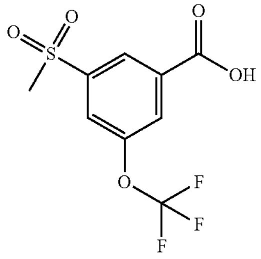 [SMILES: CS(=O)(=O)c1cc(OC(F)(F)F)cc(C(=O)O)c1]

A mixture of 2.95 g (17.5 mmol) trans-N,N-dimethylcyclohexane-1-2-diamine and 11.4 g (35 mmol) cesium carbonate in 60 mL DMF was degassed for 30 min by purging with argon. 5 g (17.5 mmol) 3-bromo-5-(trifluoromethoxy) benzoic acid, 3.58 g (35 mmol) sodium methanesulfinate and 3.34 g (17.5 mmol) copper(I) iodide were added and the mixture further purged with argon for 5 min. The mixture was stirred at 120° C. over night, cooled to room temperature and then three times extracted with dichloromethane. The aqueous layer was acidified to pH 2 using concentrated hydrochloric acid and again extracted with dichloromethane. The dichlormethane phase was washed with brine several times. The layers were separated, and the combined organic layers were dried over anhydrous $Na_2SO_4$ and filtered. The solvent was removed under reduced pressure and the residue triturated with n-pentane, filtered-off and dried to provide 3.2 g of 3-methylsulfonyl-5-(trifluromethoxy)benzoic acid.

$^1H$ NMR (DMSO-$d_6$, 400 MHz): δ=14.00 (br s, 1H, COOH), 8.42 (s, 1H), 8.20 (s, 1H), 8.14 (s, 1H), 3.39 (s, 3H).

ESI mass [m/z]: 285.0 $[M+H]^+$

In a similar way, following intermediates have been prepared:

3-(cyclopropylsulfonyl)-5-(trifluoromethoxy)benzoic acid

ESI mass [m/z]: 311.0 $[M+H]^+$ 3-chloro-5-(4-chlorophenyl)sulfonyl-benzoic acid ESI mass [m/z]: 331.0 $[M+H]^+$

Synthesis of 3-(difluoromethoxy)-5-methylsulfonyl-benzoic acid

Step 1: methyl 3-(trifluoromethoxy)-5-triisopropylsilylsulfanyl-benzoate

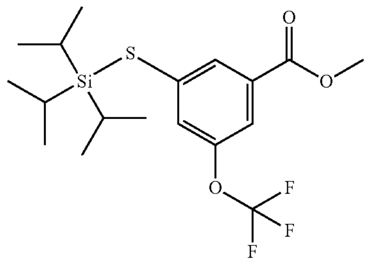 [SMILES: COC(=O)c1cc(OC(F)(F)F)cc(S[Si](C(C)C)(C(C)C)C(C)C)c1]

To a stirred solution of triisopropylsilanethiol (21.45 g, 112 mmol) in toluene (500 mL), under a stream of argon, NaH (5.03 g, 122 mmol, 60% disperse in oil) was added in portions. The mixture was stirred until no more gas evolved. Then methyl 3-bromo-5-(trifluoromethoxy)benzoate (CAS: 1306763-53-0) (30 g, 100 mmol), XantPhos (6.13 g, 11.2 mmol) and $Pd_2(dba)_3$ (4.85 g, 5.3 mmol) were added to the reaction mixture sequentially. The mixture was stirred at 100° C. overnight, cooled to r.t., diluted with EtOAc (500 mL) and filtered through a thin pad of silica gel. After evaporation, crude methyl 3-(trifluoromethoxy)-5-triisopropylsilylsulfanyl-benzoate (50 g, 50% purity by LC/MS, 64 mmol, 57% yield) was obtained and used in the next step without further purification.

Step 2: methyl 3-(difluoromethylsulfanyl)-5-(trifluoromethoxy)benzoate

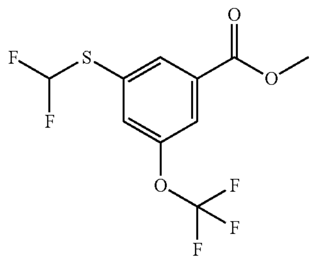 [SMILES: COC(=O)c1cc(OC(F)(F)F)cc(SC(F)F)c1]

To a stirred solution of crude methyl 3-(trifluoromethoxy)-5-triisopropylsilylsulfanyl-benzoate (50 g, 50% purity by LC/MS, 64 mmol) in DMF (1000 mL) sodium 2-chloro-2,2-difluoroacetate (29.27 g, 192 mmol) and cesium carbonate (62.55 g, 192 mmol) were added under a stream of argon. The mixture was stirred at 100° C. overnight, cooled to r.t., and evaporated under reduced pressure. The residue was dissolved in water (1000 mL) and extracted with EtOAc (5×250 mL). Methyl 3-(difluoromethylsulfanyl)-5-(trifluoromethoxy)benzoate (10.5 g, 34.7 mmol, 54.3% yield) was obtained after column chromatography.

Step 3: methyl 3-(difluoromethylsulfonyl)-5-(trifluoromethoxy)benzoate

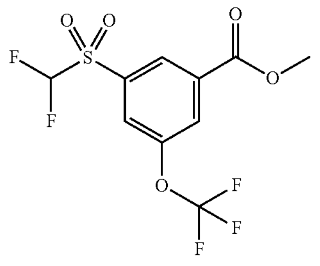 [SMILES: COC(=O)c1cc(OC(F)(F)F)cc(S(=O)(=O)C(F)F)c1]

To a solution of methyl 3-(difluoromethylsulfanyl)-5-(trifluoromethoxy)benzoate (10.5 g, 34.7 mmol) in dichloromethane (200 mL) mCPBA (16.35 g, 93.9 mmol, 75% purity) was added in portions at 0° C. under a stream of argon. The mixture was stirred overnight at room temperature and evaporated under reduced pressure. Methyl 3-(difluoromethylsulfonyl)-5-(trifluoromethoxy)benzoate (6.8 g, 20.34 mmol, 58.63%) was obtained after column chromatography on silica gel.

Step 4: 3-(difluoromethylsulfonyl)-5-(triflurómethoxy)benzoic acid

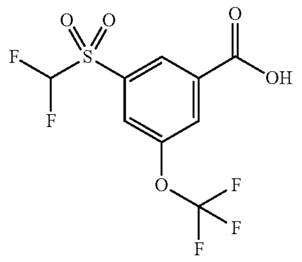 [SMILES: O=C(O)c1cc(OC(F)(F)F)cc(S(=O)(=O)C(F)F)c1]

To a stirred solution of methyl 3-(difluoromethylsulfonyl)-5-(trifluoromethoxy)benzoate (6.8 g, 20.34 mmol) in THF (80 mL)/water (20 mL) mixture at 0° C. LiOH monohydrate (1.146 g, 27.459 mmol) was added and the mixture was stirred overnight at r.t. THF was evaporated under reduced pressure, the water phase was acidified to pH=3 and extracted with MTBE (5×10 mL). Pure 3-(difluoromethylsulfonyl)-5-(trifluromethoxy)benzoic acid (3 g, 9.37 mmol, 34.12% yield) was obtained after recrystallization from 30% aqueous EtOH as white solid.

$^1H$ NMR (DMSO-$d_6$, 400 MHz): δ=7.47 (t, 1H), 8.21 (s, 1H), 8.32 (s, 1H), 8.40 (s, 1H), 13.79 (s, 1H).

ESI mass [m/z]: 319.0 $[M+H]^+$

Synthesis of 2-chloro-6-(1-cyanocyclopropyl)-N-[(1S)-1-[2-(6-cyanopyrimidin-4-yl)-1,2,4-triazol-3-yl]ethyl]pyridine-4-carboxamide (I-35)

Step 1: 2-chloro-6-(cyanomethyl)pyridine-4-carboxylic acid

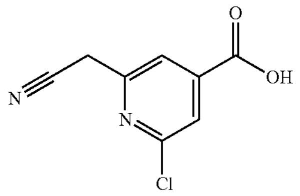 [SMILES: N#CCc1cc(C(=O)O)cc(Cl)n1]

n-BuLi (91.14 ml, 2M, 183.3 mmol)) was diluted in anhydrous THF (150 ml) and cooled to −78° C. under argon. A solution of anhydrous acetonitrile (11.4 ml, 218.8 mmol) in anhydrous THF (30 mL) was added dropwise and the reaction mixture was maintained at −78° C. for 30 min. A solution of 2,6-dichloropyridine-4-carboxylic acid (7 g, 36.5 mmol) in THF (200 ml) was added dropwise over one hour and the reaction mixture was stirred at −78° C. for further 45 min and then 1 h at room temperature. Then the reaction mixture was quenched with saturated aqueous citric acid solution (200 mL) and extracted with EtOAc (3×250 mL). The organic layer was washed with water (3×300 mL) followed by brine solution (200 mL) and dried over anhydrous $Na_2SO_4$, solvents were removed under reduced pressure. The residue was purified by flash silica gel chromatography using a gradient of 0% to 10% acetone in DCM. The obtained solid was triturated with 50% diethyl ether in n-pentane to obtained 4.2 g (58% yield) of 2-chloro-6-(cyanomethyl)pyridine-4-carboxylic acid as an off-white solid.

$^1$H NMR (400 MHz, D6-DMSO): δ=7.87 (s, 1H), 7.82 (s, 1H), 4.27 (s, 2H). COOH not detected.

ESI mass [m/z]: 195.0 $[M-H]^-$

Step 2: 2-chloro-6-(1-cyanocyclopropyl)pyridine-4-carboxylic acid (INT-12)

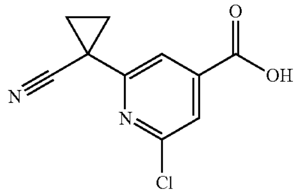 [SMILES: N#CC1(c2cc(C(=O)O)cc(Cl)n2)CC1]

To a stirred solution of 2-chloro-6-(cyanomethyl)pyridine-4-carboxylic acid (3.5 g, 17.8 mmol) in acetonitrile (50 ml) under nitrogen, tetrabutylammonium bromide (5.74 g, 17.8 mmol) was added. Then 1,2-dibromoethane (3.68 g, 19.6 mmol) was added dropwise at room temperature, then the reaction mixture was stirred at room temperature for further 30 min. The reaction mixture was cooled to 0° C. 7.5 mL of an aqueous NaOH solution (50%) was slowly added dropwise over 20 min. Then the reaction mixture was allowed to warm to room temperature and stirred for further 24 hrs. The reaction mixture was concentrated under vacuum at room temperature. The remaining residue was diluted with water and acidified with citric acid (pH~5) and extracted with EtOAc (3×150 mL). The combined organic layers were washed with water (3×100 mL) and sodium thiosulfate solution (100 mL) followed by brine solution (150 mL). The organic layer was dried over anhydrous $Na_2SO_4$, then solvents were removed under reduced pressure. The crude material was purified by flash silica gel chromatography using a gradient of 0% to 10% acetone in DCM. The resulting solid was washed with n-pentane to obtain 2 g (50% yield) of the 2-chloro-6-(1-cyanocyclopropyl)pyridine-4-carboxylic acid (INT-12) as off-white solid..

$^1$H NMR (400 MHz, DMSO-$d_6$): δ=14.20 (bs, 1H, COOH), 7.89 (s, 1H), 7.53 (s, 1H), 1.94-1.91 m, 2H), 1.76-1.73 (m, 2H).

ESI mass [m/z]: 221.0 $[M-H]^-$

Step 3: tert-butyl N-[(1S)-2-[(E)-dimethylaminomethyleneamino]-1-methyl-2-oxo-ethyl]carbamate

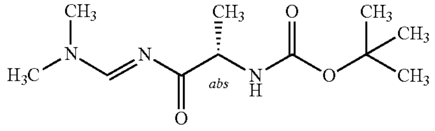 [SMILES: C[C@H](NC(=O)OC(C)(C)C)C(=O)/N=C/N(C)C]

tert-Butyl N-[(1S)-2-amino-1-methyl-2-oxo-ethyl]carbamate (40.0 g, 213 mmol) was dissolved in DCM (400 mL). Dimethylformamide dimethylacetal (38.0 g, 319 mmol, 42.4 mL) was added into the mixture. The reaction mixture was stirred at 40° C. for 2 hrs. The reaction mixture was concentrated under reduced pressure. tert-Butyl N-[(1S)-2-[(E)-dimethylaminomethyleneamino]-1-methyl-2-oxo-ethyl]carbamate (50.0 g, crude) was obtained as a colorless oil and used as crude material in the next step.

Step 4: tert-butyl N-[(1S)-1-[2-(6-cyanopyrimidin-4-yl)-1,2,4-triazol-3-yl]ethyl]carbamate (INT-3)

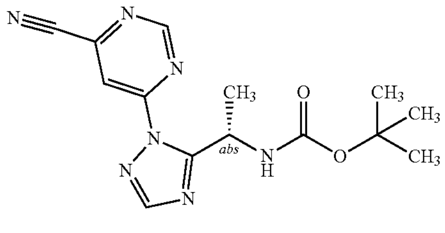 [SMILES: C[C@H](NC(=O)OC(C)(C)C)c1ncnn1-c1cc(C#N)ncn1]

tert-Butyl N-[(1S)-2-[(E)-dimethylaminomethyleneamino]-1-methyl-2-oxo-ethyl]carbamate (36.1 g, 267 mmol) was dissolved in dioxane (400 mL). 6-Hydrazinopyrimidine-4-carbonitrile (50.0 g, 206 mmol) was dissolved in AcOH (400 mL) and added into the mixture. The reaction mixture was stirred at 20° C. for 16 hrs. The reaction mixture was concentrated under vacuum. The residue was purified by column chromatography ($SiO_2$, petroleum ether/EtOAc=50/1 to 0/1). The crude product was triturated with MTBE (750 mL) at 20° C. for 30 min. tert-Butyl-N-[(1S)-1-[2-(6-cyanopyrimidin-4-yl)-1,2,4-triazol-3-yl]ethyl]carbamate (INT-3) (8.50 g, 27.0 mmol, 13.1% yield) was obtained as a white solid.

The enantiomeric excess of INT-3 has been determined via screen OD_RH (acid): ee-value=95%; $R_t$=9.49 min. Method: chiral HPLC; Chiralcel OD-RH column (4.6 mm×150 mm×5 μm), room temperature, eluting with 0.1% phosphoric acid (A) and acetonitrile (B), gradient A:B 95/5 to 10/90, detecting at X═210 nm.

$^1$H NMR (400 MHz, CDCl3): δ=1.43 (s, 9H), 1.58 (d, J=6.8 Hz, 3H), 5.45-5.58 (m, 1H), 5.97-6.10 (m, 1H), 8.02 (s, 1H), 8.32 (d, J=0.8 Hz, 1H), 9.24 (d, J=1.2 Hz, 1H). Measured with Bruker AVANCE III 400 MHz.

ESI mass [m/z]: 260.1 $[M-C_4H_8+H]^+$

Step 5: 6-[5-[(1S)-1-aminoethyl]-1,2,4-triazol-1-yl]pyrimidine-4-carbonitrile; 2,2,2-trifluoroacetic acid (INT-4)

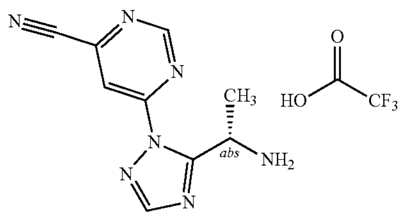 [SMILES: C[C@H](N)c1ncnn1-c1cc(C#N)ncn1 ; O=C(O)C(F)(F)F]

tert-Butyl-N-[(1S)-1-[2-(6-cyanopyrimidin-4-yl)-1,2,4-triazol-3-yl]ethyl]carbamate (2 g, 6.34 mmol) was dissolved in 20 mL dichloromethane. Trifluoroacetic acid (3.62 g, 31.7 mmol) was added slowly, then the reaction mixture was stirred at r.t. over night, followed by heating to 40° C. for 3 hrs to complete the reaction. The reaction mixture was evaporated under reduced pressure and used as crude material in the next step.

ESI mass [m/z]: 216.1 $[amine+H]^+$

Step 5: 2-chloro-6-(1-cyanocyclopropyl)-N-[(1S)-1-[2-(6-cyanopyrimidin-4-yl)-1,2,4-triazol-3-yl]ethyl]pyridine-4-carboxamide (I-35)

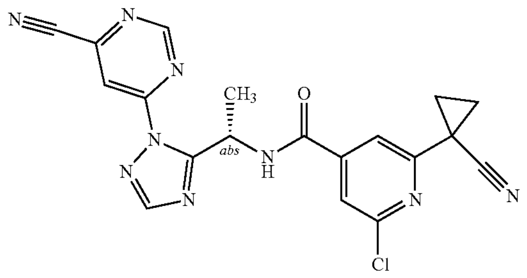 [SMILES: C[C@H](NC(=O)c1cc(Cl)nc(C2(C#N)CC2)c1)c1ncnn1-c1cc(C#N)ncn1]

2-Chloro-6-(1-cyanocyclopropyl)pyridine-4-carboxylic acid (88 mg, 0.39 mmol) was dissolved in 10 mL dichloromethane, 2 drops of DMF were added followed by oxalyl chloride (114 mg, 0.9 mmol). The reaction mixture was stirred until the gas evolution has ceased. Then the reaction mixture was evaporated under reduced pressure and dissolved in acetonitrile. This solution was slowly added dropwise to another acetonitrile solution prepared as mixture of 6-[5-[(1S)-1-aminoethyl]-1,2,4-triazol-1-yl]pyrimidine-4-carbonitrile (2,2,2-trifluoroacetic acid salt) (197 mg 60% purity, 0.36 mmol) and DIPEA (140 mg, 1.08 mmol) at r.t. The reaction mixture was stirred over night at r.t., then diluted with water and dichloromethane, the organic layer was separated and evaporated under reduced pressure. The remaining residue was purified by HPLC means to obtain the title compound as off-white solid (86 mg, 56% yield).

$^1$H NMR see peak list in table 1.

ESI mass [m/z]: 420.3 $[M+H]^+$

Synthesis of 3-bromo-N-[(1S)-1-[2-(6-cyanopyrimidin-4-yl)-5-cyclopropyl-1,2,4-triazol-3-yl]ethyl]-5-(trifluoromethoxy)benzamide (I-15) and 6-[5-[(1S)-1-[[3-bromo-5-(trifluoromethoxy)benzoyl]amino]ethyl]-3-cyclopropyl-1,2,4-triazol-1-yl]pyrimidine-4-carboxamide (I-13)

Step 1: ethyl cyclopropanecarboximidate hydrochloride

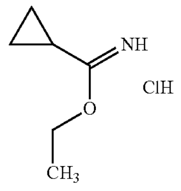

Cyclopropanecarbonitrile (10.0 g, 149 mmol, 11.0 mL) was dissolved in HCl/dioxane (70.0 mL). EtOH (6.87 g, 149 mmol, 8.71 mL) was added slowly dropwise at 0° C. The mixture was stirred at 25° C. for 16 hrs. The reaction mixture was concentrated under reduced pressure to remove HCl/dioxane. The crude product was triturated with MTBE at 25° C. for 30 min followed by filtration. The filter cake was dried under reduce pressure with rotary evaporator. The crude product (21.0 g, 140 mmol, 94.2% yield, HCl salt) was obtained as a white solid and was used in the next step without further purification.

Step 2: ethyl (Z)-N-[(2S)-2-(tert-butoxycarbonylamino)propanoyl]cyclopropanecarboximidate

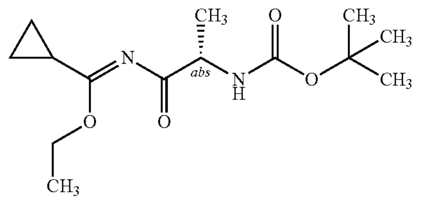 [SMILES: CCO/C(=N\C(=O)[C@H](C)NC(=O)OC(C)(C)C)C1CC1]

tert-Butyl N-[(1S)-2-amino-1-methyl-2-oxo-ethyl]carbamate (15.1 g, 79.7 mmol) was dissolved in THF (180 mL. Ethyl cyclopropanecarboximidate hydrochloride (17.8 g, 119 mmol), DIPEA (46.1 g, 357 mmol, 62.1 mL) and finally HATU (49.7 g, 131 mmol) were added. The mixture was stirred at 25° C. for 3 hrs. Ethyl (Z)-N-[(2S)-2-(tert-butoxycarbonylamino)propanoyl]cyclopropanecarboximidate (22.5 g, crude) in THF was obtained as a yellow liquid and used in the next step as solution without further work-up and purification.

Step 3: tert-butyl N-[(1S)-1-[2-(6-cyanopyrimidin-4-yl)-5-cyclopropyl-1,2,4-triazol-3-yl]ethyl]carbamate (INT-7)

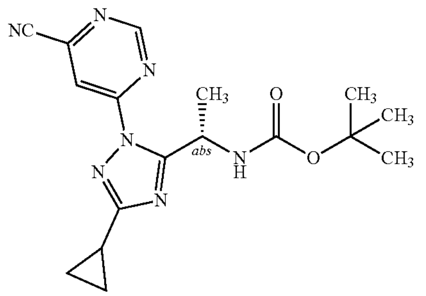 [SMILES: C[C@H](NC(=O)OC(C)(C)C)c1nc(C2CC2)nn1-c1cc(C#N)ncn1]

To the THF solution of ethyl (Z)-N-[(2S)-2-(tert-butoxycarbonylamino)propanoyl]cyclopropanecarboximidate (15.0 g, 52.8 mmol) was slowly added 6-hydrazinopyrimidine-4-carbonitrile (7.13 g, 52.8 mmol) at 0° C. The mixture was stirred at 25° C. for 16 hrs. The reaction mixture was quenched with $H_2O$ (200 mL), then extracted with ethyl acetate (3×50 mL). The combined organic layers were washed with brine (200 mL), dried with anhydrous $Na_2SO_4$, filtered and concentrated in vacuum. The obtained residue was purified by column chromatography (SiO2, petroleum ether/ethyl acetate=50/1 to 3/1) to give tert-butyl N-[(1S)-1-[2-(6-cyanopyrimidin-4-yl)-5-cyclopropyl-1,2,4-triazol-3-yl]ethyl]carbamate (INT-7, 5.60 g, 15.6 mmol, 29.6% yield, 99.1% purity) as a white solid.

The enantiomeric excess of INT-7 has been determined via screen OD_RH (acid): ee-value=92.5%; $R_t$=14.45 min. Method: chiral HPLC; Chiralcel OD-RH column (4.6 mm×150 mm×5 μm), room temperature, eluting with 0.1% phosphoric acid (A) and acetonitrile (B), gradient A:B 95/5 to 10/90, detecting at λ=210 n.

$^1H$ NMR (400 MHz, MeOD): δ=9.21 (s, 1H), 8.36 (s, 1H), 5.82 (q, J=6.8 Hz, 1H), 2.15-2.04 (m, 1H), 1.52 (d, J=6.8 Hz, 3H), 1.40 (br s, 9H), 1.09-0.98 (m, 4H). Measured with Bruker AVANCE III 400 MHz.

ESI mass [m/z]: 356.0 $[M+H]^+$

Step 4: 6-[5-[(1S)-1-aminoethyl]-3-cyclopropyl-1,2,4-triazol-1-yl]pyrimidine-4-carbonitrile hydro-chloride (INT-8) and 6-[5-[(1S)-1-aminoethyl]-3-cyclopropyl-1,2,4-triazol-1-yl]pyrimidine-4-carboxamide hydrochloride (INT-11)

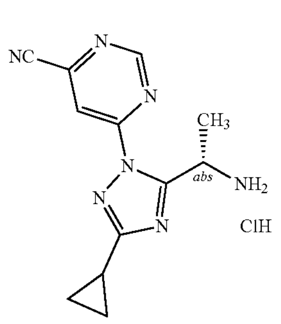

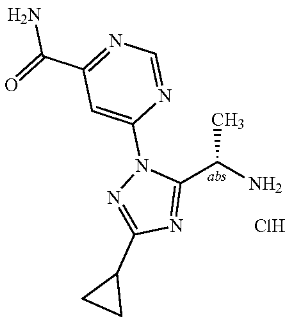

tert-Butyl N-[(1S)-1-[2-(6-cyanopyrimidin-4-yl)-5-cyclopropyl-1,2,4-triazol-3-yl]ethyl] carbamate (5.0 g, 14 mmol) was dissolved in 4M HCl/dioxane (35.0 mL) and stirred over night at r.t. HCl/dioxane was removed under reduced pressure. The remaining solid is a mixture of 6-[5-[(1S)-1-aminoethyl]-3-cyclopropyl-1,2,4-triazol-1-yl]pyrimidine-4-carbonitrile hydrochloride (1NT-8) and 6-[5-[(1S)-1-aminoethyl]-3-cyclopropyl-1,2,4-triazol-1-yl]pyrimidine-4-carboxamide hydrochloride (INT-11) and was used in the next step without further purification.

6-[5-[(1S)-1-aminoethyl]-3-cyclopropyl-1,2,4-triazol-1-yl]pyrimidine-4-carbonitrile hydrochloride (INT-8)

ESI mass [m/z]: 256.2 $[amine+H]^+$

6-[5-[(1S)-1-aminoethyl]-3-cyclopropyl-1,2,4-triazol-1-yl]pyrimidine-4-carboxamide hydrochloride (INT-11)

ESI mass [m/z]: 274.2 $[amine+H]^+$

Step 5: 3-bromo-N-[(1S)-1-[2-(6-cyanopyrimidin-4-yl)-5-cyclopropyl-1,2,4-triazol-3-yl]ethyl]-5-(trifluoromethoxy)benzamide (I-15) and 6-[5-[(1S)-1-[[3-bromo-5-(trifluoromethoxy) benzoyl]amino]ethyl]-3-cyclopropyl-1,2,4-triazol-1-yl]pyrimidine-4-carboxamide (I-13)

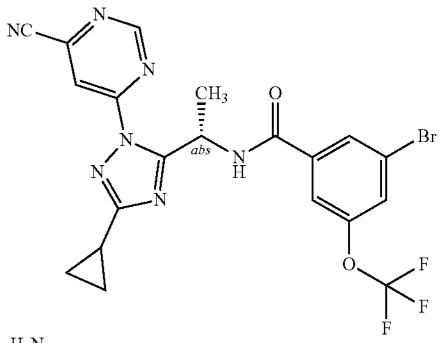

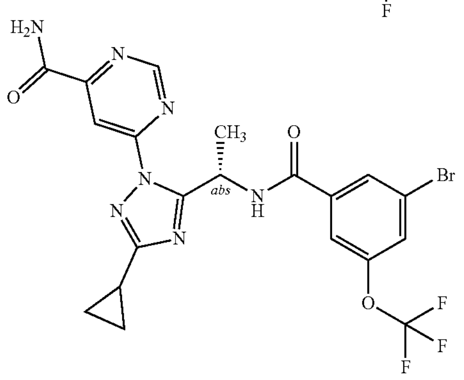

A mixture of 101 mg (0.28 mmol) 3-bromo-5-(trifluoromethoxy)benzoic acid, 245 mg (0.65 mmol) 1-[bis(dimethylamino)methylene]-1H-1,2,3-triazolo[4,5-b]pyridinium 3-oxid hexafluorophosphate (HATU), 146 mg (1.13 mmol) N,N-diisopropylethylamine and 1.3 mL DMF was stirred for 60 min at room temperature. 100 mg of the mixture from step 4 were added and the reaction mixture was stirred overnight at room temperature. The mixture was diluted with water and extracted with DCM, the DCM phase was separated, washed with brine, concentrated under reduced pressure and purified by preparative HPLC chromatography to provide 11 mg (6.5% yield) of 3-bromo-N-[(1S)-1-[2-(6-cyanopyrimidin-4-yl)-5-cyclopropyl-1,2,4-triazol-3-yl]ethyl]-5-(trifluoromethoxy)benzamide (1-15) and 94.5 mg (54.2% yield of 6-[5-[(1S)-1-[[3-bromo-5-(trifluoromethoxy)benzoyl]amino]ethyl]-3-cyclopropyl-1,2,4-triazol-1-yl]pyrimidine-4-carboxamide (1-13).

3-bromo-N-[(1S)-1-[2-(6-cyanopyrimidin-4-yl)-5-cyclopropyl-1,2,4-triazol-3-yl]ethyl]-5-(trifluoromethoxy)benzamide (I-15)

$^1$H NMR see peak list in table 1.
ESI mass [m/z]: 524.1 $[M+H]^+$

6-[5-[(1S)-1-[[3-bromo-5-(trifluoromethoxy)benzoyl]amino]ethyl]-3-cyclopropyl-1,2,4-triazol-1-yl]pyrimidine-4-carboxamide (I-13)

$^1$H NMR see peak list in table 1.
ESI mass [m/z]: 542.1 $[M+H]^+$

Synthesis of intermediate 6-hydrazinopyrimidine-4-carboxamide/(6-hydrazono-1,6-dihydropyrimidine-4-carboxamide)

Step 1: 6-chloropyrimidine-4-carbonyl chloride

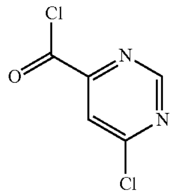

Oxalyl chloride (26.0 mL, 297.0 mmol) was added during 1 h to a heated mixture of 6-hydroxypyrimidine-4-carboxylic acid (13.86 g, 9.98 mmol) and DMF (0.13 mmol, 0.01 mL) in 80 mL ethyl acetate. Heating under reflux was continued for 3 h. The volatiles were distilled off at atmospheric pressure, then under reduced pressure. Kugelrohr distillation (diaphragm pump vacuum, 6 mbar, oven temp 110° C.) yielded 11.03 g (63% of theory).

Step 2: 6-chloropyrimidine-4-carboxamide

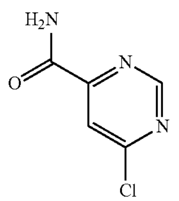

6-Chloropyrimidine-4-carbonyl chloride (11.03 g, 62.32 mmol) in THF (50 mL) was added within 10 min to aq. ammonia (33%, 20 ml, 341 mmol) in a mixture of THF/ice water (0.3 L) at ice/water cooling, then the mixture was stirred for 1 h. The mixture was acidified with aq. HCl and the organic solvent was removed under reduced pressure. The formed precipitate was filtered off, washed with water and dried to yield 7.6 g (76% of theory, corrected by purity).

ESI mass [m/z]: 158.1 $[M+H]^+$ $^1$H NMR (400 MHz, $D_6$-DMSO): δ=8.1 (m, 2H), 8.45 (br, 1H), 9.2 (s, 1H).

Step 3: 6-hydrazinopyrimidine-4-carboxamide/(6-hydrazono-1,6-dihydropyrimidine-4-carboxamide)

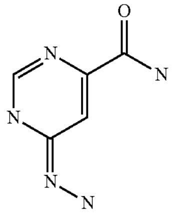 [SMILES: N/N=c1\cc(C(N)=O)nc[nH]1]

6-Chloropyrimidine-4-carboxamide (7.06 g, 48.24 mmol) and hydrazine hydrate (64%, 10.32 g, 206.1 mmol, 10.0 mL) in MeOH (250 mL) were stirred for 4 h at 65° C. Water was added and the MeOH was evaporated under reduced pressure. Aq. HCl and aq. $K_2CO_3$ were added until pH 8. The formed precipitate was filtered off, washed with water and dried to yield 7.03 g (95% of theory, corrected by purity).

ESI mass [m/z]: 154.1 $[M+H]^+$ $^1$H NMR (400 MHz, $D_6$-DMSO): δ=4.5 (br, 2H), 7.3 (br, 1H), 7.7 (br, 1H), 8.0 (br, 1H), 8.4 (br, 1H), 8.7 (br, 1H).

Synthesis of 6-[5-[(1S)-1-[(3,5-dibromobenzoyl)amino]ethyl]-1,2,4-triazol-1-yl]pyrimidine-4-carboxamide (I-34)

Step 1: 3,5-dibromo-N-[(1S)-2-[(E)-dimethylaminomethyleneamino]-1-methyl-2-oxo-ethyl]benzamide

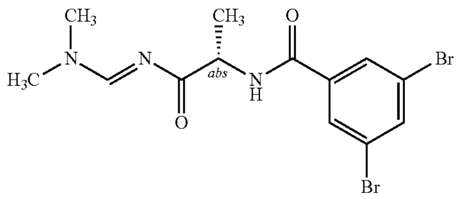 [SMILES: C[C@H](NC(=O)c1cc(Br)cc(Br)c1)C(=O)/N=C/N(C)C]

0.5 g (1.4 mmol) N-[(2S)-1-amino-1-oxopropan-2-yl]-3,5-dibromobenzamide and 3 ml DMF-DMA (22.6 mmol) in 40 mL THF were stirred in the water bath of a rotary evaporator at a bath temperature of 65° C. for 10 min, then evaporated under reduced pressure to yield 0.61 g and directly used in the subsequent step.

Step 2: 6-[5-[(1S)-1-[(3,5-dibromobenzoyl)amino]ethyl]-1,2,4-triazol-1-yl]pyrimidine-4-carboxamide (I-34)

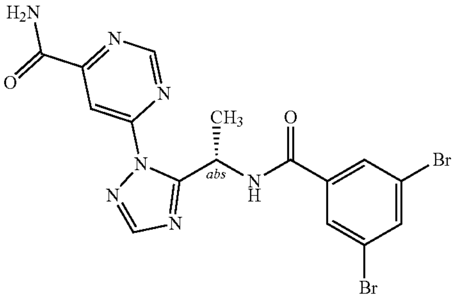 [SMILES: C[C@H](NC(=O)c1cc(Br)cc(Br)c1)c1ncnn1-c1cc(C(N)=O)ncn1]

0.61 g (1.5 mmol) 3,5-dibromo-N-[(1S)-2-[(E)-dimethylaminomethyleneamino]-1-methyl-2-oxo-ethyl]benzamide and 0.25 g (1.6 mmol) 6-hydrazinopyrimidine-4-carboxamide were stirred in 60 mL AcOH at 85° C. for 0.5 h. The mixture was evaporated under reduced pressure, aq. $K_2CO_3$, aq. NaCl and EtOAc were added. The aqueous layer was extracted three times with THF/EtOAc. The combined organic layers were dried with $Na_2SO_4$ and evaporated under reduced pressure. Crystallisation of the residue from MeOH (including heating with activated carbon and hot filtration) yielded 0.24 g (32%).

Analytical data see table 1.

Synthesis of 6-[5-[(1S)-1-aminoethyl]-1,2,4-triazol-1-yl]pyrimidine-4-carboxamide hydrochloride (INT-9)

Step 1: tert-butyl N-[(1S)-2-[(E)-dimethylaminomethyleneamino]-1-methyl-2-oxo-ethyl]carbamate

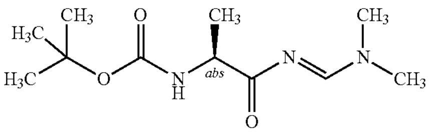 [SMILES: C[C@H](NC(=O)OC(C)(C)C)C(=O)/N=C/N(C)C]

tert-Butyl N-[(1S)-2-amino-1-methyl-2-oxo-ethyl]carbamate (150 g, 797 mmol, 1.00 eq) was dissolved in dioxane (1.50 L). N,N-Dimethylformamide dimethylacetal (142 g, 1.20 mol, 159 mL, 1.50 eq) was added into the mixture. The reaction mixture was stirred at 25° C. for 3 hrs. TLC (dichloromethane:methanol=10:1, Rf=0.67) indicated the starting material was consumed. The crude product (193 g, calculated) in dioxane was used in the next step without further purification.

Step 2: tert-butyl N-[(1S)-1-[2-(6-chloropyrimidin-4-yl)-1,2,4-triazol-3-yl]ethyl]carbamate

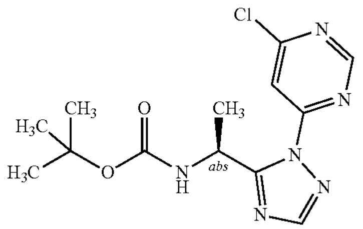 [SMILES: C[C@H](NC(=O)OC(C)(C)C)c1ncnn1-c1cc(Cl)ncn1]

The reaction mixture of tert-Butyl N-[(1S)-2-[(E)-dimethylaminomethyleneamino]-1-methyl-2-oxo-ethyl]carbamate (193 g, 793 mmol, 1.00 eq) was added dropwise to a mixture of (6-chloropyrimidin-4-yl)hydrazine (126 g, 873 mmol, 1.10 eq) dissolved in AcOH (1900 mL). The reaction mixture was stirred at 25° C. for 16 hrs. TLC (petroleum ether: ethyl acetate=3:1, Rf=0.22) indicated the strating material was consumed completely. The reaction mixture was concentrated under vacuum. The residue was purified by column chromatography (silica gel, petroleum ether/ethyl acetate=50/1 to 3/1). tert-Butyl N-[(1S)-1-[2-(6-chloropyrimidin-4-yl)-1,2,4-triazol-3-yl]ethyl]carbamate (160 g, 493 mmol, 62.1% yield) was obtained as a white solid.

Step 3: methyl 6-[5-[(1S)-1-(tert-butoxycarbonylamino)ethyl]-1,2,4-triazol-1-yl]pyrimidine-4-carboxylate

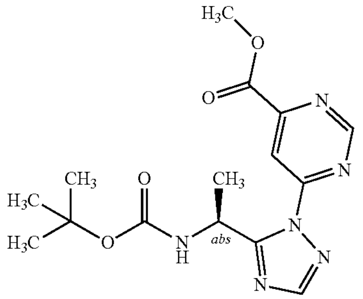 [SMILES: COC(=O)c1cc(-n2ncnc2[C@H](C)NC(=O)OC(C)(C)C)ncn1]

To a solution of tert-butyl N-[(1S)-1-[2-(6-chloropyrimidin-4-yl)-1,2,4-triazol-3-yl]ethyl]carbamate (80.0 g, 246 mmol, 1.00 eq) in MeOH (1.50 L) was added triethylamine (49.9 g, 493 mmol, 68.6 mL, 2.00 eq) and Pd(dppf)$Cl_2$ (18.0 g, 24.6 mmol, 0.100 eq) under nitrogen. The suspension was degassed under vacuum and purged with CO (carbon monoxide) several times. The mixture was stirred under CO (246 mmol, 1.00 eq) (50.0 psi) at 40° C. for 16 hrs. TLC (petroleum ether: ethyl acetate=1:1, Rf=0.27) indicated the strating material was consumed. The reaction mixture was filtered and the filter liquor was concentrated under vacuum. The residue was purified by column chromatography (silica gel, petroleum ether/ethyl acetate=50/1 to 1/1). Methyl 6-[5-[(1S)-1-(tert-butoxycarbonylamino)ethyl]-1,2,4-triazol-1-yl]pyrimidine-4-carboxylate (80.0 g, 230 mmol, 46.6% yield) was obtained as a white solid.

$^1H$ NMR (DMSO-$d_6$) δ=9.29 (s, 1H), 8.63 (s, 1H), 8.02 (s, 1H), 7.27 (s, 1H), 6.09-6.06 (m. 1H), 5.58-5.56 (d, 1H), 1.60-1.58 (d, 3H), 1.42 (s, 9H).

Step 4: tert-butyl N-[(1S)-1-[2-(6-carbamoylpyrimidin-4-yl)-1,2,4-triazol-3-yl]ethyl]carbamate

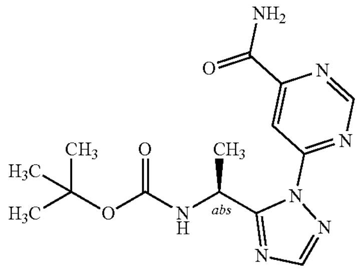 [SMILES: C[C@H](NC(=O)OC(C)(C)C)c1ncnn1-c1cc(C(N)=O)ncn1]

Methyl 6-[5-[(1S)-1-(tert-butoxycarbonylamino)ethyl]-1,2,4-triazol-1-yl]pyrimidine-4-carboxylate (40.0 g, 115 mmol, 1.00 eq) was dissolved in THF (240 mL) and MeOH (80.0 mL). $NH_4OH$ (96.6 g, 689 mmol, 106 mL, 25.0% purity, 6.00 eq) was added into the mixture. The reaction mixture was stirred at 25° C. for 6 hrs. TLC (petroleum ether: ethyl acetate=3:1, Rf=0.1) indicated the starting material was consumed completely. The reaction mixture was concentrated. The crude product was triturated with MTBE (300 mL) at 25° C. for 30 minutes. tert-Butyl N-[(1S)-1-[2-(6-carbamoylpyrimidin-4-yl)-1,2,4-triazol-3-yl]ethyl]carbamate (64.0 g, 189 mmol, 82.1% yield, 98.2% purity) was obtained as a white solid.

$^1H$ NMR (DMSO-$d_6$) δ=9.30 (s, 1H), 8.47 (s, 1H), 8.35 (s, 1H), 8.28 (s, 1H), 8.12 (s, 1H), 5.80-5.76 (m. 1H1), 1.46-1.44 (d, 3H), 1.32 (s, 9H).

Step 5: 6-[5-[(1S)-1-aminoethyl]-1,2,4-triazol-1-yl]pyrimidine-4-carboxamide hydrochloride (INT-9)

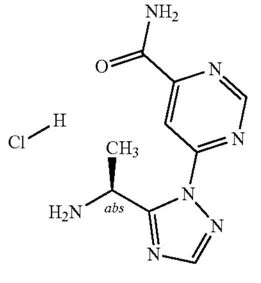

tert-Butyl N-[(1S)-1-[2-(6-carbamoylpyrimidin-4-yl)-1,2,4-triazol-3-yl]ethyl]carbamate (1 g, 3 mmol) was dissolved in 30 mL dioxane, then 4 M HCl/dioxane (7.5 mL) was added and the mixture was stirred at 50° C. for 7 hrs and additional 4 days at r.t. The mixture was evaporated under reduced pressure to obtain 1.02 g of the crude product (INT-9).

ESI mass [m/z]: 234.2 $[amine+H]^+$ $^1H$ NMR (DMSO-$d_6$) δ=9.36 (s, 1H), 8.78 (s, 2H, $NH_2$), 8.52 (s, 1H), 8.50 (bs, 1H), 8.39 (s, 1H), 8.17 (bs, 1H), 5.07-5.45 (m, 1H), 1.67-1.65 (d, 3H).

Synthesis of 3-(trifluoromethoxy)-5-(trifluoromethylsulfonyl)benzoic acid (INT-13)

Step 1: 3-bromo-5-(trifluoromethoxy)benzenethiol

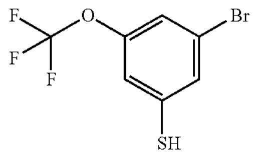 [SMILES: FC(F)(F)Oc1cc(S)cc(Br)c1]

A 2.5 M solution of n-BuLi in hexane (77 mL, 191 mmol) was added dropwise to a stirred solution of 1,3-dibromo-5-(trifluoromethoxy)benzene (48.9 g, 153 mmol) in absolute diethyl ether (430 mL) at −65° C. The reaction mixture was stirred at −65° C. for 50 min. Then ground sulfur (7.11 g, 222 mmol) was added portionwise at −65° C. The reaction mixture was stirred at −65° C. for 1.5 hrs. Then glacial acetic acid (35 mL) was added to the stirred reaction mixture. The mixture was allowed to reach 0° C. The reaction mixture was concentrated under reduced pressure to a volume of 50 mL. The residue was triturated with deionized water (500 mL) and the resulting emulsion was extracted with diethyl ether (2×300 mL). The combined diethyl ether layers were washed successively with water and brine and the solution was dried over sodium sulfate. The solvent was removed under reduced pressure to give a brown oil. The oil was subjected to vacuum distillation at a pressure of 13 mm Hg. A colorless fraction at 94-98° C. was collected.

Yield 27.7 g (66%).

$^1H$-NMR (400 MHz, $CDCl_3$): δ=7.35 (t, J=1.6 Hz, 1H), 7.19-7.16 (m, 1H), 7.08-7.05 (m, 1H), 3.61 (s, 1H). $^{19}F$-NMR (376 MHz, $CDCl_3$): δ=−57.80. $^1H$ and $^{19}F$ NMR spectra were recorded on a Varian Gemini 2000 machine.

Step 2: 1-bromo-3-(trifluoromethoxy)-5-(trifluoromethylsulfanyl)benzene

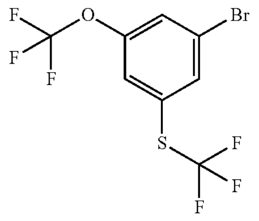 [SMILES: FC(F)(F)Oc1cc(Br)cc(SC(F)(F)F)c1]

Triethylamine (27.2 mL, 195 mmol) was added to a degassed solution of 3-bromo-5-(trifluoromethoxy)benzenethiol (17.75 g, 65 mmol) in DMF (175 mL) under argon. The stirred mixture was cooled to 0° C. and blown with trifluoroiodomethane to a weight gain of 38 g. Then 1,1'-dimethyl-[4,4'-bipyridine]-1,1'-diium dichloride (3.34 g, 13 mmol) was added to the stirred reaction mixture. The reaction mixture was stirred at room temperature overnight. The mixture was poured into deionized water (800 mL) and the resulting emulsion was extracted with diethyl ether (2×350 mL). The combined diethyl ether layers were washed successively with water and brine and the solution was dried over sodium sulfate. The solvent was removed under reduced pressure to give a dark-brown oil. The oil was subjected to vacuum distillation at a pressure of 20 mm Hg. A colorless fraction at 87-89° C. was collected. Yield 23.4 g (83%).

$^1$H-NMR (400 MHz, $CDCl_3$): δ=7.76 (t, J=1.6 Hz, 1H), 7.54-7.51 (m, 1H), 7.49-7.47 (m, 1H). $^{19}$F-NMR (376 MHz, $CDCl_3$): δ=−41.92, −58.01. $^1$H and $^{19}$F NMR spectra were recorded on a Varian Gemini 2000 machine.

Step 3: 3-(trifluoromethoxy)-5-(trifluoromethylsulfanyl)benzoic acid

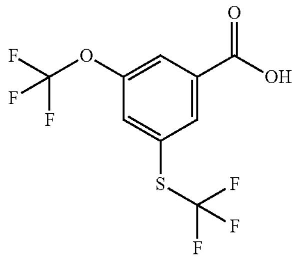 [SMILES: O=C(O)c1cc(OC(F)(F)F)cc(SC(F)(F)F)c1]

A stirred mixture of 1-bromo-3-(trifluoromethoxy)-5-(trifluoromethylsulfanyl)benzene (5.12 g, 15 mmol), ground potassium carbonate (10.4, 75 mmol), palladium (II) acetate (168 mg, 0.75 mmol), and xantphos (868 mg, 1.5 mmol) in DMF (75 mL) was heated at 100° C. under carbon monoxide atmosphere for 19 hrs. Deionized water (75 mL) was added to the reaction mixture at room temperature. The solvents were removed under reduced pressure. The residue was dissolved in deionized water (70 mL) and extracted with diethyl ether (2×50 mL). The water layer was separated and its pH was adjusted to 4 with aqueous HCl. The solvent was removed under reduced pressure and the residue was purified by column chromatography on silica gel (Combiflash). Yield 3 g (65%).

$^1$H-NMR (400 MHz, DMSO-$d_6$): δ=13.94 (s, 1H), 8.19 (t, J=1.5 Hz, 1H), 8.07-8.04 (m, 1H), 8.03-8.00 (m, 1H). $^{19}$F-NMR (376 MHz, DMSO-$d_6$): δ=−44.12, −59.52. $^1$H and $^{19}$F NMR spectra were recorded on a Varian Gemini 2000 machine.

Step 4: 3-(trifluoromethoxy)-5-(trifluoromethylsulfonyl)benzoic acid (INT-13)

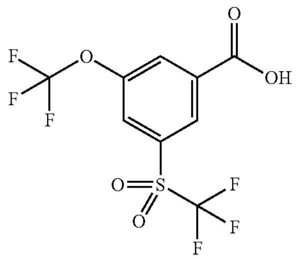 [SMILES: O=C(O)c1cc(OC(F)(F)F)cc(S(=O)(=O)C(F)(F)F)c1]

An aqueous solution of hydrogen peroxide (40%, 20 mL, 100 mmol) was added dropwise to a stirred solution of TFA (0.3 mL) in acetic anhydride (50 mL) at 0° C. for 1.5 hrs. 3-(Trifluoromethoxy)-5-(trifluoromethylsulfanyl)benzoic acid (3.06 g, 10 mmol) was added at 0° C. The resulting solution was allowed to reach room temperature. The reaction mixture was stirred at 55° C. for 4 hrs and then at room temperature overnight. The reaction mixture was diluted with deionized water to a volume of 250 mL. The mixture was cooled to 0° C. causing precipitation of a white solid. The precipitate was filtered, washed successively with water and hexane, and dried in a vacuum. Yield 3.2 g (95%).

ESI mass [m/z]: 337.0 $[M-H]^-$ $^1$H NMR (400 MHz, DMSO-$d_6$): δ=14.37 (bs, 1H, COOH), 8.48 (s, 1H), 8.46 (s, 1H), 8.42 (s, 1H).

Synthesis of 3-bromo-5-(2,2-dichlorocyclopropyl)benzoic acid (INT-14)

Step 1: 3-bromo-5-(2,2-dichlorocyclopropyl)benzonitrile

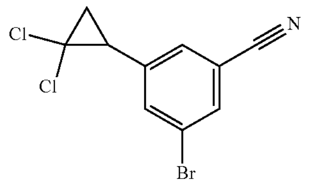 [SMILES: N#Cc1cc(Br)cc(C2CC2(Cl)Cl)c1]

Powdered potassium hydroxide (15 g, 260 mmol) was added portion-wise to a stirred solution of 3-bromo-5-vinylbenzonitrile (5.41 g, 26 mmol) and 18-crown-6 (1.03 g, 3.9 mmol) in chloroform (225 mL) at room temperature within 30 min. The reaction mixture was stirred at room temperature for 48 hrs. The reaction mixture was diluted with dichloromethane to a volume of 400 mL. The solution was washed with water and dried over sodium sulfate. The solvent was removed under reduced pressure to give a blackish oil. The oil was purified by flash chromatography (Combiflash) to obtain 4.55 g (60%).

$^1$H-NMR (400 MHz, $CDCl_3$): δ=7.73-7.71 (m, 1H), 7.64-7.62 (m, 1H), 7.47-7.45 (m, 1H), 2.93-2.83 (m, 1H), 2.06 (dd, J=10.5, 7.7 Hz, 1H), 1.90-1.81 (m, 1H). Spectrum was recorded on a Varian Gemini 2000.

Step 2: 3-bromo-5-(2,2-dichlorocyclopropyl)benzoic acid (INT-14)

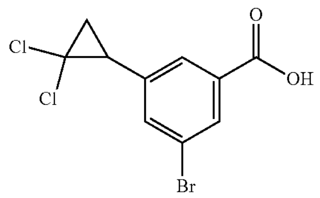 [SMILES: O=C(O)c1cc(Br)cc(C2CC2(Cl)Cl)c1]

Thionyl chloride (16.42, mL, 225 mmol) was added dropwise to a stirred solution of 3-bromo-5-(2,2-dichlorocyclopropyl)benzonitrile (4.36 g, 15 mmol) in methanol (100 mL) at 0° C. The reaction mixture was stirred at room temperature overnight. The reaction mixture was diluted with water to a volume of 300 mL and the resulting emulsion was extracted with diethyl ether (2×75 mL). The organic phase was separated, washed with brine, and dried over sodium sulfate. The solvent was removed under reduced pressure to give a yellowish oil (4.55 g). The oil was dissolved in isopropanol (35 mL) and the solution was added dropwise to a stirred solution of lithium hydroxide (1.26 g 30 mmol) in deionized water (20 mL) at room temperature and the reaction mixture was stirred for 5 hrs. The reaction mixture was diluted with water to a volume of 100 mL. Isopropanol was removed under reduced pressure. The remaining aqueous fraction was washed with diethyl ether (2×40 mL). Then a solution of concentrated aqueous HCl in deionized water (20 mL) was added to the aqueous fraction causing precipitation of a white solid. The precipitate was filtered, washed successively with water and hexane, and dried in a drying oven at 65° C. to obtain 3.2 g (69%) of the title compound.

ESI mass [m/z]: 311.0 $[M+H]^+$ $^1$H-NMR (400 MHz, DMSO-$d_6$): δ=13.45 (s, 1H), 7.97 (s, 1H), 7.87 (s, 1H), 7.81 (s, 1H), 3.27 (dd, J=10.9, 8.5 Hz, 1H), 2.40-2.28 (m, 1H), 2.17-2.06 (m, 1H). Spectrum was recorded on a Varian Gemini 2000.

Synthesis
3-bromo-5-(1,1,2,2-tetrafluoroethoxy)benzoic acid (INT-15)

Step 1: mixture of methyl 3-bromo-5-(1,1,2,2-tetrafluoroethoxy)benzoate and methyl 3-bromo-5-(2-bromo-1,1,2,2-tetrafluoroethoxy)benzoate

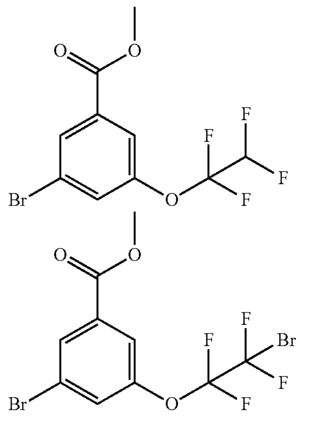

To a solution of 1,2-dibromo-1,1,2,2-tetrafluoroethane (18.0 g, 77.9 mmol, 1.0 eq) in DMSO (100 mL) was added $Cs_2CO_3$ (38.1 g, 116 mmol, 1.5 eq) and methyl 3-bromo-5-hydroxybenzoate (commercially available, 40.4 g, 155 mmol, 2.0 eq), the mixture was stirred at 60° C. for 12 hrs. To the reaction mixture was added $H_2O$ (200 mL) and extracted with ethyl acetate (150 mL×3), the organic phase was dried and concentrated to yield a mixture of products (22.0 g, 1:1) as a yellow oil.

Step 2: methyl
3-bromo-5-(1,1,2,2-tetrafluoroethoxy)benzoate

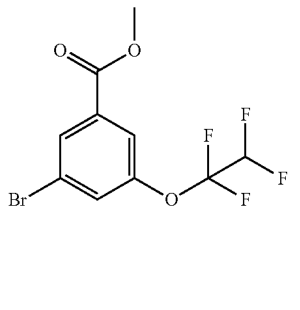 [SMILES: COC(=O)c1cc(Br)cc(OC(F)(F)C(F)F)c1]

To a solution of the mixture from the previous step (22.0 g, 53.6 mmol, 1.0 eq) in AcOH (100 mL) was added Zn (10.5 g, 161 mmol, 3.0 eq) at 50° C., the mixture was stirred at 50° C. for 12 hrs. The reaction mixture was filtered and concentrated under reduced pressure to give a residue. (16.5 g, crude) was obtained as a light yellow liquid.

Step 3:
3-bromo-5-(1,1,2,2-tetrafluoroethoxy)benzoic acid (INT-15)

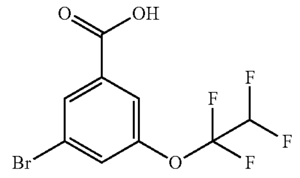 [SMILES: O=C(O)c1cc(Br)cc(OC(F)(F)C(F)F)c1]

To a solution of methyl 3-bromo-5-(1,1,2,2-tetrafluoroethoxy)benzoate from the previous step (16.5 g, 49.8 mmol, 1.0 eq) in THF (100 mL) was added $LiOH{\cdot}H_2O$ (2.0 M, 49.8 mL, 2.0 eq), the mixture was stirred at 25° C. for 2 hrs. The reaction was concentrated under reduced pressure to give a residue, diluted with water (50 mL), adjusted to pH=4 with 2M $KHSO_4$ solution and extracted with DCM (30 mL×2), the combined organic layers were washed with brine (50 mL), dried over $MgSO_4$, filtered and concentrated under reduced pressure to yield (10.0 g, 31.5 mmol, 63.3) as a white solid.

ESI mass [m/z]: 314.9 $[M-H]^-$ $^1$H-NMR: (400 MHz $CDCl_3$): =10.69 (br s, 1H), 8.17 (d, J=1.2 Hz, 1H), 7.89 (s, 1H), 7.64 (s, 1H), 5.78-6.12 (m, 1H).

Synthesis of 6-(5-{(1S)-1-[3-chloro-5-(1,1,2,2-tetrafluoroethoxy)benzamido]ethyl}-1H-1,2,4-triazol-1-yl)pyrimidine-4-carboxamide (I-113)

Step 1: mixture of 3-chloro-5-(1,1,2,2-tetrafluoroethoxy)benzoic acid and 3-chloro-5-(1,1,2,2-tetrafluoro-2-iodoethoxy)benzoic acid

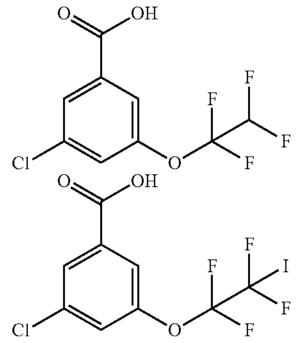

3-Chloro-5-hydroxybenzoic acid (commercially available, 9.3 g, 54 mmol), 1-chloro-1,1,2,2-tetrafluoro-2-iodoethane (10.5 g, 40 mmol), potassium carbonate (25 g, 181 mmol) in 50 ml DMSO were stirred in a thick-walled reaction tube equipped with a pressure-relieve valve at 60° C. for 3 d. The mixture was evaporated under reduced pressure. The residue was taken up in aq. citric acid/ethyl acetate, the aqueous layer was extracted three times with ethyl acetate. The combined organic layers were dried with sodium sulfate and evaporated to yield 19.5 g crude product. Chromatography (silica gel, petrolether/acetone) yielded a fraction of 10.3 g, mainly consisting of 3-chloro-5-(1,1,2,2-tetrafluoro-2-iodoethoxy)benzoic acid and an impure fraction containing 3-chloro-5-(1,1,2,2-tetrafluoroethoxy)benzoic acid, which was directly used in the subsequent step.

Step 2: 6-(5-{(1S)-1-[3-chloro-5-(1,1,2,2-tetrafluoroethoxy)benzamido]ethyl}-1H-1,2,4-triazol-1-yl) pyrimidine-4-carboxamide (I-113)

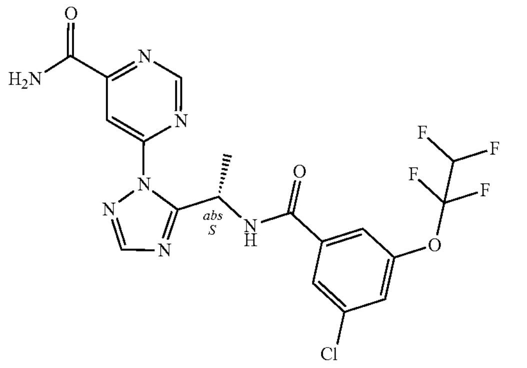

3-Chloro-5-(1,1,2,2-tetrafluoroethoxy)benzoic acid (0.19 g, 0.45 mmol) with HATU (0.34 g, 0.89 mmol) and 6-{5-[(1S)-1-aminoethyl]-1H-1,2,4-triazol-1-yl}pyrimidine-4-carboxamide hydrochloride (0.12 g (0.45 mmol) with N,N-diisopropylamine (0.31 ml, 1.78 mmol) were each stirred in 1.5 ml DMF for 1 h. Both solutions were combined and stirred at r.t. for 16 hrs. Chromatographic purification of the reaction mixture (RP18, water/ACN with 0.1% HCOOH) yielded 92 mg (42% of theory).

Analytical data see table 1.

Synthesis of 6-(5-{(1S)-1-[3-chloro-5-(1,1,2,2-tetrafluoro-2-iodoethoxy)benzamido]ethyl}-1H-1,2,4-triazol-1-yl)pyrimidine-4-carboxamide (I-114)

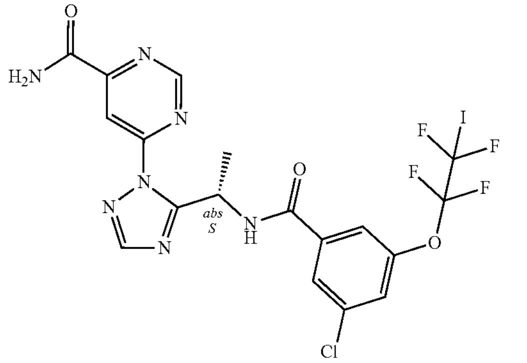

3-Chloro-5-(1,1,2,2-tetrafluoro-2-iodoethoxy)benzoic acid (from the previous sequence, 0.18 g, 0.45 mmol) with HATU (0.34 g, 0.89 mmol) and 6-{5-[(1S)-1-aminoethyl]-1H-1,2,4-triazol-1-yl}pyrimidine-4-carboxamide hydrochloride (0.12 g (0.45 mmol) with N,N-diisopropylamine (0.31 ml, 1.78 mmol) were each stirred in 1.5 ml DMF for 1 h. Both solutions were combined and stirred at r.t. for 16 hrs. Chromatographic purification of the reaction mixture (RP18, water/ACN with 0.1% HCOOH) yielded 106 mg (39% of theory).

Analytical data see table 1.

Synthesis of 3-(1-fluoro-1-methyl-ethyl)-5-(trifluoromethoxy)benzoic acid (INT-16)

Step 1: 2-[3-bromo-5-(trifluoromethoxy)phenyl] propan-2-ol

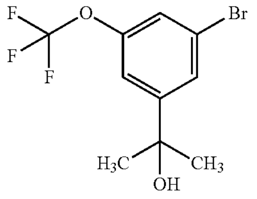 [SMILES: CC(C)(O)c1cc(Br)cc(OC(F)(F)F)c1]

To a solution of 1,3-dibromo-5-(trifluoromethoxy)benzene (20 g, 62.4 mmol) in THF (160 mL), i-PrMgCl (1.9 M in THF, 36 mL, 73.2 mmol) was added dropwise at −5° C. under argon. The mixture was stirred at the same temperature for 45 min, then acetone (9 g, 156 mmol) was added dropwise. The reaction mixture was stirred for additional 30 min and MTBE (200 mL) was added followed by 10% citric acid (200 mL). The organic phase was separated, washed with brine (3×100 mL), dried and concentrated under reduced pressure. 2-[3-Bromo-5-(trifluoromethoxy)phenyl] propan-2-ol (10.14 g, 33.91 mmol, 54.3% yield) was obtained after MPLC purification.

Step 2: methyl 3-(1-hydroxy-1-methyl-ethyl)-5-(trifluoromethoxy)benzoate

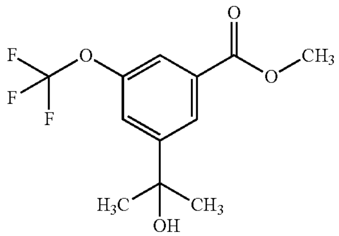 [SMILES: COC(=O)c1cc(OC(F)(F)F)cc(C(C)(C)O)c1]

To a solution of 2-[3-bromo-5-(trifluoromethoxy)phenyl] propan-2-ol (10.14 g, 33.91 mmol) in MeOH (110 mL), $Et_3N$ (6.833 g, 67.82 mmol) and Pd(dppf)Cl2 (2.47 g, 3.391 mmol) were added. The mixture was stirred at 130° C. under pressure of CO (10 Torr) for 48 h, diluted with EtOAc (600 mL) and filtered through a pad of Celite and concentrated under reduced pressure. The residue was dissolved in EtOAc (300 mL) and washed with water (2×200 mL). The organic phase was dried over Na2SO4 and concentrated under reduced pressure to afford methyl 3-(1-hydroxy-1-methyl-ethyl)-5-(trifluoromethoxy)benzoate (8.96 g, 32.21 mmol, 95% yield).

Step 3: methyl 3-(1-fluoro-1-methyl-ethyl)-5-(trifluoromethoxy)benzoate

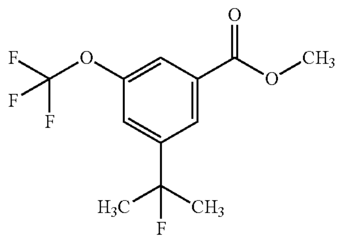 [SMILES: COC(=O)c1cc(OC(F)(F)F)cc(C(C)(C)F)c1]

To a solution of methyl 3-(1-hydroxy-1-methyl-ethyl)-5-(trifluoromethoxy)benzoate (8.96 g, 32.21 mmol) in dichloromethane (100 mL), Morph-DAST (6.2 g, 35.435 mmol) was added dropwise at −60° C. The mixture was stirred at room temperature overnight and poured into aqueous sodium bicarbonate. The organic layer was separated, dried over sodium sulfate and concentrated under reduced pressure. Pure methyl 3-(1-fluoro-1-methyl-ethyl)-5-(trifluoromethoxy)benzoate (3.8 g, 13.56 mmol, 42% yield) was obtained after MPLC.

Step 4: 3-(1-fluoro-1-methyl-ethyl)-5-(trifluoromethoxy)benzoic acid (INT-16)

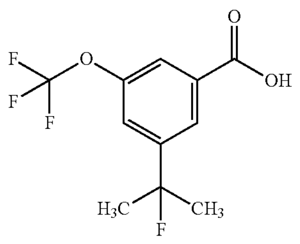 [SMILES: CC(C)(F)c1cc(OC(F)(F)F)cc(C(=O)O)c1]

To a stirred solution of 3-(1-fluoro-1-methyl-ethyl)-5-(trifluoromethoxy)benzoate (3.8 g, 13.56 mmol) in a mixture of THF (40 mL)/$H_2O$ (12.5 mL) at 0° C., LiOH monohydrate (0.766 g, 18.306 mmol) was added and the mixture was stirred overnight at r.t. THF was evaporated under reduced pressure, water was acidified to pH=4.5 and extracted with MTBE (2×25 mL). Pure 3-(1-fluoro-1-methyl-ethyl)-5-(trifluoromethoxy)benzoic acid was obtained after recrystallization from 30% aqueous EtOH (3.17 g, 11.9 mmol, 87,76% yield) as yellow solid.

ESI mass [m/z neg.]: 265.1 $[M-H]^+$ $^1$H-NMR (400 MHz, DMSO-$d_6$): δ=1.66 (s, 3H), 1.72 (s, 3H), 7.66 (s, 1H), 7.75 (m, 1H), 7.99 (m, 1H), 13.56 (s, 1H). Spectrum was recorded on a Bruker AVANCE TTT 400 MHz.

Alternative synthesis of 6-[5-[(1S)-1-aminoethyl]-3-cyclopropyl-1,2,4-triazol-1-yl]pyrimidine-4-carboxamide hydrochloride (INT-11)

Step 1: tert-butyl N-[(1S)-2-chloro-1-methyl-2-oxo-ethyl]carbamate

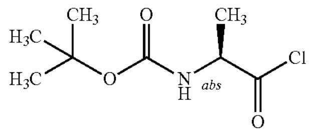

To a solution of (2S)-2-(tert-butoxycarbonylamino)propanoic acid (90.0 g, 476 mmol, 1.00 eq) in DCM (900 mL) was added $Et_3N$ (44.7 g, 442 mmol, 61.6 mL, 0.930 eq). Trimethylacetyl chloride (57.4 g, 476 mmol, 58.5 mL, 1.00 eq) was added dropwise at 0° C. After addition, the reaction mixture was stirred at 20° C. for 16 hrs. tert-Butyl N-[(1S)-2-chloro-1-methyl-2-oxo-ethyl]carbamate (98.8 g, crude) in DCM (900 mL) was obtained as a colorless liquid and used for the next step.

Step 2: ethyl (Z)-N-[(2S)-2-(tert-butoxycarbonylamino)propanoyl]cyclopropanecarboximidate

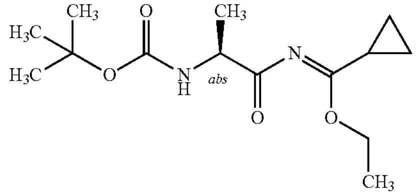 [SMILES: CCO/C(=N\C(=O)[C@H](C)NC(=O)OC(C)(C)C)C1CC1]

To a solution of tert-butyl N-[(1S)-2-chloro-1-methyl-2-oxo-ethyl]carbamate (98.8 g, 476 mmol, 1.00 eq) in DCM (900 mL) was added $Et_3N$ (116 g, 1.14 mol, 159 mL, 2.40 eq). Then ethyl cyclopropanecarboximidate hydrochloride_ (71.1 g, 476 mmol, 1.00 eq) was added in portions at 20° C. After addition, the mixture was stirred at 20° C. for 16 hrs. Ethyl (Z)-N-[(2S)-2-(tert-butoxycarbonylamino)propanoyl]cyclopropanecarboximidate (135 g, crude) in DCM was obtained as colorless liquid and used for the next step.

Step 3: tert-butyl N-[(1S)-1-[2-(6-chloropyrimidin-4-yl)-5-cyclopropyl-1,2,4-triazol-3-yl]ethyl]carbamate

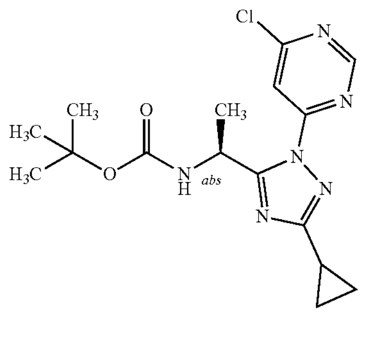 [SMILES: C[C@H](NC(=O)OC(C)(C)C)c1nc(C2CC2)nn1-c1cc(Cl)ncn1]

(6-Chloropyrimidin-4-yl)hydrazine (68.7 g, 475 mmol, 1.00 eq) was added in portions to a solution of ethyl (Z)-N-[(2S)-2-(tert-butoxycarbonylamino)propanoyl]cyclopropanecarboximidate (135 g, 475 mmol, 1.00 eq) in DCM (900 mL) below 20° C. After addition, the mixture was stirred at 20° C. for 16 hrs. To the reaction mixture was added $H_2O$ (500 mL), the separated organic phase was washed with brine (200 mL), dried and concentrated. The residue was purified by column chromatography (silca gel, petroleum ether/ethyl acetate=20/1 to 3/1). tert-Butyl N-[(1S)-1-[2-(6-chloropyrimidin-4-yl)-5-cyclopropyl-1,2,4-triazol-3-yl]ethyl]carbamate (48.0 g, 132 mmol, 27.7% yield over three steps) was obtained as yellow solid.

Step 4: methyl 6-[5-[(1S)-1-(tert-butoxycarbonylamino)ethyl]-3-cyclopropyl-1,2,4-triazol-1-yl]pyrimidine-4-carboxylate (INT-17)

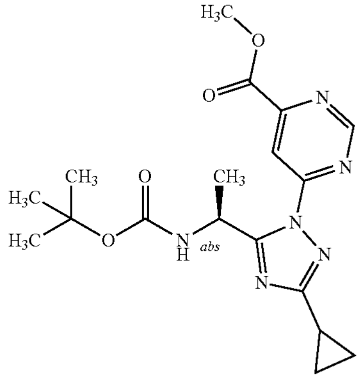 [SMILES: COC(=O)c1cc(-n2nc(C3CC3)nc2[C@H](C)NC(=O)OC(C)(C)C)ncn1]

To a solution of tert-butyl N-[(1S)-1-[2-(6-chloropyrimidin-4-yl)-5-cyclopropyl-1,2,4-triazol-3-yl]ethyl]carbamate (48.0 g, 132 mmol, 1.00 eq) in MeOH (1.00 L) was added $Et_3N$ (26.6 g, 263 mmol, 36.6 mL, 2.00 eq) and $Pd(dppf)Cl_2$ (9.63 g, 13.2 mmol, 0.100 eq). The suspension was degassed under vacuum and purged with CO several times. The mixture was stirred under CO (50 psi) at 40° C. for 16 hrs. The reaction mixture was concentrated. The residue was purified by column chromatography (silica gel, petroleum ether/ethyl acetate=20/1 to 1/1). Methyl 6-[5-[(1S)-1-(tert-butoxycarbonylamino)ethyl]-3-cyclopropyl-1,2,4-triazol-1-yl]pyrimidine-4-carboxylate (41.0 g, 106 mmol, 80.2% yield) was obtained as light yellow solid.

Step 5: tert-butyl N-[(1S)-1-[2-(6-carbamoylpyrimidin-4-yl)-5-cyclopropyl-1,2,4-triazol-3-yl]ethyl]carbamate (INT-18)

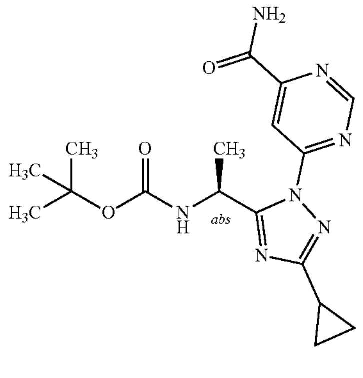 [SMILES: C[C@H](NC(=O)OC(C)(C)C)c1nc(C2CC2)nn1-c1cc(C(N)=O)ncn1]

Methyl 6-[5-[(1S)-1-(tert-butoxycarbonylamino)ethyl]-3-cyclopropyl-1,2,4-triazol-1-yl]pyrimidine-4-carboxylate (25.0 g, 64.4 mmol, 1.00 eq) was dissolved in THF (150 mL) and MeOH (50 mL). $NH_4OH$ (54.1 g, 386 mmol, 59.5 mL, 25% purity, 6.00 eq) was added dropwise at 20° C. After addition, the mixture was stirred at 20° C. for 5 hrs. The reaction mixture was concentrated. tert-Butyl N-[(1S)-1-[2-(6-carbamoylpyrimidin-4-yl)-5-cyclopropyl-1,2,4-triazol-3-yl]ethyl]carbamate (24.0 g, 60.4 mmol, 93.8% yield, 94% purity) was obtained as light yellow solid and used for the next step.

$^1H$ NMR (400 MHz, $CDCl_3$): δ 9.08 (d, J=0.73 Hz, 1H), 8.65 (s, 1H), 7.79 (br s, 1H), 5.96-6.07 (m, 1H), 5.81 (br s, 1H), 5.56-5.71 (m, 1H), 2.02-2.12 (m, 1H), 1.55 (d, J=6.8 Hz, 3H), 1.44 (s, 9H), 0.98-1.11 (m, 4H).

Step 6: 6-[5-[(1S)-1-aminoethyl]-3-cyclopropyl-1,2,4-triazol-1-yl]pyrimidine-4-carboxamide hydrochloride (INT-11)

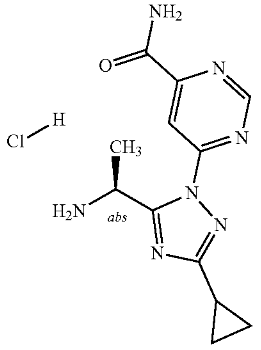 [SMILES: Cl ; C[C@H](N)c1nc(C2CC2)nn1-c1cc(C(N)=O)ncn1]

tert-Butyl N-[(1S)-1-[2-(6-carbamoylpyrimidin-4-yl)-5-cyclopropyl-1,2,4-triazol-3-yl]ethyl]carbamate (8.00 g, 21.4 mmol, 1.00 eq) in DCM (20.0 mL) was added to HCl/dioxane (80.0 mL, 4M). The mixture was stirred at 20° C. for 2 hrs. The reaction mixture was concentrated. The crude product was triturated with DCM (50.0 mL) at 20° C. for 1 h and filtrated. 6-[5-[(1S)-1-Aminoethyl]-3-cyclopropyl-1,2,4-triazol-1-yl]pyrimidine-4-carboxamide hydrochloride (5.54 g, 17.01 mmol, 79.4% yield, 95.1% purity) was obtained as white solid.

ESI mass [m/z]: 274.2 $[amine+H]^+$ $^1H$-NMR (400 MHz, DMSO-$d_6$): δ 9.30 (s, 1H), 8.75 (bs, 2H, $NH_2$), 8.48 (s, 1H), 8.32 (s, 1H), 8.15 (s, 1H), 5.44-5.41 (m, 1H), 2.20-2.14 (m, 1H), 1.64-1.61 (d, 3H), 1.12-1.07 (m, 2H), 1.03-0.98 (m, 2H).

Synthesis 6-[5-[(1S)-1-aminoethyl]-3-cyclopropyl-1,2,4-triazol-1-yl]-N-methyl-pyrimidine-4-carboxamide hydrochloride (INT-21)

Step 1: tert-butyl N-[(1S)-1-[5-cyclopropyl-2-[6-(methylcarbamoyl)pyrimidin-4-yl]-1,2,4-triazol-3-yl]ethyl]carbamate (INT-19)

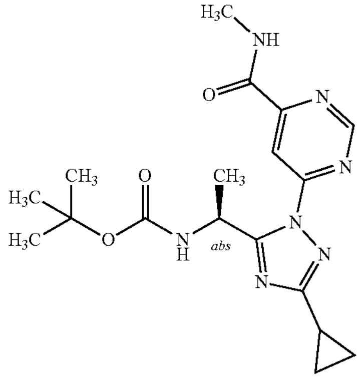 [SMILES: CNC(=O)c1cc(-n2nc(C3CC3)nc2[C@H](C)NC(=O)OC(C)(C)C)ncn1]

To as solution of methyl 6-[5-[(1S)-1-(tert-butoxycarbonylamino)ethyl]-3-cyclopropyl-1,2,4-triazol-1-yl]pyrimidine-4-carboxylate (9.00 g, 23.2 mmol, 1.00 eq) in THF (45.0 mL) was added methanamine (2 M in THF, 34.7 mL, 3.00 eq). The mixture was stirred at 20° C. for 4 hrs. After the reaction was completed, the reaction mixture was concentrated. The residue was purified by column chromatography (silica gel, petroleum ether/ethyl acetate=20/1 to 1/1). tert-Butyl N-[(1S)-1-[5-cyclopropyl-2-[6-(methylcarbamoyl)pyrimidin-4-yl]-1,2,4-triazol-3-yl]ethyl]carbamate (8.50 g, 20.8 mmol, 89.9% yield, 95% purity) was obtained as light yellow solid.

$^1$H NMR (400 MHz, $CDCl_3$): δ 9.04 (s, 1H), 8.63 (s, 1H), 7.98 (d, 1H), 6.02-5.99 (m, 1H), 5.63 (d, 1H), 3.09 (d, 3H), 2.10-2.06 (m, 1H), 1.54 (d, 1H), 1.44 (s, 9H), 1.07-1.02 (m, 4H).

Step 2: 6-[5-[(1S)-1-aminoethyl]-3-cyclopropyl-1,2,4-triazol-1-yl]-N-methyl-pyrimidine-4-carboxamide hydrochloride (INT-21)

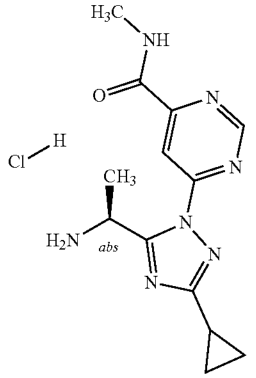 [SMILES: Cl ; CNC(=O)c1cc(-n2nc(C3CC3)nc2[C@H](C)N)ncn1]

Trimethylsilyl chloride (7.07 g, 65.0 mmol, 8.26 mL, 3.00 eq) was added to $CF_3CH_2OH$ (84.0 mL) and stirred for 30 mins. tert-Butyl N-[(1S)-1-[5-cyclopropyl-2-[6-(methylcarbamoyl)pyrimidin-4-yl]-1,2,4-triazol-3-yl]ethyl]carbamate (8.40 g, 21.7 mmol, 1.00 eq) in $CF_3CH_2OH$ (84.0 mL) was added dropwise to the above solution below 20° C. After addition, the mixture was stirred at 20° C. for 1 hr. The reaction mixture was concentrated. 6-[5-[(1S)-1-Aminoethyl]-3-cyclopropyl-1,2,4-triazol-1-yl]-N-methyl-pyrimidine-4-carboxamide hydrochloride (6.60 g, 19.7 mmol, 91.0% yield, 96.8% purity, HCl) was obtained as light yellow solid.

$^1$H NMR (400 MHz, MeOD): δ 9.19 (d, J=1.00 Hz, 1H), 8.52 (d, J=1.00 Hz, 1H), 5.59 (q, J=6.71 Hz, 1H), 3.25-3.38 (m, 2H), 3.00 (s, 3H), 2.11-2.24 (m, 1H), 1.75 (d, J=6.75 Hz, 3H), 1.01-1.16 (m, 4H).

Synthesis 6-[5-[(1S)-1-aminoethyl]-3-cyclopropyl-1,2,4-triazol-1-yl]-N,N-dimethyl-pyrimidine-4-carboxamide hydrochloride (INT-22)

Step 1: tert-butyl N-[(1S)-1-[5-cyclopropyl-2-[6-(dimethylcarbamoyl)pyrimidin-4-yl]-1,2,4-triazol-3-yl]ethyl]carbamate (INT-20)

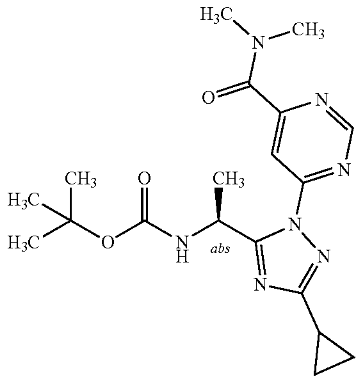 [SMILES: C[C@H](NC(=O)OC(C)(C)C)c1nc(C2CC2)nn1-c1cc(C(=O)N(C)C)ncn1]

To as solution of methyl 6-[5-[(1S)-1-(tert-butoxycarbonylamino)ethyl]-3-cyclopropyl-1,2,4-triazol-1-yl]pyrimidine-4-carboxylate (14.0 g, 36.0 mmol, 1.00 eq) was added dimethyl amine (2 M in THF, 108 mL, 6.00 eq) THF solution. The reaction mixture was stirred at 60° C. for 16 hrs. The reaction mixture was concentrated. The residue was purified by column chromatography (silica gel, petroleum ether/ethyl acetate=20/1 to 1/1). tert-Butyl N-[(1S)-1-[5-cyclopropyl-2-[6-(dimethylcarbamoyl)pyrimidin-4-yl]-1,2,4-triazol-3-yl]ethyl]carbamate (11.6 g, 27.4 mmol, 76.2% yield, 95% purity) was obtained as yellow gum.

$^1$H NMR (400 MHz, $CDCl_3$): δ 9.07 (s, 1H), 8.12 (s, 1H), 6.02-5.99 (m, 1H), 5.62 (d, 1H), 3.16 (s, 3H), 3.08 (s, 3H), 2.07-2.00 (m, 1H), 1.55 (d, 1H), 1.44 (s, 9H), 1.04-1.00 (m, 4H).

Step 2: 6-[5-[(1S)-1-aminoethyl]-3-cyclopropyl-1,2,4-triazol-1-yl]-N,N-dimethyl-pyrimidine-4-carboxamide hydrochloride (INT-22)

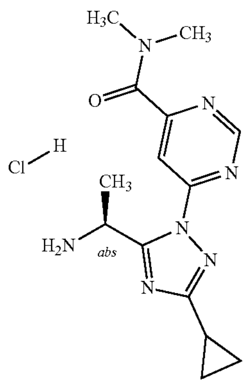

Triemethylsilyl chloride (8.93 g, 82.2 mmol, 10.4 mL, 3.00 eq) was added to $CF_3CH_2OH$ (110 mL) and stirred for 30 mins. tert-Butyl N-[(1S)-1-[5-cyclopropyl-2-[6-(dimethylcarbamoyl)pyrimidin-4-yl]-1,2,4-triazol-3-yl]ethyl]carbamate (11.0 g, 27.4 mmol, 1.00 eq) in $CF_3CH_2OH$ (84.0 mL) was added dropwise to the above solution below 20° C. After addition, the mixture was stirred at 20° C. for 1 hr. The reaction mixture was concentrated. 6 6-[5-[(1S)-1-Amino-ethyl]-3-cyclopropyl-1,2,4-triazol-1-yl]-N,N-dimethyl-pyrimidine-4-carboxamide hydrochloride (8.20 g, 23.6 mmol, 86.3% yield, 97.4% purity,) was obtained as light yellow solid.

$^1$H NMR (400 MHz, MeOD): δ 9.17 (d, J=1.00 Hz, 1H), 8.13 (d, J=1.00 Hz, 1H), 5.61 (q, J=6.67 Hz, 1H), 3.18 (s, 3H), 3.10 (s, 3H), 2.11-2.24 (m, 1H), 1.78 (d, J=6.75 Hz, 3H), 1.05-1.14 (m, 4H).

Synthesis of 3,5-bis(difluoromethylsulfonyl)benzoic acid (INT-23)

Step 1: methyl 3,5-bis(dimethylcarbamothioyloxy)benzoate

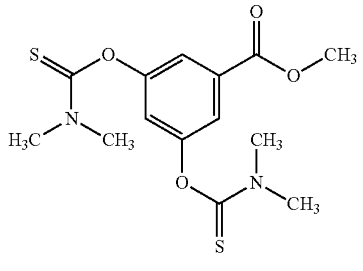 [SMILES: COC(=O)c1cc(OC(=S)N(C)C)cc(OC(=S)N(C)C)c1]

Methyl 3,5-dihydroxybenzoate (50 g, 300 mmol) was dissolved in anhydrous DMF (200 mL) under a nitrogen atmosphere. The solution was cooled to 0° C. and DABCO (133 g, 1190 mmol) was added in portions. To the resulting suspension a solution of N,N-dimethylthiocarbamoyl chloride (147 g, 1190 mmol) in DMF (200 mL) was added dropwise at 0-5° C. When the reaction mixture solidified, more DMF was added to enable efficient stirring. The suspension was allowed to warm to room temperature and stirred for 24 h. The reaction mixture was poured into water (2000 mL), filtered and the residue was washed with ethanol to give methyl 3,5-bis(dimethylcarbamothioyloxy)benzoate (92 g, 90% yield) as white crystalline powder which was used as such in the next step.

Step 2: methyl 3,5-bis(dimethylcarbamoylsulfanyl)benzoate

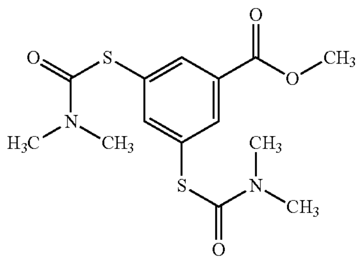 [SMILES: COC(=O)c1cc(SC(=O)N(C)C)cc(SC(=O)N(C)C)c1]

Methyl 3,5-bis(dimethylcarbamothioyloxy)benzoate (8.0 g, 23.3 mmol) was suspended in diphenyl ether (80 mL) and heated under a nitrogen atmosphere in a sand bath to 230-240° C. for 3 h. After the reaction mixture was allowed to cool to 30-40° C. it was poured into hexane (160 mL) and slowly allowed to cool to 4° C. Methyl 3,5-bis(dimethylcarbamoylsulfanyl)benzoate (7.37 g, 92% yield) was obtained after filtration and extensive washing with warm hexane as light beige crystals which was used as such in the next step.

Step 3: methyl 3,5-bis(sulfanyl)benzoate

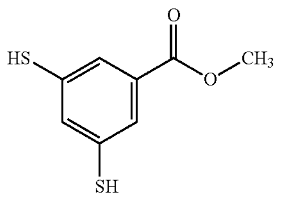

Under a nitrogen atmosphere methyl 3,5-bis(dimethylcarbamoylsulfanyl)benzoate (34.2 g, 100 mmol) was suspended in mixture of 28% solution of sodium methoxide (43 g, 230 mmol) and methanol (150 mL) and the reaction mixture was stirred overnight at r.t. Ice-water (500 mL) was added followed by neutralization with concentrated hydrochloric acid. The precipitate was filtered, washed with water and dried under vacuum to methyl 3,5-bis(sulfanyl)benzoate (12.5 g, 62% yield) as a white powder which was used as such in the next step.

Step 4: methyl 3,5-bis(difluoromethylsulfanyl)benzoate

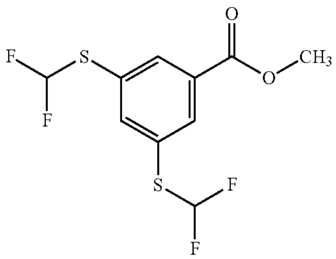 [SMILES: COC(=O)c1cc(SC(F)F)cc(SC(F)F)c1]

To a solution of methyl 3,5-bis(sulfanyl)benzoate (4 g, 20 mmol) in N,N-dimethylformamide (50 mL) were added potassium carbonate (11.4 g, 80 mmol) and sodium chlorodifluoroacetate (11.2 g, 80 mmol). The reaction mixture was heated to 95° C. for 3 hours, diluted with water and the aqueous phase was extracted with ethyl acetate. The combined organic phases were washed with water and brine, dried over sodium sulfate, filtered and then concentrated to give methyl methyl 3,5-bis(difluoromethylsulfanyl)benzoate (3.72 g, 62% yield) as an off-white powder.

$^1$H NMR (400 MHz, $CDCl_3$): δ 8.30 (s, 2H), 7.99 (s, 1H), 7.04-6.75 (t, 1H), 3.97 (s, 3H). Measured on a Bruker AVANCE III 400 MHz machine.

Step 5: methyl 3,5-bis(difluoromethylsulfonyl)benzoate

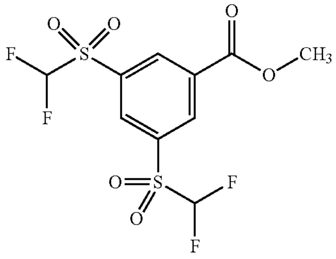 [SMILES: COC(=O)c1cc(S(=O)(=O)C(F)F)cc(S(=O)(=O)C(F)F)c1]

To a solution of methyl 3,5-bis(difluoromethylsulfanyl) benzoate (3.72 g, 12.5 mmol) in a mixture of carbon tetrachloride (15 mL), acetonitrile (15 mL) and water (35 mL), were added sodium periodate (26.4 g, 120 mmol) and trichlororuthenium hydrate (0.1 g, 0.47 mmol). The reaction mixture was stirred at r.t. for 30 min, diluted with water and extracted with dichloromethane. The combined organic layers were dried over sodium sulfate, filtered and concentrated under reduced pressure to give methyl 3,5-bis(difluoromethylsulfonyl)benzoate (2.3 g, 51% yield) as an off-white powder.

$^1$H NMR (400 MHz, $CDCl_3$): δ 9.00 (s, 2H), 8.74 (s, 1H), 6.48-6.21 (t, 1H), 4.08 (s, 3H). Measured on a Bruker AVANCE III 400 MHz machine.

Step 5: 3,5-bis(difluoromethylsulfonyl)benzoic acid (INT-23)

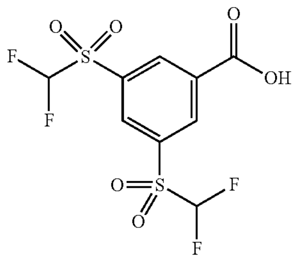 [SMILES: O=C(O)c1cc(S(=O)(=O)C(F)F)cc(S(=O)(=O)C(F)F)c1]

Methyl 3,5-bis(difluoromethylsulfonyl)benzoate (2.3 g, 6.3 mmol) was added to a mixture of lithium hydroxide (0.76 g, 12.6 mmol), THF (12 mL) and water (6 mL). The reaction was stirred at r.t. for 4 hours, acidified with 1 M hydrochloric acid and the aqueous phase was extracted with ethyl acetate. The combined organic layers were dried over sodium sulfate, filtered and concentrated under reduced pressure to give 3,5-bis(difluoromethylsulfonyl)benzoic acid (2.03 g, 92% yield) as an off-white powder.

ESI mass [m/z]: 349.0 $[M-H]^-$ $^1$H NMR (400 MHz, DMSO-d6): δ 7.53 (t, 2H), 8.57 (s, 1H), 8.79 (s, 2H), 14.53 (s, 1H). Measured on a Bruker AVANCE III 400 MHz machine.

Analytical Methods

The analytical methods described below refer to all information in the entire document, unless the procedure of the respective analytical determination is described separately at the respective passage.

Mass Spectrometry

The determination of [M+H]+ or M− by LC-MS under acidic chromatographic conditions was done with 1 ml formic acid per liter acetonitrile and 0.9 ml formic acid per liter Millipore water as eluents. The column Zorbax Eclipse Plus C18 50 mm*2.1 mm was used. The temperature of the column oven was 55° C.

The determination of 1H-NMR data was done with a Bruker Avance III 400 MHz spectrometer equipped with a 1.7 mm TCI probehead, with tetramethylsilane as reference (0.00 ppm) and the measurements were recorded usually from solutions in the solvents CD3CN, CDCl3 or d6-DMSO. Alternatively, a Bruker Avance III 600 MHz instrument equipped with a 5 mm CPNMP probehead or a Bruker Avance NEO 600 MHz instrument equipped with a 5 mm TCI probehead were used for the measurements. Usually the measurements were carried out with a probehead temperature of 298 K. Other measurement temperatures are explicitly noticed.

NMR Peak Lists Procedure

1H-NMR data of selected examples are written in form of 1H-NMR peak lists. □-Values in ppm and the signal intensity in round brackets are listed to each signal peak. Semicolons are depicted as delimiters between the □-value—signal intensity pairs.

Therefore the peak list of an example has the form:

$\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed view of a 1H-NMR spectrum in cm and shows the real relations of signal intensities. Several peaks from broad signals or the middle of the signal and their relative intensity in comparison to the most intensive signal in the spectrum can be shown.

Tetramethylsilane or the chemical shift of the solvent in cases where the sample does not contain tetramethylsilane is used for a calibration of the chemical shift for 1H spectra. Therefore, the tetramethylsilane peak can occur in 1H-NMR peak lists, but not necessarily.

1H-NMR peak lists are equivalent to classical 1H-NMR prints and contain usually all peaks, which are also listed at classical 1H-NMR-interpretations.

In addition, they can show signals of solvents, stereoisomers of the compounds which are optionally object of the invention, and/or peaks of impurities, like classical 1H-NMR prints.

1H-NMR solvent signals, the tetramethylsilane signal and the water signal in the corresponding solvent are excluded from the relative intensity calibration as they have very high intensity values.

On average, the peaks of stereoisomers of the compounds according to the invention and/or peaks of impurities have usually a lower intensity than the peaks of compounds according to the invention (for example with a purity >90%).

Such stereoisomers and/or impurities can be typical for the specific preparation process. Thus, the corresponding peaks can help to recognize the reproduction of the preparation process via "side-products-fingerprints".

An expert, who calculates the peaks of the target compounds with known methods (MestreC, ACD-simulation, but also with empirically evaluated expectation values), can assign the peaks of the target compounds as needed, optionally using additional intensity filters. This assignment would be similar to the usual peak picking at classical 1H-NMR interpretations.

The used solvent can be extracted from the JCAMP file with the parameter "solvent", the spectrometer frequency with "observe frequency" and the spectrometer type with "spectrometer/data system" 13C-NMR data are displayed analogous to 1H-NMR data as peak lists from broadband decoupled 13C-NMR spectra. 13C-NMR solvent signals and tetramethylsilane are excluded from the relative intensity calibration as these signals can have very high intensities.

Further details of NMR-data description with peak lists are disclosed in the publication "Citation of NMR Peaklist Data within Patent Applications" of the Research Disclosure Database Number 564025.

The compounds according to the invention described in table 1 below are likewise preferred compounds of the formula (1), wherein $R^1$ is hydrogen and X is oxygen and which are obtained according to or analogously to the preparation examples described above.

(I)

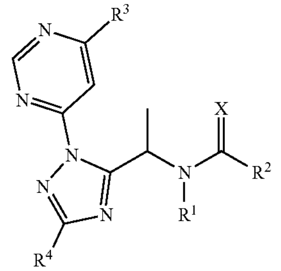

TABLE 1
| Example | Structure[1)] | NMR Peak List[2)] | ESI Mass (m/z)[3)] |
|---|---|---|---|
| I-1 | 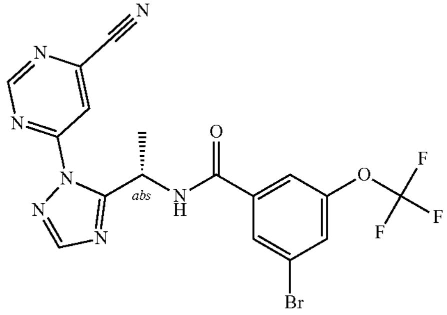 [SMILES: C[C@H](NC(=O)c1cc(Br)cc(OC(F)(F)F)c1)c1ncnn1-c1cc(C#N)ncn1] | $^1$H-NMR (400.2 MHz, $d_6$-DMSO) δ = 9.4329 (3.8); 9.4157 (3.9); 9.3849 (11.2); 9.3820 (10.9); 8.6117 (10.8); 8.6088 (10.3); 8.3605 (16.0); 8.1401 (5.5); 8.1364 (8.5); 8.1328 (5.3); 8.0040 (0.3); 7.9013 (5.6); 7.8067 (5.3); 7.8043 (5.8); 6.2097 (0.6); 6.1927 (2.6); 6.1754 (4.1); 6.1581 (2.6); 6.1409 (0.6); 5.7582 (0.5); 3.6552 (0.4); 3.3323 (68.0); 2.6774 (0.6); 2.6728 (0.9); 2.6684 (0.6); 2.5261 (3.1); 2.5125 (55.9); 2.5084 (106.6); 2.5039 (136.4); 2.4994 (100.9); 2.4951 (50.3); 2.3352 (0.6); 2.3308 (0.8); 2.3262 (0.6); 1.6421 (15.3); 1.6247 (15.2); 0.0079 (2.3); −0.0002 (57.2); −0.0084 (2.3) | 484.1 |
| I-2 | 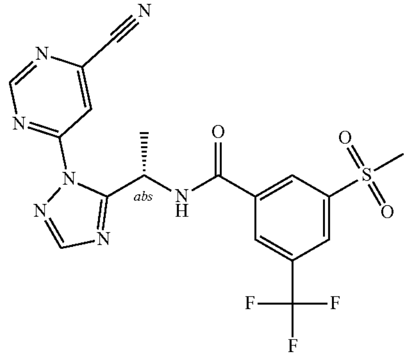 [SMILES: C[C@H](NC(=O)c1cc(C(F)(F)F)cc(S(C)(=O)=O)c1)c1ncnn1-c1cc(C#N)ncn1] | $^1$H-NMR (400.2 MHz, $d_6$-DMSO): δ = 9.7167 (3.6); 9.6994 (3.7); 9.4035 (11.3); 9.4005 (10.7); 8.6630 (7.3); 8.6243 (10.6); 8.6214 (9.7); 8.5369 (6.5); 8.4203 (6.6); 8.3804 (16.0); 6.2818 (0.5); 6.2648 (2.6); 6.2475 (4.0); 6.2301 (2.6); 6.2126 (0.5); 5.7607 (5.8); 3.3882 (38.8); 3.3325 (78.8); 2.6764 (0.8); 2.6718 (1.1); 2.6673 (0.8); 2.5252 (3.6); 2.5117 (65.5); 2.5074 (126.7); 2.5029 (163.2); 2.4984 (119.2); 2.4940 (58.0); 2.3341 (0.7); 2.3298 (1.0); 2.3254 (0.7); 1.6778 (14.9); 1.6604 (14.9); 0.0080 (1.4); −0.0002 (38.6); −0.0085 (1.4) | 466.2 |

TABLE 1-continued
| Example | Structure[1)] | NMR Peak List[2)] | ESI Mass (m/z)[3)] |
|---|---|---|---|
| I-3 | 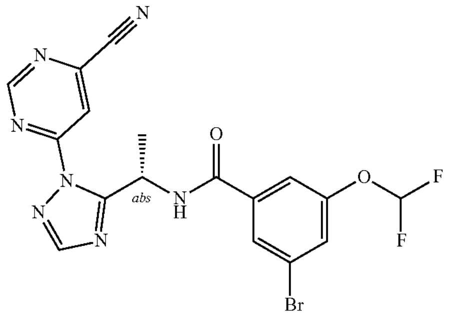 [SMILES: C[C@H](NC(=O)c1cc(Br)cc(OC(F)F)c1)c1ncnn1-c1cc(C#N)ncn1] | $^1$H-NMR (400.2 MHz, $d_6$-DMSO): δ = 9.3842 (10.8); 9.3812 (11.0); 9.3480 (3.4); 9.3307 (3.4); 8.6075 (10.9); 8.6045 (10.9); 8.3527 (16.0); 8.3154 (0.5); 7.9558 (5.0); 7.9520 (8.4); 7.9482 (5.1); 7.6476 (3.2); 7.6424 (6.6); 7.6380 (4.9); 7.6252 (5.0); 7.6221 (5.7); 7.5234 (4.1); 7.3400 (8.8); 7.1568 (4.3); 6.2026 (0.5); 6.1855 (2.4); 6.1682 (3.8); 6.1508 (2.4); 6.1334 (0.5); 3.3270 (176.3); 2.6762 (0.9); 2.6717 (1.3); 2.6670 (0.9); 2.5252 (3.9); 2.5204 (6.0); 2.5117 (78.1); 2.5072 (159.3); 2.5027 (207.6); 2.4981 (145.9); 2.4936 (68.2); 2.3385 (0.4); 2.3340 (0.9); 2.3295 (1.2); 2.3249 (0.9); 2.3204 (0.4); 2.0748 (10.8); 1.6362 (14.3); 1.6189 (14.3); 0.1459 (0.8); 0.0080 (6.5); −0.0001 (186.6); −0.0085 (6.2); −0.1496 (0.8) | 466.1 |
| I-4 | 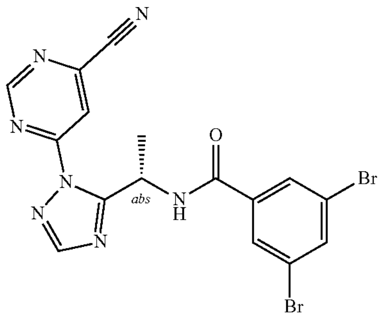 [SMILES: C[C@H](NC(=O)c1cc(Br)cc(Br)c1)c1ncnn1-c1cc(C#N)ncn1] | $^1$H-NMR (400.2 MHz, $d_6$-DMSO) δ = 9.3849 (5.5); 9.3819 (5.6); 9.3643 (1.8); 9.3470 (1.8); 8.6050 (5.3); 8.6020 (5.4); 8.3533 (8.4); 8.0367 (16.0); 6.1769 (1.3); 6.1596 (2.1); 6.1422 (1.3); 3.3288 (51.4); 2.6725 (0.4); 2.5260 (1.4); 2.5212 (2.1); 2.5125 (24.8); 2.5081 (50.5); 2.5036 (65.8); 2.4990 (46.1); 2.4994 (21.4); 2.3305 (0.4); 2.0757 (2.6); 1.6287 (8.0); 1.6114 (7.9); 0.1458 (0.6); 0.0143 (0.6); 0.0078 (4.8); −0.0002 (126.5); −0.0086 (4.2); −0.1498 (0.6) | 478.0 |
| I-5 | 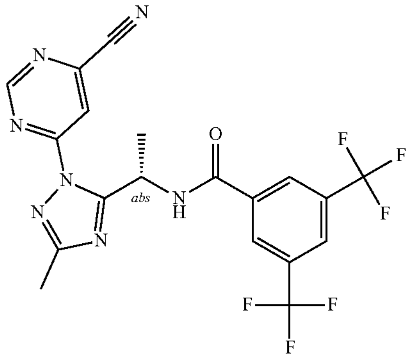 [SMILES: Cc1nc([C@H](C)NC(=O)c2cc(C(F)(F)F)cc(C(F)(F)F)c2)n(-c2cc(C#N)ncn2)n1] | $^1$H-NMR (400.2 MHz, $d_6$-DMSO) δ = 9.6507 (1.2); 9.6331 (1.2); 9.3528 (4.2); 9.3498 (4.2); 8.5251 (4.4); 8.5164 (4.4); 8.5134 (4.1); 8.3336 (1.9); 6.2483 (1.0); 6.2309 (1.6); 6.2135 (1.0); 3.3258 (38.4); 2.6769 (0.4); 2.6722 (0.5); 2.6677 (0.4); 2.5258 (1.5); 2.5211 (2.2); 2.5124 (30.8); 2.5079 (63.7); 2.5034 (83.2); 2.4987 (58.0); 2.4942 (26.7); 2.3728 (16.0); 2.3347 (0.4); 2.3301 (0.5); 2.3255 (0.4); 2.0752 (0.5); 1.6541 (5.4); 1.6367 (5.4); 0.1459 (0.7); 0.0079 (6.4); −0.0002 (175.8); −0.0086 (5.7); −0.0153 (0.6); −0.1496 (0.7) | 470.2 |

TABLE 1-continued
| Example | Structure[1)] | NMR Peak List[2)] | ESI Mass (m/z)[3)] |
|---|---|---|---|
| I-6 | 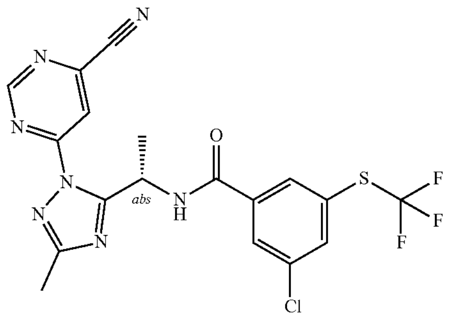 [SMILES: Cc1nc([C@H](C)NC(=O)c2cc(Cl)cc(SC(F)(F)F)c2)n(-c2cc(C#N)ncn2)n1] | $^1$H-NMR (400.2 MHz, $d_6$-DMSO) δ = 9.4418 (1.4); 9.4243 (1.5); 9.3385 (4.2); 9.3355 (4.2); 8.5101 (4.4); 8.5071 (4.3); 8.1800 (1.8); 8.1759 (3.1); 8.1714 (2.3); 8.1460 (2.9); 8.0317 (1.6); 8.0278 (2.6); 6.1913 (1.0); 6.1739 (1.7); 6.1565 (1.0); 3.3260 (38.7); 2.6765 (0.4); 2.6718 (0.5); 2.6671 (0.4); 2.5252 (1.8); 2.5204 (2.8); 2.5118 (32.5); 2.5074 (65.4); 2.5029 (84.7); 2.4983 (59.8); 2.4938 (28.3); 2.3704 (16.0); 2.3342 (0.4); 2.3296 (0.5); 2.3251 (0.4); 1.6272 (5.8); 1.6099 (5.8); 0.1458 (0.7); 0.0129 (0.9); 0.0078 (6.3); −0.0002 (154.5); −0.0086 (5.8); −0.1497 (0.7) | 468.1 |
| I-7 | 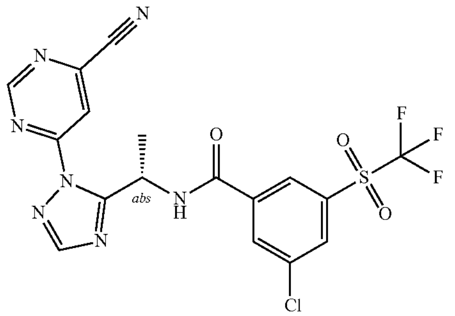 [SMILES: C[C@H](NC(=O)c1cc(Cl)cc(S(=O)(=O)C(F)(F)F)c1)c1ncnn1-c1cc(C#N)ncn1] | $^1$H-NMR (400.2 MHz, $d_6$-DMSO) δ = 9.7249 (3.1); 9.7078 (3.1); 9.3852 (11.0); 9.3821 (10.9); 8.6147 (10.5); 8.6116 (10.4); 8.5533 (4.6); 8.5491 (7.2); 8.5448 (5.4); 8.4944 (6.4); 8.4242 (3.6); 8.4201 (5.7); 8.3758 (16.0); 8.3158 (0.4); 8.1675 (0.7); 6.2561 (0.5); 6.2388 (2.3); 6.2216 (3.7); 6.2043 (2.3); 6.1869 (0.5); 3.6671 (1.3); 3.3256 (28.4); 2.6813 (0.4); 2.6768 (0.8); 2.6723 (1.1); 2.6677 (0.8); 2.6630 (0.4); 2.5258 (3.5); 2.5211 (5.2); 2.5124 (64.9); 2.5079 (134.0); 2.5033 (175.2); 2.4987 (121.7); 2.4941 (55.6); 2.3392 (0.4); 2.3347 (0.7); 2.3301 (1.0); 2.3255 (0.7); 2.3211 (0.3); 2.0752 (6.3); 1.6676 (14.0); 1.6502 (13.9); 1.4470 (0.5); 1.4288 (0.5); 0.1458 (1.5); 0.0079 (13.7); −0.0002 (377.2); −0.0086 (12.0); −0.1497 (1.5) | 486.0 |

TABLE 1-continued
| Example | Structure[1)] | NMR Peak List[2)] | ESI Mass (m/z)[3)] |
|---|---|---|---|
| I-8 | 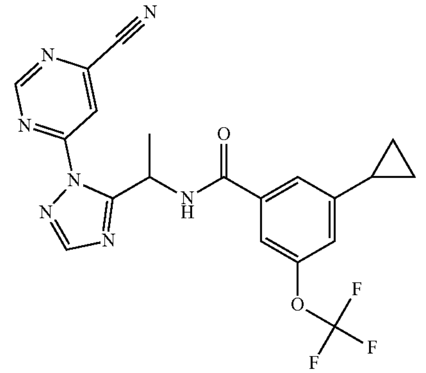 [SMILES: CC(NC(=O)c1cc(OC(F)(F)F)cc(C2CC2)c1)c1ncnn1-c1cc(C#N)ncn1] | $^1$H-NMR (400.2 MHz, $d_6$-DMSO) δ = 9.3813 (10.0); 9.3791 (10.3); 9.2542 (4.0); 9.2368 (4.1); 8.6071 (10.3); 8.6048 (10.4); 8.3493 (15.0); 7.5408 (8.3); 7.5191 (6.2); 7.2818 (6.2); 6.2015 (0.6); 6.1845 (2.7); 6.1673 (4.2); 6.1499 (2.7); 6.1326 (0.6); 3.3261 (108.4); 2.6719 (1.2); 2.6679 (1.0); 2.5072 (156.7); 2.5030 (198.3); 2.4989 (148.3); 2.3337 (0.9); 2.3298 (1.2); 2.0748 (4.9); 2.0667 (1.8); 2.0580 (1.9); 2.0457 (3.3); 2.0335 (2.0); 2.0249 (1.8); 2.0123 (0.9); 1.6437 (16.0); 1.6263 (15.9); 1.0536 (1.8); 1.0423 (5.6); 1.0368 (6.1); 1.0215 (5.7); 1.0161 (5.7); 1.0058 (2.2); 0.8029 (2.3); 0.7917 (6.9); 0.7873 (6.7); 0.7799 (6.4); 0.7750 (7.0); 0.7633 (1.9); 0.1458 (1.5); −0.0002 (288.0); −0.1497 (1.5) | 444.1 |
| I-9 | 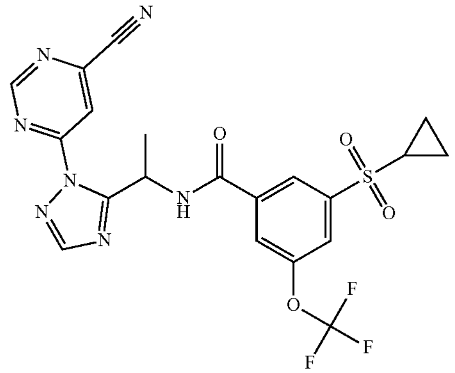 [SMILES: CC(NC(=O)c1cc(OC(F)(F)F)cc(S(=O)(=O)C2CC2)c1)c1ncnn1-c1cc(C#N)ncn1] | $^1$H-NMR (400.2 MHz, $d_6$-DMSO) δ = 9.6524 (3.5); 9.6352 (3.6); 9.3937 (10.0); 9.3907 (10.4); 8.6180 (10.4); 8.6150 (10.7); 8.4300 (4.8); 8.4264 (8.7); 8.4229 (5.0); 8.3742 (16.00); 8.1578 (5.0); 8.0682 (5.1); 6.2614 (0.5); 6.2444 (2.4); 6.2271 (3.8); 6.2098 (2.4); 6.1925 (0.5); 3.3338 (163.7); 3.0707 (0.7); 3.0589 (1.6); 3.0512 (1.7); 3.0470 (1.1); 3.0395 (3.2); 3.0311 (1.2); 3.0275 (1.8); 3.0197 (1.7); 3.0077 (0.8); 2.6775 (0.5); 2.6730 (0.7); 2.6685 (0.5); 2.5264 (2.2); 2.5215 (3.5); 2.5129 (43.2); 2.5086 (87.2); 2.0541 (113.4); 2.4995 (79.6); 2.4950 (37.2); 2.3354 (0.5); 2.3308 (0.7); 2.3264 (0.5); 2.0755 (3.4); 1.6732 (14.2); 1.6558 (14.1); 1.2468 (0.4); 1.2361 (0.6); 1.2230 (1.9); 1.2206 (1.9); 1.2115 (4.0); 1.2080 (3.7); 1.2024 (4.4); 1.1914 (2.9); 1.816 (0.9); 1.1761 (0.5); 1.1691 (0.7); 1.1555 (0.6); 1.1413 (0.7), 1.1324 (1.2); 1.1184 (4.9); 1.1124 (3.9); 1.0988 (4.7); 1.0929 (3.3); 1.0761 (0.6); 0.1457 (0.9); 0.0077 (8.0); −0.0001 (192.2); −0.0086 (6.2); −0.0150 (0.7); −0.1498 (0.9) | 508.1 |

TABLE 1-continued
| Example | Structure[1)] | NMR Peak List[2)] | ESI Mass (m/z)[3)] |
|---|---|---|---|
| I-10 | 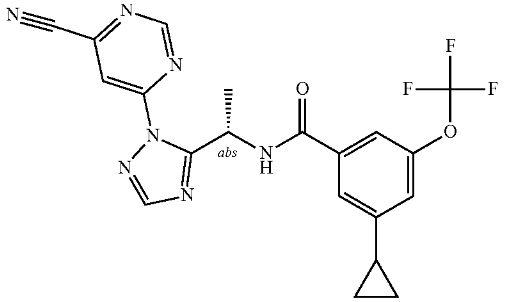 [SMILES: C[C@H](NC(=O)c1cc(OC(F)(F)F)cc(C2CC2)c1)c1ncnn1-c1cc(C#N)ncn1] | $^1$H-NMR (400.2 MHz, d6-DMSO) δ = 9.3818 (10.9); 9.3787 (10.9); 9.2543 (3.2); 9.2369 (3.2); 8.6075 (10.3); 8.6044 (10.2); 8.3585 (0.3); 8.3499 (16.0); 8.3154 (0.4); 7.5438 (3.6); 7.5404 (7.2); 7.5369 (4.7); 7.5214 (4.1); 7.5188 (4.6); 7.5163 (4.1); 7.2832 (4.5); 6.2015 (0.5); 6.1841 (2.4); 6.1667 (3.7); 6.1494 (2.4); 6.1320 (0.5); 3.3299 (205.7); 2.6812 (0.3); 2.6768 (0.7); 2.6722 (1.0); 2.6676 (0.7); 2.6631 (0.3); 2.5257 (3.2); 2.5210 (4.7); 2.5123 (61.2); 2.5078 (125.4); 2.5033 (163.8); 2.4986 (115.4); 2.4940 (53.7); 2.3346 (0.7); 2.3300 (1.0); 2.3255 (0.7); 2.3212 (0.3); 2.0796 (0.7); 2.0751 (1.0); 2.0669 (1.4); 2.0585 (1.5); 2.0546 (1.0); 2.0460 (3.0); 2.0375 (1.0); 2.0335 (1.6); 2.0251 (1.6); 2.0125 (0.8); 1.6436 (14.3); 1.6262 (14.3); 1.0539 (1.8); 1.0428 (4.9); 1.0372 (5.3); 1.0332 (2.6); 1.0267 (2.6); 1.0218 (5.1); 1.0162 (5.1); 1.0059 (2.1); 0.8031 (2.2); 0.7924 (5.6); 0.7872 (5.6); 0.7801 (5.2); 0.7749 (6.1); 0.7634 (1.8); −0.0001 (0.7) | 444.2 |
| I-11 | 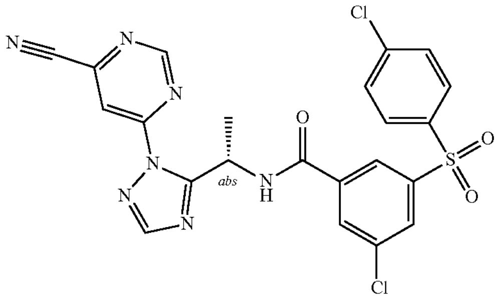 [SMILES: C[C@H](NC(=O)c1cc(Cl)cc(S(=O)(=O)c2ccc(Cl)cc2)c1)c1ncnn1-c1cc(C#N)ncn1] | $^1$H-NMR (400.2 MHz, d6-DMSO) δ = 9.5599 (3.2); 9.5428 (3.3); 9.3815 (11.3); 9.3784 (11.4); 8.6067 (11.2); 8.6036 (11.2); 8.3586 (16.0); 8.3511 (4.7); 8.3472 (8.6); 8.3434 (5.1); 8.3154 (0.9); 8.2453 (4.1); 8.2406 (8.7); 8.2362 (6.0); 8.2248 (6.2); 8.2210 (7.2); 8.2163 (3.7); 8.0834 (1.3); 8.0769 (11.8); 8.0718 (3.6); 8.0601 (3.9); 8.0549 (13.8); 8.0485 (1.5); 7.7501 (1.5); 7.7435 (13.6); 7.7385 (3.9); 7.7267 (3.6); 7.7216 (12.0); 7.7151 (1.2); 6.2206 (0.5); 6.2037 (2.2); 6.1864 (3.5); 6.1691 (2.2); 6.1517 (0.5); 3.3288 (390.4); 2.6812 (0.7); 2.6766 (1.5); 2.6720 (2.1); 2.6674 (1.5); 2.6629 (0.7); 2.5256 (7.1); 2.5209 (10.4); 2.5122 (120.2); 2.5076 (243.5); 2.5030 (322.2); 2.4984 (234.5); 2.4938 (112.7); 2.3390 (0.7); 2.3345 (1.5); 2.3299 (2.1); 2.3253 (1.5); 2.3208 (0.7); 1.6486 (13.1); 1.6312 (13.2); 0.1459 (0.9); 0.0080 (7.6); −0.0002 (239.1); −0.0085 (7.2); −0.1497 (0.9) | 529.9 |

TABLE 1-continued
| Example | Structure[1)] | NMR Peak List[2)] | ESI Mass (m/z)[3)] |
|---|---|---|---|
| I-12 | 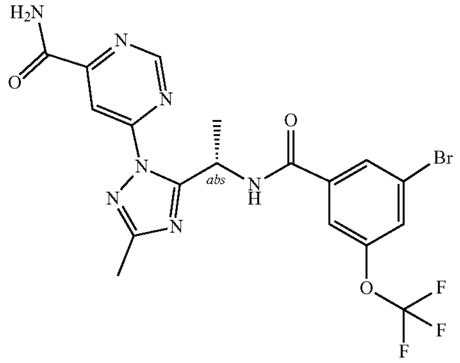 [SMILES: Cc1nc([C@H](C)NC(=O)c2cc(Br)cc(OC(F)(F)F)c2)n(-c2cc(C(N)=O)ncn2)n1] | $^1$H-NMR (400.2 MHz, d6-DMSO) δ = 9.3959 (1.4); 9.3784 (1.5); 9.2665 (4.8); 9.2636 (4.8); 8.4449 (1.4); 8.3353 (4.5); 8.3324 (4.5); 8.1541 (2.0); 8.1503 (3.3); 8.1465 (2.1); 8.1014 (1.4); 7.8981 (2.0); 7.8915 (1.8); 7.8170 (2.0); 7.8143 (1.7); 6.2486 (1.0); 6.2311 (1.6); 6.2136 (1.0); 3.3278 (444.9); 2.6796 (1.1); 2.6753 (2.3); 2.6707 (3.2); 2.6661 (2.4); 2.6616 (1.1); 2.5411 (27.6); 2.5243 (10.6); 2.5196 (16.0); 2.5108 (191.3); 2.5063 (387.0); 2.5017 (511.6); 2.4971 (375.8); 2.4926 (183.4); 2.3715 (16.0); 2.3377 (1.1); 2.3332 (2.3); 2.3286 (3.2); 2.3240 (2.3); 2.3195 (1.1); 2.0748 (0.4); 1.6333 (5.3); 1.6160 (5.3); 1.2351 (0.4); −0.0003 (6.9) | 516.1 |
| I-13 | 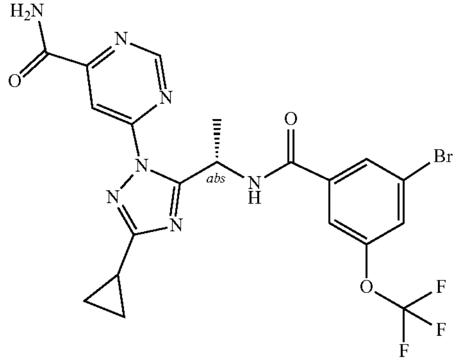 [SMILES: C[C@H](NC(=O)c1cc(Br)cc(OC(F)(F)F)c1)c1nc(C2CC2)nn1-c1cc(C(N)=O)ncn1] | $^1$H-NMR (400.2 MHz, d6-DMSO) δ = 20.0026 (0.4); 9.3634 (2.3); 9.3464 (2.5); 9.3140 (0.6); 9.2416 (6.7); 9.2388 (6.8); 8.4997 (0.4); 8.4400 (2.4); 8.3111 (6.5); 8.3083 (6.6); 8.1138 (3.9); 8.1103 (6.6); 8.1063 (5.5); 7.8937 (3.3); 7.7840 (3.4); 6.2216 (0.4); 6.2041 (1.6); 6.1865 (2.5); 6.1689 (1.7); 6.1510 (0.4); 3.5553 (0.4); 3.4791 (0.6); 3.4648 (0.6); 3.3284 (2237.4); 2.7718 (0.4); 2.7114 (0.6); 2.6797 (5.8); 2.6752 (11.6); 2.6707 (16.0); 2.6663 (11.5); 2.6250 (0.8); 2.5411 (94.1); 2.5241 (55.4); 2.5193 (84.3); 2.5017 (980.0); 2.5063 (1931.7); 2.5017 (2518.6); 2.4972 (1852.3); 2.4928 (912.2); 2.3677 (0.6); 2.3376 (5.3); 2.3330 (11.4); 2.3286 (15.5); 2.3241 (11.2); 2.2877 (0.4); 2.1294 (0.5); 2.1171 (0.9); 2.1088 (1.0); 2.0967 (2.1); 2.0841 (1.2); 2.0748 (6.3); 2.0632 (0.6); 1.6170 (8.6); 1.5996 (8.8); 1.5843 (0.8); 1.2377 (0.6); 1.0313 (3.0); 1.0259 (3.9); 1.0105 (3.0); 1.0049 (3.7); 0.9780 (0.4); 0.9377 (0.6); 0.9139 (2.2); 0.9017 (2.3); 0.8961 (1.9); 0.8898 (2.0); 0.8781 (1.8); 0.8548 (0.5); −0.0001 (23.4) | 542.1 |

TABLE 1-continued
| Example | Structure[1)] | NMR Peak List[2)] | ESI Mass (m/z)[3)] |
|---|---|---|---|
| I-14 | 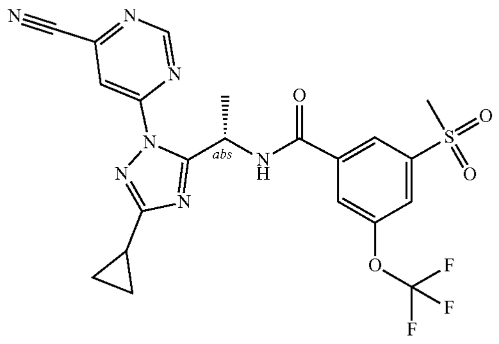 [SMILES: C[C@H](NC(=O)c1cc(OC(F)(F)F)cc(S(C)(=O)=O)c1)c1nc(C2CC2)nn1-c1cc(C#N)ncn1] | $^1$H-NMR (400.2 MHz, d6-DMSO) δ = 9.5757 (4.2); 9.5583 (4.3); 9.3249 (12.7); 9.3219 (12.8); 8.5081 (12.7); 8.5051 (12.8); 8.4375 (5.7); 8.4338 (10.2); 8.4303 (5.7); 8.2566 (0.8); 8.1247 (6.0); 8.0917 (6.0); 8.0363 (0.4); 7.9612 (0.5); 6.2023 (0.6); 6.1850 (3.0); 6.1677 (4.8); 6.1504 (3.0); 6.1324 (0.7); 3.6174 (0.3); 3.5864 (0.3); 3.5563 (0.3); 3.5337 (0.5); 3.4975 (0.5); 3.4576 (0.9); 3.4353 (1.0); 3.4012 (2.4); 3.3617 (53.1); 3.3548 (13.9); 3.3303 (1555.9); 2.7105 (0.3); 2.6797 (4.0); 2.6754 (8.5); 2.6709 (13.3); 2.6663 (8.8); 2.6619 (4.1); 2.6421 (0.6); 2.6412 (14.4); 2.5244 (38.1); 2.5196 (57.5); 2.5109 (678.0); 2.5065 (1359.2); 2.5019 (1787.4); 2.4973 (1317.9); 2.4928 (648.3); 2.4141 (0.5); 2.3378 (3.6); 2.3332 (8.0); 2.3287 (11.1); 2.3241 (7.9); 2.3196 (3.8); 2.2591 (1.0); 2.1110 (0.8); 2.0992 (1.8); 2.0905 (2.0); 2.0785 (3.9); 2.0748 (3.0); 2.0661 (2.3); 2.0577 (2.1); 2.0459 (1.0); 1.6294 (16.0); 1.6121 (16.0); 1.5865 (0.4); 1.4072 (0.8); 1.3906 (0.7); 1.3307 (1.6); 1.2362 (0.4); 1.2064 (1.7); 1.1848 (1.8); 1.1674 (0.6); 1.0666 (0.5); 1.0568 (0.6); 1.0395 (5.3); 1.0344 (7.1); 1.0189 (5.5); 1.0135 (7.0); 0.9975 (0.9); 0.9880 (0.6); 0.9690 (0.3); 0.9539 (1.0); 0.9416 (1.2); 0.9298 (4.0); 0.9236 (2.3); 0.9174 (4.7); 0.9117 (3.3); (0.8); −0.0002 (10.8); −0.0090 (0.4) | 522.2 |
| I-15 | 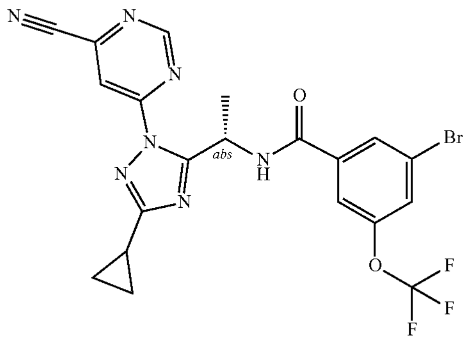 [SMILES: C[C@H](NC(=O)c1cc(Br)cc(OC(F)(F)F)c1)c1nc(C2CC2)nn1-c1cc(C#N)ncn1] | $^1$H-NMR (400.2 MHz, d6-DMSO) δ = 9.3743 (4.0); 9.3569 (4.1); 9.3147 (12.7); 9.3116 (12.7); 8.5002 (13.1); 8.4972 (12.9); 8.1184 (5.6); 8.1146 (9.3); 8.1108 (5.8); 7.9001 (5.7); 7.7899 (5.2); 7.7873 (5.8); 7.7848 (5.0); 6.1512 (0.6); 6.1340 (3.0); 6.1166 (4.7); 6.0992 (3.0); 6.0820 (0.6); 3.3286 (314.1); 2.6804 (0.7); 2.6760 (1.5); 2.6714 (2.1); 2.6668 (1.5); 2.6622 (0.7); 2.5418 (3.9); 2.5249 (6.8); 2.5202 (10.6); 2.5112 (125.6); 2.5070 (253.7); 2.5024 (335.2); 2.4978 (247.8); 2.4933 (122.4); 2.3384 (0.7); 2.3338 (1.5); 2.3293 (2.1); 2.3247 (1.5); 2.3203 (0.7); 2.1075 (0.8); 2.0953 (1.8); 2.0866 (2.0); 2.0837 (1.5); 2.0749 (4.2); 2.0626 (2.2); 2.0540 (2.0); 2.0418 (1.0); 1.6026 (16.0); 1.5852 (16.0); 1.0381 (4.5); 1.0320 (6.8); 1.0174 (4.2); 1.0112 (7.2); 0.9907 (0.6); 0.9860 (0.6); 0.9487 (1.0); 0.9364 (1.1); 0.9251 (2.8); | 524.1 |

TABLE 1-continued
| Ex-am-ple | Structure[1)] | NMR Peak List[2)] | ESI Mass (m/z)[3)] |
|---|---|---|---|
| | | 0.9223 (2.6); 0.9131 (3.0); 0.9099 (2.6); 0.9013 (2.0); 0.8964 (2.8); 0.8891 (2.1); 0.8843 (2.6); 0.8672 (1.2); 0.8585 (0.8); −0.0002 (4.5) | |
| I-16 | 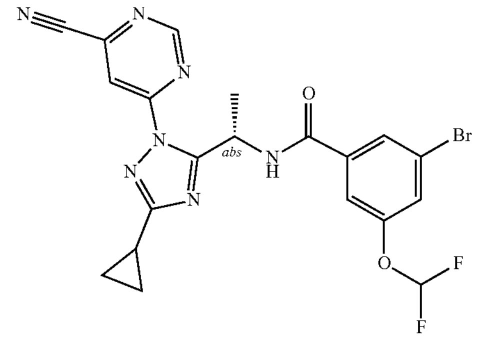 [SMILES: C[C@H](NC(=O)c1cc(Br)cc(OC(F)F)c1)c1nc(C2CC2)nn1-c1cc(C#N)ncn1] | $^1$H-NMR (400.2 MHz, d6-DMSO) δ = 9.3156 (13.1); 9.3126 (13.3); 9.2969 (4.1); 9.2795 (4.1); 8.4994 (13.7); 8.4963 (13.6); 7.9405 (5.8); 7.9367 (9.8); 7.9329 (6.0); 7.6477 (4.1); 7.6425 (7.6); 7.6379 (5.3); 7.6139 (5.4); 7.6106 (6.3); 7.5251 (4.9); 7.3418 (10.5); 7.1584 (5.2); 6.1463 (0.6); 6.1292 (3.0); 6.1118 (4.8); 6.0944 (3.0); 6.0769 (0.6); 3.3314 (831.0); 2.6801 (1.6); 2.6755 (3.4); 2.6710 (4.8); 2.6664 (3.5); 2.6618 (1.6); 2.5858 (0.4); 2.5414 (12.7); 2.5245 (15.2); 2.5198 (23.0); 2.5110 (283.6); 2.5066 (572.0); 2.5020 (754.0); 2.4974 (554.9); 2.4928 (272.0); 2.3378 (1.5); 2.3334 (3.4); 2.3288 (4.6); 2.3243 (3.4); 2.3199 (1.6); 2.1048 (0.8); 2.0926 (1.8); 2.0839 (2.0); 2.0810 (1.6); 2.0720 (3.8); 2.0599 (2.1); 2.0512 (2.0); 2.0390 (1.0); 1.6171 (0.4); 1.5970 (16.0); 1.5796 (15.9); 1.2307 (0.5); 1.2130 (0.9); 1.1957 (0.4); 1.0636 (0.3); 1.0370 (4.6); 1.0307 (7.1); 1.0163 (4.5); 1.0099 (7.4); 0.9899 (0.7); 0.9847 (0.6); 0.9471 (1.0); 0.9347 (1.1); 0.9235 (2.9); 0.9115 (3.1); 0.9082 (2.6); 0.9054 (2.2); 0.9003 (2.0); 0.8953 (2.8); 0.8883 (2.1); 0.8833 (2.5); 0.8659 (1.2); 0.8575 (0.8); −0.0002 (5.3) | 506.1 |
| I-17 | 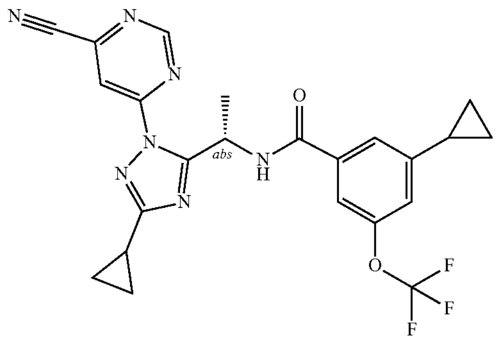 [SMILES: C[C@H](NC(=O)c1cc(OC(F)(F)F)cc(C2CC2)c1)c1nc(C2CC2)nn1-c1cc(C#N)ncn1] | $^1$H-NMR (400.2 MHz, d6-DMSO) δ = 9.3142 (12.4); 9.3112 (12.4); 9.2051 (3.9); 9.1875 (4.0); 8.5007 (12.4); 8.4977 (12.1); 7.5147 (8.5); 7.5111 (6.1); 7.5018 (5.0); 7.4992 (5.6); 7.2856 (5.5); 6.1397 (0.6); 6.1222 (2.9); 6.1048 (4.7); 6.0873 (3.0); 6.0699 (0.6); 3.3319 (423.1); 2.6804 (0.8); 2.6760 (1.7); 2.6714 (2.4); 2.6668 (1.7); 2.6624 (0.8); 2.5418 (2.0); 2.5249 (7.8); 2.5202 (11.4); 2.5115 (140.5); 2.5070 (283.2); 2.5025 (373.3); 2.4978 (272.5); 2.4933 (132.3); 2.3384 (0.7); 2.3338 (1.6); 2.3293 (2.3); 2.3247 (1.7); 2.3203 (0.7); 2.1035 (0.8); 2.0914 (1.8); 2.0825 (2.1); 2.0796 (2.2); 2.0751 (1.3); 2.0706 (4.0); 2.0585 (3.9); 2.0498 (2.6); 2.0462 (3.7); 2.0377 (2.2); 2.0337 (2.1); 2.0251 (1.8); 2.0126 (0.9); 1.6027 (16.0); 1.5853 (15.9); 1.0552 (2.2); 1.0440 (6.1); 1.0383 (9.3); 1.0349 (7.1); 1.0284 (9.2); 1.0232 (6.9); 1.0175 (8.9); 1.0076 (8.8); 0.9822 (0.8); 0.9755 (0.3); 0.9467 (1.2); 0.9346 (1.2); 0.9235 | 484.3 |

TABLE 1-continued
| Example | Structure[1)] | NMR Peak List[2)] | ESI Mass (m/z)[3)] |
|---|---|---|---|
| | | (2.6); 0.9172 (3.3); 0.9114 (2.7); 0.9052 (2.2); 0.8925 (1.8); 0.8865 (2.2); 0.8806 (2.0); 0.8747 (2.0); 0.8587 (1.3); 0.8496 (0.8); 0.8024 (2.5); 0.7917 (6.5); 0.7865 (6.4); 0.7794 (6.0); 0.7743 (7.0); 0.7628 (2.0); −0.0002 (2.0) | |
| I-18 | 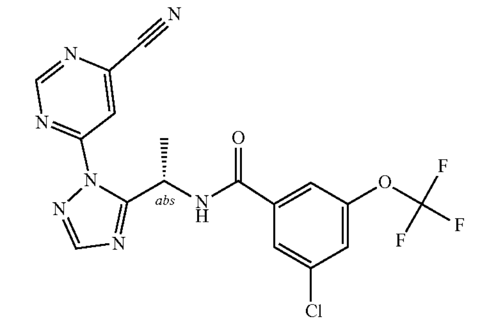 [SMILES: C[C@H](NC(=O)c1cc(Cl)cc(OC(F)(F)F)c1)c1ncnn1-c1cc(C#N)ncn1] | $^1$H-NMR (400.2 MHz, d6-DMSO) δ = 9.4262 (3.4); 9.4091 (3.4); 9.3830 (10.8); 9.3800 (10.8); 8.6086 (10.7); 8.6055 (10.7); 8.3586 (16.0); 8.3154 (0.3); 8.0062 (4.9); 8.0021 (7.7); 7.9981 (5.2); 7.7920 (5.0); 7.7897 (4.3); 7.7784 (5.3); 7.7758 (5.1); 6.2215 (0.5); 6.1942 (2.4); 6.1769 (3.8); 6.1596 (2.4); 6.1423 (0.5); 3.3302 (152.2); 2.6772 (0.6); 2.6727 (0.9); 2.6681 (0.6); 2.5261 (2.9); 2.5214 (4.4); 2.5127 (50.9); 2.5082 (101.8); 2.5037 (133.0); 2.4991 (96.4); 2.4945 (46.6); 2.3350 (0.6); 2.3305 (0.8); 2.3259 (0.6); 2.0754 (1.6); 1.6443 (14.5); 1.6269 (14.5); 0.1459 (0.4); 0.0080 (3.4); −0.0002 (97.5); −0.0085 (3.1); −0.1496 (0.4) | 438.3 |
| I-19 | 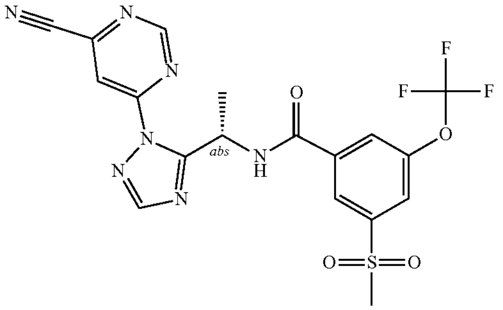 [SMILES: C[C@H](NC(=O)c1cc(OC(F)(F)F)cc(S(C)(=O)=O)c1)c1ncnn1-c1cc(C#N)ncn1] | $^1$H-NMR (400.2 MHz, d6-DMSO) δ = 9.6308 (3.4); 9.6135 (3.5); 9.3943 (10.8); 9.3913 (10.7); 8.6163 (10.4); 8.6133 (10.1); 8.4610 (5.0); 8.4574 (8.8); 8.4538 (5.0); 8.3722 (16.0); 8.3150 (0.4); 8.1430 (5.1); 8.1408 (4.8); 8.0930 (5.1); 6.2604 (0.5); 6.2432 (2.5); 6.2259 (3.9); 6.2086 (2.5); 6.1914 (0.5); 3.3605 (40.3); 3.3288 (181.2); 2.6813 (0.4); 2.6766 (0.8); 2.6720 (1.1); 2.6674 (0.8); 2.6629 (0.4); 2.5255 (4.0); 2.5207 (6.2); 2.5120 (68.8); 2.5076 (135.7); 2.5030 (176.0); 2.4984 (127.4); 2.4940 (61.5); 2.3388 (0.4); 2.3344 (0.8); 2.3298 (1.1); 2.3523 (0.8); 2.3212 (0.4); 2.0749 (2.8); 1.6699 (14.5); 1.6525 (14.4); 0.1459 (0.5); 0.0080 (4.5); −0.0001 (125.2); −0.0085 (4.2); −0.1496 (0.5) | 482.3 |

TABLE 1-continued
| Example | Structure[1)] | NMR Peak List[2)] | ESI Mass (m/z)[3)] |
|---|---|---|---|
| I-20 | 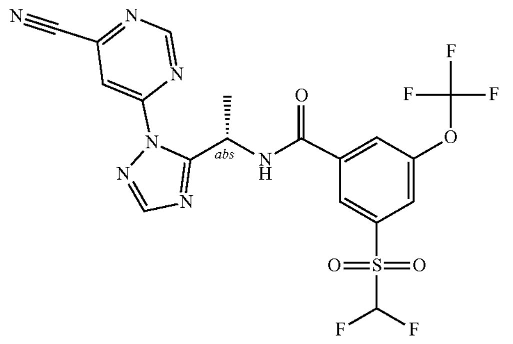 [SMILES: C[C@H](NC(=O)c1cc(OC(F)(F)F)cc(S(=O)(=O)C(F)F)c1)c1ncnn1-c1cc(C#N)ncn1] | $^{1}$H-NMR (400.2 MHz, d6-DMSO) δ = 9.7622 (1.9); 9.7452 (1.9); 9.3852 (6.1); 9.3821 (6.1); 8.6170 (6.1); 8.6139 (5.9); 8.5062 (2.4); 8.5027 (4.4); 8.4992 (2.6); 8.3761 (11.7); 8.3151 (0.4); 8.1312 (2.9); 7.5752 (1.6); 7.4454 (3.8); 7.3156 (1.9); 6.2450 (1.3); 6.2277 (2.1); 6.2104 (1.4); 3.3281 (177.6); 2.6806 (0.4); 2.6763 (0.9); 2.6717 (1.2); 2.6671 (0.9); 2.6627 (0.4); 2.5252 (4.2); 2.5204 (6.4); 2.5118 (71.1); 2.5073 (141.5); 2.5027 (185.2); 2.4981 (134.0); 2.4936 (64.3); 2.3387 (0.4); 2.3341 (0.8); 2.3296 (1.2); 2.3250 (0.8); 2.3205 (0.4); 2.0746 (16.0); 1.6727 (8.0); 1.6553 (8.0); 0.1459 (0.6); 0.0080 (4.7); −0.0002 (131.8); −0.0085 (4.0); −0.1496 (0.5) | 518.2 |
| I-21 | 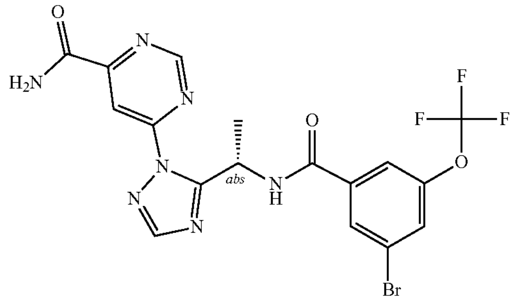 [SMILES: C[C@H](NC(=O)c1cc(Br)cc(OC(F)(F)F)c1)c1ncnn1-c1cc(C(N)=O)ncn1] | $^{1}$H-NMR (400.2 MHz, d6-DMSO) δ = 9.5390 (0.8); 9.4133 (3.4); 9.3960 (3.5); 9.3090 (11.0); 9.3061 (10.7); 9.2678 (0.5); 9.2648 (0.5); 8.4638 (3.5); 8.3793 (10.9); 8.3764 (10.5); 8.3188 (16.0); 8.2688 (0.5); 8.2659 (0.5); 8.2025 (0.4); 8.1316 (6.7); 8.1279 (11.0); 8.1242 (8.0); 7.9941 (0.4); 7.9094 (0.4); 7.8904 (4.9); 7.8008 (4.5); 7.7982 (4.9); 7.7956 (4.1); 6.2715 (0.5); 6.2546 (2.4); 6.2373 (3.7); 6.2199 (2.4); 6.2024 (0.5); 3.3268 (228.4); 2.6807 (0.7); 2.6765 (1.6); 2.6719 (2.1); 2.6673 (1.5); 2.6629 (0.7); 2.5254 (7.5); 2.5206 (11.6); 2.5120 (129.2); 2.5075 (253.5); 2.5030 (326.9); 2.4984 (235.3); 2.4939 (112.8); 2.3388 (0.7); 2.3343 (1.5); 2.3298 (2.1); 2.3253 (1.5); 2.3208 (0.7); 1.6561 (13.6); 1.6387 (14.1); 1.6200 (0.8); 1.4027 (0.4); 1.3847 (0.4); 0.1459 (0.9); 0.0079 (8.3); −0.0002 (231.3); −0.0086 (7.8); −0.1496 (1.0) | 502.2 |

TABLE 1-continued
| Example | Structure[1)] | NMR Peak List[2)] | ESI Mass (m/z)[3)] |
| --- | --- | --- | --- |
| I-22 | 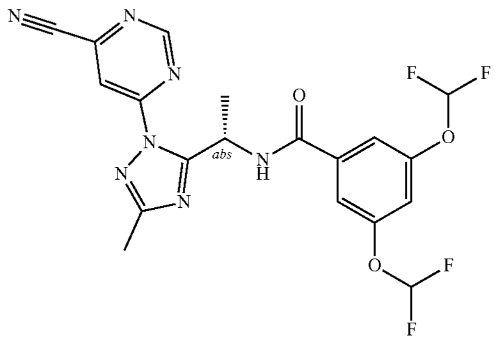 [SMILES: Cc1nc([C@H](C)NC(=O)c2cc(OC(F)F)cc(OC(F)F)c2)n(-c2cc(C#N)ncn2)n1] | $^1$H-NMR (400.2 MHz, d6-DMSO) δ = 9.3395 (4.4); 9.3364 (4.4); 9.3016 (1.2); 9.2842 (1.3); 8.5075 (4.2); 8.5045 (4.1); 7.5559 (5.4); 7.5504 (5.5); 7.5179 (3.1); 7.3346 (6.5); 7.2434 (1.4); 7.2379 (2.5); 7.2324 (1.2); 7.1512 (3.2); 6.1842 (1.0); 6.1668 (1.6); 6.1494 (1.0); 5.7544 (0.6); 3.3770 (269.2); 2.5449 (1.4); 2.5281 (0.8); 2.5234 (1.2); 2.5147 (17.9); 2.5102 (36.3); 2.5056 (47.4); 2.5010 (33.7); 2.4965 (15.7); 2.3671 (16.0); 1.6256 (5.3); 1.6082 (5.3); 0.0080 (0.4); −0.0002 (11.2) | 466.2 |
| I-23 | 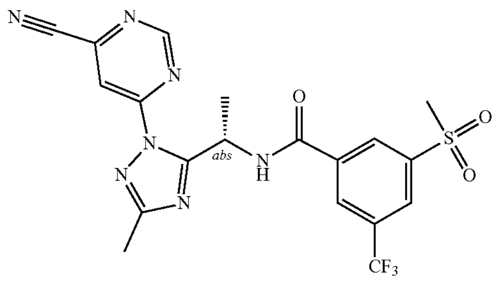 [SMILES: Cc1nc([C@H](C)NC(=O)c2cc(C(F)(F)F)cc(S(C)(=O)=O)c2)n(-c2cc(C#N)ncn2)n1] | $^1$H-NMR (400.2 MHz, d6-DMSO) δ = 9.6951 (1.4); 9.6774 (1.5); 9.3593 (4.1); 9.3563 (4.3); 8.6824 (2.7); 8.5544 (2.4); 8.5203 (4.1); 8.5173 (4.2); 8.4167 (2.4); 6.2593 (1.0); 6.2419 (1.6); 6.2244 (1.0); 5.7587 (0.4); 3.3889 (15.6); 3.3300 (42.1); 2.6716 (0.4); 2.5251 (1.0); 2.5203 (1.7); 2.5117 (23.0); 2.5072 (46.4); 2.5027 (61.0); 2.4981 (43.8); 2.4935 (20.7); 2.3761 (16.0); 2.3295 (0.4); 1.6571 (5.6); 1.6397 (5.6); 0.0080 (0.4); −0.0002 (11.5); −0.0085 (0.3) | 480.1 |
| I-24 | 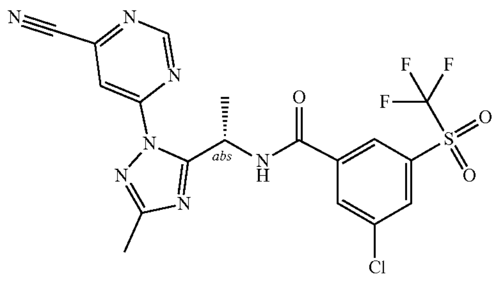 [SMILES: Cc1nc([C@H](C)NC(=O)c2cc(Cl)cc(S(=O)(=O)C(F)(F)F)c2)n(-c2cc(C#N)ncn2)n1] | $^1$H-NMR (400.2 MHz, d6-DMSO) δ = 9.7115 (1.3); 9.6941 (1.3); 9.3431 (4.2); 9.3401 (4.3); 8.5683 (1.8); 8.5641 (2.8); 8.5598 (2.1); 8.5155 (4.4); 8.5126 (5.5); 8.5092 (2.8); 8.4297 (1.4); 8.4257 (2.3); 6.2287 (1.0); 6.2114 (1.5); 6.1940 (1.0); 5.7589 (1.6); 3.3307 (51.9); 2.6764 (0.3); 2.6719 (0.4); 2.5254 (1.3); 2.5208 (2.0); 2.5120 (27.2); 2.5075 (55.3); 2.5029 (73.1); 2.4983 (52.5); 2.4938 (24.8); 2.3767 (16.0); 2.3343 (0.3); 2.3297 (0.4); 2.3250 (0.3); 1.6450 (5.3); 1.6276 (5.3); 0.0080 (0.5); −0.0002 (15.9); −0.0085 (0.4) | 500.0 |

TABLE 1-continued
| Example | Structure[1)] | NMR Peak List[2)] | ESI Mass (m/z)[3)] |
|---|---|---|---|
| I-25 | 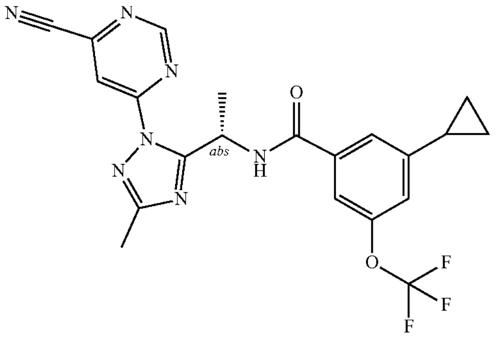 [SMILES: Cc1nc([C@H](C)NC(=O)c2cc(OC(F)(F)F)cc(C3CC3)c2)n(-c2cc(C#N)ncn2)n1] | $^1$H-NMR (400.2 MHz, d6-DMSO) δ = 9.3381 (3.8); 9.3353 (3.8); 9.2378 (1.5); 9.2201 (1.5); 8.5082 (3.6); 8.5058 (3.7); 7.5582 (3.0); 7.5388 (2.1); 7.2895 (2.1); 6.1733 (1.0); 6.1558 (1.6); 6.1384 (1.0); 5.7575 (0.9); 3.3562 (59.1); 3.3542 (60.0); 3.3509 (68.8); 3.3445 (109.7); 3.2884 (0.5); 2.6770 (0.3); 2.6727 (0.4); 3.2884 (0.5); 2.6770 (0.3); 2.6727 2.5337 (0.4); 2.5256 (1.5); 2.5209 (2.3); 2.5126 (28.8); 2.5082 (56.8); 2.5037 (73.2); 2.4990 (52.2); 2.4945 (24.5); 2.4850 (1.0); 2.4796 (0.5); 2.3655 (16.0); 2.3350 (0.3); 2.3305 (0.4); 2.3262 (0.3); 2.0691 (0.6); 2.0607 (0.7); 2.0482 (1.2); 2.0358 (0.7); 2.0275 (0.6); 1.6226 (5.8); 1.6052 (5.8); 1.0554 (0.7); 1.0442 (2.1); 1.0386 (2.3); 1.0349 (1.0); 1.0282 (1.1); 1.0233 (2.2); 1.0178 (2.2); 1.0076 (0.8); 0.8054 (0.8); 0.7949 (2.3); 0.7896 (2.2); 0.7826 (2.2); 0.7775 (2.3); 0.7662 (0.7); −0.0002 (2.9) | 458.2 |
| I-26 | 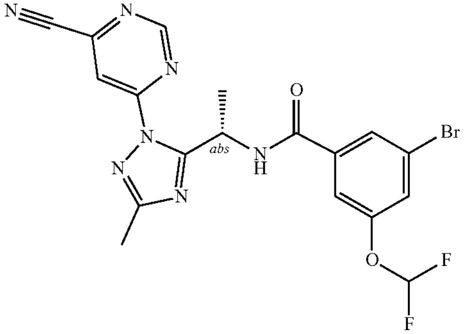 [SMILES: Cc1nc([C@H](C)NC(=O)c2cc(Br)cc(OC(F)F)c2)n(-c2cc(C#N)ncn2)n1] | $^1$H-NMR (400.2 MHz, d6-DMSO) δ = 9.3423 (3.9); 9.3393 (4.2); 9.2395 (1.4); 9.3120 (1.4); 8.5086 (3.7); 8.5056 (4.0); 7.9762 (1.8); 7.9725 (3.2); 7.9687 (1.9); 7.6529 (0.8); 7.6476 (2.9); 7.6433 (4.6); 7.5267 (1.4); 7.3435 (2.9); 7.1601 (1.4); 6.1755 (1.0); 6.1581 (1.6); 6.1406 (1.0); 5.7584 (1.2); 3.3414 (31.8); 3.3324 (50.9); 2.6718 (0.4); 2.5253 (1.2); 2.5204 (2.0); 2.5119 (25.4); 2.5074 (51.4); 2.5028 (67.5); 2.4981 (48.3); 2.4936 (22.6); 2.3670 (16.0); 2.3297 (0.4); 1.6155 (5.6); 1.5981 (5.6); 0.0080 (0.4); −0.0002 (12.5); −0.0086 (0.3) | 480.0 |
| I-27 | 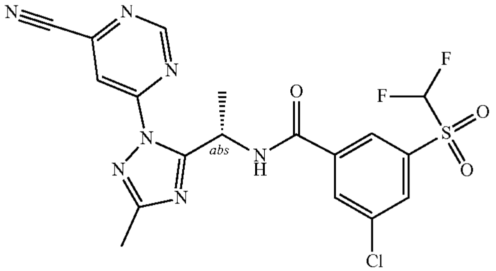 [SMILES: Cc1nc([C@H](C)NC(=O)c2cc(Cl)cc(S(=O)(=O)C(F)F)c2)n(-c2cc(C#N)ncn2)n1] | $^1$H-NMR (400.2 MHz, d6-DMSO) δ = 9.6643 (1.3); 9.6468 (1.4); 9.3446 (4.0); 9.3416 (4.1); 8.5143 (3.8); 8.5114 (3.9); 8.4481 (1.8); 8.4839 (3.0); 8.4796 (2.0); 8.3942 (1.8); 8.3905 (3.1); 8.3869 (1.7); 8.1993 (1.8); 8.1949 (3.0); 8.1905 (1.6); 7.5507 (1.0); 7.4209 (2.3); 7.2910 (1.2); 6.2230 (1.0); 6.2057 (1.6); 6.1883 (1.0); 5.7586 (0.4); 3.3375 (29.5); 2.5271 (0.6); 2.5223 (0.9); 2.5137 (12.5); 2.5092 (25.1); 2.5047 (32.8); 2.5000 (23.5); 2.4955 (11.1); 2.3762 (16.0); 1.6415 (5.5); 1.6241 (5.5); −0.0002 (6.4) | 482.0 |

TABLE 1-continued
| Example | Structure[1)] | NMR Peak List[2)] | ESI Mass (m/z)[3)] |
|---|---|---|---|
| I-28 | 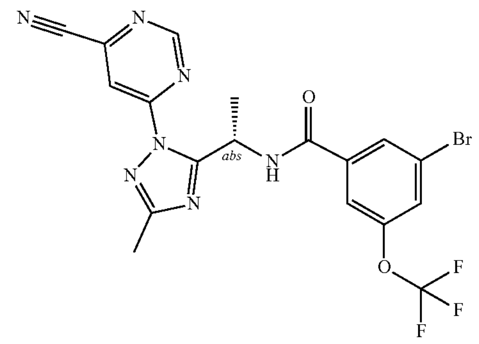 [SMILES: Cc1nc([C@H](C)NC(=O)c2cc(Br)cc(OC(F)(F)F)c2)n(-c2cc(C#N)ncn2)n1] | $^1$H-NMR (400.2 MHz, d6-DMSO) δ = 9.4111 (1.3); 9.3935 (1.3); 9.3412 (4.2); 9.3382 (4.2); 8.5094 (4.0); 8.5064 (4.0); 8.1590 (1.8); 8.1551 (3.1); 8.1513 (1.9); 7.9054 (1.8); 7.8232 (1.7); 7.8206 (1.9); 7.8181 (1.6); 6.1819 (1.0); 6.1645 (1.6); 6.1471 (1.0); 5.7585 (0.7); 3.3358 (132.4); 2.6721 (0.4); 2.6675 (0.3); 2.5256 (1.3); 2.5208 (1.9); 2.5122 (26.9); 2.5077 (54.9); 2.5031 (72.6); 2.4985 (52.2); 2.4940 (24.8); 2.3695 (16.0); 2.3300 (0.4); 1.6210 (5.4); 1.6036 (5.4); −0.0002 (9.8) | 498.0 |
| I-29 | 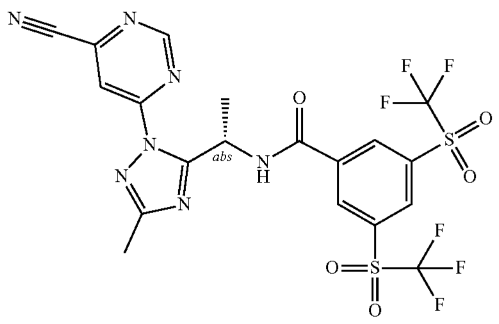 [SMILES: Cc1nc([C@H](C)NC(=O)c2cc(S(=O)(=O)C(F)(F)F)cc(S(=O)(=O)C(F)(F)F)c2)n(-c2cc(C#N)ncn2)n1] | $^1$H-NMR (400.2 MHz, d6-DMSO) δ = 10.0778 (1.3); 10.0602 (1.3); 9.3503 (4.4); 9.3472 (4.5); 9.1273 (5.8); 9.1232 (5.9); 8.6708 (2.3); 8.5271 (4.4); 8.5241 (4.4); 6.3007 (1.0); 6.2833 (1.5); 6.2659 (1.0); 5.7585 (3.0); 4.0016 (0.9); 3.3303 (60.4); 2.6763 (0.4); 2.6717 (0.6); 2.6671 (0.4); 2.5421 (5.0); 2.5252 (1.6); 2.5204 (2.5); 2.5118 (34.3); 2.5073 (69.6); 2.5027 (91.8); 2.4981 (65.9); 2.4936 (31.1); 2.3846 (16.0); 2.3341 (0.4); 2.3295 (0.5); 2.3249 (0.4); 1.6776 (5.3); 1.6603 (5.3); 0.0080 (0.6); −0.0002 (20.3); −0.0085 (0.6) | 598.0 |
| I-30 | 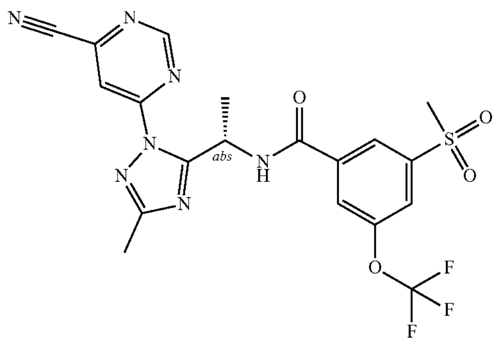 [SMILES: Cc1nc([C@H](C)NC(=O)c2cc(OC(F)(F)F)cc(S(C)(=O)=O)c2)n(-c2cc(C#N)ncn2)n1] | $^1$H-NMR (400.2 MHz, d6-DMSO) δ = 9.6164 (1.3); 9.5988 (1.4); 9.3521 (3.9); 9.3491 (3.9); 8.5172 (3.6); 8.5142 (3.6); 8.4799 (1.7); 8.4763 (3.2); 8.4727 (1.8); 8.1590 (1.8); 8.0951 (1.9); 6.2352 (1.0); 6.2177 (1.5); 6.2003 (1.0); 5.7583 (0.5); 3.3654 (15.5); 3.3401 (29.2); 3.3324 (39.5); 2.6720 (0.4); 2.5255 (1.1); 2.5208 (1.6); 2.5121 (22.5); 2.5076 (45.9); 2.5030 (60.5); 2.4984 (43.1); 2.4938 (20.1); 2.3755 (16.0); 2.3298 (0.4); 1.6481 (5.3); 1.6307 (5.3); 0.0080 (0.4); −0.0002 (12.6); −0.0086 (0.4) | 496.1 |

TABLE 1-continued
| Example | Structure[1)] | NMR Peak List[2)] | ESI Mass (m/z)[3)] |
|---|---|---|---|
| I-31 | 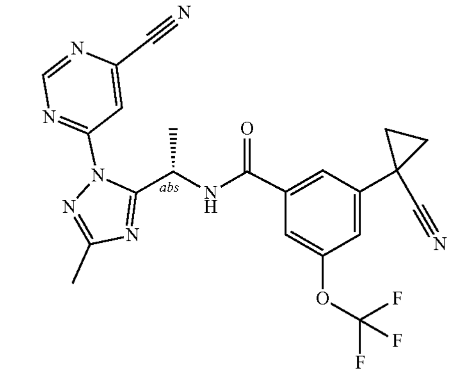 [SMILES: Cc1nc([C@H](C)NC(=O)c2cc(OC(F)(F)F)cc(C3(C#N)CC3)c2)n(-c2cc(C#N)ncn2)n1] | $^1$H-NMR (400.2 MHz, d6-DMSO) δ = 9.4118 (3.3); 9.3946 (3.6); 9.3857 (11.3); 9.3826 (11.2); 8.6108 (10.7); 8.6078 (10.5); 8.3618 (16.0); 7.8314 (4.4); 7.8276 (7.6); 7.8237 (4.8); 7.7452 (4.3); 7.7427 (4.9); 7.7402 (4.4); 7.4826 (4.9); 6.2248 (0.5); 6.2075 (2.4); 6.1902 (3.7); 6.1729 (2.4); 6.1553 (0.5); 3.8920 (0.9); 3.3313 (131.1); 3.2414 (1.0); 3.2243 (0.9); 2.6772 (0.6); 2.6726 (0.8); 2.6680 (0.6); 2.5261 (3.0); 2.5213 (4.5); 2.5127 (50.4); 2.5082 (100.3); 2.5036 (130.8); 2.4990 (94.6); 2.4945 (45.1); 2.3351 (0.6); 2.3305 (0.8); 2.3259 (0.6); 2.0758 (10.2); 1.8577 (2.6); 1.8456 (7.1); 1.8380 (7.9); 1.8267 (3.4); 1.7866 (0.4); 1.7032 (0.5); 1.6636 (6.1); 1.6584 (15.1); 1.6518 (9.5); 1.6412 (15.8); 1.6316 (3.5); 0.0080 (0.8); −0.0002 (22.7); −0.0085 (0.6) | 469.4 |
| I-32 | 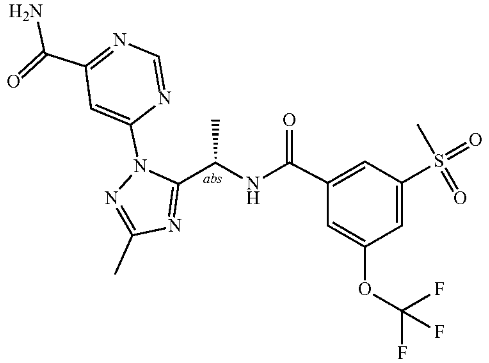 [SMILES: Cc1nc([C@H](C)NC(=O)c2cc(OC(F)(F)F)cc(S(C)(=O)=O)c2)n(-c2cc(C(N)=O)ncn2)n1] | $^1$H-NMR (400.2 MHz, d6-DMSO) δ = 9.6061 (1.4); 9.5884 (1.4); 9.2781 (4.8); 9.2752 (4.7); 8.4851 (2.0); 8.4815 (3.6); 8.4778 (2.0); 8.4432 (1.4); 8.3448 (4.8); 8.3419 (4.6); 8.3161 (2.1); 8.1548 (2.0); 8.1029 (1.4); 8.0840 (2.1); 6.9421 (0.5); 6.9339 (0.5); 6.9233 (0.5); 6.9183 (0.4); 6.3040 (0.9); 6.2864 (1.6); 6.2689 (1.0); 3.3608 (18.3); 3.3300 (947.0); 2.6804 (1.8); 2.6760 (3.6); 2.6714 (5.0); 2.6668 (3.6); 2.6623 (1.8); 2.6446 (0.4); 2.5249 (17.0); 2.5202 (24.6); 2.5116 (285.6); 2.5070 (576.7); 2.5025 (751.8); 2.4978 (538.4); 2.4933 (254.3); 2.3777 (16.0); 2.3383 (1.4); 2.3338 (3.3); 2.3292 (4.6); 2.3246 (3.2); 2.3202 (1.4); 1.6611 (5.3); 1.6437 (5.3); 1.2588 (0.4); 1.2459 (0.7); 1.2332 (0.6); 0.1460 (2.6); 0.0225 (0.3); 0.0080 (21.3); −0.0001 (669.4); −0.0085 (21.5); −0.0214 (0.8); −0.1496 (2.6) | 514.0 |

TABLE 1-continued
| Example | Structure[1)] | NMR Peak List[2)] | ESI Mass (m/z)[3)] |
|---|---|---|---|
| I-33 | 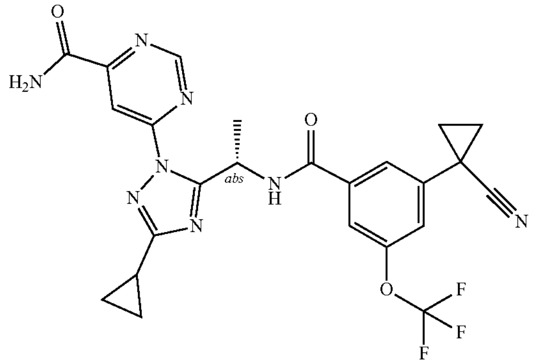 [SMILES: C[C@H](NC(=O)c1cc(OC(F)(F)F)cc(C2(C#N)CC2)c1)c1nc(C2CC2)nn1-c1cc(C(N)=O)ncn1] | $^1$H NMR (DMSO-$d_6$) δ = 9.34 (d, 1H), 9.24 (d, 1H), 8.44 (s, 1H), 8.32 (d, 1H), 8.11 (s, 1H), 7.79 (m, 1H), 7.72 (s, 1H), 7.48 (s, 1H), 6.17-6.24 (m, 1H), 2.02-2.17 (m, 1H), 1.77-1.90 (m, 2H), 1.59-1.68 (m, 5H), 0.85-1.07 (m, 4H), ppm. | 527.4 |
| I-34 | 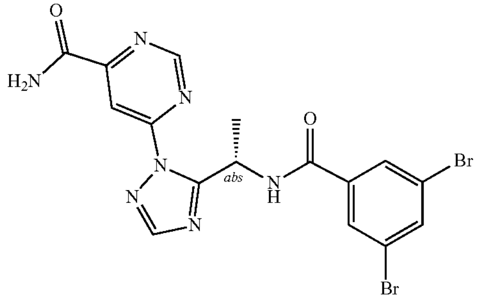 [SMILES: C[C@H](NC(=O)c1cc(Br)cc(Br)c1)c1ncnn1-c1cc(C(N)=O)ncn1] | $^1$H-NMR (400.2 MHz, d6-DMSO) δ = 9.3503 (2.1); 9.3329 (2.1); 9.3116 (7.2); 9.3087 (7.1); 8.4730 (2.1); 8.3764 (7.1); 8.3735 (6.9); 8.3174 (10.1); 8.1276 (2.0); 8.1110 (0.3); 8.1066 (0.3); 8.0451 (1.9); 8.0405 (4.2); 8.0366 (5.6); 8.0284 (16.0); 8.0242 (7.6); 6.2731 (1.4); 6.2198 (2.3); 6.2024 (1.5); 5.7587 (1.3); 3.3403 (260.0); 2.6776 (0.4); 2.6729 (0.6); 2.6684 (0.4); 2.5265 (1.6); 2.5217 (2.5); 2.5131 (36.6); 2.5085 (75.2); 2.5039 (99.0); 2.4993 (70.1); 2.4948 (32.4); 2.3353 (0.4); 2.3308 (0.6); 2.3262 (0.4); 1.6421 (8.4); 1.6248 (8.5); 1.2333 (0.4); 0.0080 (1.5); −0.0002 (5.6); −0.0085 (1.5) | 495.8 |
| I-35 | 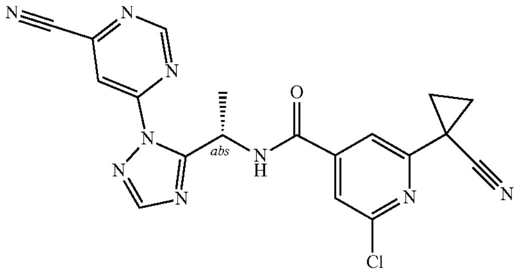 [SMILES: C[C@H](NC(=O)c1cc(Cl)nc(C2(C#N)CC2)c1)c1ncnn1-c1cc(C#N)ncn1] | $^1$H-NMR (400.2 MHz, d6-DMSO) δ = 9.6173 (3.8); 9.6000 (3.9); 9.3837 (10.2); 9.3808 (10.1); 8.6107 (10.6); 8.6078 (10.1); 8.3787 (16.0); 7.8110 (12.9); 7.8042 (12.6); 6.2188 (0.6); 6.2019 (2.6); 6.1846 (4.1); 6.1673 (2.6); 6.1500 (0.6); 3.3315 (314.1); 2.6894 (5.8); 2.6761 (1.1); 2.6717 (1.4); 2.6674 (1.1); 2.5250 (4.5); 2.5513 (89.6); 2.5072 (174.7); 2.5028 (225.3); 2.4983 (165.2); 2.4942 (82.2); 2.3340 (1.0); 2.3295 (1.4); 2.3253 (1.0); 2.0758 (0.8); 1.9156 (3.1); 1.9043 (8.0); 1.8950 (9.1); 1.8854 (4.1); 1.8451 (0.4); 1.7778 (0.4); 1.7383 (4.3); 1.7285 (8.2); 1.7190 (7.0); 1.7079 (3.0); 1.6698 (0.4); 1.6504 (15.2); 1.6330 (15.2); 1.6160 (0.6); 1.5984 (0.3); 1.4330 (1.9); −0.0001 (2.7) | 420.3 |

TABLE 1-continued
| Ex-am-ple | Structure[1)] | NMR Peak List[2)] | ESI Mass (m/z)[3)] |
|---|---|---|---|
| I-36 | 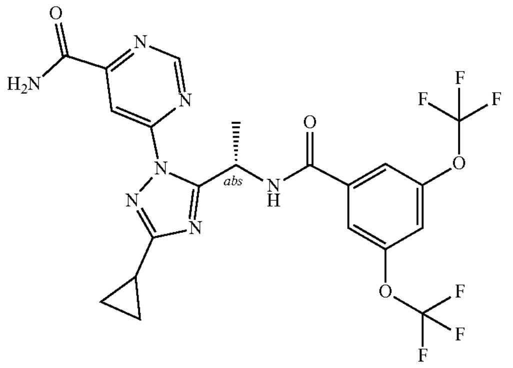 [SMILES: C[C@H](NC(=O)c1cc(OC(F)(F)F)cc(OC(F)(F)F)c1)c1nc(C2CC2)nn1-c1cc(C(N)=O)ncn1] | $^1$H-NMR (400.2 MHz, d6-DMSO) δ = 9.4372 (4.1); 9.4197 (4.2); 9.2409 (14.0); 9.2380 (13.9); 8.4410 (4.1); 8.3147 (13.8); 8.3118 (13.6); 8.1070 (4.0); 7.8780 (11.3); 7.8730 (11.8); 7.7586 (5.0); 6.2340 (0.6); 6.2169 (3.0); 6.1995 (4.8); 6.1820 (3.1); 6.1648 (0.6); 4.1850 (0.5); 4.1769 (0.5); 3.3317 (587.0); 3.0358 (0.4); 2.8152 (0.3); 2.8038 (0.4); 2.6809 (0.9); 2.6765 (1.8); 2.6719 (2.5); 2.6674 (1.8); 2.6630 (0.8); 2.5255 (7.1); 2.5207 (10.8); 2.5120 (143.7); 2.5075 (294.0); 2.5029 (387.7); 2.4983 (275.0); 2.4938 (128.1); 2.3389 (0.8); 2.3343 (1.7); 2.3298 (2.4); 2.352 (1.7); 2.3207 (0.8); 2.1313 (0.8); 2.1192 (1.9); 2.1106 (1.9); 2.1075 (1.5); 2.0985 (3.8); 2.0863 (2.2); 2.0778 (2.0); 2.0655 (1.0); 1.7236 (1.5); 1.6300 (16.0); 1.6126 (15.9); 1.5551 (3.2); 1.0601 (0.4); 1.0517 (0.4); 1.0321 (4.9); 1.0267 (7.1); 1.0114 (4.6); 1.0059 (7.2); 0.9880 (0.8); 0.9798 (0.6); 0.9385 (1.0); 0.9265 (1.0); 0.9148 (4.0); 0.9091 (2.0); 0.9026 (4.2); 0.8968 (3.4); 0.8904 (3.1); 0.8847 (2.0); 0.8784 (2.8); 0.8618 (1.1); 0.8536 (0.7); 0.0081 (2.6); −0.0001 (82.4); −0.0085 (2.4) | 546.3 |
| I-37 | 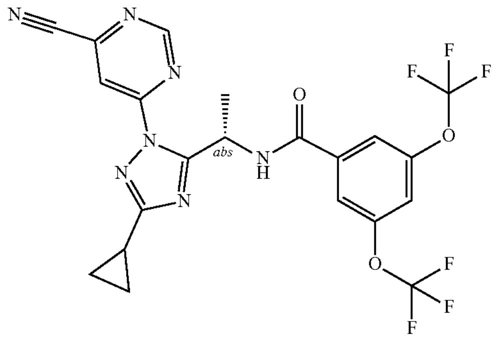 [SMILES: C[C@H](NC(=O)c1cc(OC(F)(F)F)cc(OC(F)(F)F)c1)c1nc(C2CC2)nn1-c1cc(C#N)ncn1] | $^1$H-NMR (400.2 MHz, d6-DMSO) δ = 9.4452 (4.0); 9.4279 (4.1); 9.3135 (11.8); 9.3106 (11.6); 8.5053 (11.6); 8.5024 (11.4); 7.8791 (11.4); 7.8748 (12.0); 7.7660 (5.2); 6.1622 (0.6); 6.1452 (2.9); 6.1278 (4.6); 6.1104 (2.9); 6.0934 (0.6); 3.3312 (335.7); 2.6764 (1.2); 2.6719 (1.6); 2.6672 (1.2); 2.5253 (4.5); 2.5204 (7.4); 2.5118 (100.3); 2.5074 (201.1); 2.5029 (263.4); 2.4983 (191.1); 2.4939 (92.6); 2.3342 (1.2); 2.3297 (1.6); 2.3252 (1.2); 2.1087 (0.8); 2.0966 (1.8); 2.0879 (1.9); 2.0759 (3.7); 2.0639 (2.2); 2.0553 (1.9); 2.0430 (1.0); 1.6148 (16.0); 1.5974 (15.9); 1.5000 (0.4); 1.0664 (0.3); 1.0387 (4.4); 1.0328 (6.4); 1.0180 (4.2); 1.0120 (6.8); 0.9866 (0.7); 0.9492 (1.0); 0.9370 (1.2); 0.9255 (2.8); 0.9221 (2.5); 0.9135 (2.9); 0.9097 (2.4); 0.9000 (2.1); 0.8953 (2.7); 0.8881 (2.4); 0.8832 (2.6); 0.8661 (1.3); 0.8570 (0.8); 0.0079 (2.2); −0.0002 (66.7); −0.0085 (2.2) | 528.4 |

TABLE 1-continued
| Example | Structure[1)] | NMR Peak List[2)] | ESI Mass (m/z)[3)] |
|---|---|---|---|
| I-38 | 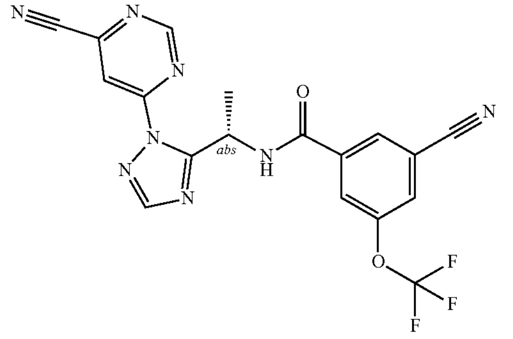 [SMILES: C[C@H](NC(=O)c1cc(C#N)cc(OC(F)(F)F)c1)c1ncnn1-c1cc(C#N)ncn1] | $^1$H-NMR (400.2 MHz, d6-DMSO) δ = 9.4920 (3.4); 9.4748 (3.4); 9.3848 (10.3); 9.3818 (10.5); 8.6133 (10.1); 8.6102 (10.2); 8.3851 (4.8); 8.3817 (9.0); 8.3783 (5.4); 8.3690 (16.0); 8.2467 (4.5); 8.1075 (4.2); 8.1052 (4.8); 8.1028 (4.2); 6.2301 (0.5); 6.2128 (2.4); 6.1955 (3.8); 6.1782 (2.4); 6.1609 (0.5); 3.3298 (94.2); 2.6770 (0.6); 2.6724 (0.8); 2.6679 (0.6); 2.5259 (2.5); 2.5212 (3.8); 2.5125 (46.6); 2.5080 (93.8); 2.5034 (122.5); 2.4988 (88.1); 2.4943 (42.2); 2.3348 (0.5); 2.3302 (0.8); 2.3257 (0.5); 2.0766 (0.7); 1.6543 (14.1); 1.6369 (14.0); 1.4334 (0.5); 0.1458 (0.4); 0.0080 (3.2); −0.0002 (92.3); −0.0085 (2.9); −0.1496 (0.4) | 429.3 |
| 1-39 | 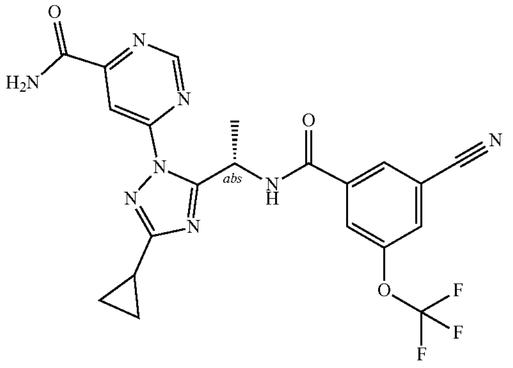 [SMILES: C[C@H](NC(=O)c1cc(C#N)cc(OC(F)(F)F)c1)c1nc(C2CC2)nn1-c1cc(C(N)=O)ncn1] | $^1$H NMR (DMSO-$d_6$) δ = 9.42 (d, 1H), 9.24 (d, 1H), 8.44 (s, 1H), 8.35-8.38 (m, 1H), 8.31 (d, 1H), 8.24 (s, 1H), 8.07-8.12 (m, 2H), 6.17-6.25 (m, 1H), 2.06-2.14 (m, 1H), 1.62 (d, 3H), 0.97-1.07 (m, 2H), 0.85-0.96 (m, 2H) ppm. | 487.3 |

TABLE 1-continued
| Example | Structure[1)] | NMR Peak List[2)] | ESI Mass (m/z)[3)] |
|---|---|---|---|
| I-40 | 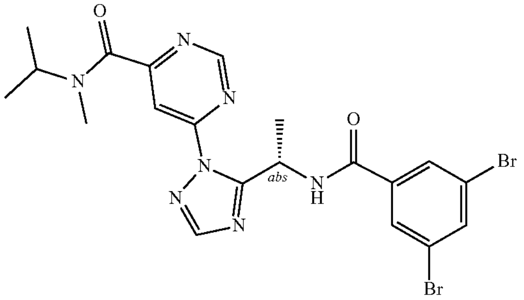 [SMILES: CC(C)N(C)C(=O)c1cc(-n2ncnc2[C@H](C)NC(=O)c2cc(Br)cc(Br)c2)ncn1] | $^1$H-NMR (400.2 MHz, CDCl3) δ = 9.1929 (1.4); 9.1901 (1.4); 9.1782 (2.0); 9.1754 (1.8); 8.1561 (1.4); 8.1535 (1.4); 8.1283 (1.9); 8.1256 (1.9); 8.0110 (2.1); 8.0043 (2.9); 7.9466 (4.5); 7.9426 (6.6); 7.9386 (3.2); 7.8005 (2.2); 7.7967 (3.0); 7.7931 (1.7); 7.7817 (0.6); 7.2904 (7.8); 6.5215 (0.6); 6.5177 (0.5); 6.5014 (0.8); 6.4847 (0.6); 5.3087 (3.6); 4.9711 (0.4); 4.9541 (0.5); 4.9371 (0.4); 3.9723 (0.5); 3.9557 (0.7); 3.9392 (0.5); 3.0101 (8.6); 2.8777 (6.3); 2.5927 (0.4); 2.5882 (0.5); 2.5834 (0.4); 2.2842 (0.4); 2.2464 (0.6); 2.1943 (0.8); 2.1750 (0.5); 2.0721 (16.0); 2.0155 (0.4); 1.9979 (0.4); 1.7219 (4.1); 1.7173 (3.1); 1.7049 (4.1); 1.7003 (3.0); 1.5684 (0.3); 1.5494 (0.5); 1.5033 (0.5); 1.3024 (0.3); 1.2778 (3.1); 1.2715 (4.1); 1.2685 (4.6); 1.2608 (3.7); 1.2545 (5.0); 1.2523 (5.0); 1.2414 (4.0); 1.2248 (3.9); 1.2069 (5.8); 1.1938 (0.4); 1.1562 (3.6); 1.1334 (0.7); 0.9387 (0.8); 0.9204 (1.5); 0.9088 (1.9); 0.9023 (0.8); 0.8915 (1.8); 0.8768 (0.8); 0.8579 (0.4); 0.0712 (0.7); −0.0002 (7.7) | 552.1 |
| I-41 | 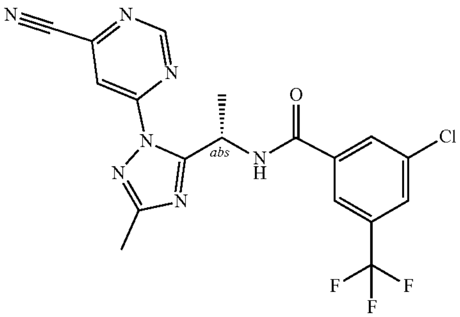 [SMILES: Cc1nc([C@H](C)NC(=O)c2cc(Cl)cc(C(F)(F)F)c2)n(-c2cc(C#N)ncn2)n1] | $^1$H-NMR (400.2 MHz, d6-DMSO) δ = 9.4967 (1.2); 9.4791 (1.3); 9.3479 (4.0); 9.3448 (4.0); 8.5121 (3.9); 8.5092 (3.8); 8.2268 (2.2); 8.1781 (2.2); 8.0923 (2.1); 6.2073 (1.0); 6.1899 (1.5); 6.1724 (1.0); 5.7589 (0.9); 3.3361 (28.6); 3.3317 (38.9); 2.6722 (0.4); 2.5258 (1.1); 2.5210 (1.6); 2.5123 (21.3); 2.5078 (43.2); 2.5032 (56.8); 2.4986 (40.5); 2.4941 (19.0); 2.3701 (16.0); 2.3301 (0.3); 1.6322 (5.4); 1.6148 (5.4); 0.0080 (0.4); −0.0002 (12.3); −0.0085 (0.4) | 436.1 |

TABLE 1-continued
| Example | Structure[1)] | NMR Peak List[2)] | ESI Mass (m/z)[3)] |
| --- | --- | --- | --- |
| I-42 | 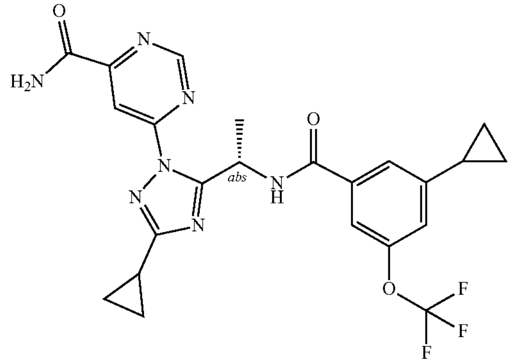 [SMILES: C[C@H](NC(=O)c1cc(OC(F)(F)F)cc(C2CC2)c1)c1nc(C2CC2)nn1-c1cc(C(N)=O)ncn1] | $^1$H-NMR (400.2 MHz, d6-DMSO) δ = 9.3068 (11.4); 9.3039 (11.4); 9.2420 (3.5); 9.2246 (3.6); 8.4724 (3.6); 8.3739 (11.0); 8.3710 (10.9); 8.3158 (16.0); 8.1317 (3.5); 7.5227 (10.4); 7.5193 (10.2); 7.2817 (4.8); 6.2602 (0.5); 6.2430 (2.3); 6.2256 (3.6); 6.2082 (2.3); 6.1908 (0.5); 3.3334 (118.6); 2.6818 (0.3); 2.6773 (0.7); 2.6728 (0.9); 2.6682 (0.7); 2.5262 (3.2); 2.5215 (5.2); 2.5128 (57.0); 2.5084 (112.6); 2.5038 (145.6); 2.4992 (104.9); 2.4947 (50.0); 2.3352 (0.7); 2.3306 (0.9); 2.3261 (0.6); 2.0773 (1.0); 2.0721 (0.7); 2.0595 (1.5); 2.0511 (1.5); 2.0474 (1.1); 2.0386 (2.9); 2.0297 (1.1); 2.0261 (1.7); 2.0177 (1.5); 2.0051 (0.8); 1.6579 (13.4); 1.6405 (13.3); 1.0459 (1.6); 1.0351 (4.8); 1.0295 (5.1); 1.0253 (2.5); 1.0192 (2.5); 1.0141 (4.9); 1.0885 (4.8); 0.9985 (1.9); 0.7948 (2.2); 0.7845 (5.1); 0.7822 (4.5); 0.7790 (4.8); 0.7721 (5.0); 0.7676 (4.9); 0.7560 (1.7); −0.0002 (6.7) | 462.3 |
| I-43 | 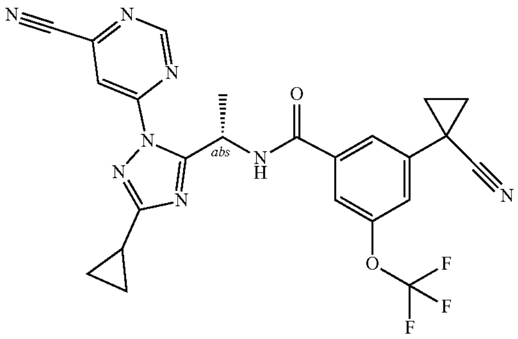 [SMILES: C[C@H](NC(=O)c1cc(OC(F)(F)F)cc(C2(C#N)CC2)c1)c1nc(C2CC2)nn1-c1cc(C#N)ncn1] | $^1$H-NMR (400.2 MHz, d6-DMSO) δ = 9.3654 (4.3); 9.3479 (4.4); 9.3207 (12.0); 9.3178 (11.6); 8.5060 (12.2); 8.5031 (11.7); 7.8089 (5.6); 7.8056 (9.1); 7.8020 (5.8); 7.7211 (6.3); 7.4804 (6.5); 6.1659 (0.6); 6.1486 (3.0); 6.1313 (4.7); 6.1138 (3.0); 6.0966 (0.6); 5.7612 (2.5); 4.0394 (0.5); 4.0217 (0.5); 3.3355 (39.3); 2.6747 (0.4); 2.5280 (1.5); 2.5143 (27.6); 2.5103 (53.2); 2.5058 (68.3); 2.5013 (50.2); 2.4970 (25.0); 2.3370 (0.3); 2.3325 (0.4); 2.1099 (0.8); 2.0977 (1.8); 2.0889 (2.0); 2.0770 (3.8); 2.0649 (2.2); 2.0563 (2.0); 2.0441 (1.0); 1.9916 (2.1); 1.8623 (3.0); 1.8509 (7.8); 1.8432 (9.2); 1.8323 (4.0); 1.7913 (0.5); 1.7073 (0.5); 1.6672 (4.9); 1.6555 (8.8); 1.6477 (7.3); 1.6359 (3.9); 1.6205 (16.0); 1.6031 (15.8); 1.3964 (0.3); 1.1943 (0.6); 1.1765 (1.1); 1.1587 (0.6); 1.0651 (0.3); 1.0386 (4.8); 1.0324 (7.0); 1.0179 (4.5); 1.0117 (7.3); 0.9914 (0.8); 0.9865 (0.7); 0.9532 (1.1); 0.9411 (1.3); 0.9292 (3.1); 0.9174 (3.2); 0.9061 (2.2); 0.9012 (3.0); 0.8942 (2.3); 0.8893 (2.8); 0.8722 (1.3); 0.8633 (0.8); 0.0079 (0.4); −0.0002 (10.0); −0.0085 (0.4) | 509.1 |

TABLE 1-continued
| Example | Structure[1)] | NMR Peak List[2)] | ESI Mass (m/z)[3)] |
|---|---|---|---|
| I-44 | 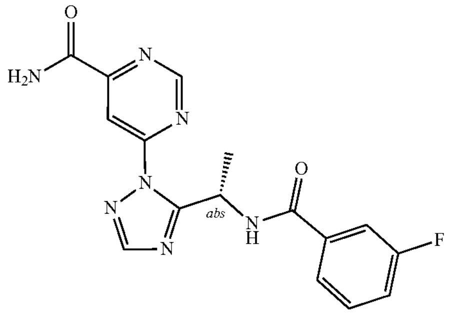 [SMILES: C[C@H](NC(=O)c1cccc(F)c1)c1ncnn1-c1cc(C(N)=O)ncn1] | $^{1}$H-NMR (400.2 MHz, d6-DMSO) δ = 9.3181 (8.0); 9.3152 (7.8); 9.1979 (2.6); 9.1804 (2.7); 8.4749 (2.6); 8.3812 (7.9); 8.3784 (7.6); 8.3104 (11.5); 8.1330 (2.6); 7.7068 (2.5); 7.6871 (3.1); 7.6661 (1.6); 7.6599 (1.9); 7.6563 (1.4); 7.6410 (1.6); 7.6369 (1.8); 7.6349 (1.8); 7.6311 (1.4); 7.5375 (1.2); 7.5227 (1.4); 7.5172 (2.2); 7.5025 (2.3); 7.4977 (1.5); 7.4828 (1.4); 7.4122 (1.2); 7.4101 (1.2); 7.4056 (1.1); 7.3901 (1.9); 7.3838 (1.8); 7.3696 (0.9); 7.3676 (0.9); 7.3630 (0.8); 6.2690 (0.4); 6.2518 (1.8); 6.2344 (2.9); 6.2170 (1.8); 6.1996 (0.4); 5.7612 (16.0); 3.3392 (29.3); 2.5294 (0.7); 2.5160 (12.9); 2.5116 (25.7); 2.5070 (33.4); 2.5024 (24.3); 2.4980 (11.7); 1.6562 (10.5); 1.6388 (10.4); −0.0002 (3.3) | 356.1 |
| I-45 | 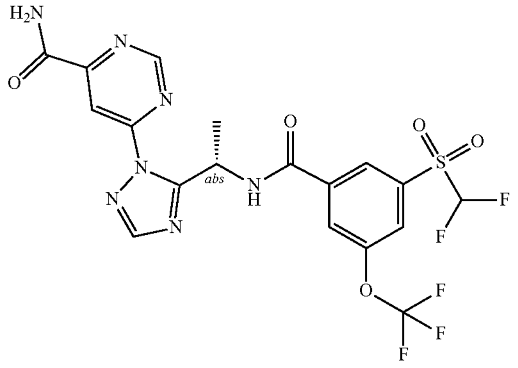 [SMILES: C[C@H](NC(=O)c1cc(OC(F)(F)F)cc(S(=O)(=O)C(F)F)c1)c1ncnn1-c1cc(C(N)=O)ncn1] | $^{1}$H-NMR (400.2 MHz, d6-DMSO) δ = 9.7619 (3.4); 9.7449 (3.4); 9.3153 (11.3); 9.3123 (11.1); 8.5111 (4.6); 8.5076 (7.8); 8.5041 (4.7); 8.4702 (3.6); 8.4156 (0.3); 8.3853 (11.3); 8.3824 (11.2); 8.3722 (4.9); 8.3395 (16.0); 8.3170 (0.8); 8.1591 (0.4); 8.1295 (8.0); 7.5730 (2.6); 7.4433 (6.2); 7.3136 (3.2); 6.3252 (0.6); 6.3089 (2.2); 6.2916 (3.5); 6.2741 (2.2); 6.2576 (0.5); 3.9430 (0.3); 3.7934 (0.3); 3.7367 (0.4); 3.6790 (0.4); 3.6676 (1.1); 3.6447 (0.4); 3.6183 (0.4); 3.5921 (0.5); 3.5584 (0.5); 3.5154 (0.7); 3.4763 (0.8); 3.4314 (1.6); 3.3413 (5036.9); 3.2953 (2.9); 3.2763 (1.1); 3.2629 (0.9); 3.2233 (0.4); 3.1821 (0.3); 2.7226 (0.3); 2.7068 (0.3); 2.6806 (4.2); 2.6762 (8.8); 2.6716 (12.0); 2.6671 (8.6); 2.6626 (3.9); 2.5693 (1.6); 2.5251 (40.1); 2.5202 (67.4); 2.5117 (762.2); 2.5072 (1490.9); 2.5027 (1910.5); 2.4980 (1368.1); 2.4935 (651.5); 2.3514 (0.5); 2.3385 (4.2); 2.3340 (8.7); 2.3294 (11.8); 2.3249 (8.4); 2.3205 (3.8); 2.0754 (0.7); 1.6851 (12.9); 1.6677 (12.7); 1.4491 (0.4); 1.4313 (0.3); 1.2362 (0.4); 0.0080 (1.5); −0.0002 (42.7); −0.0086 (1.2) | 536.2 |

TABLE 1-continued
| Example | Structure[1)] | NMR Peak List[2)] | ESI Mass (m/z)[3)] |
|---|---|---|---|
| I-46 | 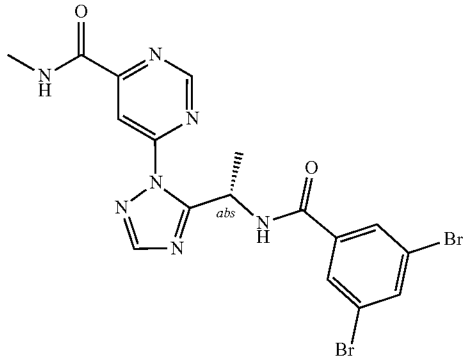 [SMILES: CNC(=O)c1cc(-n2ncnc2[C@H](C)NC(=O)c2cc(Br)cc(Br)c2)ncn1] | $^1$H-NMR (400.2 MHz, d6-DMSO) δ = 9.3478 (2.2); 9.3303 (2.2); 9.3126 (7.7); 9.3097 (7.6); 9.1699 (0.5); 9.1589 (1.5); 9.1467 (1.5); 9.1349 (0.5); 9.3689 (7.8); 8.3660 (7.6); 8.3203 (10.6); 8.0452 (2.3); 8.0408 (5.1); 8.0366 (5.0); 8.0238 (16.0); 8.0195 (9.7); 6.2529 (0.3); 6.2357 (1.5); 6.2184 (2.4); 6.2010 (1.6); 3.3336 (82.5); 2.8729 (11.9); 2.8608 (11.8); 2.6772 (0.5); 2.6726 (0.7); 2.6680 (0.5); 2.5262 (2.5); 2.5214 (3.9); 2.5127 (43.8); 2.5082 (86.9); 2.5037 (112.2); 2.4990 (79.9); 2.4945 (37.5); 2.3351 (0.5); 2.3305 (0.7); 2.3259 (0.5); 2.0872 (0.9); 1.6413 (9.0); 1.6239 (9.0); 0.0080 (2.6); −0.0002 (80.0); −0.0086 (2.6) | 510.0 |
| I-47 | 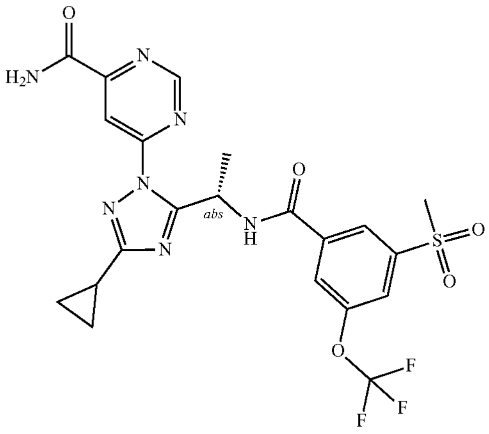 [SMILES: C[C@H](NC(=O)c1cc(OC(F)(F)F)cc(S(C)(=O)=O)c1)c1nc(C2CC2)nn1-c1cc(C(N)=O)ncn1] | $^1$H-NMR (400.2 MHz, d6-DMSO) δ = 9.5777 (4.5); 9.5601 (4.6); 9.2560 (12.2); 9.2532 (12.1); 8.5544 (0.5); 8.4456 (10.9); 8.4423 (13.3); 8.3194 (13.4); 8.3166 (12.2); 8.1225 (7.5); 8.1130 (5.2); 8.0865 (6.8); 7.9942 (0.7); 7.9907 (0.6); 7.9739 (0.5); 7.8568 (0.4); 7.6476 (0.8); 7.6443 (0.9); 7.6277 (1.5); 7.6245 (1.4); 7.6155 (1.3); 7.5981 (1.4); 7.5757 (1.0); 7.5676 (1.2); 7.5580 (0.9); 7.5499 (1.1); 7.5388 (0.4); 7.5318 (0.4); 6.2755 (0.6); 6.2583 (3.0); 6.2410 (4.7); 6.2236 (3.0); 6.2062 (0.7); 3.3740 (4.5); 3.3620 (45.8); 3.3309 (88.4); 3.2723 (0.4); 3.0155 (1.5); 2.9078 (1.5); 2.6763 (1.6); 2.6719 (2.2); 2.6676 (1.7); 2.5250 (9.4); 2.5074 (275.5); 2.5029 (350.4); 2.4985 (258.4); 2.3341 (1.7); 2.3297 (2.3); 2.3253 (1.7); 2.1339 (0.9); 2.1218 (1.9); 2.1131 (2.1); 2.1011 (3.8); 2.0889 (2.3); 2.0804 (2.1); 2.0682 (1.1); 1.6457 (15.9); 1.6283 (16.0); 1.2980 (0.7); 1.2586 (1.0); 1.2328 (1.6); 1.0610 (0.4); 1.0492 (0.9); 1.0329 (5.9); 1.0286 (7.0); 1.0125 (6.0); 1.0076 (6.6); 0.9940 (1.3); 0.9822 (0.7); 0.9595 (0.4); 0.9442 (1.0); 0.9319 (1.2); 0.9201 (3.7); 0.9078 (5.4); 0.9021 (4.8); 0.8939 (2.7); 0.8884 (2.8); 0.8766 (1.0); 0.8665 (0.8); 0.8522 (0.4); 0.8335 (0.4); 0.1459 (0.6); 0.0077 (5.8); −0.0002 (126.9); −0.0084 (5.7); −0.1495 (0.6) | 540.0 |

TABLE 1-continued
| Example | Structure[1)] | NMR Peak List[2)] | ESI Mass (m/z)[3)] |
|---|---|---|---|
| I-48 | 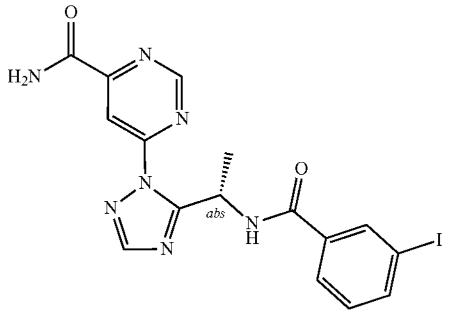 | $^{1}$H-NMR (400.2 MHz, d6-DMSO) δ = 9.3155 (11.0); 9.3127 (10.8); 9.2206 (3.5); 9.2031 (3.6); 8.4766 (3.8); 8.3788 (11.3); 8.3759 (10.8); 8.3089 (16.0); 8.2080 (4.7); 8.2040 (7.9); 8.2001 (4.5); 8.1321 (3.7); 7.9071 (2.8); 7.9046 (3.7); 7.9007 (2.8); 7.8876 (3.0); 7.8850 (3.8); 7.8811 (2.9); 7.8402 (2.8); 7.8376 (3.6); 7.8340 (2.6); 7.8207 (3.1); 7.8171 (3.8); 7.8144 (2.7); 7.2804 (4.0); 7.2608 (7.4); 7.2412 (3.6); 6.2554 (0.5); 6.2383 (2.5); 6.2209 (3.8); 6.2034 (2.5); 6.1860 (0.5); 3.3375 (62.8); 2.6787 (0.4); 2.6742 (0.6); 2.6697 (0.4); 2.5276 (1.9); 2.5141 (35.4); 2.5098 (68.2); 2.5053 (86.0); 2.5007 (61.4); 2.4963 (29.3); 2.3366 (0.4); 2.3321 (0.5); 2.3275 (0.4); 1.6432 (14.4); 1.6258 (14.3); −0.0002 (7.5) | 464.1 |
| I-49 | 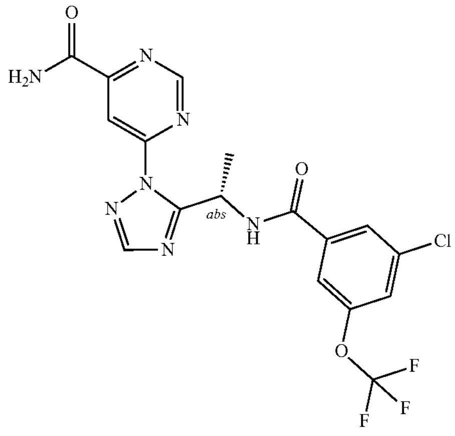 [SMILES: C[C@H](NC(=O)c1cc(Cl)cc(OC(F)(F)F)c1)c1ncnn1-c1cc(C(N)=O)ncn1] | $^{1}$H-NMR (400.2 MHz, d6-DMSO) δ = 9.4710 (4.8); 9.3997 (4.9); 9.3090 (12.4); 8.4722 (5.8); 8.3765 (12.4); 8.3239 (14.3); 8.1314 (5.8); 7.9954 (9.5); 7.7931 (7.8); 7.7728 (8.0); 6.2723 (0.6); 6.2552 (2.8); 6.2380 (4.3); 6.2208 (2.8); 6.2035 (0.7); 3.3368 (226.5); 2.6733 (1.3); 2.5044 (213.3); 2.3314 (1.3); 1.6580 (16.0); 1.6407 (16.0); 0.1454 (0.5); −0.0002 (91.3); −0.1498 (0.5) | 456.0 |

TABLE 1-continued
| Example | Structure[1)] | NMR Peak List[2)] | ESI Mass (m/z)[3)] |
|---|---|---|---|
| I-50 | 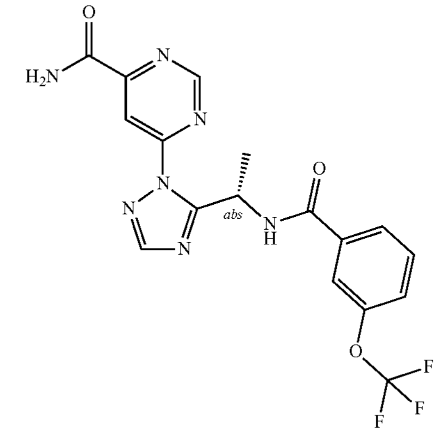 [SMILES: C[C@H](NC(=O)c1cccc(OC(F)(F)F)c1)c1ncnn1-c1cc(C(N)=O)ncn1] | $^1$H-NMR (400.2 MHz, d6-DMSO) δ = 9.3141 (11.5); 9.3115 (12.1); 9.3050 (4.7); 9.2871 (4.4); 8.4725 (4.6); 8.3808 (11.1); 8.3782 (10.9); 8.3150 (16.0); 8.1321 (4.5); 7.9056 (4.2); 7.8865 (4.8); 7.7974 (6.1); 7.6313 (2.7); 7.6112 (6.4); 7.5919 (4.8); 7.5650 (4.3); 7.5443 (2.0); 6.2775 (0.6); 6.2605 (2.7); 6.2432 (4.2); 6.2258 (2.7); 6.2088 (0.6); 3.3374 (132.5); 2.6779 (0.6); 2.6736 (0.8); 2.5091 (101.0); 2.5048 (126.1); 2.5005 (93.9); 2.3316 (0.8); 1.6612 (15.4); 1.6438 (15.4); 0.1458 (0.3); −0.0002 (72.5); −0.1497 (0.3) | 422.1 |
| I-51 | 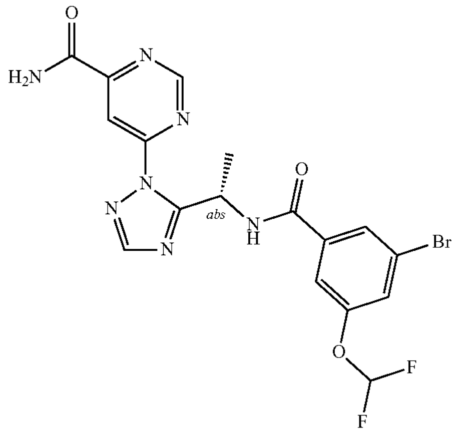 [SMILES: C[C@H](NC(=O)c1cc(Br)cc(OC(F)F)c1)c1ncnn1-c1cc(C(N)=O)ncn1] | $^1$H-NMR (400.2 MHz, d6-DMSO) δ = 10.3390 (0.4); 9.6112 (0.4); 9.3388 (3.6); 9.3214 (4.0); 9.3138 (11.1); 9.3110 (11.2); 9.2925 (0.3); 8.5899 (1.1); 8.5871 (1.2); 8.4757 (4.2); 8.3779 (10.1); 8.3752 (10.4); 8.3182 (16.0); 8.1320 (3.9); 8.0843 (0.4); 7.9497 (5.0); 7.9460 (8.3); 7.9424 (5.3); 7.7726 (0.4); 7.6457 (3.3); 7.6405 (6.8); 7.6361 (5.3); 7.6201 (6.1); 7.5523 (0.9); 7.5245 (4.0); 7.3411 (8.4); 7.1578 (4.2); 6.2640 (0.5); 6.2469 (2.4); 6.2297 (3.7); 6.2123 (2.4); 6.1953 (0.5); 3.3335 (126.3); 2.6769 (0.9); 2.6725 (1.2); 2.6680 (0.9); 2.5259 (4.1); 2.5122 (79.2); 2.5080 (156.1); 2.5035 (201.8); 2.4990 (148.4); 2.3348 (0.9); 2.3303 (1.2); 2.3258 (0.9); 2.0870 (0.3); 2.0068 (4.8); 1.9678 (4.7); 1.6506 (13.8); 1.6332 (13.7); −0.0001 (2.9) | 484.1 |

TABLE 1-continued
| Example | Structure[1)] | NMR Peak List[2)] | ESI Mass (m/z)[3)] |
|---|---|---|---|
| I-52 | 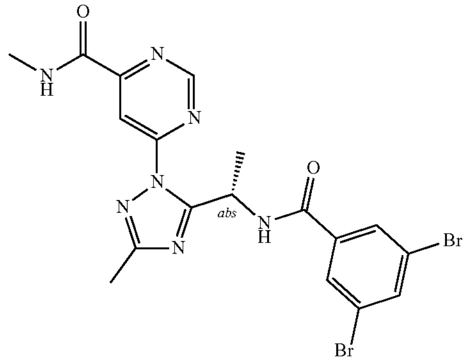 [SMILES: CNC(=O)c1cc(-n2nc(C)nc2[C@H](C)NC(=O)c2cc(Br)cc(Br)c2)ncn1] | $^{1}$H-NMR (400.2 MHz, d6-DMSO) δ = 9.3318 (1.8); 9.3140 (1.8); 9.2709 (4.7); 9.2689 (4.3); 9.1512 (0.5); 9.1396 (1.3); 9.1276 (1.3); 9.1164 (0.4); 8.3261 (4.6); 8.3240 (4.4); 8.0463 (12.9); 6.2334 (1.2); 6.2160 (1.8); 6.1985 (1.2); 3.3365 (40.0); 2.8695 (7.7); 2.8574 (7.6); 2.5092 (38.2); 2.5050 (47.6); 2.5006 (35.1); 2.3757 (16.0); 2.0787 (0.5); 1.6218 (6.4); 1.6045 (6.3); −0.0002 (0.4) | 524.0 |
| I-53 | 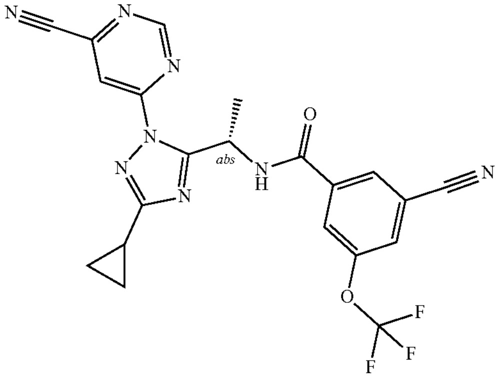 [SMILES: C[C@H](NC(=O)c1cc(C#N)cc(OC(F)(F)F)c1)c1nc(C2CC2)nn1-c1cc(C#N)ncn1] | $^{1}$H-NMR (600.1 MHz, CD3CN) δ = 9.1905 (0.9); 9.1887 (0.9); 8.3478 (1.0); 8.3458 (1.0); 8.1585 (0.5); 8.1563 (1.0); 8.1540 (0.5); 7.9670 (0.5); 7.8686 (0.5); 7.8102 (0.2); 7.7983 (0.2); 6.2382 (0.4); 6.2263 (0.5); 6.2145 (0.4); 2.1702 (16.0); 2.0854 (0.1); 2.0773 (0.2); 2.0715 (0.2); 2.0694 (0.2); 2.0633 (0.4); 2.0582 (0.1); 2.0553 (0.2); 2.0496 (0.2); 2.0415 (0.1); 1.9921 (0.7); 1.9840 (0.2); 1.9798 (0.3); 1.9760 (2.4); 1.9720 (4.4); 1.9678 (6.4); 1.9637 (4.4); 1.9596 (2.2); 1.6634 (2.4); 1.6519 (2.4); 1.0710 (0.3); 1.0640 (0.6); 1.0619 (0.3); 1.0575 (0.3); 1.0501 (0.6); 1.0481 (0.3); 1.0452 (0.3); 1.0308 (0.2); 1.0258 (0.1); 1.0235 (0.1); 1.0172 (0.2); 1.0154 (0.1); 1.0076 (0.3); 1.0038 (0.2); 0.9994 (0.3); 0.9955 (0.2); 0.9886 (0.2); 0.9827 (0.3); 0.9808 (0.2); 0.9755 (0.2); 0.9742 (0.2); 0.9680 (0.1); 0.9654 (0.1) | 469.0 |

TABLE 1-continued
| Example | Structure[1)] | NMR Peak List[2)] | ESI Mass (m/z)[3)] |
|---|---|---|---|
| I-54 | 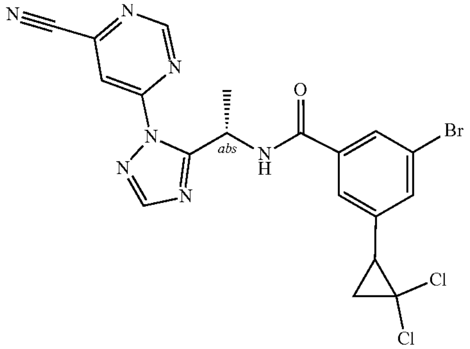 [SMILES: C[C@H](NC(=O)c1cc(Br)cc(C2CC2(Cl)Cl)c1)c1ncnn1-c1cc(C#N)ncn1] | $^1$H-NMR (400.2 MHz, d6-DMSO) δ = 9.3912 (7.0); 9.3881 (7.9); 9.3863 (7.9); 9.3831 (6.6); 9.3022 (2.1); 9.2860 (3.3); 9.2710 (2.1); 8.6134 (7.6); 8.6107 (12.1); 8.6080 (7.1); 8.3544 (15.3); 7.9788 (6.7); 7.9751 (6.7); 7.8048 (3.9); 7.7764 (3.8); 7.7233 (6.0); 7.7191 (5.7); 6.2106 (0.6); 6.1935 (2.7); 6.1762 (4.3); 6.1587 (2.7); 6.1410 (0.6); 3.631 (0.3); 3.3306 (324.0); 3.2315 (1.4); 3.2271 (1.5); 3.2052 (3.1); 3.1832 (1.7); 3.1784 (1.6); 2.6801 (0.9); 2.6757 (1.9); 2.6712 (2.6); 2.6666 (1.9); 2.6620 (0.9); 2.5247 (8.8). 25200 (13.7); 2.5112 (160.4); 2.5068 (318.2); 2.5022 (413.4); 2.4976 (299.0); 2.4931 (143.3); 2.3559 (1.7); 2.3447 (1.8); 2.3346 (4.4); 2.3290 (3.3); 2.3243 (5.0); 2.3148 (2.0); 2.3036 (1.8); 2.1393 (2.4); 2.1368 (2.4); 2.1192 (2.4); 2.1163 (2.6); 2.1124 (3.0); 2.1095 (2.7); 2.0921 (1.9); 2.0896 (1.9); 2.0758 (9.2); 1.6433 (16.0); 1.6259 (15.9); 0.0080 (0.4); −0.0002 (13.0); −0.0084 (0.4) | 508.1 |
| I-55 | 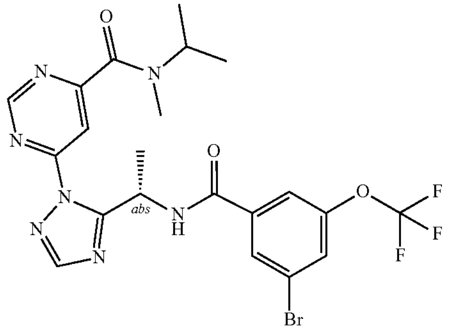 [SMILES: CC(C)N(C)C(=O)c1cc(-n2ncnc2[C@H](C)NC(=O)c2cc(Br)cc(OC(F)(F)F)c2)ncn1] | $^1$H-NMR (400.2 MHz, d6-DMSO) δ = 9.432 (1.7); 9.4059 (1.8); 9.2399 (3.9); 9.2369 (5.9); 9.2338 (2.7); 8.2958 (6.7); 8.1459 (1.8); 8.1422 (3.8); 8.1384 (3.4); 8.1349 (1.3); 8.0070 (2.8); 8.0029 (5.1); 7.9997 (3.9); 7.9037 (2.6); 7.8129 (2.8); 7.8104 (2.6); 6.2301 (1.3); 6.2128 (2.0); 6.1954 (1.3); 5.7596 (16.0); 4.7481 (0.5); 4.7310 (0.7); 4.7140 (0.6); 3.7927 (0.8); 3.7762 (1.1); 3.7599 (0.8); 3.6540 (1.3); 3.3328 (188.7); 2.8882 (13.1); 2.7497 (9.2); 2.6762 (0.8); 2.6718 (1.1); 2.6672 (0.8); 2.6627 (0.4); 2.5252 (4.0); 2.5205 (6.0); 2.5118 (68.2); 2.5073 (134.2); 2.5028 (174.6); 2.4982 (127.6); 2.4938 (61.9); 2.3386 (0.4); 2.3341 (0.8); 2.3296 (1.1); 2.3251 (0.8); 1.6638 (5.8); 1.6465 (5.8); 1.4205 (0.5); 1.4022 (0.5); 1.1923 (7.1); 1.1753 (7.1); 1.1469 (6.8); 1.1436 (6.8); 1.1305 (6.8); 1.1273 (6.6); −0.0001 (6.2) | 558.0 |

TABLE 1-continued
| Example | Structure[1)] | NMR Peak List[2)] | ESI Mass (m/z)[3)] |
|---|---|---|---|
| I-56 | 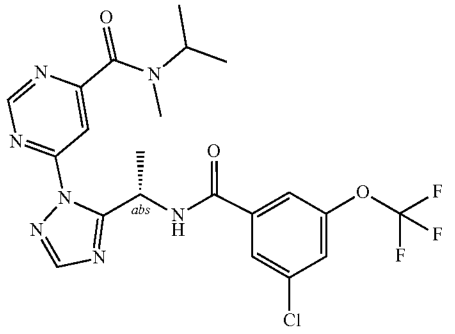 [SMILES: CC(C)N(C)C(=O)c1cc(-n2ncnc2[C@H](C)NC(=O)c2cc(Cl)cc(OC(F)(F)F)c2)ncn1] | $^1$H-NMR (400.2 MHz, d6-DMSO) δ = 9.4223 (2.0); 9.4053 (2.1); 9.2398 (4.7); 9.2368 (7.2); 9.2339 (3.2); 8.2966 (8.0); 8.0112 (2.6); 8.0080 (7.3); 8.0040 (9.9); 8.0009 (6.4); 7.7986 (3.2); 7.7924 (3.1); 7.7896 (3.6); 7.7869 (3.7); 6.2501 (0.3); 6.2326 (1.5); 6.2153 (2.4); 6.1980 (1.5); 6.1801 (0.3); 4.7485 (0.6); 4.7315 (0.9); 4.7145 (0.7); 3.8102 (0.4); 3.7940 (1.0); 3.7776 (1.4); 3.7611 (1.0); 3.7446 (0.4); 3.6549 (0.6); 3.3318 (74.5); 2.8885 (16.0); 2.7505 (11.4); 2.6765 (0.6); 2.6721 (0.9); 2.6675 (0.6); 2.5256 (2.9); 2.5208 (4.4); 2.5121 (51.9); 2.5077 (104.0); 2.5031 (136.5); 2.4985 (99.7); 2.4940 (48.1); 2.3345 (0.6); 2.3299 (0.8); 2.3254 (0.6); 2.0767 (3.7); 1.6661 (7.0); 1.6487 (7.0); 1.1925 (8.4); 1.1755 (8.4); 1.1473 (7.9); 1.1436 (7.9); 1.1309 (7.9); 1.1272 (7.7); −0.0002 (2.0) | 512.2 |
| I-57 | 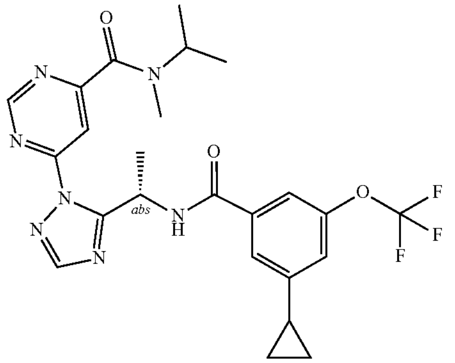 [SMILES: CC(C)N(C)C(=O)c1cc(-n2ncnc2[C@H](C)NC(=O)c2cc(OC(F)(F)F)cc(C3CC3)c2)ncn1] | $^1$H-NMR (400.2 MHz, d6-DMSO) δ = 9.2550 (2.2); 9.2423 (6.0); 9.2395 (7.0); 9.2336 (4.6); 8.2867 (8.3); 7.9996 (7.6); 7.5505 (4.4); 7.5302 (4.2); 7.2870 (3.9); 6.2365 (0.4); 6.2196 (1.8); 6.2023 (2.9); 6.1850 (1.8); 6.1679 (0.4); 4.7474 (0.7); 4.7305 (1.0); 4.7135 (0.7); 3.8021 (0.4); 3.7856 (1.1); 3.7692 (1.5); 3.7527 (1.1); 3.7363 (0.4); 3.6487 (1.1); 3.3344 (198.7); 2.8874 (16.0); 2.7392 (11.1); 2.6759 (1.0); 2.6718 (1.4); 2.6674 (1.0); 2.5070 (170.6); 2.5028 (213.6); 2.4985 (159.8); 2.3336 (1.0); 2.3295 (1.3); 2.3253 (1.0); 2.0762 (2.0); 2.0657 (1.0); 2.0566 (1.2); 2.0451 (2.0); 2.0333 (1.3); 2.0243 (1.1); 2.0117 (0.5); 1.6651 (8.1); 1.6478 (8.1); 1.4170 (0.5); 1.3988 (0.5); 1.1910 (9.0); 1.1741 (8.9); 1.1440 (8.4); 1.1384 (8.5); 1.1277 (8.5); 1.1220 (8.0); 1.0519 (1.2); 1.0406 (3.7); 1.0356 (4.0); 1.0198 (3.7); 1.0149 (3.7); 1.0045 (1.2); 0.8068 (1.3); 0.7933 (4.5); 0.7812 (4.2); 0.7690 (1.0); −0.0002 (2.2) | 518.3 |

TABLE 1-continued
| Example | Structure[1)] | NMR Peak List[2)] | ESI Mass (m/z)[3)] |
|---|---|---|---|
| I-58 | 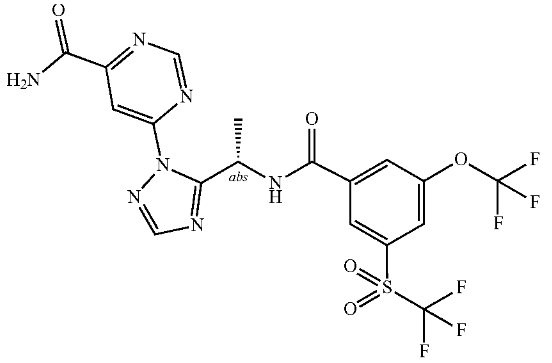 [SMILES: C[C@H](NC(=O)c1cc(OC(F)(F)F)cc(S(=O)(=O)C(F)(F)F)c1)c1ncnn1-c1cc(C(N)=O)ncn1] | $^1$H-NMR (400.2 MHz, d6-DMSO) δ = 9.8209 (3.2); 9.8038 (3.3); 9.3195 (11.7); 9.3166 (11.2); 8.6455 (6.5); 8.4724 (3.6); 8.4633 (4.8); 8.4608 (5.3); 8.4585 (4.7); 8.3900 (12.4); 8.3871 (13.3); 8.3817 (4.7); 8.3501 (16.0); 8.1383 (3.3); 7.9582 (1.8); 6.3406 (0.5); 6.3235 (2.2); 6.3062 (3.5); 6.2889 (2.2); 6.2716 (0.4); 5.7638 (7.9); 3.3435 (232.2); 2.8963 (14.2); 2.7370 (11.8); 2.7358 (11.4); 2.6863 (0.3); 2.6821 (0.7); 2.6775 (0.9); 2.6729 (0.7); 2.5310 (3.3); 2.5262 (5.1); 2.5175 (56.9); 2.5131 (111.7); 2.5085 (144.0); 2.5039 (103.6); 2.4994 (48.8); 2.3398 (0.7); 2.3354 (0.9); 2.3308 (0.6); 1.6976 (12.7); 1.6802 (12.6) | 554.2 |
| I-59 | 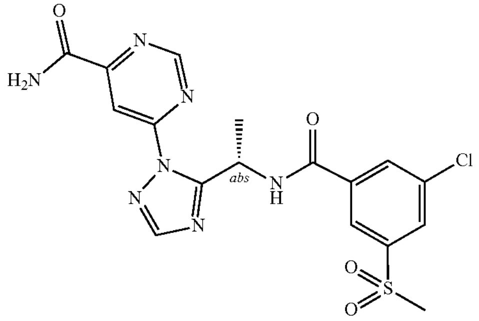 [SMILES: C[C@H](NC(=O)c1cc(Cl)cc(S(C)(=O)=O)c1)c1ncnn1-c1cc(C(N)=O)ncn1] | $^1$H-NMR (400.2 MHz, d6-DMSO) δ = 9.5501 (2.7); 9.5238 (2.7); 9.3245 (8.5); 9.3217 (8.3); 8.4796 (2.9); 8.3855 (8.9); 8.3826 (8.4); 8.3319 (16.0); 8.3277 (7.7); 8.3238 (4.4); 8.2373 (3.9); 8.2328 (5.9); 8.2287 (3.9); 8.1621 (4.3); 8.1577 (6.5); 8.1532 (3.7); 8.1328 (2.8); 6.3059 (0.4); 6.2890 (1.9); 6.2716 (2.9); 6.2542 (1.9); 6.2368 (0.4); 3.4266 (0.4); 3.3638 (289.7); 3.3307 (30.3); 2.6800 (0.4); 2.6755 (0.5); 2.6709 (0.4); 2.5289 (1.9); 2.5240 (2.9); 2.5155 (32.0); 2.5111 (62.4); 2.5065 (80.6); 2.5019 (58.3); 2.4974 (28.0); 2.3378 (0.4); 2.3334 (0.5); 2.3287 (0.4); 1.6726 (10.5); 1.6552 (10.5); −0.0002 (1.9) | 450.0 |
| I-60 | 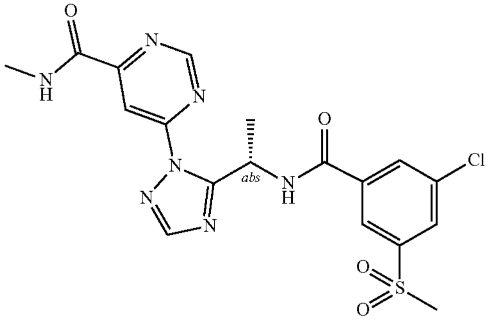 [SMILES: CNC(=O)c1cc(-n2ncnc2[C@H](C)NC(=O)c2cc(Cl)cc(S(C)(=O)=O)c2)ncn1] | $^1$H-NMR (400.2 MHz, d6-DMSO) δ = 9.5444 (3.2); 9.5269 (3.3); 9.3252 (10.5); 9.3223 (10.4); 9.1709 (0.8); 9.1591 (2.3); 9.1469 (2.3); 9.1345 (0.8); 8.3761 (10.4); 8.3732 (10.2); 8.3336 (15.3); 8.3259 (4.8); 8.3221 (8.6); 8.3183 (5.1); 8.2335 (4.6); 8.2290 (6.9); 8.2249 (4.7); 8.1613 (5.2); 8.1569 (7.6); 8.1523 (4.3); 6.3047 (0.5); 6.2876 (2.1); 6.2702 (3.4); 6.2528 (2.2); 6.2357 (0.5); 3.6613 (0.5); 3.3315 (231.5); 2.8720 (16.0); 2.8599 (15.9); 2.6805 (0.7); 2.6761 (1.5); 2.6716 (2.1); 2.6669 (1.5); 2.6624 (0.7); 2.5250 (7.5); 2.5203 (11.4); 2.5116 (125.0); 2.5071 (249.5); 2.5026 (326.0); 2.4980 (237.4); 2.4935 (114.4); 2.3382 (0.7); 2.3340 (1.5); 2.3295 (2.0); 2.3248 (1.5); 1.6692 (12.3); 1.6518 (12.2); −0.0002 (1.6) | 464.1 |

TABLE 1-continued
| Example | Structure[1)] | NMR Peak List[2)] | ESI Mass (m/z)[3)] |
|---|---|---|---|
| I-61 | 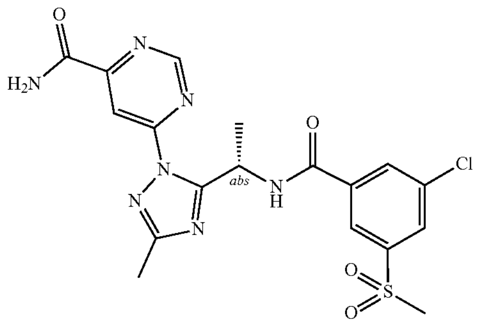 [SMILES: Cc1nc([C@H](C)NC(=O)c2cc(Cl)cc(S(C)(=O)=O)c2)n(-c2cc(C(N)=O)ncn2)n1] | $^1$H-NMR (400.2 MHz, d6-DMSO) δ = 9.5297 (1.5); 9.5120 (1.5); 9.2817 (4.6); 9.2788 (4.5); 8.4536 (1.6); 8.3527 (2.2); 8.3489 (4.1); 8.3448 (3.0); 8.3423 (5.2); 8.3394 (4.8); 8.2565 (2.1); 8.2522 (3.2); 8.2480 (2.1); 8.1610 (2.3); 8.1567 (3.5); 8.1522 (2.0); 8.1073 (1.6); 6.2875 (1.1); 6.2700 (1.7); 6.2524 (1.1); 3.3820 (0.4); 3.3322 (93.6); 2.6763 (0.6); 2.6717 (0.8); 2.6673 (0.6); 2.5252 (2.8); 2.5204 (4.4); 2.5118 (49.2); 2.5074 (97.0); 2.5028 (126.1); 2.4982 (91.5); 2.4937 (44.2); 2.3767 (16.0); 2.3341 (0.6); 2.3296 (0.8); 2.3251 (0.6); 2.0764 (0.8); 1.6486 (5.6); 1.6313 (5.6); −0.0002 (0.5) | 464.0 |
| I-62 | 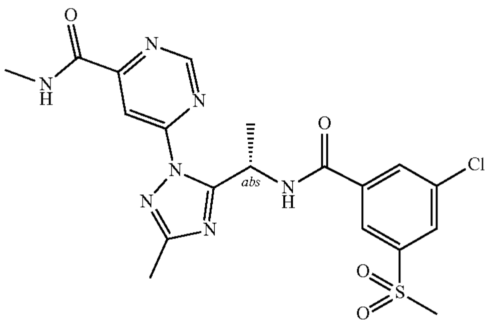 [SMILES: CNC(=O)c1cc(-n2nc(C)nc2[C@H](C)NC(=O)c2cc(Cl)cc(S(C)(=O)=O)c2)ncn1] | $^1$H-NMR (400.2 MHz, d6-DMSO) δ = 9.5295 (1.5); 9.5117 (1.6); 9.2837 (4.7); 9.2808 (4.6); 9.1506 (0.4); 9.1390 (1.1); 9.1270 (1.1); 9.1156 (0.4); 8.3512 (2.1); 8.3475 (3.9); 8.3437 (2.3); 8.3341 (4.8); 8.3313 (4.7); 8.2556 (2.1); 8.2511 (3.2); 8.2470 (2.1); 8.1626 (2.3); 8.1582 (3.5); 8.1537 (2.0); 6.2882 (1.1); 6.2707 (1.7); 6.2532 (1.1); 3.3361 (40.8); 2.8694 (7.4); 2.8573 (7.4); 2.5272 (1.0); 2.5224 (1.4); 2.5137 (16.0); 2.5093 (31.6); 2.5048 (41.1); 2.5002 (29.9); 2.4957 (14.5); 2.3821 (16.0); 1.6501 (5.7); 1.6327 (5.7) | 478.3 |

TABLE 1-continued
| Example | Structure[1)] | NMR Peak List[2)] | ESI Mass (m/z)[3)] |
|---|---|---|---|
| I-63 | 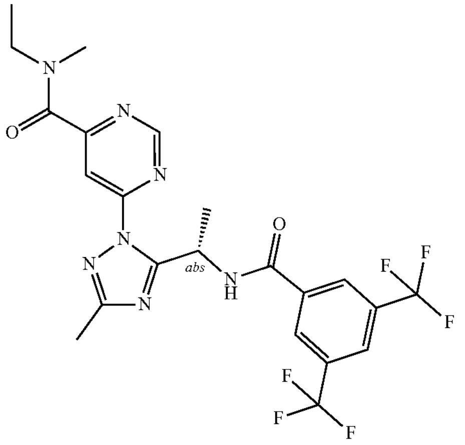 [SMILES: CCN(C)C(=O)c1cc(-n2nc(C)nc2[C@H](C)NC(=O)c2cc(C(F)(F)F)cc(C(F)(F)F)c2)ncn1] | $^{1}$H-NMR (400.2 MHz, d6-DMSO) δ = 9.6511 (1.8); 9.6334 (1.8); 9.2165 (6.0); 9.2135 (5.9); 8.5365 (6.3); 8.3404 (2.8); 7.9521 (2.8); 7.9490 (2.8); 7.9448 (3.5); 7.9418 (3.2); 6.2966 (0.7); 6.2920 (0.8); 6.2790 (1.1); 6.2745 (1.3); 6.2616 (0.8); 6.2571 (0.8); 3.6666 (0.5); 3.5287 (0.5); 3.5107 (1.7); 3.4928 (1.8); 3.4750 (0.6); 3.3340 (110.8); 3.2853 (0.6); 3.2675 (1.8); 3.2498 (1.8); 3.2320 (0.6); 3.0049 (11.2); 2.9161 (10.3); 2.6770 (0.6); 2.6724 (0.8); 2.6680 (0.6); 2.5260 (3.0); 2.5212 (4.5); 2.5125 (49.1); 2.5080 (96.9); 2.5035 (126.2); 2.4989 (91.2); 2.4944 (43.3); 2.3521 (16.0); 2.3397 (0.5); 2.3349 (0.7); 2.3302 (0.8); 2.3258 (0.6); 2.0770 (1.0); 1.6723 (6.5); 1.6549 (6.5); 1.1810 (2.2); 1.1631 (4.8); 1.1452 (2.1); 1.1260 (2.3); 1.1085 (5.2); 1.0908 (2.2); 0.0080 (0.4); −0.0002 (13.3); −0.0085 (0.4) | 530.4 |
| I-64 | 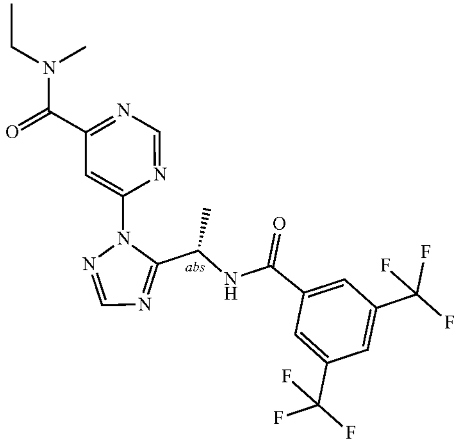 [SMILES: CCN(C)C(=O)c1cc(-n2ncnc2[C@H](C)NC(=O)c2cc(C(F)(F)F)cc(C(F)(F)F)c2)ncn1] | $^{1}$H-NMR (600.1 MHz, CD3CN lowT) δ = 9.1541 (2.5); 9.1523 (2.4); 9.1429 (3.5); 9.1411 (3.3); 8.6133 (0.2); 8.5147 (2.7); 8.4501 (0.1); 8.4082 (0.3); 8.3848 (8.4); 8.2816 (1.1); 8.2382 (0.1); 8.2196 (3.6); 8.1344 (1.6); 8.1223 (1.6); 8.1001 (0.2); 8.0788 (6.4); 8.0336 (2.6); 8.0318 (2.5); 8.0275 (3.6); 8.0257 (3.4); 6.3983 (0.4); 6.3865 (1.6); 6.3747 (2.5); 6.3629 (1.6); 6.3512 (0.4); 3.7060 (0.8); 3.5650 (0.6); 3.5533 (2.0); 3.5413 (2.0); 3.5294 (0.7); 3.2856 (0.9); 3.2738 (3.0); 3.2620 (3.0); 3.2503 (0.9); 3.0467 (16.0); 2.9293 (12.4); 2.3212 (23.6); 2.1524 (0.2); 2.1358 (0.1); 2.1212 (0.1); 2.1047 (0.2); 2.0962 (0.1); 2.0924 (0.1); 2.0881 (0.4); 2.0840 (0.7), 2.0799 (1.0); 2.0758 (0.7); 2.0717 (0.4); 2.0089 (0.1); 2.0048 (0.2); 2.0008 (0.4); 1.9932 (27.7); 1.9851 (8.1); 1.9809 (10.0); 1.9772 (66.1); 1.9731 (117.9); 1.9690 (172.4); 1.9649 (118.3); 1.9608 (59.8); 1.9520 (1.1); 1.9351 (0.2); 1.9312 (0.2); 1.9273 (0.2); 1.9236 (0.2); 1.9199 (0.2); 1.9164 (0.2); 1.9123 (0.2); 1.9047 (0.1); 1.8998 (0.1); 1.8954 (0.1); 1.8917 (0.2); 1.8873 (0.2); 1.8833 (0.2); 1.8776 (0.3); 1.8697 (0.1); 1.8620 (0.4); 1.8580 (0.7); 1.8539 (1.0); 1.8498 (0.7); 1.8457 (0.4); 1.8128 (0.1); 1.8015 | 516.2 |

TABLE 1-continued
| Example | Structure[1)] | NMR Peak List[2)] | ESI Mass (m/z)[3)] |
|---|---|---|---|
| | | (0.1); 1.7066 (10.4); 1.6950 (10.5); 1.6461 (0.1); 1.6340 (0.1); 1.4965 (0.4); 1.4843 (0.4); 1.2681 (0.3); 1.2247 (2.6); 1.2127 (5.5); 1.2007 (2.6); 1.1616 (3.3); 1.1499 (7.1); 1.1381 (3.2) | |
| I-65 | 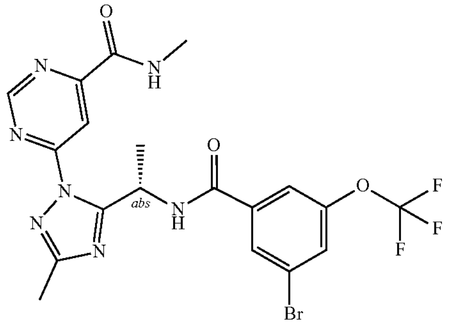 [SMILES: CNC(=O)c1cc(-n2nc(C)nc2[C@H](C)NC(=O)c2cc(Br)cc(OC(F)(F)F)c2)ncn1] | $^1$H-NMR (400.2 MHz, d6-DMSO) δ = 9.4038 (1.5); 9.3861 (1.6); 9.2720 (4.7); 9.2691 (4.6); 9.1512 (0.4); 9.1399 (1.2); 9.1278 (1.2); 9.1165 (0.4); 8.3307 (4.8); 8.3279 (4.7); 8.1553 (2.1); 8.1516 (3.4); 8.1478 (2.1); 7.8989 (2.2); 7.8228 (2.1); 7.8204 (2.2); 6.2528 (1.1); 6.2353 (1.7); 6.2179 (1.1); 3.3440 (43.3); 2.8715 (7.5); 2.8594 (7.4); 2.5303 (0.6); 2.1568 (12.0); 2.5125 (23.3); 2.5079 (30.0); 2.5034 (21.7); 2.4989 (10.5); 2.3793 (16.0); 2.0810 (0.8); 1.6378 (5.8); 1.6204 (5.8) | 530.0 |
| I-66 | 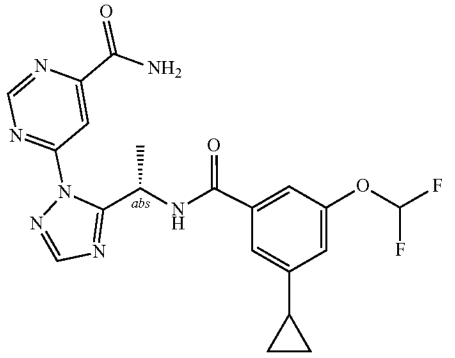 [SMILES: C[C@H](NC(=O)c1cc(OC(F)F)cc(C2CC2)c1)c1ncnn1-c1cc(C(N)=O)ncn1] | $^1$H-NMR (400.2 MHz, d6-DMSO) δ = 9.3086 (10.8); 9.3058 (10.6); 9.1515 (3.4); 9.1341 (3.5); 8.4747 (3.7); 8.3717 (10.7); 8.3688 (10.4); 8.3107 (16.0); 8.1316 (3.6); 7.4339 (4.0); 7.3734 (7.4); 7.3701 (5.2); 7.3592 (4.4); 7.3543 (5.4); 7.2489 (8.3); 7.0639 (8.0); 6.2527 (0.5); 6.2356 (2.3); 6.2181 (3.6); 6.2007 (2.3); 6.1832 (0.5); 3.3331 (183.0); 2.6807 (0.6); 2.6764 (1.2); 2.6719 (1.6); 2.6673 (1.2); 2.6628 (0.6); 2.5253 (5.6); 2.5205 (8.6); 2.5118 (96.3); 2.5074 (191.0); 2.5029 (249.1); 2.4983 (182.5); 2.4939 (89.2); 2.3387 (0.5); 2.3342 (1.1); 2.3297 (1.5); 2.3252 (1.1); 2.0765 (0.4); 2.0170 (0.7); 2.0043 (1.5); 1.9958 (1.6); 1.9834 (2.9); 1.9710 (1.7); 1.9626 (1.6); 1.9499 (0.8); 1.6254 (13.3); 1.6351 (13.3); 1.0188 (1.7); 1.0078 (5.0); 1.0022 (5.4); 0.9983 (2.7); 0.9919 (2.7); 0.9869 (5.1); 0.9813 (5.0); 0.9711 (2.0); 0.7688 (2.1); 0.7583 (5.6); 0.7532 (5.5); 0.7460 (5.3); 0.7409 (5.8); 0.7295 (1.7); −0.0001 (0.9) | 444.1 |

TABLE 1-continued
| Ex-am-ple | Structure[1)] | NMR Peak List[2)] | ESI Mass (m/z)[3)] |
|---|---|---|---|
| I-67 | 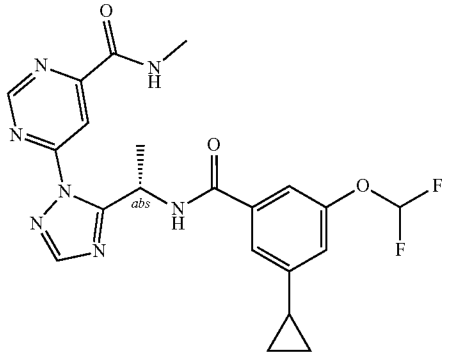 [SMILES: CNC(=O)c1cc(-n2ncnc2[C@H](C)NC(=O)c2cc(OC(F)F)cc(C3CC3)c2)ncn1] | $^1$H-NMR (400.2 MHz, d6-DMSO) δ = 9.3133 (9.8); 9.3105 (9.2); 9.1747 (1.0); 9.1636 (2.8); 9.1527 (5.5); 9.1360 (3.8); 8.3704 (9.9); 8.3676 (9.3); 8.3159 (14.7); 7.4362 (3.6); 7.3721 (7.2); 7.3689 (5.2); 7.3609 (4.6); 7.3561 (5.3); 7.2512 (7.4); 7.0660 (8.2); 6.2577 (0.5); 6.2404 (2.2); 6.2231 (3.4); 6.2056 (2.2); 6.1883 (0.5); 3.3385 (138.4); 2.8774 (16.0); 2.8653 (15.8); 2.6811 (0.9); 2.6767 (1.2); 2.6722 (0.8); 2.5300 (4.7); 2.5164 (79.1); 2.5122 (149.2); 2.5077 (188.4); 2.5032 (136.4); 2.4989 (66.5); 2.3390 (0.9); 2.3345 (1.2); 2.3301 (0.8); 2.0809 (3.4); 2.0185 (0.6); 2.0060 (1.4); 1.9975 (1.5); 1.9852 (2.8); 1.9726 (1.6); 1.9642 (1.5); 1.9517 (0.7); 1.6564 (12.7); 1.6391 (12.6); 1.0213 (1.6); 1.0104 (4.8); 1.0047 (5.0); 0.9945 (2.6); 0.9894 (4.8); 0.9839 (4.7); 0.9738 (1.8); 0.7699 (2.0); 0.7594 (5.3); 0.743 (5.2); 0.7471 (5.1); 0.7421 (5.3); 0.7308 (1.6) | 458.2 |
| I-68 | 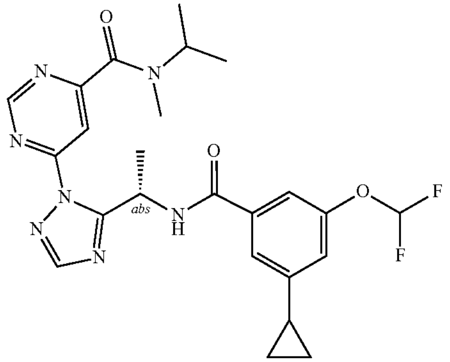 [SMILES: CC(C)N(C)C(=O)c1cc(-n2ncnc2[C@H](C)NC(=O)c2cc(OC(F)F)cc(C3CC3)c2)ncn1] | $^1$H-NMR (400.2 MHz, d6-DMSO) δ = 20.0123 (0.3); 9.2472 (6.8); 9.1536 (4.0); 8.2894 (8.3); 8.1834 (0.5); 8.0037 (8.7); 7.4447 (2.6); 7.4140 (6.6); 7.3670 (7.2); 7.2604 (4.7); 7.0730 (8.6); 6.2200 (2.6); 6.2037 (3.7); 6.1870 (2.6); 4.7382 (1.3); 4.7217 (1.0); 3.7954 (1.6); 3.7795 (2.0); 3.7626 (1.5); 3.3400 (127.5); 2.8952 (15.8); 2.7490 (10.7); 2.6780 (2.8); 2.5104 (372.3); 2.3367 (3.0); 1.9995 (3.4); 1.6660 (13.1); 1.6503 (13.0); 1.4197 (0.4); 1.1986 (11.8); 1.1825 (12.1); 1.1499 (16.0); 1.1374 (15.6); 1.0175 (7.4); 1.0006 (7.1); 0.7752 (8.7) | 500.2 |

TABLE 1-continued
| Example | Structure[1)] | NMR Peak List[2)] | ESI Mass (m/z)[3)] |
|---|---|---|---|
| I-69 | 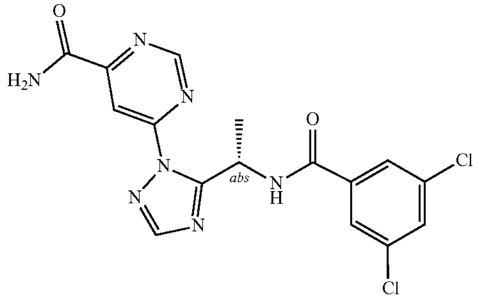 [SMILES: C[C@H](NC(=O)c1cc(Cl)cc(Cl)c1)c1ncnn1-c1cc(C(N)=O)ncn1] | $^1$H-NMR (400.2 MHz, d6-DMSO) δ = 9.3503 (2.5); 9.3229 (2.6); 9.3111 (8.1); 9.3083 (7.9); 8.4725 (2.6); 8.3752 (8.0); 8.3723 (7.8); 8.3180 (12.3); 8.1301 (2.6); 7.8666 (13.1); 7.8618 (16.0); 7.8270 (4.5); 7.8223 (6.5); 7.8175 (2.9); 6.2572 (0.4); 6.2399 (1.8); 6.2225 (2.8); 6.2053 (1.8); 6.1881 (0.4); 3.3309 (542.7); 2.7298 (0.4); 2.6756 (4.2); 2.6711 (5.7); 2.6665 (4.2); 2.6622 (2.0); 2.5245 (20.9); 2.5196 (34.9); 2.5111 (350.5); 2.5066 (680.5); 2.5021 (880.6); 2.4975 (638.4); 2.4930 (308.7); 2.3381 (1.8); 2.3334 (3.9); 2.3289 (5.4); 2.3244 (3.8); 2.0758 (0.6); 1.6448 (10.4); 1.6274 (10.4); 0.1459 (5.4); 0.0209 (2.0); 0.0079 (55.8); −0.0002 (1198.0); −0.0086 (42.4); −0.1496 (5.3) | 406.2 |
| I-70 | 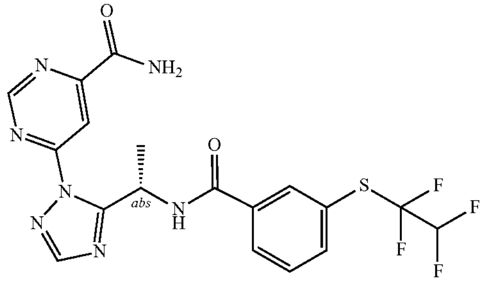 [SMILES: C[C@H](NC(=O)c1cccc(SC(F)(F)C(F)F)c1)c1ncnn1-c1cc(C(N)=O)ncn1] | $^1$H-NMR (400.2 MHz, d6-DMSO) δ = 9.3346 (3.5); 9.3164 (13.9); 9.3136 (12.3); 8.4707 (3.8); 8.3845 (10.5); 8.3817 (10.4); 8.3145 (16.0); 8.1417 (8.1); 8.1375 (6.7); 8.0567 (2.6); 8.0539 (3.6); 8.0504 (2.5); 8.0371 (2.9); 8.0340 (3.8); 7.8319 (3.1); 7.8123 (3.6); 7.6289 (3.9); 7.6094 (6.8); 7.5899 (3.1); 6.8952 (0.7); 6.8866 (1.4); 6.8776 (0.7); 6.7644 (1.4); 6.7557 (2.9); 6.7468 (1.4); 6.6334 (0.7); 6.6249 (1.4); 6.6159 (0.7); 6.2870 (0.5); 6.2699 (2.4); 6.2526 (3.8); 6.2352 (2.4); 6.2179 (0.5); 3.3355 (51.8); 2.6782 (0.4); 2.6738 (0.6); 2.6694 (0.4); 2.5272 (2.1); 2.5137 (37.3); 2.5093 (72.4); 2.508 (93.3); 2.5003 (68.3); 2.4959 (33.5); 2.3361 (0.4); 2.3316 (0.6); 2.3271 (0.4); 1.6633 (13.8); 1.6459 (13.8); 0.1459 (0.6); 0.0079 (5.9); −0.0002 (122.4); −0.0085 (4.4); −0.1496 (0.6) | 530.0 |

TABLE 1-continued
| Example | Structure[1)] | NMR Peak List[2)] | ESI Mass (m/z)[3)] |
| --- | --- | --- | --- |
| I-71 | 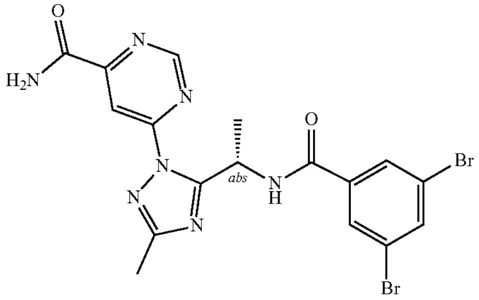 [SMILES: Cc1nc([C@H](C)NC(=O)c2cc(Br)cc(Br)c2)n(-c2cc(C(N)=O)ncn2)n1] | $^1$H-NMR (400.2 MHz, d6-DMSO) δ = 9.3348 (1.5); 9.3171 (1.5); 9.2715 (4.6); 9.2686 (4.4); 8.4543 (1.6); 8.3367 (4.8); 8.3339 (4.5); 8.1091 (1.6); 8.0550 (4.8); 8.0512 (10.8); 8.0460 (4.3); 8.0425 (2.6); 8.0377 (1.0); 6.2353 (1.1); 6.2179 (1.7); 6.2004 (1.1); 3.3359 (45.0); 2.6736 (0.4); 2.5271 (1.2); 2.5136 (22.6); 2.5092 (43.6); 2.5046 (55.7); 2.5001 (40.0); 2.4956 (19.0); 2.3718 (16.0); 2.3314 (0.4); 1.6222 (5.8); 1.6049 (5.8); 0.1461 (0.4); 0.0079 (3.6); −0.0002 (78.7); −0.0086 (2.7); −0.1495 (0.4) | 510.1 |
| I-72 | 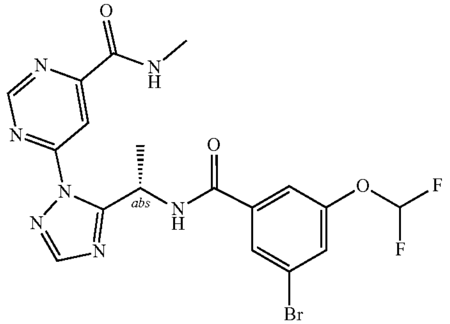 [SMILES: CNC(=O)c1cc(-n2ncnc2[C@H](C)NC(=O)c2cc(Br)cc(OC(F)F)c2)ncn1] | $^1$H-NMR (400.2 MHz, d6-DMSO) δ = 9.3370 (3.2); 9.3191 (4.0); 9.3149 (10.9); 9.3121 (10.2); 9.1696 (0.8); 9.1584 (2.4); 9.1463 (2.4); 9.1351 (0.8); 8.3720 (10.2); 8.3692 (9.9); 8.3200 (15.2); 7.9450 (4.7); 7.9413 (7.7); 7.9376 (4.6); 7.6449 (3.1); 7.6398 (6.1); 7.6353 (4.4); 7.6212 (4.8); 7.6182 (5.3); 7.5238 (3.7); 7.3405 (7.8); 7.1571 (3.9); 6.2646 (0.5); 6.2472 (2.2); 6.2299 (3.4); 6.2125 (2.2); 6.1949 (0.4); 3.3356 (93.6); 2.8737 (16.0); 2.8616 (15.9); 2.6779 (0.5); 2.6734 (0.7); 2.6689 (0.5); 2.5267 (2.3); 2.5133 (42.7); 2.5089 (83.0); 2.5043 (106.9); 2.4998 (77.4); 2.4953 (37.2); 2.3357 (0.5); 2.3312 (0.7); 2.3266 (0.5); 2.0778 (3.7); 1.6509 (12.6); 1.6335 (12.6); 0.1459 (0.7); 0.0078 (7.0); −0.0002 (154.7); −0.0086 (5.6); −0.1496 (0.7) | 498.1 |
| I-73 | 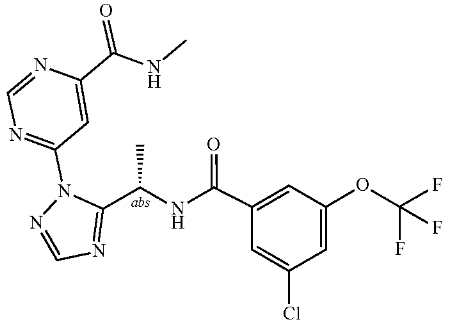 | $^1$H-NMR (400.2 MHz, d6-DMSO) δ = 9.4168 (3.5); 9.3995 (3.6); 9.3133 (9.4); 9.3107 (9.7); 9.1686 (0.9); 9.1579 (2.6); 9.1457 (2.5); 9.1343 (0.9); 8.3727 (9.5); 8.3700 (9.8); 8.3259 (14.7); 7.9970 (4.5); 7.9931 (7.2); 7.9894 (4.8); 7.7927 (5.2); 7.7734 (5.1); 7.7713 (5.2); 6.2735 (0.5); 6.2562 (2.2); 6.2389 (3.5); 6.2216 (2.3); 6.2044 (0.5); 3.3385 (131.7); 2.8734 (16.0); 2.8613 (15.9); 2.6788 (0.5); 2.6744 (0.7); 2.6698 (0.5); 2.5275 (2.7); 2.5138 (44.3); 2.5098 (85.2); 2.5053 (110.1); 2.5008 (82.3); 2.3365 (0.5); 2.3322 (0.7); 2.3277 (0.5); 2.0784 (1.5); 1.6584 (13.0); 1.6411 (12.9); 0.0078 (1.0); −0.0002 (27.1); −0.0084 (1.0) | 470.2 |

TABLE 1-continued
| Ex-am-ple | Structure[1)] | NMR Peak List[2)] | ESI Mass (m/z)[3)] |
|---|---|---|---|
| I-74 | 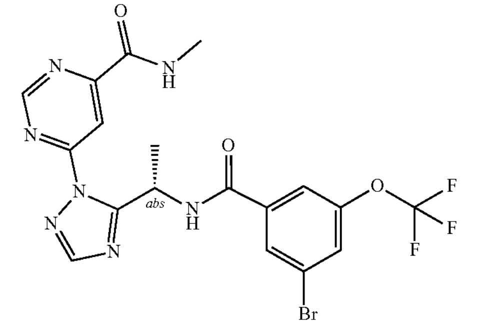 [SMILES: CNC(=O)c1cc(-n2ncnc2[C@H](C)NC(=O)c2cc(Br)cc(OC(F)(F)F)c2)ncn1] | $^1$H-NMR (400.2 MHz, d6-DMSO) δ = 9.4157 (3.4); 9.3984 (3.5); 9.3118 (9.2); 9.3093 (9.5); 9.1566 (2.5); 9.1442 (2.5); 8.3715 (9.5); 8.3690 (9.7); 8.3236 (14.6); 8.3191 (5.8); 8.1270 (4.6); 8.1236 (7.6); 8.1201 (4.9); 7.8953 (5.2); 7.7967 (5.3); 6.2705 (0.5); 6.2532 (2.3); 6.2359 (3.5); 6.2186 (2.3); 6.2008 (0.5); 3.3313 (138.8); 3.3075 (2.7); 2.8722 (15.7); 2.8601 (16.0); 2.6765 (1.2); 2.6723 (1.6); 2.6679 (1.2); 2.5254 (5.6); 2.5076 (203.4); 2.5032 (261.8); 2.4989 (197.4); 2.3344 (1.2); 2.3301 (1.6); 2.3257 (1.2); 1.6549 (13.3); 1.6375 (13.3); 1.1101 (0.7); 0.1458 (0.8); −0.0003 (172.8); −0.0082 (7.7); −0.1498 (0.8) | 516.1 |
| I-75 | 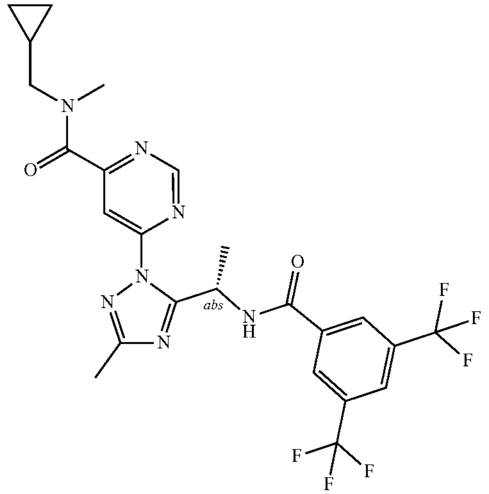 [SMILES: Cc1nc([C@H](C)NC(=O)c2cc(C(F)(F)F)cc(C(F)(F)F)c2)n(-c2cc(C(=O)N(C)CC3CC3)ncn2)n1] | $^1$H-NMR (400.2 MHz, d6-DMSO) δ = 9.6516 (1.5); 9.6473 (1.7); 9.6343 (1.6); 9.6300 (1.6); 9.2255 (3.6); 9.2225 (3.6); 9.2123 (4.2); 9.2093 (4.2); 8.5372 (8.0); 8.3374 (3.6); 7.9427 (3.6); 7.9397 (3.8); 7.9349 (4.4); 7.9319 (4.4); 6.3008 (0.9); 6.2930 (1.1); 6.2834 (1.4); 6.2757 (1.6); 6.2658 (0.9); 6.2582 (1.0); 3.3866 (2.6); 3.3693 (2.8); 3.3324 (130.8); 3.1510 (3.0); 3.1337 (3.1); 3.0938 (14.2); 2.9865 (13.5); 2.6769 (0.7); 2.6724 (1.0); 2.6679 (0.7); 2.6632 (0.3); 2.5259 (3.1); 2.5213 (4.5); 2.5125 (57.4); 2.5080 (118.0); 2.5034 (157.2); 2.4988 (115.2); 2.4943 (55.9); 2.3545 (13.8); 2.3503 (16.0); 2.3349 (0.9); 2.3303 (1.1); 2.3258 (0.8); 2.3212 (0.4); 2.0767 (1.6); 1.6739 (9.2); 1.6565 (9.2); 1.1208 (0.4); 1.1142 (0.4); 1.1025 (0.6); 1.0904 (0.4); 1.0830 (0.4); 1.0704 (0.4); 1.0647 (0.3); 1.0528 (0.4); 1.0451 (0.4); 1.0331 (0.7); 1.0208 (0.4); 1.0134 (0.4); 0.5496 (0.5); 0.5389 (1.5); 0.5346 (1.6); 0.5300 (0.8); 0.5245 (0.8); 0.5188 (1.6); 0.5144 (1.6); 0.5044 (0.6); 0.4640 (0.4); 0.4599 (0.4); 0.4523 (1.8); 0.4482 (1.9); 0.4405 (0.8); 0.4371 (0.7); 0.4322 (1.8); 0.4281 (1.9); 0.4210 (0.4); 0.4170 (0.4); 0.3337 (0.6); 0.3202 (1.9); 0.3114 (1.6); 0.3079 (1.9); 0.2967 (0.5); 0.1456 (1.2); 0.1331 (2.0); 0.1220 (2.0); 0.1099 (0.6); 0.0079 (3.8); −0.0002 (128.8); −0.0086 (4.5); −0.1498 (0.5) | 556.2 |

TABLE 1-continued
| Example | Structure[1)] | NMR Peak List[2)] | ESI Mass (m/z)[3)] |
|---|---|---|---|
| I-76 | 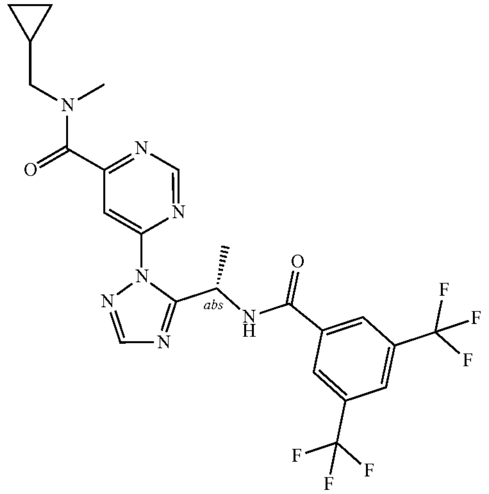 [SMILES: C[C@H](NC(=O)c1cc(C(F)(F)F)cc(C(F)(F)F)c1)c1ncnn1-c1cc(C(=O)N(C)CC2CC2)ncn1] | $^1$H-NMR (400.2 MHz, d6-DMSO) δ = 9.6644 (2.0); 9.6478 (2.1); 9.2662 (3.8); 9.2631 (3.8); 9.2534 (4.6); 9.2504 (4.5); 8.5153 (8.5); 8.3392 (3.8); 8.3190 (0.3); 8.3117 (5.9); 8.3072 (7.0); 8.0143 (4.0); 8.0112 (4.2); 8.0080 (5.0); 8.0050 (4.7); 6.3007 (0.9); 6.2952 (1.1); 6.2836 (1.4); 6.2779 (1.7); 6.2660 (0.9); 6.2607 (1.0); 3.6657 (0.6); 3.3929 (2.8); 3.3755 (3.1); 3.3316 (292.2); 3.1476 (3.3); 3.1303 (3.4); 3.1004 (16.0); 2.9893 (14.7); 2.6804 (0.9); 2.6761 (1.9); 2.6714 (2.6); 2.6669 (1.9); 2.6622 (0.9); 2.5250 (8.6); 2.5203 (12.4); 2.5116 (152.4); 2.5071 (309.6); 2.5024 (409.0); 2.4978 (296.3); 2.4933 (141.0); 2.3386 (0.8); 2.3339 (1.8); 2.3293 (2.6); 2.3247 (1.8); 2.3202 (0.8); 1.6949 (9.8); 1.6775 (9.7); 1.1217 (0.4); 1.1142 (0.4); 1.1022 (0.7); 1.0903 (0.4); 1.0823 (0.4); 1.0717 (0.4); 1.0619 (0.5); 1.0539 (0.5); 1.0420 (0.8); 1.0297 (0.5); 1.0220 (0.5); 0.5511 (0.5); 0.5402 (1.6); 0.5360 (1.7); 0.5313 (0.8); 0.5257 (0.8); 0.5202 (1.7); 0.5158 (1.6); 0.5058 (0.6); 0.4651 (0.4); 0.4535 (1.9); 0.4495 (2.0); 0.4417 (0.8); 0.4385 (0.8); 0.4334 (2.0); 0.4293 (2.0); 0.4184 (0.5); 0.3347 (0.6); 0.3209 (1.9); 0.3124 (1.7); 0.3088 (1.9); 0.2975 (0.5); 0.1514 (0.8); 0.1456 (2.0); 0.1390 (2.2); 0.1286 (2.0); 0.1152 (0.6); 0.0079 (11.7); −0.0003 (378.7); −0.0086 (12.3); −0.0173 (0.7); −0.1496 (1.5) | 542.2 |
| I-77 | 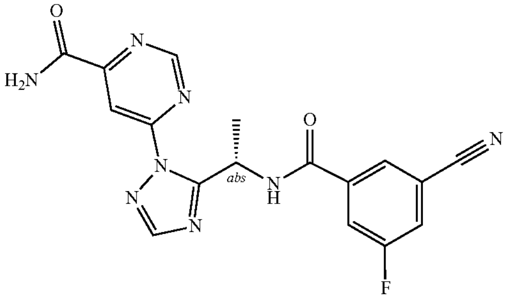 [SMILES: C[C@H](NC(=O)c1cc(F)cc(C#N)c1)c1ncnn1-c1cc(C(N)=O)ncn1] | $^1$H-NMR (400.2 MHz, d6-DMSO) δ = 9.3938 (3.4); 9.3767 (3.5); 9.3138 (10.3); 9.3109 (10.6); 8.4702 (3.5); 8.3782 (10.4); 8.3754 (10.4); 8.3222 (16.0); 8.1870 (4.8); 8.1837 (8.9); 8.1804 (5.3); 8.1298 (3.4); 8.0881 (2.1); 8.0851 (2.3); 8.0819 (2.6); 8.0788 (2.3); 8.0673 (2.1); 8.0639 (2.5); 8.0610 (2.5); 8.0578 (2.2); 8.0057 (2.2); 8.0022 (2.5); 7.9996 (2.4); 7.9959 (2.0); 7.9821 (2.4); 7.9784 (2.7); 7.9722 (2.0); 7.9527 (1.6); 6.2818 (0.5); 6.2647 (2.4); 6.2473 (3.8); 6.2299 (2.4); 6.2121 (0.5); 3.3960 (0.4); 3.3307 (602.4); 2.8908 (11.8); 2.7309 (9.9); 2.6802 (2.0); 2.6758 (4.2); 2.6712 (5.8); 2.6667 (4.2); 2.6620 (2.0); 2.5247 (19.0); 2.5199 (28.9); 2.5112 (344.3); 2.5068 (689.9); 2.5022 (907.1); 2.4977 (666.3); 2.4932 (326.0); 2.3382 (1.7); 2.3336 (4.0); 2.3291 (5.6); 2.3246 (4.1); 2.3202 (1.9); 1.6597 (13.9); 1.6424 | 381.2 |

TABLE 1-continued
| Example | Structure[1)] | NMR Peak List[2)] | ESI Mass (m/z)[3)] |
|---|---|---|---|
| | | (13.8); 0.1458 (3.2); 0.0079 (25.4); −0.0002 (722.4); −0.0085 (24.6); −0.0383 (0.3); −0.1497 (3.1) | |
| I-78 | 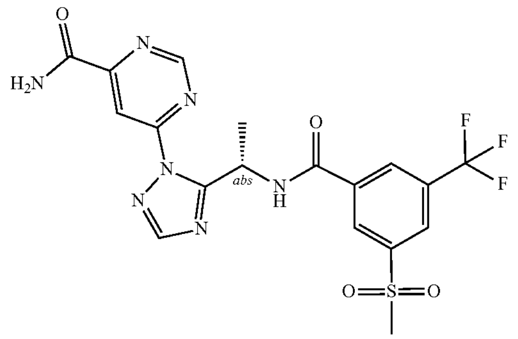 [SMILES: C[C@H](NC(=O)c1cc(C(F)(F)F)cc(S(C)(=O)=O)c1)c1ncnn1-c1cc(C(N)=O)ncn1] | $^1$H-NMR (400.2 MHz, d6-DMSO) δ = 9.7016 (3.4); 9.6842 (3.5); 9.3298 (10.9); 9.3269 (11.1); 8.6640 (6.6); 8.5273 (5.9); 8.4732 (3.6); 8.4099 (5.9); 8.3880 (10.9); 8.3851 (11.0); 8.3402 (16.0); 8.1316 (3.4); 6.3441 (0.5); 6.3272 (2.3); 6.3098 (3.7); 6.2924 (2.4); 6.2750 (0.5); 3.3847 (37.9); 3.3304 (146.4); 2.6765 (1.3); 2.6719 (1.8); 2.6674 (1.4); 2.5254 (6.1); 2.5207 (9.2); 2.5120 (104.7); 2.5075 (211.0); 2.5029 (278.6); 2.4983 (203.3); 2.4938 (98.4); 2.3388 (0.6); 2.3343 (1.2); 2.3298 (1.7); 2.3252 (1.2); 2.3207 (0.6); 1.6922 (13.3); 1.6748 (13.4); 0.0081 (2.3); −0.0001 (71.6); −0.0084 (2.2) | 484.2 |
| I-79 | 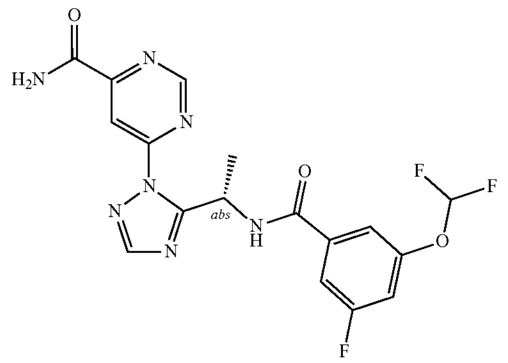 [SMILES: C[C@H](NC(=O)c1cc(F)cc(OC(F)F)c1)c1ncnn1-c1cc(C(N)=O)ncn1] | $^1$H-NMR (400.2 MHz, d6-DMSO) δ = 9.3134 (11.5); 9.3104 (11.5); 9.2947 (3.2); 9.2774 (3.2); 8.4724 (3.1); 8.3771 (11.1); 8.3742 (10.9); 8.3159 (16.0); 8.1325 (3.0); 7.9172 (0.9); 7.5972 (2.0); 7.5939 (2.4); 7.5915 (2.3); 7.5881 (2.1); 7.5740 (2.0); 7.5706 (2.6); 7.5683 (2.2); 7.5648 (2.1); 7.5217 (4.5); 7.5080 (4.8); 7.3657 (1.8); 7.3600 (3.1); 7.3544 (1.6); 7.3384 (10.6); 7.3306 (1.5); 7.1552 (4.5); 6.2672 (0.5); 6.2498 (2.2); 6.2325 (3.5); 6.2151 (2.2); 6.1977 (0.4); 3.3591 (6.3); 3.2618 (2.8); 3.1806 (0.5); 3.1463 (2.2); 2.7956 (0.4); 2.7841 (0.4); 2.6813 (0.4); 2.6769 (0.9); 2.6723 (1.2); 2.6677 (0.9); 2.6631 (0.4); 2.5258 (4.3); 2.5211 (6.5); 2.5124 (74.7); 2.5079 (151.0); 2.5033 (198.6); 2.4987 (143.1); 2.4941 (67.8); 2.3392 (0.4); 2.3347 (0.9); 2.3302 (1.3); 2.3256 (0.9); 2.3211 (0.4); 2.0765 (2.6); 1.6558 (13.0); 1.6385 (12.9); 0.0081 (1.7); −0.0001 (55.4); −0.0085 (1.6) | 422.3 |

TABLE 1-continued
| Example | Structure[1)] | NMR Peak List[2)] | ESI Mass (m/z)[3)] |
|---|---|---|---|
| I-80 | 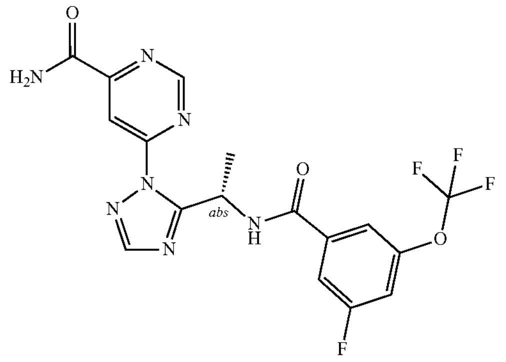 [SMILES: C[C@H](NC(=O)c1cc(F)cc(OC(F)(F)F)c1)c1ncnn1-c1cc(C(N)=O)ncn1] | $^1$H-NMR (400.2 MHz, d6-DMSO) δ = 9.3786 (3.3); 9.3612 (3.4); 9.3103 (10.5); 9.3073 (10.4); 8.4702 (3.2); 8.3776 (10.7); 8.3747 (10.5); 8.3217 (16.0); 8.1303 (3.2); 7.7882 (1.9); 7.7847 (2.3); 7.7826 (2.4); 7.7791 (2.1); 7.7651 (2.0); 7.7617 (2.5); 7.7595 (2.3); 7.7561 (2.1); 7.6915 (4.5); 7.6423 (2.1); 7.6213 (2.1); 6.2734 (0.5); 6.2562 (2.3); 6.2389 (3.6); 6.2215 (2.3); 6.2044 (0.5); 3.3323 (162.2); 2.6814 (0.4); 2.6770 (1.0); 2.6724 (1.3); 2.6678 (0.9); 2.6635 (0.4); 2.5259 (4.5); 2.5212 (6.9); 2.5125 (79.7); 2.5080 (158.7); 2.5034 (206.8); 2.4988 (148.5); 2.4943 (70.2); 2.3394 (0.4); 2.3348 (0.9); 2.3303 (1.3); 2.3257 (0.9); 2.3214 (0.4); 1.6607 (13.3); 1.6433 (13.3); 0.0080 (1.7); −0.0001 (51.9); −0.0085 (1.5) | 440.3 |
| I-81 | 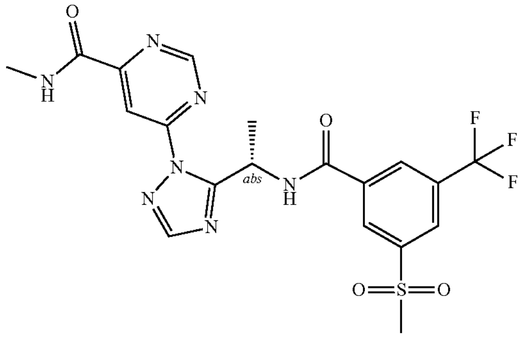 [SMILES: CNC(=O)c1cc(-n2ncnc2[C@H](C)NC(=O)c2cc(C(F)(F)F)cc(S(C)(=O)=O)c2)ncn1] | $^1$H-NMR (400.2 MHz, d6-DMSO) δ = 9.7001 (3.4); 9.6826 (3.5); 9.3314 (9.9); 9.3286 (10.0); 9.1685 (0.9); 9.1572 (2.5); 9.1450 (2.5); 9.1337 (0.8); 8.6605 (6.3); 8.5266 (5.7); 8.4113 (5.7); 8.3811 (9.5); 8.3784 (9.7); 8.3419 (15.6); 8.3185 (0.6); 6.3440 (0.5); 6.3270 (2.2); 6.3096 (3.4); 6.2922 (2.2); 6.2744 (0.5); 3.4042 (0.5); 3.3838 (36.0); 3.3311 (151.5); 3.3078 (0.4); 2.8727 (16.0); 2.8606 (15.9); 2.6766 (1.0); 2.6721 (1.4); 2.6676 (1.0); 2.5255 (4.6); 2.5207 (7.0); 2.5120 (83.6); 2.5076 (167.5); 2.5031 (219.7); 2.4986 (160.9); 2.4942 (78.7); 2.3345 (1.0); 2.3299 (1.4); 2.3255 (1.0); 1.6916 (12.5); 1.6743 (12.5); 0.0080 (1.6); −0.0001 (53.2); −0.0085 (1.7) | 498.2 |

TABLE 1-continued
| Example | Structure[1)] | NMR Peak List[2)] | ESI Mass (m/z)[3)] |
|---|---|---|---|
| I-82 | 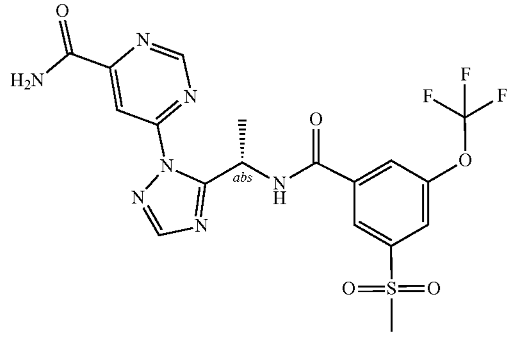 [SMILES: C[C@H](NC(=O)c1cc(OC(F)(F)F)cc(S(C)(=O)=O)c1)c1ncnn1-c1cc(C(N)=O)ncn1] | $^1$H-NMR (400.2 MHz, d6-DMSO) δ = 9.6221 (4.6); 9.6046 (4.7); 9.3203 (12.8); 8.4687 (6.4); 8.4590 (11.5); 8.3819 (13.3); 8.3358 (13.3); 8.3183 (0.4); 8.1346 (11.4); 8.0867 (8.1); 6.3198 (0.7); 6.3035 (2.8); 6.2865 (4.4); 6.2692 (2.9); 6.2517 (0.7); 3.3596 (37.5); 3.3309 (144.3); 2.6710 (2.2); 2.5023 (350.8); 2.3290 (2.2); 1.6814 (16.0); 1.6641 (16.0); −0.0008 (39.6); −0.0023 (38.0) | 500.2 |
| I-83 | 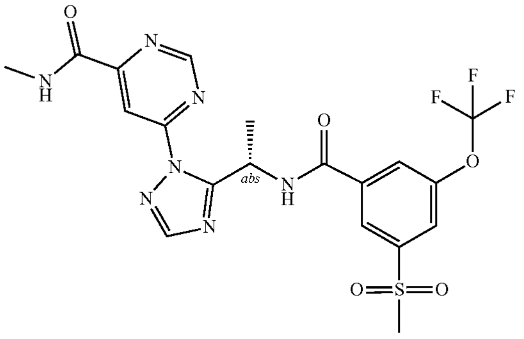 [SMILES: CNC(=O)c1cc(-n2ncnc2[C@H](C)NC(=O)c2cc(OC(F)(F)F)cc(S(C)(=O)=O)c2)ncn1] | $^1$H-NMR (400.2 MHz, d6-DMSO) δ = 9.622 (3.1); 9.6047 (3.1); 9.3252 (10.2); 9.3223 (10.1); 9.1678 (0.8); 9.1569 (2.3); 9.1448 (2.2); 9.1331 (0.7); 8.4586 (4.5); 8.4549 (7.9); 8.4513 (4.4); 8.3784 (10.4); 8.3755 (10.1); 8.3386 (15.0); 8.1379 (4.4); 8.1357 (4.2); 8.0895 (4.4); 6.3217 (0.4); 6.3049 (2.1); 6.2875 (3.3); 6.2701 (2.1); 6.2527 (0.4); 3.6663 (0.6); 3.3778 (1.0); 3.3597 (35.9); 3.3314 (113.4); 2.8721 (16.0); 2.8600 (15.9); 2.6809 (0.6); 2.6764 (1.2); 2.6719 (1.6); 2.6673 (1.1); 2.6628 (0.5); 2.5253 (5.8); 2.5206 (8.8); 2.5119 (95.5); 2.5074 (189.1); 2.5029 (246.2); 2.4982 (177.6); 2.4937 (84.5); 2.3389 (0.5); 2.3343 (1.1); 2.3297 (1.5); 2.3251 (1.1); 2.3206 (0.5); 1.9089 (0.8); 1.6822 (12.0); 1.6648 (12.0); 0.0080 (1.9); −0.0002 (58.8); −0.0085 (1.8) | 514.2 |

TABLE 1-continued
| Example | Structure[1)] | NMR Peak List[2)] | ESI Mass (m/z)[3)] |
|---|---|---|---|
| I-84 | 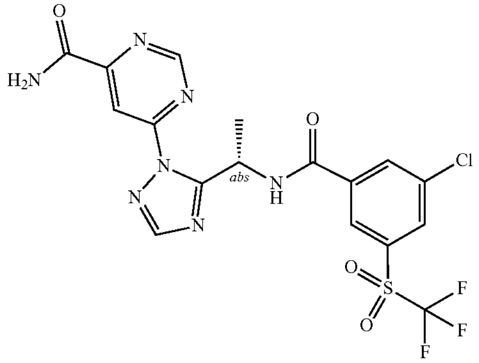 [SMILES: C[C@H](NC(=O)c1cc(Cl)cc(S(=O)(=O)C(F)(F)F)c1)c1ncnn1-c1cc(C(N)=O)ncn1] | $^{1}$H-NMR (400.2 MHz, d6-DMSO) δ = 9.7216 (3.5); 9.7043 (3.6); 9.3152 (10.7); 9.3124 (10.4); 8.5508 (4.4); 8.5467 (7.2); 8.5424 (5.1); 8.4957 (6.9); 8.4704 (3.7); 8.4252 (4.0); 8.4214 (6.4); 8.3837 (10.1); 8.3809 (9.7); 8.3412 (16.0); 8.1324 (3.6); 6.3206 (0.5); 6.3035 (2.3); 6.2862 (3.6); 6.2688 (2.3); 6.2513 (0.5); 3.3330 (135.4); 2.6776 (0.8); 2.6731 (1.1); 2.6686 (0.8); 2.5265 (3.8); 2.5217 (5.8); 2.5129 (67.3); 2.5086 (132.4); 2.5041 (172.0); 2.4995 (125.7); 2.4952 (61.3); 2.3354 (0.8); 2.3309 (1.1); 2.3264 (0.8); 2.0774 (2.3); 1.6814 (13.1); 1.6640 (13.0); 0.0080 (1.2); −0.0001 (37.5); −0.0085 (1.2) | 504.1 |
| I-85 | 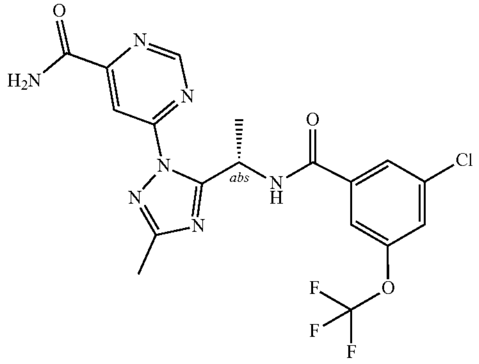 [SMILES: Cc1nc([C@H](C)NC(=O)c2cc(Cl)cc(OC(F)(F)F)c2)n(-c2cc(C(N)=O)ncn2)n1] | $^{1}$H-NMR (400.2 MHz, d6-DMSO) δ = 9.4001 (1.3); 9.3826 (1.4); 9.2689 (4.7); 9.2659 (4.7); 8.4518 (1.3); 8.3377 (4.8); 8.3348 (4.7); 8.1089 (1.3); 8.0222 (2.0); 8.0182 (3.4); 8.0141 (2.0); 7.7938 (4.6); 6.2515 (1.0); 6.2340 (1.6); 6.2166 (1.0); 3.3338 (45.5); 2.6729 (0.4); 2.5266 (1.6); 2.5218 (2.4); 2.5131 (26.9); 2.5086 (53.5); 2.5040 (69.6); 2.4994 (49.9); 2.4948 (23.4); 2.4678 (0.4); 2.3731 (16.0); 2.3354 (0.3); 2.3308 (0.4); 2.3263 (0.3); 1.6371 (5.4); 1.6197 (5.3); −0.0002 (3.6) | 470.3 |

TABLE 1-continued
| Example | Structure[1)] | NMR Peak List[2)] | ESI Mass (m/z)[3)] |
|---|---|---|---|
| I-86 | 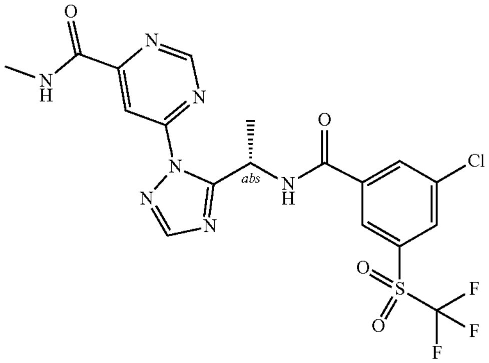 [SMILES: CNC(=O)c1cc(-n2ncnc2[C@H](C)NC(=O)c2cc(Cl)cc(S(=O)(=O)C(F)(F)F)c2)ncn1] | $^1$H-NMR (400.2 MHz, d6-DMSO) δ = 9.7215 (3.2); 9.7042 (3.3); 9.3181 (10.2); 9.3153 (10.1); 9.1678 (0.8); 9.1561 (2.4); 9.1440 (2.4); 9.1325 (0.8); 8.5498 (4.3); 8.5457 (7.0); 8.5413 (5.1); 8.4953 (6.4); 8.4254 (3.8); 8.4215 (5.9); 8.3769 (10.1); 8.3741 (9.9); 8.3433 (15.0); 6.3214 (0.5); 6.3041 (2.2); 6.2868 (3.4); 6.2695 (2.2); 6.2521 (0.5); 3.3358 (87.8); 2.8732 (16.0); 2.8610 (15.9); 2.6789 (0.5); 2.6745 (0.7); 2.6699 (0.5); 2.5279 (2.3); 2.5231 (3.7); 2.5144 (41.6); 2.5100 (82.2); 2.5054 (107.0); 2.5009 (78.6); 2.4965 (38.6); 2.3368 (0.5); 2.3323 (0.6); 2.3278 (0.5); 1.6817 (12.5); 1.6643 (12.5); −0.0002 (8.8) | 518.2 |
| I-87 | 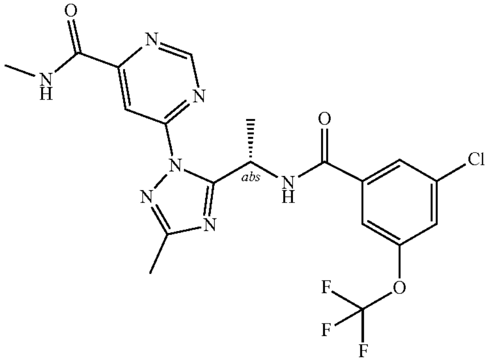 [SMILES: CNC(=O)c1cc(-n2nc(C)nc2[C@H](C)NC(=O)c2cc(Cl)cc(OC(F)(F)F)c2)ncn1] | $^1$H-NMR (400.2 MHz, d6-DMSO) δ = 9.4003 (1.4); 9.3826 (1.5); 9.2712 (4.7); 9.2683 (4.6); 9.1495 (0.4); 9.1378 (1.0); 9.1257 (1.0); 9.1146 (0.3); 8.3299 (4.9); 8.3270 (4.7); 8.0207 (2.1); 8.0167 (3.7); 8.0126 (2.1); 7.7934 (5.0); 6.2527 (1.0); 6.2353 (1.7); 6.2178 (1.1); 3.3364 (31.4); 2.8696 (7.3); 2.8574 (7.2); 2.5283 (0.9); 2.5236 (1.4); 2.5148 (15.7); 2.5104 (31.0); 2.5058 (40.1); 2.5012 (28.8); 2.4967 (13.5); 2.3778 (16.0); 2.0791 (4.3); 1.6380 (5.6); 1.6206 (5.6); −0.0002 (2.1) | 484.3 |

TABLE 1-continued
| Example | Structure[1)] | NMR Peak List[2)] | ESI Mass (m/z)[3)] |
|---|---|---|---|
| I-88 | 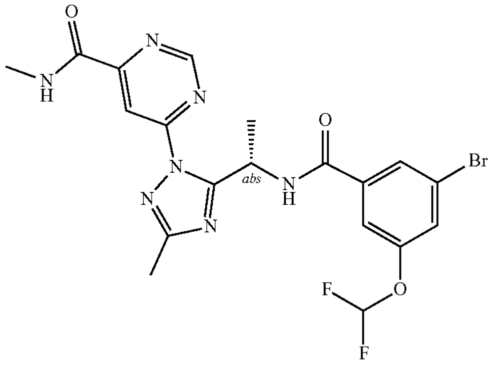 [SMILES: CNC(=O)c1cc(-n2nc(C)nc2[C@H](C)NC(=O)c2cc(Br)cc(OC(F)F)c2)ncn1] | $^1$H-NMR (400.2 MHz, d6-DMSO) δ = 9.3171 (1.4); 9.2994 (1.5); 9.2723 (4.7); 9.2694 (4.6); 9.1487 (0.4); 9.1377 (1.1); 9.1254 (1.1); 9.1139 (0.4); 8.3287 (4.6); 8.3258 (4.6); 7.9695 (2.1); 7.9657 (3.7); 7.9620 (2.1); 7.6420 (5.7); 7.6385 (5.9); 7.5252 (1.7); 7.3418 (3.7); 7.1585 (1.8); 6.2438 (1.0); 6.2263 (1.7); 6.2088 (1.1); 3.3347 (35.1); 2.8694 (7.4); 2.8572 (7.3); 2.5269 (1.1); 2.5221 (1.6); 2.5135 (18.3); 2.5090 (36.5); 2.5044 (47.6); 2.4998 (34.5); 2.4953 (16.5); 2.3748 (16.0); 2.0779 (3.7); 1.6301 (5.6); 1.6128 (5.6); −0.0002 (2.1) | 512.2 |
| I-89 | 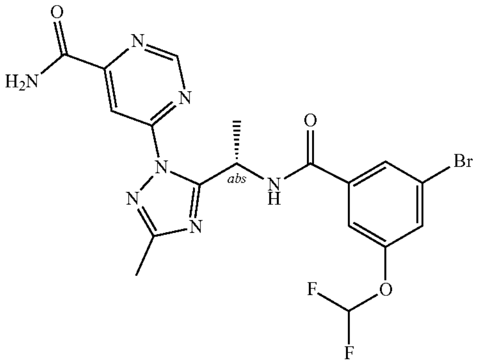 [SMILES: Cc1nc([C@H](C)NC(=O)c2cc(Br)cc(OC(F)F)c2)n(-c2cc(C(N)=O)ncn2)n1] | $^1$H-NMR (400.2 MHz, d6-DMSO) δ = 9.3179 (1.5); 9.3003 (1.5); 9.2706 (4.7); 9.2677 (4.7); 8.4508 (1.5); 8.3367 (4.4); 8.3339 (4.4); 8.1073 (1.5); 7.9731 (2.0); 7.9693 (3.7); 7.9655 (2.1); 7.6426 (6.3); 7.6390 (6.3); 7.5254 (1.8); 7.3421 (3.8); 7.1587 (1.9); 6.2434 (1.0); 6.2259 (1.7); 6.2084 (1.0); 3.3321 (67.3); 2.6765 (0.4); 2.6720 (0.6); 2.6674 (0.4); 2.5255 (2.1); 2.5208 (3.2); 2.5121 (36.2); 2.5077 (72.3); 2.5031 (94.8); 2.4985 (68.7); 2.4940 (33.0); 2.3701 (16.0); 2.3346 (0.4); 2.3299 (0.6); 2.3253 (0.4); 1.6294 (5.6); 1.6120 (5.6); −0.0002 (3.7) | 498.1 |

TABLE 1-continued
| Example | Structure[1)] | NMR Peak List[2)] | ESI Mass (m/z)[3)] |
|---|---|---|---|
| I-90 | 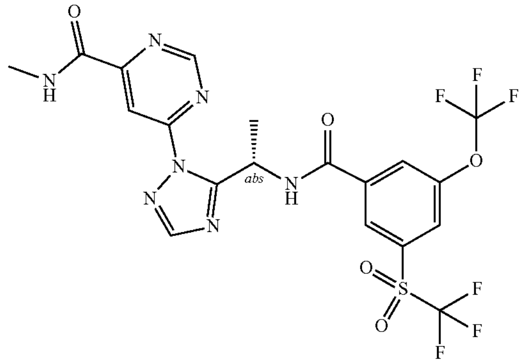 [SMILES: CNC(=O)c1cc(-n2ncnc2[C@H](C)NC(=O)c2cc(OC(F)(F)F)cc(S(=O)(=O)C(F)(F)F)c2)ncn1] | $^1$H-NMR (400.2 MHz, d6-DMSO) δ = 9.8225 (2.7); 9.8054 (2.7); 9.3200 (9.6); 9.3172 (9.4); 9.1742 (0.7); 9.1640 (2.0); 9.1519 (1.9); 9.1406 (0.6); 8.6410 (5.7); 8.4568 (4.2); 8.4545 (3.9); 8.3848 (4.0); 8.3780 (12.4); 8.3751 (11.2); 8.3499 (14.7); 6.3360 (0.4); 6.3187 (2.0); 6.3014 (3.2); 6.2840 (2.0); 6.2667 (0.4); 3.5073 (0.4); 3.3460 (396.6); 2.8710 (16.0); 2.8588 (16.0); 2.7130 (0.6); 2.6823 (0.7); 2.6776 (1.5); 2.6730 (2.0); 2.6684 (1.4); 2.6639 (0.7); 2.5776 (0.4); 2.5434 (189.4); 2.5266 (6.7); 2.5218 (10.3); 2.5131 (117.8); 2.5086 (238.4); 2.5040 (310.5); 2.4994 (223.7); 2.4948 (105.4); 2.3694 (0.5); 2.3399 (0.6); 2.3354 (1.4); 2.3308 (1.9); 2.3263 (1.4); 2.3217 (0.6); 2.0779 (2.3); 1.6913 (11.8); 1.6739 (11.7); −0.0002 (6.7) | 568.0 |
| I-91 | 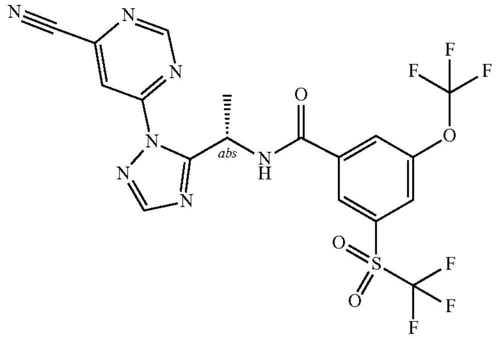 [SMILES: C[C@H](NC(=O)c1cc(OC(F)(F)F)cc(S(=O)(=O)C(F)(F)F)c1)c1ncnn1-c1cc(C#N)ncn1] | $^1$H-NMR (400.2 MHz, d6-DMSO) δ = 9.8262 (2.5); 9.8090 (2.6); 9.3882 (9.5); 9.3852 (9.5); 8.6382 (5.5); 8.6253 (7.6); 8.6231 (7.0); 8.6224 (6.7); 8.4575 (4.0); 8.4552 (3.7); 8.3871 (16.0); 6.2684 (0.4); 6.2515 (2.0); 6.2342 (3.1); 6.2169 (2.0); 6.1992 (0.4); 3.3447 (422.2); 2.7131 (0.5); 2.6815 (0.8); 2.6769 (1.7); 2.6724 (2.3); 2.6678 (1.7); 2.6632 (0.8); 2.5563 (1.0); 2.5428 (168.2); 2.5259 (7.8); 2.5213 (11.5); 2.5125 (135.0); 2.5080 (273.3); 2.5034 (357.3); 2.4987 (257.9); 2.4942 (121.7); 2.3687 (0.5); 2.3393 (0.7); 2.3348 (1.6); 2.3302 (2.2); 2.3256 (1.6); 2.3211 (0.7); 2.0774 (3.9); 1.6772 (11.6); 1.6598 (11.5); −0.0002 (8.3) | 536.0 |
| I-92 | 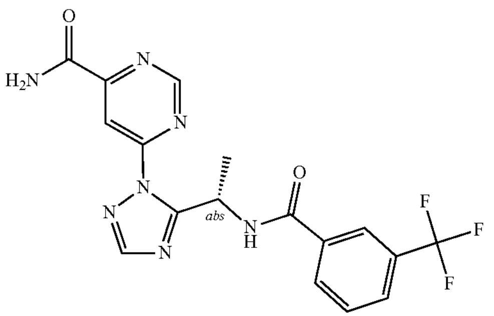 [SMILES: C[C@H](NC(=O)c1cccc(C(F)(F)F)c1)c1ncnn1-c1cc(C(N)=O)ncn1] | $^1$H-NMR (400.2 MHz, d6-DMSO) δ = 9.4041 (4.6); 9.3866 (4.4); 9.3221 (4.9); 9.3173 (11.3); 8.4716 (5.3); 8.3816 (11.7); 8.3403 (0.4); 8.3175 (13.9); 8.1930 (7.8); 8.1440 (5.6); 8.1275 (8.4); 7.9248 (4.0); 7.9057 (4.6); 7.7290 (3.2); 7.7096 (5.3); 7.6900 (2.3); 6.2975 (0.8); 6.2804 (2.9); 6.2629 (4.3); 6.2456 (2.7); 6.2288 (0.6); 3.3346 (42.0); 3.3313 (84.3); 2.6762 (1.5); 2.6722 (1.6); 2.5074 (247.0); 2.5031 (263.1); 2.4989 (179.2); 2.3343 (1.5); 2.3298 (1.6); 1.6691 (16.0); 1.6518 (15.3); 0.0041 (21.5); −0.0004 (38.1) | 406.3 |

TABLE 1-continued
| Example | Structure[1)] | NMR Peak List[2)] | ESI Mass (m/z)[3)] |
|---|---|---|---|
| I-93 | 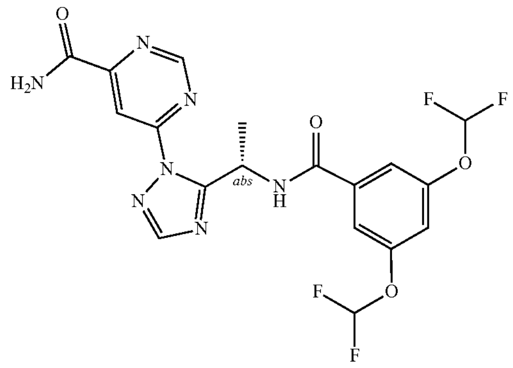 [SMILES: C[C@H](NC(=O)c1cc(OC(F)F)cc(OC(F)F)c1)c1ncnn1-c1cc(C(N)=O)ncn1] | $^1$H-NMR (400.2 MHz, d6-DMSO) δ = 9.3175 (14.2); 9.3147 (12.2); 9.3006 (3.5); 8.4812 (3.7); 8.3817 (10.8); 8.3790 (10.1); 8.3206 (16.0); 8.1418 (3.7); 7.5420 (14.5); 7.5365 (14.6); 7.5227 (7.6); 7.3392 (15.8); 7.2387 (3.9); 7.2333 (6.7); 7.2280 (3.4); 7.1559 (7.9); 6.2778 (0.5); 6.2606 (2.4); 6.2433 (3.8); 6.2259 (2.4); 6.2085 (0.5); 3.3430 (68.0); 2.6786 (0.5); 2.6741 (0.7); 2.6697 (0.5); 2.5275 (2.6); 2.5227 (4.0); 2.5141 (41.4); 2.5097 (80.0); 2.5052 (102.2); 2.5006 (74.0); 2.4963 (35.5); 2.3365 (0.5); 2.3320 (0.6); 2.3275 (0.4); 1.6621 (13.7); 1.6447 (13.6); −0.0002 (2.8) | 470.3 |
| I-94 | 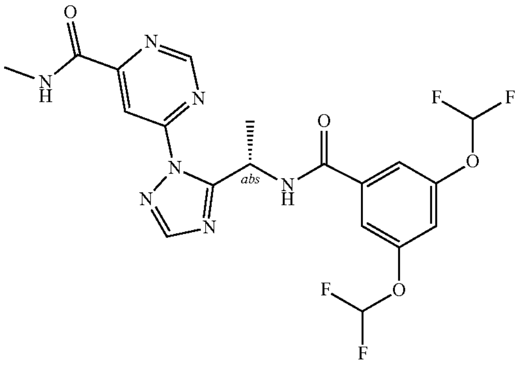 [SMILES: CNC(=O)c1cc(-n2ncnc2[C@H](C)NC(=O)c2cc(OC(F)F)cc(OC(F)F)c2)ncn1] | $^1$H-NMR (400.2 MHz, d6-DMSO) δ = 9.3185 (13.0); 9.3157 (13.6); 9.2987 (3.1); 9.1753 (0.8); 9.1650 (2.3); 9.1529 (2.2); 9.1411 (0.7); 8.3737 (10.4); 8.3708 (10.2); 8.3215 (15.8); 7.5376 (13.3); 7.5321 (13.6); 7.5210 (7.6); 7.3376 (15.9); 7.2383 (3.5); 7.2328 (6.2); 7.2275 (3.2); 7.1542 (7.9); 6.2765 (0.5); 6.2593 (2.2); 6.2419 (3.4); 6.2244 (2.2); 6.2071 (0.4); 3.3414 (124.0); 2.8726 (16.0); 2.8605 (15.9); 2.6823 (0.4); 2.6776 (0.8); 2.6731 (1.1); 2.6686 (0.8); 2.6644 (0.4); 2.5266 (4.0); 2.5218 (6.1); 2.5131 (63.2); 2.5087 (125.4); 2.5041 (162.9); 2.4995 (118.5); 2.4950 (56.4); 2.3398 (0.3); 2.3354 (0.7); 2.3309 (1.0); 2.3263 (0.7); 2.3220 (0.3); 2.0779 (1.1); 1.6596 (12.5); 1.6422 (12.4); −0.0001 (4.8) | 484.3 |

TABLE 1-continued
| Example | Structure[1)] | NMR Peak List[2)] | ESI Mass (m/z)[3)] |
|---|---|---|---|
| I-95 | 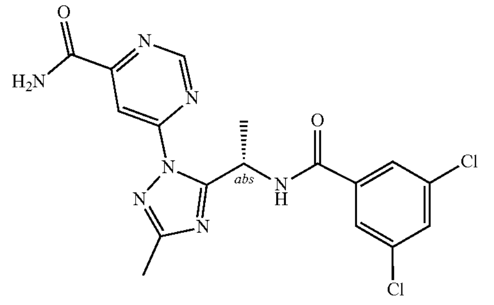 [SMILES: Cc1nc([C@H](C)NC(=O)c2cc(Cl)cc(Cl)c2)n(-c2cc(C(N)=O)ncn2)n1] | $^1$H-NMR (400.2 MHz, d6-DMSO) δ = 9.3314 (1.6); 9.3131 (1.6); 9.2696 (4.7); 9.2667 (4.6); 8.4526 (1.5); 8.3751 (0.5); 8.3723 (0.5); 8.3345 (4.5); 8.3316 (4.4); 8.3185 (0.8); 8.1064 (1.4); 7.8894 (7.7); 7.8846 (8.8); 7.8666 (0.8); 7.8619 (1.0); 7.8294 (2.5); 7.8246 (4.0); 7.8199 (1.9); 6.2360 (1.1); 6.2184 (1.7); 6.2010 (1.1); 3.3310 (183.4); 2.8907 (1.7); 2.7305 (1.5); 2.6759 (1.2); 2.6713 (1.7); 2.6668 (1.2); 2.6622 (0.6); 2.5248 (5.7); 2.5201 (8.7); 2.5113 (102.5); 2.5069 (203.4); 2.5024 (264.3); 2.4978 (191.2); 2.4933 (91.4); 2.3703 (16.0); 2.3383 (0.6); 2.3338 (1.2); 2.3292 (1.6); 2.3247 (1.2); 1.6449 (0.7); 1.6243 (5.8); 1.6069 (5.6); 0.0081 (0.5); −0.0001 (17.3); −0.0084 (0.5) | 420.1 |
| I-96 | 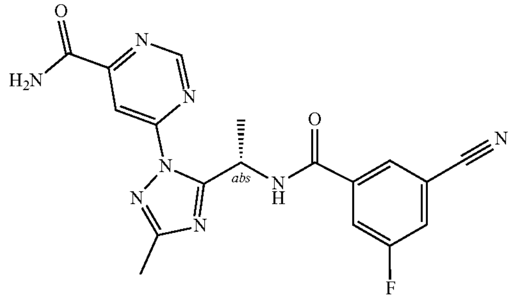 [SMILES: Cc1nc([C@H](C)NC(=O)c2cc(F)cc(C#N)c2)n(-c2cc(C(N)=O)ncn2)n1] | $^1$H-NMR (400.2 MHz, d6-DMSO) δ = 9.3758 (1.5); 9.3581 (1.5); 9.2725 (4.5); 9.2696 (4.4); 8.4503 (1.4); 8.3373 (4.6); 8.3345 (4.5); 8.3238 (0.4); 8.2048 (2.1); 8.2014 (3.8); 8.1981 (2.1); 8.1073 (1.4); 8.0896 (1.0); 8.0864 (1.1); 8.0833 (1.2); 8.0802 (1.0); 8.0687 (1.0); 8.0655 (1.1); 8.0624 (1.1); 8.0593 (1.0); 8.0219 (1.0); 8.0183 (1.1); 8.0157 (1.0); 8.0120 (0.8); 7.9982 (1.1); 7.9946 (1.2); 7.9921 (1.0); 7.9883 (0.8); 6.2600 (1.1); 6.2426 (1.7); 6.2251 (1.1); 5.7598 (1.8); 3.3313 (57.1); 2.8913 (1.9); 2.7311 (1.6); 2.6765 (0.5); 2.6720 (0.7); 2.6674 (0.5); 2.5255 (2.4); 2.5208 (3.5); 2.5120 (42.8); 2.5076 (85.3); 2.5030 (111.2); 2.4984 (80.1); 2.4939 (38.1); 2.3722 (16.0); 2.3344 (0.5); 2.3299 (0.7); 2.3253 (0.5); 1.6606 (0.4); 1.6389 (5.7); 1.6215 (5.6); 0.0081 (1.0); −0.0001 (31.7); −0.0085 (1.0) | 395.3 |

TABLE 1-continued
| Example | Structure[1)] | NMR Peak List[2)] | ESI Mass (m/z)[3)] |
|---|---|---|---|
| I-97 | 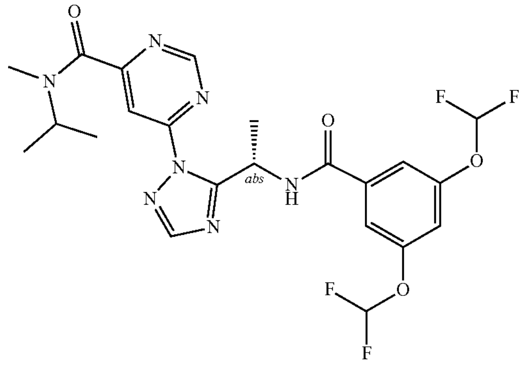 | $^1$H-NMR (400.2 MHz, d6-DMSO) δ = 9.3124 (1.8); 9.2952 (1.9); 9.2407 (4.8); 9.2375 (7.2); 9.2345 (3.4); 8.2917 (8.1); 8.0064 (3.9); 8.0043 (7.5); 8.0016 (5.6); 7.5464 (6.4); 7.5410 (10.1); 7.5356 (4.6); 7.5255 (5.1); 7.3422 (10.4); 7.2353 (3.8); 7.1588 (5.2); 6.2502 (0.4); 6.2334 (1.6); 6.2163 (2.5); 6.1989 (1.6); 6.1816 (0.3); 4.7488 (0.7); 4.7319 (0.9); 4.7149 (0.7); 4.0376 (0.9); 4.0198 (0.9); 3.8141 (0.4); 3.7977 (1.0); 3.7813 (1.4); 3.7649 (1.0); 3.7487 (0.4); 3.3323 (87.1); 2.8892 (16.0); 2.7497 (11.2); 2.6761 (0.8); 2.6716 (1.1); 2.6670 (0.9); 2.5250 (4.0); 2.5202 (6.6); 2.5115 (70.2); 2.5072 (140.9); 2.5026 (183.8); 2.4981 (132.9); 2.4937 (6.47); 2.3341 (0.8); 2.3294 (1.1); 2.3249 (0.8); 1.9897 (4.1); 1.6673 (7.6); 1.6500 (7.6); 1.3973 (1.3); 1.1923 (9.4); 1.1749 (10.4); 1.1568 (2.1); 1.1501 (8.2); 1.1463 (8.5); 1.1337 (8.2); 1.1299 (8.2); −0.0002 (1.6) | 526.3 |
| I-98 | 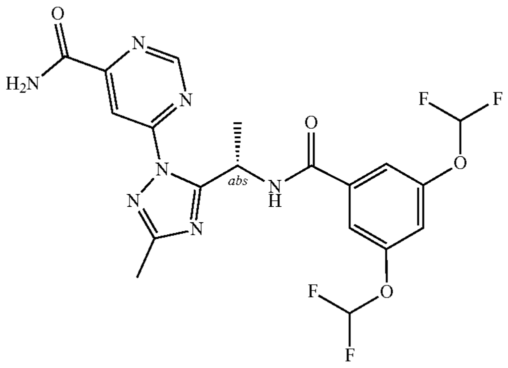 [SMILES: Cc1nc([C@H](C)NC(=O)c2cc(OC(F)F)cc(OC(F)F)c2)n(-c2cc(C(N)=O)ncn2)n1] | $^1$H-NMR (400.2 MHz, d6-DMSO) δ = 9.2912 (1.5); 9.2731 (5.6); 9.2704 (5.2); 8.4530 (1.7); 8.3404 (4.5); 8.3377 (4.5); 8.1134 (1.6); 7.5610 (6.1); 7.5556 (6.2); 7.5231 (3.0); 7.3398 (6.2); 7.2394 (1.6); 7.2341 (2.9); 7.2288 (1.5); 7.1564 (3.1); 6.2549 (1.1); 6.2394 (1.7); 6.2219 (1.1); 5.7606 (1.9); 3.3367 (17.9); 2.5273 (0.9); 2.5138 (16.5); 2.5095 (32.5); 2.5050 (41.8); 2.5004 (29.8); 2.4961 (14.3); 2.3716 (16.0); 1.6411 (5.9); 1.6237 (5.9); −0.0002 (0.5) | 484.3 |

TABLE 1-continued
| Example | Structure[1)] | NMR Peak List[2)] | ESI Mass (m/z)[3)] |
|---|---|---|---|
| I-99 | 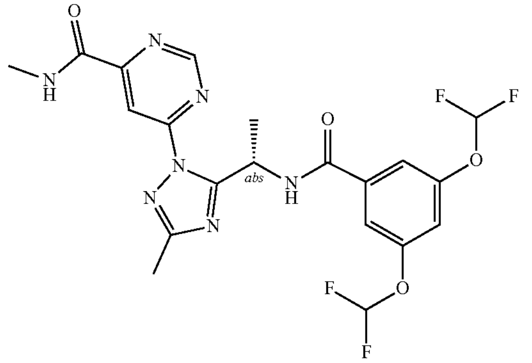 [SMILES: CNC(=O)c1cc(-n2nc(C)nc2[C@H](C)NC(=O)c2cc(OC(F)F)cc(OC(F)F)c2)ncn1] | $^1$H-NMR (400.2 MHz, d6-DMSO) δ = 9.2958 (1.3); 9.2755 (5.9); 9.2726 (5.3); 9.1451 (1.0); 9.1332 (1.0); 9.1218 (0.3); 8.3298 (4.7); 8.3269 (4.6); 7.5571 (6.0); 7.5515 (6.1); 7.5236 (3.5); 7.3402 (7.5); 7.2410 (1.6); 7.2356 (2.8); 7.2301 (1.4); 7.1568 (3.7); 6.2551 (1.0); 6.2375 (1.6); 6.2200 (1.0); 3.3395 (48.0); 2.8674 (7.1); 2.8553 (7.0); 2.6770 (0.4); 2.6725 (0.6); 2.6679 (0.4); 2.5260 (2.2); 2.5213 (3.4); 2.5126 (34.4); 2.5081 (68.1); 2.5035 (88.0); 2.4989 (63.2); 2.4944 (29.6); 2.3734 (16.0); 2.3350 (0.4); 2.3303 (0.6); 2.3258 (0.4); 2.0779 (4.6); 1.6378 (5.5); 1.6204 (5.4); −0.0002 (2.0) | 498.3 |
| I-100 | 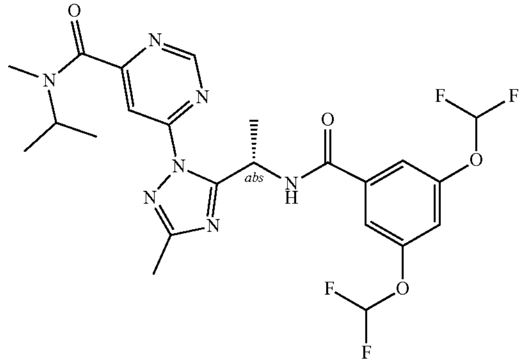 [SMILES: Cc1nc([C@H](C)NC(=O)c2cc(OC(F)F)cc(OC(F)F)c2)n(-c2cc(C(=O)N(C)C(C)C)ncn2)n1] | $^1$H-NMR (400.2 MHz, d6-DMSO) δ = 9.2959 (1.5); 9.2790 (1.5); 9.2010 (3.2); 9.1978 (4.5); 9.1943 (2.4); 7.9356 (2.2); 7.9328 (2.3); 7.9277 (3.3); 7.9249 (3.3); 7.5654 (4.8); 7.5605 (7.1); 7.5564 (3.8); 7.5300 (3.6); 7.3466 (7.6); 7.2390 (2.8); 7.1632 (3.8); 6.2295 (1.2); 6.2121 (1.9); 6.1946 (1.2); 4.7412 (0.5); 4.7243 (0.7); 4.7073 (0.5); 3.7949 (0.7); 3.7786 (0.9); 3.7623 (0.7); 3.3388 (74.3); 2.8811 (11.0); 2.7428 (8.0); 2.6764 (0.7); 2.6720 (1.0); 2.6677 (0.7); 2.5253 (3.3); 2.5075 (112.0) 2.5030 (147.0); 2.4986 (109.5); 2.3466 (16.0); 2.3349 (1.1); 2.3300 (1.1); 2.3256 (0.8); 1.6452 (5.7); 1.6279 (5.7); 1.1888 (6.5); 1.1718 (6.5); 1.1447 (6.8); 1.1284 (6.7); 0.0000 (1.7) | 540.3 |

TABLE 1-continued
| Example | Structure[1)] | NMR Peak List[2)] | ESI Mass (m/z)[3)] |
|---|---|---|---|
| I-101 | 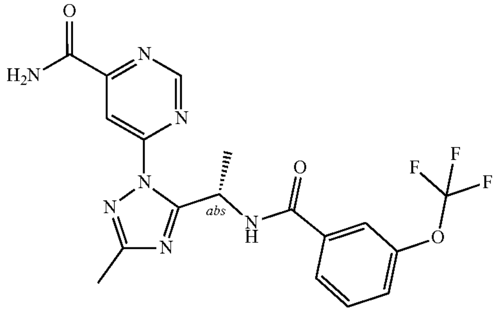 [SMILES: Cc1nc([C@H](C)NC(=O)c2cccc(OC(F)(F)F)c2)n(-c2cc(C(N)=O)ncn2)n1] | $^{1}$H-NMR (400.2 MHz, d6-DMSO) δ = 9.2876 (1.5); 9.2718 (5.6); 9.2691 (6.1); 8.4522 (1.7); 8.3399 (4.3); 8.3373 (4.3); 8.3201 (0.5); 8.1100 (1.6); 7.9246 (1.6); 7.9054 (1.8); 7.8189 (2.2); 7.6353 (1.2); 7.6152 (2.6); 7.5958 (2.0); 7.5673 (1.6); 7.5466 (0.7); 6.2558 (1.1); 6.2382 (1.8); 6.2207 (1.1); 3.3358 (29.3); 2.6732 (0.4); 2.5267 (1.1); 2.5219 (1.5); 2.5130 (19.2); 2.5087 (39.6); 2.5043 (52.4); 2.4998 (37.9); 2.3693 (16.0); 2.3310 (0.4); 1.6397 (6.2); 1.6223 (6.2); −0.0002 (0.4) | 436.4 |
| I-102 | 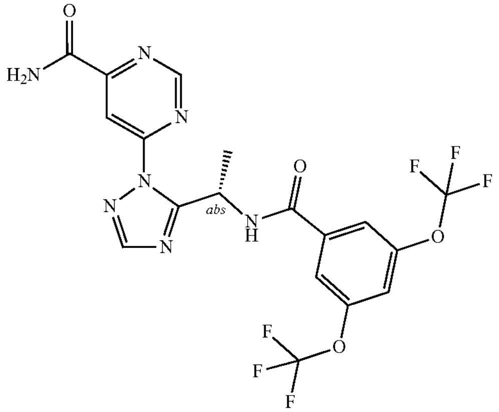 [SMILES: C[C@H](NC(=O)c1cc(OC(F)(F)F)cc(OC(F)(F)F)c1)c1ncnn1-c1cc(C(N)=O)ncn1] | $^{1}$H-NMR (400.2 MHz, d6-DMSO) δ = 9.4915 (3.1); 9.4742 (3.2); 9.3106 (11.6); 9.3076 (11.8); 8.4735 (3.2); 8.3813 (11.4); 8.3783 (11.4); 8.3294 (16.0); 8.3204 (0.4); 8.1351 (3.2); 7.9064 (8.9); 7.9014 (9.4); 7.7643 (3.9); 6.2875 (0.5); 6.2705 (2.3); 6.2532 (3.6); 6.2358 (2.3); 6.2184 (0.5); 3.3365 (124.1); 2.6826 (0.4); 2.6780 (0.8); 2.6734 (1.2); 2.6688 (0.8); 2.6642 (0.4); 2.5270 (3.8); 2.5223 (5.8); 2.5136 (68.6); 2.5091 (141.1); 2.5044 (185.4); 2.4998 (132.2); 2.4952 (62.1); 2.3405 (0.4); 2.3359 (0.8); 2.3312 (1.2); 2.3266 (0.8); 2.3224 (0.4); 2.0780 (0.4); 1.6700 (13.3); 1.6526 (13.2); −0.0002 (2.6) | 506.3 |

TABLE 1-continued
| Example | Structure[1)] | NMR Peak List[2)] | ESI Mass (m/z)[3)] |
|---|---|---|---|
| I-103 | 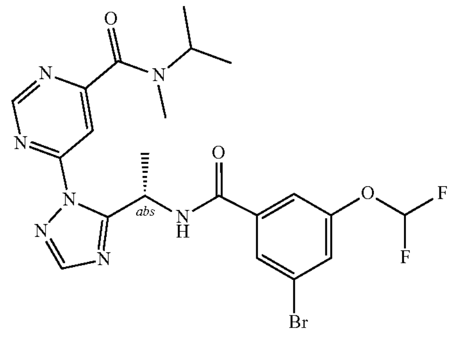 [SMILES: CC(C)N(C)C(=O)c1cc(-n2ncnc2[C@H](C)NC(=O)c2cc(Br)cc(OC(F)F)c2)ncn1] | $^1$H-NMR (400.2 MHz, d6-DMSO) δ = 9.3423 (1.8); 9.3251 (1.9); 9.2405 (4.4); 9.2372 (5.8); 9.2332 (3.1); 8.2904 (7.9); 8.0060 (3.1); 8.0018 (5.8); 7.9986 (4.8); 7.9860 (0.4); 7.9653 (2.2); 7.9613 (4.1); 7.9574 (3.6); 7.9525 (1.5); 7.6719 (0.7); 7.6685 (0.7); 7.6444 (3.6); 7.6409 (3.8); 7.6258 (3.8); 7.5286 (2.7); 7.3706 (0.4); 7.3453 (5.6); 7.1620 (2.8); 6.2402 (0.4); 6.2233 (1.7); 6.2060 (2.7); 6.1887 (1.7); 6.1712 (0.4); 4.7491 (0.6); 4.7321 (0.9); 4.7152 (0.7); 3.8108 (0.4); 3.7943 (1.0); 3.7780 (1.4); 3.7615 (1.0); 3.7455 (0.4); 3.6506 (2.1); 3.3325 (38.7); 2.8887 (16.0); 2.7515 (11.2); 2.6764 (0.6); 2.6719 (0.9); 2.6675 (0.6); 2.5254 (2.9); 2.5205 (4.6); 2.5118 (56.2); 2.5075 (114.3); 2.5030 (149.5); 2.4984 (107.7); 2.4940 (51.9); 2.3342 (0.7); 2.3298 (0.9); 2.3253 (0.7); 2.0766 (3.1); 1.6584 (7.4); 1.6411 (7.4); 1.4146 (0.8); 1.3963 (0.8); 1.9128 (8.9); 1.1758 (8.9); 1.1494 (8.1); 1.1457 (8.4); 1.1330 (8.1); 1.1293 (8.1); −0.0002 (1.6) | 540.1 |
| I-104 | 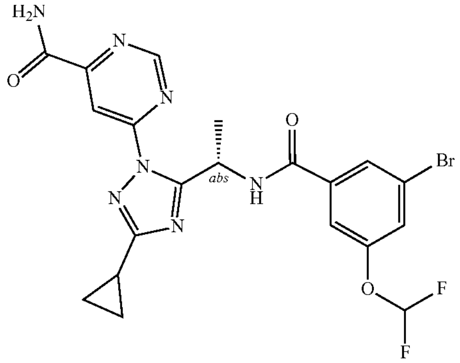 [SMILES: C[C@H](NC(=O)c1cc(Br)cc(OC(F)F)c1)c1nc(C2CC2)nn1-c1cc(C(N)=O)ncn1] | $^1$H-NMR (400.2 MHz, d6-DMSO) δ = 10.1909 (1.2); 9.3128 (1.2); 9.2976 (3.5); 9.2801 (3.8); 9.2471 (13.3); 9.2442 (14.2); 8.4976 (1.1); 8.4573 (4.1); 8.3116 (14.0); 8.3087 (14.7); 8.1162 (4.0); 7.9385 (5.5); 7.9347 (10.0); 7.9310 (6.6); 7.6450 (3.6); 7.6398 (7.5); 7.6353 (5.6); 7.6109 (6.6); 7.5265 (4.6); 7.4656 (1.0); 7.3431 (9.5); 7.1889 (0.8); 7.1598 (4.8); 7.0880 (0.9); 6.1999 (3.0); 6.1825 (4.8); 6.1651 (3.1); 3.8939 (1.4); 3.3444 (2993.9). 2.7118 (1.6); 2.6764 (11.4); 2.6718 (15.6); 2.6672 (11.5); 2.6628 (5.5); 2.5422 (314.3); 2.5254 (54.6); 2.5207 (81.2); 2.5120 (893.4); 2.5074 (1802.7). 2.5028 (2349.1); 2.4982 (1693.6); 2.4936 (798.3); 2.3681 (0.8); 2.3388 (4.6); 2.3343 (10.3); 2.3297 (14.5); 2.3251 (10.0); 2.3205 (4.4); 2.1156 (1.8); 2.1065 (1.9); 2.0947 (3.9); 2.0822 (2.6); 2.0769 (14.3); 2.0615 (1.2); 1.6118 (16.0); 1.5944 (15.8); 1.5702 (1.7); 1.5523 (1.7); 1.4455 (0.9); 1.2347 (1.2); 1.0308 (5.9); 1.0252 (7.2); 1.0099 (5.9); 1.0045 (7.2); 0.9118 (4.2); 0.8998 (4.5); 0.8892 (5.8); 0.8768 (3.3); −0.0002 (15.3) | 523.9 |

TABLE 1-continued
| Example | Structure[1)] | NMR Peak List[2)] | ESI Mass (m/z)[3)] |
|---|---|---|---|
| I-105 | 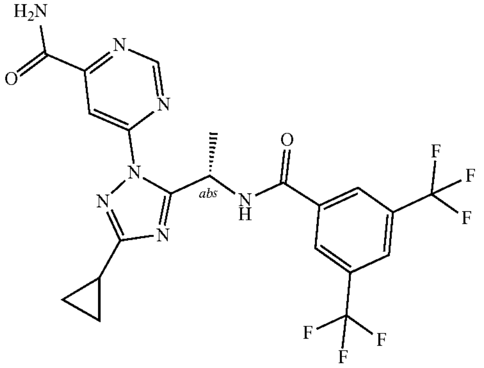 [SMILES: C[C@H](NC(=O)c1cc(C(F)(F)F)cc(C(F)(F)F)c1)c1nc(C2CC2)nn1-c1cc(C(N)=O)ncn1] | $^1$H-NMR (400.2 MHz, d6-DMSO) δ = 20.0064 (0.8); 9.6110 (3.5); 9.5936 (3.8); 9.2559 (13.7); 9.2530 (14.4); 8.4843 (14.0); 8.4553 (4.2); 8.3364 (6.0); 8.3183 (14.2); 8.3153 (14.5); 8.1167 (4.1); 6.2680 (3.0); 6.2506 (4.8); 6.2332 (3.1); 3.3439 (2293.8); 2.9969 (0.8); 2.7118 (1.5); 2.6809 (4.8); 2.6764 (9.9), 2.6719 (13.5); 2.6673 (9.8); 2.6628 (4.7); 2.5423 (313.9); 2.5254 (47.1); 2.5207 (70.8); 2.5120 (790.4); 2.5075 (1588.1); 2.5029 (2065.4); 2.4983 (1491.3); 2.4937 (704.7); 2.3689 (1.1); 2.3389 (4.2); 2.3343 (9.2); 2.3297 (12.8); 2.3252 (9.1); 2.3206 (4.0); 2.1319 (0.9); 2.1206 (1.8); 2.1118 (2.0); 2.0996 (3.8); 2.0875 (2.2); 2.0770 (13.0); 2.0667 (1.0); 1.6493 (16.0); 1.6319 (15.8); 1.2352 (0.6); 1.0310 (5.0); 1.0264 (6.6); 1.0101 (5.1); 1.0055 (6.6); 0.9882 (0.9); 0.9391 (1.1); 0.9159 (3.6); 0.9034 (4.2); 0.8892 (4.0); 0.8798 (2.7); −0.0001 (17.2) | 514.1 |
| I-106 | 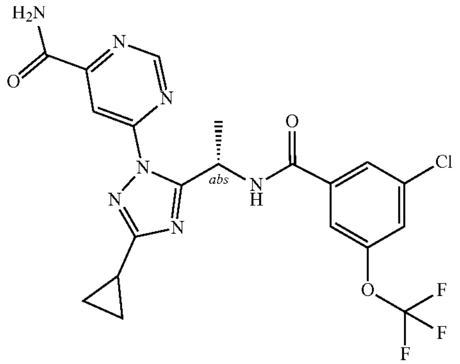 [SMILES: C[C@H](NC(=O)c1cc(Cl)cc(OC(F)(F)F)c1)c1nc(C2CC2)nn1-c1cc(C(N)=O)ncn1] | $^1$H-NMR (400.2 MHz, d6-DMSO) δ = 9.3755 (3.7); 9.3579 (3.8); 9.2444 (13.5); 9.2415 (13.4); 8.4567 (4.2); 8.3121 (14.5); 8.3092 (14.1); 8.1171 (4.1); 7.9840 (5.7); 7.9800 (8.8); 7.9760 (5.9); 7.7969 (5.6); 7.7615 (5.7); 7.7589 (6.0); 7.7563 (4.8); 6.2230 (0.6); 6.2057 (3.0); 6.1883 (4.9); 6.1709 (3.1); 6.1534 (0.6); 3.8433 (0.3); 3.4745 (0.3); 3.3450 (1069.3); 2.7120 (0.8); 2.6811 (2.4); 2.6766 (5.1); 2.6721 (7.0); 2.6675 (5.0); 2.6629 (2.4); 2.5425 (227.1); 2.5256 (24.4); 2.5209 (36.9); 2.5122 (413.5); 2.5077 (834.8); 2.5031 (1087.8). 2.4985 (785.7); 2.4939 (370.9); 2.3689 (0.7); 2.3391 (2.2); 2.3345 (4.9); 2.3299 (6.7); 2.3253 (4.8); 2.3208 (2.1); 2.1307 (0.9); 2.1182 (1.8); 2.1095 (1.9); 2.0975 (3.9); 2.0855 (2.3); 2.0773 (11.6); 2.0646 (1.0); 1.6185 (16.0); 1.6011 (15.8); 1.2338 (0.4); 1.0595 (0.4); 1.0504 (0.5); 1.0321 (5.1); 1.0266 (7.0); 1.0113 (5.1); 1.0057 (7.0); 0.9890 (0.8); 0.9801 (0.6); 0.9366 (0.9); 0.9241 (1.0); 0.9131 (4.0); 0.9074 (2.1); 0.9009 (4.3); 0.8955 (3.4); 0.8892 (4.2); 0.8846 (2.1); 0.8774 (3.0); 0.8622 (1.0); 0.8532 (0.8); 0.0080 (0.40); −0.0002 (13.7); 0.0085 (0.4) | 496.0 |

TABLE 1-continued
| Example | Structure[1)] | NMR Peak List[2)] | ESI Mass (m/z)[3)] |
|---|---|---|---|
| I-107 | 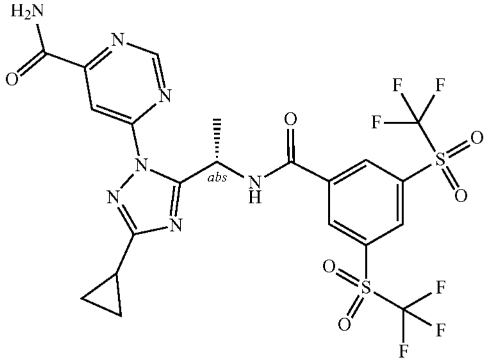 [SMILES: C[C@H](NC(=O)c1cc(S(=O)(=O)C(F)(F)F)cc(S(=O)(=O)C(F)(F)F)c1)c1nc(C2CC2)nn1-c1cc(C(N)=O)ncn1] | $^1$H-NMR (400.2 MHz, d6-DMSO) δ = 10.0426 (3.3); 10.0253 (3.4); 9.2591 (11.4); 9.2563 (11.4); 9.0928 (15.9); 9.0887 (16.0); 9.0467 (0.4); 9.0346 (0.4); 8.6659 (6.5); 8.4540 (3.8); 8.3237 (13.0); 8.3208 (12.9); 8.1224 (3.7); 6.3456 (0.6); 6.3278 (2.6); 6.3105 (4.2); 6.2929 (2.7); 6.2751 (0.5); 3.8943 (0.7); 3.3416 (951.7). 3.2850 (0.4); 2.7311 (0.4); 2.7123 (0.8); 2.6950 (0.4); 2.6808 (2.6); 2.6764 (5.5); 2.6718 (7.5); 2.6672 (5.4); 2.6628 (2.6); 2.5935 (0.8); 2.5423 (191.3); 2.5254 (28.0); 2.5207 (41.7); 2.5120 (444.9); 2.5074 (889.8); 2.5028 (1158.3); 2.4892 (837.6); 2.4937 (395.8); 2.3684 (0.6); 2.3388 (2.3); 2.3343 (5.2); 2.3296 (7.2); 2.3251 (5.1); 2.3205 (2.2); 2.1398 (0.7); 2.1275 (1.6); 2.1187 (1.7); 2.1067 (3.5); 2.0946 (2.0); 2.0860 (1.8); 2.0771 (12.0); 1.6748 (13.9); 1.6575 (13.8); 1.2354 (0.3); 1.0562 (0.7); 1.0393 (4.9); 1.0354 (5.6); 1.0187 (4.8); 1.0145 (5.2); 1.008 (1.1); 0.9879 (0.5); 0.9481 (0.6); 0.9353 (0.8); 0.9297 (2.0); 0.9236 (2.7); 0.9173 (3.9); 0.9119 (4.5); 0.9070 (3.6); 0.8940 (1.7); 0.8892 (1.7); 0.8724 (0.5); 0.0079 (0.7); −0.0002 (22.6); −0.0086 (0.6) | 642.0 |
| I-108 | 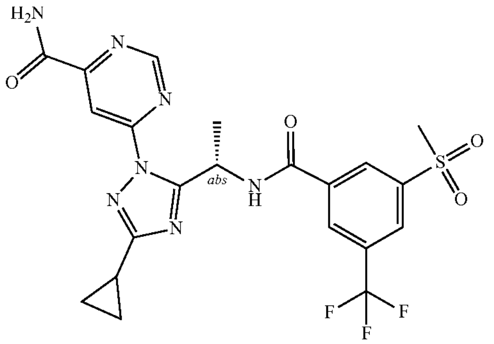 [SMILES: C[C@H](NC(=O)c1cc(C(F)(F)F)cc(S(C)(=O)=O)c1)c1nc(C2CC2)nn1-c1cc(C(N)=O)ncn1] | $^1$H-NMR (400.2 MHz, d6-DMSO) δ = 9.6571 (3.7); 9.6394 (3.7); 9.2632 (13.2); 9.2603 (13.5); 8.6531 (8.1); 8.5162 (7.1); 8.4585 (4.3); 8.4091 (7.1) 8.3209 (14.7); 8.3179 (14.7); 8.1182 (4.2); 6.2993 (0.6); 6.2825 (3.1); 6.2650 (4.9); 6.2475 (3.1); 6.2303 (0.6); 3.4173 (0.5); 3.3870 (46.5); 3.3400 (679.1); 2.9972 (2.8); 2.7119 (1.6); 2.6809 (2.0); 2.6764 (4.3); 2.6718 (5.9); 2.6672 (4.3); 2.6627 (2.0); 2.6132 (0.5); 2.5424 (463.8); 2.5254 (21.0); 2.5207 (31.5); 2.5120 (339.5); 2.5075 (690.6); 2.5029 (909.4); 2.4982 (663.3); 2.4937 (317.5); 2.3683 (1.4); 2.3389 (1.8); 2.3342 (4.0); 2.3297 (5.7); 2.3251 (4.0); 2.3206 (1.8); 2.1345 (0.8); 2.1224 (1.9); 2.1139 (1.9); 2.1108 (1.6); 2.1017 (4.0); 2.0895 (2.3); 2.0810 (2.2); 2.0774 (9.0); 2.0687 (1.0); 1.6541 (16.0); 1.6368 (15.9); 1.0612 (0.4); 1.0491 (0.8); 1.0330 (5.5); 1.0285 (6.9); 1.0123 (5.3); 1.0075 (6.4); 0.9940 (1.1); 0.9825 (0.6); 0.9436 (0.8); 0.9310 (0.9); 0.9243 (2.3); 0.9196 (3.2); 0.9116 (4.4); 0.9071 (5.1); 0.9020 (4.2); 0.8947 (2.3); 0.8891 (2.8); 0.8763 (0.8); 0.8657 (0.6); 0.0081 (0.6); −0.0002 (21.3); −0.0085 (0.6) | 524.1 |

TABLE 1-continued
| Example | Structure[1)] | NMR Peak List[2)] | ESI Mass (m/z)[3)] |
|---|---|---|---|
| I-109 | 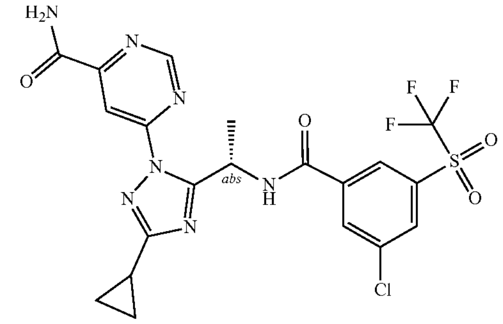 [SMILES: C[C@H](NC(=O)c1cc(Cl)cc(S(=O)(=O)C(F)(F)F)c1)c1nc(C2CC2)nn1-c1cc(C(N)=O)ncn1] | $^1$H-NMR (400.2 MHz, d6-DMSO) δ = 9.6757 (3.8); 9.6582 (3.8); 9.2477 (13.2); 9.2448 (13.6); 8.5362 (5.6); 8.5317 (9.2); 8.5277 (6.7); 8.4729 (8.8); 8.4550 (4.5); 8.4218 (7.1); 8.3746 (0.6); 8.3163 (13.3); 8.3134 (13.3); 8.1170 (4.3); 6.2697 (0.6); 6.2527 (3.1); 6.2354 (4.9); 6.2179 (3.0); 6.2000 (0.6); 3.3400 (585.8); 2.8905 (0.4); 2.7304 (0.4); 2.7121 (0.6); 2.6764 (4.5); 2.6718 (6.2); 2.6673 (4.6); 2.6628 (2.2); 2.6075 (0.4); 2.5424 (144.2); 2.5253 (21.2); 2.5206 (32.3); 2.5119 (366.4); 2.5074 (740.1); 2.5029 (973.1); 2.4983 (713.5); 2.4938 (346.0); 2.4505 (0.9); 2.3683 (0.5); 2.3387 (2.0); 2.3342 (4.3); 2.3297 (6.0); 2.3251 (4.4); 2.3208 (2.0); 2.1354 (0.8); 2.1233 (1.9); 2.1144 (1.9); 2.1116 (1.6); 2.1025 (3.8); 2.0902 (2.2); 2.0818 (2.1); 2.0776 (5.6); 2.0696 (1.0); 1.6411 (16.0); 1.6237 (15.9); 1.2347 (0.6); 1.0637 (0.4); 1.0520 (0.6); 1.0347 (5.4); 1.0302 (6.6); 1.0141 (5.8); 1.0092 (6.4); 0.9940 (1.0); 0.9837 (0.6); 0.9416 (0.9); 0.9319 (0.9); 0.9189 (3.1); 0.9120 (2.6); 0.9058 (5.0); 0.9006 (4.0); 0.8967 (3.5); 0.8891 (2.6); 0.8845 (2.8); 0.8706 (0.9); 0.8618 (0.6); 0.0079 (0.7); −0.0003 (23.2); −0.0084 (0.7) | 544.0 |
| I-110 | 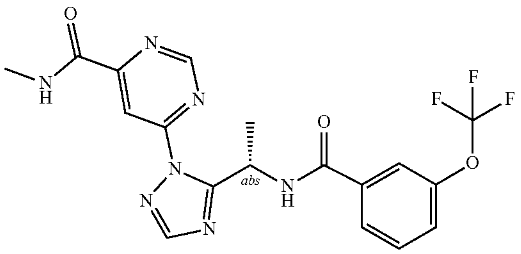 [SMILES: CNC(=O)c1cc(-n2ncnc2[C@H](C)NC(=O)c2cccc(OC(F)(F)F)c2)ncn1] | $^1$H-NMR (400.2 MHz, d6-DMSO) δ = 9.3151 (9.3); 9.3122 (9.8); 9.3036 (3.4); 9.2862 (3.4); 9.1690 (0.8); 9.1578 (2.3); 9.1456 (2.3); 9.1342 (0.8); 8.3726 (8.8); 8.3698 (9.1); 8.3157 (14.4); 7.9053 (2.0); 7.9021 (3.5); 7.8991 (2.4); 7.8864 (2.3); 7.8831 (3.9); 7.8801 (2.6); 7.7936 (4.4); 7.6296 (2.5); 7.6094 (5.6); 7.5901 (4.4); 7.5670 (2.9); 7.5646 (3.2); 7.5619 (2.9); 7.5466 (1.3); 7.5439 (1.4); 7.5414 (1.3); 6.2765 (0.5); 6.2595 (2.3); 6.2421 (3.6); 6.2247 (2.3); 6.2074 (0.5); 3.3339 (174.3); 2.8717 (16.0); 2.8596 (16.0); 2.6809 (0.5); 2.6766 (1.0); 2.6721 (1.3); 2.6676 (1.0); 2.5256 (4.1); 2.5209 (5.7); 2.5120 (70.1); 2.5076 (147.9); 2.5031 (198.8); 2.4986 (143.7); 2.4942 (68.7); 2.3389 (0.4); 2.3344 (0.9); 2.3299 (1.3); 2.3254 (0.9); 1.6584 (13.3); 1.6410 (13.2); −0.0002 (1.2) | 436.3 |

TABLE 1-continued
| Example | Structure[1)] | NMR Peak List[2)] | ESI Mass (m/z)[3)] |
|---|---|---|---|
| I-111 | 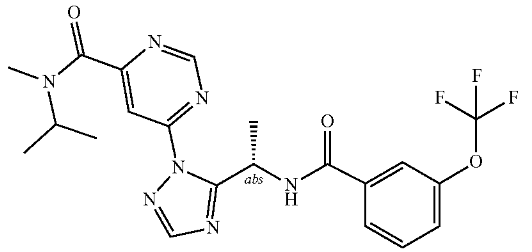 [SMILES: CC(C)N(C)C(=O)c1cc(-n2ncnc2[C@H](C)NC(=O)c2cccc(OC(F)(F)F)c2)ncn1] | $^1$H-NMR (400.2 MHz, d6-DMSO) δ = 9.3113 (2.1); 9.2940 (2.1); 9.2431 (4.9); 9.2406 (6.3); 8.2888 (8.2); 8.0108 (3.1); 8.0078 (7.2); 8.0048 (4.9); 7.9076 (2.2); 7.8886 (2.6); 7.8129 (3.2); 7.6743 (0.3); 7.6345 (1.5); 7.6143 (3.5); 7.5951 (2.6); 7.5699 (2.3); 7.5673 (2.3); 7.5493 (1.1); 7.5467 (1.1); 6.2558 (0.4); 6.2386 (1.7); 6.2213 (2.7); 6.2039 (1.7); 6.1864 (0.4); 4.7516 (0.7); 4.7346 (0.9); 4.7177 (0.7); 3.8111 (0.4); 3.7947 (1.0); 3.7783 (1.4); 3.7619 (1.0); 3.7454 (0.4); 3.6554 (0.9); 3.3394 (39.9); 2.8907 (16.0); 2.7477 (11.3); 2.5280 (0.8); 2.5233 (1.2); 2.5145 (15.2); 2.5101 (32.1); 2.5055 (43.2); 2.5010 (31.2); 2.4965 (14.9); 2.0788 (3.5); 1.6701 (7.7); 1.6527 (7.6); 1.5650 (1.0); 1.5471 (1.0); 1.4259 (0.4); 1.4075 (0.4); 1.1933 (8.4); 1.1763 (8.4); 1.1475 (8.2); 1.1440 (8.5); 1.1311 (8.2); 1.1276 (8.2); −0.0002 (0.4) | 478.3 |
| I-112 | 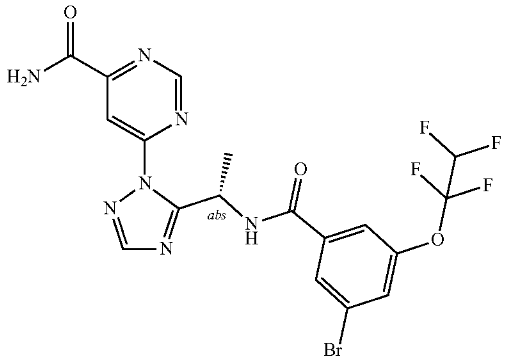 [SMILES: C[C@H](NC(=O)c1cc(Br)cc(OC(F)(F)C(F)F)c1)c1ncnn1-c1cc(C(N)=O)ncn1] | $^1$H-NMR (400.2 MHz, d6-DMSO) δ = 9.4246 (2.7); 9.4072 (2.8); 9.3153 (10.0); 9.3214 (10.0); 8.4748 (2.8); 8.3827 (9.8); 8.3797 (9.7); 8.3225 (14.1); 8.1331 (2.7); 8.1005 (4.2); 8.0967 (7.1); 8.0928 (4.3); 7.7555 (4.6); 7.7533 (4.2); 7.7467 (4.0); 7.7423 (4.6); 6.9796 (0.5); 6.9721 (1.1); 6.9644 (0.5); 6.8501 (1.1); 6.8428 (2.4); 6.8350 (1.2); 6.7206 (0.5); 6.7135 (1.2); 6.7058 (0.6); 6.2760 (0.4); 6.2586 (1.9); 6.2412 (3.0); 6.2238 (1.9); 6.2067 (0.4); 3.3362 (60.2); 2.6788 (0.4); 2.6743 (0.6); 2.6698 (0.4); 2.5279 (1.7); 2.5232 (2.7); 2.5145 (34.1); 2.5100 (70.8); 2.5054 (92.9); 2.5007 (65.1); 2.4962 (30.1); 2.3368 (0.4); 2.3322 (0.6); 2.3276 (0.4); 2.0786 (16.0); 1.6551 (10.9); 1.6377 (10.9); −0.0002 (0.4) | 534.1 |

TABLE 1-continued
| Example | Structure[1)] | NMR Peak List[2)] | ESI Mass (m/z)[3)] |
|---|---|---|---|
| I-113 | 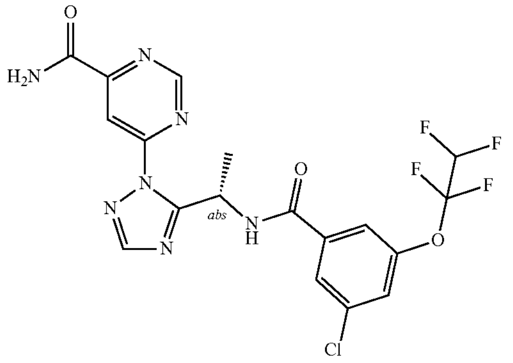 [SMILES: C[C@H](NC(=O)c1cc(Cl)cc(OC(F)(F)C(F)F)c1)c1ncnn1-c1cc(C(N)=O)ncn1] | $^1$H-NMR (400.2 MHz, d6-DMSO) δ = 9.4245 (2.1); 9.4071 (2.1); 9.3162 (7.2); 9.3132 (7.2); 8.4750 (2.1); 8.3912 (0.4); 8.3841 (6.4); 8.3812 (6.5); 8.3235 (10.5); 8.1348 (2.0); 7.9668 (3.0); 7.9626 (4.5); 7.9587 (3.0); 7.7295 (3.0); 7.6417 (2.2); 7.6368 (3.6); 7.6316 (1.9); 6.9854 (0.4); 6.9870 (0.8); 6.9703 (0.4); 6.8560 (0.8); 6.8487 (1.9); 6.8409 (0.9); 6.7266 (4); 6.7194 (0.9); 6.7117 (0.4); 6.2610 (1.4); 6.2437 (2.2); 6.2263 (1.4); 3.3390 (41.1); 2.5290 (1.0); 2.5243 (1.6); 2.5156 (19.0); 2.5112 (38.8); 2.5066 (50.6); 2.5020 (35.4); 2.4974 (16.3); 2.0797 (16.0); 1.6582 (7.9); 1.6408 (7.9); 1.6280 (0.5) | 488.2 |
| I-114 | 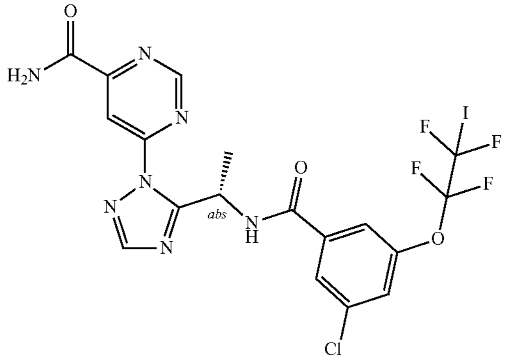 [SMILES: C[C@H](NC(=O)c1cc(Cl)cc(OC(F)(F)C(F)(F)I)c1)c1ncnn1-c1cc(C(N)=O)ncn1] | $^1$H-NMR (400.2 MHz, d6-DMSO) δ = 9.4501 (3.0); 9.4328 (3.2); 9.3160 (11.0); 9.3131 (11.4); 8.4720 (3.3); 8.3818 (10.5); 8.3789 (10.9); 8.3234 (16.0); 8.1310 (3.2); 7.9962 (0.4); 7.9803 (4.5); 7.9761 (6.8); 7.9722 (4.7); 7.7505 (0.4); 7.7352 (4.5); 7.6645 (3.1); 7.6596 (5.2); 7.6548 (2.8); 6.2806 (0.4); 6.2637 (2.1); 6.2464 (3.4); 6.2290 (2.2); 6.2116 (0.4); 3.3316 (93.7); 2.6815 (0.4); 2.6769 (1.0); 2.6723 (1.4); 2.6678 (1.0); 2.6632 (0.4); 2.5260 (4.3); 2.5213 (6.2); 2.5125 (81.2); 2.5080 (169.2); 2.5034 (222.6); 2.4988 (156.2); 2.4942 (72.1); 2.3393 (0.4); 2.3348 (1.0); 2.3302 (1.3); 2.3257 (1.0); 2.3211 (0.4); 2.0771 (3.9); 1.6585 (12.2); 1.6411 (12.2); −0.0002 (0.4 | 614.1 |

TABLE 1-continued
| Example | Structure[1)] | NMR Peak List[2)] | ESI Mass (m/z)[3)] |
|---|---|---|---|
| I-115 | 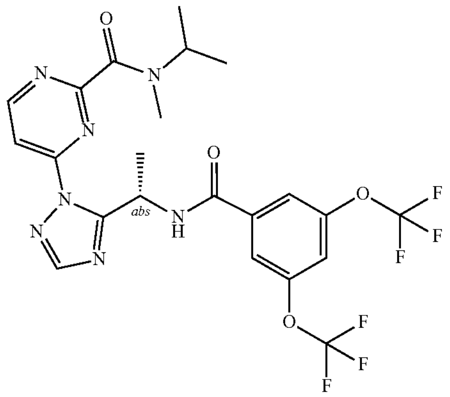 [SMILES: CC(C)N(C)C(=O)c1nccc(-n2ncnc2[C@H](C)NC(=O)c2cc(OC(F)(F)F)cc(OC(F)(F)F)c2)n1] | $^1$H-NMR (400.2 MHz, d6-DMSO) δ = 9.4997 (1.9); 9.4825 (2.0); 9.2411 (5.2); 9.2383 (6.9); 9.2359 (3.6); 8.3013 (8.1); 8.0098 (6.6); 8.0086 (5.4); 8.0069 (5.9); 7.9173 (6.4); 7.7718 (2.6); 6.2653 (0.3); 6.2481 (1.6); 6.2308 (2.5); 6.2135 (1.6); 4.7487 (0.6); 4.7318 (0.9); 4.7147 (0.6); 3.8154 (0.3); 3.7992 (0.9); 3.7827 (1.3); 3.7663 (1.0); 3.7499 (0.3); 3.3324 (115.7); 2.8894 (16.0); 2.7479 (11.2); 2.6813 (0.3); 2.6767 (0.8); 2.6722 (1.0); 2.6676 (0.7); 2.6630 (0.3); 2.5258 (3.3); 2.5211 (5.0); 2.5123 (63.4); 2.5079 (131.1); 2.5033 (171.7); 2.4986 (120.4); 2.4941 (55.6); 2.3393 (0.4); 2.3347 (0.8); 2.3301 (1.0); 2.3255 (0.7); 2.3210 (0.3); 2.0768 (10.7); 1.6778 (6.7); 1.6604 (6.7); 1.1919 (7.6); 1.749 (7.6); 1.1482 (7.4); 1.438 (7.5); 1.318 (7.4); 1.274 (7.2); −0.0002 (0.6) | 562.3 |
| I-116 | 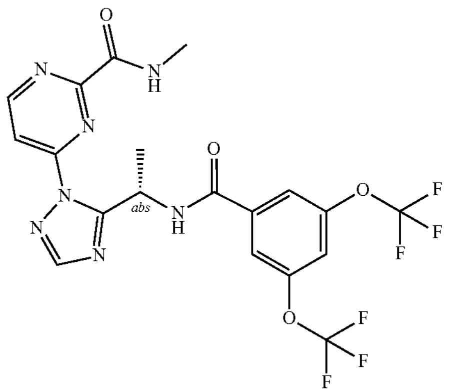 [SMILES: CNC(=O)c1nccc(-n2ncnc2[C@H](C)NC(=O)c2cc(OC(F)(F)F)cc(OC(F)(F)F)c2)n1] | $^1$H-NMR (400.2 MHz, d6-DMSO) δ = 9.4881 (3.2); 9.4708 (3.2); 9.3119 (10.0); 9.3090 (9.8); 9.1677 (0.8); 9.1564 (2.3); 9.1442 (2.3); 9.1329 (0.8); 8.3738 (9.9); 8.3710 (9.8); 8.3299 (14.7); 8.3193 (0.5); 7.9029 (9.0); 7.8982 (9.3); 7.7630 (4.1); 6.2870 (0.4); 6.2699 (2.2); 6.2526 (3.4); 6.2353 (2.2); 6.2177 (0.4); 3.3334 (182.0); 2.8718 (16.0); 2.8597 (15.9); 2.6773 (1.1); 2.6727 (1.4); 2.6682 (1.0); 2.6641 (0.5); 2.5262 (4.9); 2.5214 (7.9); 2.5127 (89.6); 2.5083 (179.3); 2.5038 (231.9); 2.4992 (164.3); 2.4947 (77.3); 2.3397 (0.5); 2.3350 (1.0); 2.3306 (1.4); 2.3261 (1.0); 1.6687 (12.6); 1.6514 (12.5); −0.0001 (1.0) | 520.3 |

TABLE 1-continued
| Example | Structure[1)] | NMR Peak List[2)] | ESI Mass (m/z)[3)] |
|---|---|---|---|
| I-117 | 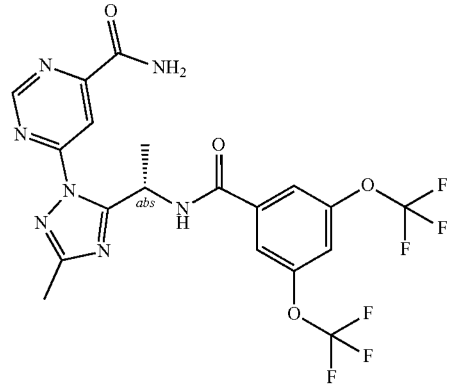 [SMILES: Cc1nc([C@H](C)NC(=O)c2cc(OC(F)(F)F)cc(OC(F)(F)F)c2)n(-c2cc(C(N)=O)ncn2)n1] | $^{1}$H-NMR (400.2 MHz, d6-DMSO) δ = 9.4737 (1.4); 9.4560 (1.4); 9.2660 (4.9); 9.2630 (4.8); 8.4490 (1.4); 8.3393 (4.6); 8.3364 (4.5); 8.1092 (1.3); 7.9241 (3.8); 7.9191 (3.9); 7.7642 (1.7); 6.2651 (1.0); 6.2476 (1.6); 6.2301 (1.0); 3.3327 (77.4); 2.6771 (0.5); 2.6725 (0.7); 2.6679 (0.5); 2.5260 (2.4); 2.5213 (3.7); 2.5126 (43.9); 2.5081 (89.2); 2.5035 (115.4); 2.4989 (80.3); 2.4943 (36.6); 2.3742 (16.0); 2.3348 (0.5); 2.3303 (0.7); 2.3257 (0.5); 1.6479 (5.3); 1.6305 (5.3); −0.0002 (0.5) | 520.3 |
| I-118 | 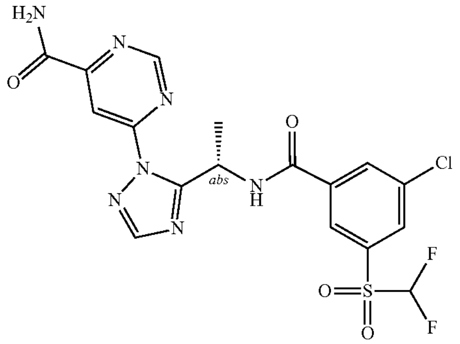 [SMILES: C[C@H](NC(=O)c1cc(Cl)cc(S(=O)(=O)C(F)F)c1)c1ncnn1-c1cc(C(N)=O)ncn1] | $^{1}$H-NMR (400.2 MHz, d6-DMSO) δ = 9.6729 (3.2); 9.6556 (3.3); 9.3169 (10.0); 9.3141 (10.3); 9.2764 (0.4); 9.2544 (0.4); 9.0075 (0.4); 8.8942 (0.3); 8.8886 (0.3); 8.5173 (0.3); 8.5021 (0.4); 8.4956 (0.4); 8.4860 (0.7); 8.4669 (7.4); 8.4627 (8.6); 8.4584 (5.7); 8.4058 (0.3); 8.3863 (10.0); 8.3834 (11.0); 8.3772 (7.8); 8.3735 (4.4); 8.3426 (0.4); 8.3344 (16.0); 8.3183 (0.5); 8.1921 (4.2); 8.1877 (7.2); 8.1833 (4.0); 8.1315 (3.3); 7.9055 (0.7); 7.8840 (0.6); 7.5474 (2.7); 7.4174 (6.2); 7.2875 (3.2); 6.3133 (0.5); 6.2963 (2.3); 6.2791 (3.6); 6.2617 (2.2); 6.2441 (0.5); 4.0041 (1.2); 3.9875 (0.6); 3.9663 (2.5); 3.9575 (1.6); 3.9522 (0.9); 3.9468 (2.2); 3.3311 (83.2); 2.6769 (0.8); 2.6725 (1.2); 2.6679 (0.9); 2.5259 (3.0); 2.5211 (4.4); 2.5124 (66.5); 2.5080 (140.0); 2.5035 (187.0); 2.4989 (132.7); 2.4944 (61.8); 2.3391 (0.3); 2.3348 (0.8); 2.3303 (1.1); 2.3257 (0.8); 2.3212 (0.3); 2.0765 (11.2); 2.0428 (0.4); 1.9099 (0.7); 1.6750 (13.1); 1.6577 (13.0); 1.6365 (0.4); 1.5438 (0.8); 1.5275 (1.5); 1.5109 (1.0); 1.3263 (0.5); 1.3063 (0.4); 1.2987 (1.2); 1.2847 (0.4); 1.2590 (1.4); 1.2336 (1.8); 0.8536 (0.3); 0.1457 (1.4); 0.0079 (9.8); −0.0001 (304.2); −0.0086 (9.6); −0.0179 (0.5); −0.1498 (1.3) | 486.1 |

TABLE 1-continued
| Example | Structure[1)] | NMR Peak List[2)] | ESI Mass (m/z)[3)] |
|---|---|---|---|
| I-119 | 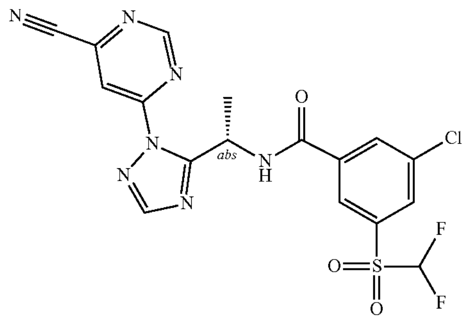 [SMILES: C[C@H](NC(=O)c1cc(Cl)cc(S(=O)(=O)C(F)F)c1)c1ncnn1-c1cc(C#N)ncn1] | $^{1}$H-NMR (400.2 MHz, d6-DMSO) δ = 9.6828 (4.4); 9.6656 (2.5); 9.3883 (8.9); 9.3852 (9.0); 8.6180 (8.6); 8.6149 (8.8); 8.6100 (0.5); 8.4724 (3.6); 8.4679 (5.5); 8.4637 (4.1); 8.3743 (16.0); 8.3694 (3.7); 8.1992 (3.2); 8.1947 (5.5); 8.1903 (3.1); 8.1147 (0.4); 8.1112 (0.4); 8.0793 (0.5); 7.9343 (0.4); 7.5521 (2.2); 7.4222 (5.3); 7.2924 (2.7); 6.2485 (0.3); 6.2315 (1.7); 6.2143 (2.7); 6.1970 (1.7); 6.1796 (0.4); 5.7595 (14.0); 4.0126 (1.7); 3.9817 (1.2); 3.3316 (20.5); 3.0057 (1.0); 2.8940 (1.1); 2.6728 (0.4); 2.5264 (1.0); 2.5216 (1.5); 2.5130 (26.6); 2.5085 (56.4); 2.5039 (75.5); 2.4993 (53.2); 2.4947 (24.6); 2.3353 (0.3); 2.3308 (0.4); 2.3261 (0.3); 2.0772 (0.9); 1.9103 (0.5); 1.7466 (0.7); 1.7290 (0.7); 1.6618 (10.1); 1.6444 (10.1); 1.2993 (0.4); 1.2592 (0.6); 1.2335 (3.3); 0.8532 (0.4); 0.1458 (0.6); 0.0080 (4.7); −0.0002 (141.8); −0.0086 (4.6); −0.0156 (0.4); −0.1496 (0.6) | 468.1 |
| I-120 | 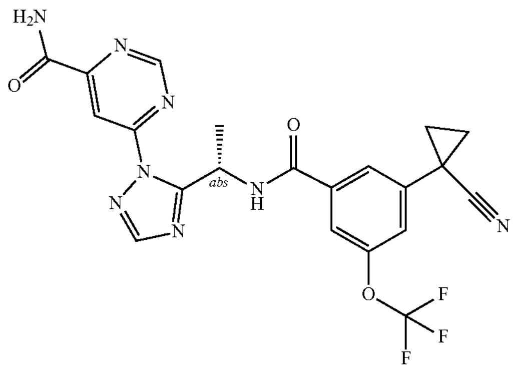 [SMILES: C[C@H](NC(=O)c1cc(OC(F)(F)F)cc(C2(C#N)CC2)c1)c1ncnn1-c1cc(C(N)=O)ncn1] | $^{1}$H-NMR (400.2 MHz, d6-DMSO) δ = 9.4026 (3.8); 9.3852 (3.9); 9.3137 (10.0); 9.3112 (9.9); 8.4719 (4.4); 8.3823 (10.2); 8.3800 (9.9); 8.3264 (14.8); 8.1344 (4.3); 7.8215 (8.0); 7.7420 (5.9); 7.4842 (6.0); 6.2898 (0.6); 6.2723 (2.5); 6.2550 (3.9); 6.2377 (2.5); 6.2205 (0.6); 5.7602 (7.6); 3.3492 (26.5); 2.6746 (0.5); 2.6705 (0.4); 2.5101 (64.7); 2.5058 (81.7); 2.5015 (60.6); 2.3325 (0.5); 1.8550 (3.0); 1.8422 (8.3); 1.8349 (8.9); 1.8235 (3.9); 1.7837 (0.5); 1.7000 (0.7); 1.6744 (14.4); 1.6570 (16.0); 1.6493 (10.4); 1.6420 (8.6); 1.6287 (3.2); 1.2318 (0.6); 0.1458 (0.5); −0.0002 (96.3); −0.1494 (0.5) | 487.2 |

TABLE 1-continued
| Example | Structure[1)] | NMR Peak List[2)] | ESI Mass (m/z)[3)] |
|---|---|---|---|
| I-121 | 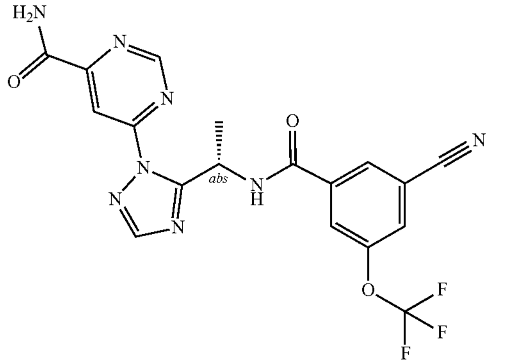 [SMILES: C[C@H](NC(=O)c1cc(C#N)cc(OC(F)(F)F)c1)c1ncnn1-c1cc(C(N)=O)ncn1] | $^1$H-NMR (400.2 MHz, d6-DMSO) δ = 9.4842 (3.2); 9.4669 (3.4); 9.3136 (11.0); 9.3106 (10.8); 8.4694 (3.4); 8.3863 (5.4); 8.3814 (15.2); 8.3785 (13.7); 8.3289 (16.0); 8.3186 (0.6); 8.2408 (4.5); 8.1323 (3.3); 8.1049 (4.3); 8.1025 (4.8); 8.1000 (4.1); 6.2955 (0.5); 6.2782 (2.3); 6.2609 (3.6); 6.2436 (2.3); 6.2264 (0.5); 3.9121 (0.3); 3.3308 (167.6); 2.6809 (0.6); 2.6765 (1.2); 2.6719 (1.7); 2.6674 (1.2); 2.6628 (0.6); 2.5254 (4.8); 2.5206 (7.8); 2.5120 (102.4); 2.5075 (208.9); 2.5030 (273.1); 2.4984 (191.1); 2.4939 (87.3); 2.3390 (0.5); 2.3343 (1.2); 2.3298 (1.6); 2.3252 (1.2); 1.6681 (13.2); 1.6508 (13.1); 0.1458 (1.8); 0.0252 (0.4); 0.0079 (16.3); −0.0002 (442.0); −0.0086 (14.3); −0.0174 (0.6); −0.0218 (0.5); −0.1496 (1.8) | 447.1 |
| I-122 | 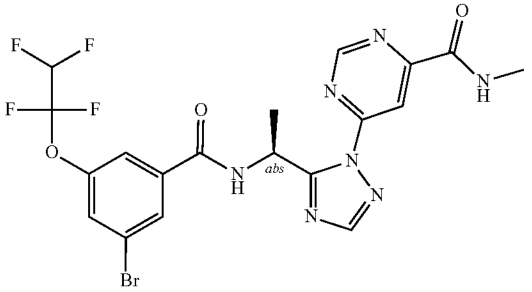 [SMILES: CNC(=O)c1cc(-n2ncnc2[C@H](C)NC(=O)c2cc(Br)cc(OC(F)(F)C(F)F)c2)ncn1] | $^1$H-NMR (400.2 MHz, d6-DMSO) δ = 9.4179 (2.9); 9.4005 (3.0); 9.3129 (9.1); 9.3100 (9.3); 9.1681 (0.7); 9.1564 (2.1); 9.1442 (2.2); 9.1324 (0.7); 8.3735 (8.5); 8.3707 (8.5); 8.3223 (14.1); 8.0931 (4.0); 8.0892 (7.2); 8.0854 (4.3); 7.7433 (7.6); 7.7386 (5.4); 6.9763 (0.6); 6.9688 (1.2); 6.9612 (0.6); 6.8468 (1.2); 6.8395 (2.6); 6.8317 (1.3); 6.7172 (0.6); 6.7102 (1.3); 6.7025 (0.6); 6.2723 (0.4); 6.2552 (2.0); 6.2379 (3.1); 6.2205 (2.0); 6.2033 (0.4); 3.3321 (71.2); 2.8728 (14.7); 2.8607 (14.7); 2.6774 (0.5); 2.6728 (0.7); 2.6682 (0.5); 2.5263 (1.6); 2.5216 (2.4); 2.5128 (38.0); 2.5084 (81.7); 2.5038 (110.4); 2.4992 (78.2); 2.4947 (36.1); 2.3352 (0.5); 2.3306 (0.7); 2.3262 (0.5); 2.0770 (16.0); 1.6530 (11.5); 1.6356 (11.5); 0.1458 (0.8); 0.0079 (5.7); −0.0002 (185.4); −0.0086 (5.7); −0.1497 (0.8) | 548.1 |

TABLE 1-continued
| Example | Structure[1)] | NMR Peak List[2)] | ESI Mass (m/z)[3)] |
|---|---|---|---|
| I-123 | 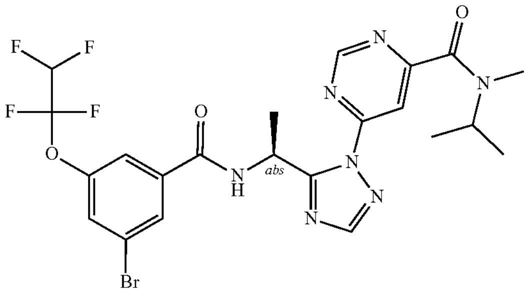 [SMILES: CC(C)N(C)C(=O)c1cc(-n2ncnc2[C@H](C)NC(=O)c2cc(Br)cc(OC(F)(F)C(F)F)c2)ncn1] | $^1$H-NMR (400.2 MHz, d6-DMSO) δ = 9.4265 (2.0); 9.4093 (2.1); 9.2420 (4.7); 9.2389 (6.3); 9.2357 (2.9); 8.2949 (8.1); 8.1341 (0.4); 8.1128 (2.4); 8.1091 (4.8); 8.1053 (4.2); 8.0095 (3.3); 8.0060 (5.8); 8.0022 (4.4); 7.7651 (3.6); 7.7628 (3.7); 7.7448 (4.1); 6.9825 (0.5); 6.9753 (0.9); 6.9680 (0.5); 6.8532 (1.1); 6.8459 (2.0); 6.8384 (1.0); 6.7236 (0.5); 6.7168 (1.0); 6.7091 (0.5); 6.2512 (0.4); 6.2338 (1.7); 6.2166 (2.7); 6.1992 (1.7); 6.1819 (0.4); 4.7518 (0.7); 4.7347 (0.9); 4.7178 (0.7); 3.8126 (0.4); 3.7962 (1.0); 3.7798 (1.4); 3.7633 (1.0); 3.7469 (0.4); 3.6561 (2.2); 3.3342 (36.9); 2.8902 (16.0); 2.7514 (11.3); 2.6739 (0.4); 2.5272 (1.1); 2.5138 (24.3); 2.5095 (48.3); 2.5050 (62.2); 2.5005 (44.2); 2.4963 (21.0); 2.3317 (0.4); 2.0778 (8.2); 1.6643 (7.6); 1.6470 (7.6); 1.4216 (0.8); 1.4032 (0.8); 1.1938 (9.0); 1.1768 (8.9); 1.1489 (8.4); 1.1446 (8.4); 1.1325 (8.4); 1.1283 (8.0); 0.1462 (0.4); 0.0078 (4.1); −0.0002 (98.2); −0.0085 (3.9); −0.1494 (0.4) | 590.1 |
| I-124 | 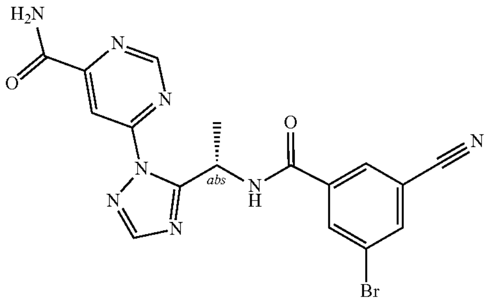 [SMILES: C[C@H](NC(=O)c1cc(Br)cc(C#N)c1)c1ncnn1-c1cc(C(N)=O)ncn1] | $^1$H-NMR (400.2 MHz, d6-DMSO) δ = 9.4188 (2.7); 9.4014 (2.8); 9.3148 (9.7); 9.3119 (9.8); 8.5699 (0.4); 8.5668 (0.4); 8.4721 (2.8); 8.3790 (10.0); 8.3761 (9.8); 8.3600 (3.4); 8.3557 (6.3); 8.3519 (4.9); 8.3304 (4.9); 8.3236 (16.0); 8.2861 (5.0); 8.2824 (8.2); 8.2788 (3.9); 8.1311 (2.7); 6.2784 (0.4); 6.2608 (2.0); 6.2434 (3.1); 6.2262 (2.0); 6.2086 (0.4); 3.3324 (257.4); 2.6808 (0.7); 2.6763 (1.6); 2.6718 (2.1); 2.6672 (1.5); 2.6626 (0.7); 2.5253 (6.5); 2.5206 (9.5); 2.5119 (124.8); 2.5074 (259.8); 2.5028 (343.0); 2.4982 (239.0); 2.4936 (108.4); 2.3388 (0.6); 2.3342 (1.4); 2.3297 (2.0); 2.3250 (1.4); 2.3206 (0.6); 2.0760 (6.8); 1.9895 (0.4); 1.9455 (0.5); 1.9086 (1.6); 1.6537 (11.6); 1.6363 (11.5); 1.3550 (0.4); 0.1458 (1.4); 0.0199 (0.4); 0.0191 (0.4); 0.0155 (0.6); 0.0080 (11.6); −0.0002 (375.1); −0.0085 (11.5); −0.1496 (1.4) | 443.0 |

TABLE 1-continued
| Example | Structure[1)] | NMR Peak List[2)] | ESI Mass (m/z)[3)] |
|---|---|---|---|
| I-125 | 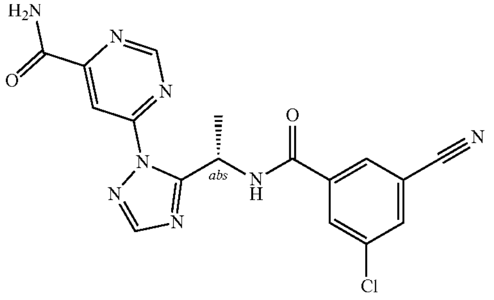 [SMILES: C[C@H](NC(=O)c1cc(Cl)cc(C#N)c1)c1ncnn1-c1cc(C(N)=O)ncn1] | $^1$H-NMR (400.2 MHz, d6-DMSO) δ = 9.4226 (3.1); 9.4052 (3.2); 9.3181 (10.5); 9.3152 (10.5); 8.4742 (3.2); 8.3836 (10.9); 8.3807 (10.7); 8.3266 (1.6); 8.2634 (3.8); 8.2598 (9.3); 8.2562 (6.8); 8.2510 (5.4); 8.2462 (7.1); 8.2425 (3.9); 8.1999 (5.8); 8.1956 (6.9); 8.1910 (4.3); 8.1362 (3.1); 6.2837 (0.5); 6.2665 (2.2); 6.2493 (3.5); 6.2318 (2.2); 6.2144 (0.4); 3.3394 (19.0); 2.6763 (0.3); 2.5299 (1.0); 2.5251 (1.5); 2.5165 (19.7); 2.5120 (40.8); 2.5074 (53.6); 2.5028 (37.5); 2.4983 (17.2); 2.0801 (0.7); 1.6606 (13.0); 1.6432 (12.8); 0.0080 (1.9); −0.0002 (56.9); −0.0086 (1.8) | 397.1 |
| I-126 | 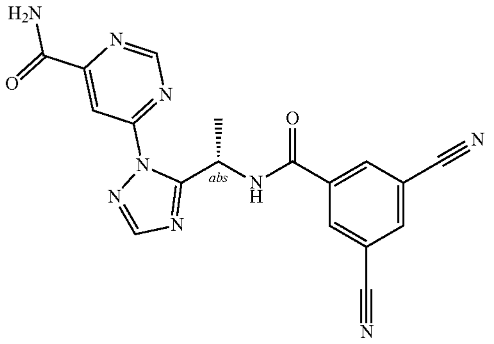 [SMILES: C[C@H](NC(=O)c1cc(C#N)cc(C#N)c1)c1ncnn1-c1cc(C(N)=O)ncn1] | $^1$H-NMR (400.2 MHz, d6-DMSO) δ = 9.4722 (2.4); 9.4548 (2.5); 9.3169 (8.3); 9.3140 (8.4); 8.6500 (3.3); 8.6463 (6.8); 8.6425 (4.0); 8.5725 (16.0); 8.5687 (14.5); 8.4694 (2.4); 8.3817 (8.3); 8.3788 (8.3); 8.3309 (12.6); 8.3178 (0.4); 8.1317 (2.4); 6.2989 (0.4); 6.2820 (1.7); 6.2647 (2.7); 6.2473 (1.7); 6.2299 (0.4); 3.3324 (179.9); 2.6811 (0.4); 2.6766 (0.9); 2.6719 (1.2); 2.6674 (0.8); 2.6628 (0.4); 2.5255 (3.3); 2.5208 (5.0); 2.5121 (71.4); 2.5076 (149.2); 2.5030 (196.9); 2.4984 (137.4); 2.4938 (62.6); 2.3389 (0.4); 2.3344 (0.8); 2.3298 (1.2); 2.3252 (0.8); 2.3209 (0.4); 1.6660 (10.0); 1.6486 (10.0); 0.1458 (0.8); 0.0079 (6.3); −0.0002 (199.5); −0.0086 (5.9); −0.1497 (0.8) | 388.2 |
| I-127 | 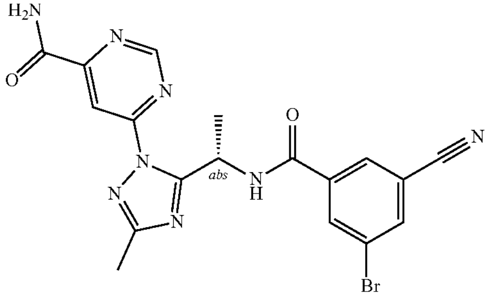 [SMILES: Cc1nc([C@H](C)NC(=O)c2cc(Br)cc(C#N)c2)n(-c2cc(C(N)=O)ncn2)n1] | $^1$H-NMR (400.2 MHz, d6-DMSO) δ = 9.4011 (1.5); 9.3834 (1.5); 9.2727 (4.6); 9.2698 (4.5); 8.4510 (1.5); 8.3607 (1.3); 8.3563 (3.6); 8.3524 (4.2); 8.3469 (3.8); 8.3422 (1.5); 6.3378 (4.7); 8.3349 (4.5); 8.3182 (1.2); 8.3036 (2.6); 8.3000 (3.9); 8.2963 (2.1); 8.1068 (1.5); 8.2566 (1.0); 6.2393 (1.7); 6.2218 (1.0); 5.7585 (4.4); 3.3314 (177.9); 3.3077 (0.6); 2.6761 (1.2); 2.6716 (1.6); 2.6669 (1.1); 2.6625 (0.5); 2.5251 (4.6); 2.5203 (7.3); 2.5116 (99.6); 2.5072 (202.6); 2.5026 (264.0); 2.4981 (185.3); 2.9436 (86.1); 2.3723 (16.0); 2.3385 (0.6); 2.3340 (1.2); 2.3294 (1.6); 2.3249 (1.1); 2.3204 (0.5); 1.6322 (5.6); 1.6149 (5.6); 0.1460 (1.0); 0.0080 (8.6); −0.0001 (255.3); −0.0085 (8.5); −0.0152 (0.8); −0.0219 (0.4); −0.0226 (0.4); −0.1495 (1.1) | 457.0 |

TABLE 1-continued
| Example | Structure[1)] | NMR Peak List[2)] | ESI Mass (m/z)[3)] |
|---|---|---|---|
| I-128 | 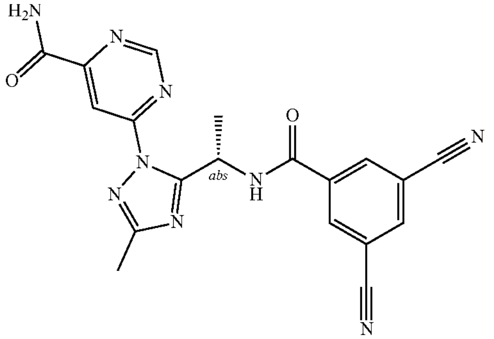 [SMILES: Cc1nc([C@H](C)NC(=O)c2cc(C#N)cc(C#N)c2)n(-c2cc(C(N)=O)ncn2)n1] | $^1$H-NMR (400.2 MHz, d6-DMSO) δ = 9.4565 (1.4); 9.4388 (1.4); 9.3182 (0.4); 9.3152 (0.4); 9.2761 (4.7); 9.2732 (4.8); 8.6506 (2.0); 8.6469 (4.1); 8.6431 (2.5); 8.5883 (9.0); 8.5845 (8.1); 8.5737 (0.7); 8.5699 (0.7); 8.4493 (1.4); 8.3825 (0.4); 8.3797 (0.4); 8.3408 (4.8); 8.3379 (4.7); 8.3320 (0.6); 8.1095 (1.3); 6.2777 (1.0); 6.2602 (1.6); 6.2428 (1.0); 3.3338 (29.2); 2.5271 (0.8); 2.5224 (1.1); 2.5136 (16.4); 2.5091 (34.7); 2.5045 (46.2); 2.4999 (32.5); 2.4953 (15.0); 2.3761 (16.0); 1.6672 (0.5); 1.6452 (5.4); 1.6279 (5.3); 0.0080 (1.5); −0.0002 (48.0); −0.0086 (1.4) | 402.2 |
| I-129 | 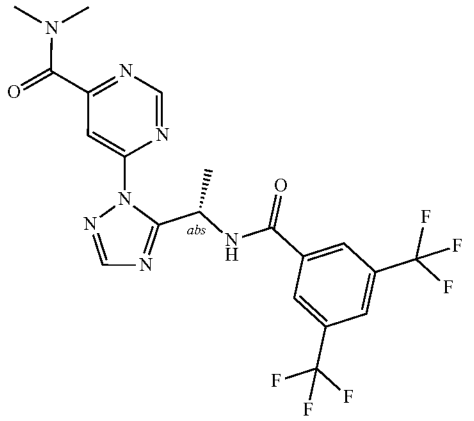 [SMILES: C[C@H](NC(=O)c1cc(C(F)(F)F)cc(C(F)(F)F)c1)c1ncnn1-c1cc(C(=O)N(C)C)ncn1] | $^1$H-NMR (400.2 MHz, d6-DMSO) δ = 9.6691 (1.0); 9.6520 (1.0); 9.2604 (3.8); 9.2573 (3.7); 8.5159 (3.5); 8.3375 (1.6); 8.3091 (5.3); 8.0379 (4.1); 8.0348 (3.9); 6.2991 (0.8); 6.2817 (1.2); 6.2643 (0.7); 3.3334 (64.6); 3.0422 (13.3); 2.9509 (16.0); 2.6767 (0.6); 2.6721 (0.8); 2.6676 (0.5); 2.5257 (2.3); 2.5210 (3.6); 2.5122 (46.9); 2.5077 (96.6); 2.5032 (126.2); 2.4985 (87.3); 2.4939 (39.3); 2.3345 (0.6); 2.3300 (0.8); 2.3254 (0.5); 1.6926 (4.4); 1.6752 (4.4); 0.1459 (0.7); 0.0132 (0.5); 0.0080 (6.2); −0.0002 (179.6); −0.0086 (5.3); −0.1496 (0.7) | 502.3 |

TABLE 1-continued
| Example | Structure[1)] | NMR Peak List[2)] | ESI Mass (m/z)[3)] |
|---|---|---|---|
| I-130 | 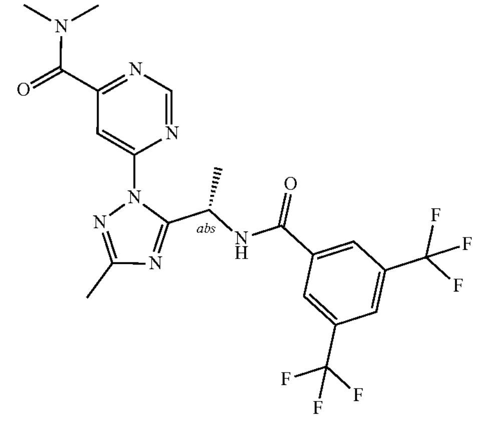 [SMILES: Cc1nc([C@H](C)NC(=O)c2cc(C(F)(F)F)cc(C(F)(F)F)c2)n(-c2cc(C(=O)N(C)C)ncn2)n1] | $^1$H-NMR (400.2 MHz, d6-DMSO) δ = 9.6533 (1.1); 9.6358 (1.2); 9.2206 (4.0); 9.2176 (4.0); 8.5374 (4.0); 8.3388 (1.8); 7.9673 (4.2); 7.9642 (4.1); 6.2971 (0.9); 6.2797 (1.4); 6.2622 (0.9); 3.3337 (31.7); 3.0353 (13.6); 2.9476 (16.0); 2.6729 (0.4); 2.5265 (1.4); 2.5218 (2.2); 2.5131 (24.4); 2.5086 (49.4); 2.5040 (64.1); 2.4994 (45.4); 2.4948 (21.1); 2.3529 (13.9); 2.3354 (0.4); 2.3309 (0.4); 2.3263 (0.3); 2.0775 (0.9); 1.6718 (4.7); 1.6544 (4.7); −0.0002 (0.7) | 516.2 |
| I-131 | 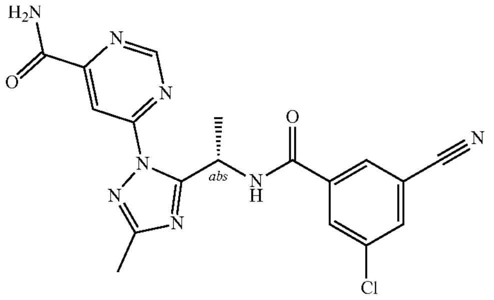 [SMILES: Cc1nc([C@H](C)NC(=O)c2cc(Cl)cc(C#N)c2)n(-c2cc(C(N)=O)ncn2)n1] | $^1$H-NMR (400.2 MHz, d6-DMSO) δ = 9.4038 (1.4); 9.3862 (1.4); 9.2731 (4.4); 9.2702 (4.3); 8.4530 (1.4); 8.3382 (4.5); 8.3353 (4.3); 8.3247 (0.4); 8.2777 (1.9); 8.2741 (3.8); 8.2705 (2.4); 8.2530 (2.1); 8.2480 (2.7); 8.2445 (1.7); 8.2170 (2.5); 8.2130 (2.8); 8.2081 (1.6); 8.1106 (1.3); 6.2585 (1.0); 6.2410 (1.6); 6.2235 (1.0); 3.3353 (115.1); 2.6770 (0.6); 2.6723 (0.7); 2.6677 (0.5); 2.5258 (2.8); 2.5210 (4.8); 2.5124 (45.0); 2.5079 (88.8); 2.5033 (114.1); 2.4987 (78.4); 2.4942 (35.0); 2.3728 (16.0); 2.3347 (0.6); 2.3301 (0.8); 2.3256 (0.5); 1.6563 (0.4); 1.6350 (5.5); 1.6176 (5.4); 0.0080 (2.3); −0.0002 (56.7); −0.0086 (1.6) | 411.1 |

TABLE 1-continued
| Example | Structure[1)] | NMR Peak List[2)] | ESI Mass (m/z)[3)] |
|---|---|---|---|
| I-132 | 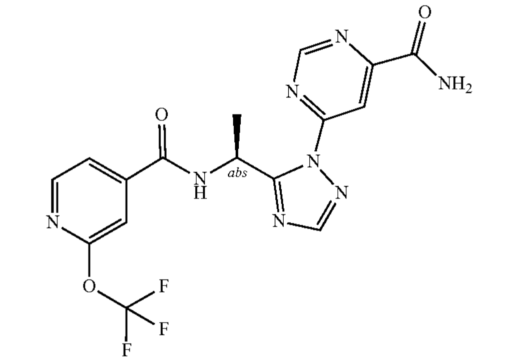 [SMILES: C[C@H](NC(=O)c1ccnc(OC(F)(F)F)c1)c1ncnn1-c1cc(C(N)=O)ncn1] | $^1$H-NMR (400.2 MHz, d6-DMSO) δ = 9.5375 (3.8); 9.5201 (3.9); 9.3109 (10.5); 9.3082 (11.3); 8.5173 (6.8); 8.5044 (7.1); 8.4729 (4.2); 8.3809 (10.4); 8.3783 (10.6); 8.3320 (16.0); 8.3193 (0.9); 8.1343 (4.1); 7.7959 (4.9); 7.7929 (5.2); 7.7830 (4.7); 7.7800 (5.1); 7.6216 (9.5); 6.2829 (0.6); 6.2657 (2.7); 6.2484 (4.3); 6.2310 (2.7); 6.2137 (0.6); 3.3345 (124.1); 3.3113 (0.5); 2.6769 (1.0); 2.6725 (1.5); 2.6681 (1.1); 2.5259 (3.7); 2.5213 (5.4); 2.5079 (167.0); 2.5035 (224.3); 2.4991 (164.0); 2.3347 (1.0); 2.3304 (1.4); 2.3258 (1.1); 1.6624 (16.0); 1.6451 (15.9); −0.0002 (11.4); −0.0084 (0.4) | 423.1 |
| I-133 | 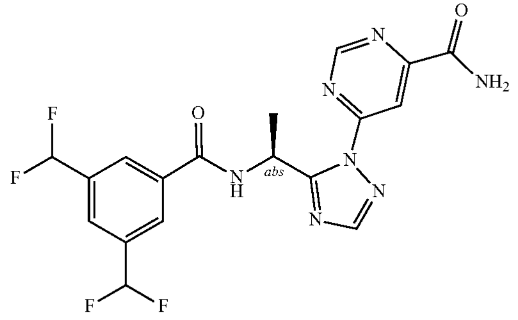 [SMILES: C[C@H](NC(=O)c1cc(C(F)F)cc(C(F)F)c1)c1ncnn1-c1cc(C(N)=O)ncn1] | $^1$H-NMR (400.2 MHz, d6-DMSO) δ = 9.5144 (3.5); 9.4971 (3.6); 9.3213 (9.9); 9.3185 (10.6); 8.4753 (3.8); 8.3873 (9.5); 8.3846 (10.0); 8.3213 (16.0); 8.2306 (11.8); 8.1351 (3.7); 7.9434 (5.3); 7.3216 (5.4); 7.1829 (12.6); 7.0443 (5.9); 6.3061 (0.5); 6.2890 (2.5); 6.2716 (3.9); 6.2542 (2.5); 6.2367 (0.5); 3.3369 (45.8); 2.6783 (0.4); 2.6737 (0.6); 2.6692 (0.5); 2.5272 (1.6); 2.5226 (2.4); 2.5135 (34.4); 2.5092 (73.0); 2.5047 (98.4); 2.5002 (70.4); 2.4958 (33.1); 2.3360 (0.4); 2.3315 (0.6); 2.3271 (0.5); 1.6726 (14.5); 1.6552 (14.4); −0.0002 (5.4) | 438.1 |
| I-134 | 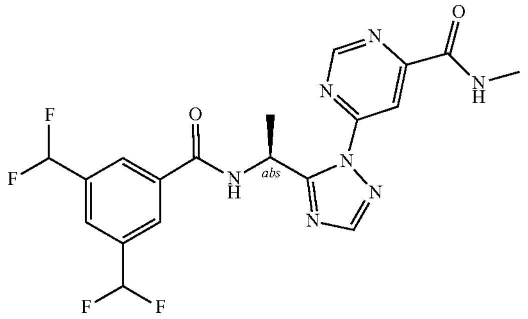 [SMILES: CNC(=O)c1cc(-n2ncnc2[C@H](C)NC(=O)c2cc(C(F)F)cc(C(F)F)c2)ncn1] | $^1$H-NMR (400.2 MHz, d6-DMSO) δ = 9.5123 (3.1); 9.4949 (3.2); 9.3218 (9.3); 9.3189 (9.4); 9.1698 (0.8); 9.1584 (2.2); 9.1462 (2.2); 9.1344 (0.8); 8.3790 (9.0); 8.3762 (9.0); 8.3221 (14.5); 8.2276 (10.1); 7.9421 (4.6); 7.3194 (4.8); 7.1807 (11.2); 7.0421 (5.2); 6.3050 (0.4); 6.2879 (2.2); 6.2705 (3.5); 6.2531 (2.2); 6.2354 (0.5); 3.3344 (115.2); 2.8728 (16.0); 2.8608 (15.9); 2.6812 (0.4); 2.6769 (0.8); 2.6723 (1.2); 2.6679 (0.9); 2.6633 (0.4); 2.5259 (3.4); 2.5212 (4.8); 2.5124 (64.0); 2.5079 (135.5); 2.5034 (181.0); 2.4988 (127.6); 2.4944 (58.7); 2.3392 (0.3); 2.3347 (0.8); 2.3303 (1.1); 2.3257 (0.8); 2.0769 (5.8); 1.6702 (12.9); 1.6528 (12.8); −0.0002 (6.4) | 452.1 |

TABLE 1-continued
| Example | Structure[1)] | NMR Peak List[2)] | ESI Mass (m/z)[3)] |
|---|---|---|---|
| I-135 | 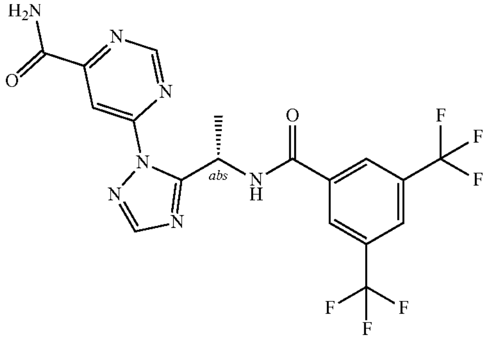 [SMILES: C[C@H](NC(=O)c1cc(C(F)(F)F)cc(C(F)(F)F)c1)c1ncnn1-c1cc(C(N)=O)ncn1] | $^1$H-NMR (400.2 MHz, d6-DMSO) δ = 9.6598 (2.7); 9.6424 (2.8); 9.3236 (7.9); 9.3207 (8.4); 8.4981 (9.9); 8.4732 (2.8); 8.3863 (7.8); 8.3835 (8.0); 8.3354 (16.0); 8.3194 (0.6); 8.1345 (2.8); 6.3340 (0.4); 6.3170 (1.9); 6.2997 (3.0); 6.2824 (1.9); 6.2650 (0.4); 3.3341 (90.4); 2.6775 (0.8); 2.6729 (1.2); 2.6683 (0.9); 2.6637 (0.4); 2.5356 (0.4); 2.5264 (3.1); 2.5217 (4.4); 2.5128 (62.2); 2.5084 (132.6); 2.5039 (178.0); 2.4994 (126.9); 2.4949 (59.2); 2.3398 (0.4); 2.3353 (0.8); 2.3307 (1.1); 2.3262 (0.8); 2.0875 (0.6); 1.6886 (11.1); 1.6712 (11.1); 1.3717 (0.4); 1.3536 (0.4); −0.0002 (3.1) | 474.3 |
| I-136 | 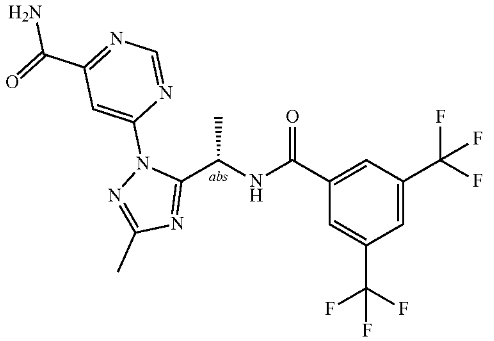 [SMILES: Cc1nc([C@H](C)NC(=O)c2cc(C(F)(F)F)cc(C(F)(F)F)c2)n(-c2cc(C(N)=O)ncn2)n1] | $^1$H-NMR (400.2 MHz, d6-DMSO) δ = 9.6482 (1.5); 9.6305 (1.5); 9.2827 (4.3); 9.2799 (4.4); 8.5238 (5.3); 8.4542 (1.6); 8.3479 (4.3); 8.3452 (4.3); 8.3336 (2.3); 8.1143 (1.5); 7.9561 (0.7); 6.3183 (1.1); 6.3009 (1.7); 6.2834 (1.1); 3.3385 (23.4); 2.8944 (5.6); 2.7347 (4.6); 2.6921 (1.0); 2.5292 (0.7); 2.5245 (1.0); 2.5157 (13.9); 2.5113 (29.2); 2.5068 (38.8); 2.5022 (27.3); 2.4978 (12.6); 2.3780 (16.0); 1.6697 (5.8); 1.6523 (5.8); 1.3970 (1.3); −0.0002 (0.7) | 488.4 |

TABLE 1-continued
| Example | Structure[1)] | NMR Peak List[2)] | ESI Mass (m/z)[3)] |
|---|---|---|---|
| I-137 | 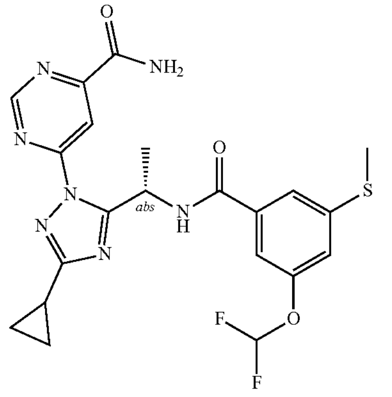 [SMILES: CSc1cc(OC(F)F)cc(C(=O)N[C@@H](C)c2nc(C3CC3)nn2-c2cc(C(N)=O)ncn2)c1] | $^1$H-NMR (400.2 MHz, d6-DMSO) δ = 9.2469 (11.9); 9.2443 (11.4); 9.2040 (4.6); 9.1863 (4.8); 8.4500 (4.9); 8.3188 (1.3); 8.3120 (11.5); 8.3097 (11.0); 8.1118 (4.9); 7.5529 (9.5); 7.4878 (4.5); 7.3423 (7.0); 7.3034 (9.5); 7.2004 (5.1); 7.1961 (7.8); 7.1918 (4.7); 7.1190 (4.8); 6.2131 (0.6); 6.1955 (2.9); 6.1782 (4.7); 6.1607 (2.9); 6.1431 (0.6); 3.3312 (302.2); 2.7025 (0.4); 2.6759 (3.6); 2.6715 (5.0); 2.6671 (3.6); 2.5764 (0.5); 2.5723 (0.5); 2.5289 (55.6); 2.5200 (22.1); 2.5069 (588.9); 2.5025 (772.3); 2.4981 (558.2); 2.3517 (0.4); 2.3338 (3.6); 2.3294 (5.0); 2.3250 (3.6); 2.1262 (0.8); 2.1134 (1.8); 2.1046 (2.0); 2.0930 (3.7); 2.0808 (2.3); 2.0723 (2.0); 2.0598 (1.0); 1.6147 (16.0); 1.5973 (15.9); 1.0473 (0.4); 1.0282 (5.4); 1.0224 (7.2); 1.0075 (5.2); 1.0016 (7.2); 0.9837 (0.8); 0.9768 (0.6); 0.9639 (0.3); 0.9513 (0.3); 0.9360 (1.0); 0.9236 (1.2); 0.9116 (3.8); 0.8995 (3.9); 8.8936 (3.5); 0.8872 (3.6); 0.8752 (3.3); 0.8588 (1.1); 0.8491 (0.7); 0.1462 (1.1); 0.0079 (7.6); −0.0002 (240.4); −0.0082 (8.1); −0.1494 (1.1) | 490.1 |
| I-138 | 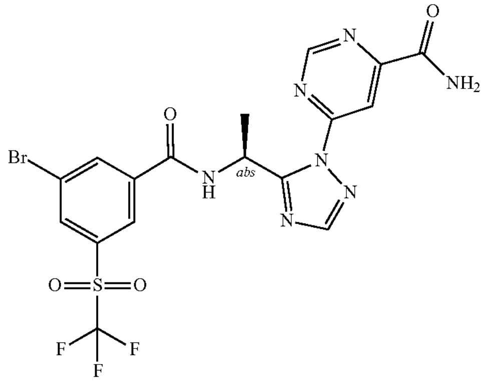 [SMILES: C[C@H](NC(=O)c1cc(Br)cc(S(=O)(=O)C(F)(F)F)c1)c1ncnn1-c1cc(C(N)=O)ncn1] | $^1$H-NMR (400.2 MHz, d6-DMSO) δ = 9.7188 (3.9); 9.7016 (4.0); 9.3158 (9.7); 9.3134 (10.1); 8.6852 (4.7); 8.6813 (8.5); 8.6775 (5.2); 8.5209 (7.5); 8.4925 (7.2); 8.4716 (4.2); 8.3848 (9.7); 8.3826 (9.8); 8.3692 (0.5); 8.3399 (16.0); 8.3291 (0.4); 8.3250 (0.6); 8.3204 (0.6); 8.1572 (0.6); 8.1342 (4.0); 7.9541 (0.4); 6.3197 (0.6); 6.3027 (2.6); 6.2855 (4.0); 6.2681 (2.6); 6.2508 (0.5); 4.3934 (0.5); 3.3626 (0.5); 3.3350 (96.1); 3.3098 (0.5); 3.2957 (0.4); 3.0028 (1.50); 2.8926 (3.4); 2.8867 (1.7); 2.7329 (2.7); 2.6905 (0.4); 2.6778 (0.8); 2.6735 (1.1); 2.6691 (0.8); 2.6434 (0.5); 2.5268 (3.0); 2.5220 (4.4); 2.5132 (60.9); 2.5089 (127.0); 2.5045 (169.6); 2.5001 (122.0); 2.4959 (58.5); 2.3358 (0.8); 2.3312 (1.1); 2.3269 (0.8); 2.0774 (0.9); 1.6792 (14.7); 1.6618 (14.7); 0.0079 (1.7); −0.0002 (55.2); −0.0084 (1.8) | 550.0 |

TABLE 1-continued
| Example | Structure[1)] | NMR Peak List[2)] | ESI Mass (m/z)[3)] |
|---|---|---|---|
| I-139 | 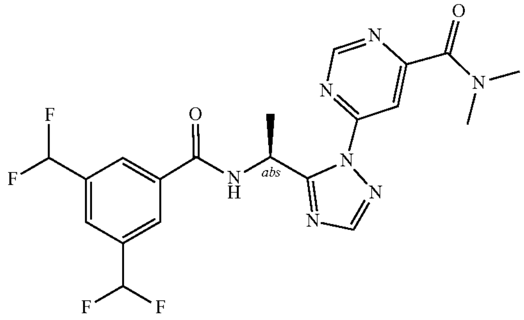 [SMILES: C[C@H](NC(=O)c1cc(C(F)F)cc(C(F)F)c1)c1ncnn1-c1cc(C(=O)N(C)C)ncn1] | $^1$H-NMR (400.2 MHz, d6-DMSO) δ = 9.5119 (1.4); 9.4945 (1.5); 9.2519 (3.3); 9.2496 (3.6); 8.2936 (5.7); 8.2353 (4.6); 8.0332 (3.5); 8.0311 (3.7); 7.9420 (2.1); 7.3222 (2.0); 7.1836 (4.6); 7.0450 (2.2); 6.2664 (0.9); 6.2491 (1.5); 6.2318 (0.9); 5.7585 (1.9); 3.3334 (43.8); 3.0417 (14.1); 2.9473 (16.0); 2.6719 (0.4); 2.5253 (1.2); 2.5202 (1.7); 2.5115 (22.8); 2.5074 (47.2); 2.5030 (63.3); 2.4986 (45.9); 2.4944 (22.3); 2.3297 (0.4); 1.6748 (5.4); 1.6574 (5.4); 1.2343 (1.4); 0.0077 (0.8); −0.0002 (26.7); −0.0085 (0.9) | 466.1 |
| I-140 | 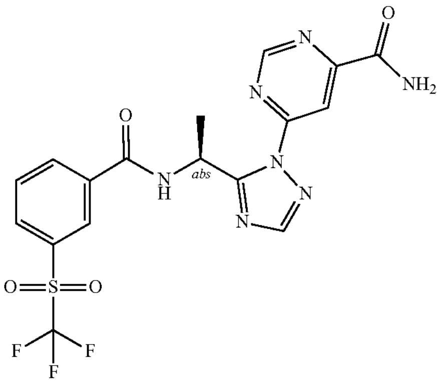 [SMILES: C[C@H](NC(=O)c1cccc(S(=O)(=O)C(F)(F)F)c1)c1ncnn1-c1cc(C(N)=O)ncn1] | $^1$H-NMR (400.2 MHz, d6-DMSO) δ = 9.6727 (3.5); 9.6554 (3.6); 9.3174 (8.9); 9.3153 (9.1); 8.5680 (6.2); 8.4921 (3.8); 8.4724 (7.6); 8.3912 (9.0); 8.3891 (9.1); 8.3355 (16.0); 8.3103 (3.2); 8.1392 (3.9); 7.8945 (3.7); 7.9647 (6.7); 7.9450 (3.2); 6.3255 (0.5); 6.3084 (2.4); 6.2911 (3.8); 6.2737 (2.4); 6.2563 (0.5); 3.3422 (30.3); 2.6772 (0.4); 2.5307 (1.1); 2.5258 (1.5); 2.1571 (19.4); 2.5128 (40.1); 2.5084 (53.2); 2.5040 (38.3); 2.5000 (18.4); 2.3352 (0.3); 2.0810 (6.1); 1.6873 (13.7); 1.6699 (13.7); −0.0002 (8.1) | 470.1 |

TABLE 1-continued
| Example | Structure[1)] | NMR Peak List[2)] | ESI Mass (m/z)[3)] |
| --- | --- | --- | --- |
| I-141 | 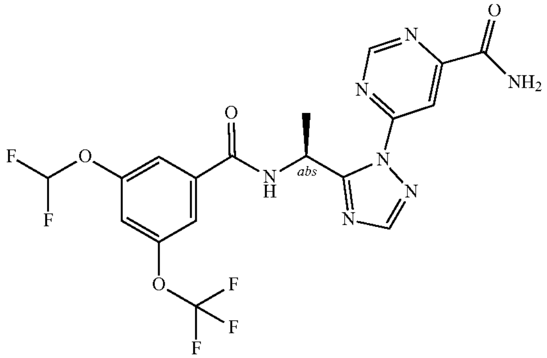 [SMILES: C[C@H](NC(=O)c1cc(OC(F)F)cc(OC(F)(F)F)c1)c1ncnn1-c1cc(C(N)=O)ncn1] | $^1$H-NMR (400.2 MHz, d6-DMSO) δ = 9.4024 (3.4); 9.3851 (3.5); 9.3116 (10.7); 9.3088 (10.7); 8.4705 (3.7); 8.3809 (10.7); 8.3780 (10.6); 8.3226 (16.0); 8.1334 (3.6); 7.7157 (11.2); 7.7106 (10.1); 7.5590 (4.1); 7.4707 (4.9); 7.3928 (0.4); 7.3761 (8.6); 7.1932 (4.3); 6.2815 (0.5); 6.2644 (2.5); 6.2471 (4.0); 6.2997 (2.5); 6.2125 (0.5); 3.3334 (85.5); 2.9872 (0.8); 2.8845 (0.8); 2.6818 (0.3); 2.6773 (0.7); 2.6728 (0.9); 2.6682 (0.6); 2.5262 (2.6); 2.5215 (4.1); 2.128 (52.3); 2.5084 (108.7); 2.5039 (144.2); 2.4993 (101.0); 2.4948 (45.7); 2.3352 (0.7); 2.3307 (0.9); 2.3261 (0.6); 1.6657 (14.7); 1.6483 (14.6); 0.1459 (0.7); 0.0080 (5.9); −0.0002 (170.5); −0.0086 (4.9); −0.1496 (0.7) | 488.0 |
| I-142 | 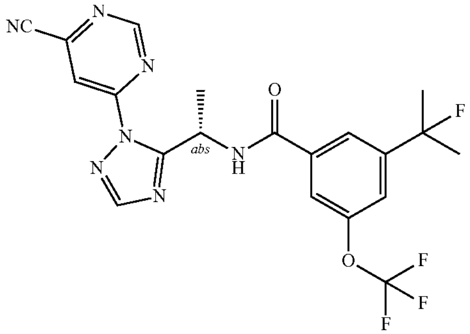 [SMILES: C[C@H](NC(=O)c1cc(OC(F)(F)F)cc(C(C)(C)F)c1)c1ncnn1-c1cc(C#N)ncn1] | $^1$H-NMR (400.2 MHz, d6-DMSO) δ = 9.3876 (5.4); 9.3723 (1.6); 8.6139 (4.1); 8.3611 (5.4); 7.9263 (3.0); 7.7370 (2.3); 7.5558 (2.3); 6.2085 (1.0); 6.1914 (1.6); 6.1741 (1.0); 3.3308 (64.7); 2.6715 (0.8); 2.5026 (121.6); 2.3293 (0.8); 2.0760 (0.9); 1.7099 (13.1); 1.6545 (16.0); 1.6401 (6.2); 0.1458 (0.4); 0.0074 (2.5); −0.0002 (76.5); −0.1497 (0.4) | 464.1 |

TABLE 1-continued
| Example | Structure[1)] | NMR Peak List[2)] | ESI Mass (m/z)[3)] |
|---|---|---|---|
| I-143 | 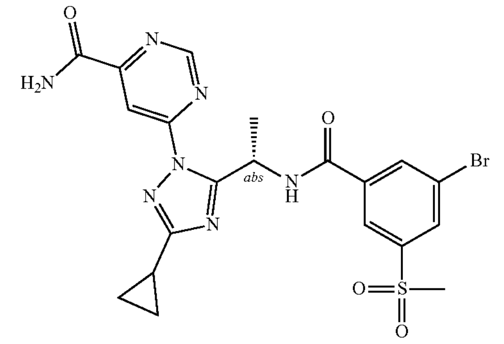 [SMILES: C[C@H](NC(=O)c1cc(Br)cc(S(C)(=O)=O)c1)c1nc(C2CC2)nn1-c1cc(C(N)=O)ncn1] | $^1$H-NMR (400.2 MHz, d6-DMSO) δ = 9.4936 (4.2); 9.4759 (4.4); 9.2561 (11.0); 9.2535 (11.8); 8.4496 (4.6); 8.3631 (4.0); 8.3594 (9.6); 8.3547 (9.1); 8.3533 (9.3); 8.3488 (10.8); 8.3177 (11.5); 8.3151 (11.7); 8.2673 (5.7); 8.2632 (9.8); 8.2591 (5.1); 8.1103 (4.5); 6.2610 (0.6); 6.2439 (3.0); 6.2266 (4.8); 6.2091 (3.0); 6.1916 (0.6); 3.3308 (195.2); 2.6764 (1.4); 2.6718 (2.0); 2.6674 (1.5); 2.5622 (0.4); 2.5252 (4.9); 2.5205 (7.4); 2.5117 (108.6); 2.5074 (230.0); 2.5029 (310.4); 2.4984 (223.6); 2.4941 (106.1); 2.3342 (1.4); 2.3297 (2.0); 2.3252 (1.4); 2.1327 (0.8); 2.1202 (1.8); 2.1115 (1.9); 2.0996 (3.8); 2.0875 (2.2); 2.0789 (2.0); 2.0667 (1.0); 1.8918 (0.5); 1.6320 (16.0); 1.6146 (15.9); 1.0608 (0.3); 1.0483 (0.8); 1.0322 (5.2); 1.0281 (7.2); 1.0127 (5.3); 1.0072 (6.6); 0.9945 (1.2); 0.9824 (0.6); 0.9709 (0.3); 0.9445 (0.8); 0.9320 (1.0); 0.9201 (3.5); 0.9122 (4.7); 0.9077 (5.5); 0.9014 (4.6); 0.8951 (2.3); 0.8899 (2.3); 0.8792 (0.8); 0.8681 (0.6); 0.1460 (1.6); 0.0079 (10.6); −0.0002 (338.3); −0.0084 (11.4); −0.0192 (0.7); −0.0228 (0.6); −0.0278 (0.4); −0.1496 (1.6) | 536.0 |
| I-144 | 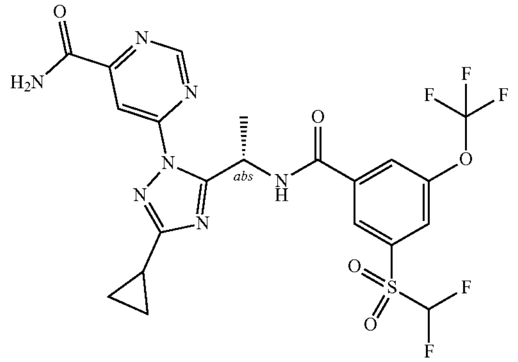 [SMILES: C[C@H](NC(=O)c1cc(OC(F)(F)F)cc(S(=O)(=O)C(F)F)c1)c1nc(C2CC2)nn1-c1cc(C(N)=O)ncn1] | $^1$H-NMR (400.2 MHz, d6-DMSO) δ = 9.7110 (4.4); 9.6935 (4.6); 9.2475 (10.3); 9.2450 (12.0); 8.4829 (9.4); 8.4416 (5.0); 8.3503 (6.6); 8.3184 (15.7); 8.1222 (7.2); 7.5741 (3.2); 7.4443 (7.2); 7.3145 (3.8); 6.2782 (0.7); 6.2611 (2.9); 6.2437 (4.7); 6.2263 (3.0); 6.2090 (0.6); 3.3298 (288.0); 3.3059 (2.3); 2.6758 (2.8); 2.6715 (4.0); 2.6672 (3.1); 2.5883 (0.4); 2.5512 (0.7); 2.5245 (8.8); 2.5068 (439.7); 2.5025 (599.9); 2.4983 (456.8); 2.3292 (3.7); 2.3250 (3.0); 2.1342 (0.7); 2.1216 (1.8); 2.1135 (2.0); 2.1012 (3.6); 2.0894 (2.2); 2.0805 (1.9); 2.0683 (0.9); 1.6471 (16.0); 1.6297 (16.0); 1.0614 (0.4); 1.0511 (0.6); 1.0288 (7.0); 1.0123 (5.8); 1.0077 (6.7); 0.9920 (1.0); 0.9810 (0.6); 0.9436 (1.0); 0.9308 (1.1); 0.9196 (3.4); 0.9072 (5.3); 0.9024 (4.4); 0.8854 (2.8); 0.8720 (0.9); 0.8613 (0.7); 0.1457 (2.4); 0.0079 (15.9); −0.0002 (505.3); −0.0083 (18.2); −0.0347 (0.4) −0.1498 (2.4) | 576.0 |

TABLE 1-continued
| Example | Structure[1)] | NMR Peak List[2)] | ESI Mass (m/z)[3)] |
|---|---|---|---|
| I-145 | 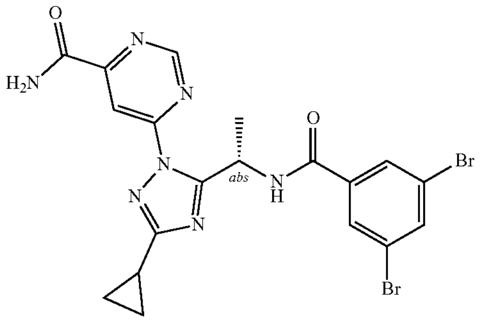 [SMILES: C[C@H](NC(=O)c1cc(Br)cc(Br)c1)c1nc(C2CC2)nn1-c1cc(C(N)=O)ncn1] | $^{1}$H-NMR (400.2 MHz, d6-DMSO) δ = 9.3025 (2.4); 9.2852 (2.4); 9.2446 (6.8); 9.2418 (7.0); 8.4484 (2.6); 8.3182 (1.6); 8.3117 (7.1); 8.3088 (7.2); 8.1098 (2.5); 8.0416 (2.0); 8.0374 (4.7); 8.0333 (5.4); 8.0247 (16.0); 8.0206 (8.7); 6.2097 (0.4); 6.1927 (1.7); 6.1753 (2.8); 6.1578 (1.8); 6.1403 (0.4); 3.3300 (127.6); 3.3070 (0.6); 2.6762 (1.2); 2.6716 (1.7); 2.6671 (1.2); 2.6628 (0.6); 2.5593 (0.4); 2.5539 (0.4); 2.5495 (0.4); 2.5250 (6.0); 2.5200 (9.8); 2.5116 (98.3); 2.5072 (199.8); 2.5027 (263.8); 2.4982 (188.0); 2.4937 (87.9); 2.4703 (0.7); 2.3381 (0.6); 2.3341 (1.2); 2.3295 (1.7); 2.3250 (1.2); 2.3206 (0.6); 2.1283 (0.5); 2.1161 (1.1); 2.1074 (1.2); 2.0954 (2.2); 2.0832 (1.3); 2.0748 (1.3); 2.0623 (0.6); 1.6050 (9.6); 1.5876 (9.5); 1.0483 (0.4); 1.0311 (3.3); 1.0257 (4.0); 1.0103 (3.5); 1.0048 (3.9); 0.9895 (0.5); 0.9801 (0.3); 0.9379 (0.6); 0.9259 (0.6); 0.9146 (2.5); 0.9086 (1.5); 0.9022 (2.9); 0.8959 (2.1); 0.8921 (2.2); 0.8800 (1.9); 0.8655 (0.5); 0.8562 (0.4); 0.1458 (1.4); 0.0239 (0.5); 0.0079 (14.0); −0.0002 (338.2); −0.0085 (11.3); −0.0331 (0.4); −0.1496 (1.4) | 536.0 |
| I-146 | 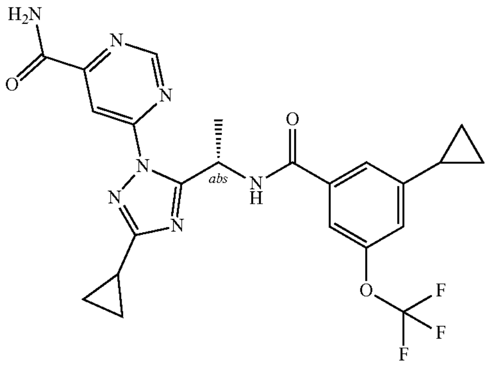 [SMILES: C[C@H](NC(=O)c1cc(OC(F)(F)F)cc(C2CC2)c1)c1nc(C2CC2)nn1-c1cc(C(N)=O)ncn1] | $^{1}$H-NMR (400.2 MHz, d6-DMSO) δ = 9.2396 (11.4); 9.1972 (4.2); 9.1796 (4.3); 8.4484 (4.8); 8.3111 (11.5); 8.1119 (4.8); 7.5020 (14.9); 7.4988 (14.7); 7.2804 (6.4); 6.2090 (0.6); 6.1916 (2.9); 6.1742 (4.6); 6.1568 (2.9); 6.1392 (0.6); 3.3317 (70.6); 2.8915 (2.2); 2.7319 (2.0); 2.6763 (0.9); 2.6723 (1.2); 2.6682 (0.8); 2.5074 (141.0); 2.5033 (175.6); 2.4991 (124.0); 2.3341 (0.9); 2.3303 (1.1); 2.1268 (0.8); 2.1146 (1.8); 2.1059 (2.0); 2.0939 (3.6); 2.0819 (2.2); 2.0729 (2.5); 2.0597 (2.4); 2.0505 (2.0); 2.0382 (3.6); 2.0258 (2.1); 2.0174 (1.9); 2.0046 (1.0); 1.6186 (16.0); 1.6013 (15.8); 1.2313 (0.4); 1.2044 (0.4); 1.1873 (0.4); 1.0475 (2.4); 1.0364 (7.1); 1.0305 (10.8); 1.0221 (9.6); 1.0156 (7.4); 1.0098 (10.1); 1.0015 (8.8); 0.9823 (1.0); 0.9766 (0.7); 0.9635 (0.5); 0.9513 (0.4); 0.9368 (1.1); 0.9246 (1.3); 0.9123 (3.6); 0.9003 (3.7); 0.8941 (2.7); 0.8861 (3.4); 0.8794 (2.4); 0.8743 (3.1); 0.8573 (1.2); 0.8483 (0.8); 0.7947 (2.5); 0.7840 (6.9); 0.7794 (6.6); 0.7722 (6.4); 0.7673 (6.7); 0.7558 (1.9); 0.1456 (0.6); 0.0068 (6.3); −0.0002 (112.3); −0.0007 (110.6); −0.0084 (4.1); −0.1500 (0.6) | 502.1 |

TABLE 1-continued
| Example | Structure[1)] | NMR Peak List[2)] | ESI Mass (m/z)[3)] |
|---|---|---|---|
| I-147 | 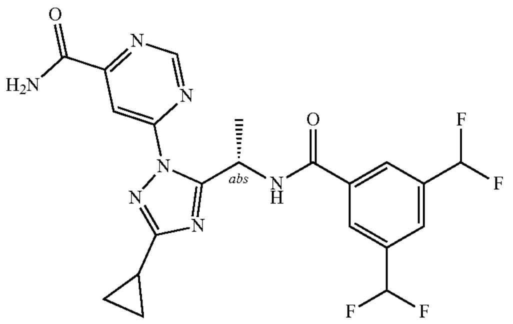 [SMILES: C[C@H](NC(=O)c1cc(C(F)F)cc(C(F)F)c1)c1nc(C2CC2)nn1-c1cc(C(N)=O)ncn1] | $^1$H-NMR (400.2 MHz, d6-DMSO) δ = 9.4665 (4.4); 9.4490 (4.6); 9.2485 (10.7); 8.7078 (0.6); 8.6974 (0.7); 8.4638 (4.7); 8.4437 (6.5); 8.3178 (11.8); 8.2770 (3.3); 8.2582 (3.6); 8.2199 (16.0); 8.1094 (5.6); 7.9380 (7.5); 7.5072 (0.6); 7.4961 (0.6); 7.4860 (0.7); 7.4752 (0.6); 7.4129 (0.4); 7.3950 (0.4); 7.3683 (0.4); 7.3192 (6.0); 7.2968 (3.0); 7.2875 (3.3); 7.2769 (3.3); 7.2664 (3.1); 7.1195 (0.7); 7.1806 (12.4); 7.1276 (0.5); 7.0848 (0.4); 7.0705 (0.4); 7.0419 (6.1); 6.2559 (0.6); 6.2402 (2.6); 6.2231 (4.2); 6.2054 (2.8); 6.1872 (0.7); 3.5763 (0.4); 3.5193 (0.8); 3.3311 (59.6); 3.1977 (0.5); 3.1679 (0.4); 3.1323 (0.4); 3.0937 (0.4); 3.0670 (0.4); 3.0523 (0.6); 3.0302 (0.7); 3.0251 (0.7); 2.9595 (0.5); 2.9364 (0.6); 2.9214 (0.4); 2.8907 (10.1); 2.8383 (1.4); 2.7506 (1.1); 2.7310 (6.9); 2.6717 (4.3); 2.5028 (677.1); 2.4053 (0.8); 2.3296 (4.4); 2.1265 (0.8); 2.1147 (1.7); 2.1063 (2.2); 2.0942 (3.4); 2.0822 (2.4); 2.0740 (2.1); 2.0608 (1.0); 1.6344 (14.5); 1.6171 (15.0); 1.3498 (0.3); 1.2972 (0.7); 1.2585 (1.2); 1.2099 (15.8); 1.1941 (13.0); 1.1510 (0.8); 1.1354 (0.4); 1.0206 (7.4); 0.9996 (7.6); 0.9812 (1.0); 0.9239 (1.4); 0.9127 (3.8); 0.9006 (4.5); 0.8948 (4.4); 0.8883 (4.1); 0.8761 (3.6); 0.8598 (1.5); 0.1459 (1.8); 0.0243 (0.4); 0.0076 (17.8); −0.0002 (409.2); −0.0067 (130.3); −0.0617 (0.5); −0.0731 (0.4); −0.0812 (0.4); −0.1498 (2.1) | 478.1 |
| I-148 | 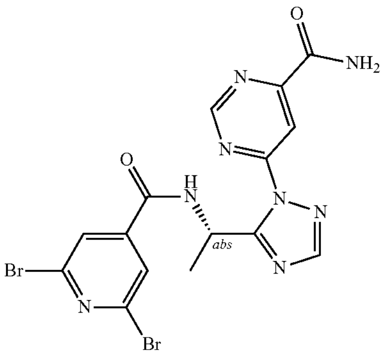 [SMILES: C[C@H](NC(=O)c1cc(Br)nc(Br)c1)c1ncnn1-c1cc(C(N)=O)ncn1] | $^1$H-NMR (400.2 MHz, d6-DMSO) δ = 9.5711 (1.7); 9.5538 (1.8); 9.3102 (4.4); 9.3074 (4.8); 8.5893 (0.4); 8.5865 (0.4); 8.4746 (2.0); 8.3772 (4.4); 8.3745 (4.6); 8.3365 (6.8); 8.1326 (1.8); 8.0355 (16.0); 6.2443 (1.1); 6.2269 (1.8); 6.2096 (1.2); 3.3330 (28.0); 2.5269 (0.6); 2.5222 (0.9); 2.5089 (36.4); 2.5045 (48.9); 2.5001 (36.2); 2.0075 (1.6); 1.9685 (1.6); 1.6477 (6.5); 1.6304 (6.5); 0.0079 (1.4); −0.0002 (46.2); −0.0084 (1.6) | 497.0 |

TABLE 1-continued
| Example | Structure[1)] | NMR Peak List[2)] | ESI Mass (m/z)[3)] |
|---|---|---|---|
| I-149 | 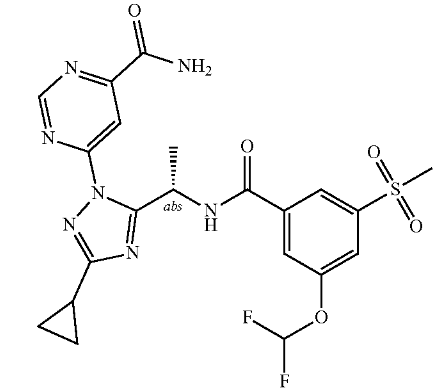 [SMILES: C[C@H](NC(=O)c1cc(OC(F)F)cc(S(C)(=O)=O)c1)c1nc(C2CC2)nn1-c1cc(C(N)=O)ncn1] | $^1$H-NMR (400.2 MHz, d6-DMSO) δ = 9.4967 (4.9); 9.4791 (5.1); 9.2574 (10.9); 9.2556 (11.7); 8.4474 (5.3); 8.3188 (11.4); 8.3173 (11.8); 8.2749 (10.1); 8.1111 (5.2); 7.9411 (7.1); 7.8665 (7.4); 7.6148 (4.3); 7.4322 (9.0); 7.2496 (4.5); 6.2715 (0.7); 6.2548 (3.0); 6.2374 (4.7); 6.2200 (3.0); 6.2023 (0.7); 3.3385 (26.3); 3.3172 (48.0); 2.6758 (1.5); 2.6717 (2.1); 2.6677 (1.6); 2.5248 (5.9); 2.5070 (245.5); 2.5028 (327.4); 2.4987 (246.6); 2.4490 (0.4); 2.3338 (1.5); 2.3296 (2.1); 2.1310 (0.8); 2.1187 (1.8); 2.1101 (2.0); 2.0982 (3.7); 2.0863 (2.3); 2.0775 (2.0); 2.0651 (1.0); 1.6411 (16.0); 1.6237 (16.0); 1.2328 (0.6); 1.0597 (0.4); 1.0474 (0.8); 1.0314 (5.8); 1.0270 (7.2); 1.0109 (5.9); 1.0060 (6.7); 0.9928 (1.3); 0.9808 (0.6); 0.9719 (0.4); 0.9582 (0.3); 0.9432 (1.0); 0.9299 (1.1); 0.9188 (3.7); 0.9063 (5.6); 0.9003 (5.0); 0.8877 (2.8); 0.8767 (0.9); 0.8659 (0.7); 0.1460 (1.0); 0.0234 (0.5); 0.0076 (6.8); −0.0002 (186.0); −0.0076 (8.0); −0.1496 (0.9) | 522.2 |
| I-150 | 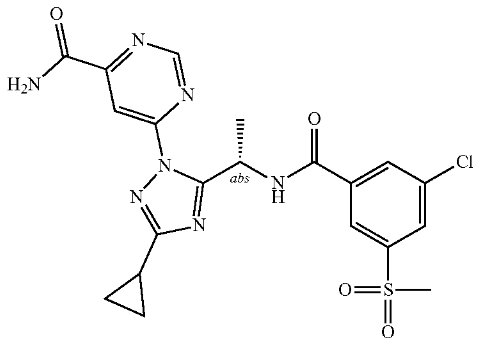 [SMILES: C[C@H](NC(=O)c1cc(Cl)cc(S(C)(=O)=O)c1)c1nc(C2CC2)nn1-c1cc(C(N)=O)ncn1] | $^1$H-NMR (400.2 MHz, d6-DMSO) δ = 9.4968 (3.6); 9.4792 (3.7); 9.2561 (9.1); 9.2534 (10.0); 8.4493 (3.9); 8.3228 (4.7); 8.3182 (16.0); 8.3153 (14.8); 8.2297 (4.4); 8.2243 (7.6); 8.2204 (5.0); 8.1577 (4.8); 8.1533 (7.8); 8.1490 (4.3); 8.1101 (3.8); 6.2626 (0.5); 6.2455 (2.4); 6.2280 (3.9); 6.2106 (2.5); 6.1931 (0.5); 3.9696 (0.4); 3.3320 (155.3); 3.3090 (0.8); 2.6762 (0.9); 2.6718 (1.3); 2.6674 (1.0); 2.5252 (3.2); 2.5204 (4.8); 2.5115 (71.7); 2.5073 (151.0); 2.5029 (203.8); 2.4984 (147.0); 2.4941 (70.0); 2.3340 (0.9); 2.3297 (1.3); 2.3253 (0.9); 2.1323 (0.7); 2.1202 (1.5); 2.1115 (1.6); 2.0995 (3.1); 2.0875 (1.9); 2.0787 (1.7); 2.0665 (0.8); 1.6340 (13.2); 1.6167 (13.2); 1.3319 (0.5); 1.0481 (0.6); 1.0330 (4.3); 1.0278 (6.0); 1.0126 (4.4); 1.0071 (5.6); 0.9944 (1.0); 0.9823 (0.5); 0.9440 (0.7); 0.9315 (0.8); 0.9198 (3.0); 0.9122 (4.0); 0.9075 (4.7); 0.9012 (4.0); 0.8892 (1.9); 0.8989 (0.6); 0.8683 (0.5); 0.1456 (0.5); 0.0079 (3.3); −0.0002 (110.8); −0.0085 (3.6); −0.1498 (0.5) | 490.0 |

TABLE 1-continued
| Example | Structure[1)] | NMR Peak List[2)] | ESI Mass (m/z)[3)] |
|---|---|---|---|
| I-151 | 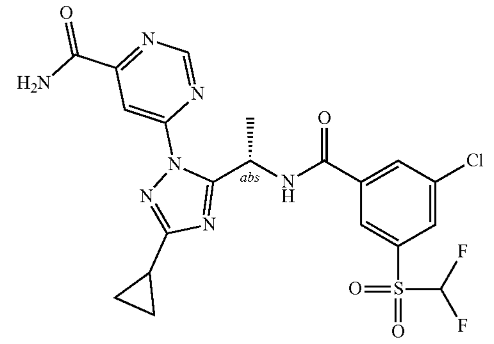 [SMILES: C[C@H](NC(=O)c1cc(Cl)cc(S(=O)(=O)C(F)F)c1)c1nc(C2CC2)nn1-c1cc(C(N)=O)ncn1] | $^1$H-NMR (400.2 MHz, d6-DMSO) δ = 9.6218 (4.4); 9.6043 (4.6); 9.2479 (10.6); 9.2454 (12.3); 8.4462 (13.7); 8.4425 (10.5); 8.3597 (9.4); 8.3184 (11.6); 8.3168 (12.5); 8.1881 (5.0); 8.1838 (8.8); 8.1797 (5.2); 8.1101 (4.8); 7.5466 (3.3); 7.4167 (7.6); 7.2868 (3.9); 6.2656 (0.6); 6.2482 (3.0); 6.2309 (4.7); 6.2135 (3.0); 6.1960 (0.6); 3.3633 (0.4); 3.3318 (254.9); 3.3080 (0.9); 2.6761 (1.7); 2.6718 (2.4); 2.6675 (1.8); 2.5578 (0.4); 2.5524 (0.4); 2.5251 (5.2); 2.5072 (264.4); 2.5028 (357.2); 2.4985 (262.6); 2.3339 (1.5); 2.3297 (2.2); 2.3252 (1.6); 2.1333 (0.8); 2.1212 (1.8); 2.1127 (1.9); 2.1006 (3.7); 2.0885 (2.2); 2.0799 (2.0); 2.0765 (1.5); 2.0678 (1.0); 1.9895 (0.4); 1.6368 (16.0); 1.6195 (16.0); 1.2980 (0.6); 1.2585 (0.8); 1.2327 (1.4); 1.0610 (0.4); 1.0497 (0.7); 1.0321 (5.6); 1.0282 (6.8); 1.0118 (5.9); 1.0073 (6.5); 0.9929 (1.1); 0.9813 (0.6); 0.9720 (0.3); 0.9434 (0.9); 0.9308 (1.0); 0.9192 (3.4); 0.9072 (5.3); 0.9009 (4.3); 0.8861 (2.8); 0.8729 (0.9); 0.8637 (0.7); 0.1456 (0.8); 0.0080 (4.9); −0.0002 (165.4); −0.0084 (5.7); −0.1498 (0.8) | 526.2 |
| I-152 | 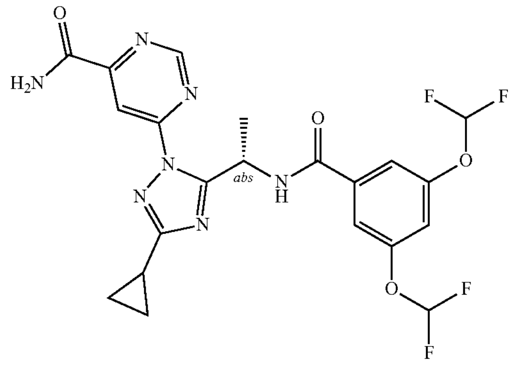 [SMILES: C[C@H](NC(=O)c1cc(OC(F)F)cc(OC(F)F)c1)c1nc(C2CC2)nn1-c1cc(C(N)=O)ncn1] | $^1$H-NMR (400.2 MHz, d6-DMSO) δ = 9.2683 (3.6); 9.2504 (9.0); 9.2475 (12.2); 8.4525 (4.7); 8.3155 (9.5); 8.1140 (4.6); 7.9537 (1.1); 7.5216 (16.0); 7.5183 (15.8); 7.3352 (9.2); 7.3322 (10.8); 7.2272 (6.0); 7.1518 (4.6); 7.1488 (5.4); 6.2276 (0.5); 6.2100 (2.1); 6.1927 (3.2); 6.1753 (2.1); 6.1590 (0.5); 3.5530 (0.4); 3.5475 (0.4); 3.5400 (0.4); 3.5312 (0.4); 3.4951 (0.9); 3.4891 (0.9); 3.4647 (0.8); 3.4471 (1.2); 3.4367 (1.5); 3.4283 (1.9); 3.3790 (1197.9); 3.3001 (0.9); 3.2379 (0.4); 2.8963 (5.1); 2.8928 (6.0); 2.7360 (4.5); 2.7332 (5.2); 2.6946 (7.9); 2.6907 (8.6); 2.6792 (1.3); 2.6751 (1.2); 2.5100 (180.8); 2.5059 (184.9); 2.4642 (0.4); 2.3367 (1.1); 2.3326 (1.2); 2.1267 (0.6); 2.1150 (1.3); 2.1066 (1.8); 2.0943 (2.6); 2.0856 (1.8); 2.0772 (1.4); 2.0646 (0.7); 2.0615 (0.6); 1.6235 (11.6); 1.6062 (11.4); 1.1912 (0.4); 1.1759 (0.4); 1.0491 (0.4); 1.0303 (6.0); 1.0095 (6.0); 0.9931 (0.7); 0.9393 (0.8); 9.9130 (3.2); 0.9007 (4.2); 0.8947 (3.8); 0.8816 (2.7); 0.8664 (1.0); 0.8546 (0.6); 0.0117 (1.7); 0.0036 (46.5); −0.0002 (49.6) | 510.1 |

TABLE 1-continued
| Example | Structure[1)] | NMR Peak List[2)] | ESI Mass (m/z)[3)] |
|---|---|---|---|
| I-153 | 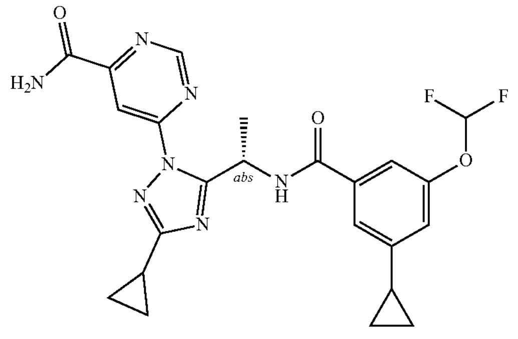 [SMILES: C[C@H](NC(=O)c1cc(OC(F)F)cc(C2CC2)c1)c1nc(C2CC2)nn1-c1cc(C(N)=O)ncn1] | $^1$H-NMR (400.2 MHz, d6-DMSO) δ = 9.2420 (10.2); 9.2395 (12.9); 9.1059 (4.7); 9.0881 (4.7); 8.4484 (5.8); 8.3181 (1.2); 8.3064 (13.0); 8.1098 (5.6); 7.4344 (3.9); 7.3557 (9.8); 7.3532 (9.8); 7.3429 (8.0); 7.2495 (8.0); 7.0621 (9.8); 6.2036 (0.6); 6.1866 (2.9); 6.1692 (4.4); 6.1514 (2.8); 6.1340 (0.6); 3.4053 (0.4); 3.3967 (0.3); 3.3308 (532.9); 3.2984 (0.5); 3.2746 (0.4); 2.7267 (0.3); 2.6713 (5.6); 2.5736 (0.8); 2.5023 (844.0); 2.4462 (0.9); 2.3915 (0.4); 2.3292 (5.2); 2.1230 (0.9); 2.1114 (1.8); 2.1019 (2.2); 2.0906 (3.5); 2.0786 (2.3); 2.0699 (1.9); 2.0571 (1.0); 2.0159 (0.8); 2.0038 (1.8); 1.9947 (2.1); 1.9827 (3.4); 1.9705 (2.3); 1.9627 (1.9); 1.9493 (0.9); 1.9072 (1.0); 1.6130 (16.0); 1.5958 (15.8); 1.3302 (0.8); 1.2975 (0.9); 1.2586 (1.2); 1.2335 (2.2); 1.1958 (0.3); 1.1897 (0.3); 1.0209 (9.2); 1.0037 (12.7); 1.0007 (12.6); 0.9884 (6.8); 0.9830 (7.1); 0.9727 (2.7); 0.9498 (0.5); 0.9345 (1.4); 0.9217 (1.5); 0.9098 (4.0); 0.8982 (4.4); 0.8932 (4.2); 0.8859 (4.0); 0.8742 (3.6); 0.8576 (1.5); 0.8257 (0.3); 0.8046 (0.4); 0.7682 (2.5); 0.7559 (8.0); 0.7533 (8.0); 0.7451 (7.1); 0.7408 (7.7); 0.7292 (1.9); 0.1456 (1.5); −0.0002 (320.3); −0.1500 (1.5) | 484.3 |
| I-154 | 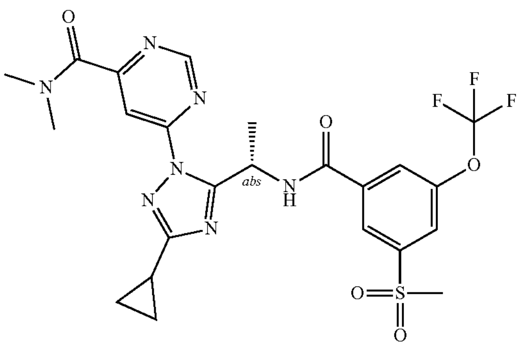 [SMILES: C[C@H](NC(=O)c1cc(OC(F)(F)F)cc(S(C)(=O)=O)c1)c1nc(C2CC2)nn1-c1cc(C(=O)N(C)C)ncn1] | $^1$H-NMR (400.2 MHz, d6-DMSO) δ = 9.5814 (1.6); 9.5640 (1.6); 9.1935 (3.5); 9.190 (3.8); 8.4514 (3.3); 8.1363 (2.0); 8.0879 (2.1); 7.9496 (3.6); 7.9470 (4.0); 6.2391 (1.0); 6.2217 (1.6); 6.2042 (1.0); 3.3626 (15.6); 3.3316 (98.6); 3.0340 (14.1); 2.9437 (16.0); 2.6758 (0.5); 2.6714 (0.6); 2.6672 (0.5); 2.5246 (1.6); 2.5110 (36.3); 2.5069 (75.4); 2.5026 (101.5); 2.4982 (74.0); 2.3339 (0.4); 2.3926 (0.6); 2.3252 (0.5); 2.0823 (0.6); 2.0736 (0.6); 2.0616 (1.2); 2.0497 (0.7); 2.0410 (0.6); 1.6490 (5.3); 1.6316 (5.2); 1.0166 (1.8); 1.0119 (2.3); 0.9961 (1.9); 0.9910 (2.2); 0.9198 (0.4); 0.9093 (1.3); 0.9029 (0.8); 0.8967 (1.8); 0.8908 (1.3); 0.8876 (1.3); 0.8751 (1.0); 0.0078 (1.4); −0.0002 (44.6); −0.0084 (1.5) | 568.2 |

TABLE 1-continued
| Example | Structure[1)] | NMR Peak List[2)] | ESI Mass (m/z)[3)] |
|---|---|---|---|
| I-155 | 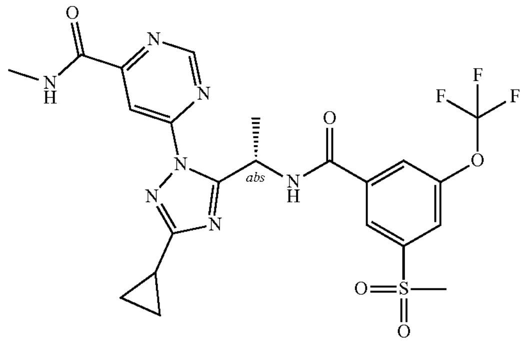 [SMILES: CNC(=O)c1cc(-n2nc(C3CC3)nc2[C@H](C)NC(=O)c2cc(OC(F)(F)F)cc(S(C)(=O)=O)c2)ncn1] | $^1$H-NMR (400.2 MHz, d6-DMSO) δ = 9.5753 (3.5); 9.5576 (3.6); 9.2592 (9.4); 9.2565 (10.0); 9.1324 (2.7); 9.1204 (2.7); 9.1086 (0.9); 8.4419 (8.4); 8.4387 (5.6); 8.3140 (9.6); 8.3113 (10.0); 8.1249 (5.5); 8.0892 (5.6); 6.2778 (0.5); 6.2607 (2.4); 6.2433 (3.8); 6.2258 (2.5); 6.2083 (0.5); 3.3639 (36.0); 3.3375 (38.0); 2.8940 (2.0); 2.8689 (16.0); 2.8569 (15.9); 2.7344 (1.6); 2.6801 (0.4); 2.6754 (0.4); 2.5288 (1.0); 2.5108 (47.6); 2.5065 (62.0); 2.5022 (45.8); 2.3334 (0.4); 2.1464 (0.6); 2.1343 (1.5); 2.1255 (1.7); 2.1136 (3.0); 2.1015 (1.8); 2.0930 (1.6); 2.0807 (0.8); 1.6482 (13.0); 1.6308 (13.0); 1.0517 (0.6); 1.0350 (5.0); 1.0311 (5.7); 1.0145 (5.0); 1.0101 (5.4); 0.9963 (0.9); 0.9846 (0.5); 0.9466 (0.8); 0.9340 (0.9); 0.9222 (2.9); 0.9098 (4.5); 0.9045 (4.0); 0.8909 (2.1); 0.8784 (0.7); 0.8691 (0.5); 0.0076 (1.0); −0.0002 (28.3); −0.0083 (1.0) | 554.2 |
| I-156 | 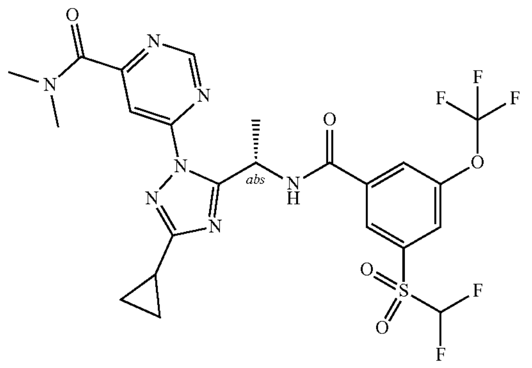 [SMILES: C[C@H](NC(=O)c1cc(OC(F)(F)F)cc(S(=O)(=O)C(F)F)c1)c1nc(C2CC2)nn1-c1cc(C(=O)N(C)C)ncn1] | $^1$H-NMR (600.1 MHz, d6-DMSO) δ = 9.7036 (1.3); 9.6919 (1.3); 9.1858 (3.3); 9.1838 (3.3); 8.4952 (1.6); 8.4928 (2.8); 8.4904 (1.6); 8.3598 (1.7); 8.1206 (1.6); 7.9518 (3.5); 7.9498 (3.5); 7.5300 (0.8); 7.4434 (1.8); 7.3569 (0.9); 6.2480 (0.2); 6.2365 (0.9); 6.2249 (1.5); 6.2133 (1.0); 6.2018 (0.2); 3.3232 (10.6); 3.3222 (13.0); 3.3199 (24.4); 3.0362 (13.9); 2.9456 (16.0); 2.8927 (0.2); 2.7332 (0.1); 2.6915 (0.2); 2.6188 (0.2); 2.6157 (0.2); 2.6127 (0.2); 2.5247 (0.5); 2.5216 (0.6); 2.5185 (0.6); 2.5097 (11.2); 2.5067 (24.4); 2.5037 (34.0); 2.5006 (24.6); 2.4976 (11.4); 2.3906 (0.2); 2.3875 (0.2); 2.3846 (0.2); 2.0854 (0.2); 2.0773 (0.6); 2.0716 (0.6); 2.0695 (0.4); 2.0635 (1.1); 2.0554 (0.6); 2.0497 (0.6); 2.0415 (0.3); 1.6513 (4.9); 1.6397 (4.9); 1.0349 (0.1); 1.0187 (0.6); 1.0166 (0.7); 1.0132 (1.4); 1.0116 (1.6); 1.0067 (0.8); 1.0051 (0.7); 1.0026 (0.6); 0.9993 (1.3); 0.9976 (1.6); 0.9931 (0.6); 0.9804 (0.1); 0.9769 (0.2); 0.9303 (0.2); 0.9270 (0.3); 0.9224 (0.4); 0.9189 (0.3); 0.9103 (0.7); 0.9073 (0.6); 0.9023 (0.8); 0.8992 (0.6); 0.8887 (0.6); 0.8857 (0.8); 0.8820 (0.6); 0.8777 (0.7); 0.8696 (0.4); 0.8666 (0.4); 0.8618 (0.2); 0.8583 (0.2); 0.0968 (0.1); 0.0053 (0.8); −0.0001 (27.1); −0.0057 (0.9); 0.1002 (0.1) | 604.2 |

TABLE 1-continued
| Example | Structure[1)] | NMR Peak List[2)] | ESI Mass (m/z)[3)] |
|---|---|---|---|
| I-157 | 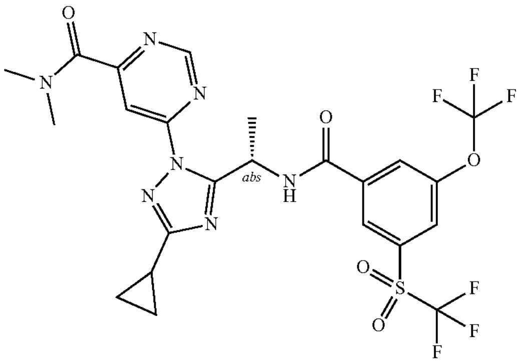 [SMILES: C[C@H](NC(=O)c1cc(OC(F)(F)F)cc(S(=O)(=O)C(F)(F)F)c1)c1nc(C2CC2)nn1-c1cc(C(=O)N(C)C)ncn1] | $^1$H-NMR (600.1 MHz, d6-DMSO) δ = 9.7579 (1.6); 9.7462 (1.6); 9.1851 (3.6); 9.1834 (3.4); 8.6237 (2.9); 8.4422 (2.2); 8.3642 (2.1); 8.3146 (0.3); 7.9511 (3.7); 7.9494 (3.6); 6.2553 (0.2); 6.2439 (1.0); 6.2324 (1.6); 6.2207 (1.0); 6.2093 (0.2); 3.3190 (46.3); 3.2951 (0.2); 3.0593 (0.1); 3.0355 (14.6); 2.9455 (16.0); 2.6179 (0.3); 2.6149 (0.4); 2.5239 (0.9); 2.5209 (1.2); 2.5178 (1.1); 2.5058 (49.7); 2.5029 (68.2); 2.5000 (51.5); 2.3896 (0.3); 2.3871 (0.4); 2.3838 (0.3); 2.0856 (0.3); 2.0774 (0.6); 2.0714 (0.7); 2.0636 (1.3); 2.0556 (0.8); 2.0497 (0.7); 2.0416 (0.4); 1.6558 (5.8); 1.6442 (5.8); 1.0362 (0.1); 1.0127 (2.0); 1.0068 (1.2); 0.9986 (2.0); 0.9853 (0.1); 0.9778 (0.2); 0.9266 (0.4); 0.9216 (0.5); 0.9188 (0.4); 0.9096 (1.0); 0.9017 (1.0); 0.8838 (1.0); 0.8794 (0.8); 0.8755 (1.0); 0.8672 (0.5); 0.8641 (0.5); 0.8597 (0.3); 0.8558 (0.2); 0.0970 (0.2); 0.0053 (1.6); −0.0001 (45.8); −0.1002 (0.2) | 622.2 |
| I-158 | 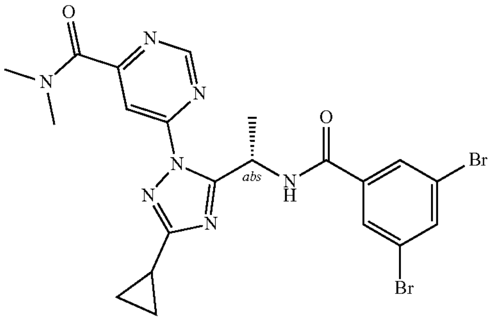 [SMILES: C[C@H](NC(=O)c1cc(Br)cc(Br)c1)c1nc(C2CC2)nn1-c1cc(C(=O)N(C)C)ncn1] | $^1$H-NMR (600.1 MHz, d6-DMSO) δ = 9.2933 (1.4); 9.2816 (1.5); 9.1767 (2.8); 9.1753 (3.5); 8.0281 (11.1); 7.9525 (2.4); 7.9371 (3.0); 7.9359 (3.5); 6.1743 (0.2); 6.1629 (1.0); 6.1513 (1.5); 6.1397 (1.0); 6.1282 (0.2); 3.5078 (0.1); 3.4858 (0.1); 3.4699 (0.2); 3.4646 (0.2); 3.4568 (0.2); 3.4510 (0.5); 3.4407 (0.2); 2.4350 (0.4); 3.3984 (522.7); 3.3974 (544.0); 3.3757 (0.9); 3.3688 (0.6); 3.3577 (0.3); 3.3530 (0.2); 3.0583 (0.1); 3.0369 (12.9); 3.0072 (0.1); 2.9448 (14.0); 2.8947 (16.0); 2.7351 (14.1); 2.6931 (0.2); 2.6181 (0.2); 2.5267 (0.6); 2.5236 (0.6); 2.5115 (22.8); 2.5088 (31.3); 2.5061 (23.9); 2.3926 (0.2); 2.0804 (0.2); 2.0722 (0.6); 2.0663 (0.6); 2.0585 (1.1); 2.0505 (0.7); 2.0446 (0.6); 2.0365 (0.3); 1.6095 (5.2); 1.5980 (5.2); 1.0342 (0.1); 1.0147 (1.5); 1.0112 (1.8); 1.0008 (1.4); 0.9972 (1.9); 0.9875 (0.2); 0.9217 (0.3); 0.9165 (0.4); 0.9054 (0.8); 0.8973 (0.9); 0.8883 (0.3); 0.8793 (0.9); 0.8709 (0.8); 8.609 (0.4); 0.8535 (0.3); 0.0053 (0.7); −0.0001 (19.1) | 564.0 |

TABLE 1-continued
| Example | Structure[1)] | NMR Peak List[2)] | ESI Mass (m/z)[3)] |
|---|---|---|---|
| I-159 | 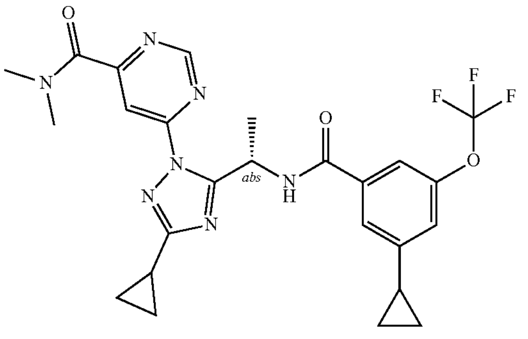 [SMILES: C[C@H](NC(=O)c1cc(OC(F)(F)F)cc(C2CC2)c1)c1nc(C2CC2)nn1-c1cc(C(=O)N(C)C)ncn1] | $^1$H-NMR (600.1 MHz, d6-DMSO) δ = 9.1895 (1.2); 9.1799 (3.9); 9.1779 (4.7); 7.9387 (3.6); 7.9367 (3.6); 7.5283 (1.2); 7.5261 (2.4); 7.5237 (1.6); 7.5122 (1.5); 7.5106 (1.3); 7.2760 (1.5); 6.1779 (0.2); 6.1662 (0.9); 6.1546 (1.4); 6.1429 (0.9); 6.1312 (0.2); 3.3245 (13.7); 3.3222 (36.0); 3.0505 (0.1); 3.0350 (14.1); 2.9371 (16.0); 2.6184 (0.1); 2.6153 (0.2); 2.6122 (0.1); 2.5244 (0.4); 2.5213 (0.5); 2.5181 (0.5); 2.5094 (9.5); 2.5064 (21.2); 2.5033 (29.7); 2.5002 (21.1); 2.4972 (9.4); 2.3902 (0.1); 2.3872 (0.2); 2.3841 (0.1); 2.0766 (0.2); 2.0685 (0.6); 2.0628 (0.6); 2.0606 (0.5); 2.0548 (1.3); 2.0511 (0.7); 2.0486 (0.7); 2.0467 (0.8); 2.0427 (1.1); 2.0372 (0.4); 2.0343 (0.6); 2.0289 (0.5); 2.0205 (0.3); 1.6214 (4.8); 1.6098 (4.8); 1.0445 (0.5); 1.0371 (1.7); 1.0335 (1.8); 1.0306 (0.7); 1.0264 (0.7); 1.0231 (1.8); 1.0195 (1.8); 1.0122 (1.0); 1.0076 (1.3); 1.0041 (1.6); 1.0005 (0.8); 0.9980 (0.7); 0.9937 (1.2); 0.9901 (1.7); 0.9868 (0.7); 0.9758 (0.1); 0.9714 (0.2); 0.9227 (0.2); 9.198 (0.3); 0.9150 (0.4); 0.9118 (0.4); 0.9039 (0.6); 0.9002 (0.6); 0.8957 (0.6); 0.8920 (0.5); 0.8888 (0.2); 0.8856 (0.1); 0.8801 (0.1); 0.8773 (0.2); 0.8733 (0.5); 0.8707 (0.6); 0.8652 (0.5); 0.8628 (0.6); 0.8608 (0.6); 0.8580 (0.3); 0.8529 (0.4); 0.8499 (0.4); 0.8450 (0.3); 0.8418 (0.2); 0.7988 (0.7); 0.7918 (1.5); 0.7905 (1.4); 0.7881 (1.5); 0.7835 (1.6); 0.7805 (1.5); 0.7730 (0.6); 0.0053 (0.6); −0.0001 (22.3); −0.0057 (0.7) | 530.2 |
| I-160 | 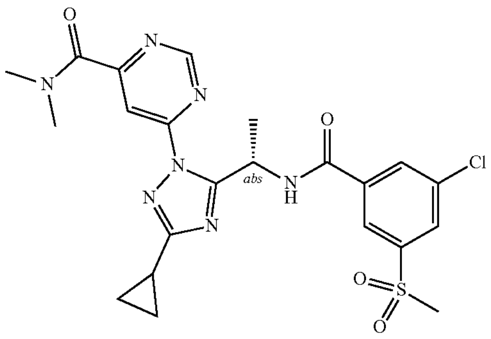 [SMILES: C[C@H](NC(=O)c1cc(Cl)cc(S(C)(=O)=O)c1)c1nc(C2CC2)nn1-c1cc(C(=O)N(C)C)ncn1] | $^1$H-NMR (600.1 MHz, d6-DMSO) δ = 9.4837 (1.8); 9.4721 (1.8); 9.1880 (4.2); 9.1869 (3.9); 8.3254 (3.5); 8.3140 (0.2); 8.2299 (3.2); 8.1517 (3.1); 7.9436 (4.4); 7.9423 (3.9); 6.2304 (0.3); 6.2189 (1.1); 6.2073 (1.7); 6.1957 (1.1); 6.1838 (0.2); 3.3285 (15.9); 3.3180 (51.4); 3.2933 (0.1); 3.0604 (0.1); 3.0345 (14.9); 2.9463 (16.0); 2.6138 (0.5); 2.5456 (0.1); 2.5197 (1.4); 2.5177 (1.4); 2.5018 (82.6); 2.3857 (0.5); 2.0827 (0.3); 2.0745 (0.6); 2.0683 (0.8); 2.0608 (1.3); 2.0531 (0.8); 2.0471 (0.7); 2.0388 (0.3); 1.6356 (6.2); 1.6240 (6.2); 1.0318 (0.1); 1.0248 (0.1); 1.0091 (2.4); 0.9952 (2.5); 0.9814 (0.2); 0.9762 (0.2); 0.9254 (0.4); 0.9202 (0.4); 0.9087 (1.4); 0.9007 (1.4); 0.8909 (1.2); 0.8831 (1.2); 0.8718 (0.5); 0.8662 (0.3); 0.0969 | 518.2 |

TABLE 1-continued
| Example | Structure[1)] | NMR Peak List[2)] | ESI Mass (m/z)[3)] |
|---|---|---|---|
| | | (0.2); 0.0052 (1.7); −0.0001 (47.6); −0.1000 (0.2) | |
| I-161 | 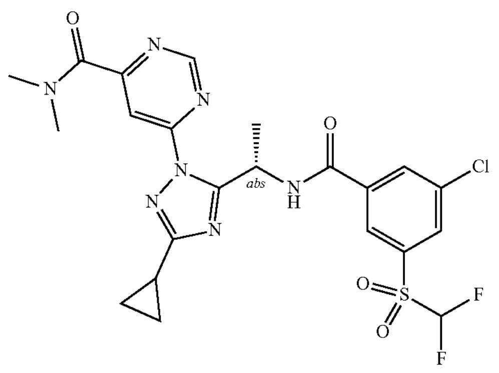 [SMILES: C[C@H](NC(=O)c1cc(Cl)cc(S(=O)(=O)C(F)F)c1)c1nc(C2CC2)nn1-c1cc(C(=O)N(C)C)ncn1] | $^1$H-NMR (600.1 MHz, d6-DMSO) δ = 9.6096 (1.2); 9.5980 (1.3); 9.1827 (3.5); 9.1807 (3.4); 8.4533 (1.6); 8.4504 (2.5); 8.4475 (1.7); 8.3698 (1.6); 8.3672 (2.8); 8.3647 (1.5); 8.3141 (0.1); 8.1842 (1.4); 8.1812 (2.3); 8.1782 (1.3); 7.9471 (3.6); 7.9451 (3.6); 7.5010 (0.8); 7.4143 (1.8); 7.3277 (0.9); 6.2328 (0.2); 6.2214 (0.9); 6.2097 (1.5); 6.1981 (0.9); 6.1866 (0.2); 3.3176 (34.9); 3.0596 (0.1); 3.0351 (14.0); 2.9461 (16.0); 2.6204 (0.1); 2.6174 (0.2); 2.6145 (0.3); 2.6114 (0.2); 2.6083 (0.1); 2.5235 (0.8); 2.5204 (0.9); 2.5173 (0.9); 2.5085 (16.6); 2.5055 (36.6); 2.5024 (51.1); 2.4993 (36.1); 2.4963 (16.1); 2.3924 (0.1); 2.3893 (0.2); 2.3862 (0.3); 2.3833 (0.2); 2.3803 (0.1); 2.0837 (0.2); 2.0744 (1.2); 2.0699 (0.6); 2.0677 (0.4); 2.0619 (1.1); 2.0561 (0.4); 2.0538 (0.6); 2.0480 (0.6); 2.0398 (0.3); 1.6392 (4.8); 1.6276 (4.8); 1.0330 (0.1); 1.0167 (0.6); 1.0150 (0.6); 1.0120 (1.3); 1.0098 (1.5); 1.0059 (0.7); 1.0029 (0.6); 0.9981 (1.2); 0.9959 (1.5); 0.9921 (0.6); 0.9757 (0.2); 0.9284 (0.2); 0.9251 (0.3); 0.9204 (0.3); 0.9168 (0.3); 0.9084 (0.8); 0.9051 (0.6); 0.9002 (0.8); 0.8971 (0.6); 0.8902 (0.6); 0.8880 (0.5); 0.8859 (0.6); 0.8821 (0.6); 0.8801 (0.5); 0.8776 (0.7); 0.8696 (0.3); 0.8665 (0.3); 0.8615 (0.2); 0.8583 (0.2); 0.0969 (0.2); 0.0053 (1.4); −0.0001 (48.6); −0.0057 (1.4); −0.1003 (0.2) | 554.2 |

TABLE 1-continued
| Example | Structure[1)] | NMR Peak List[2)] | ESI Mass (m/z)[3)] |
|---|---|---|---|
| I-162 | 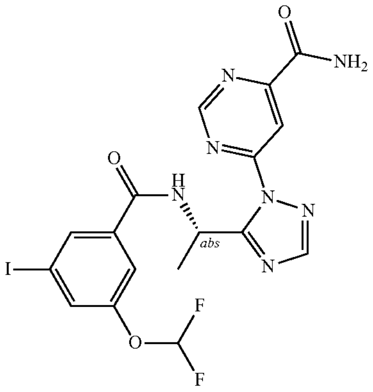 [SMILES: C[C@H](NC(=O)c1cc(I)cc(OC(F)F)c1)c1ncnn1-c1cc(C(N)=O)ncn1] | $^1$H-NMR (600.1 MHz, d6-DMSO) δ = 9.6038 (0.2); 9.3103 (12.5); 9.3083 (12.4); 9.2989 (0.4); 9.2873 (4.2); 8.5881 (0.1); 8.5860 (0.1); 8.4705 (0.4); 8.4570 (3.6); 8.3798 (11.1); 8.3779 (10.9); 8.3106 (15.7); 8.3050 (0.3); 8.1605 (0.1); 8.1581 (0.2); 8.1559 (0.1); 8.1202 (3.6); 8.1023 (5.9); 8.1000 (10.8); 8.0977 (5.8); 7.7397 (4.2); 7.7362 (5.2); 7.7336 (4.2); 7.6112 (4.3); 7.6084 (5.2); 7.6052 (3.9); 7.4318 (3.9); 7.3327 (0.1); 7.3094 (8.8); 7.1869 (4.2); 6.2491 (0.6); 6.2377 (2.7); 6.2261 (4.3); 6.2145 (2.7); 6.2027 (0.6); 3.3209 (53.7); 2.6224 (0.2); 2.6194 (0.4); 2.6164 (0.5); 2.6133 (0.3); 2.6105 (0.2); 2.5254 (1.1); 2.5223 (1.3); 2.5192 (1.2); 2.5105 (23.8); 2.5074 (52.8); 2.5043 (73.7); 2.5012 (51.9); 2.4982 (22.8); 2.3943 (0.2); 2.3913 (0.3); 2.3882 (0.5); 2.3852 (0.3); 2.3819 (0.1); 2.0877 (2.7); 2.0083 (0.5); 1.9696 (0.5); 1.6458 (15.9); 1.6342 (16.0); 1.3316 (0.2); 1.3195 (0.2); 1.1721 (0.1); 1.1619 (0.1); 1.1489 (0.1); 1.1378 (0.1); 0.0967 (0.2); 0.0054 (2.0); 0.0001 (70.0); −0.0057 (1.9); −0.1002 (0.2) | 530.1 |
| I-163 | 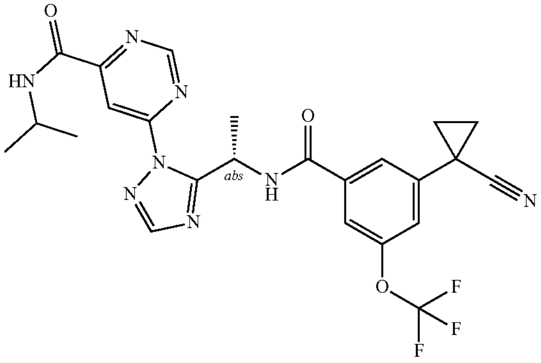 [SMILES: CC(C)NC(=O)c1cc(-n2ncnc2[C@H](C)NC(=O)c2cc(OC(F)(F)F)cc(C3(C#N)CC3)c2)ncn1] | $^1$H-NMR (600.1 MHz, d6-DMSO) δ = 9.3691 (1.9); 9.3574 (2.0); 9.2962 (5.0); 9.2943 (4.9); 8.8793 (1.6); 8.8653 (1.6); 8.3639 (5.1); 8.3620 (4.9); 8.3248 (7.0); 7.9634 (0.2); 7.8091 (2.3); 7.8065 (3.9); 7.8040 (2.4); 7.7370 (0.2); 7.7211 (2.4); 7.4776 (2.4); 6.2683 (0.3); 6.2568 (1.3); 6.2452 (2.0); 6.2335 (1.3); 6.2219 (0.3); 4.1982 (0.3); 4.1872 (0.7); 4.1762 (1.0); 4.1733 (0.8); 4.1651 (0.8); 4.1622 (1.0); 4.1512 (0.7); 4.1401 (0.3); 3.3198 (50.5); 2.6212 (0.1); 2.6182 (0.3); 2.6151 (0.4); 2.6120 (0.3); 2.6089 (0.1); 2.5242 (0.9); 2.5211 (1.1); 2.5180 (1.0); 2.5092 (20.6); 2.5061 (45.8); 2.5031 (64.4); 2.5000 (45.8); 2.4970 (20.6); 2.4775 (0.1); 2.3901 (0.3); 2.3870 (0.4); 2.3839 (0.3); 2.3807 (0.1); 2.0750 (6.3); 1.8689 (0.1); 1.8600 (0.3); 1.8557 (0.2); 1.8426 (1.7); 1.8343 (3.7); 1.8298 (4.2); 1.8221 (1.9); 1.7946 (0.2); 1.6684 (7.5); 1.6568 (7.6); 1.6462 (2.1); 1.6403 (2.2); 1.6381 (3.8); 1.6331 (3.0); 1.6253 (1.6); 1.6168 (0.1); 1.5997 (0.1); 1.2231 (16.0); 1.2120 (16.0); 1.1939 (0.1); 1.1049 (0.1); 0.0969 (0.2); 0.0053 (1.0); −0.0001 (36.8); −0.0057 (1.1); −0.1002 (0.2) | 529.3 |

TABLE 1-continued
| Example | Structure[1)] | NMR Peak List[2)] | ESI Mass (m/z)[3)] |
|---|---|---|---|
| I-164 | 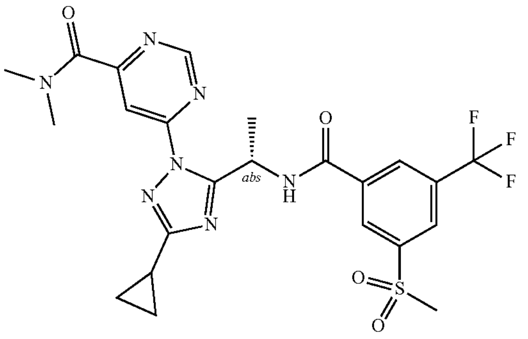 [SMILES: C[C@H](NC(=O)c1cc(C(F)(F)F)cc(S(C)(=O)=O)c1)c1nc(C2CC2)nn1-c1cc(C(=O)N(C)C)ncn1] | $^1$H-NMR (600.1 MHz, d6-DMSO) δ = 9.6454 (1.3); 9.6336 (1.4); 9.1997 (3.3); 9.1977 (3.4); 8.6655 (2.2); 8.5351 (2.0); 8.4086 (1.9); 7.9542 (4.0); 7.9523 (3.7); 6.2735 (0.2); 6.2621 (1.0); 6.2504 (1.5); 6.2388 (1.0); 6.2272 (0.2); 3.3863 (13.6); 3.3222 (23.3); 3.0620 (0.1); 3.0373 (14.0); 2.9485 (16.0); 2.8930 (4.6); 2.7336 (3.6); 2.6165 (0.1); 2.5254 (0.3); 2.5224 (0.3); 2.5193 (0.3); 2.5104 (6.0); 2.5074 (13.2); 2.5044 (18.3); 2.5013 (13.0); 2.4983 (5.8); 2.3883 (0.1); 2.0862 (0.2); 2.0781 (0.6); 2.0723 (0.6); 2.0702 (0.4); 2.0643 (1.1); 2.0562 (0.6); 2.0505 (0.6); 2.0423 (0.3); 1.6602 (4.9); 1.6486 (4.9); 1.0342 (0.1); 1.0167 (0.8); 1.0130 (1.4); 1.0111 (1.5); 1.0032 (0.7); 0.9992 (1.3); 0.9971 (1.6); 0.9841 (0.1); 0.9805 (0.1); 0.9770 (0.2); 0.9319 (0.2); 0.9288 (0.3); 0.9240 (0.3); 0.9205 (0.3); 0.9128 (0.8); 0.9093 (0.6); 0.9047 (0.9); 0.9010 (0.6); 0.8964 (0.7); 0.8922 (0.8); 0.8883 (0.7); 0.8841 (0.8); 0.8763 (0.3); 0.8733 (0.3); 0.8684 (0.2); 0.8651 (0.2); 0.00533 (0.4); −0.0001 (12.6); −0.0057 (0.4) | 552.2 |
| I-165 | 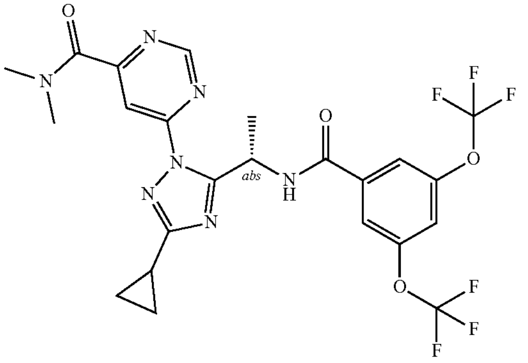 [SMILES: C[C@H](NC(=O)c1cc(OC(F)(F)F)cc(OC(F)(F)F)c1)c1nc(C2CC2)nn1-c1cc(C(=O)N(C)C)ncn1] | $^1$H-NMR (600.1 MHz, d6-DMSO) δ = 9.4358 (1.2); 9.4242 (1.3); 9.1791 (3.2); 9.1770 (3.2); 7.9536 (0.5); 7.9449 (3.4); 7.9429 (3.4); 7.8889 (3.1); 7.8856 (3.2); 7.7467 (1.3); 6.2041 (0.2); 6.1925 (0.9); 6.1809 (1.5); 6.1692 (1.0); 6.1576 (0.2); 3.4043 (0.3); 3.3925 (0.2); 3.3890 (0.2); 3.3829 (0.2); 3.3808 (0.2); 3.3771 (0.6); 3.3528 (479.8); 3.3326 (0.3); 3.3263 (0.2); 3.3186 (0.2); 3.3090 (0.2); 3.3047 (0.1); 3.0548 (0.1); 3.0359 (14.0); 2.9413 (16.0); 2.8936 (4.3); 2.7341 (3.3); 2.6207 (0.2); 2.6178 (0.3); 2.6146 (0.2); 2.5267 (0.6); 2.5236 (0.7); 2.5205 (0.7); 2.5117 (12.2); 2.5087 (27.2); 2.5057 (38.2); 2.5026 (27.2); 2.4996 (12.2); 2.3926 (0.2); 2.3896 (0.2); 2.3864 (0.2); 2.0814 (0.2); 2.0733 (0.5); 2.0675 (0.6); 2.0654 (0.4); 2.0595 (1.1); 2.0514 (0.6); 2.0456 (0.6); 2.0375 (0.3); 1.6335 (4.9); 1.6219 (4.9); 1.0329 (0.1); 1.0174 (0.6); 1.0122 (1.3); 1.0096 (1.5); 1.0051 (0.7); 0.9984 (1.2); 0.9956 (1.5); 0.9915 (0.6); 0.9758 (0.2); 0.9253 (0.2); 0.9221 (0.3); 0.9176 (0.4); 0.9141 (0.4); 0.9049 (0.7); 0.9025 (0.5); 0.8968 (0.7); 0.8942 (0.6); 0.8878 (0.2); 0.8854 (0.2); 0.8786 (0.5); 0.8760 (0.7); 0.8705 (0.5); 0.8679 (0.7); 0.8581 (0.4); 0.8549 (0.4); 0.8501 | 574.2 |

TABLE 1-continued
| Ex-am-ple | Structure[1)] | NMR Peak List[2)] | ESI Mass (m/z)[3)] |
| --- | --- | --- | --- |
| | | (0.2); 0.8468 (0.2); 0.0968 (0.1); 0.0054 (0.9); −0.0001 (30.1); −0.0057 (0.9); −0.1002 (0.1) | |
| I-166 | 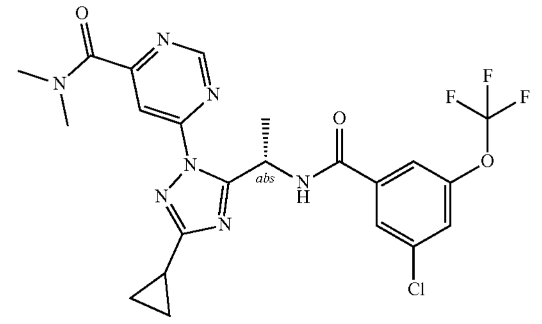 [SMILES: C[C@H](NC(=O)c1cc(Cl)cc(OC(F)(F)F)c1)c1nc(C2CC2)nn1-c1cc(C(=O)N(C)C)ncn1] | $^1$H-NMR (600.1 MHz, d6-DMSO) δ = 9.3582 (1.1); 9.3465 (1.2); 9.1784 (3.4); 9.1763 (3.4); 7.9882 (1.7); 7.9855 (2.4); 7.9828 (1.7); 7.9421 (3.8); 7.9401 (3.7); 7.7821 (1.3); 7.7706 (1.5); 7.7688 (1.5); 7.7671 (1.1); 6.1934 (0.2); 6.1818 (0.9); 6.1702 (1.4); 6.1586 (0.9); 6.1469 (0.2); 3.3193 (32.4); 3.0353 (13.9); 2.9432 (16.0); 2.6184 (0.1); 2.6154 (0.2); 2.6123 (0.1); 2.5244 (0.4); 2.5213 (0.5); 2.5182 (0.5); 2.5095 (9.5); 2.5064 (21.0); 2.5034 (29.2); 2.5003 (20.7); 2.4972 (9.2); 2.3903 (0.1); 2.3872 (0.2); 2.3842 (0.1); 2.0806 (0.2); 2.0725 (0.5); 2.0667 (0.5); 2.0645 (0.4); 2.0587 (1.1); 2.0528 (0.4); 2.0505 (0.6); 2.0448 (0.6); 2.0367 (0.3); 1.6227 (4.6); 1.6111 (4.7); 1.0153 (0.6); 1.0108 (1.2); 1.0078 (1.5); 1.0041 (0.7); 1.0014 (0.6); 0.9970 (1.2); 0.9938 (1.6); 0.9904 (0.6); 0.9746 (0.2); 0.9249 (0.2); 0.9218 (0.3); 0.9171 (0.3); 0.9137 (0.3); 0.9092 (0.2); 0.9051 (0.6); 0.9020 (0.5); 0.8969 (0.6); 0.8939 (0.5); 0.8877 (0.2); 0.8810 (0.5); 0.8785 (0.7); 0.8765 (0.5); 0.8730 (0.5); 0.8703 (0.7); 0.8683 (0.6); 0.8656 (0.3); 0.8604 (0.4); 0.8575 (0.4); 0.8526 (0.2); 0.8493 (0.2); 0.0054 (0.8); −0.0001 (28.3); −0.0057 (0.8) | 524.2 |
| I-167 | 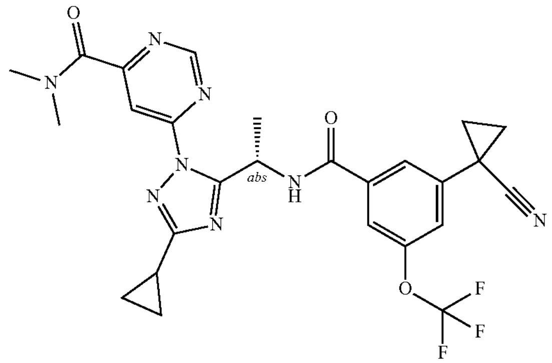 [SMILES: C[C@H](NC(=O)c1cc(OC(F)(F)F)cc(C2(C#N)CC2)c1)c1nc(C2CC2)nn1-c1cc(C(=O)N(C)C)ncn1] | $^1$H-NMR (600.1 MHz, d6-DMSO) δ = 9.3447 (1.2); 9.3329 (1.3); 9.1855 (3.6); 9.1834 (3.6); 7.9452 (3.7); 7.9431 (3.6); 7.8123 (1.5); 7.8097 (2.6); 7.8071 (1.6); 7.7345 (1.4); 7.7327 (1.6); 7.7310 (1.4); 7.4782 (1.6); 6.2039 (0.2); 6.1925 (0.9); 6.1808 (1.5); 6.1691 (1.0); 6.1573 (0.2); 3.3201 (24.6); 3.0363 (14.2); 2.9429 (16.0); 2.8925 (0.4); 2.7332 (0.3); 2.6188 (0.1); 2.6158 (0.2); 2.6127 (0.1); 2.5248 (0.3); 2.5217 (0.4); 2.5186 (0.4); 2.5098 (7.4); 2.5068 (16.6); 2.5037 (23.3); 2.5006 (16.5); 2.4976 (7.4); 2.3906 (0.1); 2.3876 (0.2); 2.3846 (0.1); 2.0812 (0.2); 2.0756 (1.6); 2.0731 (0.6); 2.0673 (0.6); 2.0651 (0.4); 2.0593 (1.2); 2.0534 (0.4); 2.0511 (0.6); 2.0454 (0.6); 2.0373 (0.3); 1.9898 (0.4); 1.8524 (0.6); 1.8510 (0.8); 1.8431 (2.0); 1.8388 (2.8); 1.8368 (1.4); 1.8315 (1.0); 1.8042 (0.1); 1.6869 (0.1); 1.6605 (1.4); 1.6544 (1.4); 1.6523 (2.7); 1.6480 (2.3); 1.6391 (1.8); 1.6360 (4.9); 1.6244 (4.9); 1.6142 (0.2); 1.1833 | 555.2 |

TABLE 1-continued
| Example | Structure[1)] | NMR Peak List[2)] | ESI Mass (m/z)[3)] |
|---|---|---|---|
| | | (0.1); 1.1764 (0.2); 1.646 (0.1); 1.0298 (0.1); 1.0141 (0.6); 1.0098 (1.3); 1.0067 (1.6); 1.0032 (0.7); 1.0002 (0.6); 0.9960 (1.2); 0.9927 (1.7); 0.9895 (0.6); 0.9736 (0.2); 0.9267 (0.2); 0.9238 (0.3); 0.9189 (0.3); 0.9157 (0.3); 0.9073 (0.6); 0.9041 (0.5); 0.8991 (0.7); 0.8959 (0.5); 0.8901 (0.2); 0.8838 (0.5); 0.8812 (0.8); 0.8757 (0.5); 0.8730 (0.7); 0.8710 (0.6); 0.8632 (0.4); 0.8603 (0.4); 0.8554 (0.2); 0.8523 (0.2); 0.0054 (0.5); 0.0001 (18.5); −0.0057 (0.5) | |
| I-168 | 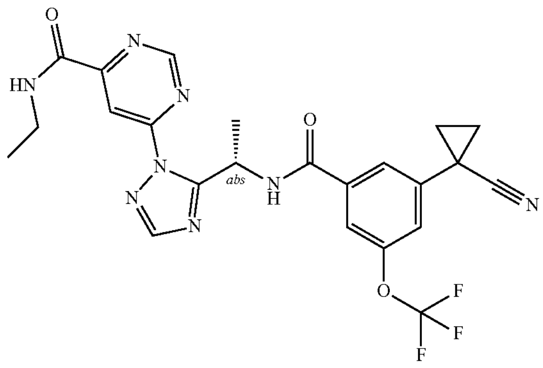 [SMILES: CCNC(=O)c1cc(-n2ncnc2[C@H](C)NC(=O)c2cc(OC(F)(F)F)cc(C3(C#N)CC3)c2)ncn1] | $^1$H-NMR (600.1 MHz, d6-DMSO) δ = 9.3871 (0.3); 9.3744 (2.6); 9.3659 (1.2); 9.3628 (2.6); 9.3040 (6.6); 9.3020 (6.4); 9.2134 (0.1); 9.2120 (0.1); 9.1939 (1.1); 9.1839 (2.1); 9.1740 (1.0); 8.3717 (7.2); 8.3698 (6.9); 8.3317 (0.8); 8.3236 (9.1); 8.3143 (0.1); 8.2684 (0.1); 7.8122 (3.4); 7.8097 (5.3); 7.8071 (3.1); 7.7291 (2.8); 7.7275 (3.1); 7.4784 (3.3); 6.2725 (0.4); 6.2611 (1.6); 6.2494 (2.6); 6.2378 (1.7); 6.2260 (0.4); 6.2221 (0.2); 5.7548 (11.1); 3.9747 (2.4); 3.3888 (0.9); 3.3769 (3.1); 3.3665 (3.6); 3.3650 (3.6); 3.3547 (3.2); 3.3428 (1.0); 3.3197 (83.9); 2.9908 (0.1); 2.8750 (0.1); 2.6216 (0.2); 2.6186 (0.4); 2.6155 (0.5); 2.6125 (0.3); 2.6093 (0.2); 2.5245 (1.1); 2.5214 (1.3); 2.5183 (1.2); 2.5096 (23.9); 2.5065 (52.9); 2.5035 (73.9); 2.5004 (52.4); 2.4974 (23.4); 2.3935 (0.2); 2.3905 (0.4); 2.3873 (0.5); 2.3843 (0.3); 1.8696 (0.1); 1.8435 (2.1); 1.8352 (4.9); 1.8307 (5.6); 1.8229 (2.4); 1.8126 (0.1); 1.7957 (0.2); 1.6692 (10.3); 1.6576 (10.5); 1.6480 (3.0); 1.6419 (3.1); 1.6399 (5.2); 1.6350 (4.0); 1.6270 (2.1); 1.6191 (0.2); 1.6013 (0.1); 0.13527 (0.2); 1.3272 (0.2); 1.2597 (0.1); 1.2548 (0.2); 1.2496 (0.1); 1.2331 (0.4); 1.1762 (0.1); 1.1632 (7.4); 1.1512 (16.0); 1.1392 (7.4); 1.0460 (0.2); 1.0437 (0.1); 0.8528 (0.1); 0.8506 (0.1); 0.8198 (0.1); 0.0968 (0.2); 0.0053 (1.4); −0.0001 (48.4); −0.0057 (1.5); −0.1002 (0.2) | 515.2 |

TABLE 1-continued
| Example | Structure[1)] | NMR Peak List[2)] | ESI Mass (m/z)[3)] |
| --- | --- | --- | --- |
| I-169 | 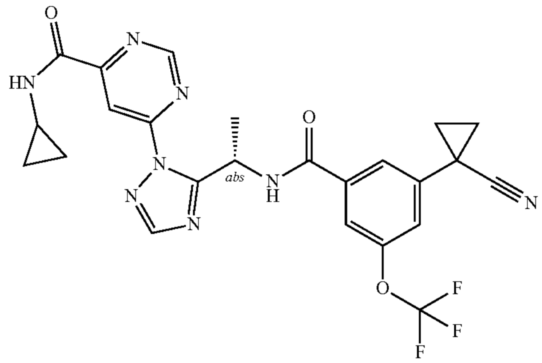 [SMILES: C[C@H](NC(=O)c1cc(OC(F)(F)F)cc(C2(C#N)CC2)c1)c1ncnn1-c1cc(C(=O)NC2CC2)ncn1] | $^1$H-NMR (600.1 MHz, d6-DMSO) δ = 9.3880 (0.2); 9.3752 (1.8); 9.3637 (1.9); 9.2781 (4.8); 9.2761 (4.7); 9.1473 (1.8); 9.1388 (1.8); 8.3723 (0.3); 8.3704 (0.3); 8.3602 (4.8); 8.3583 (4.6); 8.3392 (0.2); 8.3315 (0.5); 8.3250 (7.0); 8.3144 (0.1); 7.8119 (2.3); 7.8093 (3.8); 7.8067 (2.3); 7.7309 (2.0); 7.7293 (2.2); 7.7277 (2.0); 7.4781 (2.4); 6.2684 (0.3); 6.2570 (1.2); 6.2454 (2.0); 6.2338 (1.3); 6.2223 (0.3); 5.7549 (16.0); 3.9751 (1.3); 3.3202 (31.1); 2.9952 (0.2); 2.9862 (0.7); 2.9767 (1.2); 2.9721 (0.4); 2.9678 (1.2); 2.9577 (0.6); 2.9488 (0.2); 2.6191 (0.2); 2.6160 (0.3); 2.6129 (0.2); 2.5250 (0.6); 2.5219 (0.7); 2.5188 (0.7); 2.5101 (14.0); 2.5070 (31.2); 2.5040 (43.9); 2.5009 (31.1); 2.4979 (13.9); 2.3909 (0.2); 2.3879 (0.3); 2.3848 (0.2); 1.8436 (1.5); 1.8353 (3.5); 1.8308 (4.1); 1.8231 (1.8); 1.7958 (0.2); 1.6668 (7.0); 1.6551 (7.2); 1.6477 (2.2); 1.6417 (2.2); 1.6396 (3.8); 1.6346 (2.9); 1.6267 (1.5); 1.6186 (0.1); 1.4589 (0.3); 1.4475 (0.3); 1.3532 (0.1); 1.3261 (0.7); 1.2330 (0.2); 1.0463 (0.1); 0.7441 (1.6); 0.7404 (5.2); 7.350 (2.0); 0.7302 (14.4); 0.7197 (0.2); 0.0968 (0.1); 0.0053 (0.9); −0.0001 (32.2); −0.0057 (1.0); −0.1001 (0.1) | 527.2 |
| I-170 | 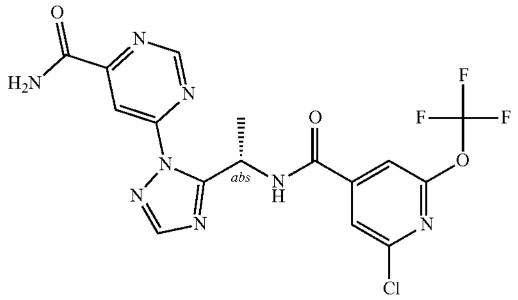 [SMILES: C[C@H](NC(=O)c1cc(Cl)nc(OC(F)(F)F)c1)c1ncnn1-c1cc(C(N)=O)ncn1] | $^1$H-NMR (600.1 MHz, d6-DMSO) δ = 9.5815 (3.7); 9.5699 (3.8); 9.3208 (0.2); 9.3187 (0.2); 9.3067 (11.9); 9.3047 (11.6); 8.4555 (3.3); 8.3923 (0.1); 8.3895 (0.2); 8.3786 (11.5); 8.3766 (11.2); 8.3493 (0.1); 8.3354 (15.3); 8.3138 (0.3); 8.1573 (0.1); 8.1205 (3.2); 7.9381 (10.8); 7.9364 (10.7); 7.8618 (0.1); 7.6384 (11.6); 7.6367 (11.2); 7.6043 (0.1); 7.2669 (0.6); 6.2555 (2.7); 6.2440 (4.2); 6.2324 (2.7); 6.2208 (0.6); 3.5952 (0.1); 3.3605 (0.1); 3.3202 (139.4); 2.9885 (0.3); 2.8920 (0.1); 2.8676 (0.3); 2.6210 (0.3); 2.6179 (0.7); 2.6148 (1.1); 2.6117 (0.8); 2.6087 (0.3); 2.5238 (2.3); 2.5207 (2.8); 2.5176 (2.6); 2.5089 (53.4); 2.5058 (119.4); 2.5028 (167.5); 2.4997 (118.1); 2.4966 (51.9); 2.4770 (0.2); 2.3927 (0.4); 2.3897 (0.8); 2.3867 (1.1); 2.3835 (0.8); 2.3804 (0.3); 1.6828 (0.2); 1.6800 (0.2); 1.6580 (15.9); 1.6464 (16.0); 1.5478 (0.1); 0.0968 (0.4); 0.0054 (2.8); −0.0001 (104.4); −0.0057 (3.0); −0.0168 (0.1); −0.1002 (0.4) | 457.2 |

TABLE 1-continued
| Example | Structure[1)] | NMR Peak List[2)] | ESI Mass (m/z)[3)] |
|---|---|---|---|
| I-171 | 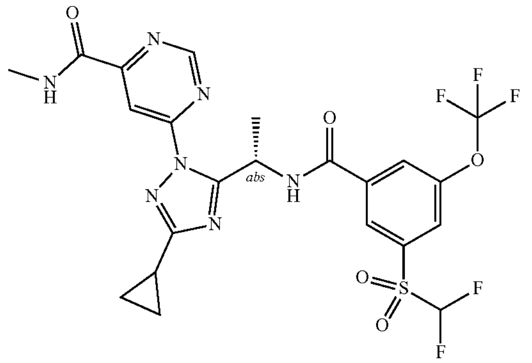 [SMILES: CNC(=O)c1cc(-n2nc(C3CC3)nc2[C@H](C)NC(=O)c2cc(OC(F)(F)F)cc(S(=O)(=O)C(F)F)c2)ncn1] | $^1$H-NMR (600.1 MHz, d6-DMSO) δ = 9.6924 (2.8); 9.6807 (2.9); 9.2459 (9.5); 9.2440 (9.3); 9.1186 (0.7); 9.1108 (2.1); 9.1027 (2.0); 9.0948 (0.6); 8.4789 (3.5); 8.4764 (6.4); 8.4740 (3.5); 8.3447 (3.5); 8.3432 (3.1); 8.3140 (0.9); 8.3117 (9.1); 8.3098 (8.8); 8.1170 (3.2); 7.9528 (0.1); 7.5251 (1.7); 7.4386 (4.4); 7.3520 (2.2); 6.2648 (0.4); 6.2532 (2.2); 6.2416 (3.5); 6.2299 (2.3); 6.2181 (0.4); 3.3462 (0.1); 3.3174 (176.0); 3.2939 (0.1); 2.8914 (1.3); 2.8648 (15.9); 2.8567 (16.0); 2.7326 (1.0); 2.7317 (1.0); 2.6904 (1.0); 2.6203 (0.5); 2.6172 (1.0); 2.6141 (1.4); 2.6110 (1.0); 2.6080 (0.5); 2.5535 (0.1); 2.5508 (0.1); 2.5358 (0.1); 2.5338 (0.1); 2.5304 (0.1); 2.5232 (3.0); 2.5201 (3.7); 2.5170 (3.4); 2.5082 (72.1); 2.5052 (161.7); 2.5021 (227.4); 2.4990 (159.9); 2.4959 (70.0); 2.4725 (0.2); 2.3922 (0.5); 2.3891 (1.0); 2.3860 (1.4); 2.3829 (1.0); 2.3798 (0.5); 2.1328 (0.6); 2.1296 (0.2); 2.1247 (1.3); 2.1189 (1.4); 2.1167 (1.0); 2.1109 (2.7); 2.1050 (0.8); 2.1027 (1.6); 2.0970 (1.5); 2.0888 (0.8); 1.9091 (0.1); 1.6441 (11.2); 1.6325 (11.3); 1.2708 (0.2); 1.2592 (0.4); 1.2465 (0.3); 1.2321 (0.1); 1.0505 (0.3); 1.0469 (0.2); 1.0421 (0.2); 1.0336 (1.3); 1.0321 (1.4); 1.0269 (3.7); 1.0241 (1.7); 1.0217 (1.5); 1.0199 (1.5); 1.0181 (1.2); 1.0129 (3.8); 1.0103 (1.8); 1.0081 (1.4); 0.9995 (0.2); 0.9948 (0.4); 0.9913 (0.4); 0.9497 (0.1); 0.9389 (0.5); 0.9351 (0.6); 0.9307 (0.8); 0.9268 (0.6); 0.9196 (1.8); 0.9156 (1.7); 0.9114 (1.9); 0.9073 (1.7); 0.9017 (1.8); 0.8971 (1.7); 0.8936 (1.8); 0.8889 (1.7); 0.8813 (0.6); 0.8782 (0.7); 0.8734 (0.5); 0.8699 (0.4); 0.0968 (1.3); 0.0054 (11.4); −0.0001 (427.5); −0.0057 (12.1); −0.0184 (0.4); −0.0202 (0.3); −0.0225 (0.3); −0.0267 (0.3); −0.0300 (0.2); −0.0326 (0.1); −0.0360 (0.1); −0.0427 (0.1); −0.1003 (1.4) | 590.2 |

TABLE 1-continued
| Example | Structure[1)] | NMR Peak List[2)] | ESI Mass (m/z)[3)] |
|---|---|---|---|
| I-172 | 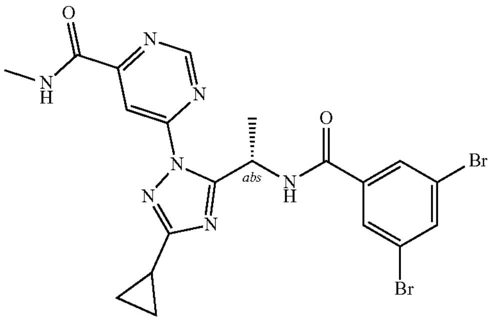 [SMILES: CNC(=O)c1cc(-n2nc(C3CC3)nc2[C@H](C)NC(=O)c2cc(Br)cc(Br)c2)ncn1] | $^1$H-NMR (600.1 MHz, d6-DMSO) δ = 9.2825 (2.6); 9.2708 (2.7); 9.2408 (7.2); 9.2389 (7.1); 9.1230 (0.6); 9.1154 (1.8); 9.1072 (1.8); 9.0992 (0.6); 8.4569 (0.3); 8.3380 (0.1); 8.3142 (0.5); 8.3011 (7.1); 8.2992 (7.0); 8.0338 (2.5); 8.0308 (5.6); 8.0279 (4.6); 8.1056 (16.0); 8.0127 (11.3); 6.1946 (0.4); 6.1829 (2.0); 6.1712 (3.2); 6.1596 (2.0); 6.1480 (0.4); 3.6184 (0.1); 3.3549 (0.2); 3.3453 (0.2); 3.3191 (95.3); 3.3171 (122.8); 3.2914 (0.1); 3.1456 (0.1); 2.8649 (13.8); 2.8569 (13.8); 2.7476 (0.1); 2.6198 (0.6); 2.6167 (1.3); 2.6138 (1.8); 2.6107 (1.3); 2.6076 (0.6); 2.5515 (0.2); 2.5228 (3.8); 2.5197 (4.7); 2.5166 (4.6); 2.5078 (92.3); 2.5048 (203.2); 2.5017 (284.3); 2.4987 (200.9); 2.4956 (89.2); 2.3917 (0.6); 2.3887 (1.3); 2.3856 (1.8); 2.3826 (1.3); 2.3794 (0.5); 2.1265 (0.5); 2.1184 (1.2); 2.1126 (1.2); 2.1105 (0.9); 2.1046 (2.4); 2.0988 (0.8); 2.0965 (1.4); 2.0907 (1.3); 2.0825 (0.6); 2.0738 (0.5); 1.6015 (10.5); 1.5899 (10.5); 1.2982 (0.1); 1.2712 (0.7); 1.2598 (0.9); 1.2572 (1.0); 1.2462 (0.9); 1.2318 (0.3); 1.0462 (0.2); 1.0260 (2.8); 1.0232 (3.3); 1.0200 (1.5); 1.0161 (1.4); 1.0121 (2.6); 1.0092 (3.4); 1.0063 (1.4); 0.9957 (0.2); 0.9899 (0.4); 0.9419 (0.1); 0.9327 (0.4); 0.9295 (0.6); 0.9250 (0.7); 0.9213 (0.6); 0.9127 (1.7); 0.9097 (1.3); 0.9046 (1.8); 0.9015 (1.3); 0.8947 (1.1); 0.8915 (1.5); 0.8866 (1.2); 0.8834 (1.5); 0.8738 (0.6); 0.8709 (0.8); 0.8661 (0.5); 0.8628 (0.4); 0.0968 (1.4); 0.0113 (0.3); 0.0053 (10.3); −0.0001 (365.1); −0.0057 (10.7); −0.0233 (0.2); −0.0263 (0.2); −0.0520 (0.1); −0.0949 (0.1); −0.1002 (1.5) | 550.0 |

TABLE 1-continued
| Example | Structure[1)] | NMR Peak List[2)] | ESI Mass (m/z)[3)] |
|---|---|---|---|
| I-173 | 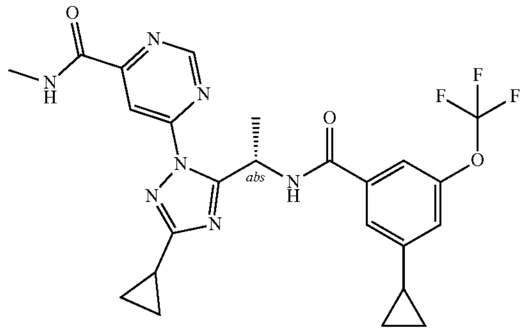 [SMILES: CNC(=O)c1cc(-n2nc(C3CC3)nc2[C@H](C)NC(=O)c2cc(OC(F)(F)F)cc(C3CC3)c2)ncn1] | $^1$H-NMR (600.1 MHz, d6-DMSO) δ = 9.2370 (8.6); 9.2350 (8.7); 9.1764 (2.8); 9.1646 (3.0); 9.1231 (0.7); 9.1154 (2.0); 9.1074 (2.0); 0.0994 (0.7); 8.3147 (0.2); 8.3022 (8.8); 8.3003 (8.7); 7.9536 (0.5); 7.4949 (7.9); 7.4922 (9.0); 7.2737 (3.5); 6.1954 (0.4); 6.1838 (2.2); 6.1721 (3.6); 6.1604 (2.3); 6.1487 (0.4); 3.3215 (40.8); 3.3193 (66.1); 2.8919 (4.6); 2.8660 (16.0); 2.8579 (16.0); 2.7331 (3.4); 2.7323 (3.5); 2.6210 (0.2); 2.6180 (0.5); 2.6149 (0.7); 2.6119 (0.5); 2.6087 (0.2); 2.5240 (1.4); 2.5209 (1.7); 2.5177 (1.6); 2.5090 (32.6); 2.5059 (73.3); 2.5029 (103.3); 2.4998 (73.0); 2.4967 (32.2); 2.3929 (0.2); 2.3898 (0.4); 2.3868 (0.6); 2.3837 (0.5); 2.3806 (0.2); 2.1253 (0.6); 2.1172 (1.3); 2.1114 (1.3); 2.1091 (1.0); 2.1033 (2.7); 2.0975 (0.9); 2.0952 (1.5); 2.0895 (1.4); 2.0813 (0.7); 2.0574 (0.6); 2.0490 (1.2); 2.0435 (1.2); 2.0408 (0.8); 2.0351 (2.4); 2.0294 (0.8); 2.0267 (1.3); 2.0212 (1.2); 2.0128 (0.6); 1.9893 (0.1); 1.6150 (11.5); 1.6034 (11.6); 1.2593 (0.2); 1.2331 (0.1); 1.0439 (0.3); 1.0370 (1.1); 1.0356 (1.1); 1.0296 (4.4); 1.0260 (5.3); 1.0232 (4.5); 1.0205 (4.9); 1.0158 (5.3); 1.0121 (5.2); 1.0094 (3.5); 1.0065 (4.6); 1.0025 (1.6); 0.9921 (0.3); 0.9867 (0.4); 0.9783 (0.1); 0.9496 (0.1); 0.9418 (0.1); 0.9321 (0.5); 0.9287 (0.7); 0.9243 (0.9); 0.9207 (0.8); 0.9162 (0.6); 0.9115 (1.6); 0.9090 (1.2); 0.9034 (1.7); 0.9009 (1.4); 0.8935 (0.5); 0.8865 (1.4); 0.8840 (1.6); 0.8821 (1.2); 0.8784 (1.2); 0.8758 (1.6); 0.8739 (1.4); 0.8711 (0.7); 0.8660 (1.0); 0.8628 (0.9); 0.8581 (0.6); 0.8546 (0.4); 0.8105 (0.1); 0.8018 (0.1); 0.7942 (0.2); 0.7902 (0.1); 0.7834 (1.8); 0.7748 (3.8); 0.7723 (2.9); 0.7708 (2.5); 0.7668 (3.2); 0.7641 (2.5); 0.7586 (1.5); 0.7523 (0.2); 0.7479 (0.2); 0.0967 (0.4); 0.0054 (3.1); −0.0001 (117.0); −0.0057 (3.2); −0.1003 (0.4) | 516.3 |

TABLE 1-continued
| Ex-am-ple | Structure[1)] | NMR Peak List[2)] | ESI Mass (m/z)[3)] |
|---|---|---|---|
| I-174 | 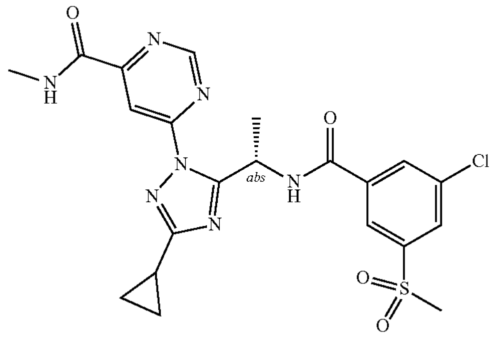 [SMILES: CNC(=O)c1cc(-n2nc(C3CC3)nc2[C@H](C)NC(=O)c2cc(Cl)cc(S(C)(=O)=O)c2)ncn1] | $^1$H-NMR (600.1 MHz, d6-DMSO) δ = 9.4760 (2.9); 9.4643 (3.0); 9.2525 (8.6); 9.2505 (8.5); 9.2447 (0.1); 9.1220 (0.7); 9.1143 (2.1); 9.1063 (2.0); 9.0983 (0.7); 8.3137 (4.6); 8.3111 (7.8); 8.3083 (5.4); 8.3072 (9.8); 8.3052 (8.7); 8.2200 (4.0); 8.2169 (6.0); 8.2143 (4.1); 8.1518 (4.3); 8.1488 (6.2); 8.1458 (3.6); 8.0153 (0.1); 7.9523 (0.4); 6.2478 (0.5); 6.2363 (2.2); 6.2247 (3.5); 6.2130 (2.2); 6.2014 (0.4); 3.4382 (0.2); 3.3244 (49.0); 3.3200 (133.8); 3.3168 (197.6); 3.2983 (0.4); 3.2067 (0.2); 2.9775 (0.1); 2.8908 (4.4); 2.8644 (15.9); 2.8563 (16.0); 2.7473 (0.1); 2.7385 (0.1); 2.7319 (3.1); 2.7311 (3.2); 2.6196 (0.8); 2.6166 (1.7); 2.6135 (2.4); 2.6105 (1.7); 2.6073 (0.8); 2.5369 (0.2); 2.5301 (0.3); 2.5225 (4.8); 2.5195 (5.8); 2.5163 (5.5); 2.5076 (115.2); 2.5045 (257.1); 2.5015 (360.4); 2.4984 (253.5); 2.4953 (110.9); 2.4710 (0.2); 2.3915 (0.7); 2.3885 (1.6); 2.3854 (2.2); 2.3823 (1.6); 2.3792 (0.7); 2.1304 (0.6); 2.1222 (1.3); 2.1164 (1.3); 2.1142 (1.0); 2.1084 (2.7); 2.1003 (1.5); 2.0946 (1.4); 2.0863 (0.7); 2.0735 (1.5); 1.9882 (0.1); 1.6490 (0.2); 1.6301 (11.4); 1.6185 (11.4); 1.5898 (0.1); 1.2590 (0.2); 1.2350 (0.2); 1.1750 (0.1); 1.1635 (0.1); 1.1486 (0.1); 1.0484 (0.3); 1.0419 (0.5); 1.0304 (2.1); 1.0276 (3.4); 1.0254 (3.7); 1.0165 (2.0); 1.0137 (3.2); 1.0115 (3.8); 1.0054 (0.6); 0.9986 (0.5); 0.9917 (0.4); 0.9726 (0.1); 0.9553 (0.1); 0.9467 (0.1); 0.9376 (0.4); 0.9342 (0.6); 0.9299 (0.6); 0.9261 (0.6); 0.9193 (2.1); 0.9148 (1.4); 0.9111 (2.3); 0.9090 (1.8); 0.9068 (2.5); 0.9021 (1.9); 0.89900 (1.5); 0.8941 (1.7); 0.8868 (0.5); 0.8837 (0.7); 0.8786 (0.4); 0.8753 (0.4); 0.0967 (1.3); 0.0054 (10.1); −0.0001 (370.3); −0.0057 (10.4); −0.0273 (0.1); −0.1003 (1.4) | 504.1 |

TABLE 1-continued
| Example | Structure[1)] | NMR Peak List[2)] | ESI Mass (m/z)[3)] |
|---|---|---|---|
| I-175 | 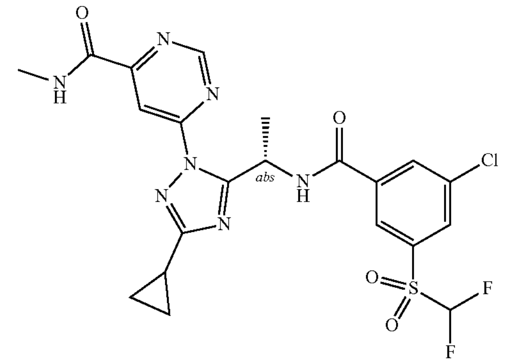 [SMILES: CNC(=O)c1cc(-n2nc(C3CC3)nc2[C@H](C)NC(=O)c2cc(Cl)cc(S(=O)(=O)C(F)F)c2)ncn1] | $^1$H-NMR (600.1 MHz, d6-DMSO) δ = 9.6028 (3.2); 9.5911 (3.4); 9.2457 (7.9); 9.2438 (8.2); 9.1193 (0.8); 9.1114 (2.4); 9.1033 (2.4); 9.0955 (0.8); 8.4435 (3.8); 8.4406 (6.4); 8.4379 (4.2); 8.3583 (3.8); 8.3558 (6.9); 8.3534 (3.9); 8.3015 (8.0); 8.3086 (8.3); 8.1811 (3.5); 8.1781 (6.1); 8.1752 (3.4); 7.4974 (2.0); 7.4108 (4.8); 7.3242 (2.4); 6.2527 (0.5); 6.2413 (2.4); 6.2296 (3.7); 6.2180 (2.4); 6.2064 (0.5); 3.3187 (46.8); 2.8659 (16.0); 2.8578 (16.0); 2.6182 (0.4); 2.6152 (0.6); 2.6122 (0.4); 2.5242 (1.2); 2.51212 (1.4); 2.5181 (1.4); 2.5092 (31.1); 2.5062 (68.9); 2.5032 (97.0); 2.5002 (69.9); 2.4972 (32.0); 2.3901 (0.4); 2.3871 (0.6); 2.3840 (0.4); 2.1324 (0.6); 2.1243 (1.4); 2.1185 (1.4); 2.1165 (1.1); 2.1105 (2.8); 2.1024 (1.6); 2.0966 (1.5); 2.0885 (0.8); 2.0750 (0.8); 1.6350 (12.3); 1.6234 (12.3); 1.2597 (0.1); 0.10500 (0.3); 1.0464 (0.2); 1.0417 (0.2); 1.0319 (1.8); 1.0268 (4.0); 1.0187 (1.7); 1.0128 (4.0); 0.9956 (0.3); 0.9916 (0.4); 0.9388 (0.5); 0.9354 (0.6); 0.9310 (0.8); 0.9272 (0.7); 0.9199 (2.0); 0.9177 (1.8); 0.9118 (2.2); 0.9095 (1.8); 0.9078 (1.7); 0.9032 (1.9); 0.8993 (1.9); 0.8952 (1.9); 0.8912 (1.9); 0.8835 (0.6); 0.8805 (0.8); 0.8757 (0.5); 0.8723 (0.4); 0.0967 (0.4); 0.0053 (2.3); −0.0001 (81.8); −0.0056 (2.5); −0.1003 (0.4) | 540.2 |
| I-176 | 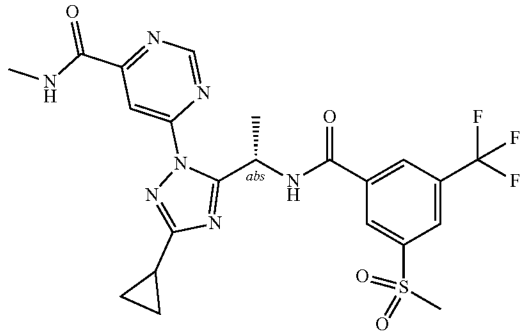 [SMILES: CNC(=O)c1cc(-n2nc(C3CC3)nc2[C@H](C)NC(=O)c2cc(C(F)(F)F)cc(S(C)(=O)=O)c2)ncn1] | $^1$H-NMR (600.1 MHz, d6-DMSO) δ = 9.6310 (3.0); 9.6192 (3.0); 9.2586 (9.2); 9.2567 (8.9); 9.1215 (0.7); 9.1136 (2.1); 9.1054 (2.1); 9.0974 (0.7); 8.6474 (5.1); 8.5095 (4.4); 8.4032 (4.2); 8.4024 (4.2); 8.3119 (9.2); 8.3099 (8.8); 6.2860 (0.5); 6.2745 (2.2); 6.2629 (3.6); 6.2511 (2.3); 6.2395 (0.4); 4.0235 (0.1); 3.4938 (0.2); 3.3798 (33.1); 3.3567 (1.1); 3.3520 (0.1); 3.3478 (0.2); 3.3169 (246.4); 3.2624 (0.1); 2.8646 (15.9); 2.8565 (16.0); 2.6198 (0.5); 2.6169 (1.2); 2.6138 (1.7); 2.6107 (1.2); 2.6077 (0.5); 2.5383 (0.2); 2.5228 (3.5); 2.5197 (4.3); 2.5166 (4.0); 2.5079 (84.4); 2.5048 (187.8); 2.5017 (262.5); 2.4987 (184.9); 2.4956 (81.0); 2.4723 (0.2); 2.3919 (0.5); 2.3887 (1.2); 2.3856 (1.7); 2.3825 (1.2); 2.3796 (0.5); 2.1322 (0.6); 2.1241 (1.3); 2.1184 (1.4); 2.1162 (1.0); 2.1103 (2.8); 2.1045 (0.9); 2.1022 (1.6); 2.0965 (1.5); 2.0883 (0.7); 2.0737 (3.0); 1.9886 (0.6); 1.6516 (11.4); 1.6400 (11.5); 1.2328 (0.1); 1.1872 (0.2); 1.1753 (0.3); 1.1635 (0.2); 1.0492 (0.3); | 538.2 |

TABLE 1-continued
| Example | Structure[1)] | NMR Peak List[2)] | ESI Mass (m/z)[3)] |
|---|---|---|---|
| | | 1.0463 (0.2); 1.0425 (0.3); 1.0313 (1.8); 1.0272 (3.5); 1.0260 (3.7); 1.0233 (2.1); 1.0174 (1.8); 1.0120 (4.0); 1.0095 (2.2); 1.0049 (0.5); 0.9977 (0.4); 0.9944 (0.3); 0.9910 (0.4); 0.9500 (0.1); 0.9395 (0.4); 0.9362 (0.6); 0.9317 (0.7); 0.9280 (0.6); 0.9208 (1.8); 0.9180 (1.4); 0.9165 (1.5); 0.9128 (2.0); 0.9080 (2.6); 0.9026 (1.6); 0.8995 (1.6); 0.8943 (1.5); 0.8873 (0.5); 0.8841 (0.7); 0.8792 (0.5); 0.8759 (0.3); 0.0968 (0.9); 0.0054 (7.1); −0.0001 (268.3); −0.0057 (7.7); −0.0323 (0.1); −0.1003 (0.9) | |
| I-177 | 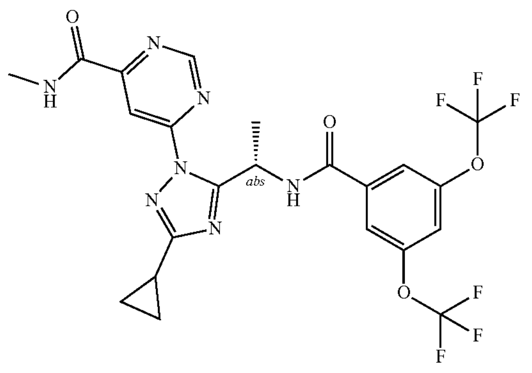 [SMILES: CNC(=O)c1cc(-n2nc(C3CC3)nc2[C@H](C)NC(=O)c2cc(OC(F)(F)F)cc(OC(F)(F)F)c2)ncn1] | $^1$H-NMR (600.1 MHz, d6-DMSO) δ = 9.4239 (3.2); 9.4122 (3.3); 9.2404 (8.2); 9.2385 (8.0); 9.1198 (0.8); 9.1119 (2.3); 9.1038 (2.3); 9.0958 (0.7); 8.3149 (0.3); 8.3080 (8.2); 8.3062 (8.0); 7.9549 (0.3); 7.8733 (8.0); 7.8701 (8.2); 7.7499 (3.4); 6.2237 (0.5); 6.2122 (2.3); 6.2005 (3.7); 6.1189 (2.4); 6.1772 (0.5); 3.3497 (0.1); 3.3213 (69.8); 3.3203 (80.5); 2.8932 (2.6); 2.8660 (16.0); 2.8579 (15.9); 2.7339 (2.0); 2.6223 (0.2); 2.6191 (0.4); 2.6161 (0.6); 2.6130 (0.4); 2.6100 (0.2); 2.5251 (1.2); 2.5220 (1.5); 2.5189 (1.4); 2.5101 (30.8); 2.5071 (67.5); 2.5041 (94.2); 2.5010 (66.9); 2.4980 (30.1); 2.4769 (0.1); 2.3939 (0.2); 2.3909 (0.4); 2.3879 (0.6); 2.3848 (0.4); 2.3819 (0.2); 2.1300 (0.6); 2.1220 (1.4); 2.1162 (1.4); 2.1141 (1.0); 2.1082 (2.8); 2.1001 (1.6); 2.0943 (1.5); 2.0861 (0.8); 1.9900 (0.2); 1.6280 (12.3); 1.6164 (12.4); 1.2601 (0.1); 1.2325 (0.1); 1.1768 (0.1); 1.0484 (0.3); 1.0446 (0.2); 1.0400 (0.2); 1.0324 (1.4); 1.0298 (1.6); 1.0266 (3.5); 1.0250 (3.7); 1.0193 (2.0); 1.0128 (3.2); 1.0110 (3.8); 1.0061 (1.4); 0.9974 (0.2); 0.9938 (0.2); 0.9901 (0.4); 0.9453 (0.1); 0.9352 (0.5); 0.9317 (0.7); 0.9274 (1.0); 0.9238 (0.8); 0.9148 (1.8); 0.9121 (1.4); 0.9069 (2.0); 0.9040 (1.3); 0.8987 (0.6); 0.8888 (1.7); 0.8843 (1.4); 0.8804 (1.8); 0.8722 (1.0); 0.8690 (0.9); 0.8644 (0.6); 0.8607 (0.4); 0.0968 (0.2); 0.0053 (1.3); −0.0001 (45.9); −0.0057 (1.4); −0.1001 (0.2) | 560.2 |

TABLE 1-continued
| Example | Structure[1)] | NMR Peak List[2)] | ESI Mass (m/z)[3)] |
|---|---|---|---|
| I-178 | 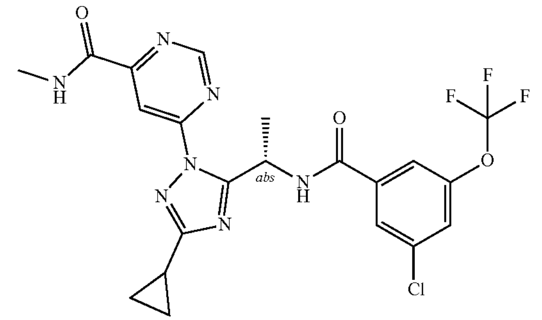 [SMILES: CNC(=O)c1cc(-n2nc(C3CC3)nc2[C@H](C)NC(=O)c2cc(Cl)cc(OC(F)(F)F)c2)ncn1] | $^1$H-NMR (600.1 MHz, d6-DMSO) δ = 20.2466 (0.1); 9.3512 (3.1); 9.3395 (3.2); 9.2384 (8.2); 9.2364 (8.1); 9.1217 (0.7); 9.1141 (2.2); 8.1060 (2.2); 9.0980 (0.7); 8.3084 (0.5); 8.3043 (8.2); 8.3024 (8.0); 7.9725 (3.9); 7.9698 (6.2); 7.9671 (4.1); 7.9527 (0.6); 7.7764 (3.6); 7.7523 (3.7); 7.7507 (4.0); 6.2088 (0.5); 6.1974 (2.3); 6.1858 (3.6); 6.1741 (2.3); 6.1624 (0.5); 3.4413 (0.3); 3.4238 (0.4); 3.4128 (0.5); 3.3609 (595.7); 3.3584 (1495.0); 3.3176 (0.4); 3.3099 (0.5); 3.2854 (0.3); 3.2703 (0.1); 2.8932 (5.2); 2.8664 (16.0); 2.8583 (16.0); 2.7338 (3.9); 2.6205 (0.7); 2.6175 (1.0); 2.6144 (0.7); 2.5264 (2.2); 2.5233 (2.6); 2.5202 (2.6); 2.5115 (50.1); 2.5085 (110.0); 2.5054 (153.2); 2.5023 (108.4); 2.4993 (48.3); 2.3923 (0.7); 2.3893 (1.0); 2.3862 (0.7); 2.1278 (0.6); 2.1197 (1.3); 2.1139 (1.4); 2.1118 (1.0); 2.1059 (2.8); 2.0978 (1.6); 2.0920 (1.4); 2.0839 (0.7); 2.0732 (2.5); 1.6171 (12.2); 1.6055 (12.2); 1.0583 (0.1); 1.0489 (0.3); 1.0327 (1.4); 1.0276 (3.3); 1.0253 (3.7); 1.0210 (1.7); 1.0189 (1.6); 1.0138 (3.1); 1.0114 (3.8); 1.0073 (1.5); 0.9909 (0.4); 0.9337 (0.5); 0.9304 (0.7); 0.9259 (0.9); 0.9224 (0.8); 0.9134 (1.9); 0.9108 (1.3); 0.9053 (2.0); 0.9026 (1.3); 0.8987 (0.5); 0.8923 (1.3); 0.8886 (1.8); 0.8842 (1.4); 0.8801 (1.6); 0.8717 (0.9); 0.8686 (0.9); 0.8640 (0.6); 8.606 (0.4); 0.0969 (0.4); 0.0053 (3.0); −0.0001 (101.2); −0.0057 (3.0); −0.1002 (0.4) | 510.1 |
| I-179 | 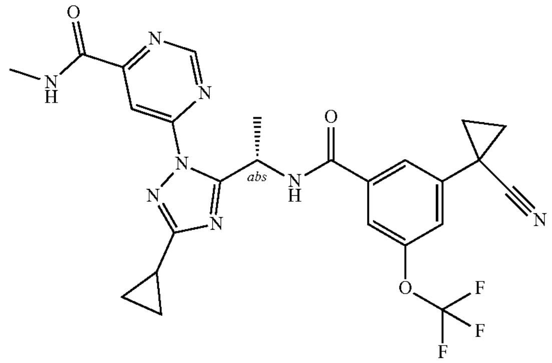 [SMILES: CNC(=O)c1cc(-n2nc(C3CC3)nc2[C@H](C)NC(=O)c2cc(OC(F)(F)F)cc(C3(C#N)CC3)c2)ncn1] | $^1$H-NMR (600.1 MHz, d6-DMSO) δ = 9.3318 (3.3); 9.3199 (3.4); 9.2430 (8.2); 9.2412 (8.0); 9.1213 (0.8); 9.1135 (2.4); 9.1053 (2.4); 0.0973 (0.8); 8.3148 (0.2); 8.3062 (8.5); 8.3044 (8.1); 7.9538 (0.3); 7.7896 (3.8); 7.7871 (6.4); 7.7847 (3.9); 7.7127 (4.2); 7.4740 (4.3); 6.2205 (0.5); 6.2091 (2.3); 6.1974 (3.6); 6.1857 (2.3); 6.1740 (0.5); 3.3205 (50.0); 3.3191 (53.5); 2.8922 (2.9); 2.8660 (16.0); 2.8579 (16.0); 2.7329 (2.3); 2.6211 (0.2); 2.6181 (0.5); 2.6151 (0.7); 2.6121 (0.5); 2.6091 (0.2); 2.5241 (1.4); 2.5210 (1.8); 2.5179 (1.7); 2.5091 (37.8); 2.5061 (82.6); 2.5030 (115.0); 2.5000 (81.8); 2.4970 (37.0); 2.4733 (0.1); 2.3931 (0.2); 2.3899 (0.5); 2.3869 (0.7); 2.3838 (0.5); 2.1292 (0.6); 2.1211 (1.3); 2.1153 (1.4); 2.1073 (2.8); 2.0992 (1.6); 2.0934 (1.4); 2.0852 (0.8); 2.0751 (0.2); 1.8735 (0.1); 1.8550 (0.1); 1.8454 (2.6); | 541.2 |

TABLE 1-continued
| Example | Structure[1)] | NMR Peak List[2)] | ESI Mass (m/z)[3)] |
|---|---|---|---|
| | | 1.8377 (5.3); 1.8334 (6.7); 1.8309 (3.2); 1.8263 (3.2); 1.8160 (0.2); 1.8073 (0.1); 1.7974 (0.2); 1.6765 (0.3); 1.6612 (0.2); 1.6580 (0.4); 1.6485 (3.6); 1.6448 (3.1); 1.6410 (4.7); 1.6381 (4.2); 1.6355 (4.2); 1.6290 (14.9); 1.6173 (12.4); 1.6026 (0.3); 1.2592 (0.1); 1.0436 (0.6); 1.0332 (0.9); 1.0250 (3.4); 1.0228 (3.8); 1.0189 (1.7); 1.0159 (1.7); 1.0112 (3.2); 1.0088 (3.9); 1.0052 (1.6); 0.9948 (0.2); 0.9921 (0.2); 0.9890 (0.5); 0.9535 (0.1); 0.9458 (0.1); 0.9355 (0.5); 0.9322 (0.7); 0.9276 (0.9); 0.9241 (0.8); 0.9154 (2.0); 0.9125 (1.5); 0.9073 (2.1); 0.9044 (1.4); 0.8961 (1.4); 0.8920 (1.8); 0.8881 (1.5); 0.8839 (1.7); 0.8755 (0.8); 0.8726 (0.9); 0.8678 (0.6); 0.8645 (0.4); 0.0969 (0.2); 0.0053 (1.7); −0.0001 (59.9); −0.0057 (1.9); −0.1002 (0.3) | |
| I-180 | 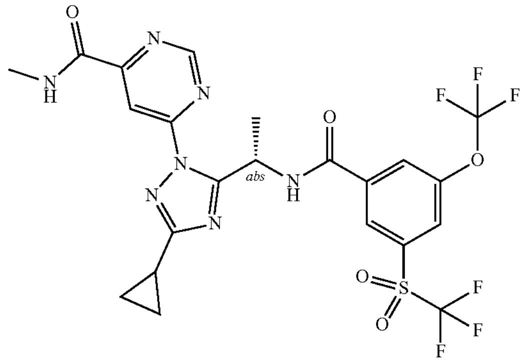 [SMILES: CNC(=O)c1cc(-n2nc(C3CC3)nc2[C@H](C)NC(=O)c2cc(OC(F)(F)F)cc(S(=O)(=O)C(F)(F)F)c2)ncn1] | $^1$H-NMR (600.1 MHz, d6-DMSO) δ = 9.7444 (3.0); 9.7327 (3.1); 9.2452 (8.6); 9.2433 (8.3); 9.1185 (0.8); 9.1105 (2.2); 9.1023 (2.2); 9.0945 (0.7); 8.6017 (5.4); 8.4300 (3.8); 8.3609 (3.4); 8.3141 (0.8); 8.3101 (8.6); 8.3082 (8.3); 7.9530 (0.4); 6.2716 (0.5); 6.2597 (2.3); 6.2481 (3.6); 6.2364 (2.3); 6.2247 (0.4); 4.0354 (0.3); 4.0237 (0.3); 3.3163 (205.4); 2.8914 (3.5); 2.8638 (16.0); 2.8557 (16.0); 2.7317 (2.6); 2.6170 (1.5); 2.6139 (2.2); 2.6109 (1.5); 2.5229 (4.4); 2.5198 (5.3); 2.5167 (5.0); 2.5080 (104.3); 2.5049 (230.1); 2.5109 (321.9); 2.4988 (227.2); 2.4957 (100.6); 2.3888 (1.5); 2.3858 (2.0); 2.3826 (1.4); 2.1337 (0.6); 2.1257 (1.4); 2.1199 (1.4); 2.1119 (2.7); 2.1037 (1.6); 2.0980 (1.4); 2.0899 (0.7); 1.9887 (1.2); 1.6494 (11.8); 1.6378 (11.8); 1.2592 (0.7); 1.1873 (0.4); 1.1755 (0.7); 1.1635 (0.4); 1.0521 (0.3); 1.0355 (1.3); 1.0333 (1.4); 1.0285 (4.2); 1.0253 (1.8); 1.0221 (2.1); 1.0144 (4.2); 1.0114 (1.9); 1.0087 (1.4); 0.9923 (0.4); 0.9390 (0.5); 0.9354 (0.7); 0.9311 (0.9); 0.9272 (0.7); 0.9198 (1.8); 0.9155 (1.8); 0.9117 (1.9); 0.9074 (1.7); 0.9005 (1.7); 0.8957 (1.8); 0.8924 (1.8); 0.8876 (1.8); 0.8799 (0.8); 0.8768 (0.8); 0.8721 (0.6); 0.8684 (0.4); 0.0968 (1.4); 0.0053 (10.4); −0.0001 (386.1); −0.0057 (11.7); −0.1003 (1.5) | 608.2 |

TABLE 1-continued
| Example | Structure[1)] | NMR Peak List[2)] | ESI Mass (m/z)[3)] |
|---|---|---|---|
| I-181 | 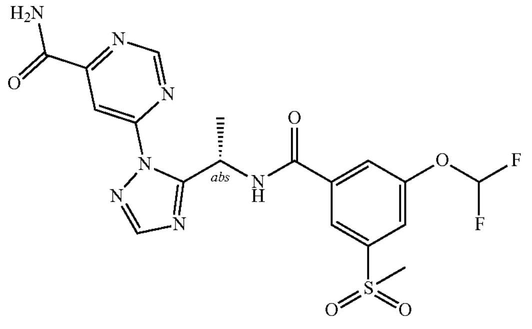 [SMILES: C[C@H](NC(=O)c1cc(OC(F)F)cc(S(C)(=O)=O)c1)c1ncnn1-c1cc(C(N)=O)ncn1] | $^1$H-NMR (600.1 MHz, d6-DMSO) δ = 9.5280 (4.1); 9.5163 (4.2); 9.3687 (0.1); 9.3570 0.1); 9.3214 (11.5); 9.3194 (11.3); 8.5296 (0.1); 8.4990 (0.1); 8.4916 (0.1); 8.4558 (4.0); 8.4260 (0.1); 8.4055 (0.1); 8.3844 (11.3); 8.3825 (11.0); 8.3669 (0.2); 8.3435 (0.1); 8.3253 (15.3); 8.3135 (0.6); 8.2893 (5.7); 8.2868 (10.1); 8.2844 (5.6); 8.1772 (0.2); 8.1191 (3.9); 7.9533 (4.4); 7.9498 (5.7); 7.9472 (4.4); 7.8690 (4.6); 7.8660 (5.8); 7.8626 (3.9); 7.5482 (3.7); 7.4264 (8.2); 7.3046 (4.0); 6.5282 (0.1); 6.3046 (0.6); 6.2929 (2.8); 6.2813 (4.3); 6.2696 (2.8); 6.2581 (0.6); 4.6463 (0.2); 3.7137 (0.1); 3.7053 (0.1); 3.6802 (0.1); 3.6718 (0.1); 3.5940 (0.3); 3.4264 (0.2); 3.3641 (0.1); 3.3174 (171.9); 3.3127 (53.1); 3.2773 (0.1); 3.2341 (0.1); 3.1950 (0.2); 2.8844 (1.2); 2.6197 (0.6); 2.6168 (1.3); 2.6138 (1.8); 2.6107 (1.3); 2.6076 (0.6); 2.5228 (4.0); 2.5197 (5.1); 2.5166 (5.4); 2.5078 (95.2); 2.5048 (202.0); 2.5017 (277.5); 2.4987 (198.6); 2.4956 (90.2); 2.4743 (0.4); 2.3917 (0.6); 2.3887 (1.3); 2.3856 (1.8); 2.3825 (1.3); 2.3797 (0.6); 1.6756 (16.0); 1.6640 (16.0); 1.5653 (0.1); 1.5546 (0.1); 1.1866 (0.1); 0.0968 (0.9); 0.0053 (8.4); −0.0001 (244.2); −0.0057 (8.3); −0.0363 (0.2); −0.1003 (0.9) | 482.1 |
| I-182 | 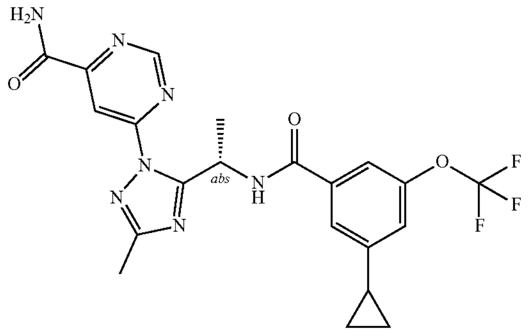 [SMILES: Cc1nc([C@H](C)NC(=O)c2cc(OC(F)(F)F)cc(C3CC3)c2)n(-c2cc(C(N)=O)ncn2)n1] | $^1$H-NMR (400.2 MHz, $d_6$-DMSO): δ = 9.2645 (4.3); 9.2616 (4.4); 9.2241 (1.6); 9.2063 (1.6); 8.4488 (1.6); 8.3377 (4.2); 8.3349 (4.2); 8.1090 (1.6); 7.5475 (4.6); 7.5442 (4.6); 7.2836 (2.2); 6.2430 (1.1); 6.2255 (1.7); 6.2080 (1.1); 3.3341 (5.4); 2.5289 (0.4); 2.5242 (0.5); 2.5154 (7.9); 2.5109 (17.0); 2.5063 (23.0); 2.5018 (16.5); 2.4973 (7.8); 2.3718 (16.0); 2.2124 (0.8); 2.0756 (0.4); 2.0632 (0.7); 2.0547 (0.7); 2.0511 (0.6); 2.0423 (1.3); 2.0299 (0.8); 2.0214 (0.7); 2.0088 (0.4); 1.6400 (5.9); 1.6226 (5.8); 1.3899 (0.4); 1.3720 (0.3); 1.0494 (0.9); 1.0382 (2.4); 1.0326 (2.6); 1.0221 (1.3); 1.0173 (2.3); 1.0117 (2.3); 1.0014 (1.0); 0.8008 (1.1); 0.7901 (2.5); 0.7850 (2.5); 0.7778 (2.4); 0.7727 (2.7); 0.7612 (0.9); −0.0002 (0.4) | 476.1 |

TABLE 1-continued
| Example | Structure[1)] | NMR Peak List[2)] | ESI Mass (m/z)[3)] |
|---|---|---|---|
| I-183 | 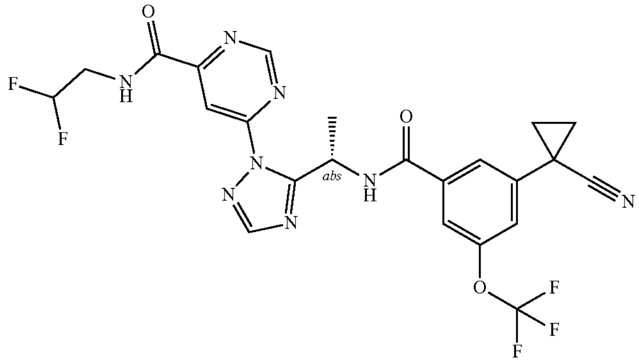 [SMILES: C[C@H](NC(=O)c1cc(OC(F)(F)F)cc(C2(C#N)CC2)c1)c1ncnn1-c1cc(C(=O)NCC(F)F)ncn1] | $^1$H-NMR (600.1 MHz, $d_6$-DMSO): δ = 9.7810 (4.4); 9.0664 (4.6); 9.0078 (1.0); 8.6665 (5.5); 8.5454 (0.1); 8.5344 (0.1); 8.4182 (1.2); 8.4061 (1.2); 8.3735 (0.1); 8.2720 (3.9); 8.1981 (2.9); 8.0053 (0.1); 7.9816 (2.8); 6.9298 (0.3); 6.9181 (1.3); 6.9062 (2.0); 6.8944 (1.3); 6.8828 (0.4); 6.7448 (0.4); 6.7385 (0.7); 6.7321 (0.4); 6.6520 (0.8); 6.6457 (1.5); 6.6393 (0.8); 6.5591 (0.4); 6.5528 (0.8); 6.5465 (0.4); 6.0361 (5.8); 4.6666 (0.1); 4.6547 (0.4); 4.6428 (0.4); 4.6310 (0.1); 4.4555 (0.7); 4.4490 (0.8); 4.4450 (0.8); 4.4385 (0.8); 4.4301 (1.4); 4.4235 (1.6); 4.4194 (1.6); 4.4129 (1.4); 4.4045 (0.8); 4.3978 (0.8); 4.3939 (0.8); 4.3873 (0.7); 2.7363 (16.0); 2.6482 (0.4); 2.6442 (0.4); 2.6402 (0.5); 2.6362 (0.4); 2.6149 (0.1); 2.6104 (0.1); 2.6062 (0.1); 2.5772 (0.1); 2.5613 (1.8); 2.5536 (1.7); 2.5372 (21.8); 2.5333 (38.5); 2.5293 (53.9); 2.5253 (38.1); 2.5213 (20.9); 2.4779 (0.1); 2.4224 (0.2); 2.4184 (0.3); 2.4138 (0.4); 2.4103 (0.3); 2.4062 (0.2); 2.3883 (1.7); 2.3792 (4.8); 2.3751 (4.7); 2.3662 (1.9); 2.3406 (0.2); 2.2828 (8.6); 2.2712 (8.7); 2.2307 (0.2); 2.2189 (0.2); 2.1585 (0.2); 2.1457 (0.1); 2.1324 (1.9); 2.1238 (4.9); 2.1196 (4.8); 2.1103 (1.6); 2.0859 (0.2); 1.9757 (0.2); 1.8741 (0.2); 1.8587 (0.8); 1.8364 (0.2); 1.8170 (0.1); 1.8053 (0.5); 1.7934 (0.9); 1.7816 (0.5); 1.6958 (0.2); 1.4710 (0.2); 1.4592 (0.2); 0.5894 (0.5) | 551.2 |
| I-184 | 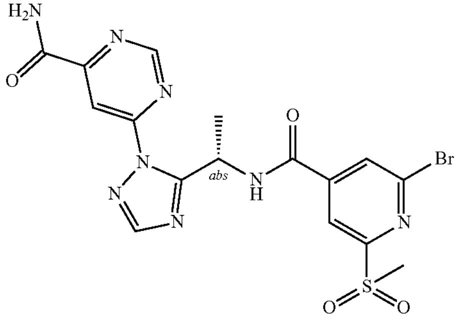 [SMILES: C[C@H](NC(=O)c1cc(Br)nc(S(C)(=O)=O)c1)c1ncnn1-c1cc(C(N)=O)ncn1] | $^1$H-NMR (600.4 MHz, $d_6$-DMSO): δ = 9.7884 (3.1); 9.7768 (3.2); 9.3104 (8.2); 9.3085 (8.0); 8.4432 (2.9); 8.4116 (8.8); 8.4096 (9.0); 8.3831 (8.6); 8.3812 (8.2); 8.3368 (16.0); 8.3093 (0.4); 8.1683 (0.3); 8.1078 (2.8); 6.2986 (0.4); 6.2873 (2.2); 6.2756 (3.4); 6.2640 (2.2); 6.2523 (0.5): 4.3846 (0.4); 4.3728 (0.3); 3.3321 (41.9); 3.3051 (110.2); 3.2830 (0.4); 3.2516 (1.0); 2.7969 (1.6); 2.6190 (0.4); 2.6159 (1.0); 2.6129 (1.5); 2.6100 (1.0); 2.6068 (0.4); 2.5220 (2.9); 2.5189 (3.6); 2.5158 (3.5); 2.5070 (71.0); 2.5040 (158.5); 2.5009 (222.5); 2.4979 (159.1); 2.4948 (72.4); 2.4761 (0.8); 2.4130 (0.3); 2.3911 (0.5); 2.3880 (1.0); 2.3849 (1.5); 2.3891 (1.0); 2.3785 (0.5); 2.0716 (0.5); 1.6669 (12.5); 1.6554 (12.7); 1.3551 (0.3); 1.3432 (0.8); 1.3313 (0.3); 0.0052 (2.3); −0.0002 (86.3); −0.0057 (2.8); −0.1003 (0.4) | 497.0 |

TABLE 1-continued
| Example | Structure[1)] | NMR Peak List[2)] | ESI Mass (m/z)[3)] |
|---|---|---|---|
| I-185 | 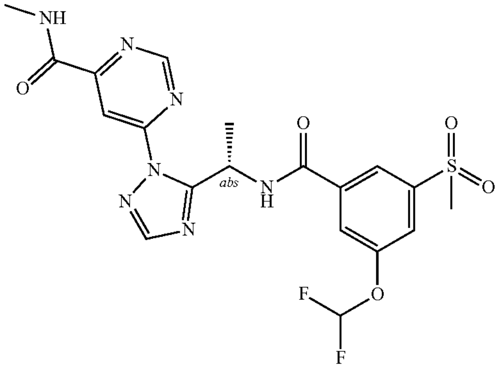 [SMILES: CNC(=O)c1cc(-n2ncnc2[C@H](C)NC(=O)c2cc(OC(F)F)cc(S(C)(=O)=O)c2)ncn1] | $^1$H-NMR (400.2 MHz, $d_6$-DMSO): δ = 9.5390 (3.5); 9.5215 (3.6); 9.3252 (8.9); 9.3224 (8.9); 9.1636 (0.9); 9.1521 (2.6); 9.1400 (2.6); 9.1281 (0.8); 8.3787 (8.4); 8.3759 (8.4); 8.3308 (13.4); 8.2875 (4.4); 8.2840 (8.1); 8.2805 (4.6); 8.1469 (1.3); 7.9532 (3.5); 7.9485 (5.0); 7.9448 (4.0); 7.8734 (3.8); 7.8690 (5.1); 7.8642 (3.3); 7.6121 (3.7); 7.4294 (8.0); 7.2468 (4.0); 6.3158 (0.5); 6.2989 (2.2); 6.2815 (3.5); 6.2641 (2.2); 6.2469 (0.4); 3.3292 (55.8); 3.3146 (42.0); 2.8733 (16.0); 2.8611 (15.9); 2.6763 (0.7); 2.6718 (0.9); 2.6673 (0.7); 2.5253 (2.6); 2.5206 (3.6); 2.5118 (46.4); 2.5074 (97.2); 2.5028 (130.7); 2.4983 (93.4); 2.4939 (43.7); 2.3343 (0.6); 2.3296 (0.9); 2.3250 (0.6); 1.6778 (12.8); 1.6604 (12.8); 0.1462 (0.3); 0.0080 (2.3); −0.0002 (75.6); −0.0085 (2.3); −0.1494 (0.3); | 496.1 |
| I-186 | 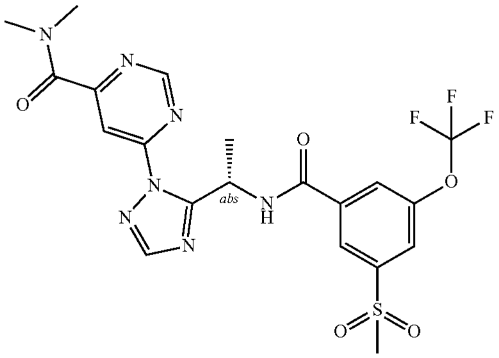 [SMILES: C[C@H](NC(=O)c1cc(OC(F)(F)F)cc(S(C)(=O)=O)c1)c1ncnn1-c1cc(C(=O)N(C)C)ncn1] | $^1$H-NMR (400.2 MHz, $d_6$-DMSO) δ = 9.6268 (1.3); 9.6095 (1.4); 9.2579 (3.1); 9.2551 (3.4); 8.4699 (1.7); 8.4665 (3.0); 8.4631 (1.9); 8.3091 (4.9); 8.1506 (1.9); 8.1485 (1.8); 8.0891 (1.8); 8.0360 (3.2); 8.0331 (3.4); 6.2853 (0.9); 6.2681 (1.4); 6.2508 (0.9); 3.3607 (14.3); 3.3262 (35.3); 3.0417 (13.7); 2.9544 (16.0); 2.6756 (0.5); 2.6710 (0.7); 2.6666 (0.6); 2.5245 (1.9); 2.5198 (2.6); 2.5109 (33.5); 2.5066 (70.2); 2.5021 (94.7); 2.4976 (68.8); 2.4933 (33.2); 2.3335 (0.5); 2.3290 (0.6); 2.3244 (0.5); 1.6872 (5.2); 1.6698 (5.2); 0.0079 (2.1); −0.0002 (66.4); −0.0084 (2.4) | 528.1 |

TABLE 1-continued
| Example | Structure[1)] | NMR Peak List[2)] | ESI Mass (m/z)[3)] |
|---|---|---|---|
| I-187 | 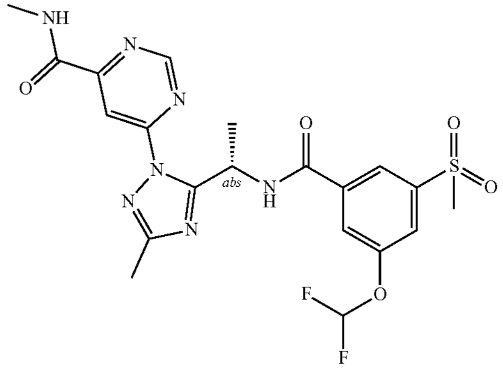 [SMILES: CNC(=O)c1cc(-n2nc(C)nc2[C@H](C)NC(=O)c2cc(OC(F)F)cc(S(C)(=O)=O)c2)ncn1] | $^{1}$H-NMR (400.2 MHz, $d_6$-DMSO) δ = 9.5222 (1.8); 9.5044 (1.8); 9.2828 (4.0); 9.2803 (4.3); 9.1448 (0.4); 9.1336 (1.3); 9.1213 (1.3); 9.1091 (0.4); 8.3360 (3.9); 8.3336 (4.2); 8.3098 (2.1); 8.3064 (3.8); 8.3032 (2.3); 7.9676 (2.5); 7.8743 (1.9); 7.8698 (2.6); 7.8654 (1.7); 7.6147 (1.7); 7.4321 (3.6) 7.2495 (1.8); 6.2986 (1.1); 6.2811 (1.8); 6.2636 (1.2); 3.3280 (36.2); 3.3186 (18.2); 2.8691 (7.7); 2.8570 (7.6); 2.6722 (0.4); 2.5255 (1.0); 2.5207 (1.4); 2.5120 (18.2); 2.5077 (38.3); 2.5033 (51.8); 2.4988 (37.5); 2.4945 (17.9); 2.3804 (16.0); 2.3301 (0.4); 2.0764 (0.5); 1.6565 (6.2); 1.6392 (6.1); −0.0002 (0.4) | 510.1 |
| I-188 | 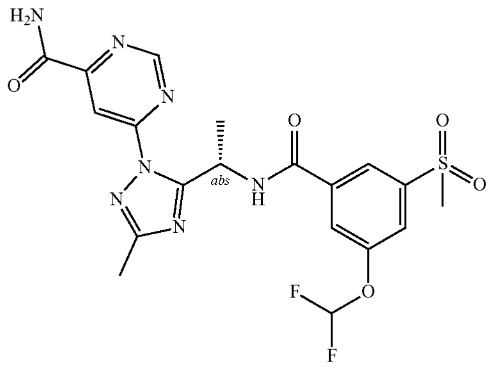 [SMILES: Cc1nc([C@H](C)NC(=O)c2cc(OC(F)F)cc(S(C)(=O)=O)c2)n(-c2cc(C(N)=O)ncn2)n1] | $^{1}$H-NMR (400.2 MHz, $d_6$-DMSO) δ = 9.5231 (1.6); 9.5053 (1.6); 9.2813 (4.2); 9.2785 (4.3); 8.4463 (1.7); 8.3445 (4.0); 8.3417 (4.2); 8.3137 (2.0); 8.3102 (3.7); 8.3067 (2.2); 8.1053 (1.6); 7.9696 (2.3); 7.9659 (1.9); 7.8735 (1.8); 7.8689 (2.5); 7.8644 (1.7); 7.6151 (1.7); 7.4324 (3.7); 7.2498 (1.8); 6.2987 (1.1); 6.2813 (1.8); 6.2637 (1.1); 3.3279 (50.1); 3.3192 (18.1); 2.6764 (0.3); 2.6720 (0.4); 2.6673 (0.3); 2.5254 (1.2); 2.5206 (1.8); 2.5119 (21.9); 2.5075 (46.4); 2.5029 (62.7); 2.4984 (45.0); 2.4940 (21.2); 2.3763 (16.0); 2.3297 (0.4); 2.0757 (1.2); 1.6569 (5.9); 1.6395 (5.8); −0.0002 (1.0) | 496.1 |

TABLE 1-continued
| Example | Structure[1)] | NMR Peak List[2)] | ESI Mass (m/z)[3)] |
|---|---|---|---|
| I-189 | 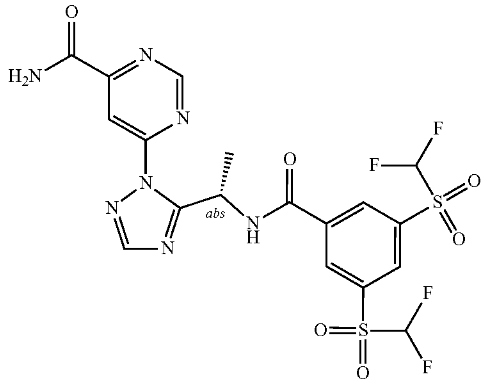 [SMILES: C[C@H](NC(=O)c1cc(S(=O)(=O)C(F)F)cc(S(=O)(=O)C(F)F)c1)c1ncnn1-c1cc(C(N)=O)ncn1] | $^{1}$H-NMR (400.2 MHz, $d_6$-DMSO) δ = 10.0304 (3.3); 10.0132 (3.5); 9.3238 (8.8); 9.3210 (9.3); 8.9390 (15.3); 8.9350 (16.0); 8.4986 (3.8); 8.4950 (6.8); 8.4663 (3.6); 8.3949 (8.6); 8.3922 (8.9); 8.3496 (14.0); 8.3171 (0.3); 8.1319 (3.5); 7.6398 (4.9); 7.5099 (11.6); 7.3802 (5.9); 6.3726 (0.5); 6.3556 (2.2); 6.3383 (3.4); 6.3210 (2.2); 6.3040 (0.5); 3.3279 (89.9); 2.6814 (0.4); 2.6768 (0.8); 2.6723 (1.1); 2.6678 (0.8); 2.5400 (0.3); 2.5257 (2.7); 2.5210 (4.1); 2.5122 (58.1); 2.5078 (123.7); 2.5033 (167.4); 2.4988 (120.8); 2.4945 (57.6); 2.3390 (0.4); 2.3346 (0.8); 2.3301 (1.1); 2.3256 (0.8); 2.0760 (8.7); 1.7042 (12.6); 1.6868 (12.6); 1.1787 (0.4); −0.0002 (10.6); −0.0085 (0.3) | 566.1 |
| I-190 | 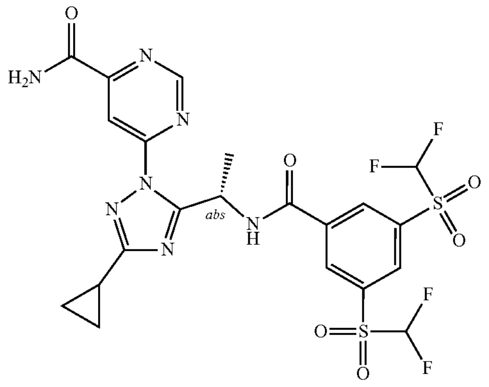 [SMILES: C[C@H](NC(=O)c1cc(S(=O)(=O)C(F)F)cc(S(=O)(=O)C(F)F)c1)c1nc(C2CC2)nn1-c1cc(C(N)=O)ncn1] | $^{1}$H-NMR (400.2 MHz, $d_6$-DMSO) δ = 9.9761 (3.5); 9.9585 (3.6); 9.2546 (9.3); 9.2519 (9.2); 8.9123 (16.0); 8.9084 (15.6); 8.4921 (7.3); 8.4414 (4.2); 8.3265 (0.4); 8.3238 (9.0); 8.1104 (4.1); 7.9532 (0.8); 7.6390 (4.9); 7.5091 (11.3); 7.3793 (5.8); 6.2354 (0.6); 6.3081 (2.4); 6.2907 (3.8); 6.2734 (2.4); 6.2560 (0.5); 3.8626 (0.3); 3.3629 (0.4); 3.3279 (170.0); 2.8915 (5.8); 2.7320 (4.8); 2.6760 (1.6); 2.6717 (2.2); 2.6673 (1.6); 2.5250 (6.5); 2.5071 (244.2); 2.5027 (315.8); 2.4983 (229.1); 2.3340 (1.6); 2.3296 (2.1); 2.3252 (1.5); 2.2886 (0.5); 2.1370 (0.6); 2.1246 (1.5); 2.1160 (1.7); 2.1039 (3.0); 2.0918 (1.9); 2.0833 (1.6); 2.0755 (0.7); 2.0710 (0.8); 1.6655 (13.1); 1.6481 (13.1); 1.0523 (0.6); 1.0348 (5.2); 1.0316 (5.6); 1.0144 (5.1); 1.0106 (5.2); 0.9963 (1.0); 0.9838 (0.6); 0.9494 (0.8); 0.9296 (2.0); 0.9241 (2.8); 0.9123 (4.6); 0.9072 (4.0); 0.8941 (2.0); 0.8823 (0.7); 0.8717 (0.5); 0.0078 (0.7); −0.0002 (19.8); −0.0084 (0.9) | 606.1 |

TABLE 1-continued
| Example | Structure[1)] | NMR Peak List[2)] | ESI Mass (m/z)[3)] |
|---|---|---|---|
| I-191 | 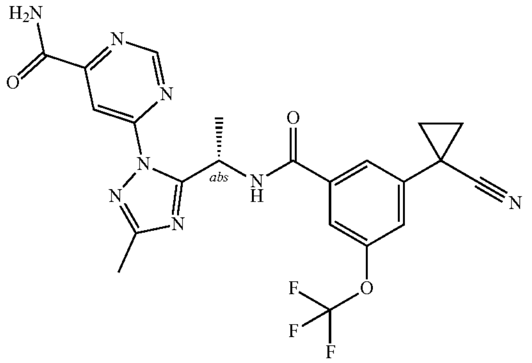 [SMILES: Cc1nc([C@H](C)NC(=O)c2cc(OC(F)(F)F)cc(C3(C#N)CC3)c2)n(-c2cc(C(N)=O)ncn2)n1] | $^1$H-NMR (400.2 MHz, $d_6$-DMSO) δ = 9.3800 (1.6); 9.3623 (1.6); 9.2667 (4.2); 9.2639 (4.6); 8.4452 (1.7); 8.3383 (4.1); 8.3355 (4.4); 8.1043 (1.7); 7.8407 (1.9); 7.8371 (3.4); 7.8335 (2.3); 7.7590 (2.3); 7.4847 (2.4); 6.2649 (1.1); 6.2473 (1.7); 6.2298 (1.1); 3.3287 (35.3); 2.6767 (0.4); 2.6720 (0.5); 2.6677 (0.4); 2.5255 (1.4); 2.5028 (2.1); 2.5119 (28.0); 2.5076 (59.6); 2.5031 (80.6); 2.4986 (59.2); 2.3737 (16.0); 2.3343 (0.4); 2.3299 (0.6); 2.3255 (0.4); 1.8529 (1.2); 1.8406 (3.3); 1.8331 (3.6); 1.8217 (1.6); 1.6612 (2.0); 1.6494 (9.4); 1.6419 (4.2); 1.6322 (6.4); −0.0002 (2.4) | 501.1 |
| I-192 | 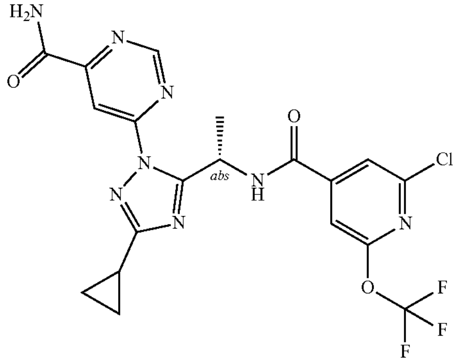 [SMILES: C[C@H](NC(=O)c1cc(Cl)nc(OC(F)(F)F)c1)c1nc(C2CC2)nn1-c1cc(C(N)=O)ncn1] | $^1$H-NMR (400.2 MHz, $d_6$-DMSO) δ = 9.5400 (4.2); 9.5225 (4.4); 9.2419 (10.1); 9.2392 (11.2); 8.4413 (4.8); 8.3134 (10.1); 8.3108 (11.2); 8.1086 (4.7); 7.9300 (12.0); 7.6304 (12.0); 6.2306 (0.6); 6.2136 (2.9); 6.1963 (4.6); 6.1789 (3.0); 6.1619 (0.6); 3.3276 (68.6); 2.6764 (0.9); 2.6722 (1.2); 2.6679 (1.0); 2.5255 (2.9); 2.5076 (133.3); 2.5033 (180.8); 2.4989 (137.9); 2.3343 (0.8); 2.3301 (1.2); 2.3256 (0.9); 2.1364 (0.7); 2.1241 (1.7); 2.1154 (2.0); 2.1035 (3.6); 2.0914 (2.2); 2.0828 (1.9); 2.0705 (1.0); 1.6221 (16.0); 1.6048 (16.0); 1.0524 (1.0); 1.0394 (4.6); 1.0336 (6.6); 1.0187 (4.6); 1.0129 (6.4); 1.0025 (1.5); 0.9895 (0.5); 0.9820 (0.4); 0.9582 (0.4); 0.9447 (0.6); 0.9284 (2.0); 0.9198 (4.9); 0.9154 (5.4); 0.9089 (6.5); 0.9033 (5.0); 0.8749 (0.4); −0.0002 (5.6) | 497.1 |

TABLE 1-continued
| Example | Structure[1)] | NMR Peak List[2)] | ESI Mass (m/z)[3)] |
|---|---|---|---|
| I-193 | 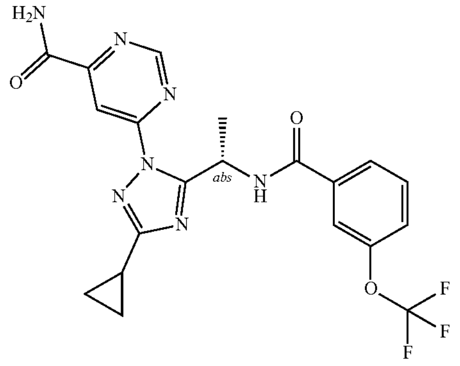 [SMILES: C[C@H](NC(=O)c1cccc(OC(F)(F)F)c1)c1nc(C2CC2)nn1-c1cc(C(N)=O)ncn1] | $^1$H-NMR (400.2 MHz, $d_6$-DMSO) δ = 9.2563 (4.5); 9.2461 (11.5); 9.2433 (12.9); 8.4417 (4.7); 8.3163 (10.6); 8.3137 (11.2); 8.1067 (4.6); 7.8871 (4.3); 7.8679 (4.9); 7.7775 (5.9); 7.6307 (3.0); 7.6106 (6.8); 7.5912 (5.0); 7.5605 (4.1); 7.5399 (2.0); 6.2272 (0.6); 6.2099 (2.9); 6.1924 (4.6); 6.1750 (2.9); 6.1576 (0.6); 3.3288 (115.6); 2.6765 (1.0); 2.6721 (1.4); 2.6677 (1.0); 2.5255 (3.7); 2.5206 (5.7); 2.5075 (148.8); 2.5031 (199.3); 2.4987 (147.9); 2.3344 (1.0); 2.3299 (1.3); 2.3258 (1.0); 2.1265 (0.8); 2.1143 (1.7); 2.1055 (1.9); 2.0936 (3.6); 2.0816 (2.2); 2.0729 (1.9); 2.0607 (0.9); 1.9897 (0.8); 1.6220 (16.0); 1.6046 (16.0); 1.1753 (0.4); 1.0544 (0.3); 1.0475 (0.3); 1.0264 (4.9); 1.0207 (6.8); 1.0057 (4.6); 0.9999 (7.1); 0.9802 (0.7); 0.9743 (0.6); 0.9361 (1.1); 0.9240 (1.2); 0.9115 (3.5); 0.8997 (3.5); 0.8912 (2.5); 0.8855 (3.1); 0.8788 (2.2); 0.8734 (2.9); 0.8563 (1.2); 0.8475 (0.7); −0.0002 (6.5) | 462.1 |
| I-194 | 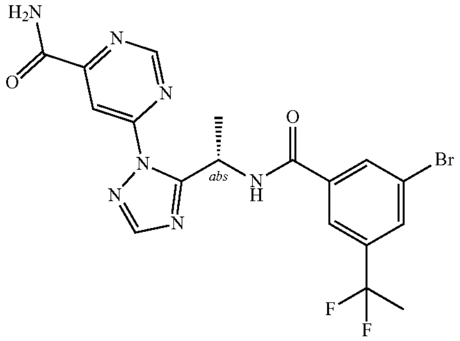 [SMILES: C[C@H](NC(=O)c1cc(Br)cc(C(C)(F)F)c1)c1ncnn1-c1cc(C(N)=O)ncn1] | $^1$H-NMR (400.2 MHz, $d_6$-DMSO) δ = 9.4034 (3.3); 9.3859 (3.4); 9.3155 (7.7); 9.3129 (8.5); 8.4689 (3.5); 8.3786 (7.6); 8.3761 (8.4); 8.3189 (12.5); 8.1599 (5.8); 8.1269 (3.4); 8.0021 (5.8); 7.9277 (5.5); 6.2819 (0.5); 6.2647 (2.1); 6.2474 (3.3); 6.2300 (2.1); 6.2129 (0.4); 3.3527 (0.4); 3.3286 (268.6); 2.8823 (0.4); 2.6757 (1.0); 2.6715 (1.5); 2.6670 (1.1); 2.5247 (3.4); 2.5068 (172.6); 2.5024 (233.0); 2.4980 (171.9); 2.3333 (1.1); 2.3292 (1.5); 2.3249 (1.1); 2.0440 (7.2); 1.9965 (16.0); 1.9488 (8.1); 1.6605 (12.2); 1.6431 (12.2); 0.1457 (0.6); 0.0079 (4.3); −0.0002 (138.6); −0.0083 (5.6); −0.0247 (0.4); −0.1498 (0.6) | 482.0 |

TABLE 1-continued
| Example | Structure[1)] | NMR Peak List[2)] | ESI Mass (m/z)[3)] |
|---|---|---|---|
| I-195 | 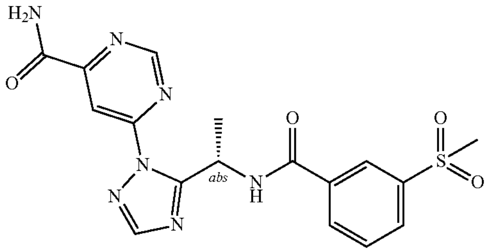 [SMILES: C[C@H](NC(=O)c1cccc(S(C)(=O)=O)c1)c1ncnn1-c1cc(C(N)=O)ncn1] | $^1$H-NMR (400.2 MHz, $d_6$-DMSO) δ = 9.4435 (4.0); 9.4259 (4.2); 9.3253 (10.4); 9.3225 (11.7); 8.4695 (4.3); 8.3963 (4.5); 8.3923 (8.2); 8.3848 (11.6); 8.3820 (11.7); 8.3218 (15.8); 8.1715 (4.0); 8.1683 (3.2); 8.1515 (4.5); 8.1488 (3.6); 8.1268 (4.2); 8.0956 (2.7); 8.0929 (3.6); 8.0916 (3.7); 8.0889 (3.1); 8.0761 (3.0); 8.0719 (4.2); 8.0693 (3.4); 7.7666 (4.1); 7.7470 (7.4); 7.7275 (3.5); 6.3125 (0.6); 6.2955 (2.7); 6.2781 (4.3); 6.2606 (2.7); 6.2430 (0.6); 3.3279 (149.9); 3.2596 (46.6); 2.6759 (1.0); 2.6714 (1.5); 2.6669 (1.1); 2.5249 (3.4); 2.5202 (5.0); 2.5112 (72.8); 2.5069 (157.6); 2.5024 (216.8); 2.4979 (161.0); 2.4937 (79.4); 2.3338 (1.0); 2.3293 (1.4); 2.3248 (1.1); 1.6744 (16.0); 1.6570 (16.0); 0.1458 (0.9); 0.0080 (6.3); −0.0002 (208.7); −0.0085 (8.0); −0.1497 (0.9) | 416.2 |
| I-196 | 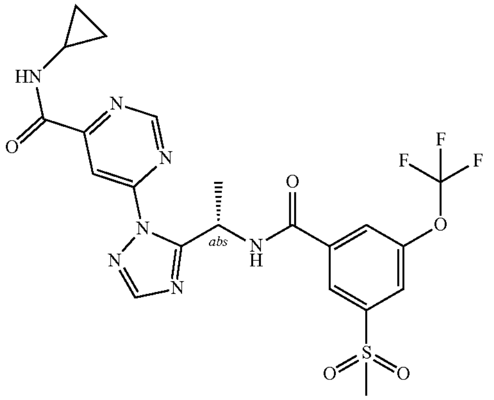 [SMILES: C[C@H](NC(=O)c1cc(OC(F)(F)F)cc(S(C)(=O)=O)c1)c1ncnn1-c1cc(C(=O)NC2CC2)ncn1] | $^1$H-NMR (400.2 MHz, $d_6$-DMSO) δ = 9.6144 (2.2); 9.5969 (2.3); 9.2926 (5.9); 9.2898 (6.1); 9.1655 (2.2); 9.1528 (2.3); 8.4548 (2.9); 8.4513 (5.3); 8.4478 (3.1); 8.3664 (5.8); 8.3636 (5.8); 8.3390 (9.1); 8.1311 (3.1); 8.1291 (3.0); 8.0873 (3.1); 6.2983 (1.5); 6.2809 (2.3); 6.2635 (1.5); 6.2461 (0.3); 3.3577 (24.8); 3.3274 (50.9); 2.9917 (0.9); 2.9778 (1.6); 2.9643 (1.5); 2.9500 (0.9); 2.6764 (0.6); 2.6717 (0.8); 2.6673 (0.6); 2.5253 (1.6); 2.5205 (2.5); 2.5117 (40.4); 2.5073 (85.4); 2.5028 (114.8); 2.4983 (82.6); 2.4939 (39.3); 2.3341 (0.5); 2.3296 (0.8); 2.3252 (0.6); 1.6794 (8.5); 1.6620 (8.5); 0.7404 (8.9); 0.7262 (16.0); −0.0002 (6.2) | 540.1 |

TABLE 1-continued
| Example | Structure[1)] | NMR Peak List[2)] | ESI Mass (m/z)[3)] |
|---|---|---|---|
| I-197 | 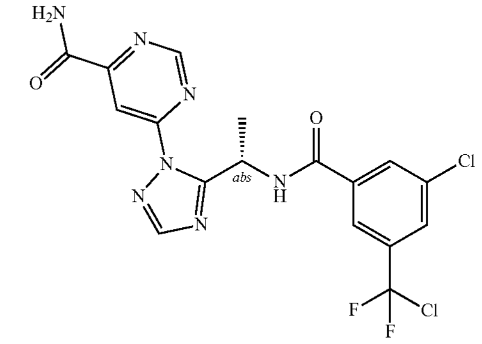 [SMILES: C[C@H](NC(=O)c1cc(Cl)cc(C(F)(F)Cl)c1)c1ncnn1-c1cc(C(N)=O)ncn1] | $^1$H-NMR (400.2 MHz, $d_6$-DMSO) δ = 9.6091 (0.6); 9.5097 (4.3); 9.4924 (4.4); 9.3154 (10.6); 9.3127 (10.7); 9.2917 (0.4); 9.2890 (0.4); 8.5863 (0.7); 8.5324 (0.8); 8.4689 (4.5); 8.3815 (10.5); 8.3789 (10.4); 8.3265 (15.8); 8.3177 (0.6); 8.3051 (0.4); 8.1820 (0.4); 8.1597 (7.8); 8.1287 (4.6); 8.1135 (8.2); 8.0270 (7.2); 7.5535 (0.5); 7.1487 (0.9); 6.2928 (0.6); 6.2755 (2.7); 6.2582 (4.3); 6.2407 (2.8); 6.2237 (0.6); 3.3310 (206.1); 3.1185 (2.0); 2.6773 (0.8); 2.6727 (1.1); 2.6682 (0.8); 2.5260 (2.8); 2.5122 (60.8); 2.5081 (126.0); 2.5037 (168.7); 2.4933 (122.9); 2.3349 (0.8); 2.3305 (1.1); 2.3263 (0.8); 2.0872 (1.7); 2.0071 (2.9); 1.9681 (2.9); 1.6688 (16.0); 1.6514 (15.9); 1.3538 (0.7); 1.3360 (0.7); 1.2590 (0.4); 1.2334 (0.8); 1.1466 (0.4); 1.1353 (0.4); 0.0080 (0.6); −0.0002 (18.3); −0.0084 (0.7) | 456.2 |
| I-198 | 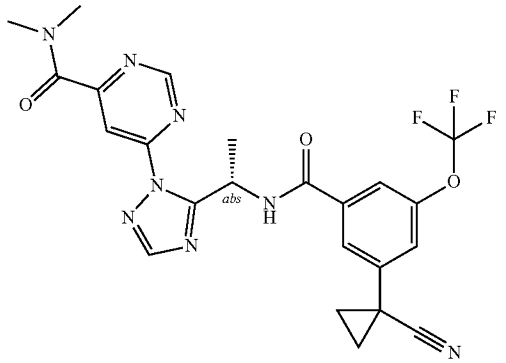 [SMILES: C[C@H](NC(=O)c1cc(OC(F)(F)F)cc(C2(C#N)CC2)c1)c1ncnn1-c1cc(C(=O)N(C)C)ncn1] | $^1$H-NMR (400.2 MHz, $d_6$-DMSO) δ = 9.4061 (1.3); 9.3889 (1.4); 9.2504 (3.4); 9.2476 (3.9); 8.2979 (5.2); 8.1490 (1.6); 8.0302 (3.5); 8.0273 (3.9); 7.8316 (2.9); 7.8283 (2.1); 7.7545 (2.0); 7.4838 (2.1); 6.2481 (0.9); 6.2307 (1.4); 6.2133 (0.9); 3.3323 (6.3); 3.0624 (1.4); 3.0421 (14.0); 2.9495 (16.0); 2.8497 (1.3); 2.6721 (0.4); 2.5256 (0.8); 2.5076 (43.4); 2.5031 (59.0); 2.4987 (44.2); 2.3297 (0.4); 2.0759 (1.2); 1.8559 (1.1); 1.8429 (3.3); 1.8357 (3.3); 1.8241 (1.4); 1.6762 (5.6); 1.6589 (5.8); 1.6523 (4.0); 1.6449 (3.3); 1.6312 (1.1); 1.3075 (0.6); 1.2900 (0.6); −0.0002 (6.8) | 515.3 |

TABLE 1-continued

| Example | Structure[1)] | NMR Peak List[2)] | ESI Mass (m/z)[3)] |
|---|---|---|---|
| I-199 | 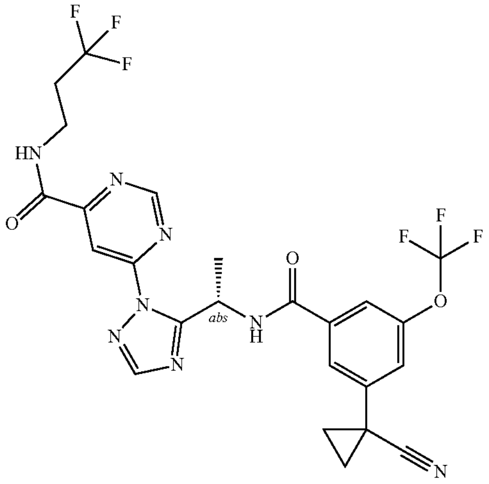 [SMILES: C[C@H](NC(=O)c1cc(OC(F)(F)F)cc(C2(C#N)CC2)c1)c1ncnn1-c1cc(C(=O)NCCC(F)(F)F)ncn1] | $^1$H-NMR (400.2 MHz, $d_6$-DMSO) δ = 9.3882 (4.5); 9.3711 (7.1); 9.3558 (1.8); 9.3343 (0.6); 9.3315 (10.1); 8.3779 (9.4); 8.3751 (9.9); 8.3324 (14.3); 8.3171 (0.3); 7.8153 (4.2); 7.8116 (7.4); 7.8079 (4.9); 7.7281 (4.9); 7.7257 (4.5); 7.4786 (5.0); 6.2820 (0.5); 6.2650 (2.3); 6.2476 (3.6); 6.2302 (2.3); 6.2129 (0.5); 3.6188 (2.1); 3.6017 (5.3); 3.5859 (5.4); 3.5688 (2.3); 3.3676 (0.5); 3.3319 (207.8); 2.6764 (1.0); 2.6724 (1.7); 2.6677 (1.0); 2.6635 (0.6); 2.6556 (1.2); 2.6446 (1.9); 2.6271 (3.5); 2.6161 (2.2); 2.6097 (2.0); 2.5986 (3.6); 2.5874 (1.0); 2.5183 (1.8); 2.5700 (1.3); 2.5526 (0.8); 2.5427 (0.5); 2.5257 (2.5); 2.5209 (3.8); 2.5121 (58.0); 2.5077 (124.2); 2.5032 (168.3); 2.4987 (121.5); 2.4943 (57.4); 2.3388 (0.4); 2.3346 (0.8); 2.3300 (1.1); 2.3255 (0.8); 2.0758 (1.3); 1.8507 (2.8); 1.8384 (7.0); 1.8310 (7.8); 1.8197 (3.6); 1.7791 (0.4); 1.6926 (0.6); 1.6713 (13.1); 1.6536 (16.0); 1.6409 (7.9); 1.6330 (6.7); 1.6210 (2.9); 0.0080 (0.7); −0.0002 (23.0); −0.0085 (0.7) | 583.3 |

1) 'abs' denotes that the compound was obtained in an enantiomerically enriched or pure form with the major stereoisomer having the absolute configuration depicted in the drawing.
2) 'lowT' denotes that the measurement was conducted at a temperature of 260 Kelvin.
3) The stated mass corresponds to the peak from the isotope pattern of the $[M + H]^+$ ion with the highest intensity. # denotes that the $[M - H]^-$ ion was recorded.

TABLE 2

(Intermediates)

| Example | Structure[1)] | NMR Peak List | ESI Mass (m/z)[2)] |
|---|---|---|---|
| INT-1 | 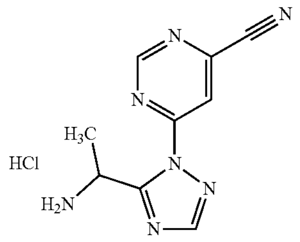 [SMILES: Cl ; CC(N)c1ncnn1-c1cc(C#N)ncn1] | $^1$H-NMR (400 MHz, DMSO-$d_6$): □ = 9.42 (d, J = 1.2 Hz, 1H), 8.74 (brs, 3H), 8.67 (d, J = 1.2 Hz, 1H), 8.56 (s, 1H), 5.50-5.40 (m, 1H), 1.64 (d, J = 6.8 Hz, 3H). | 216.1 [amine + H]$^+$ |
| INT-2 | 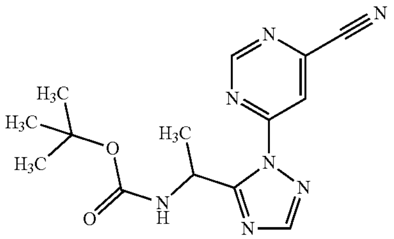 [SMILES: CC(NC(=O)OC(C)(C)C)c1ncnn1-c1cc(C#N)ncn1] | $^1$H-NMR (400 MHz, DMSO-$d_6$): □ = 9.38 (s, 1H), 8.58 (s, 1H), 8.33 (s, 1H), 7.61 (d, J = 7.6 Hz, 1H), 5.78-5.68 (m, 1H), 1.44 (d, J = 7.6 Hz, 3H), 1.33 (s, 9H). | 316.1 [M + H]$^+$ |
| INT-3 | 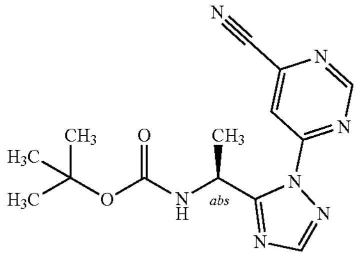 [SMILES: C[C@H](NC(=O)OC(C)(C)C)c1ncnn1-c1cc(C#N)ncn1] | $^1$H-NMR (400 MHz, $CDCl_3$): δ = 1.43 (s, 9H), 1.58 (d, J = 6.8 Hz, 3H), 5.45-5.58 (m, 1H), 5.97-6.10 (m, 1H), 8.02 (s, 1H), 8.32 (d, J = 0.8 Hz, 1H), 9.24 (d, J = 1.2 Hz, 1H). Measured with Bruker AVANCE III 400 MHz. | 260.0 [M − $C_4H_8$ + H]$^+$ |
| INT-4 | 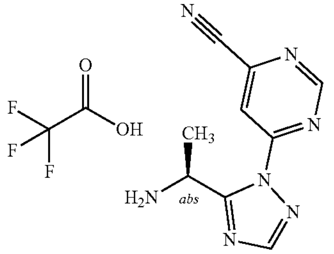 [SMILES: O=C(O)C(F)(F)F ; C[C@H](N)c1ncnn1-c1cc(C#N)ncn1] | | 216.1 [amine + H]$^+$ |
| INT-5 | 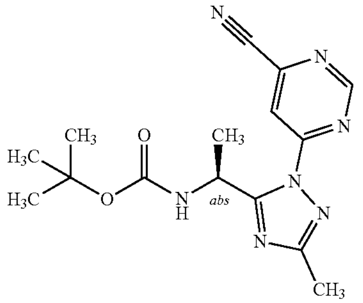 [SMILES: Cc1nc([C@H](C)NC(=O)OC(C)(C)C)n(-c2cc(C#N)ncn2)n1] | $^1$H-NMR (400 MHz, $CDCl_3$): δ = 1.43 (s, 9H), 1.56 (d, J = 6.8 Hz, 3H), 2.45 (s, 3H), 5.37-5.68 (m, 1H), 5.92-6.17 (m, 1H), 8.25 (d, J = 1.2 Hz, 1H), 9.19 (d, J = 1.2 Hz, 1H). Measured with Bruker AVANCE III 400 MHz. | 330.1 |

TABLE 2-continued
(Intermediates)
| Example | Structure[1)] | NMR Peak List | ESI Mass (m/z)[2)] |
| --- | --- | --- | --- |
| INT-6 | 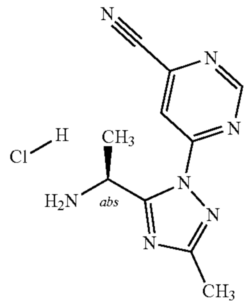 | | 230.1 [amine + H]$^+$ |
| INT-7 | 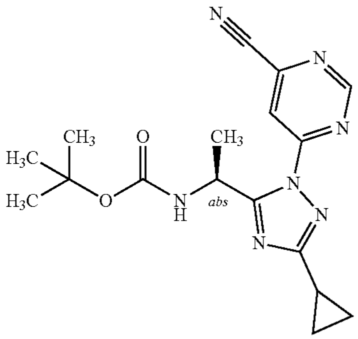 [SMILES: C[C@H](NC(=O)OC(C)(C)C)c1nc(C2CC2)nn1-c1cc(C#N)ncn1] | $^1$H-NMR (400 MHz, MeOD): δ = 9.21 (s, 1H), 8.36 (s, 1H), 5.82 (q, J = 6.8 Hz, 1H), 2.15-2.04 (m, 1H), 1.52 (d, J = 6.8 Hz, 3H), 1.40 (brs, 9H), 1.09-0.98 (m, 4H). Measured with Bruker AVANCE III 400 MHz | 356.0 |
| INT-8 | 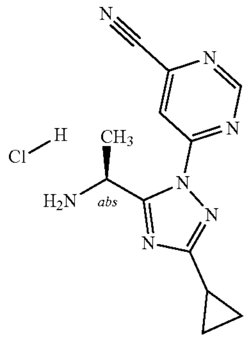 | | 256.2 [amine + H]$^+$ |
| INT-9 | 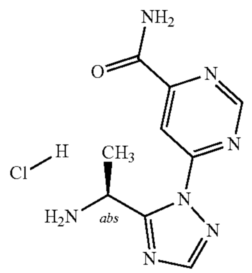 | $^1$H-NMR (400 MHz, DMSO-d$_6$): δ = 9.36 (s, 1H), 8.78 (s, 2H, NH$_2$), 8.52 (s, 1H), 8.50 (bs, 1H), 8.39 (s, 1H), 8.17 (bs, 1H), 5.07-5.45 (m, 1H), 1.67-1.65 (d, 3H). | 234.2 [amine + H]$^+$ |

TABLE 2-continued (Intermediates)

| Example | Structure[1)] | NMR Peak List | ESI Mass (m/z)[2)] |
|---|---|---|---|
| INT-10 | 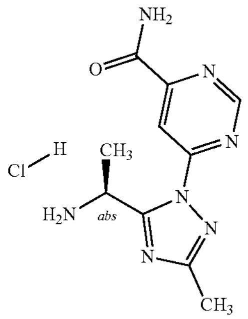 | | 248.2 [amine + H]$^+$ |
| INT-11 | 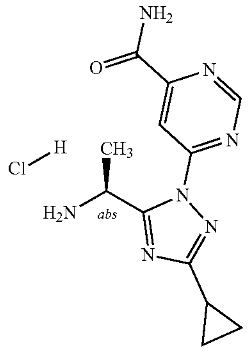 | $^1$H-NMR (400 MHz, DMSO-$d_6$): δ = 9.30 (s, 1H), 8.75 (bs, 2H, $NH_2$), 8.48 (s, 1H), 8.32 (s, 1H), 8.15 (s, 1H), 5.44-5.41 (m, 1H), 2.20-2.14 (m, 1H), 1.64-1.61 (d, 3H), 1.12-1.07 (m, 2H), 1.03-0.98 (m, 2H). | 274.2 [amine + H]$^+$ |
| INT-12 | 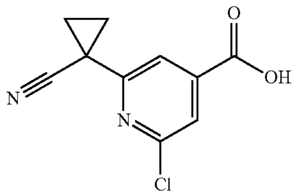 [SMILES: N#CC1(c2cc(C(=O)O)cc(Cl)n2)CC1] | $^1$H NMR (400 MHz, DMSO-$d_6$): δ = 14.20 (bs, 1H, COOH), 7.89 (s, 1H), 7.53 (s, 1H), 1.94-1.91 m, 2H), 1.76-1.73 (m, 2H). | 221.0[#] |
| INT-13 | 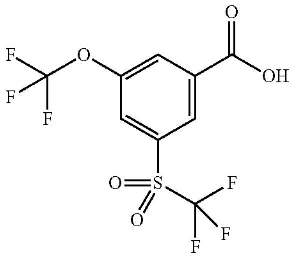 [SMILES: O=C(O)c1cc(OC(F)(F)F)cc(S(=O)(=O)C(F)(F)F)c1] | $^1$H NMR (400 MHz, DMSO-$d_6$): δ = 14.37 (bs, 1H, COOH), 8.48 (s, 1H), 8.46 (s, 1H), 8.42 (s, 1H). | 337.0[#] |
| INT-14 | 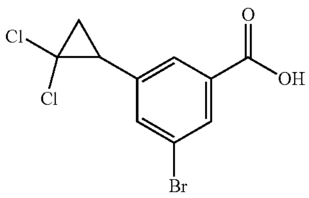 [SMILES: O=C(O)c1cc(Br)cc(C2CC2(Cl)Cl)c1] | $^1$H-NMR (400 MHz, DMSO-$d_6$): δ = 13.45 (s, 1H), 7.97 (s, 1H), 7.87 (s, 1H), 7.81 (s, 1H), 3.27 (dd, J = 10.9, 8.5 Hz, 1H), 2.40-2.28 (m, 1H), 2.17-2.06 (m, 1H). Spectrum was recorded on a Varian Gemini 2000. | 311.0 |
| INT-15 | 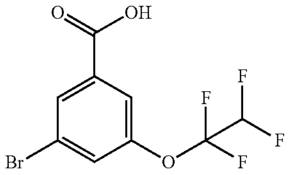 [SMILES: O=C(O)c1cc(Br)cc(OC(F)(F)C(F)F)c1] | $^1$H-NMR: (400 MHz $CDCl_3$): δ = 10.69 (brs, 1H), 8.17 (d, J = 1.2 Hz, 1H), 7.89 (s, 1H), 7.64 (s, 1H), 5.78-6.12 (m, 1H). | 314.9[#] |

TABLE 2-continued
| (Intermediates) | | | |
|---|---|---|---|
| Example | Structure[1)] | NMR Peak List | ESI Mass (m/z)[2)] |
| INT-16 | 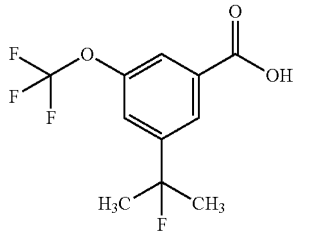 [SMILES: CC(C)(F)c1cc(OC(F)(F)F)cc(C(=O)O)c1] | $^1$H-NMR (400 MHz, DMSO-$d_6$): δ = 1.66 (s, 3H), 1.72 (s, 3H), 7.66 (s, 1H), 7.75 (m, 1H), 7.99 (m, 1H), 13.56 (s, 1H). Spectrum was recorded on a Bruker AVANCE III 400 MHz. | 265.1[#] |
| INT-17 | 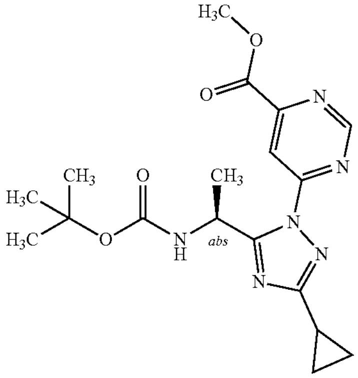 [SMILES: COC(=O)c1cc(-n2nc(C3CC3)nc2[C@H](C)NC(=O)OC(C)(C)C)ncn1] | | |
| INT-18 | 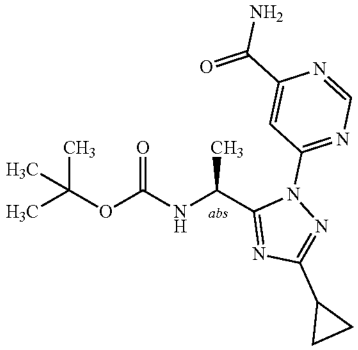 [SMILES: C[C@H](NC(=O)OC(C)(C)C)c1nc(C2CC2)nn1-c1cc(C(N)=O)ncn1] | $^1$H NMR (400 MHz, $CDCl_3$): δ 9.08 (d, J = 0.73 Hz, 1H), 8.65 (s, 1H), 7.79 (brs, 1H), 5.96-6.07 (m, 1H), 5.81 (brs, 1H), 5.56-5.71 (m, 1H), 2.02-2.12 (m, 1H), 1.55 (d, J = 6.8 Hz, 3H), 1.44 (s, 9H), 0.98-1.11 (m, 4H). | |
| INT-19 | 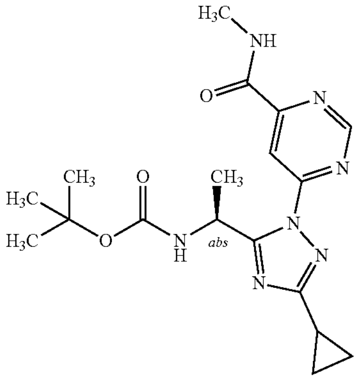 | $^1$H NMR (400 MHz, $CDCl_3$): δ 9.04 (s, 1H), 8.63 (s, 1H), 7.98 (d, 1H), 6.02-5.99 (m, 1H), 5.63 (d, 1H), 3.09 (d, 3H), 2.10-2.06 (m, 1H), 1.54 (d, 1H), 1.44 (s, 9H), 1.07-1.02 (m, 4H). | |

TABLE 2-continued

| (Intermediates) | | | |
|---|---|---|---|
| Example | Structure[1)] | NMR Peak List | ESI Mass (m/z)[2)] |
| INT-20 | 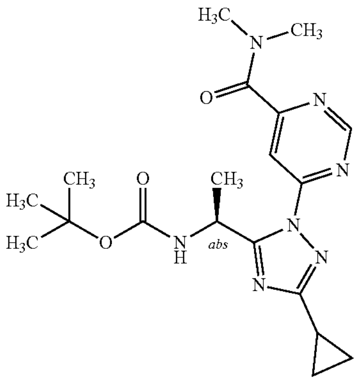 [SMILES: C[C@H](NC(=O)OC(C)(C)C)c1nc(C2CC2)nn1-c1cc(C(=O)N(C)C)ncn1] | $^1$H NMR (400 MHz, $CDCl_3$): δ 9.07 (s, 1H), 8.12 (s, 1H), 6.02-5.99 (m, 1H), 5.62 (d, 1H), 3.16 (s, 3H), 3.08 (s, 3H), 2.07-2.00 (m, 1H), 1.55 (d, 1H), 1.44 (s, 9H), 1.04-1.00 (m, 4H). | |
| INT-21 | 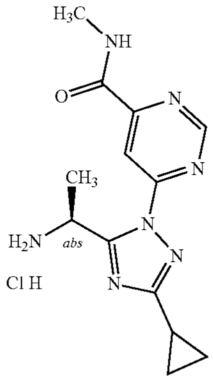 | $^1$H NMR (400 MHz, MeOD): δ 9.19 (d, J = 1.00 Hz, 1H), 8.52 (d, J = 1.00 Hz, 1H), 5.59 (q, J = 6.71 Hz, 1H), 3.25-3.38 (m, 2H), 3.00 (s, 3H), 2.11-2.24 (m, 1H), 1.75 (d, J = 6.75 Hz, 3H), 1.01-1.16 (m, 4H). | |
| INT-22 | 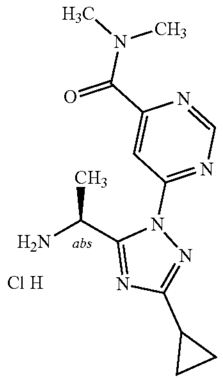 | $^1$H NMR (400 MHz, MeOD): δ 9.17 (d, J = 1.00 Hz, 1H), 8.13 (d, J = 1.00 Hz, 1H), 5.61 (q, J = 6.67 Hz, 1H), 3.18 (s, 3H), 3.10 (s, 3H), 2.11-2.24 (m, 1H), 1.78 (d, J = 6.75 Hz, 3H), 1.05-1.14 (m, 4H). | |
| INT-23 | 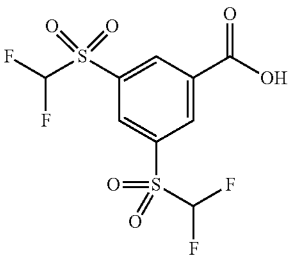 [SMILES: O=C(O)c1cc(S(=O)(=O)C(F)F)cc(S(=O)(=O)C(F)F)c1] | $^1$H NMR (400 MHz, DMSO-$d_6$): δ 7.53 (t, 2H), 8.57 (s, 1H), 8.79 (s, 2H), 14.53 (s, 1H). Measured on a Bruker AVANCE III 400 MHz machine. | 349.0[#] |

[1)]'abs' denotes that the compound was obtained in an enantiomerically enriched or pure form with the major stereoisomer having the absolute configuration depicted in the drawing.

[2)]The stated mass corresponds to the peak from the isotope pattern of the $[M + H]^+$ ion with the highest intensity.

[#]denotes that the $[M - H]^-$ ion was recorded.

BIOLOGICAL EXAMPLES

*Rhipicephalus* (*Boophilus*) *Microplus*—In-Vitro Contact Tests Larval Cattle Tick (Strain Parkhurst, Resistant Against Synthetic Pyrethroids)

9 mg compound is solved in 1 mL acetone and diluted with acetone to the desired concentration. 250 μL of the test solution is filled in 25 mL glass test tubes and homogeneously distributed on the inner walls by rotation and tilting on a shaking device (2 h at 30 rpm). With a compound concentration of 900 ppm, an inner surface of 44.7 $cm^2$ and a homogeneous distribution, a dose of 5 $\mu g/cm^2$ is achieved.

After the solvent has evaporated, each test tube is filled with 20-50 cattle tick larvae (*Rhipicephalus microplus*), closed with a perforated lid and incubated in a horizontal position at 85% relative humidity and 27° C. in an incubator. After 48 hours efficacy is determined. The larvae are patted on the ground of the tubes and negative geotactic behavior is recorded. Larvae that climb back to the top of the vial in a manner comparable to untreated control larvae are marked as alive, larvae not climbing back up comparable to untreated control larvae but are moving uncoordinatedly or only twitching their legs are marked as moribund, tick larvae remaining on the bottom and not moving at all are counted as dead.

A compound shows a good efficacy against *Rhipicephalus microplus*, if at a compound concentration of 5 $\mu g/cm^2$ an efficacy of at least 80% is monitored. An efficacy of 100% means all larvae are dead or moribund; 0% means no larvae are dead or moribund.

In this test, for example, the following compounds from the preparation examples showed good activity of 100% at an application rate of 5 $\mu g/cm^2$ (=500 g/ha): I-1, I-2, I-3, I-4, I-5, I-6, I-8, I-10, I-18, I-21, I-22, I-28, I-33, I-34, I-35, I-36, I-37, I-38, I-42, I-46, I-49, I-50, I-51, I-52, I-55, I-56, I-57, I-63, I-64, I-65, I-66, I-67, I-68, I-69, I-73, I-74, I-75, I-76, I-80, I-85, I-87, I-89, I-95, I-98, I-102, I-135, I-141.

*Rhipicephalus* (*Boophilus*) *Microplus*—Dip Test

Test animal: cattle ticks (*Rhipicephalus microplus*) strain Parkhurst, SP-resistant Solvent: dimethyl sulfoxide To produce a suitable preparation of active compound, 10 mg of active compound are dissolved in 0.5 mL solvent, and the concentrate is diluted with water to the desired concentration.

This compound solution is pipetted into tubes. 8-10 engorged, adult, female cattle ticks (*Rhipicephalus microplus*) are placed in perforated tubes. These tubes are immersed in the aqueous compound solution until the ticks are completely moistened. After the liquid has drained off, the ticks are transferred to a filter paper in a plastic tray and stored in a climate chamber.

After 7 days egg deposition of fertile eggs is monitored. Eggs where fertility is not visible are stored in a climate chamber till hatching after about 42 days. An efficacy of 100% means all eggs are infertile; 0% means all eggs are fertile.

In this test, for example, the following compounds from the preparation examples showed good activity of 100% at an application rate of 100 ppm: I-1.

*Rhipicephalus* (*Boophilus*) *Microplus*—Injection Test

Solvent: dimethyl sulfoxide

To produce a suitable preparation of active compound, 10 mg of active compound are dissolved in 0.5 mL solvent, and the concentrate is diluted with solvent to the desired concentration.

Five adult engorged female ticks (*Rhipicephalus microplus*) are injected with 1 μL compound solution into the abdomen. The ticks are transferred into replica plates and incubated in a climate chamber.

After 7 days egg deposition of fertile eggs is monitored. Eggs where fertility is not visible are stored in a climate chamber till hatching after about 42 days. An efficacy of 100% means all eggs are infertile; 0% means all eggs are fertile.

In this test, for example, the following compounds from the preparation examples showed good activity of 100% at an application rate of 4 μg/animal: I-1, 1-2.

*Ctenocephalides felis*—Oral Test

Solvent: dimethyl sulfoxide

To produce a suitable preparation of active compound, 10 mg of active compound are dissolved in 0.5 mL solvent, and the concentrate is diluted with citrated cattle blood to the desired concentration.

Approximately 20 adult unfed cat fleas (*Ctenocephalides felis*) are placed in a flea chamber whose top and bottom is covered with gauze. A chamber whose bottom is sealed with parafilm, is filled with the blood-compound solution and placed on top of the flea chamber, so that the fleas can suck the blood. The blood chamber is heated to 37° C. whereas the flea chamber is kept at room temperature.

After 2 days mortality in % is determined. 100% means all the fleas have been killed; 0% means none of the fleas have been killed.

In this test, for example, the following compounds from the preparation examples showed good activity of 100% at an application rate of 100 ppm: 1-1, 1-2.

*Ctenocephalides felis*—In-Vitro Contact Tests Adult Cat Flea 9 mg compound is solved in 1 mL acetone and diluted with acetone to the desired concentration. 250 μL of the test solution is filled in 25 mL glass test tubes and homogeneously distributed on the inner walls by rotation and tilting on a shaking device (2 h at 30 rpm). With a compound concentration of 900 ppm, an inner surface of 44.7 $cm^2$ and a homogeneous distribution, a dose of 5 $\mu g/cm^2$ is achieved.

After the solvent has evaporated, each test tube is filled with 5-10 adult cat fleas (*Ctenocephalides felis*), closed with a perforated lid and incubated in a lying position at room temperature and relative humidity. After 48 hours efficacy is determined. The fleas are patted on the ground of the tubes and are incubated on a heating plate at 45-50° C. for at most 5 minutes. Immotile or uncoordinated moving fleas, which are not able to escape the heat by climbing upwards, are marked as dead or moribund.

A compound shows a good efficacy against *Ctenocephalides felis*, if at a compound concentration of 5 $\mu g/cm^2$ an efficacy of at least 80% is monitored. An efficacy of 100% means all fleas are dead or moribund; 0% means no fleas are dead or moribund.

In this test, for example, the following compounds from the preparation examples showed good activity of 100% at an application rate of 5 $\mu g/cm^2$ (=500 g/ha): I-3, I-21, I-33, I-34, I-46, I-49, I-50, I-51, I-52, I-55, I-56, I-57, I-63, I-64, I-65, I-67, I-68, I-69, I-73, I-74, I-75, I-76, I-80, I-85, I-87, I-89, I-95, I-98, I-102, 1-135, I-141.

In this test, for example, the following compounds from the preparation examples showed good activity of 90% at an application rate of 5 $\mu g/cm^2$ (=500 g/ha): I-5, I-18, I-38, I-42, I-66.

*Rhipicephalus sanguineus*—In-Vitro Contact Tests with Adult Brown Dog Ticks 9 mg compound is solved in 1 mL acetone and diluted with acetone to the desired concentration. 250 μL of the test solution is filled in 25 mL glass test tubes and homogeneously distributed on the inner walls by rotation and tilting on a shaking device (2 h at 30 rpm). With a compound concentration of 900 ppm, an inner surface of 44.7 $cm^2$ and a homogeneous distribution, a dose of 5 μg/$cm^2$ is achieved.

After the solvent has evaporated, each test tube is filled with 5-10 adult brown dog ticks (*Rhipicephalus sanguineus*), closed with a perforated lid and incubated in a lying position at room temperature and relative humidity. After 48 hours efficacy is determined. The ticks are patted on the ground of the tubes and are incubated on a heating plate at 45-50° C. for at most 5 minutes. Immotile or uncoordinated moving ticks, which are not able to escape the heat by climbing upwards, are marked as dead or moribund.

A compound shows a good efficacy against *Rhipicephalus sanguineus*, if at a compound concentration of 5 μg/$cm^2$ an efficacy of at least 80% is monitored. An efficacy of 100% means all ticks are dead or moribund; 0% means no ticks are dead or moribund.

In this test, for example, the following compounds from the preparation examples showed good activity of 100% at an application rate of 5 μg/$cm^2$ (=500 g/ha): 1-1, I-3, I-4, I-5, I-6, I-18, I-21, I-28, I-34, I-42, 1-46, I-50, I-51, I-52, I-55, I-56, I-57, I-63, I-64, I-65, I-67, I-68, I-69, I-73, I-74, I-75, I-76, I-80, I-85, I-87, I-89, I-95, I-98, I-135, I-141.

In this test, for example, the following compounds from the preparation examples showed good activity of 80% at an application rate of 5 μg/$cm^2$ (=500 g/ha): 1-33, I-36, I-49, I-102.

*Diabrotica balteata*—Spray Test

Solvent: 78.0 parts by weight of acetone 1.5 parts by weight of dimethylformamide Emulsifier: alkylarylpolyglycol ether To produce a suitable preparation of active compound, 1 part by weight of active compound is mixed with the stated amount of solvent, and the concentrate is diluted with water, containing an emulsifier concentration of 1000 ppm, to the desired concentration. Further test concentrations are prepared by dilution with emulsifier containing water.

Soaked wheat seeds (*Triticum aestivum*) are placed in a multiple well plate filled with agar and some water and are incubated for 1 day to germinate (5 seeds per well). The germinated wheat seeds are sprayed with a test solution containing the desired concentration of the active ingredient. Afterwards each unit is infected with 10-20 larvae of the banded cucumber beetle (*Diabrotica* balteata).

After 7 days efficacy in % is determined. 100% means all the seedlings have grown up like in the untreated, uninfected control; 0% means none of the seedlings have grown.

In this test, for example, the following compounds from the preparation examples showed good activity of 100% at an application rate of 100 g/ha (=32 μg/well): I-3, I-4, I-5, I-6, I-7, I-8, I-10, I-12, I-13, I-14, I-15, I-16, I-17, I-18, I-19, I-20, I-21, I-22, I-23, I-24, I-25, I-26, I-27, I-28, I-29, I-30, I-31, I-33, I-34, I-35, I-36, I-38, I-39, I-40, I-41, I-42, I-44, I-45, I-46, I-47, I-48, I-49, I-50, I-51, I-52, I-53, I-54, I-55, I-56, I-58, I-59, I-60, I-63, I-64, I-65, I-66, I-67, I-69, I-71, I-73, I-75, I-76, I-77, I-78, I-79, I-80, I-81, I-82, I-83, I-84, I-85, I-86, I-87, I-88, I-89, I-90, I-91, I-92, I-93, I-94, I-95, I-98, I-99, I-101, I-102, I-103, I-104, I-105, I-106, I-107, I-109, I-110, I-112, I-114, I-116, I-117, I-118, I-119, I-120, I-121, I-122, I-124, I-125, I-127, I-128, I-129, I-130, I-131, I-132, I-133, I-134, I-136, I-139, I-140, I-141, I-142, I-145, I-146, I-148, 1-150, I-152, I-153, I-156, I-157, I-158, I-159, I-160, I-161, I-162, I-163, I-165, I-166, I-168, I-169.

In this test, for example, the following compounds from the preparation examples showed good activity of 80% at an application rate of 100 g/ha (=32 μg/well): I-1, I-2, I-11, I-37, I-43, I-72, I-74, I-115, I-135, 1-137, I-138, I-164, I-167.

*Meloidogyne incognita*—test Solvent: 125.0 parts by weight of acetone To produce a suitable preparation of active compound, 1 part by weight of active compound is mixed with the stated amount of solvent, and the concentrate is diluted with water to the desired concentration.

Vessels are filled with sand, a solution of the active ingredient, a suspension containing eggs and larvae of the southern root-knot nematode (*Meloidogyne incognita*) and salad seeds. The salad seeds germinate and the seedlings grow. Galls develop in the roots.

After 14 days the nematicidal activity is determined based on the percentage of gall formation. 100% means no galls were found and 0% means the number of galls found on the roots of the treated plants was equal to that in untreated control plants.

In this test, for example, the following compounds from the preparation examples showed good activity of 90% at an application rate of 20 ppm: 1-21.

*Myzus persicae*—Oral Test

Solvent: 100 parts by weight acetone

To produce a suitable preparation of active compound, 1 part by weight of active compound is mixed with the stated amount of solvent, and the concentrate is diluted with water to the desired concentration.

50 μL compound solution is filled in microtiter plates and 150 μL IPL41 insect medium (33%+15% sugar) is added to obtain a total volume of 200 μL per well. Afterwards the plates are sealed with parafilm through which a mixed population of the green peach aphid (*Myzus persicae*) can suck on the compound preparation.

After 5 days mortality in % is determined. 100% means all aphids have been killed and 0% means none of the aphids have been killed.

In this test, for example, the following compounds from the preparation examples showed good activity of 100% at an application rate of 4 ppm: I-1, 1-2.

*Myzus persicae*—Spray Test

Solvent: 78.0 parts by weight acetone 1.5 parts by weight dimethylformamide

Emulsifier: alkylarylpoly glycol ether

To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks infected with all instars of the green peach aphid (*Myzus persicae*), are sprayed with a preparation of the active ingredient of the desired concentration.

After 5 days mortality in % is determined. 100% means all aphids have been killed and 0% means none of the aphids have been killed.

In this test, for example, the following compounds from the preparation examples showed good activity of 100% at an application rate of 100 g/ha: I-7, I-19, I-20, I-41, I-49, I-55, I-77, I-79, I-80, I-81, I-83, I-85, I-86, I-87, I-88, I-89, I-90, I-92, I-93, I-94, I-98, I-102, I-112, I-116, I-129, I-133, I-139, I-140, I-142, I-143, I-152, I-160, I-163, I-164, I-166, I-167, I-168.

In this test, for example, the following compounds from the preparation examples showed good activity of 90% at an application rate of 100 g/ha: I-1, I-3, I-5, I-8, I-12, I-18, I-21, I-32, I-34, I-40, I-42, I-45, I-46, I-48, I-50, I-51, I-56, I-58, I-59, I-60, I-64, I-65, I-66, I-67, I-71, I-72, I-74, I-78, I-82, I-84, I-95, I-97, I-99, I-101, I-103, I-110, I-113, I-115, I-118, I-120, I-121, I-124, I-134, I-136, I-141, I-150, I-154, I-156, I-159, I-161, I-162, I-169.

In this test, for example, the following compounds from the preparation examples showed good activity of 70% at an application rate of 100 g/ha: I-69, I-73, I-125.

*Nezara viridula*—Spray Test

Solvent: 78.0 parts by weight of acetone 1.5 parts by weight of dimethylformamide Emulsifier: alkylarylpolyglycol ether To produce a suitable preparation of active compound, 1 part by weight of active compound is mixed with the stated amount of solvent, and the concentrate is diluted with water, containing an emulsifier concentration of 1000 ppm, to the desired concentration. Further test concentrations are prepared by dilution with emulsifier containing water.

Barley plants (*Hordeum vulgare*) are sprayed with a test solution containing the desired concentration of the active ingredient and are infested with larvae of the southern green stink bug (*Nezara viridula*).

After 4 days mortality in % is determined. 100% means all the stink bugs have been killed; 0% means none of the stink bugs have been killed.

In this test, for example, the following compounds from the preparation examples showed good activity of 100% at an application rate of 500 g/ha: I-7, I-12, I-18, I-19, I-21, I-22, I-23, I-25, I-30, I-31, I-32, 1-33, I-34, I-38, I-42, I-44, I-45, I-46, I-48, I-49, I-51, I-58, I-59, I-60, I-61, I-62, I-64, I-65, I-66, I-67, I-69, I-72, I-73, I-74, I-75, I-76, I-77, I-78, I-79, I-80, I-81, I-82, I-83, I-84, I-85, I-86, I-87, I-88, I-89, I-90, I-92, I-93, I-94, I-95, I-96, I-98, I-99, I-101, I-102, I-110, I-116, I-117, I-118, I-119, I-120, I-121, I-122, I-124, I-125, I-126, I-127, I-128, I-129, I-130, I-131, I-132, I-135, I-136, I-138, I-139, I-140, I-141, I-142, I-143, I-147, I-148, I-150, I-154, I-155, I-162.

In this test, for example, the following compounds from the preparation examples showed good activity of 90% at an application rate of 500 g/ha: I-3, I-28, I-41, I-70, I-71.

In this test, for example, the following compounds from the preparation examples showed good activity of 100% at an application rate of 100 g/ha: I-21, I-34, I-44, I-49, I-51, I-116, I-118, I-120, I-121, I-124, I-125, I-126, I-128, I-135.

In this test, for example, the following compounds from the preparation examples showed good activity of 90% at an application rate of 100 g/ha: I-3, I-7, I-19, I-32, I-42, I-127.

*Nilaparvata lugens*—Spray Test

Solvent: 78.0 parts by weight of acetone 1.5 parts by weight of dimethylformamide Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Rice plants (*Oryza sativa*) are sprayed with a preparation of the active ingredient of the desired concentration and the plants are infested with the brown planthopper (*Nilaparvata lugens*).

After 4 days mortality in % is determined. 100% means all planthoppers have been killed and 0% means none of the planthoppers have been killed.

In this test, for example, the following compounds from the preparation examples showed good activity of 100% at an application rate of 500 g/ha: I-8, I-23, I-29, I-31, I-33, I-38, I-39, I-44, I-49, I-50, I-51, I-57, I-59, I-60, I-63, I-64, I-67, I-72, I-73, I-74, I-75, I-76, I-77, I-78, I-79, I-80, I-81, I-82, I-83, I-92, I-93, I-94, I-101, I-116, I-118, I-120, I-121, I-122, I-125, I-126, I-128, I-129, I-130, I-133, I-134, I-135, I-136, I-139, I-141, I-142, I-154.

In this test, for example, the following compounds from the preparation examples showed good activity of 90% at an application rate of 500 g/ha: I-7, I-32, I-61, I-85, I-90, I-102, I-115, I-140.

*Spodoptera frugiperda*—Spray Test

Solvent: 78.0 parts by weight acetone 1.5 parts by weight dimethylformamide

Emulsifier: alkylarylpolyglycol ether

To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Maize (*Zea mays*) leaf sections are sprayed with a preparation of the active ingredient of the desired concentration. Once dry, the leaf sections are infested with fall armyworm larvae (*Spodoptera frugiperda*).

After 7 days mortality in % is determined. 100% means all caterpillars have been killed and 0% means none of the caterpillars have been killed.

In this test, for example, the following compounds from the preparation examples showed good activity of 100% at an application rate of 100 g/ha: I-1, I-3, I-4, I-5, I-6, I-7, I-8, I-9, I-10, I-11, I-12, I-13, I-15, 1-16, I-18, I-19, I-20, I-21, I-22, I-24, I-25, I-26, I-27, I-28, I-29, I-30, I-31, I-32, I-33, I-34, I-35, I-36, I-38, I-39, I-40, I-41, I-42, I-43, I-45, I-46, I-47, I-48, I-49, I-50, I-51, I-52, I-54, I-55, I-56, I-57, I-58, I-63, I-64, I-65, I-66, I-67, I-68, I-69, I-70, I-71, I-72, I-73, I-74, I-75, I-76, I-78, I-79, I-80, I-81, I-82, I-83, I-84, I-85, I-86, I-87, I-88, I-89, I-90, I-91, I-92, I-93, I-94, I-95, I-97, I-98, I-99, I-101, I-102, I-103, I-104, I-105, I-106, I-107, I-108, I-109, I-110, I-111, I-112, I-113, I-114, I-115, I-116, I-117, I-118, I-119, I-120, I-121, I-122, I-123, I-124, I-125, I-127, I-129, I-130, I-132, I-133, I-134, I-135, I-136, I-137, I-138, I-140, I-141, I-142, I-143, I-144, I-145, I-146, I-147, I-148, I-150, I-152, I-153, I-154, I-155, I-156, I-157, I-158, I-159, I-161, I-162, I-163, I-165, I-166, I-167, I-168, I-169.

In this test, for example, the following compounds from the preparation examples showed good activity of 83% at an application rate of 100 g/ha: I-62, I-100, I-151, I-160.

*Aedes aegypti* Test (AEDSAE Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/ml/RME 2000 ppm). This solution is pipetted onto a glazed tile and after evaporation of the acetone, adult mosquitoes of the species *Aedes aegypti* strain MONHEIM are placed onto the dried surface. The exposure time is 30 minutes. Mortality in percent (%) is determined 24 hours after contact of the insects to the treated surface. 100% mortality means that all tested insects are dead, whereas 0% means that no insect died.

The following examples showed in this test efficacy of 80-100% at a surface concentration of 20 $mg/m^2$: I-1, I-2, I-3, I-4, I-5, I-7, I-8, I-10, I-19, I-20, I-21, I-25, I-33, I-34, I-36, I-40, I-42, I-49, I-51, I-73, I-74, I-86, I-90, I-93, I-102.

The following examples showed in this test efficacy of 80-100% at a surface concentration of 4 mg/m$^2$: I-1, I-2, I-8, I-10, I-19, I-20, I-21, I-25, I-33, I-34, I-41, I-42, I-49, I-51, I-73, I-74, I-86, I-90, I-93, I-102.

*Culex quinquefasciatus* Test (CULXFA Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/ml/RME 2 000 ppm). This solution is pipetted onto a glazed tile and after evaporation of the acetone, adult mosquitoes of the species *Culex quinquefasciatus* strain P00 are placed onto the dried surface. The exposure time is 30 minutes. Mortality in percent (%) is determined 24 hours after contact of the insects to the treated surface. 100% mortality means that all tested insects are dead, whereas 0% means that no insect died.

The following examples showed in this test efficacy of 80-100% at a surface concentration of 20 mg/m$^2$: I-20, I-33, I-49, I-51, I-73, I-74, I-90, I-93, I-102.

The following examples showed in this test efficacy of 80-100% at a surface concentration of 4 mg/m$^2$: I-21, I-33, I-42, I-49, I-51, I-73, I-74, I-90, I-93, I-102.

*Musca domestica* Test (MUSCDO Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/ml/RME 2000 ppm). This solution is pipetted onto a glazed tile and after evaporation of the acetone, adult flies of the species *Musca domestica* strain WHO-N are placed onto the dried surface. The exposure time is 30 minutes. Mortality in percent (%) is determined 24 hours after contact of the insects to the treated surface. 100% mortality means that all tested insects are dead, whereas 0% means that no insect died.

The following examples showed in this test efficacy of 80-100% at a surface concentration of 20 mg/m$^2$: I-1, I-10, I-20, I-21, I-33, I-36, I-39, I-42, I-49, I-51, I-73, I-74, I-8, I-86, I-90, I-93, I-102.

The following examples showed in this test efficacy of 80-100% at a surface concentration of 4 mg/m$^2$: I-21, I-33, I-36, I-39, I-42, I-49, I-51, I-73, I-74, I-90, I-93, I-102.

*Blattella germanica* Test (BLTTGE Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/ml/RME 2000 ppm). This solution is pipetted onto a glazed tile and after evaporation of the acetone, adult animals of the species *Blattella germanica* strain PAULINIA are placed onto the dried surface. The exposure time is 30 minutes.

Mortality in percent (%) is determined 24 hours after contact of the insects to the treated surface. 100% mortality means that all tested insects are dead, whereas 0% means that no insect died.

The following examples showed in this test efficacy of 80-100% at a surface concentration of 20 mg/m$^2$: I-21, I-49, I-51, I-73, I-74, I-90, I-93, I-102.

The following examples showed in this test efficacy of 80-100% at a surface concentration of 4 mg/m$^2$: I-21, I-49, I-51, I-73, I-74, I-93, I-102.

Comparison Examples

*Spodoptera frugiperda*—Spray Test (SPODFR)

Solvent: 78.0 parts by weight acetone 1.5 parts by weight dimethylformamide

Emulsifier: alkylarylpolyglycol ether

To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Maize (*Zea mays*) leaf sections are sprayed with a preparation of the active ingredient of the desired concentration. Once dry, the leaf sections are infested with fall armyworm larvae (*Spodoptera frugiperda*).

After the specified period of time, mortality in % is determined. 100% means all caterpillars have been killed and 0% means none of the caterpillars have been killed.

In this test, for example, the following compound from the preparation examples shows a superior level of activity compared to the prior state of the art: see table 3 and 4.

*Myzus persicae*—Oral Test (MYZUPE Oral)

Solvent: 100 parts by weight acetone

To produce a suitable preparation of active compound, 1 part by weight of active compound is mixed with the stated amount of solvent, and the concentrate is diluted with water to the desired concentration.

50 μL compound solution is filled in microtiter plates and 150 μL IPL41 insect medium (33%+15% sugar) is added to obtain a total volume of 200 μL per well. Afterwards the plates are sealed with parafilm through which a mixed population of the green peach aphid (*Myzus persicae*) can suck on the compound preparation.

After 5 days mortality in % is determined. 100% means all aphids have been killed and 0% means none of the aphids have been killed.

In this test, for example, the following compound from the preparation examples shows a superior level of activity compared to the prior state of the art: see table 3.

*Myzus persicae*—Spray Test (MYZUPE)

Solvent: 78.0 parts by weight acetone 1.5 parts by weight dimethylformamide

Emulsifier: alkylarylpolyglycol ether

To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks infected with all instars of the green peach aphid (*Myzus persicae*), are sprayed with a preparation of the active ingredient of the desired concentration.

After the specified period of time, mortality in % is determined. 100% means all aphids have been killed and 0% means none of the aphids have been killed.

In this test, for example, the following compounds from the preparation examples show a superior level of activity compared to the prior state of the art: see table 4.

TABLE 3

| Comparison Examples (I) | | | | |
|---|---|---|---|---|
| Substance | Structure | Object | Concentration | % Efficacy dat |
| Ex.-No. I-146<br>Known from<br>WO 2019197468 | 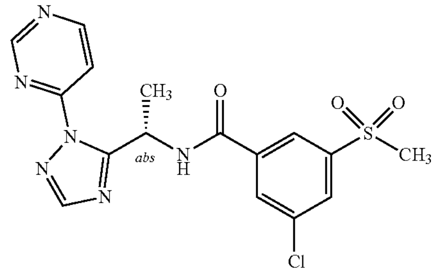 [SMILES: C[C@H](NC(=O)c1cc(Cl)cc(S(C)(=O)=O)c1)c1ncnn1-c1ccncn1] | SPODFR<br>MYZUPE<br>oral | 20 g ai/ha<br>0.16 ppm | 33 7 dat<br>0 5 dat |
| Ex.-No. I-148<br>Known from<br>WO 2019197468 | 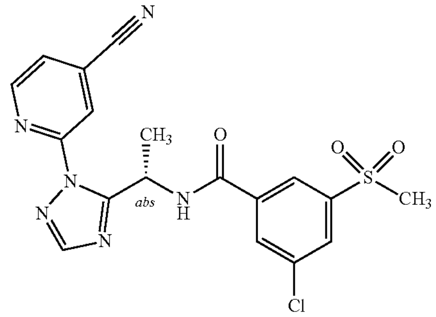 [SMILES: C[C@H](NC(=O)c1cc(Cl)cc(S(C)(=O)=O)c1)c1ncnn1-c1cc(C#N)ccn1] | SPODFR<br>MYZUPE<br>oral | 20 g ai/ha<br>0.16 ppm | 33 7 dat<br>0 5 dat |
| Ex.-No. I-1<br>According to the<br>invention | 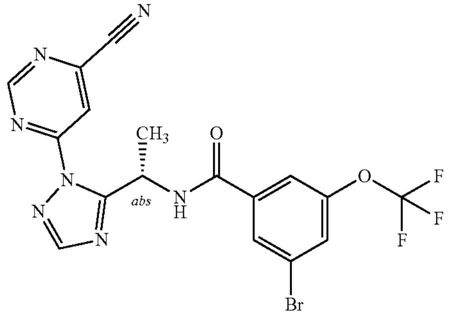 [SMILES: C[C@H](NC(=O)c1cc(Br)cc(OC(F)(F)F)c1)c1ncnn1-c1cc(C#N)ncn1] | SPODFR<br>MYZUPE<br>oral | 20 g ai/ha<br>0.16 ppm | 100 7 dat<br>100 5 dat |

dat = days after treatment

TABLE 4

| Comparison Examples (II) | | | | |
|---|---|---|---|---|
| Substance | Structure | Object | Concentration | % Efficacy dat |
| Ex.-No. I-068<br>Known from<br>WO 2019197468 | 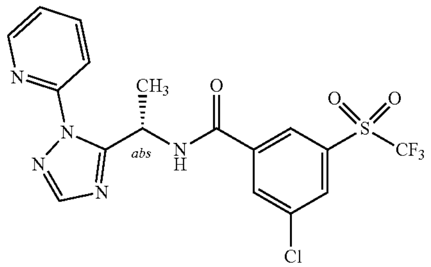 [SMILES: C[C@H](NC(=O)c1cc(Cl)cc(S(=O)(=O)C(F)(F)F)c1)c1ncnn1-c1ccccn1] | MYZUPE | 100 g ai/ha<br>20 g ai/ha | 0 5 dat<br>0 5 dat |

TABLE 4-continued

| Comparison Examples (II) | | | | |
|---|---|---|---|---|
| Substance | Structure | Object | Concentration | % Efficacy dat |
| Ex.-No. I-075 Known from WO 2019197468 | 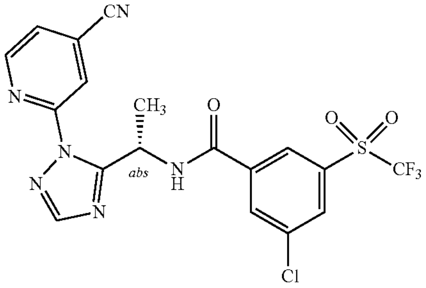 [SMILES: C[C@H](NC(=O)c1cc(Cl)cc(S(=O)(=O)C(F)(F)F)c1)c1ncnn1-c1cc(C#N)ccn1] | SPODFR | 100 g ai/ha | 100 7 dat |
| | | MYZUPE | 20 g ai/ha | 33 7 dat |
| | | | 100 g ai/ha | 90 5 dat |
| | | | 20 g ai/ha | 70 5 dat |
| Ex.-No. I-84 According to the invention | 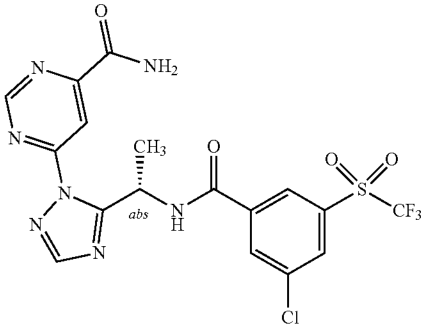 [SMILES: C[C@H](NC(=O)c1cc(Cl)cc(S(=O)(=O)C(F)(F)F)c1)c1ncnn1-c1cc(C(N)=O)ncn1] | SPODFR | 100 g ai/ha | 100 7 dat |
| | | MYZUPE | 20 g ai/ha | 100 7 dat |
| | | | 100 g ai/ha | 90 5 dat |
| | | | 20 g ai/ha | 100 5 dat |
| | | | 4 g ai/ha | 90 5 dat |
| Ex.-No. I-86 According to the invention | 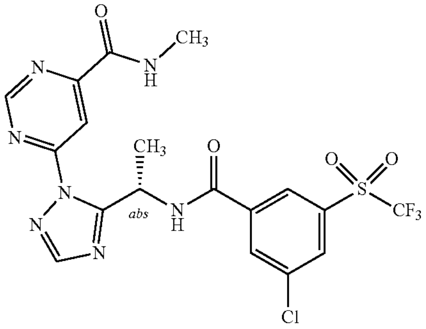 [SMILES: CNC(=O)c1cc(-n2ncnc2[C@H](C)NC(=O)c2cc(Cl)cc(S(=O)(=O)C(F)(F)F)c2)ncn1] | SPODFR | 100 g ai/ha | 100 7 dat |
| | | MYZUPE | 20 g ai/ha | 100 7 dat |
| | | | 100 g ai/ha | 100 5 dat |
| | | | 20 g ai/ha | 100 5 dat |
| | | | 4 g ai/ha | 100 5 dat |

dat = days after treatment

The invention claimed is:

1. A compound of formula (I) or an enantiomer thereof or a salt thereof (I)

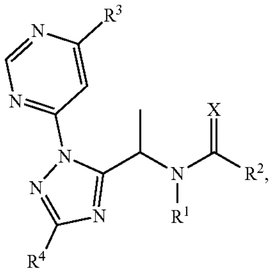

in which

X is O or S;

$R^1$ is hydrogen;

$R^2$ is selected from the following substructures Q1 and Q2, in which the bond to the C═X-group is marked with a #:

Q1

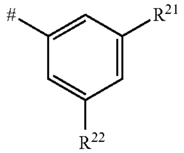

Q2

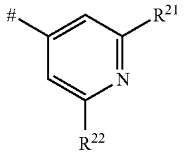

wherein $R^{21}$ is halogen, —CN, —$SF_5$, $C_1$-$C_3$haloalkyl, $C_1$-$C_3$haloalkoxy, $C_1$-$C_3$haloalkylthio, $C_1$-$C_3$haloalkylsulfinyl, $C_1$-$C_3$haloalkylsulfonyl, $C_1$-$C_3$alkylthio, $C_1$-$C_3$alkylsulfinyl, $C_1$-$C_3$alkylsulfonyl, $C_3$-$C_4$cycloalkylthio, $C_3$-$C_4$cycloalkylsulfinyl, $C_3$-$C_4$cycloalkylsulfonyl, substituted or unsubstituted phenylsulfonyl, or substituted or unsubstituted cyclopropyl $R^{22}$ is hydrogen, halogen, —CN, $C_1$-$C_3$haloalkyl, $C_1$-$C_3$haloalkoxy or $C_1$-$C_3$haloalkylsulfonyl;

$R^3$ is —CN or a substituent selected from the following substructure S1, in which the bond to the pyrimidine is marked with a #:

S1

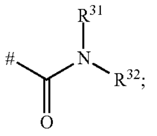

$R^{31}$ is hydrogen or $C_1$-$C_3$alkyl;

$R^{32}$ is hydrogen, substituted or unsubstituted $C_3$-$C_6$cycloalkyl or substituted or unsubstituted $C_1$-$C_3$alkyl, $R^4$ is hydrogen, $C_1$-$C_3$alkyl, $C_1$-$C_3$alkoxy or $C_3$-$C_4$cycloalkyl.

2. The compound according to claim 1, in which

X is O or S;

$R^1$ is hydrogen;

$R^2$ is selected from the following substructures Q1 or Q2, in which the bond to the C═X-group is marked with a #:

Q1

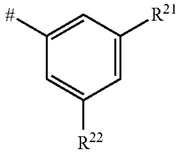

Q2

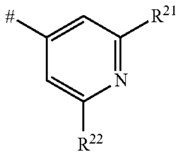

wherein $R^{21}$ is fluorine, chlorine, bromine, iodine, —CN, cyclopropyl, 1-cyanocyclopropyl, 2,2-dichlorocyclopropyl, difluoromethyl, 1,1-difluoroethyl, trifluoromethyl, chlorodifluoromethyl, 2-fluoropropan-2-yl, difluoromethoxy, trifluoromethoxy, 1,1,2,2-tetrafluoroethoxy, 1,1,2,2-tetrafluoro-2-iodoethoxy difluoromethylthio, trifluoromethylthio, 1,1,2,2-tetrafluoroethylthio difluoromethylsulfonyl, trifluoromethylsulfonyl, 1,1,2,2-tetrafluoroethylsulfonyl, methylsulfanyl, methylsulfinyl, methylsulfonyl, ethylsulfonyl, cyclopropylsulfonyl or 4-chlorophenyl-sulfonyl;

$R^{22}$ is hydrogen, fluorine, chlorine, bromine, iodine, —CN, difluoromethyl, trifluoromethyl, difluoromethoxy, trifluoromethoxy, difluoromethylsulfonyl, or trifluoromethylsulfonyl;

$R^3$ is —CN or a substituent selected from the following substructure S1, in which the bond to the pyrimidine is marked with a #:

S1

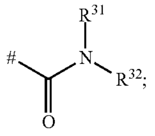

$R^{31}$ is hydrogen or methyl;

$R^{32}$ is hydrogen, substituted or unsubstituted cyclopropyl or substituted or unsubstituted $R^4$ is hydrogen, methyl or cyclopropyl.

3. The compound according to claim 1, in which

X is O;

R is hydrogen;

$R^2$ is (3,5-dibromophenyl), (3,5-dichlorophenyl), (3-chloro-5-methylsulfonylphenyl), 3-bromo-5-methylsulfonylphenyl, (3-cyano-5-fluorophenyl), 3-chloro-5-cyanophenyl, 3-bromo-5-cyanophenyl, 3,5-dicyanophenyl, 3-(1, 1,2,2-tetrafluoroethylthio) phenyl, 3-(1-cyanocyclopropyl)-5-(trifluoromethoxy) phenyl, 3-(difluoromethoxy)-5-fluorophenyl, 3-(difluoromethoxy)-5-iodophenyl, 3~ (difluoromethylsulfonyl)-5-(trifluoromethoxy) phenyl, 3-(trifluoromethoxy)-5-(trifluoromethylsulfonyl) phenyl 3-(trifluoromethoxy) phenyl, 3-(trifluoromethyl) phenyl, 3-(trifluoromethylsulfonyl) phenyl, 3,5-bis(difluoromethoxy) phenyl, 3-(2-fluoropropan-2-yl)-5-(trifluoromethoxy) phenyl, 3,5-bis(trifluoromethoxy) phenyl, 3,5-bis(difluoromethyl) phenyl, 3,5-bis(trifluoromethyl) phenyl, 3-(difluoromethoxy)-5-(trifluoromethoxy) phenyl, 3,5-bis(difluoromethylsulfonyl) phenyl, 3,5-bis(trifluoromethylsulfonyl) phenyl, 3-bromo-5-(1,1,2,2-tetrafluoroethoxy) phenyl, 3-bromo-5-(2,2-dichlorocyclopropyl) phenyl, 3-bromo-5-(difluoromethoxy) phenyl, 3-bromo-5-(trifluoromethoxy) phenyl, 3-chloro-5-(1,1,2,2-tetrafluoro-2-iodoethoxy) phenyl, 3-chloro-5-(1,1,2,2-tetrafluoroethoxy) phenyl, 3-chloro-5-(4-chlorophenyl) sulfonylphenyl, 3-chloro-5-(difluoromethylsulfonyl) phenyl, 3-chloro-5-(trifluoromethoxy) phenyl, 3-chloro-5-(trifluoromethyl) phenyl, 3-chloro-5-(1,1-difluoroethyl) phenyl, 3-chloro-5-(chlorodifluoromethyl) phenyl, 3-chloro-5-(trifluoromethylsulfonyl) phenyl, 3-bromo-5-(trifluoromethylsulfonyl) phenyl, 3-chloro-5-(trifluoromethylthio) phenyl, 3-cyano-5-(trifluoromethoxy) phenyl, 3-cyclopropyl-5-(difluoromethoxy) phenyl, 3-cyclopropyl-5-(trifluoromethoxy) phenyl, 3-cyclopropylsulfonyl-5-(trifluoromethoxy) phenyl, 3-fluoro-5-(trifluoromethoxy) phenyl, 3-methylsulfonylphenyl, 3-(difluoromethoxy)-5-methylsulfanylphenyl, 3~ (difluoromethoxy)-5-methylsulfonylphenyl, 3-methylsulfonyl-5-(trifluoromethoxy) phenyl, 3-methylsulfonyl-5-(trifluoromethyl) phenyl, 2,6-dibromopyridin-4-yl, 2-(trifluoromethoxy) pyridin-4-yl, 2-chloro-6-(trifluoromethoxy) pyridin-4-yl, 2-bromo-6-methylsulfonyl-pyridin-4-yl or 2-chloro-6-(1-cyanocyclopropyl) pyridin-4-yl;

$R^3$ is —CN, aminocarbonyl, methylcarbamoyl, ethylcarbamoyl, (isopropylamino) carbonyl, (difluoroethylamino) carbonyl, (3,3,3-trifluoropropylamino) carbonyl, (cyclopropylamino) carbonyl, dimethylaminocarbonyl, [ethyl (methyl) amino] carbonyl, [isopropyl (methyl) amino] carbonyl [cyclopropylmethyl (methyl) amino] carbonyl; or $R^4$ is hydrogen, methyl or cyclopropyl.

4. The compound according to claim 1, wherein X is O according to formula (I')

(I')

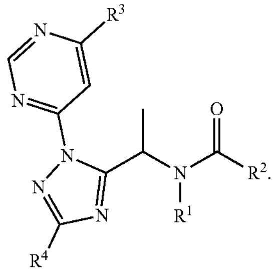

5. The compound according to claim 4, wherein $R^1$ is hydrogen and the compound is an R enantiomer according to formula (I")

(I")

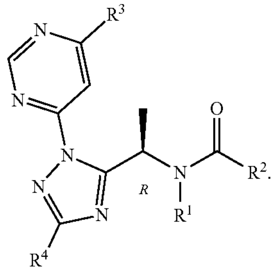

6. The compound according to claim 4, wherein $R^1$ is hydrogen and the compound is an S enantiomer according to formula (I'")

(I''')

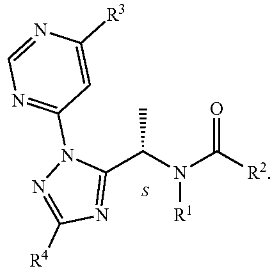

7. A compound of formula (a)

(a)

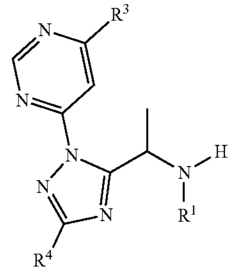

wherein $R^1$, $R^3$, and $R^4$ are as defined in claim 1.

8. A compound selected from tert-butyl {1-[1~ (6-cyanopyrimidin-4-yl)-1H-1,2,4-triazol-5-yl] ethyl}carbamate, tert-butyl N-[(IS)-1-[2-(6-cyanopyrimidin-4-yl)-1,2,4-triazol-3-yl] ethyl]carbamate, tert-butyl N-[(IS)-1-[2-(6-cyanopyrimidin-4-yl)-5-methyl-1,2,4-triazol-3-yl] ethyl] carbamate, tert-butyl N-[(IS)-1-[2-(6-cyanopyrimidin-4-yl)-5-cyclopropyl-1,2,4-triazol-3-yl] ethyl]-carbamate, tert-butyl N-[(1S)-1-[2-(6-carbamoylpyrimidin-4-yl)-5-cyclopropyl-1,2,4-triazol-3-yl] ethyl] carbamate, tert-butyl N-[(IS)-1-[5-cyclopropyl-2-[6-(methylcarbamoyl) pyrimidin-4-yl]-1,2,4-triazol-3-yl] ethyl] carbamate, and tert-butyl N-[(IS)-1-[5-cyclopropyl-2-[6-(dimethylcarbamoyl) pyrimidin-4-yl]-1,2,4-triazol-3-yl]ethyl]carbamate, or salts thereof.

9. A formulation comprising at least one compound of the formula (I) according to claim 1.

10. The formulation according to claim 9, further comprising at least one extender and/or at least one surface-active substance.

11. The formulation according to claim 9, wherein the compound of the formula (I) is in a mixture with at least one further active compound.

12. A method for controlling one or more pests comprising allowing a compound of formula (I) according to claim 1 or a formulation thereof to act on the one or more pests and/or a habitat thereof.

13. The method according to claim 12, wherein the one or more pests is an animal pest and comprises an insect, an arachnid or a nematode, or the pest is an insect, an arachnid or a nematode.

14. A product comprising a compound of formula (I) according to claim 1 of a formulation thereof for controlling one or more animal pests.

15. The product according to claim 14, wherein the one or more animal pests comprises an insect, an arachnid or a nematode, or in that the animal pest is an insect, an arachnid or a nematode.

16. A method for protecting seed or a germinating plant from one or more pests comprising contacting seed with a compound of the formula (I) according to claim 1 or a formulation thereof.

17. The compound according to claim 1, wherein $R^{21}$ is a substituted phenylsulfonyl, wherein the substituted phenylsulfonyl is substituted with one or two substituents selected from the group consisting of a halogen, —CN, methyl, trifluoromethyl, and trifluoromethoxy, or $R^{21}$ is a substituted cyclopropyl, wherein the substituted cyclopropyl is substituted with one or two substituents selected from the group consisting of halogen, —CN, methyl, and trifluoromethyl.

18. The compound according to claim 1, wherein $R^{32}$ is a substituted $C_3$-$C_6$cycloalkyl, wherein the substituted $C_3$-$C_6$cycloalkyl is substituted with one, two, or three substituents selected from the group consisting of a halogen, —CN, $C_3$-$C_6$cycloalkyl and $C_1$-$C_3$alkoxy, or $R^{32}$ is a substituted $C_1$-$C_3$alkyl, wherein the substituted $C_1$-$C_3$alkyl is substituted with one, two, or three substituents selected from the group consisting of a halogen, —CN, $C_3$-$C_6$cycloalkyl and $C_1$-$C_3$alkoxy.

19. The compound according to claim 2, wherein $R^{32}$ is a substituted $C_1$-$C_3$alkyl, wherein the substituted $C_1$-$C_3$alkyl is substituted with one, two, or three substituents selected from the group consisting of fluorine, chlorine, —CN, cyclopropyl and methoxy.

20. A compound selected from 6-[5-(1-aminoethyl)-1H-1,2,4-triazol~]-yl] pyrimidine-4-carbonitrile hydrochloride, 6-[5-[(1S)-1-aminoethyl]-1,2,4-triazol-1-yl] pyrimidine-4-carbonitrile, 6-[5-[(IS)-1-aminoethyl]-3-methyl-1,2,4-triazol-1-yl] pyrimidine-4-carbonitrile hydrochloride, 6-[5-[(IS)-1-aminoethyl]-3-cyclopropyl-1,2,4-triazol-1-yl] pyrimidine-4-carbonitrile hydro-chloride, 6-[5-[(IS)-1-aminoethyl]-3-methyl-1,2,4-triazol-1-yl] pyrimidine-4-carboxamide hydrochloride, 6-[5-[(1S)-1-aminoethyl]-3-cyclopropyl-1,2,4-triazol-1-yl] pyrimidine-4-carboxamide hydrochloride, 6-[5-[(IS)-1-aminoethyl]-1,2,4-triazol-1-yl] pyrimidine-4-carboxamide hydrochloride, methyl 6-[5-[(IS)-1-(tert-butoxycarbonylamino) ethyl]-3-cyclopropyl-1,2,4-triazol-1-yl] pyrimidine-4-carboxylate, 6-[5-[(IS)-1-aminoethyl]-3-cyclopropyl-1,2,4-triazol-1-yl]-N-methyl-pyrimidine-4-carboxamide hydrochloride, 6-[5-[(1S)-1-aminoethyl]-3-cyclopropyl-1,2,4-triazol-1-yl]-N,N-dimethyl-pyrimidine-4-carboxamide hydrochloride, or salts thereof, or free amines thereof.

21. A compound selected from 2-chloro-6-(1-cyanocyclopropyl) pyridine-4-carboxylic acid, 3-(trifluoromethoxy)-S-(trifluoromethylsulfonyl) benzoic acid, 3-bromo-5-(2,2-dichlorocyclopropyl) benzoic acid 3-bromo-5-(1,1,2,2-tetrafluoroethoxy) benzoic acid, 3-(1-fluoro-1-methylethyl)-5-(trifluoromethoxy) benzoic acid, or 3,5-bis (difluoromethylsulfonyl) benzoic acid, or salts thereof.

* * * * *